United States Patent
Tran et al.

(10) Patent No.: US 11,098,034 B2
(45) Date of Patent: *Aug. 24, 2021

(54) PYRAZOLYL SUBSTITUTED CARBONIC ACID DERIVATIVES AS MODULATORS OF THE PROSTACYCLIN (PGI2) RECEPTOR USEFUL FOR THE TREATMENT OF DISORDERS RELATED THERETO

(71) Applicant: Arena Pharmaceuticals, Inc., San Diego, CA (US)

(72) Inventors: Thuy-Anh Tran, San Diego, CA (US); Jason B. Ibarra, Las Vegas, NV (US); Young-Jun Shin, San Diego, CA (US); Brett Ullman, San Diego, CA (US); Ning Zou, San Diego, CA (US); Xi Zeng, San Diego, CA (US)

(73) Assignee: ARENA PHARMACEUTICALS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/863,625

(22) Filed: Apr. 30, 2020

(65) Prior Publication Data

US 2020/0392123 A1  Dec. 17, 2020

Related U.S. Application Data

(63) Continuation of application No. 16/181,457, filed on Nov. 6, 2018, now Pat. No. 10,689,372, which is a continuation of application No. 15/486,600, filed on Apr. 13, 2017, now Pat. No. 10,214,518, which is a continuation of application No. 14/659,293, filed on Mar. 16, 2015, now Pat. No. 9,663,500, which is a continuation of application No. 13/934,439, filed on (Continued)

(51) Int. Cl.
| | |
|---|---|
| *C07D 409/04* | (2006.01) |
| *C07D 231/12* | (2006.01) |
| *C07D 231/54* | (2006.01) |
| *C07D 231/56* | (2006.01) |
| *C07D 401/04* | (2006.01) |
| *C07D 405/04* | (2006.01) |
| *A61P 11/00* | (2006.01) |
| *A61P 9/00* | (2006.01) |
| *C07D 231/18* | (2006.01) |

(52) U.S. Cl.
CPC .............. *C07D 409/04* (2013.01); *A61P 9/00* (2018.01); *A61P 11/00* (2018.01); *C07D 231/12* (2013.01); *C07D 231/18* (2013.01); *C07D 231/54* (2013.01); *C07D 231/56* (2013.01); *C07D 401/04* (2013.01); *C07D 405/04* (2013.01)

(58) Field of Classification Search
CPC ........... C07D 231/12; A61P 9/00; A61P 11/00
See application file for complete search history.

(56) References Cited

U.S. PATENT DOCUMENTS

| | | |
|---|---|---|
| 5,849,919 A | 12/1998 | Hamanaka et al. |
| 6,746,729 B1 | 6/2004 | Cherkaoui et al. |

(Continued)

FOREIGN PATENT DOCUMENTS

| | | |
|---|---|---|
| CA | 2125074 A1 | 12/1994 |
| EP | 0028829 A1 | 5/1981 |

(Continued)

OTHER PUBLICATIONS

Aguilar et al. Epoprostenol (prostacyclin) therapy in HIV-associated pulmonary hypertension. Am. J. Respir. Crit. Care Med. 162:1846-1850 (2000).

(Continued)

*Primary Examiner* — Kamal A Saeed
(74) *Attorney, Agent, or Firm* — Wilson Sonsini Goodrich & Rosati

(57) ABSTRACT

Pyrazole derivatives of Formula Ia and pharmaceutical compositions thereof that modulate the activity of the PGI2 receptor. Compounds of the present invention and pharmaceutical compositions thereof are directed to methods useful in the treatment of: pulmonary arterial hypertension (PAH) and related disorders; platelet aggregation; coronary artery disease; myocardial infarction; transient ischemic attack; angina; stroke; ischemia-reperfusion injury; restenosis; atrial fibrillation; blood clot formation in an angioplasty or coronary bypass surgery individual or in an individual suffering from atrial fibrillation; atherosclerosis; atherothrombosis; asthma or a symptom thereof; a diabetic-related disorder such as diabetic peripheral neuropathy, diabetic nephropathy or diabetic retinopathy; glaucoma or other disease of the eye with abnormal intraocular pressure; hypertension; inflammation; psoriasis; psoriatic arthritis; rheumatoid arthritis; Crohn's disease; transplant rejection; multiple sclerosis; systemic lupus erythematosus (SLE); ulcerative colitis; ischemia-reperfusion injury; restenosis; atherosclerosis; acne; type 1 diabetes; type 2 diabetes; sepsis; and chronic obstructive pulmonary disorder (COPD).

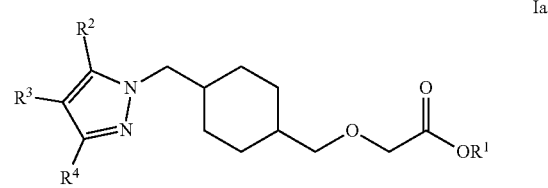

4 Claims, 9 Drawing Sheets

Related U.S. Application Data

Jul. 3, 2013, now Pat. No. 9,012,478, which is a continuation of application No. 13/131,203, filed as application No. PCT/US2009/006251 on Nov. 24, 2009, now abandoned.

(60) Provisional application No. 61/200,393, filed on Nov. 26, 2008.

(56) References Cited

U.S. PATENT DOCUMENTS

| | | |
|---|---|---|
| 7,115,746 B2 | 10/2006 | Snoonian et al. |
| 7,202,253 B2 | 4/2007 | Lloyd et al. |
| 7,226,550 B2 | 6/2007 | Hou et al. |
| 8,895,776 B2 | 11/2014 | Tran et al. |
| 9,012,478 B2 | 4/2015 | Tran et al. |
| 9,663,500 B2 | 5/2017 | Tran et al. |
| 1,021,451 A1 | 2/2019 | Tran et al. |
| 2003/0144350 A1 | 7/2003 | Stevenson et al. |
| 2004/0048844 A1 | 3/2004 | Nugiel et al. |
| 2006/0063930 A1 | 3/2006 | Agoston et al. |
| 2006/0258728 A1 | 11/2006 | Tani et al. |
| 2011/0053958 A1 | 3/2011 | Tran et al. |
| 2011/0224262 A1 | 9/2011 | Tran et al. |
| 2011/0245251 A1 | 10/2011 | Tran et al. |
| 2012/0225937 A1 | 9/2012 | Blackburn et al. |
| 2013/0217706 A1 | 8/2013 | Tran et al. |
| 2014/0171469 A1 | 6/2014 | Tran et al. |
| 2015/0126527 A1 | 5/2015 | Tran et al. |
| 2015/0191455 A1 | 7/2015 | Tran et al. |
| 2019/0270731 A1 | 9/2019 | Tran et al. |

FOREIGN PATENT DOCUMENTS

| | | |
|---|---|---|
| EP | 0442448 A2 | 8/1991 |
| EP | 1046631 A1 | 10/2000 |
| EP | 1716087 A1 | 11/2006 |
| JP | H03160438 A | 7/1991 |
| JP | H06329598 A | 11/1994 |
| JP | H11269138 A | 10/1999 |
| JP | 2005104853 A | 4/2005 |
| JP | 2006083085 A | 3/2006 |
| JP | 2006137856 A | 6/2006 |
| JP | 2007161867 A | 6/2007 |
| WO | WO-02055484 A1 | 7/2002 |
| WO | WO-2007051255 A1 | 5/2007 |
| WO | WO-2007096151 A2 | 8/2007 |
| WO | WO-2007133653 A2 | 11/2007 |
| WO | WO-2009117095 A1 | 9/2009 |
| WO | WO-2010068242 A1 | 6/2010 |
| WO | WO-2010077275 A1 | 7/2010 |
| WO | WO-2011037613 A1 | 3/2011 |
| WO | WO-2019032626 A1 | 2/2019 |

OTHER PUBLICATIONS

Archer et al., Nitric oxide deficiency in fenfluramine- and dexfenfluramine-induced pulmonary hypertension. Am. J. Respir. Crit. Care Med. 158:1061-1067 (1998).
Arehart et al., Acceleration of cardiovascular disease by a dysfunctional prostacyclin receptor mutation: potential implications for cyclooxygenase-2 inhibition. Circ. Res. 102(8):986-993 (2008).
Arehart et al., Prostacyclin, atherothrombosis, and cardiovascular disease. Curr. Med. Chem. 14:2161-2169 (2007).
Asada et al., Discovery of a series of acrylic acids and their derivatives as chemical leads for selective EP3 receptor antagonists, Bioorganic & Medicinal Chemistry, Pergamon, GB 17(18):6567-6582 (2009).
Badesch et al., Continuous intravenous epoprostenol for pulmonary hypertension due to the scleroderma spectrum of disease. A randomized, controlled trial. Ann. Intern. Med. 132:425-434 (2000).
Badesch et al., Prostanoid therapy for pulmonary arterial hypertension. Journal of the American College of Cardiology 43(12 Suppl. S):56S-61S (2004).
Baradia et al., Inhalation therapy to treat pulmonary arterial hypertension. Pharm. Pat. Analyst 1(5):577-588 (2012).
Berge et al. Pharmaceutical Salts. Journal of Pharmaceutical Sciences 66(1):1-19 (Jan. 1977).
Bernabei et al., Iloprost and echistatin protect platelets during simulated extracorporeal circulation. Ann. Thorac. Surg. 59:149-153 (1995).
Boehme et al., Decrease in circulating endothelial cell adhesion molecule and thrombomodulin levels during oral iloprost treatment in rheumatoid arthritis patients: preliminary results. Rheu matol. Int. 26:340-347 (2006).
Burnette et al. PGI2 opens potassium channels in retinal pericytes by cyclic AMP-stimulated, cross-activation of PKG. Exp. Eye Res. 83:1359-1365 (2006).
Cameron et al., The effects of 5-hydroxytryptamine 5-HT2 receptor antagonists on nerve conduction velocity and endoneurial perfusion in diabetic rats. Naunyn Schmiedebergs Arch. Pharmacol. 367:607-614 (2003).
Cameron. Vascular factors and metabolic interactions in the pathogenesis of diabetic neuropathy. Diabetologia 44:1973-1988 (2001).
Caojin et al, Comparison of acute hemodynamic effects of aerosolized iloprost and inhaled nitric oxide in adult congenital heart disease with severe pulmonary arterial hypertension. Department of Cardiology, Guangdong General Hospital & Guangdong Cardiovascular Institute, China, Intern Med. 51:2857-2862 (2012).
Chan. Vitamin E and atherosclerosis. J. Nutr. 128:1593-1596 (1998).
Cheng et al., Role of prostacyclin in the cardiovascular response to thromboxane A2. Science 296:539-541 (2002).
Clinical Trials—Cancer. Genetic Engineering and Biotechnology News 32(20):54 (Nov. 15, 2012).
Collier et al, Radiosynthesis and in vivo evaluation of the pseudopeptide δopioid antagonist [125I]-ITIPP(ψ) J. Labelled Compd. Radiopharm 42:S264-S266 (1999).
Cote et al., Disruption of the nonneuronal tph1 gene demonstrates the importance of peripheral serotonin in cardiac function. PNAS 100(23):13525-13530 (2003).
Cotter et al., Prevention and reversal of motor and sensory peripheral nerve conduction abnormalities in streptozotocin-diabetic rats by the prostacyclin analogue iloprost. Naunyn Schmiedebergs Arch. Pharmacol. 347:534-540 (1993).
Czeslick et al., Inhibition of intracellular tumour necrosis factor (TNF)-alpha and interleukin (IL)-6 production in human monocytes by iloprost. Eur. J. Clin. Invest. 33:1013-1017 (2003).
Davi et al, Platelet activation and atherothrombosis. N. Eng. J. Med. 357:2482-2494 (2007).
Di Renzo et al., Iloprost treatment reduces TNF-alpha production and TNF-RII expression in critical limb ischemia patients without affecting IL6. Prostaglandin Leukot. Essent. Fatty Acids 73:405-410 (2005).
Dogan et al., Effect of the prostacyclin analogue, iloprost, on infarct size after permanent focal cerebral ischemia. Gen. Pharmacol. 27:1163-1166 (1996).
Driscoll et al., Medical therapy for pulmonary arterial hypertension. Expert Opin. Pharmacother. 9:65-81 (2008).
Egan et al., COX-2-derived prostacyclin confers atheroprotection on female mice. Science 306:1954-1957 (2004).
Fang et al, Induction of prostacyclin/PGI2 synthase expression after cerebral ischemia-reperfusion. J. Cereb. Blood Flow Metab. 26:491-501 (2006).
Fetalvero et al., Cardioprotective prostacyclin signaling in vascular smooth muscle. Prostaglandins Other Lipid Mediat. 82:109-118 (2007).
Fetalvero et al., The prostacyclin receptor induces human vascular smooth muscle cell differentiation via the protein kinase a pathway. Am. J. Physiol. Heart. Circ. Physiol. 290:H1337-H1346 (2006).
Fries et al., The cardiovascular pharmacology of COX-2 inhibition. Hematology Am. Soc. Hematol. Educ.Program, 2005:445-451 (2005).
Fujiwara et al., A stable prostacyclin analogue reduces high serum TNF-alpha levels in diabetic patients. Exp. Clin. Endocrinol. Diabetes 112:390-394 (2004).

(56) References Cited

OTHER PUBLICATIONS

Gabriel et al., High throughput screening technologies for direct cyclic AMP measurement. ASSAY and Drug Development Technologies, 1:291-303 (2003).
Gainza et al., Role of prostacyclin (epoprostenol) as anticoagulant in continuous renal replacement therapies: efficacy, security and cost analysis. J. Nephrol. 19:648-655 (2006).
Gao et al., A 7-day oral treatment of patients with active rheumatoid arthritis using the prostacyclin analog iloprost: cytokine modulation, safety, and clinical effects. Rheumatol. Int. 22:45-51 (2002).
GenBank Accession No. NP 000951 Human PGI2 receptor (2019).
Goya et al., Effects of the prostaglandin I2 analogue, beraprost sodium, on vascular cell adhesion molecule-1 expression in human vascular endothelial cells and circulating vascular cell adhesion molecule-1 level in patients with type 2 diabetes mellitus. Metabolism Clinical and Experimental 52:192-198 (2003).
Harada et al., Role of neutrophil elastase in development of pulmonary vascular injury and septic shock in rats. Shock 30(4):379-387 (2008).
Higuchi et al. Pro-drugs as Novel Delivery Systems, vol. 14 of the A.C.S. Symposium Series; and in Bioreversible Carriers in Drug Design, ed. Edward B. Roche, American Pharmaceutical Association and Pergamon Press (1987).
Hoeper et al., Bosentan therapy for portopulmonary hypertension. Eur. Respir. J. 25:502-508 (2005).
Hoeper et al., Pulmonary hypertension after splenectomy? Ann. Intern. Med. 130(6):506-509 (1999).
Hotta et al, Effects of beraprost sodium and insulin on the electroretinogram, nerve conduction, and nerve blood flow in rats with streptozotocin-induced diabetes. Diabetes 45:361-366 (1996).
Hotta et al. Prevention of abnormalities in motor nerve conduction and nerve blood-flow by a prostacyclin analog, beraprost sodium, in streptozotocin-induced diabetic rats. Prostaglandins 49:339-349 (1995).
Hoyng et al., Iloprost, a stable prostacyclin analog, reduces intraocular pressure. Invest. Ophthalmol Vis. Sci. 28:470-476 (1987).
Humbert et al., Cellular and molecular pathobiology of pulmonary arterial hypertension. J. Am. Coll. Cardiol. 43:13S-24S (2004).
Humbert et al, Short-term and long-term epoprostenol (prostacyclin) therapy in pulmonary hypertension secondary to connective tissue diseases: results of a pilot study Eur. Respir. J. 13:1351-1356 (1999).
Idzko et al, Inhaled iloprost suppresses the cardinal features of asthma via inhibition of airway dendritic cell function. J. Clin. Invest. 117:464-472 (2007).
Jaffar et al., Prostaglandin 12-IP signaling blocks allergic pulmonary inflammation by preventing recruitment of CD4+ Th2 cells into the airways in a mouse model of asthma. J. Immunol 179:6193-6203 (2007).
Jozefowski et al., Exogenous but not endogenous prostanoids regulate cytokine secretion from murine bone marrow dendritic cells: EP2, DP, and IP but not EP1, EP3, and FP prostanoid receptors are involved. Int. Immunopharmcol. 3:865-878 (2003).
Klapars et al., A general and efficient copper catalyst for the amidation of aryl halides. J. Am. Chem. Soc. 124: 7421-7428 (2002).
Kobayashi et al., Roles of thromboxane A(2) and prostacyclin in the development of atherosclerosis in apoE-deficient mice. J. Clin. Invest. 114:784-794 (2004).
Koike et al., Enhanced angiogenesis and improvement of neuropathy by cotransfection of human hepatocyte growth factor and prostacyclin synthase gene. FASEB J. 17:779-781 (2003).
Le Bas et al., Radioiodinated analogs of EP 00652218 for the exploration of the tachykinin NK1 receptor by spect. J Labelled Compd. Radiopharm 44:S280-S282 (2001).
Liu et al., Treatments for pulmonary arterial hypertension. Respiratory Medicine, Baillier Tindall, London, GB 100(5):765-774 (2006).

Lundblad et al., Increased cortical cell loss and prolonged hemodynamic depression after traumatic brain injury in mice lacking the IP receptor for prostacyclin. Journal of Cerebral Blood Flow & Metabolism 28:367-376 (2008).
Mardla et al., Potentiation of antiaggregating effect of prostaglandins by alpha-tocopherol and quercetin. Platelets 15:319-324 (2004).
Mccormick et al., Prostacyclin analogues: the next drug-eluting stent? Biochem. Soc. Trans. 35:910-911 (2007).
McGoon et al., Screening, early detection, and diagnosis of pulmonary arterial hypertension: ACCP evidence-based clinical practice guidelines. Chest 126:14S-34S (2004).
McLaughlin et al, Pulmonary arterial hypertension. Pulmonary arterial hypertension. Circulation 114(13):1417-1431 (2006).
Miwa et al., Combination therapy with oral sildenafil and beraprost for pulmonary arterial hypertension associated with CREST syndrome. Int. Heart J. 48:417-422 (2007).
Moncada et al., Human arterial and venous tissues generate prostacyclin (prostaglandin x), a potent inhibitor of platelet aggregation. Lancet 1:18-20 (1977).
Morecroft et al., Effect of tryptophan hydroxylase 1 deficiency on the development of hypoxia-induced pulmonary hypertension. Hypertension 49:232-236 (2007).
Moss. Basic terminology of stereochemistry (IUPAC Recommendations 1996). Pure & Appl. Chem. 68(12):2193-2222 (1996).
Muller et al, Iloprost has potent anti-inflammatory properties on human monocyte-derived dendritic cells. Clinical & Experimental Allergy, Department of Pneumology, University of Freiburg, Germany 40:1214-1221 (2010).
Murata et al., Altered pain perception and inflammatory response in mice lacking prostacyclin receptor. Nature 388:678-682 (1997).
Naeije et al., Expert opinion on available options treating pulmonary arterial hypertension. Expert Opin.Pharmacother. 8:2247-2265 (2007).
Nagao et al., Role of prostaglandin I2 in airway remodeling induced by repeated allergen challenge in mice. Am. J. Respir. Cell Mol. Biol. 29:314-320 (2003).
Okuda et al., Acute effect of beraprost sodium on lower limb circulation in patients with non-insulin-dependent diabetes mellitus-evaluation by color Doppler ultrasonography and laser cutaneous blood flowmetry. Prostaglandins 52:375-384 (1996).
Osol (Editor), Remington's Pharmaceutical Sciences, 1980, Philadelphia College of Pharmaceutical Science, Chapter 27: Structure-Activity Relationship and Drug Design, pp. 420-435.
Owada et al., Effect of long-term administration of prostaglandin I(2) in incipient diabetic nephropathy. Nephron 92:788-796 (2002).
PCT/US2009/001688 International Search Report and Written Opinion dated Jul. 22, 2009.
PCT/US2009/006251 International Search Report and Written Opinion dated Mar. 19, 2010.
Potapov. Stereochemistry. 2nd Ed [Textbook for Chemistry Majors]. USSR. (1988), p. 202, Publisher (Khimiya, Moscow, USSR) (English translation).
Rabinovitch. Pathobiology of pulmonary hypertension. Annu. Rev. Pathol. Mech. Dis. 2:369-399 (2007).
Raychaudhuri et al., The prostacyclin analogue treprostinil blocks NFkappaB nuclear translocation in human alveolar macrophages. J. Biol. Chem. 277:33344-33348 (2002).
Robbins et al, Epoprostenol for treatment of pulmonary hypertension in patients with systemic lupus erythematosus. Chest 117:14-18 (2000).
Rosenkranz. Pulmonary hypertension: Current diagnosis and treatment. Clin. Res. Cardiol. 96(8):527-541 (2007).
Rosenzweig. Emerging treatments for pulmonary arterial hypertension. Expert Opin. Emerging Drugs 11(4):609-619 (2006).
Rosenzweig et al., Long-term prostacyclin for pulmonary hypertension with associated congenital heart defects. Circulation 99:1858-1865 (1999).
Sato et al., Effect of OP-2507, a novel prostacyclin analogue on ischemia and reperfusion induced arrhythmias in isolated perfused rat heart. Journal of Molecular and Cellular Cardiology, Academic Press, GB, 22:S74 (1990).

(56) References Cited

OTHER PUBLICATIONS

Schermuly et al., Antiremodeling effects of iloprost and the dual-selective phosphodiesterase 3/4 inhibitor tolafentrine in chronic experimental pulmonary hypertension. Circ. Res. 94:1101-1108 (2004).
Seiler et al., 2-[3-[2-(4,5-Diphenyl-2-oxazolyl) ethyl] phenoxy] acetic acid (BMY 42393): a new, structurally-novel prostacyclin partial agonist: 1). Inhibition of platelet aggregation and mechanism of action. Thrombosis Research 74(2):115-123 (1994).
Shindo et al., Clinical efficacy of a stable prostacyclin analog, iloprost, in diabetic neuropathy. Prostaglandins 41:85-96 (1991).
Shinomiya et al., Regulation of TNFalpha and interleukin-10 production by prostaglandins I(2) and E(2): studies with prostaglandin receptor-deficient mice and prostaglandin E-receptor subtype-selective synthetic agonists. Biochem. Pharmacol. 61:1153-1160 (2001).
Simonneau et al., Clinical classification of pulmonary hypertension. J. Am. Coll. Cardiol. 43:5S-12S (2004).
Stitham et al., Human prostacyclin receptor structure and function from naturally-occurring and synthetic mutations. Prostaglandins Other Lipid Mediat. 82:95-108 (2007).
Strauss et al., Prostanoid therapy for pulmonary arterial hypertension. Clin. Chest. Med. 28:127-142 (2007).
Streiter et al., the role of chelating diamine ligands in the gold berg reaction: a kinetic study on the copper-catalyzed amidation of aryl iodides. JACS Communications, J. Am. Chem. Soc. 127:4120-4121 (2005).
Szekeres et al., Delayed antiischemic effect of PgI2 and of a new stable PgI2 analogue 7-oxo-prostacyclin-Na in experimental model angina in dogs. Journal of Molecular and Cellular Cardiology, Academic Press, GB 15:132 (1983).
Taichman et al., Epidemiology of pulmonary arterial hypertension. Clin. Chest. Med., 28:1-22 (2007).
Takahashi et al., Augmentation of allergic inflammation in prostanoid IP receptor deficient mice. Br. J. Pharmacol, 137:315-322 (2002).
Tawara et al., Effects of combined therapy with a Rho-kinase inhibitor and prostacyclin on monocrotaline-induced pulmonary hypertension in rats. Journal of Cardiovascular Pharmacology 50(2):195-200 (2007).
Tennis et al, The role of prostacyclin in lung cancer. Translation Research, Division of Pulmonary Sciences and Critical Care Medicine, Department of Medicine, University of Colorado Denver Health Sciences, Denver, Colorado 155(2):57-61 (2010).
Tuder et al., Prostacyclin synthase expression is decreased in lungs from patients with severe pulmonary hypertension. Am. J. Respir. Crit. Care Med. 159:1925-1932 (1999).
Ueno et al., Effects of beraprost sodium, a prostacyclin analogue, on diabetic neuropathy in streptozotocin-induced diabetic rats. Jpn. J. Pharmacol, 70:177-182 (1996).
Ueno et al., Effects of beraprost sodium, a prostacyclin analogue, on tail flick response in two models of diabetic-neuropathy in rats and its mechanism. Life Sci. 59:PL105-PL110 (1996).
Van Rijt et al., In vivo depletion of lung CD11c+ dendritic cells during allergen challenge abrogates the characteristic features of asthma. J. Exp. Med., 201:981-991 (2005).
Vippagunta et al., Crystalline solids. Advanced Drug Delivery Reviews 48:3-26 (2001).
Walther et al., Synthesis of serotonin by a second tryptophan hydroxylase isoform. Science 299:76 (2003).
Wang et al. Deletion of microsomal prostaglandin E synthase-1 augments prostacyclin and retards atherogenesis. Proc. Natl. Acad. Sci. USA 103:14507-14512 (2006).
Xiao et al., Roles of prostaglandin I(2) and thromboxane A(2) in cardiac ischemia-reperfusion injury: a study using mice lacking their respective receptors. Circulation 104:2210-2215 (2001).
Yamada et al., Hypotensive activity of novokinin, a potent analogue of ovokinin(2-7), is mediated by angiotensin AT(2) receptor and prostaglandin IP receptor. Peptides, 29:412-418 (2008).
Yamagishi et al., Beraprost sodium, a prostaglandin I2 analogue, protects against advanced gycation end products-induced injury in cultured retinal pericytes. Mol. Med. 8:546-550 (2002).
Yamashita et al., Beraprost sodium, prostacyclin analogue, attenuates glomerular hyperfiltration and glomerular macrophage infiltration by modulating ecNOS expression in diabetic rats. Diabetes Res. Clin. Pract. 57:149-161 (2002).
Zhang et al, Characterization of the molecular mechanisms of the coupling between intracellular loops of prostacyclin receptor with the C-terminal domain of the Galphas protein in human coronary artery smooth muscle cells. Arch. Biochem. Biophys. 454:80-88 (2006).
Zhou et al., Prostaglandin I2 analogs inhibit proinflammatory cytokine production and T cell stimulatory function of dendritic cells. J. Immunol. 178:702-710 (2007).
Zhu et al, Synthesis and mode of action of (125)I- and (3)H-labeled thieno[2,3-c]pyridine antagonists of cell adhesion molecule expression. J. Org. Chem. 67:943-948 (2002).

PYRAZOLYL SUBSTITUTED CARBONIC ACID DERIVATIVES AS MODULATORS OF THE PROSTACYCLIN (PGI2) RECEPTOR USEFUL FOR THE TREATMENT OF DISORDERS RELATED THERETO

CROSS-REFERENCE TO RELATED APPLICATIONS

This application is a continuation of U.S. application Ser. No. 16/181,457, filed Nov. 6, 2018, now U.S. Pat. No. 10,689,372, issued Jun. 23, 2020, which is a continuation of U.S. application Ser. No. 15/486,600, filed Apr. 13, 2017, now U.S. Pat. No. 10,214,518, issued Feb. 26, 2019, which is a continuation of U.S. application Ser. No. 14/659,293, filed Mar. 16, 2015, now U.S. Pat. No. 9,663,500, issued May 30, 2017, which is a continuation of U.S. application Ser. No. 13/934,439, filed Jul. 3, 2013, now U.S. Pat. No. 9,012,478, issued Apr. 21, 2015, which is a continuation of U.S. application Ser. No. 13/131,203, filed May 25, 2011, which is a U.S. National Stage entry of International Application No. PCT/US2009/006251, filed Nov. 24, 2009, which claims the benefit of priority from U.S. Provisional Application No. 61/200,393, filed Nov. 26, 2008, all of which are hereby incorporated by reference in their entirety.

FIELD OF THE INVENTION

The present invention relates to certain compounds of Formula Ia and pharmaceutical compositions thereof that modulate the activity of the PGI2 receptor. Compounds of the present invention and pharmaceutical compositions thereof are directed to methods useful in the treatment of: pulmonary arterial hypertension (PAH); idiopathic PAH; familial PAH; PAH associated with: a collagen vascular disease, a congenital heart disease, portal hypertension, HIV infection, ingestion of a drug or toxin, hereditary hemorrhagic telangiectasia, splenectomy, pulmonary veno-occlusive disease (PVOD) or pulmonary capillary hemangiomatosis (PCH); PAH with significant venous or capillary involvement; platelet aggregation; coronary artery disease; myocardial infarction; transient ischemic attack; angina; stroke; ischemia-reperfusion injury; restenosis; atrial fibrillation; blood clot formation in an angioplasty or coronary bypass surgery individual or in an individual suffering from atrial fibrillation; atherothrombosis; asthma or a symptom thereof; a diabetic-related disorder such as diabetic peripheral neuropathy, diabetic nephropathy or diabetic retinopathy; glaucoma or other disease of the eye with abnormal intraocular pressure; hypertension; inflammation; psoriasis; psoriatic arthritis; rheumatoid arthritis; Crohn's disease; transplant rejection; multiple sclerosis; systemic lupus erythematosus (SLE); ulcerative colitis; atherosclerosis; acne; type 1 diabetes; type 2 diabetes; sepsis; and chronic obstructive pulmonary disorder (COPD).

BACKGROUND OF THE INVENTION

Prostacyclin (PGI2) is a lipid molecule derived from arachidonic acid through the cyclooxygenase pathway. It is a potent vasodilator, antiproliferative, anti-thrombotic and antiplatelet agent that mediates its effects as an agonist of a G protein-coupled receptor (PGI2 receptor; e.g., human PGI2 receptor, GenBank® Accession No. NP_000951 and alleles thereof). It is known that the binding of PGI2 (or other such agonist) to the PGI2 receptor leads to coupling with the Gs protein and increases intracellular cAMP levels. (See, e.g., Zhang et al., Arch. Biochem. Biophys., 2006, 454:80-88.)

Pulmonary arterial hypertension (PAH) is a life-threatening disease characterized by a progressive pulmonary vasculopathy leading to right ventricular hypertrophy. Right heart failure occurs if left untreated. Prostacyclin, which has vasodilatory and antiproliferative effects on the pulmonary vasculature has been found to be low in patients with PAH compared with normal controls. Exogenous administration of prostacyclin or an analog of prostacyclin (i.e., an agonist of the PGI2 receptor) has become an important strategy in the treatment of PAH. (See, e.g., Tuder et al., Am. J. Respir. Crit. Care. Med., 1999, 159:1925-1932; Humbert et al., J. Am. Coll. Cardiol., 2004, 43:13S-24S; Rosenzweig, Expert Opin. Emerging Drugs, 2006, 11:609-619; McLaughlin et al., Circulation, 2006, 114:1417-1431; Rosenkranz, Clin. Res. Cardiol., 2007, 96:527-541; Driscoll et al., Expert Opin. Pharmacother., 2008, 9:65-81.)

Trepostinil and iloprost are FDA-approved analogs of prostacyclin which, like prostacyclin, are not orally-active. Beraprost is an orally-active analog of prostacyclin approved for the treatment of PAH in Japan, but it has failed registration for the treatment of PAH in Europe and in the US. Of the three FDA-approved drugs, prostacyclin is the best studied in PAH patients. The approximate annual cost of treating PAH with these drugs is $25,000 to $200,000 depending on the dose. At present, many experts consider intravenous prostacyclin to be the most reliable agent for managing the sickest PAH patients. Due to the short half-life of prostacyclin, intravenous treatment is complicated by the need for a continuous infusion. Patients are at risk for potentially fatal rebound pulmonary hypertension if the infusion is abruptly disrupted, as well as significant risk of catheter-related complications including sepsis. (See, e.g., Rosenzweig, Expert Opin. Emerging Drugs, 2006, 11:609-619; Naeije et al, Expert Opin. Pharmacother., 2007, 8:2247-2265; Strauss et al, Clin. Chest. Med., 2007, 28:127-142; Driscoll et al., Expert Opin. Pharmacother., 2008, 9:65-81.)

There is considerable interest in developing prostacyclin analogs (i.e., agonists of the PGI2 receptor) for use in the treatment of other diseases, such as atherothrombosis. Developing stable, orally-active analogs of prostacyclin (i.e., stable, orally-active agonists of the PGI2 receptor) is a rate-limiting step in achieving this goal (see, e.g., Arehart et al., Curr. Med. Chem., 2007, 14:2161-2169; Arehart et al., Circ. Res., 2008, 102(8), 986-93, as well as in the improved management of PAH.

SUMMARY OF THE INVENTION

One aspect of the present invention encompasses certain cyclohexane derivatives selected from compounds of Formula Ia and pharmaceutically acceptable salts, solvates and hydrates thereof:

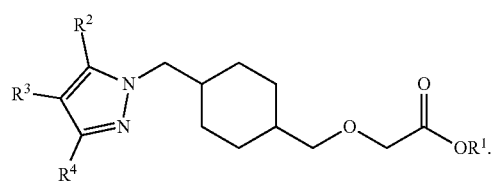

Ia wherein:
R$^1$ is selected from: H and C$_1$-C$_6$ alkyl;
and
R$^2$, R$^3$, and R$^4$ are each independently selected from: H, C$_1$-C$_6$ alkoxy, C$_1$-C$_6$ alkyl, C$_1$-C$_6$ alkylsulfinyl, C$_1$-C$_6$ alkylsulfonyl, C$_1$-C$_6$ alkylthio, aryl, C$_3$-C$_7$ cycloalkyl and heteroaryl; wherein said C$_1$-C$_6$ alkoxy, C$_1$-C$_6$ alkyl, C$_1$-C$_6$ alkylsulfinyl, C$_1$-C$_6$ alkylsulfonyl, C$_1$-C$_6$ alkylthio, aryl, C$_3$-C$_7$ cycloalkyl and heteroaryl are each optionally substituted with one or more groups selected from: C$_1$-C$_6$ alkoxy, C$_1$-C$_6$ alkyl, C$_1$-C$_6$ alkylsulfinyl, C$_1$-C$_6$ alkylsulfonyl, C$_1$-C$_6$ alkylthio, aryl, amino, carboxamide, cyano, C$_1$-C$_6$ haloalkyl, halogen and hydroxy;
or
R$^2$ and R$^3$ together with the pyrazole ring to which they are both attached to form a tricyclic heteroaryl; and R$^4$ is selected from: H, C$_1$-C$_6$ alkoxy, C$_1$-C$_6$ alkyl, C$_1$-C$_6$ alkylsulfinyl, C$_1$-C$_6$ alkylsulfonyl, C$_1$-C$_6$ alkylthio, aryl, C$_3$-C$_7$ cycloalkyl and heteroaryl; wherein said C$_1$-C$_6$ alkoxy, C$_1$-C$_6$ alkyl, C$_1$-C$_6$ alkylsulfinyl, C$_1$-C$_6$ alkylsulfonyl, C$_1$-C$_6$ alkylthio, aryl, C$_3$-C$_7$ cycloalkyl and heteroaryl are each optionally substituted with one or more groups selected from: C$_1$-C$_6$ alkoxy, C$_1$-C$_6$ alkyl, C$_1$-C$_6$ alkylsulfinyl, C$_1$-C$_6$ alkylsulfonyl, C$_1$-C$_6$ alkylthio, aryl, cyano, C$_1$-C$_6$ haloalkyl, halogen and hydroxy.

One aspect of the present invention pertains to methods for the treatment of a PGI2 receptor mediated disorder in an individual, comprising administering to said individual in need thereof, a therapeutically effective amount of a compound of the present invention or a pharmaceutical composition thereof.

One aspect of the present invention pertains to methods for the treatment of PAH in an individual, comprising administering to said individual in need thereof, a therapeutically effective amount of a compound of the present invention or a pharmaceutical composition thereof.

One aspect of the present invention pertains to methods for the treatment of idiopathic PAH in an individual, comprising administering to said individual in need thereof, a therapeutically effective amount of a compound of the present invention or a pharmaceutical composition thereof.

One aspect of the present invention pertains to methods for the treatment of familial PAH in an individual, comprising administering to said individual in need thereof, a therapeutically effective amount of a compound of the present invention or a pharmaceutical composition thereof.

One aspect of the present invention pertains to methods for the treatment of PAH associated with a collagen vascular disease in an individual, comprising administering to said individual in need thereof, a therapeutically effective amount of a compound of the present invention or a pharmaceutical composition thereof.

One aspect of the present invention pertains to methods for the treatment of PAH associated with a collagen vascular disease selected from: scleroderma, CREST syndrome, systemic lupus erythematosus (SLE), rheumatoid arthritis, Takayasu's arteritis, polymyositis, and dermatomyositis in an individual, comprising administering to said individual in need thereof, a therapeutically effective amount of a compound of the present invention or a pharmaceutical composition thereof.

One aspect of the present invention pertains to methods for the treatment of PAH associated with a congenital heart disease in an individual, comprising administering to said individual in need thereof, a therapeutically effective amount of a compound of the present invention or a pharmaceutical composition thereof.

One aspect of the present invention pertains to methods for the treatment of PAH associated with a congenital heart disease selected from: atrial septic defect (ASD), ventricular septic defect (VSD) and patent ductus arteriosus in an individual, comprising administering to said individual in need thereof, a therapeutically effective amount of a compound of the present invention or a pharmaceutical composition thereof.

One aspect of the present invention pertains to methods for the treatment of PAH associated with portal hypertension in an individual, comprising administering to said individual in need thereof, a therapeutically effective amount of a compound of the present invention or a pharmaceutical composition thereof.

One aspect of the present invention pertains to methods for the treatment of PAH associated with HIV infection in an individual, comprising administering to said individual in need thereof, a therapeutically effective amount of a compound of the present invention or a pharmaceutical composition thereof.

One aspect of the present invention pertains to methods for the treatment of PAH associated with ingestion of a drug or toxin in an individual, comprising administering to said individual in need thereof, a therapeutically effective amount of a compound of the present invention or a pharmaceutical composition thereof.

One aspect of the present invention pertains to methods for the treatment of PAH associated with hereditary hemorrhagic telangiectasia in an individual, comprising administering to said individual in need thereof, a therapeutically effective amount of a compound of the present invention or a pharmaceutical composition thereof.

One aspect of the present invention pertains to methods for the treatment of PAH associated with splenectomy in an individual, comprising administering to said individual in need thereof, a therapeutically effective amount of a compound of the present invention or a pharmaceutical composition thereof.

One aspect of the present invention pertains to methods for the treatment of PAH associated with significant venous or capillary involvement in an individual, comprising administering to said individual in need thereof, a therapeutically effective amount of a compound of the present invention or a pharmaceutical composition thereof.

One aspect of the present invention pertains to methods for the treatment of PAH associated with pulmonary veno-occlusive disease (PVOD) in an individual, comprising administering to said individual in need thereof, a therapeutically effective amount of a compound of the present invention or a pharmaceutical composition thereof.

One aspect of the present invention pertains to methods for the treatment of PAH associated with pulmonary capillary hemangiomatosis (PCH) in an individual, comprising administering to said individual in need thereof, a therapeutically effective amount of a compound of the present invention or a pharmaceutical composition thereof.

One aspect of the present invention pertains to methods for the treatment of platelet aggregation in an individual, comprising administering to said individual in need thereof, a therapeutically effective amount of a compound of the present invention or a pharmaceutical composition thereof.

One aspect of the present invention pertains to methods for the treatment of: coronary artery disease, myocardial infarction, transient ischemic attack, angina, stroke, ischemia-reperfusion injury, restenosis or atrial fibrillation in an individual, comprising administering to said individual in need thereof, a therapeutically effective amount of a compound of the present invention or a pharmaceutical composition thereof.

One aspect of the present invention pertains to methods for the treatment of blood clot formation in an angioplasty or coronary bypass surgery individual comprising administering to said individual in need thereof, a therapeutically effective amount of a compound of the present invention or a pharmaceutical composition thereof.

One aspect of the present invention pertains to methods for the treatment of blood clot formation in an individual suffering from atrial fibrillation comprising administering to said individual in need thereof, a therapeutically effective amount of a compound of the present invention or a pharmaceutical composition thereof.

One aspect of the present invention pertains to methods for the treatment of atherosclerosis in an individual, comprising administering to said individual in need thereof, a therapeutically effective amount of a compound of the present invention or a pharmaceutical composition thereof.

One aspect of the present invention pertains to methods for the treatment of atherothrombosis in an individual, comprising administering to said individual in need thereof a therapeutically effective amount of a compound of the present invention or a pharmaceutical composition thereof.

One aspect of the present invention pertains to methods for the treatment of asthma in an individual, comprising administering to said individual in need thereof, a therapeutically effective amount of a compound of the present invention or a pharmaceutical composition thereof.

One aspect of the present invention pertains to methods for the treatment of a symptom of asthma in an individual, comprising administering to said individual in need thereof, a therapeutically effective amount of a compound of the present invention or a pharmaceutical composition thereof.

One aspect of the present invention pertains to methods for the treatment of a diabetic-related disorder in an individual, comprising administering to said individual in need thereof, a therapeutically effective amount of a compound of the present invention or a pharmaceutical composition thereof.

One aspect of the present invention pertains to methods for the treatment of diabetic peripheral neuropathy in an individual, comprising administering to said individual in need thereof, a therapeutically effective amount of a compound of the present invention or a pharmaceutical composition thereof.

One aspect of the present invention pertains to methods for the treatment of diabetic nephropathy in an individual, comprising administering to said individual in need thereof, a therapeutically effective amount of a compound of the present invention or a pharmaceutical composition thereof.

One aspect of the present invention pertains to methods for the treatment of diabetic retinopathy in an individual, comprising administering to said individual in need thereof, a therapeutically effective amount of a compound of the present invention or a pharmaceutical composition thereof.

One aspect of the present invention pertains to methods for the treatment of glaucoma or other disease of the eye with abnormal intraocular pressure in an individual, comprising administering to said individual in need thereof, a therapeutically effective amount of a compound of the present invention or a pharmaceutical composition thereof.

One aspect of the present invention pertains to methods for the treatment of hypertension in an individual, comprising administering to said individual in need thereof, a therapeutically effective amount of a compound of the present invention or a pharmaceutical composition thereof.

One aspect of the present invention pertains to methods for the treatment of hypertension intended to confer protection against cerebral ischemia in an individual, comprising administering to said individual in need thereof, a therapeutically effective amount of a compound of the present invention or a pharmaceutical composition thereof.

One aspect of the present invention pertains to methods for the treatment of inflammation in an individual, comprising administering to said individual in need thereof, a therapeutically effective amount of a compound of the present invention or a pharmaceutical composition thereof.

One aspect of the present invention pertains to methods for the treatment of an inflammatory disease in an individual, comprising administering to said individual in need thereof, a therapeutically effective amount of a compound of the present invention or a pharmaceutical composition thereof.

One aspect of the present invention pertains to methods for the treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma in an individual, comprising administering to said individual in need thereof, a therapeutically effective amount of a compound of the present invention or a pharmaceutical composition thereof.

One aspect of the present invention pertains to methods of modulating the activity of a PGI2 receptor by contacting the receptor with a compound of the present invention.

One aspect of the present invention pertains to methods of agonizing a PGI2 receptor by contacting the receptor with a compound of the present invention.

One aspect of the present invention pertains to methods for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drag or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH) in an individual comprising administering to said individual in need thereof, a therapeutically effective amount of a compound of the present invention or a pharmaceutical composition thereof.

One aspect of the present invention pertains to methods for the treatment of a disorder selected from: platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD) in an individual comprising administering to said individual in need thereof, a therapeutically effective amount of a compound of the present invention or a pharmaceutical composition thereof.

One aspect of the present invention pertains to the use of a compound of the present invention in the manufacture of a medicament for the treatment of a PGI2 receptor mediated disorder.

One aspect of the present invention pertains to the use of a compound of the present invention in the manufacture of a medicament for the treatment of PAH.

One aspect of the present invention pertains to the use of a compound of the present invention in the manufacture of a medicament for the treatment of idiopathic PAH.

One aspect of the present invention pertains to the use of a compound of the present invention in the manufacture of a medicament for the treatment of familial PAH.

One aspect of the present invention pertains to the use of a compound of the present invention in the manufacture of a medicament for the treatment of PAH associated with collagen vascular disease.

One aspect of the present invention pertains to the use of a compound of the present invention in the manufacture of a medicament for the treatment of PAH associated with a collagen vascular disease selected from: scleroderma, CREST syndrome, systemic lupus erythematosus (SLE), rheumatoid arthritis, Takayasu's arteritis, polymyositis, and dermatomyositis.

One aspect of the present invention pertains to the use of a compound of the present invention in the manufacture of a medicament for the treatment of PAH associated with a congenital heart disease.

One aspect of the present invention pertains to the use of a compound of the present invention in the manufacture of a medicament for the treatment of PAH associated with a congenital heart disease selected from: atrial septic defect (ASD), ventricular septic defect (VSD) and patent ductus arteriosus.

One aspect of the present invention pertains to the use of a compound of the present invention in the manufacture of a medicament for the treatment of PAH associated with portal hypertension.

One aspect of the present invention pertains to the use of a compound of the present invention in the manufacture of a medicament for the treatment of PAH associated with HIV infection.

One aspect of the present invention pertains to the use of a compound of the present invention in the manufacture of a medicament for the treatment of PAH associated with ingestion of a drug or toxin.

One aspect of the present invention pertains to the use of a compound of the present invention in the manufacture of a medicament for the treatment of PAH associated with hereditary hemorrhagic telangiectasia.

One aspect of the present invention pertains to the use of a compound of the present invention in the manufacture of a medicament for the treatment of PAH associated with splenectomy.

One aspect of the present invention pertains to the use of a compound of the present invention in the manufacture of a medicament for the treatment of PAH associated with significant venous or capillary involvement.

One aspect of the present invention pertains to the use of a compound of the present invention in the manufacture of a medicament for the treatment of PAH associated with pulmonary veno-occlusive disease (PVOD).

One aspect of the present invention pertains to the use of a compound of the present invention in the manufacture of a medicament for the treatment of PAH associated with pulmonary capillary hemangiomatosis (PCH).

One aspect of the present invention pertains to the use of a compound of the present invention in the manufacture of a medicament for the treatment of platelet aggregation.

One aspect of the present invention pertains to the use of a compound of the present invention in the manufacture of a medicament for the treatment of a PGI2 receptor mediated disorder selected from: coronary artery disease, myocardial infarction, transient ischemic attack, angina, stroke, ischemia-reperfusion injury, restenosis and atrial fibrillation.

One aspect of the present invention pertains to the use of a compound of the present invention in the manufacture of a medicament for the treatment of blood clot formation in an angioplasty or coronary bypass surgery individual.

One aspect of the present invention pertains to the use of a compound of the present invention in the manufacture of a medicament for the treatment of blood clot formation in an individual suffering from atrial fibrillation.

One aspect of the present invention pertains to the use of a compound of the present invention in the manufacture of a medicament for the treatment of atherosclerosis.

One aspect of the present invention pertains to the use of a compound of the present invention in the manufacture of a medicament for the treatment of atherothrombosis.

One aspect of the present invention pertains to the use of a compound of the present invention in the manufacture of a medicament for the treatment of asthma.

One aspect of the present invention pertains to the use of a compound of the present invention in the manufacture of a medicament for the treatment of a symptom of asthma.

One aspect of the present invention pertains to the use of a compound of the present invention in the manufacture of a medicament for the treatment of a diabetic-related disorder.

One aspect of the present invention pertains to the use of a compound of the present invention in the manufacture of a medicament for the treatment of diabetic peripheral neuropathy.

One aspect of the present invention pertains to the use of a compound of the present invention in the manufacture of a medicament for the treatment of diabetic nephropathy.

One aspect of the present invention pertains to the use of a compound of the present invention in the manufacture of a medicament for the treatment of diabetic retinopathy.

One aspect of the present invention pertains to the use of a compound of the present invention in the manufacture of a medicament for the treatment of glaucoma or other disease of the eye with abnormal intraocular pressure.

One aspect of the present invention pertains to the use of a compound of the present invention in the manufacture of a medicament for the treatment of hypertension.

One aspect of the present invention pertains to the use of a compound of the present invention in the manufacture of a medicament for the treatment of hypertension intended to confer protection against cerebral ischemia.

One aspect of the present invention pertains to the use of a compound of the present invention in the manufacture of a medicament for the treatment of inflammation.

One aspect of the present invention pertains to the use of a compound of the present invention in the manufacture of a medicament for the treatment of an inflammatory disease.

One aspect of the present invention pertains to the use of a compound of the present invention in the manufacture of a medicament for the treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma.

One aspect of the present invention pertains to the use of a compound of the present invention in the manufacture of a medicament for modulating the activity of a PGI2 receptor.

One aspect of the present invention pertains to the use of a compound of the present invention in the manufacture of a medicament for agonizing a PGI2 receptor.

One aspect of the present invention pertains to the use of a compound of the present invention in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drag or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

One aspect of the present invention pertains to the use of a compound of the present invention in the manufacture of a medicament for the treatment of a disorder selected from: platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

One aspect of the present invention pertains to compounds of the present invention for use in a method of treatment of the human or animal body by therapy.

One aspect of the present invention pertains to compounds of the present invention for use in a method of treatment of a PGI2 receptor mediated disorder.

One aspect of the present invention pertains to compounds of the present invention for use in a method of treatment of PAH.

One aspect of the present invention pertains to compounds of the present invention for use in a method of treatment of idiopathic PAH.

One aspect of the present invention pertains to compounds of the present invention for use in a method of treatment of familial PAH One aspect of the present invention pertains to compounds of the present invention for use in a method of treatment of PAH associated with a collagen vascular disease.

One aspect of the present invention pertains to compounds of the present invention for use in a method of treatment of PAH associated with a collagen vascular disease selected from: scleroderma, CREST syndrome, systemic lupus erythematosus (SLE), rheumatoid arthritis, Takayasu's arteritis, polymyositis, and dermatomyositis.

One aspect of the present invention pertains to compounds of the present invention for use in a method of treatment of PAH associated with a congenital heart disease.

One aspect of the present invention pertains to compounds of the present invention for use in a method of treatment of PAH associated with a congenital heart disease selected from: atrial septic defect (ASD), ventricular septic defect (VSD) and patent ductus arteriosus.

One aspect of the present invention pertains to compounds of the present invention for use in a method of treatment of PAH associated with portal hypertension.

One aspect of the present invention pertains to compounds of the present invention for use in a method of treatment of PAH associated with HIV infection.

One aspect of the present invention pertains to compounds of the present invention for use in a method of treatment of PAH associated with ingestion of a drug or toxin.

One aspect of the present invention pertains to compounds of the present invention for use in a method of treatment of PAH associated with hereditary hemorrhagic telangiectasia.

One aspect of the present invention pertains to compounds of the present invention for use in a method of treatment of PAH associated with splenectomy.

One aspect of the present invention pertains to compounds of the present invention for use in a method of treatment of PAH associated with significant Venous or capillary involvement.

One aspect of the present invention pertains to compounds of the present invention for use in a method of treatment of PAH associated with pulmonary veno-occlusive disease (PVOD).

One aspect of the present invention pertains to compounds of the present invention for use in a method of treatment of PAH associated with pulmonary capillary hemangiomatosis (PCH).

One aspect of the present invention pertains to compounds of the present invention for use in a method of treatment of platelet aggregation.

One aspect of the present invention pertains to compounds of the present invention for use in a method of treatment of: coronary artery disease, myocardial infarction, transient ischemic attack, angina, stroke, ischemia-reperfusion injury, restenosis or atrial fibrillation.

One aspect of the present invention pertains to compounds of the present invention for use in a method of treatment of blood clot formation in an angioplasty or coronary bypass surgery individual.

One aspect of the present invention pertains to compounds of the present invention for use in a method of treatment of blood clot formation in an individual suffering from atrial fibrillation.

One aspect of the present invention pertains to compounds of the present invention for use in a method of treatment of atherosclerosis.

One aspect of the present invention pertains to compounds of the present invention for use in a method of treatment of atherothrombosis.

One aspect of the present invention pertains to compounds of the present invention for use in a method of treatment of asthma.

One aspect of the present invention pertains to compounds of the present invention for use in a method of treatment of a symptom of asthma.

One aspect of the present invention pertains to compounds of the present invention for use in a method of treatment of a diabetic-related disorder.

One aspect of the present invention pertains to compounds of the present invention for use in a method of treatment of diabetic peripheral neuropathy.

One aspect of the present invention pertains to compounds of the present invention for use in a method of treatment of diabetic nephropathy.

One aspect of the present invention pertains to compounds of the present invention for use in a method of treatment of diabetic retinopathy.

One aspect of the present invention pertains to compounds of the present invention for use in a method of treatment of glaucoma or other disease of the eye with abnormal intraocular pressure.

One aspect of the present invention pertains to compounds of the present invention for use in a method of treatment of hypertension.

One aspect of the present invention pertains to compounds of the present invention for use in a method of treatment of hypertension intended to confer protection against cerebral ischemia.

One aspect of the present invention pertains to compounds of the present invention for use in a method of treatment of inflammation.

One aspect of the present invention pertains to compounds of the present invention for use in a method of treatment of an inflammatory disease.

One aspect of the present invention pertains to compounds of the present invention for use in a method of treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma.

One aspect of the present invention pertains to compounds of the present invention for use in a method of modulating the activity of a PGI2 receptor.

One aspect of the present invention pertains to compounds of the present invention for use in a method of agonizing a PGI2 receptor.

One aspect of the present invention pertains to compounds of the present invention for use in a method of treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arterious in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

One aspect of the present invention pertains to compounds of the present invention for use in a method of treatment of a disorder selected from: platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

One aspect of the present invention pertains to compounds for preparing a composition comprising admixing a compound of the present invention and a pharmaceutically acceptable carrier.

These and other aspects of the invention disclosed herein will be set forth in greater detail as the patent disclosure proceeds.

DETAILED DESCRIPTION OF THE INVENTION

Definitions

Figure 1:
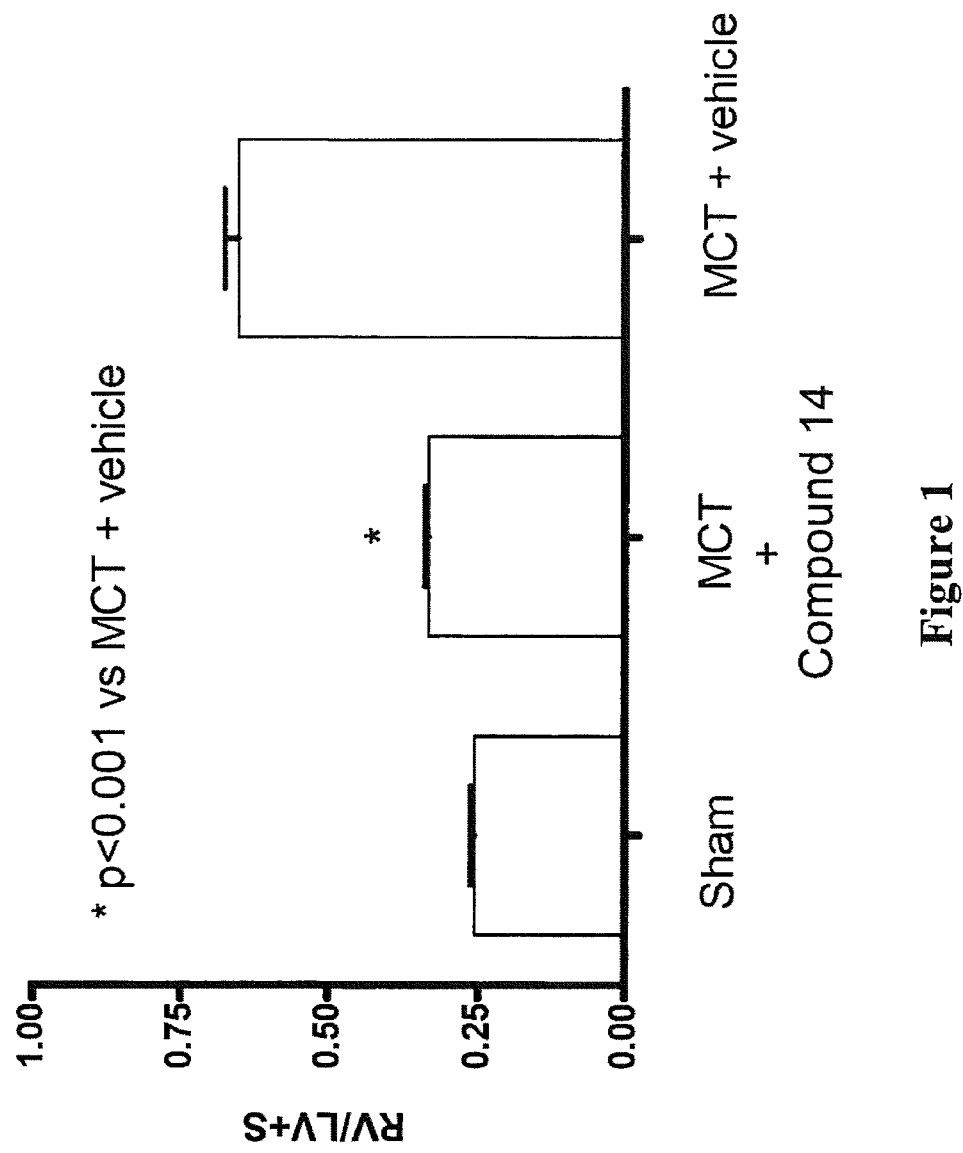
FIG. 1 shows the results of an experiment which measured the ability of Compound 14 to inhibit the right ventricle hypertrophic response to MCT-induced pulmonary arterial hypertension in rat.

For clarity and consistency, the following definitions will be used throughout this patent document.

The term "agonists" is intended to mean moieties that interact and activate the receptor, such as, the PGI2 receptor and initiate a physiological or pharmacological response characteristic of that receptor. For example, when moieties activate the intracellular response upon binding to the receptor, or enhance GTP binding to membranes.

The term "contact or contacting" is intended to mean bringing the indicated moieties together, whether in an in vitro system or an in vivo system. Thus, "contacting" a PGI2 receptor with a compound of the invention includes the administration of a compound of the present invention to an individual, preferably a human, having a PGI2 receptor, as well as, for example, introducing a compound of the invention into a sample containing a cellular or more purified preparation containing a PGI2 receptor.

The term "hydrate" as used herein means a compound of the invention or a salt thereof, that further includes a stoichiometric or non-stoichiometric amount of water bound by non-covalent intermolecular forces.

The terms "including" and "such as" are illustrative and not limitative.

The term "in need of treatment" and the term "in need thereof," when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" is intended to mean any animal, including mammals, preferably mice, rats, other rodents, rabbits, dogs, cats, swine, cattle, sheep, horses, or primates and most preferably humans.

The term "modulate or modulating" is intended to mean an increase or decrease in the amount, quality, response or effect of a particular activity, function or molecule.

The term "pharmaceutical composition" is intended to mean a composition comprising at least one active ingredient; including but not limited to, salts, solvates and hydrates of compounds of the present invention; whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "therapeutically effective amount" is intended to mean the amount of active compound or pharmaceutical agent that elicits the biological or medicinal response in a tissue, system, animal, individual or human that is being sought by a researcher, veterinarian, medical doctor or other clinician or caregiver; or in an individual, which includes one or more of the following:

(1) Preventing the disease; for example, preventing a disease, condition or disorder in an individual that may be predisposed to the disease, condition or disorder but does not yet experience or display the pathology or symptomatology of the disease;

(2) Inhibiting the disease; for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Chemical Group, Moiety or Radical

The term "AD-mix-α" is intended to mean a mixture of potassium osmate, potassium ferricyanide, potassium carbonate and hydroquinine 1,4-phthalazinediyl diether.

The term "AD-mix-β" is intended to mean a mixture of potassium osmate, potassium ferricyanide, potassium carbonate and hydroquinidine 1,4-phthalazinediyl diether.

The term "$C_1$-$C_6$ alkoxy" is intended to mean a $C_1$-$C_6$ alkyl radical, as defined herein, attached directly to an oxygen atom. Some embodiments are 1 to 5 carbons; some embodiments are 1 to 4 carbons; some embodiments are 1 to 3 carbons; and some embodiments are 1 or 2 carbons. Examples include methoxy, ethoxy, n-propoxy, isopropoxy, n-butoxy, t-butoxy, isobutoxy, sec-butoxy and the like.

The term "$C_1$-$C_6$ alkyl" is intended to mean a straight or branched carbon radical containing 1 to 6 carbons. Some embodiments are 1 to 5 carbons. Some embodiments are 1 to 4 carbons. Some embodiments are 1 to 3 carbons. Some embodiments are 1 or 2 carbons. Some embodiments are 1 carbon. Examples of an alkyl include, but are not limited to, methyl, ethyl, n-propyl, isopropyl, n-butyl, sec-butyl, isobutyl, t-butyl, pentyl, isopentyl, t-pentyl, neo-pentyl, 1-methylbutyl [i.e., —CH(CH₃)CH₂CH₂CH₃], 2-methylbutyl [i.e., —CH₂CH(CH₃)CH₂CH₃], n-hexyl and the like.

The term "$C_1$-$C_6$ alkylsulfinyl" is intended to mean a $C_1$-$C_6$ alkyl radical attached to the sulfur of a sulfoxide radical having the formula: —S(O)— wherein the alkyl radical has the same definition as described herein. Examples include, but are not limited to, methylsulfinyl, ethylsulfinyl, n-propylsulfinyl, isopropylsulfinyl, n-butylsulfinyl, sec-butylsulfinyl, isobutylsulfinyl, t-butylsulfinyl, and the like.

The term "$C_1$-$C_6$ alkylsulfonyl" is intended to mean a $C_1$-$C_6$ alkyl radical attached to the sulfur of a sulfone radical having the formula: —S(O)₂— wherein the alkyl radical has the same definition as described herein. Examples include, but are not limited to, methylsulfonyl, ethylsulfonyl, n-propylsulfonyl, isopropylsulfonyl, n-butylsulfonyl, sec-butylsulfonyl, isobutylsulfonyl, t-butylsulfonyl, and the like.

The term "$C_1$-$C_6$ alkylthio" is intended to mean a $C_1$-$C_6$ alkyl radical attached to a sulfur atom (i.e., —S—) wherein the alkyl radical has the same definition as described herein. Examples include, but are not limited to, methylsulfanyl (i.e., CH₃S—), ethylsulfanyl, n-propylsulfanyl, iso-propylsulfanyl, n-butylsulfanyl, sec-butylsulfanyl, iso-butylsulfanyl, t-butylsulfanyl, and the like.

The term "amino" is intended to mean the group —NH₂.

The term "aryl" is intended to mean an aromatic ring radical containing 6 to 10 ring carbons. Examples include phenyl and naphthyl. In some embodiments aryl is intended to mean phenyl.

The term "carboxamide" is intended to mean the group —CONH₂.

The term "cyano" is intended to mean the group —CN.

The term "$C_3$-$C_7$ cycloalkyl" is intended to mean a saturated ring radical containing 3 to 7 carbons. Some embodiments contain 3 to 6 carbons. Some embodiments contain 3 to 5 carbons Some embodiments contain 5 to 7 carbons. Some embodiments contain 3 to 4 carbons. Examples include cyclopropyl, cyclobutyl, cyclopentyl, cyclohexyl, cycloheptyl and the like.

The term "$C_1$-$C_6$ haloalkyl" is intended to mean a $C_1$-$C_6$ alkyl group, defined herein, wherein the alkyl is substituted with one halogen up to fully substituted and a fully substituted $C_1$-$C_6$ haloalkyl can be represented by the formula $C_nL_{2n+1}$ wherein L is a halogen and "n" is 1, 2, 3, 4, 5 or 6. When more than one halogen is present then they may be the same or different and selected from the group consisting of F, Cl, Br and I, preferably F. Some embodiments are 1 to 5 carbons, some embodiments are 1 to 4 carbons, some embodiments are 1 to 3 carbons, and some embodiments are 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl and the like.

The term "halogen" or "halo" is intended to mean to a fluoro, chloro, bromo or iodo group.

The term "heteroaryl" is intended to mean an aromatic ring system containing 5 to 14 aromatic ring atoms that may be a single ring, two fused rings or three fused rings wherein at least one aromatic ring atom is a heteroatom selected from, but not limited to, the group consisting of O, S and N wherein the N can be optionally substituted with H, $C_1$-$C_4$ acyl or $C_1$-$C_4$ alkyl. Some embodiments contain 5 to 6 ring atoms for example furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, triazinyl and the like. Some embodiments contain 8 to 14 ring atoms for example carbazolyl, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl. phenazinyl, phenothiazinyl, phenoxazinyl, benzoxazolyl, benzothiazolyl, 1H-benzimidazolyl, imidazopyridinyl, benzothienyl, benzofuranyl, isobenzofuran and the like.

The term "hydroxyl" or "hydroxy" is intended to mean the group —OH.

The term "MP-carbonate" is intended to mean macroporous triethylammonium methylpolystyrene carbonate.

Compounds of the Invention:

One aspect of the present invention pertains to certain compounds as shown in Formula Ia:

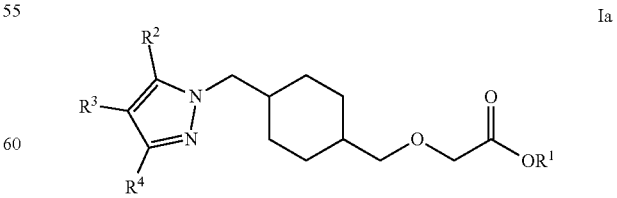

Ia and pharmaceutically acceptable salts, solvates and hydrates thereof;

wherein $R^1$, $R^2$, $R^3$ and $R^4$ have the same definitions as described herein, supra and infra.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R^1$, $R^2$, $R^3$ and $R^4$) contained within the generic chemical formulae described herein, for example, Ia, Ic, Ie, Ig, Ii, etc., are specifically embraced by the present invention just as if each and every combination was individually explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one group they can be identical or they can be different.

Compounds of the invention can also include tautomeric forms, such as keto-enol tautomers and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

It is understood and appreciated that compounds of Formula Ia and formulae related thereto may have one or more chiral centers and therefore can exist as enantiomers and/or diastereoisomers. The invention is understood to extend to and embrace all such enantiomers, diastereoisomers and mixtures thereof, including but not limited to racemates. It is understood that compounds of Formula Ia and formulae used throughout this disclosure are intended to represent all individual enantiomers and mixtures thereof, unless stated or shown otherwise.

It is understood and appreciated that compounds of Formula Ia exist as meso isomers. Such meso isomers may be referred to as cis and trans. Certain cis meso isomers of compounds of Formula Ia are named herein using the prefix (1s,4s) and certain trans meso isomers of compounds of Formula Ia are named herein using the prefix (1r,4r) as shown below.

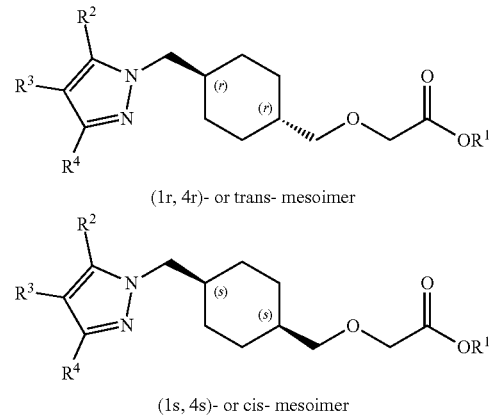

(1r, 4r)- or trans- mesoimer (1s, 4s)- or cis- mesoimer

It is further understood and appreciated that certain compounds of Formula Ia bear a 3,4-dihydroxybutyl substituent on the pyrazole ring. When the absolute stereochemistry of the dihydroxybutyl group is (S) then certain cis compounds of Formula Ia are named herein using the prefix (1R,4s). When the absolute stereochemistry of the dihydroxybutyl group is (R) then certain cis compounds of Formula Ia are named herein using the prefix (1S,4s) as shown below.

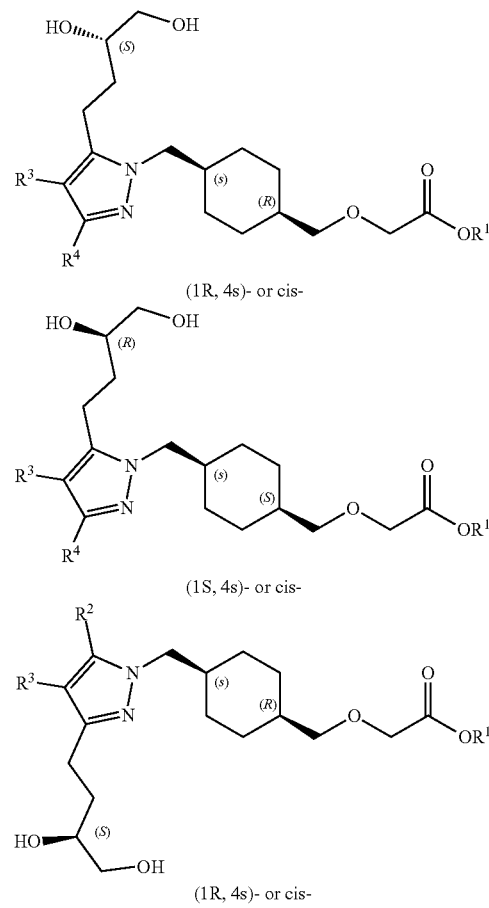

(1R, 4s)- or cis- (1S, 4s)- or cis- (1R, 4s)- or cis-

-continued

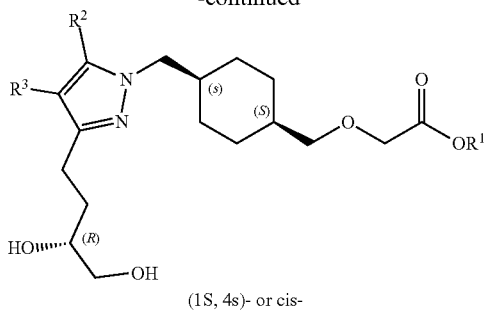

(1S, 4s)- or cis-

It is well understood and appreciated in the art that pyrazoles can exist in various tautomeric forms. Two possible tautomeric forms of certain intermediates useful in the preparation of compounds of the present invention are illustrated below:

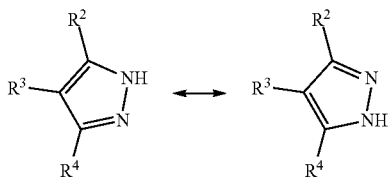

It is further understood that tautomeric forms can also have corresponding nomenclature for each represented tautomer. The present invention includes all tautomers and the various nomenclature designations.

The Group $R^1$:

In some embodiments, $R^1$ is selected from: H and $C_1$-$C_6$ alkyl.

In some embodiments, $R^1$ is H.

In some embodiments, $R^1$ is $C_1$-$C_6$ alkyl.

In some embodiments, $R^1$ is methyl.

The Group $R^2$:

In some embodiments, $R^2$ is selected from: H, $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, amino, carboxamide, cyano, halogen and hydroxy.

In some embodiments, $R^2$ is selected from: H, $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl are each optionally substituted with one or more groups selected from: amino, carboxamide, chloro, cyano, ethoxy, fluoro, hydroxy, methoxy, methyl, methylsulfinyl, methylsulfonyl and methylthio.

In some embodiments, $R^2$ is selected from: H, butyl, cyclopropyl, ethoxy, ethyl, ethylsulfinyl, ethylthio, isopropyl, methoxy, methyl, methylsulfinyl, methylsulfonyl, methylthio, phenyl, propyl and propylthio; wherein said butyl, cyclopropyl, ethoxy, ethyl, ethylsulfinyl, ethylthio, isopropyl, methoxy, methyl, methylsulfinyl, methylsulfonyl, methylthio, phenyl, propyl and propylthio are each optionally substituted with one or more groups selected from: amino, carboxamide, chloro, cyano, ethoxy, fluoro, hydroxy, methoxy, methyl, methylsulfinyl, methylsulfonyl and methylthio.

In some embodiments, $R^2$ is selected from: H, 2-(methylsulfinyl)ethyl, 2-(methylsulfonyl)ethyl, 2-(methylthio)ethyl, 2,3-difluorophenyl, 2-aminoethylthio, 2-amino-2-oxoethoxy, 2-cyanoethyl, 2-ethoxyethylthio, 2-fluoro-4-methoxyphenyl, 2-fluorophenyl, 2-hydroxyethyl, 2-hydroxyethylsulfinyl, 2-hydroxyethylthio, 2-methoxyethyl, 2-methoxyethylthio, 3,4-difluorophenyl, 3,4-dihydroxy butyl, 3-chloro-2-fluorophenyl, 3-fluoro-5-methoxyphenyl, 3-fluorophenyl, 3-hydroxypropyl, 3-hydroxypropylthio, 3-methoxyphenyl, 4-chloro-3-fluorophenyl, 4-chlorophenyl, 4-fluorophenyl, 4-methoxyphenyl, cyanomethoxy, cyanomethylthio, cyclopropyl, ethoxy, ethyl, ethylthio, isopropyl, methyl, methylsulfinyl, methylsulfonyl, methylthio, m-tolyl, n-propyl, phenyl and trifluoromethyl.

In some embodiments, $R^2$ is selected from: H, 2-(methylsulfinyl)ethyl, 2-(methylsulfonyl)ethyl, 2-(methylthio)ethyl, 2,3-difluorophenyl, 2-aminoethylthio, 2-amino-2-oxoethoxy, 2-cyanoethyl, 2-ethoxyethylthio, 2-fluoro-4-methoxyphenyl, 2-fluorophenyl, 2-hydroxyethyl, 2-hydroxyethylsulfinyl, 2-hydroxyethylthio, 2-methoxyethyl, 2-methoxyethylthio, 3,4-difluorophenyl, 3,4-dihydroxybutyl, 3-chloro-2-fluorophenyl, 3-fluoro-5-methoxyphenyl, 3-fluorophenyl, 3-hydroxypropyl, 3-hydroxypropylthio, 3-methoxyphenyl, 4-chloro-3-fluorophenyl, 4-chlorophenyl, 4-fluorophenyl, 4-methoxyphenyl, cyanomethoxy, cyanomethylthio, cyclopropyl, ethoxy, ethyl, ethylthio, isopropyl, methyl, methylsulfinyl, methylsulfonyl, methylthio, m-tolyl, n-propyl, phenyl, p-tolyl and trifluoromethyl.

In some embodiments, $R^2$ is H.
In some embodiments, $R^2$ is 2-(methylsulfinyl)ethyl.
In some embodiments, $R^2$ is 2-(methylsulfonyl)ethyl.
In some embodiments, $R^2$ is 2-(methylthio)ethyl.
In some embodiments, $R^2$ is 2,3-difluorophenyl.
In some embodiments, $R^2$ is 2-aminoethylthio.
In some embodiments, $R^2$ is 2-amino-2-oxoethoxy.
In some embodiments, $R^2$ is 2-cyanoethyl.
In some embodiments, $R^2$ is 2-ethoxy ethylthio.
In some embodiments, $R^2$ is 2-fluoro-4-methoxyphenyl.
In some embodiments, $R^2$ is 2-fluorophenyl.
In some embodiments, $R^2$ is 2-hydroxyethyl.
In some embodiments, $R^2$ is 2-hydroxyethylsulfinyl.
In some embodiments, $R^2$ is 2-hydroxyethylthio.
In some embodiments, $R^2$ is 2-methoxyethyl.
In some embodiments, $R^2$ is 2-methoxyethylthio.
In some embodiments, $R^2$ is 3,4-difluorophenyl.
In some embodiments, $R^2$ is 3,4-dihydroxybutyl.
In some embodiments, $R^2$ is 3-chloro-2-fluorophenyl.
In some embodiments, $R^2$ is 3-fluoro-5-methoxyphenyl.
In some embodiments, $R^2$ is 3-fluorophenyl.
In some embodiments, $R^2$ is 3-hydroxypropyl.
In some embodiments, $R^2$ is 3-hydroxypropylthio.
In some embodiments, $R^2$ is 3-methoxyphenyl.
In some embodiments, $R^2$ is 4-chloro-3-fluorophenyl.
In some embodiments, $R^2$ is 4-chlorophenyl.
In some embodiments, $R^2$ is 4-fluorophenyl.
In some embodiments, $R^2$ is 4-chlorophenyl.
In some embodiments, $R^2$ is 4-chlorophenyl.
In some embodiments, $R^2$ is 4-methoxyphenyl.
In some embodiments, $R^2$ is cyanomethoxy.
In some embodiments, $R^2$ is 4-chlorophenyl.
In some embodiments, $R^2$ is cyanomethylthio.
In some embodiments, $R^2$ is cyclopropyl.

In some embodiments, $R^2$ is ethoxy.
In some embodiments, $R^2$ is ethyl.
In some embodiments, $R^2$ is ethylthio.
In some embodiments, $R^2$ is isopropyl.
In some embodiments, $R^2$ is methyl.
In some embodiments, $R^2$ is methylsulfinyl.
In some embodiments, $R^2$ is methyl.
In some embodiments, $R^2$ is methylsulfonyl.
In some embodiments, $R^2$ is methylthio.
In some embodiments, $R^2$ is m-tolyl.
In some embodiments, $R^2$ is n-propyl.
In some embodiments, $R^2$ is phenyl.
In some embodiments, $R^2$ is/j-tolyl.
In some embodiments, $R^2$ is trifluoromethyl.

The Group $R^3$:

In some embodiments, $R^3$ is selected from: $C_1$-$C_6$ alkyl, aryl and heteroaryl; wherein said $C_1$-$C_6$ alkyl, aryl and heteroaryl are each optionally substituted with one or more groups selected from: $C_1$-$C_6$ alkoxy, $C_1$-$C_6$ alkyl, aryl, cyano, $C_1$-$C_6$ haloalkyl, halogen and hydroxy.

In some embodiments, $R^3$ is selected from: $C_1$-$C_6$ alkyl, aryl and heteroaryl; wherein said $C_1$-$C_6$ alkyl, aryl and heteroaryl are each optionally substituted with one or more groups selected from: chloro, cyano, ethoxy, fluoro, hydroxy, isopropoxy, methoxy, methyl, phenyl and trifluoromethyl.

In some embodiments, $R^3$ is selected from: furan-2-yl, methyl, phenyl, pyridin-3-yl, pyridin-4-yl, thiophen-2-yl and thiophen-3-yl; wherein said furan-2-yl, methyl, phenyl, pyridin-3-yl, pyridin-4-yl, thiophen-2-yl and thiophen-3-yl are each optionally substituted with one or more groups selected from: chloro, cyano, ethoxy, fluoro, hydroxy, isopropoxy, methoxy, methyl, phenyl and trifluoromethyl.

In some embodiments, $R^3$ is selected from: 2,3-difluorophenyl, 2,4-difluorophenyl, 2,5-difluorophenyl, 2-chlorophenyl. 2-fluoro-3-hydroxyphenyl, 2-fluoro-3-methoxyphenyl, 2-fluoro-3-methylphenyl, 2-fluoro-4-methylphenyl, 2-fluorophenyl, 2-methoxyphenyl, 2-methoxypyridin-4-yl, 3-(trifluoromethyl)phenyl, 3,4-difluorophenyl, 3-chloro-2-fluorophenyl, 3-chloro-4-fluorophenyl, 3-chlorophenyl, 3-fluoro-5-methoxyphenyl, 3-fluoro-5-methylphenyl, 3-fluorophenyl, 3-hydroxyphenyl, 3-isopropoxyphenyl, 3-methoxyphenyl, 4-chlorophenyl, 4-fluorophenyl, 4-methoxyphenyl, 5-cyano-2-fluorophenyl, 5-fluoropyridin-3-yl, 5-methoxypyridin-3-yl, 5-methylthiophen-2-yl, 6-methoxypyridin-3-yl, benzhydryl, furan-2-yl, m-tolyl, phenyl, p-tolyl, thiophen-2-yl and thiophen-3-yl.

In some embodiments, $R^3$ is 2,3-difluorophenyl.
In some embodiments, $R^3$ is 2,4-difluorophenyl.
In some embodiments, $R^3$ is 2,5-difluorophenyl.
In some embodiments, $R^3$ is 2-chiorophenyl.
In some embodiments. $R^3$ is 2-fluoro-3-hydroxyphenyl.
In some embodiments, $R^3$ is 2-fluoro-3-methoxyphenyl.
In some embodiments, $R^3$ is 2-fluoro-3-methylphenyl.
In some embodiments, $R^3$ is 2-fluoro-4-methylphenyl.
In some embodiments, $R^3$ is 2-fluorophenyl.
In some embodiments, $R^3$ is 2-methoxyphenyl.
In some embodiments, $R^3$ is 2-methoxypyridin-4-yl.
In some embodiments, $R^3$ is 3-(trifluoromethyl)phenyl.
In some embodiments, $R^3$ is 3,4-difluorophenyl.
In some embodiments, $R^3$ is 3-chloro-2-fluorophenyl.
In some embodiments, $R^3$ is 3-chloro-4-fluorophenyl.
In some embodiments, $R^3$ is 3-chlorophenyl.
In some embodiments, $R^3$ is 3-fluoro-5-methoxyphenyl.
In some embodiments, $R^3$ is 3-fluoro-5-methylphenyl.
In some embodiments, $R^3$ is 3-fluorophenyl.
In some embodiments, $R^3$ is 3-hydroxyphenyl.
In some embodiments, $R^3$ is 3-isopropoxyphenyl.
In some embodiments, $R^3$ is 3-methoxyphenyl.
In some embodiments, $R^3$ is 4-chlorophenyl.
In some embodiments, $R^3$ is 4-fluorophenyl.
In some embodiments, $R^3$ is 4-methoxyphenyl.
In some embodiments, $R^3$ is 5-cyano-2-fluorophenyl.
In some embodiments, $R^3$ is 5-fluoropyridin-3-yl.
In some embodiments, $R^3$ is 5-methoxypyridin-3-yl.
In some embodiments, $R^3$ is 5-methylthiophen-2-yl.
In some embodiments, $R^3$ is 6-methoxypyridin-3-yl.
In some embodiments, $R^3$ is benzhydryl, furan-2-yl.
In some embodiments, $R^3$ is m-tolyl.
In some embodiments, $R^3$ is phenyl.
In some embodiments, $R^3$ is p-tolyl.
In some embodiments, $R^3$ is thiophen-2-yl.
In some embodiments, $R^3$ is thiophen-3-yl.

The Group $R^4$:

In some embodiments, $R^4$ is H, $C_1$-$C_6$ alkoxy, $C_1$-$C_6$ alkyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, carboxamide, cyano, halogen and hydroxy.

In some embodiments, $R^4$ is selected from: H, $C_1$-$C_6$ alkoxy, $C_1$-$C_6$ alkyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylthio, aryl and $C_3$-$C_7$ cycloalkyl are each optionally substituted with one or more groups selected from: carboxamide, chloro, cyano, ethoxy, fluoro, hydroxy, methoxy, methyl and trifluoromethyl.

In some embodiments, $R^4$ is selected from: H, butyl, cyclopropyl, ethyl, ethylthio, isopropyl, methoxy, methyl, methylthio, phenyl and propyl; wherein said butyl, cyclopropyl, ethyl, ethylthio, isopropyl, methoxy, methyl, methylthio, phenyl and propyl are each optionally substituted with one or more groups selected from: carboxamide, chloro, cyano, ethoxy, fluoro, hydroxy, methoxy, methyl and trifluoromethyl.

In some embodiments, $R^4$ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethylthio, 2-methoxyethyl, 2-methoxyethylthio, 3,4-difluorophenyl, 3,4-dihydroxy butyl, 3-chloro-2-fluorophenyl, 3-chlorophenyl, 3-fluoro-5-methoxyphenyl, 3-fluorophenyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

In some embodiments, $R^4$ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-hydroxypropyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

In some embodiments, $R^4$ is H.
In some embodiments, $R^4$ is 2,3-difluorophenyl.
In some embodiments, $R^4$ is 2,4-difluorophenyl.
In some embodiments, $R^4$ is 2-amino-2-oxoethoxy.

In some embodiments, $R^4$ is 2-cyanoethyl.
In some embodiments, $R^4$ is 2-ethoxyethylthio.
In some embodiments, $R^4$ is 2-fluoro-4-methoxyphenyl.
In some embodiments, $R^4$ is 2-fluoro-4-methylphenyl.
In some embodiments, $R^4$ is 2-fluorophenyl.
In some embodiments, $R^4$ is 2-hydroxyethyl.
In some embodiments, $R^4$ is 2-hydroxyethylthio.
In some embodiments, $R^4$ is 2-methoxyethyl.
In some embodiments, $R^4$ is 2-methoxyethylthio.
In some embodiments, $R^4$ is 3,4-difluorophenyl.
In some embodiments, $R^4$ is 3,4-dihydroxybutyl.
In some embodiments, $R^4$ is 3-chloro-2-fluorophenyl.
In some embodiments, $R^4$ is 3-chlorophenyl.
In some embodiments, $R^4$ is 3-fluoro-5-methoxyphenyl.
In some embodiments, $R^4$ is 3-fluorophenyl.
In some embodiments, $R^4$ is 3-hydroxypropyl.
In some embodiments, $R^4$ is 3-methoxyphenyl.
In some embodiments, $R^4$ is 4-chloro-2-fluorophenyl.
In some embodiments, $R^4$ is 4-chloro-3-fluorophenyl.
In some embodiments, $R^4$ is 4-chlorophenyl.
In some embodiments, $R^4$ is 4-fluorophenyl.
In some embodiments, $R^4$ is 4-hydroxyphenyl.
In some embodiments, $R^4$ is 4-methoxyphenyl.
In some embodiments, $R^4$ is cyanomethylthio.
In some embodiments, $R^4$ is cyclopropyl.
In some embodiments, $R^4$ is ethyl.
In some embodiments, $R^4$ is isopropyl.
In some embodiments, $R^4$ is methyl.
In some embodiments, $R^4$ is methylthio.
In some embodiments, $R^4$ is m-tolyl.
In some embodiments, $R^4$ is n-propyl.
In some embodiments, $R^4$ is phenyl.
In some embodiments, $R^4$ is p-tolyl.
In some embodiments, $R^4$ is trifluoromethyl.

Certain Combinations of the Present Invention:

In some embodiments, $R^2$, $R^3$, and $R^4$ are each independently selected from; H, $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl, $C_3$-$C_7$ cycloalkyl and heteroaryl; wherein said $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl, $C_3$-$C_7$ cycloalkyl and heteroaryl are each optionally substituted with one or more groups selected from: $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl, amino, carboxamide, cyano, $C_1$-$C_6$ haloalkyl, halogen and hydroxy.

In some embodiments, $R^2$, $R^3$, and $R^4$ are each independently selected from: H, $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl, $C_3$-$C_7$ cycloalkyl and heteroaryl; wherein said $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl, $C_3$-$C_7$ cycloalkyl and heteroaryl are each optionally substituted with one or more groups selected from: amino, carboxamide, chloro, cyano, ethoxy, fluoro, hydroxy, isopropoxy, methoxy, methyl, methylsulfinyl, methylsulfonyl, methylthio, phenyl and trifluoromethyl.

In some embodiments, $R^2$, $R^3$, and $R^4$ are each independently selected from: H, butyl, cyclopropyl, ethoxy, ethyl, ethylsulfinyl, ethylthio, furan-2-yl, isopropyl, methoxy, methyl, methylsulfinyl, methylsulfonyl, methylthio, phenyl, propyl, propylthio, pyridin-3-yl, pyridin-4-yl, thiophen-2-yl and thiophen-3-yl; wherein said butyl, cyclopropyl, ethoxy, ethyl, ethylsulfinyl, ethylthio, furan-2-yl, isopropyl, methoxy, methyl, methylsulfinyl, methylsulfonyl, methylthio, phenyl, propyl, propylthio, pyridin-3-yl, pyridin-4-yl, thiophen-2-yl and thiophen-3-yl are each optionally substituted with one or more groups selected from: amino, carboxamide, chloro, cyano, ethoxy, fluoro, hydroxy, isopropoxy, methoxy, methyl, methylsulfinyl, methylsulfonyl, methylthio, phenyl and trifluoromethyl.

In some embodiments, $R^2$, $R^3$, and $R^4$ are each independently selected from: H, 2-(methylsulfinyl)ethyl, 2-(methylsulfonyl)ethyl, 2-(methylthio)ethyl, 2,3-difluorophenyl, 2,4-difluorophenyl, 2,5-difluorophenyl, 2-aminoethylthio, 2-amino-2-oxoethoxy, 2-chlorophenyl, 2-cyanoethyl, 2-ethoxyethylthio, 2-fluoro-3-hydroxyphenyl, 2-fluoro-3-methoxyphenyl, 2-fluoro-3-methylphenyl, 2-fluoro-4-methoxyphenyl, 2-fluoro-4-methylphenyl, 2-fluorophenyl, 2-hydroxyethyl, 2-hydroxyethylsulfinyl, 2-hydroxyethylthio, 2-methoxyethyl, 2-methoxyethylthio, 2-methoxyphenyl, 2-methoxypyridin-4-yl, 3-(trifluoromethyl)phenyl, 3,4-difluorophenyl, 3,4-dihydroxybutyl, 3-chloro-2-fluorophenyl, 3-chloro-4-fluorophenyl, 3-chlorophenyl, 3-fluoro-5-methoxyphenyl, 3-fluoro-5-methylphenyl, 3-fluorophenyl, 3-hydroxyphenyl, 3-hydroxypropyl, 3-hydroxypropylthio, 3-isopropoxyphenyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, 5-cyano-2-fluorophenyl, 5-fluoropyridin-3-yl, 5-methoxypyridin-3-yl, 5-methylthiophen-2-yl, 6-methoxypyridin-3-yl, benzhydryl, cyanomethoxy, cyanomethylthio, cyclopropyl, ethoxy, ethyl, ethylthio, furan-2-yl, isopropyl, methyl, methylsulfinyl, methylsulfonyl, methylthio, m-tolyl, n-propyl, phenyl, p-tolyl, thiophen-2-yl, thiophen-3-yl and trifluoromethyl.

In some embodiments, $R^2$ and $R^3$ together with the pyrazole ring to which they are both attached to form a tricyclic heteroaryl.

In some embodiments, wherein $R^2$ and $R^3$ together with the pyrazole ring to which they are both attached to form 4,5-dihydro-3H-benzo[e]indazol-3-yl or indeno[2,1-c]pyrazol-1(8H)-yl.

In some embodiments, wherein $R^2$ and $R^3$ together with the pyrazole ring to which they are both attached to form 4,5-dihydro-3H-benzo[e]indazol-3-yl.

In some embodiments, wherein $R^2$ and $R^3$ together with the pyrazole ring to which they are both attached to form indeno[2,1-c]pyrazol-1(8H)-yl.

One aspect of the present invention encompasses certain pyrazole derivatives selected from compounds of Formula Ic and pharmaceutically acceptable salts, solvates and hydrates thereof:

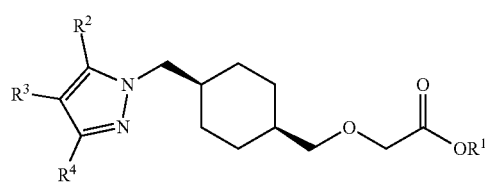

Ic wherein:

$R^1$ is selected from: H and $C_1$-$C_6$ alkyl;

$R^2$ is selected from: H, $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, amino, carboxamide, cyano, halogen and hydroxy;

$R^3$ is selected from: $C_1$-$C_6$ alkyl, aryl and heteroaryl; wherein said $C_1$-$C_6$ alkyl, aryl and heteroaryl are each optionally substituted with one or more groups selected from: $C_1$-$C_6$ alkoxy, $C_1$-$C_6$ alkyl, aryl, cyano, $C_1$-$C_6$ haloalkyl, halogen and hydroxy;

and $R^4$ is selected from: H, $C_1$-$C_6$ alkoxy, $C_1$-$C_6$ alkyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, carboxamide, cyano, halogen and hydroxy.

One aspect of the present invention encompasses certain pyrazole derivatives selected from compounds of Formula Ic and pharmaceutically acceptable salts, solvates and hydrates thereof:

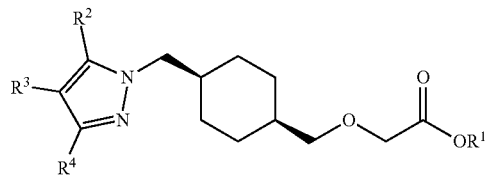

Ic wherein:

$R^1$ is selected from: H and methyl;

$R^2$ is selected from: H, 2-(methylsulfinyl)ethyl, 2-(methylsulfonyl)ethyl, 2-(methylthio)ethyl, 2,3-difluorophenyl, 2-aminoethylthio, 2-amino-2-oxoethoxy, 2-cyanoethyl, 2-ethoxyethylthio, 2-fluoro-4-methoxyphenyl, 2-fluorophenyl, 2-hydroxyethyl, 2-hydroxyethylsulfinyl, 2-hydroxyethylthio, 2-methoxyethyl, 2-methoxyethylthio, 3,4-difluorophenyl, 3,4-dihydroxybutyl, 3-chloro-2-fluorophenyl, 3-fluoro-5-methoxyphenyl, 3-fluorophenyl, 3-hydroxypropyl, 3-hydroxypropylthio, 3-methoxyphenyl, 4-chloro-3-fluorophenyl, 4-chlorophenyl, 4-fluorophenyl, 4-methoxyphenyl, cyanomethoxy, cyanomethylthio, cyclopropyl, ethoxy, ethyl, ethylthio, isopropyl, methyl, methylsulfinyl, methylsulfonyl, methylthio, m-tolyl, n-propyl, phenyl and trifluoromethyl;

$R^3$ is selected from: 2,3-difluorophenyl, 2,4-difluorophenyl, 2,5-difluorophenyl, 2-chlorophenyl, 2-fluoro-3-hydroxyphenyl, 2-fluoro-3-methoxyphenyl, 2-fluoro-3-methylphenyl, 2-fluoro-4-methylphenyl, 2-fluorophenyl, 2-methoxyphenyl, 2-methoxypyridin-4-yl, 3-(trifluoromethyl)phenyl, 3,4-difluorophenyl, 3-chloro-2-fluorophenyl, 3-chloro-4-fluorophenyl, 3-chlorophenyl, 3-fluoro-5-methoxyphenyl, 3-fluoro-5-methylphenyl, 3-fluorophenyl, 3-hydroxyphenyl, 3-isopropoxyphenyl, 3-methoxyphenyl, 4-chlorophenyl, 4-fluorophenyl, 4-methoxyphenyl, 5-cyano-2-fluorophenyl, 5-fluoropyridin-3-yl, 5-methoxypyridin-3-yl, 5-methylthiophen-2-yl, 6-methoxypyridin-3-yl, benzhydryl, furan-2-yl, m-tolyl, phenyl, p-tolyl, thiophen-2-yl and thiophen-3-yl;

and $R^4$ is selected from: H, 2,3-difluorophenyl, 2,4-difluorophenyl, 2-amino-2-oxoethoxy, 2-cyanoethyl, 2-ethoxy ethylthio, 2-fluoro-4-methoxyphenyl, 2-fluoro-4-methylphenyl, 2-fluorophenyl, 2-hydroxyethyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-hydroxypropyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ic and pharmaceutically acceptable salts, solvates and hydrates thereof:

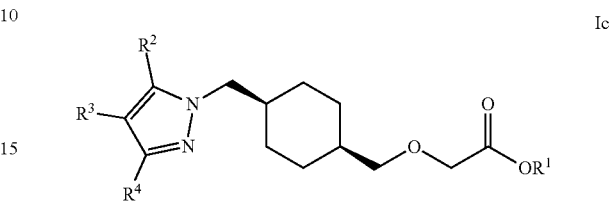

Ic wherein:

$R^1$ is selected from: H and methyl;

$R^2$ is selected from: H, 2-(methylsulfinyl)ethyl, 2-(methylsulfonyl)ethyl, 2-(methylthio)ethyl, 2,3-difluorophenyl, 2-aminoethylthio, 2-amino-2-oxoethoxy, 2-cyanoethyl, 2-ethoxyethylthio, 2-fluoro-4-methoxyphenyl, 2-fluorophenyl, 2-hydroxyethyl, 2-hydroxyethylsulfinyl, 2-hydroxyethylthio, 2-methoxyethyl, 2-methoxyethylthio, 3,4-difluorophenyl, 3,4-dihydroxybutyl, 3-chloro-2-fluorophenyl, 3-fluoro-5-methoxyphenyl, 3-fluorophenyl, 3-hydroxypropyl, 3-hydroxypropylthio, 3-methoxyphenyl, 4-chloro-3-fluorophenyl, 4-chlorophenyl, 4-fluorophenyl, 4-methoxyphenyl, cyanomethoxy, cyanomethylthio, cyclopropyl, ethoxy, ethyl, ethylthio, isopropyl, methyl, methylsulfinyl, methylsulfonyl, methylthio, m-tolyl, n-propyl, phenyl, p-tolyl and trifluoromethyl;

$R^3$ is selected from: 2,3-difluorophenyl, 2,4-difluorophenyl, 2,5-difluorophenyl, 2-chlorophenyl, 2-fluoro-3-hydroxyphenyl, 2-fluoro-3-methoxyphenyl, 2-fluoro-3-methylphenyl, 2-fluoro-4-methylphenyl, 2-fluorophenyl, 2-methoxyphenyl, 2-methoxypyridin-4-yl, 3-(trifluoromethyl)phenyl, 3,4-difluorophenyl, 3-chloro-2-fluorophenyl, 3-chloro-4-fluorophenyl, 3-chlorophenyl, 3-fluoro-5-methoxyphenyl, 3-fluoro-5-methylphenyl, 3-fluorophenyl, 3-hydroxyphenyl, 3-isopropoxyphenyl, 3-methoxyphenyl, 4-chlorophenyl, 4-fluorophenyl, 4-methoxyphenyl, 5-cyano-2-fluorophenyl, 5-fluoropyridin-3-yl, 5-methoxypyridin-3-yl, 5-methylthiophen-2-yl, 6-methoxypyridin-3-yl, benzhydryl, furan-2-yl, m-tolyl, phenyl, p-tolyl, thiophen-2-yl and thiophen-3-yl;

and $R^4$ is selected from: H, 2,3-difluorophenyl, 2,4-difluorophenyl, 2-amino-2-oxoethoxy, 2-cyanoethyl, 2-ethoxy ethylthio, 2-fluoro-4-methoxyphenyl, 2-fluoro-4-methylphenyl, 2-fluorophenyl, 2-hydroxyethyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-hydroxypropyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ic and pharmaceutically acceptable salts, solvates and hydrates thereof:

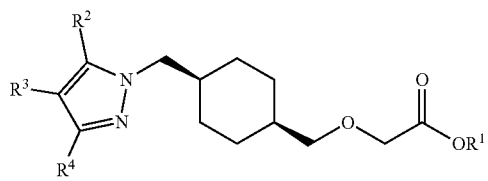

wherein:

R¹ is selected from: H and $C_1$-$C_6$ alkyl;

R² and R³ together with the pyrazole ring to which they are both attached to form a tricyclic heteroaryl; and R⁴ is selected from: H, $C_1$-$C_6$ alkoxy, $C_1$-$C_6$ alkyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, carboxamide, cyano, halogen and hydroxy.

One aspect of the present invention encompasses certain pyrazole derivatives selected from compounds of Formula Ic and pharmaceutically acceptable salts, solvates and hydrates thereof:

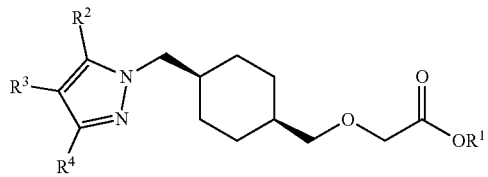

wherein:

R¹ is selected from: H and methyl;

R² and R³ together with the pyrazole ring to which they are both attached to form 4,5-dihydro-3H-benzo[e]indazol-3-yl or indeno[2,1-c]pyrazol-1(8H)-yl; and R⁴ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ic and pharmaceutically acceptable salts, solvates and hydrates thereof:

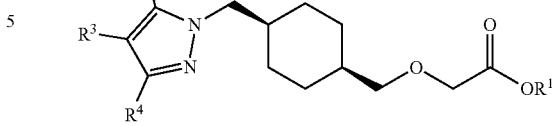

wherein:

R¹ is selected from: H and methyl;

R² and R³ together with the pyrazole ring to which they are both attached to form 4,5-dihydro-3H-benzo[e]indazol-3-yl or indeno[2,1-c]pyrazol-1(8H)-yl; and R⁴ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-hydroxypropyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ie and pharmaceutically acceptable salts, solvates and hydrates thereof:

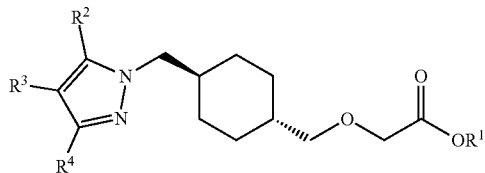

wherein:

R¹ is selected from: H and $C_1$-$C_6$ alkyl;

R² is selected from: H, $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, amino, carboxamide, cyano, halogen and hydroxy;

R³ is selected from: $C_1$-$C_6$ alkyl, aryl and heteroaryl; wherein said $C_1$-$C_6$ alkyl, aryl and heteroaryl are each optionally substituted with one or more groups selected from: $C_1$-$C_6$ alkoxy, $C_1$-$C_6$ alkyl, aryl, cyano, $C_1$-$C_6$ haloalkyl, halogen and hydroxy; and R⁴ is selected from: H, $C_1$-$C_6$ alkoxy, $C_1$-$C_6$ alkyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, carboxamide, cyano, halogen and hydroxy.

One aspect of the present invention encompasses certain pyrazole derivatives selected from compounds of Formula Ie and pharmaceutically acceptable salts, solvates and hydrates thereof:

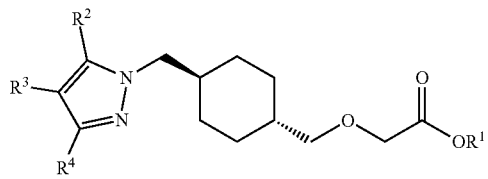

wherein:
R¹ is selected from: H and methyl;
R² is selected from: H, 2-(methylsulfinyl)ethyl, 2-(methylsulfonyl)ethyl, 2-(methylthio)ethyl, 2,3-difluorophenyl, 2-aminoethylthio, 2-amino-2-oxoethoxy, 2-cyanoethyl, 2-ethoxyethylthio, 2-fluoro-4-methoxyphenyl, 2-fluorophenyl, 2-hydroxyethyl, 2-hydroxyethylsulfinyl, 2-hydroxyethylthio, 2-methoxyethyl, 2-methoxyethylthio, 3,4-difluorophenyl, 3,4-dihydroxybutyl, 3-chloro-2-fluorophenyl, 3-fluoro-5-methoxyphenyl, 3-fluorophenyl, 3-hydroxypropyl, 3-hydroxypropylthio, 3-methoxyphenyl, 4-chloro-3-fluorophenyl, 4-chlorophenyl, 4-fluorophenyl, 4-methoxyphenyl, cyanomethoxy, cyanomethylthio, cyclopropyl, ethoxy, ethyl, ethylthio, isopropyl, methyl, methylsulfinyl, methylsulfonyl, methylthio, m-tolyl, n-propyl, phenyl and trifluoromethyl;
R³ is selected from: 2,3-difluorophenyl, 2,4-difluorophenyl, 2,5-difluorophenyl, 2-chlorophenyl, 2-fluoro-3-hydroxyphenyl, 2-fluoro-3-methoxyphenyl, 2-fluoro-3-methylphenyl, 2-fluoro-4-methylphenyl, 2-fluorophenyl, 2-methoxyphenyl, 2-methoxypyridin-4-yl, 3-(trifluoromethyl)phenyl, 3,4-difluorophenyl, 3-chloro-2-fluorophenyl, 3-chloro-4-fluorophenyl, 3-chlorophenyl, 3-fluoro-5-methoxyphenyl, 3-fluoro-5-methylphenyl, 3-fluorophenyl, 3-hydroxyphenyl, 3-isopropoxyphenyl, 3-methoxyphenyl, 4-chlorophenyl, 4-fluorophenyl, 4-methoxyphenyl, 5-cyano-2-fluorophenyl, 5-fluoropyridin-3-yl, 5-methoxypyridin-3-yl, 5-methylthiophen-2-yl, 6-methoxypyridin-3-yl, benzhydryl, furan-2-yl, m-tolyl, phenyl, p-tolyl, thiophen-2-yl and thiophen-3-yl;
and
R⁴ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-hydroxypropyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ie and pharmaceutically acceptable salts, solvates and hydrates thereof:

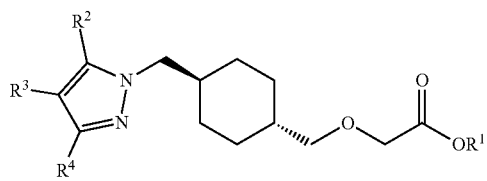

wherein:
R¹ is selected from: H and methyl;
R² is selected from: H, 2-(methylsulfinyl)ethyl, 2-(methylsulfonyl)ethyl, 2-(methylthio)ethyl, 2,3-difluorophenyl, 2-aminoethylthio, 2-amino-2-oxoethoxy, 2-cyanoethyl, 2-ethoxyethylthio, 2-fluoro-4-methoxyphenyl, 2-fluorophenyl, 2-hydroxyethyl, 2-hydroxyethylsulfinyl, 2-hydroxyethylthio, 2-methoxyethyl, 2-methoxyethylthio, 3,4-difluorophenyl, 3,4-dihydroxybutyl, 3-chloro-2-fluorophenyl, 3-fluoro-5-methoxyphenyl, 3-fluorophenyl, 3-hydroxypropyl, 3-hydroxypropylthio, 3-methoxyphenyl, 4-chloro-3-fluorophenyl, 4-chlorophenyl, 4-fluorophenyl, 4-methoxyphenyl, cyanomethoxy, cyanomethylthio, cyclopropyl, ethoxy, ethyl, ethylthio, isopropyl, methyl, methylsulfinyl, methylsulfonyl, methylthio, m-tolyl, n-propyl, phenyl, p-tolyl and trifluoromethyl;
R³ is selected from: 2,3-difluorophenyl, 2,4-difluorophenyl, 2,5-difluorophenyl, 2-chlorophenyl, 2-fluoro-3-hydroxyphenyl, 2-fluoro-3-methoxyphenyl, 2-fluoro-3-methylphenyl, 2-fluoro-4-methylphenyl, 2-fluorophenyl, 2-methoxyphenyl, 2-methoxypyridin-4-yl, 3-(trifluoromethyl)phenyl, 3,4-difluorophenyl, 3-chloro-2-fluorophenyl, 3-chloro-4-fluorophenyl, 3-chlorophenyl, 3-fluoro-5-methoxyphenyl, 3-fluoro-5-methylphenyl, 3-fluorophenyl, 3-hydroxyphenyl, 3-isopropoxyphenyl, 3-methoxyphenyl, 4-chlorophenyl, 4-fluorophenyl, 4-methoxyphenyl, 5-cyano-2-fluorophenyl, 5-fluoropyridin-3-yl, 5-methoxypyridin-3-yl, 5-methylthiophen-2-yl, 6-methoxypyridin-3-yl, benzhydryl, furan-2-yl, m-tolyl, phenyl, p-tolyl, thiophen-2-yl and thiophen-3-yl;
and
R⁴ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-hydroxypropyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ie and pharmaceutically acceptable salts, solvates and hydrates thereof:

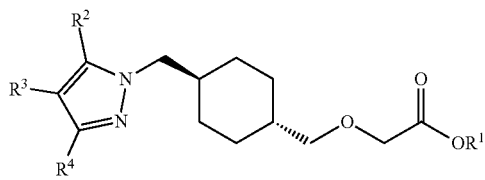

wherein:
R¹ is selected from: H and $C_1$-$C_6$ alkyl;
R² and R³ together with the pyrazole ring to which they are both attached to form a tricyclic heteroaryl;
and
R⁴ is selected from: H, $C_1$-$C_6$ alkoxy, $C_1$-$C_6$ alkyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, carboxamide, cyano, halogen and hydroxy.

One aspect of the present invention encompasses certain pyrazole derivatives selected from compounds of Formula Ie and pharmaceutically acceptable salts, solvates and hydrates thereof:

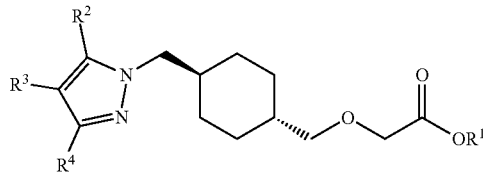

Ie wherein:
$R^1$ is selected from: H and methyl;
$R^2$ and $R^3$ together with the pyrazole ring to which they are both attached to form 4,5-dihydro-3H-benzo[e]indazol-3-yl or indeno[2,1-c]pyrazol-1(8H)-yl;
and
$R^4$ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ie and pharmaceutically acceptable salts, solvates and hydrates thereof:

Ie

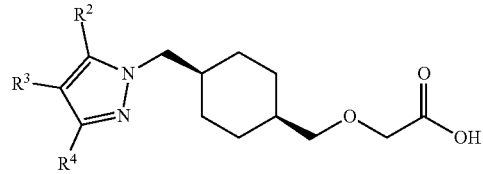

wherein:
$R^1$ is selected from: H and methyl;
$R^2$ and $R^3$ together with the pyrazole ring to which they are both attached to form 4,5-dihydro-3/i-benzo[e]indazol-3-yl or indeno[2,1-c]pyrazol-1(8H)-yl;
and
$R^4$ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-hydroxypropyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ig and pharmaceutically acceptable salts, solvates and hydrates thereof:

Ig wherein:
$R^2$ is selected from: H, $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, amino, carboxamide, cyano, halogen and hydroxy;
$R^3$ is selected from: $C_1$-$C_6$ alkyl, aryl and heteroaryl; wherein said $C_1$-$C_6$ alkyl, aryl and heteroaryl are each optionally substituted with one or more groups selected from: $C_1$-$C_6$ alkoxy, $C_1$-$C_6$ alkyl, aryl, cyano, $C_1$-$C_6$ haloalkyl, halogen and hydroxy;
and
$R^4$ is selected from: H, $C_1$-$C_6$ alkoxy, $C_1$-$C_6$ alkyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, carboxamide, cyano, halogen and hydroxy.

One aspect of the present invention encompasses certain pyrazole derivatives selected from compounds of Formula Ig and pharmaceutically acceptable salts, solvates and hydrates thereof:

Ig

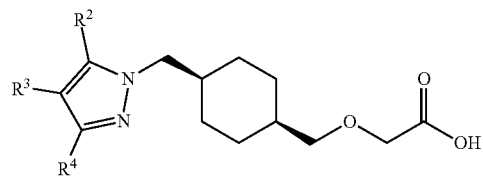

wherein:
$R^2$ is selected from: H, 2-(methylsulfinyl)ethyl, 2-(methylsulfonyl)ethyl, 2-(methylthio)ethyl, 2,3-difluorophenyl, 2-aminoethylthio, 2-amino-2-oxoethoxy, 2-cyanoethyl, 2-ethoxyethylthio, 2-fluoro-4-methoxyphenyl, 2-fluorophenyl, 2-hydroxy ethyl, 2-hydroxyethylsulfinyl, 2-hydroxyethylthio, 2-methoxyethyl, 2-methoxyethylthio, 3,4-difluorophenyl, 3,4-dihydroxybutyl, 3-chloro-2-fluorophenyl, 3-fluoro-5-methoxyphenyl, 3-fluorophenyl, 3-hydroxypropyl, 3-hydroxypropylthio, 3-methoxyphenyl, 4-chloro-3-fluorophenyl, 4-chlorophenyl, 4-fluorophenyl, 4-methoxyphenyl, cyanomethoxy, cyanomethylthio, cyclopropyl, ethoxy, ethyl, ethylthio, isopropyl, methyl, methylsulfinyl, methylsulfonyl, methylthio, m-tolyl, H-propyl, phenyl and trifluoromethyl;

$R^3$ is selected from: 2,3-difluorophenyl, 2,4-difluorophenyl, 2,5-difluorophenyl, 2-chlorophenyl, 2-fluoro-3-hydroxyphenyl, 2-fluoro-3-methoxyphenyl, 2-fluoro-3-methylphenyl, 2-fluoro-4-methylphenyl, 2-fluorophenyl, 2-methoxyphenyl, 2-methoxypyridin-4-yl, 3-(trifluoromethyl)phenyl, 3,4-difluorophenyl, 3-chloro-2-fluorophenyl, 3-chloro-4-fluorophenyl, 3-chlorophenyl, 3-fluoro-5-methoxyphenyl, 3-fluoro-5-methylphenyl, 3-fluorophenyl, 3-hydroxyphenyl, 3-isopropoxyphenyl, 3-methoxyphenyl, 4-chlorophenyl, 4-fluorophenyl, 4-methoxyphenyl, 5-cyano-2-fluorophenyl, 5-fluoropyridin-3-yl, 5-methoxypyridin-3-yl, 5-methylthiophen-2-yl, 6-methoxypyridin-3-yl, benzhydryl, furan-2-yl, m-tolyl, phenyl, p-tolyl, thiophen-2-yl and thiophen-3-yl;

and $R^4$ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ig and pharmaceutically acceptable salts, solvates and hydrates thereof:

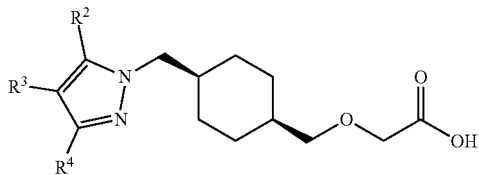

Ig wherein:

$R^2$ is selected from: H, 2-(methylsulfinyl)ethyl, 2-(methylsulfonyl)ethyl, 2-(methylthio)ethyl, 2,3-difluorophenyl, 2-aminoethylthio, 2-amino-2-oxoethoxy, 2-cyanoethyl, 2-ethoxyethylthio, 2-fluoro-4-methoxyphenyl, 2-fluorophenyl, 2-hydroxyethyl, 2-hydroxyethylsulfinyl, 2-hydroxyethylthio, 2-methoxyethyl, 2-methoxyethylthio, 3,4-difluorophenyl, 3,4-dihydroxybutyl, 3-chloro-2-fluorophenyl, 3-fluoro-5-methoxyphenyl, 3-fluorophenyl, 3-hydroxypropyl, 3-hydroxypropylthio, 3-methoxyphenyl, 4-chloro-3-fluorophenyl, 4-chlorophenyl, 4-fluorophenyl, 4-methoxyphenyl, cyanomethoxy, cyanomethylthio, cyclopropyl, ethoxy, ethyl, ethylthio, isopropyl, methyl, methylsulfinyl, methylsulfonyl, methylthio, m-tolyl, n-propyl, phenyl, p-tolyl and trifluoromethyl;

$R^3$ is selected from: 2,3-difluorophenyl, 2,4-difluorophenyl, 2,5-difluorophenyl, 2-chlorophenyl, 2-fluoro-3-hydroxyphenyl, 2-fluoro-3-methoxyphenyl, 2-fluoro-3-methylphenyl, 2-fluoro-4-methylphenyl, 2-fluorophenyl, 2-methoxyphenyl, 2-methoxypyridin-4-yl, 3-(trifluoromethyl)phenyl, 3,4-difluorophenyl, 3-chloro-2-fluorophenyl, 3-chloro-4-fluorophenyl, 3-chlorophenyl, 3-fluoro-5-methoxyphenyl, 3-fluoro-5-methylphenyl, 3-fluorophenyl, 3-hydroxyphenyl, 3-isopropoxyphenyl, 3-methoxyphenyl, 4-chlorophenyl, 4-fluorophenyl, 4-methoxyphenyl, 5-cyano-2-fluorophenyl, 5-fluoropyridin-3-yl, 5-methoxypyridin-3-yl, 5-methylthiophen-2-yl, 6-methoxypyridin-3-yl, benzhydryl, furan-2-yl, m-tolyl, phenyl, p-tolyl, thiophen-2-yl and thiophen-3-yl;

and $R^4$ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-hydroxypropyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ig and pharmaceutically acceptable salts, solvates and hydrates thereof:

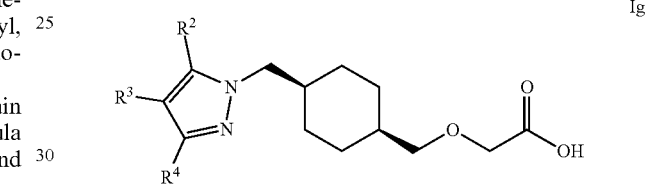

Ig wherein:

$R^2$ and $R^3$ together with the pyrazole ring to which they are both attached to form a tricyclic heteroaryl;

and $R^4$ is selected from: H, $C_1$-$C_6$ alkoxy, $C_1$-$C_6$ alkyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, carboxamide, cyano, halogen and hydroxy.

One aspect of the present invention encompasses certain pyrazole derivatives selected from compounds of Formula Ig and pharmaceutically acceptable salts, solvates and hydrates thereof:

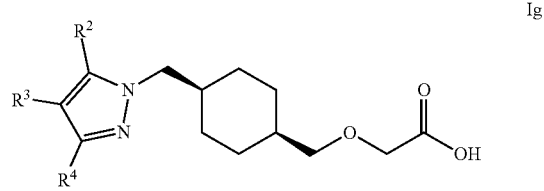

Ig wherein:

$R^2$ and $R^3$ together with the pyrazole ring to which they are both attached to form 4,5-dihydro-3H-benzo[e]indazol-3-yl or indeno[2,1-c]pyrazol-1(8H)-yl;

and $R^4$ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-methoxyphenyl, 4-chloro-2-fluorophenyl, 4-chloro-3-fluorophenyl 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ig and pharmaceutically acceptable salts, solvates and hydrates thereof:

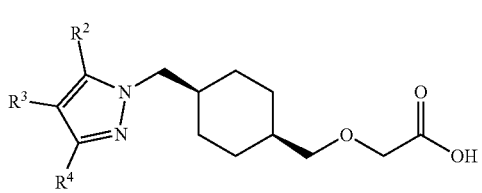

Ig wherein:
$R^2$ and $R^3$ together with the pyrazole ring to which they are both attached to form 4,5-dihydro-3H-benzo[e]indazol-3-yl or indeno[2,1-c]pyrazol-1(8H)-yl;
and
$R^4$ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-hydroxypropyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ii and pharmaceutically acceptable salts, solvates and hydrates thereof:

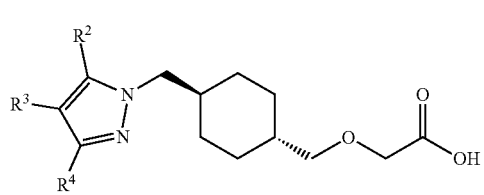

Ii wherein:
$R^2$ is selected from: H, $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, $C_1$-$C_6$ alkylsulfinyl, $C_1$-$C_6$ alkylsulfonyl, $C_1$-$C_6$ alkylthio, amino, carboxamide, cyano, halogen and hydroxy;

$R^3$ is selected from: $C_1$-$C_6$ alkyl, aryl and heteroaryl; wherein said $C_1$-$C_6$ alkyl, aryl and heteroaryl are each optionally substituted with one or more groups selected from: $C_1$-$C_6$ alkoxy, $C_1$-$C_6$ alkyl, aryl, cyano, $C_1$-$C_6$ haloalkyl, halogen and hydroxy;

and
$R^4$ is selected from: H, $C_1$-$C_6$ alkoxy, $C_1$-$C_6$ alkyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, carboxamide, cyano, halogen and hydroxy.

One aspect of the present invention encompasses certain pyrazole derivatives selected from compounds of Formula Ii and pharmaceutically acceptable salts, solvates and hydrates thereof:

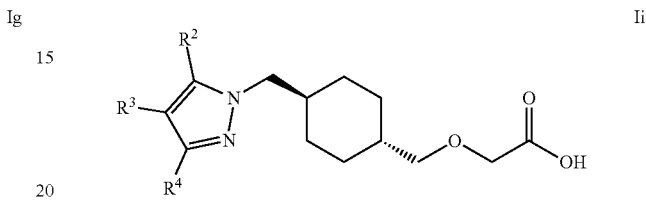

Ii wherein:
$R^2$ is selected from: H, 2-(methylsulfinyl)ethyl, 2-(methylsulfonyl)ethyl, 2-(methylthio)ethyl, 2,3-difluorophenyl, 2-aminoethylthio, 2-amino-2-oxoethoxy, 2-cyanoethyl, 2-ethoxyethylthio, 2-fluoro-4-methoxyphenyl, 2-fluorophenyl, 2-hydroxyethyl, 2-hydroxyethylsulfinyl, 2-hydroxyethylthio, 2-methoxyethyl, 2-methoxyethylthio, 3,4-difluorophenyl, 3,4-dihydroxybutyl, 3-chloro-2-fluorophenyl, 3-fluoro-5-methoxyphenyl, 3-fluorophenyl, 3-hydroxypropyl, 3-hydroxypropylthio, 3-methoxyphenyl, 4-chloro-3-fluorophenyl, 4-chlorophenyl, 4-fluorophenyl, 4-methoxyphenyl, cyanomethoxy, cyanomethylthio, cyclopropyl, ethoxy, ethyl, ethylthio, isopropyl, methyl, methylsulfinyl, methylsulfonyl, methylthio, m-tolyl, n-propyl, phenyl and trifluoromethyl;

$R^3$ is selected from: 2,3-difluorophenyl, 2,4-difluorophenyl, 2,5-difluorophenyl, 2-chlorophenyl, 2-fluoro-3-hydroxyphenyl, 2-fluoro-3-methoxyphenyl, 2-fluoro-3-methylphenyl, 2-fluoro-4-methylphenyl, 2-fluorophenyl, 2-methoxyphenyl, 2-methoxypyridin-4-yl, 3-(trifluoromethyl)phenyl, 3,4-difluorophenyl, 3-chloro-2-fluorophenyl, 3-chloro-4-fluorophenyl, 3-chlorophenyl, 3-fluoro-5-methoxyphenyl, 3-fluoro-5-methylphenyl, 3-fluorophenyl, 3-hydroxyphenyl, 3-isopropoxyphenyl, 3-methoxyphenyl, 4-chlorophenyl, 4-fluorophenyl, 4-methoxyphenyl, 5-cyano-2-fluorophenyl, 5-fluoropyridin-3-yl, 5-methoxypyridin-3-yl, 5-methylthiophen-2-yl, 6-methoxypyridin-3-yl, benzhydryl, furan-2-yl, m-tolyl, phenyl, p-tolyl, thiophen-2-yl and thiophen-3-yl;

and
$R^4$ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ii and pharmaceutically acceptable salts, solvates and hydrates thereof:

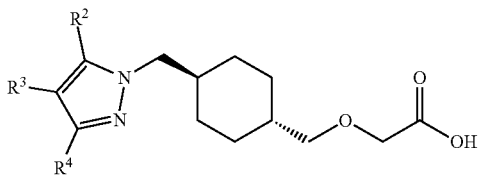

wherein:

R² is selected from: H, 2-(methylsulfinyl)ethyl, 2-(methylsulfonyl)ethyl, 2-(methylthio)ethyl, 2,3-difluorophenyl, 2-aminoethylthio, 2-amino-2-oxoethoxy, 2-cyanoethyl, 2-ethoxyethylthio, 2-fluoro-4-methoxyphenyl, 2-fluorophenyl, 2-hydroxyethyl, 2-hydroxyethylsulfinyl, 2-hydroxyethylthio, 2-methoxyethyl, 2-methoxyethylthio, 3,4-difluorophenyl, 3,4-dihydroxy butyl, 3-chloro-2-fluorophenyl, 3-fluoro-5-methoxyphenyl, 3-fluorophenyl, 3-hydroxypropyl, 3-hydroxypropylthio, 3-methoxyphenyl, 4-chloro-3-fluorophenyl, 4-chlorophenyl, 4-fluorophenyl, 4-methoxyphenyl, cyanomethoxy, cyanomethylthio, cyclopropyl, ethoxy, ethyl, ethylthio, isopropyl, methyl, methylsulfinyl, methylsulfonyl, methylthio, m-tolyl, n-propyl, phenyl, p-tolyl and trifluoromethyl;

R³ is selected from: 2,3-difluorophenyl, 2,4-difluorophenyl, 2,5-difluorophenyl, 2-chlorophenyl, 2-fluoro-3-hydroxyphenyl, 2-fluoro-3-methoxyphenyl, 2-fluoro-3-methylphenyl, 2-fluoro-4-methylphenyl, 2-fluorophenyl, 2-methoxyphenyl, 2-methoxypyridin-4-yl, 3-(trifluoromethyl)phenyl, 3,4-difluorophenyl, 3-chloro-2-fluorophenyl, 3-chloro-4-fluorophenyl, 3-chlorophenyl, 3-fluoro-5-methoxyphenyl, 3-fluoro-5-methylphenyl, 3-fluorophenyl, 3-hydroxyphenyl, 3-isopropoxyphenyl, 3-methoxyphenyl, 4-chlorophenyl, 4-fluorophenyl, 4-methoxyphenyl, 5-cyano-2-fluorophenyl, 5-fluoropyridin-3-yl, 5-methoxypyridin-3-yl, 5-methylthiophen-2-yl, 6-methoxypyridin-3-yl, benzhydryl, furan-2-yl, m-tolyl, phenyl, p-tolyl, thiophen-2-yl and thiophen-3-yl;
and R⁴ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-hydroxypropyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxy phenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ii and pharmaceutically acceptable salts, solvates and hydrates thereof:

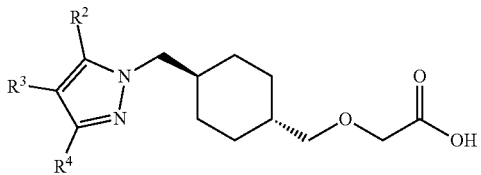

wherein:

R² and R³ together with the pyrazole ring to which they are both attached to form a tricyclic heteroaryl;
and R⁴ is selected from: H, $C_1$-$C_6$ alkoxy, $C_1$-$C_6$ alkyl, $C_1$-$C_6$ alkylthio, aryl and $C_3$-$C_7$ cycloalkyl; wherein said $C_1$-$C_6$ alkoxy, $C_1$-$C_6$ alkyl, $C_1$-$C_6$ alkylthio, aryl and $C_3$-$C_7$ cycloalkyl are each optionally substituted with one or more groups selected from: $C_1$-$C_6$ alkoxy, $C_1$-$C_6$ alkyl, carboxamide, cyano, halogen and hydroxy.

One aspect of the present invention encompasses certain pyrazole derivatives selected from compounds of Formula Ii and pharmaceutically acceptable salts, solvates and hydrates thereof:

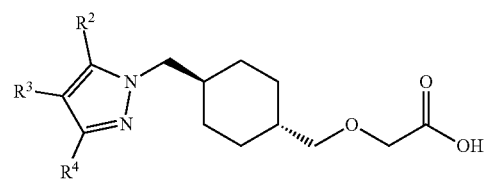

wherein:

R² and R³ together with the pyrazole ring to which they are both attached to form 4,5-dihydro-3H-benzo[e]indazol-3-yl or indeno[2,1-c]pyrazol-1(8H)-yl;
and R⁴ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethylthio, 2-methoxyethyl, 2-methoxyethylthio, 3,4-difluorophenyl, 3,4-dihydroxybutyl, 3-chloro-2-fluorophenyl, 3-chlorophenyl, 3-fluoro-5-methoxyphenyl, 3-fluorophenyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

One aspect of the present invention encompasses certain pyrazole derivatives selected from compounds of Formula Ii and pharmaceutically acceptable salts, solvates and hydrates thereof:

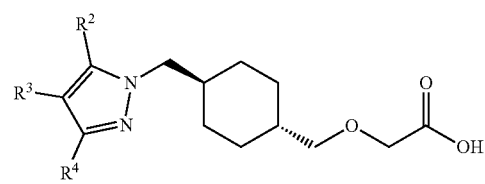

wherein:

R² and R³ together with the pyrazole ring to which they are both attached to form 4,5-dihydro-3H-benzo[e]indazol-3-yl or indeno[2,1-c]pyrazol-1(8H)-yl;
and R⁴ is selected from: H, 2,3-difluorophenyl, 2,4-difluorophenyl, 2-amino-2-oxoethoxy, 2-cyanoethyl, 2-ethoxyethylthio, 2-fluoro-4-methoxyphenyl, 2-fluoro-4-methylphenyl, 2-fluorophenyl, 2-hydroxyethyl, 2-hydroxyethylthio, 2-methoxyethyl, 2-methoxyethylthio, 3,4-difluorophenyl, 3,4-dihydroxy butyl, 3-chloro-2-fluorophenyl, 3-chlorophenyl, 3-fluoro-5-methoxyphenyl, 3-fluorophenyl, 3-hydroxypropyl, 3-methoxyphenyl, 4-chloro-2-fluorophenyl, 4-chloro-3-fluorophenyl, 4-chlorophenyl, 4-fluorophenyl, 4-hydroxyphenyl, 4-methoxyphenyl, cyanomethylthio, cyclopropyl, ethyl, isopropyl, methyl, methylthio, m-tolyl, n-propyl, phenyl, p-tolyl and trifluoromethyl.

Some embodiments of the present invention include every combination of one or more compounds selected from the following group shown in TABLE A.

TABLE A

| Cpd No. | Chemical Structure | Chemical Name |
|---|---|---|
| 1 | 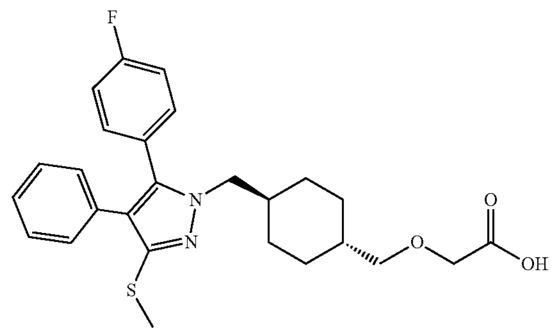 [SMILES: CSc1nn(C[C@H]2CC[C@H](COCC(=O)O)CC2)c(-c2ccc(F)cc2)c1-c1ccccc1] | 2-(((1r,4r)-4-((5-(4-fluorophenyl)-3-(methylthio)-4-phenyl-1H-pyrazol-1-yl)methyl)cyclohexyl)methoxy)acetic acid |
| 2 | 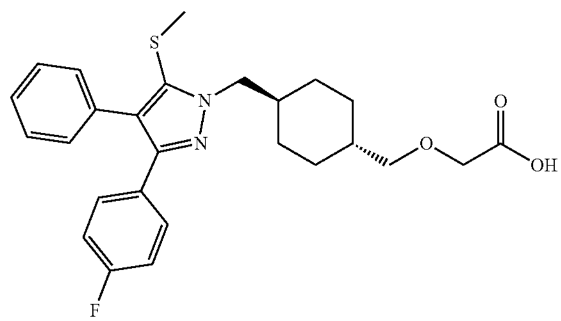 [SMILES: CSc1c(-c2ccccc2)c(-c2ccc(F)cc2)nn1C[C@H]1CC[C@H](COCC(=O)O)CC1] | 2-(((1r,4r)-4-((3-(4-fluorophenyl)-5-(methylthio)-4-phenyl-1H-pyrazol-1-yl)methyl)cyclohexyl)methoxy)acetic acid |
| 3 | 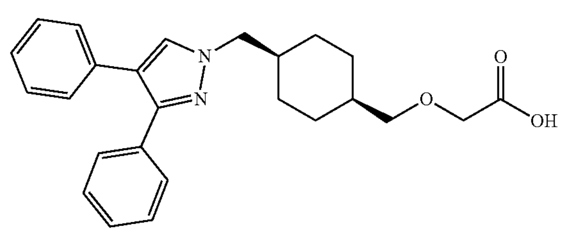 [SMILES: O=C(O)COC[C@H]1CC[C@@H](Cn2cc(-c3ccccc3)c(-c3ccccc3)n2)CC1] | 2-(((1s,4s)-4-((3,4-diphenyl-1H-pyrazol-1-yl)methyl)cyclohexyl)methoxy)acetic acid |
| 4 | 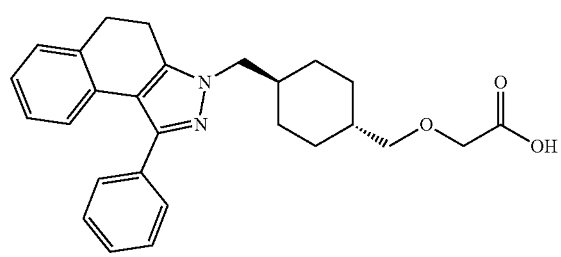 [SMILES: O=C(O)COC[C@H]1CC[C@H](Cn2nc(-c3ccccc3)c3c2CCc2ccccc2-3)CC1] | 2-(((1r,4r)-4-((1-phenyl-4,5-dihydro-3H-benzo[e]indazol-3-yl)methyl)cyclohexyl)methoxy)acetic acid |
| 5 | 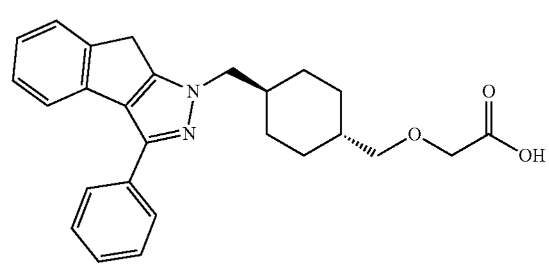 [SMILES: O=C(O)COC[C@H]1CC[C@H](Cn2nc(-c3ccccc3)c3c2Cc2ccccc2-3)CC1] | 2-(((1r,4r)-4-((3-phenylindeno[2,1-c]pyrazol-1(8H)-yl)methyl)cyclohexyl)methoxy)acetic acid |

TABLE A-continued

| Cpd No. | Chemical Structure | Chemical Name |
|---|---|---|
| 6 | 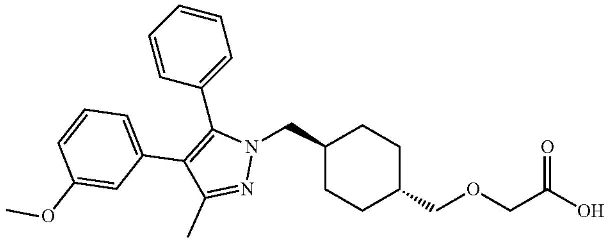 [SMILES: COc1cccc(-c2c(C)nn(C[C@H]3CC[C@H](COCC(=O)O)CC3)c2-c2ccccc2)c1] | 2-(((1r,4r)-4-((4-(3-methoxyphenyl)-3-methyl-5-phenyl-1H-pyrazol-1-yl)methyl)cyclohexyl)methoxy)acetic acid |
| 7 | 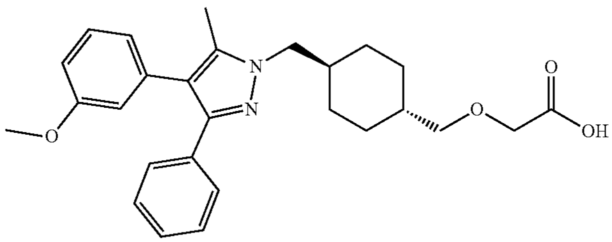 [SMILES: COc1cccc(-c2c(-c3ccccc3)nn(C[C@H]3CC[C@H](COCC(=O)O)CC3)c2C)c1] | 2-(((1r,4r)-4-((4-(3-methoxyphenyl)-5-methyl-3-phenyl-1H-pyrazol-1-yl)methyl)cyclohexyl)methoxy)acetic acid |
| 8 | 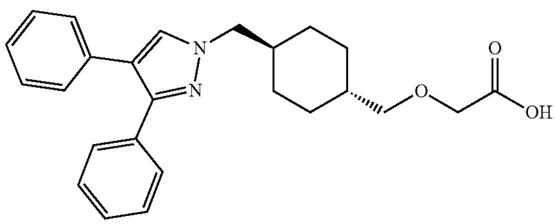 [SMILES: O=C(O)COC[C@H]1CC[C@H](Cn2cc(-c3ccccc3)c(-c3ccccc3)n2)CC1] | 2-(((1r,4r)-4-((3,4-diphenyl-1H-pyrazol-1-yl)methyl)cyclohexyl)methoxy)acetic acid |
| 9 | 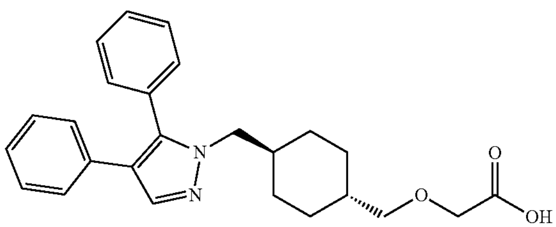 [SMILES: O=C(O)COC[C@H]1CC[C@H](Cn2ncc(-c3ccccc3)c2-c2ccccc2)CC1] | 2-(((1r,4r)-4-((4,5-diphenyl-1H-pyrazol-1-yl)methyl)cyclohexyl)methoxy)acetic acid |
| 10 | 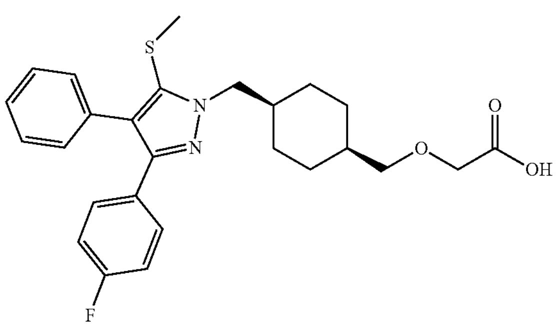 [SMILES: CSc1c(-c2ccccc2)c(-c2ccc(F)cc2)nn1C[C@H]1CC[C@@H](COCC(=O)O)CC1] | 2-(((1s,4s)-4-((3-(4-fluorophenyl)-5-(methylthio)-4-phenyl-1H-pyrazol-1-yl)methyl)cyclohexyl)methoxy)acetic acid |
| 11 | 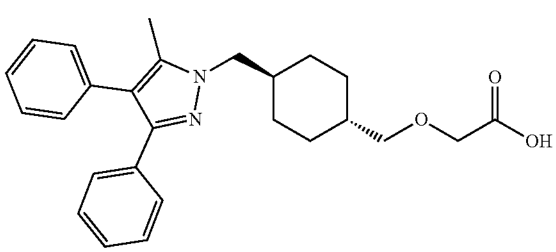 [SMILES: Cc1c(-c2ccccc2)c(-c2ccccc2)nn1C[C@H]1CC[C@H](COCC(=O)O)CC1] | 2-(((1r,4r)-4-((5-methyl-3,4-diphenyl-1H-pyrazol-1-yl)methyl)cyclohexyl)methoxy)acetic acid |

TABLE A-continued

| Cpd No. | Chemical Structure | Chemical Name |
|---|---|---|
| 12 | 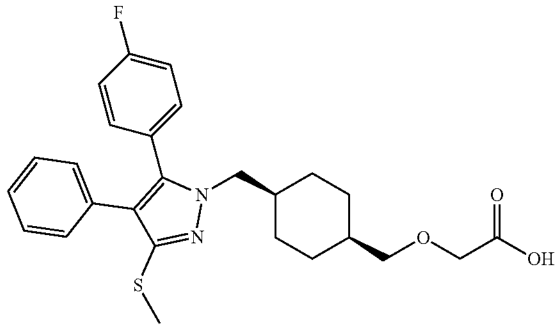 [SMILES: CSc1nn(C[C@H]2CC[C@@H](COCC(=O)O)CC2)c(-c2ccc(F)cc2)c1-c1ccccc1] | 2-(((1s,4s)-4-((5-(4-fluorophenyl)-3-(methylthio)-4-phenyl-1H-pyrazol-1-yl)methyl)cyclohexyl)methoxy)acetic acid |
| 13 | 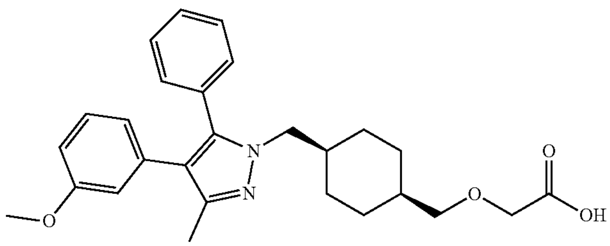 [SMILES: COc1cccc(-c2c(C)nn(C[C@H]3CC[C@@H](COCC(=O)O)CC3)c2-c2ccccc2)c1] | 2-(((1s,4s)-4-((4-(3-methoxyphenyl)-3-methyl-5-phenyl-1H-pyrazol-1-yl)methyl)cyclohexyl)methoxy)acetic acid |
| 14 | 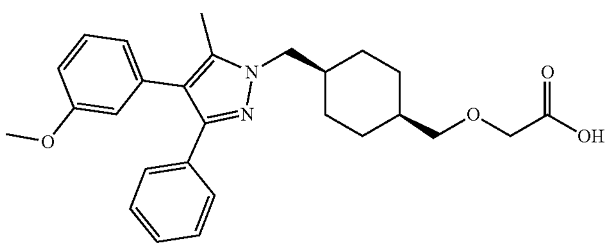 [SMILES: COc1cccc(-c2c(-c3ccccc3)nn(C[C@H]3CC[C@@H](COCC(=O)O)CC3)c2C)c1] | 2-(((1s,4s)-4-((4-(3-methoxyphenyl)-5-methyl-3-phenyl-1H-pyrazol-1-yl)methyl)cyclohexyl)methoxy)acetic acid |
| 15 | 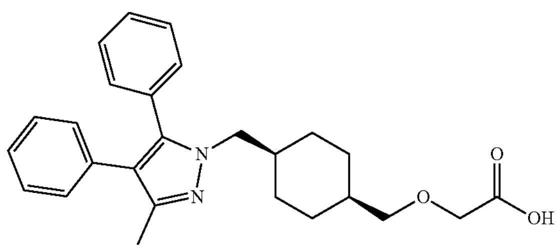 [SMILES: Cc1nn(C[C@H]2CC[C@@H](COCC(=O)O)CC2)c(-c2ccccc2)c1-c1ccccc1] | 2-(((1s,4s)-4-((3-methyl-4,5-diphenyl-1H-pyrazol-1-yl)methyl)cyclohexyl)methoxy)acetic acid |
| 16 | 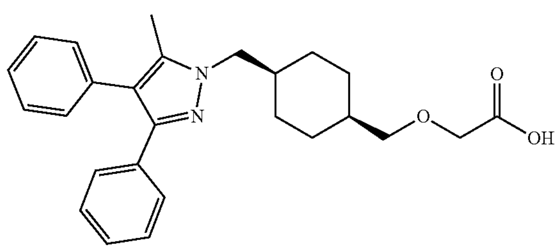 [SMILES: Cc1c(-c2ccccc2)c(-c2ccccc2)nn1C[C@H]1CC[C@@H](COCC(=O)O)CC1] | 2-(((1s,4s)-4-((5-methyl-3,4-diphenyl-1H-pyrazol-1-yl)methyl)cyclohexyl)methoxy)acetic acid |
| 17 | 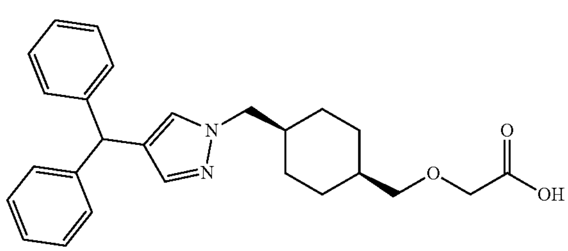 [SMILES: O=C(O)COC[C@H]1CC[C@@H](Cn2cc(C(c3ccccc3)c3ccccc3)cn2)CC1] | 2-(((1s,4s)-4-((4-benzhydryl-1H-pyrazol-1-yl)methyl)cyclohexyl)methoxy)acetic acid |

TABLE A-continued

| Cpd No. | Chemical Structure | Chemical Name |
| --- | --- | --- |
| 18 | 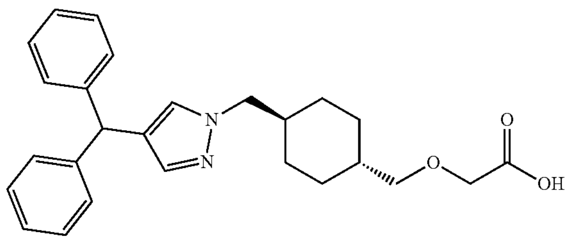 [SMILES: O=C(O)COC[C@H]1CC[C@H](Cn2cc(C(c3ccccc3)c3ccccc3)cn2)CC1] | 2-(((1r,4r)-4-((4-benzhydryl-1H-pyrazol-1-yl)methyl)cyclohexyl)methoxy)acetic acid |
| 19 | 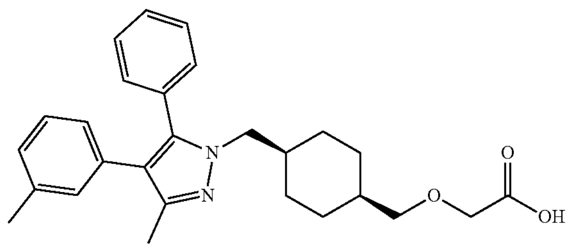 [SMILES: Cc1cccc(-c2c(C)nn(C[C@H]3CC[C@@H](COCC(=O)O)CC3)c2-c2ccccc2)c1] | 2-(((1s,4s)-4-((3-methyl-5-phenyl-4-m-tolyl-1H-pyrazol-1-yl)methyl)cyclohexyl)methoxy)acetic acid |
| 20 | 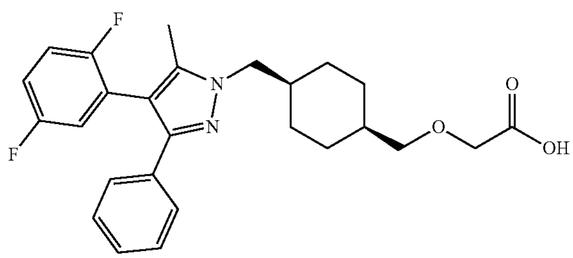 [SMILES: Cc1c(-c2cc(F)ccc2F)c(-c2ccccc2)nn1C[C@H]1CC[C@@H](COCC(=O)O)CC1] | 2-(((1s,4s)-4-((4-(2,5-difluorophenyl)-5-methyl-3-phenyl-1H-pyrazol-1-yl)methyl)cyclohexyl)methoxy)acetic acid |
| 21 | 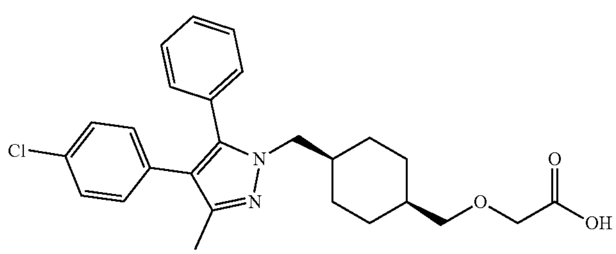 [SMILES: Cc1nn(C[C@H]2CC[C@@H](COCC(=O)O)CC2)c(-c2ccccc2)c1-c1ccc(Cl)cc1] | 2-(((1s,4s)-4-((4-(4-chlorophenyl)-3-methyl-5-phenyl-1H-pyrazol-1-yl)methyl)cyclohexyl)methoxy)acetic acid |
| 22 | 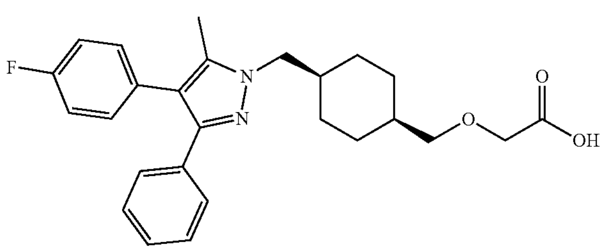 [SMILES: Cc1c(-c2ccc(F)cc2)c(-c2ccccc2)nn1C[C@H]1CC[C@@H](COCC(=O)O)CC1] | 2-(((1s,4s)-4-((4-(4-fluorophenyl)-5-methyl-3-phenyl-1H-pyrazol-1-yl)methyl)cyclohexyl)methoxy)acetic acid |
| 23 | 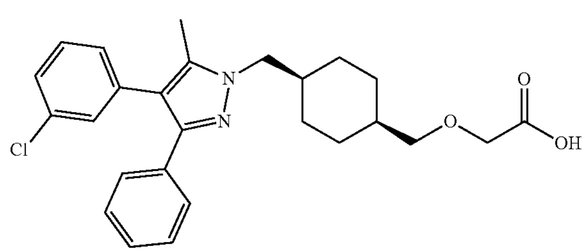 [SMILES: Cc1c(-c2cccc(Cl)c2)c(-c2ccccc2)nn1C[C@H]1CC[C@@H](COCC(=O)O)CC1] | 2-(((1s,4s)-4-((4-(3-chlorophenyl)-5-meth-3-phenyl-1H-pyrazol-1-yl)methyl)cyclohexyl)methoxy)acetic acid |

TABLE A-continued

| Cpd No. | Chemical Structure | Chemical Name |
|---|---|---|
| 24 | 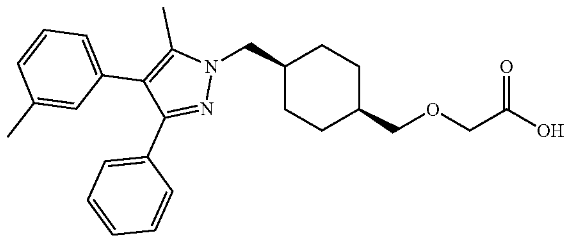 [SMILES: Cc1cccc(-c2c(-c3ccccc3)nn(C[C@H]3CC[C@@H](COCC(=O)O)CC3)c2C)c1] | 2-(((1s,4s)-4-((5-methyl-3-phenyl-4-m-tolyl-1H-pyrazol-1-yl)methyl)cyclohexyl)methoxy)acetic acid |
| 25 | 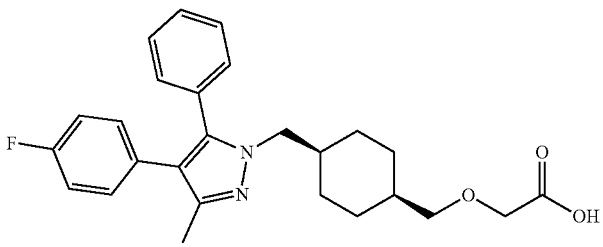 [SMILES: Cc1nn(C[C@H]2CC[C@@H](COCC(=O)O)CC2)c(-c2ccccc2)c1-c1ccc(F)cc1] | 2-(((1s,4s)-4-((4-(4-fluorophenyl)-3-methyl-5-phenyl-1H-pyrazol-1-yl)methyl)cyclohexyl)methoxy)acetic acid |
| 26 | 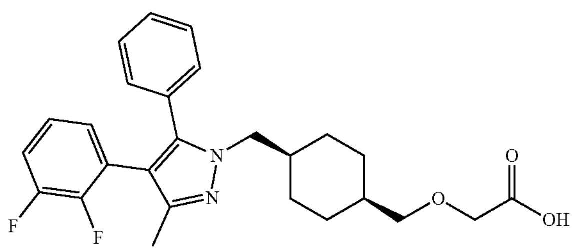 [SMILES: Cc1nn(C[C@H]2CC[C@@H](COCC(=O)O)CC2)c(-c2ccccc2)c1-c1cccc(F)c1F] | 2-(((1s,4s)-4-((4-(2,3-difluorophenyl)-3-methyl-5-phenyl-1H-pyrazol-1-yl)methyl)cyclohexyl)methoxy)acetic acid |
| 27 | 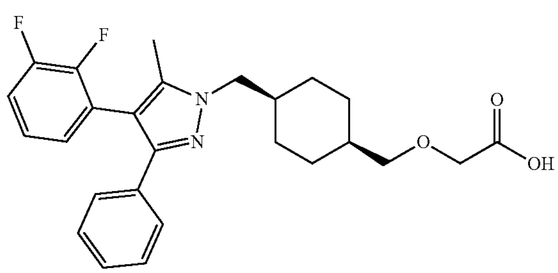 [SMILES: Cc1c(-c2cccc(F)c2F)c(-c2ccccc2)nn1C[C@H]1CC[C@@H](COCC(=O)O)CC1] | 2-(((1s,4s)-4-((4-(2,3-difluorophenyl)-5-methyl-3-phenyl-1H-pyrazol-1-yl)methyl)cyclohexyl)methoxy)acetic acid |
| 28 | 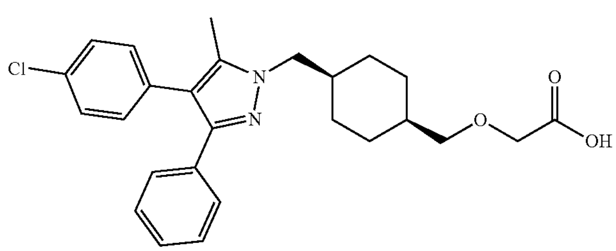 [SMILES: Cc1c(-c2ccc(Cl)cc2)c(-c2ccccc2)nn1C[C@H]1CC[C@@H](COCC(=O)O)CC1] | 2-(((1s,4s)-4-((4-(4-chlorophenyl)-5-methyl-3-phenyl-1H-pyrazol-1-yl)methyl)cyclohexyl)methoxy)acetic acid |
| 29 | 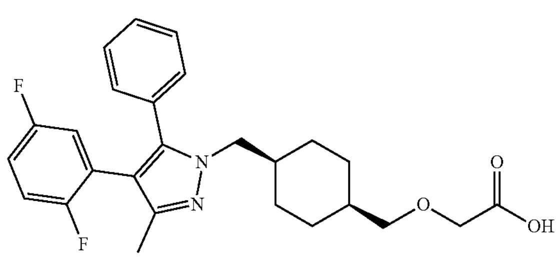 [SMILES: Cc1nn(C[C@H]2CC[C@@H](COCC(=O)O)CC2)c(-c2ccccc2)c1-c1cc(F)ccc1F] | 2-(((1s,4s)-4-((4-(2,5-difluorophenyl)-3-methyl-5-phenyl-1H-pyrazol-1-yl)methyl)cyclohexyl)methoxy)acetic acid |

TABLE A-continued

| Cpd No. | Chemical Structure | Chemical Name |
|---|---|---|
| 30 | 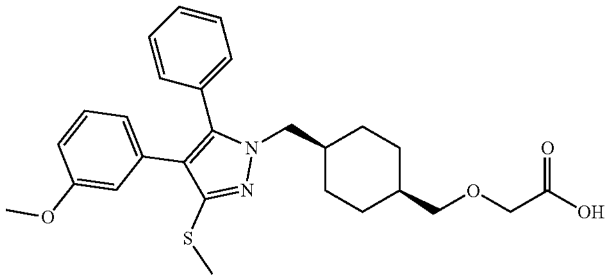 [SMILES: COc1cccc(-c2c(SC)nn(C[C@H]3CC[C@@H](COCC(=O)O)CC3)c2-c2ccccc2)c1] | 2-(((1s,4s)-4-((4-(3-methoxyphenyl)-3-(methylthio)-5-phenyl-1H-pyrazol-1-yl)methyl)cyclohexyl)methoxy)acetic acid |
| 31 | 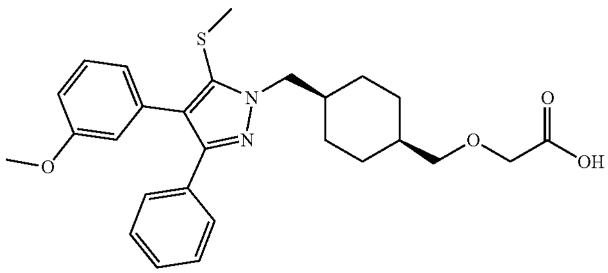 [SMILES: COc1cccc(-c2c(-c3ccccc3)nn(C[C@H]3CC[C@@H](COCC(=O)O)CC3)c2SC)c1] | 2-(((1s,4s)-4-((4-(3-methoxyphenyl)-5-(methylthio)-3-phenyl-1H-pyrazol-1-yl)methyl)cyclohexyl)methoxy)acetic acid |
| 32 | 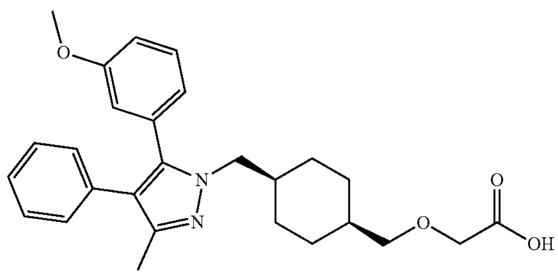 [SMILES: COc1cccc(-c2c(-c3ccccc3)c(C)nn2C[C@H]2CC[C@@H](COCC(=O)O)CC2)c1] | 2-(((1s,4s)-4-((5-(3-methoxyphenyl)-3-methyl-4-phenyl-1H-pyrazol-1-yl)methyl)cyclohexyl)methoxy)acetic acid |
| 33 | 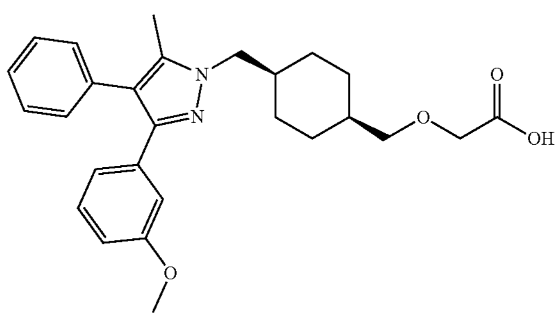 [SMILES: COc1cccc(-c2nn(C[C@H]3CC[C@@H](COCC(=O)O)CC3)c(C)c2-c2ccccc2)c1] | 2-(((1s,4s)-4-((3-(3-methoxyphenyl)-5-methyl-4-phenyl-1H-pyrazol-1-yl)methyl)cyclohexyl)methoxy)acetic acid |
| 34 | 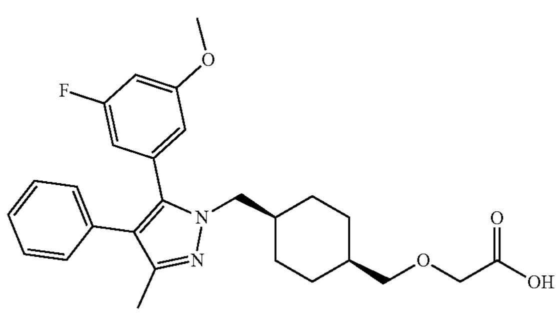 [SMILES: COc1cc(F)cc(-c2c(-c3ccccc3)c(C)nn2C[C@H]2CC[C@@H](COCC(=O)O)CC2)c1] | 2-(((1s,4s)-4-((5-(3-fluoro-5-methoxyphenyl)-3-methyl-4-phenyl-1H-pyrazol-1-yl)methyl)cyclohexyl)methoxy)acetic acid |

TABLE A-continued

| Cpd No. | Chemical Structure | Chemical Name |
|---|---|---|
| 35 | 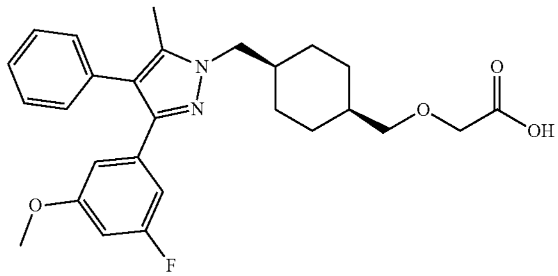 [SMILES: COc1cc(F)cc(-c2nn(C[C@H]3CC[C@@H](COCC(=O)O)CC3)c(C)c2-c2ccccc2)c1] | 2-(((1s,4s)-4-((3-(3-fluoro-5-methoxyphenyl)-5-methyl-4-phenyl-1H-pyrazol-1-yl)methyl)cyclohexyl)methoxy)acetic acid |
| 36 | 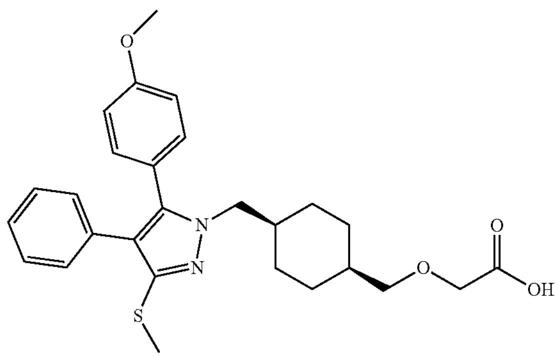 [SMILES: COc1ccc(-c2c(-c3ccccc3)c(SC)nn2C[C@H]2CC[C@@H](COCC(=O)O)CC2)cc1] | 2-(((1s,4s)-4-((5-(4-methoxyphenyl)-3-(methylthio)-4-phenyl-1H-pyrazol-1-yl)methyl)cyclohexyl)methoxy)acetic acid |
| 37 | 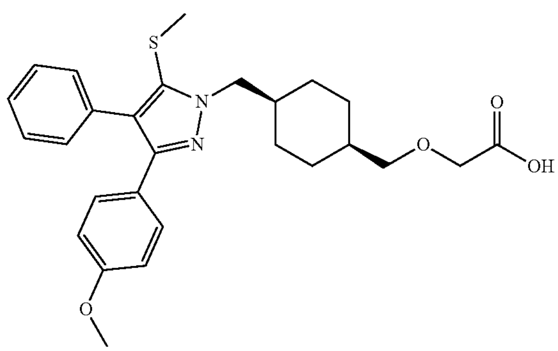 [SMILES: COc1ccc(-c2nn(C[C@H]3CC[C@@H](COCC(=O)O)CC3)c(SC)c2-c2ccccc2)cc1] | 2-(((1s,4s)-4-((3-(4-methoxyphenyl)-5-(methylthio)-4-phenyl-1H-pyrazol-1-yl)methyl)cyclohexyl)methoxy)acetic acid |
| 38 | 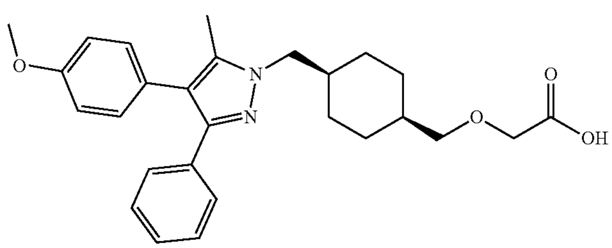 [SMILES: COc1ccc(-c2c(-c3ccccc3)nn(C[C@H]3CC[C@@H](COCC(=O)O)CC3)c2C)cc1] | 2-(((1s,4s)-4-((4-(4-methoxyphenyl)-5-methyl-3-phenyl-1H-pyrazol-1-yl)methyl)cyclohexyl)methoxy)acetic acid |
| 39 | 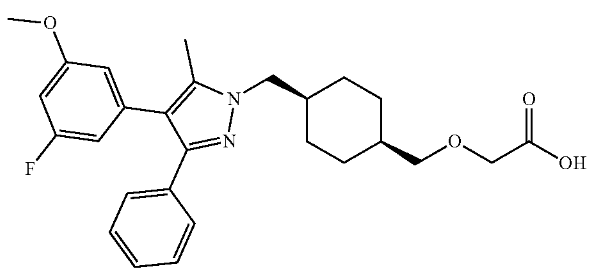 [SMILES: COc1cc(F)cc(-c2c(-c3ccccc3)nn(C[C@H]3CC[C@@H](COCC(=O)O)CC3)c2C)c1] | 2-(((1s,4s)-4-((4-(3-fluoro-5-methoxyphenyl)-5-methyl-3-phenyl-1H-pyrazol-1-yl)methyl)cyclohexyl)methoxy)acetic acid |

TABLE A-continued

| Cpd No. | Chemical Structure | Chemical Name |
|---|---|---|
| 40 | 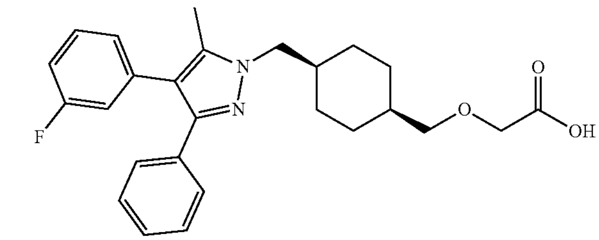 [SMILES: Cc1c(-c2cccc(F)c2)c(-c2ccccc2)nn1C[C@H]1CC[C@@H](COCC(=O)O)CC1] | 2-(((1s,4s)-4-((4-(3-fluorophenyl)-5-methyl-3-phenyl-1H-pyrazol-1-yl)methyl)cyclohexyl)methoxy)acetic acid |
| 41 | 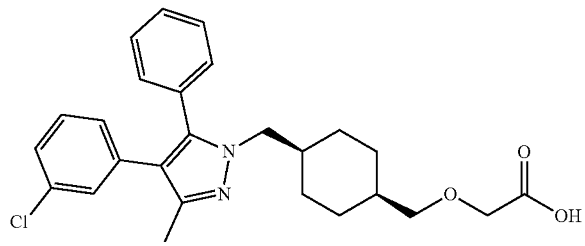 [SMILES: Cc1nn(C[C@H]2CC[C@@H](COCC(=O)O)CC2)c(-c2ccccc2)c1-c1cccc(Cl)c1] | 2-(((1s,4s)-4-((4-(3-chlorophenyl)-3-methyl-5-phenyl-1H-pyrazol-1-yl)methyl)cyclohexyl)methoxy)acetic acid |
| 42 | 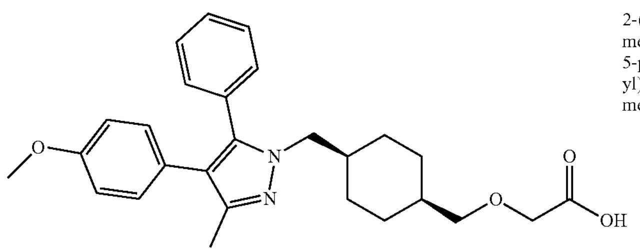 | 2-(((1s,4s)-4-((4-(4-methoxyphenyl)-3-methyl-5-phenyl-1H-pyrazol-1-yl)methyl)cyclohexyl)methoxy)acetic acid |
| 43 | 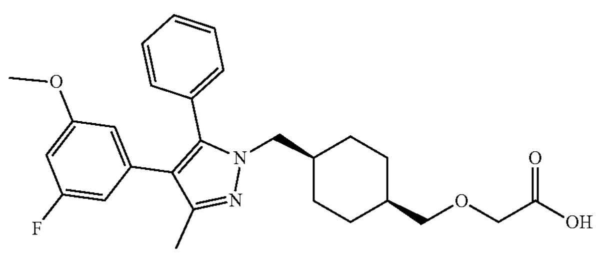 [SMILES: COc1cc(F)cc(-c2c(C)nn(C[C@H]3CC[C@@H](COCC(=O)O)CC3)c2-c2ccccc2)c1] | 2-(((1s,4s)-4-((4-(3-fluoro-5-methoxyphenyl)-3-methyl-5-phenyl-1H-pyrazol-1-yl)methyl)cyclohexyl)methoxy)acetic acid |
| 44 | 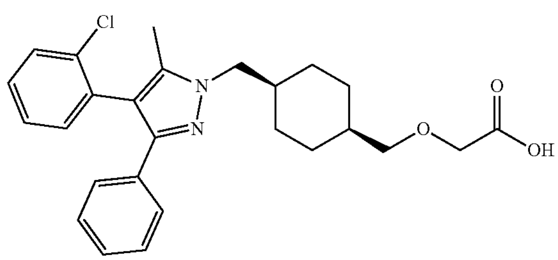 [SMILES: Cc1c(-c2ccccc2Cl)c(-c2ccccc2)nn1C[C@H]1CC[C@@H](COCC(=O)O)CC1] | 2-(((1s,4s)-4-((4-(2-chlorophenyl)-5-methyl-3-phenyl-1H-pyrazol-1-yl)methyl)cyclohexyl)methoxy)acetic acid |
| 45 | 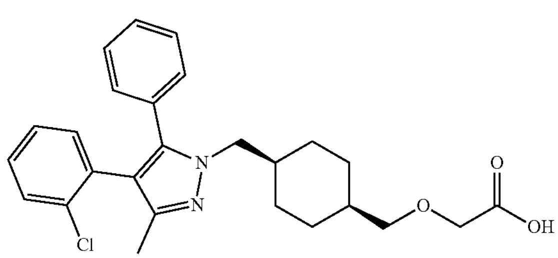 [SMILES: Cc1nn(C[C@H]2CC[C@@H](COCC(=O)O)CC2)c(-c2ccccc2)c1-c1ccccc1Cl] | 2-(((1s,4s)-4-((4-(2-chlorophenyl)-3-methyl-5-phenyl-1H-pyrazol-1-yl)methyl)cyclohexyl)methoxy)acetic acid |

TABLE A-continued

| Cpd No. | Chemical Structure | Chemical Name |
|---|---|---|
| 46 | 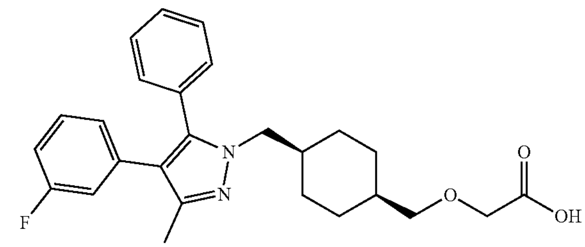 [SMILES: Cc1nn(C[C@H]2CC[C@@H](COCC(=O)O)CC2)c(-c2ccccc2)c1-c1cccc(F)c1] | 2-(((1s,4s)-4-((4-(3-fluorophenyl)-3-methyl-5-phenyl-1H-pyrazol-1-yl)methyl)cyclohexyl)methoxy)acetic acid |
| 47 | 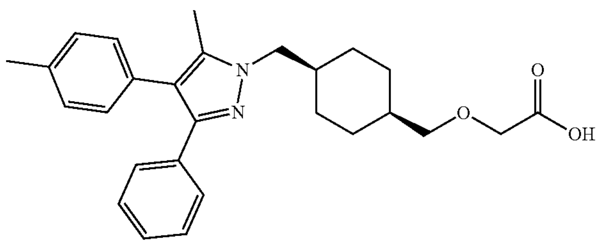 [SMILES: Cc1ccc(-c2c(-c3ccccc3)nn(C[C@H]3CC[C@@H](COCC(=O)O)CC3)c2C)cc1] | 2-(((1s,4s)-4-((5-methyl-3-phenyl-4-p-tolyl-1H-pyrazol-1-yl)methyl)cyclohexyl)methoxy)acetic acid |
| 48 | 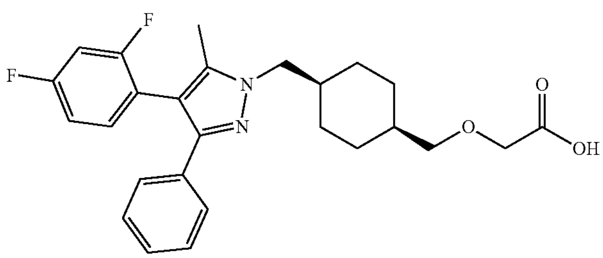 [SMILES: Cc1c(-c2ccc(F)cc2F)c(-c2ccccc2)nn1C[C@H]1CC[C@@H](COCC(=O)O)CC1] | 2-((1s,4s)-4-((4-(2,4-difluorophenyl)-5-methyl-3-phenyl-1H-pyrazol-1-yl)methyl)cyclohexyl)methoxy)acetic acid |
| 49 | 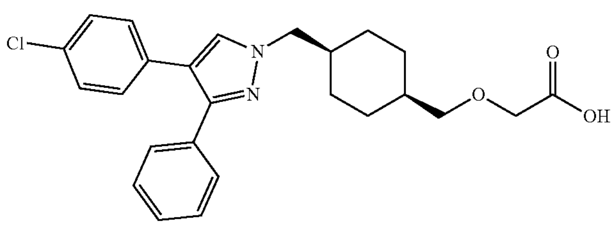 [SMILES: O=C(O)COC[C@H]1CC[C@@H](Cn2cc(-c3ccc(Cl)cc3)c(-c3ccccc3)n2)CC1] | 2-(((1s,4s)-4-((4-(4-chlorophenyl)-3-phenyl-1H-pyrazol-1-yl)methyl)cyclohexyl)methoxy)acetic acid |
| 50 | 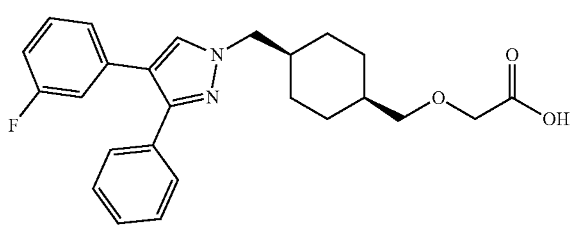 [SMILES: O=C(O)COC[C@H]1CC[C@@H](Cn2cc(-c3cccc(F)c3)c(-c3ccccc3)n2)CC1] | 2-(((1s,4s)-4-((4-(3-fluorophenyl)-3-phenyl-1H-pyrazol-1-yl)methyl)cyclohexyl)methoxy)acetic acid |
| 51 | 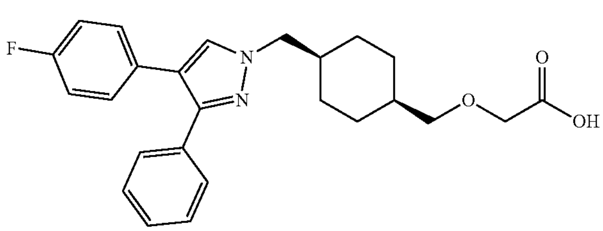 [SMILES: O=C(O)COC[C@H]1CC[C@@H](Cn2cc(-c3ccc(F)cc3)c(-c3ccccc3)n2)CC1] | 2-(((1s,4s)-4-((4-(4-fluorophenyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 52 | 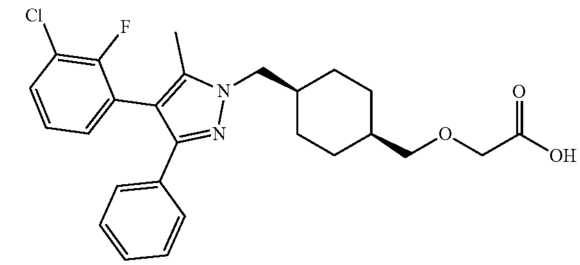 [SMILES: Cc1c(-c2cccc(Cl)c2F)c(-c2ccccc2)nn1C[C@H]1CC[C@@H](COCC(=O)O)CC1] | 2-(((1s,4s)-4-((4-(3-chloro-2-fluorophenyl)-5-methyl-3-phenyl-1H-pyrazol-1-yl)methyl)cyclohexyl)methoxy)acetic acid |
| 53 | 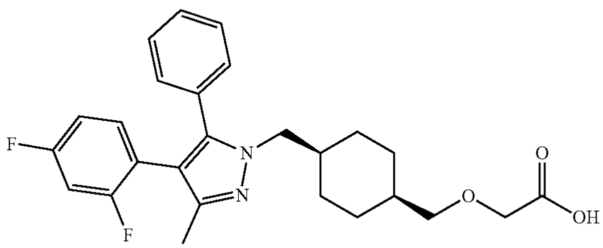 [SMILES: Cc1nn(C[C@H]2CC[C@@H](COCC(=O)O)CC2)c(-c2ccccc2)c1-c1ccc(F)cc1F] | 2-(((1s,4s)-4-((4-(2,4-difluorophenyl)-3-methyl-5-phenyl-1H-pyrazol-l-yl)methyl)cyclohexyl)methoxy)acetic acid |
| 54 | 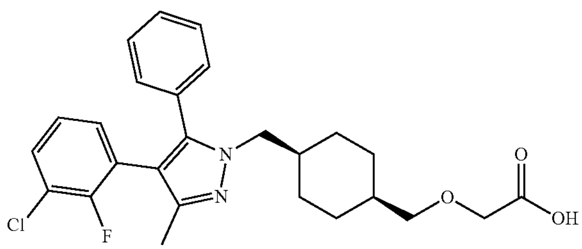 [SMILES: Cc1nn(C[C@H]2CC[C@@H](COCC(=O)O)CC2)c(-c2ccccc2)c1-c1cccc(Cl)c1F] | 2-(((1s,4s)-4-((4-(3-chloro-2-fluorophenyl)-3-methyl-5-phenyl-1H-pyrazol-l-yl)methyl)cyclohexyl)methoxy)acetic acid |
| 55 | 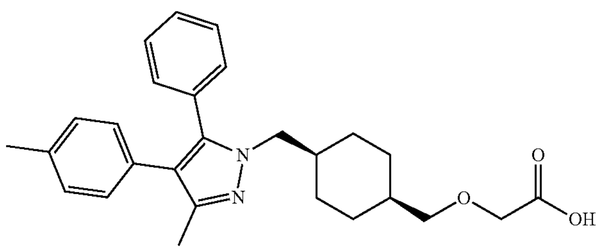 [SMILES: Cc1ccc(-c2c(C)nn(C[C@H]3CC[C@@H](COCC(=O)O)CC3)c2-c2ccccc2)cc1] | 2-(((1s,4s)-4-((3-methyl-5-phenyl-4-p-tolyl-1H-pyrazol-1-yl)methyl)cyclohexyl)methoxy)acetic acid |
| 56 | 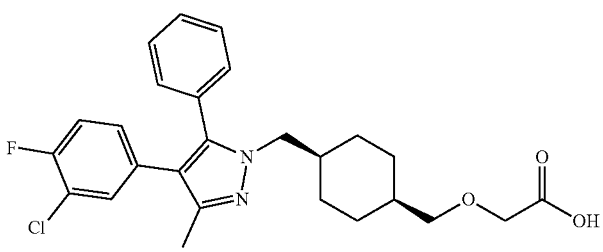 [SMILES: Cc1nn(C[C@H]2CC[C@@H](COCC(=O)O)CC2)c(-c2ccccc2)c1-c1ccc(F)c(Cl)c1] | 2-(1s,4s)-4-((4-(3-chloro-4-fluorophenyl)-3-methyl-5-phenyl-1H-pyrazol-1-yl)methyl)cyclohexyl)methoxy)acetic acid |
| 57 | 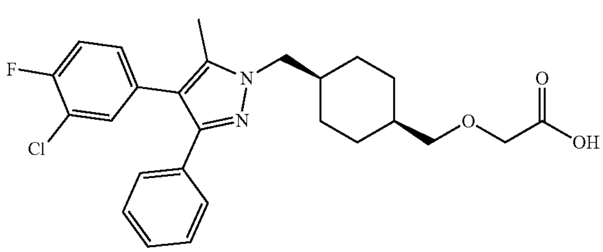 [SMILES: Cc1c(-c2ccc(F)c(Cl)c2)c(-c2ccccc2)nn1C[C@H]1CC[C@@H](COCC(=O)O)CC1] | 2-(((1s,4s)-4-((4-(3-chloro-4-fluorophenyl)-5-methyl-3-phenyl-1H-pyrazol-1-yl)methyl)cyclohexyl)methoxy)acetic acid |

TABLE A-continued

| Cpd No. | Chemical Structure | Chemical Name |
|---|---|---|
| 58 | 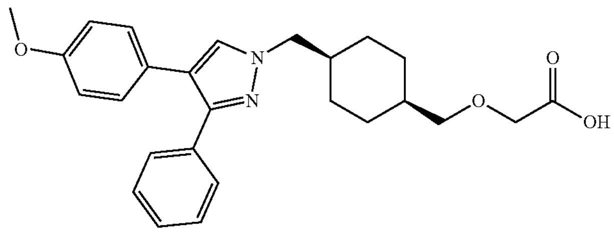 [SMILES: COc1ccc(-c2cn(C[C@H]3CC[C@@H](COCC(=O)O)CC3)nc2-c2ccccc2)cc1] | 2-(((1s,4s)-4-((4-(4-methoxyphenyl)-3-phenyl-1H-pyrazol-1-yl)methyl)cyclohexyl)methoxy)acetic acid |
| 59 | 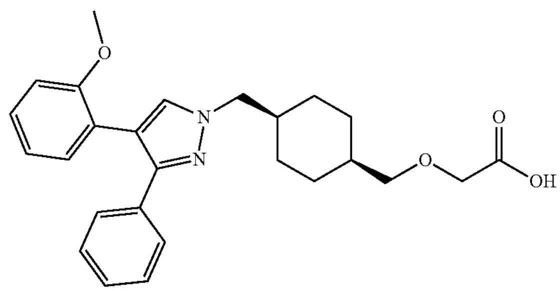 [SMILES: COc1ccccc1-c1cn(C[C@H]2CC[C@@H](COCC(=O)O)CC2)nc1-c1ccccc1] | 2-(((1s,4s)-4-((4-(2-methoxyphenyl)-3-phenyl-1H-pyrazol-1-yl)methyl)cyclohexyl)methoxy)acetic acid |
| 60 | 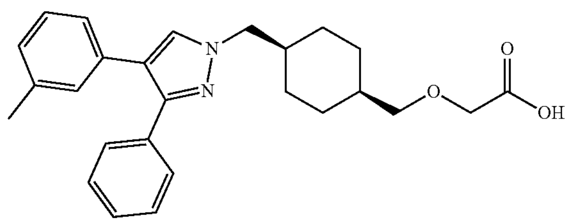 [SMILES: Cc1cccc(-c2cn(C[C@H]3CC[C@@H](COCC(=O)O)CC3)nc2-c2ccccc2)c1] | 2-(((1s,4s)-4-((3-phenyl-4-m-tolyl-1H-pyrazol-1-yl)methyl)cyclohexyl)methoxy)acetic acid |
| 61 | 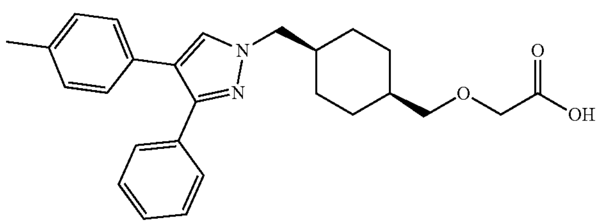 [SMILES: Cc1ccc(-c2cn(C[C@H]3CC[C@@H](COCC(=O)O)CC3)nc2-c2ccccc2)cc1] | 2-(((1s,4s)-4-((3-phenyl-4-p-tolyl-1H-pyrazol-1-yl)methyl)cyclohexyl)methoxy)acetic acid |
| 62 | 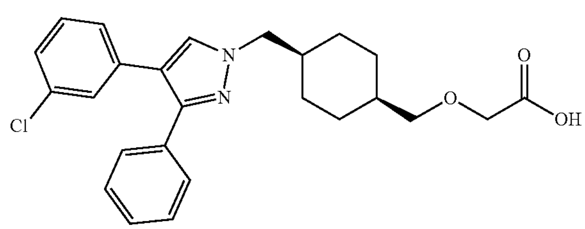 [SMILES: O=C(O)COC[C@H]1CC[C@@H](Cn2cc(-c3cccc(Cl)c3)c(-c3ccccc3)n2)CC1] | 2-(((1s,4s)-4-((4-(3-chlorophenyl)-3-phenyl-1H-pyrazol-1-yl)methyl)cyclohexyl)methoxy)acetic acid |
| 63 | 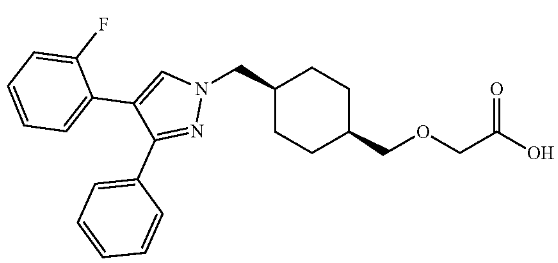 [SMILES: O=C(O)COC[C@H]1CC[C@@H](Cn2cc(-c3ccccc3F)c(-c3ccccc3)n2)CC1] | 2-(((1s,4s)-4-((4-(2-fluorophenyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 64 | 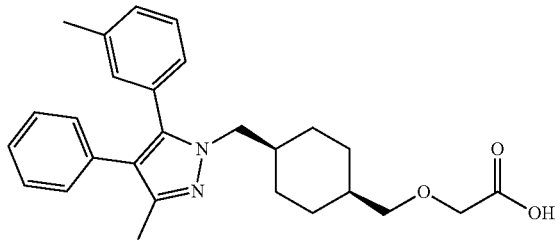 [SMILES: Cc1cccc(-c2c(-c3ccccc3)c(C)nn2C[C@H]2CC[C@@H](COCC(=O)O)CC2)c1] | 2-(((1s,4s)-4-((3-methyl-4-phenyl-5-m-tolyl-1H-pyrazol-1-yl)methyl)cyclohexyl)methoxy)acetic acid |
| 65 | 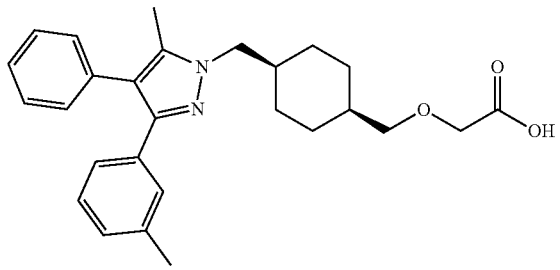 [SMILES: Cc1cccc(-c2nn(C[C@H]3CC[C@@H](COCC(=O)O)CC3)c(C)c2-c2ccccc2)c1] | 2-(((1s,4s)-4((5-methyl-4-phenyl-3-m-tolyl-1H-pyrazol-1-yl)methyl)cyclohexyl)methoxy)acetic acid |
| 66 | 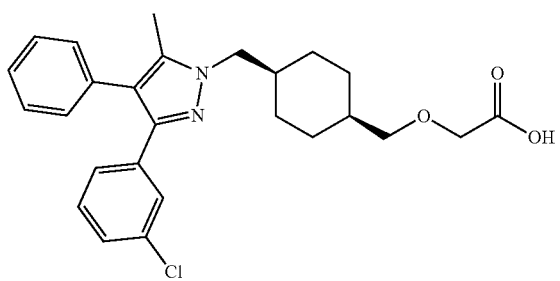 | 2-(((1s,4s)-4-((3-(3-chlorophenyl)-5-methyl-4-phenyl-1H-pyrazol-1-yl)methyl)cyclohexyl)methoxy)acetic acid |
| 67 | 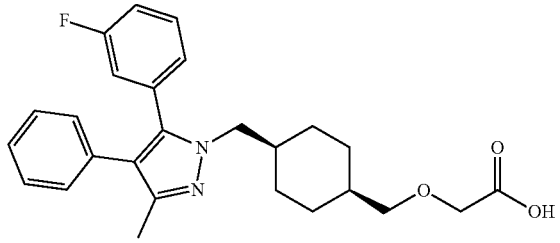 [SMILES: Cc1nn(C[C@H]2CC[C@@H](COCC(=O)O)CC2)c(-c2cccc(F)c2)c1-c1ccccc1] | 2-(((1s,4s)-4-((5-(3-fluorophenyl)-3-methyl-4-phenyl-1H-pyrazol-1-yl)methyl)cyclohexyl)methoxy)acetic acid |
| 68 | 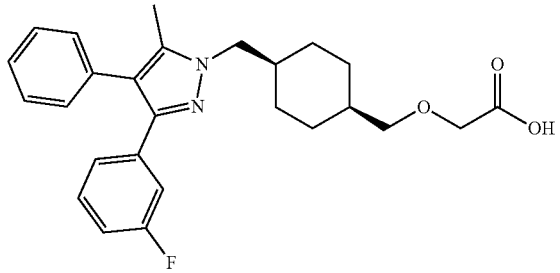 [SMILES: Cc1c(-c2ccccc2)c(-c2cccc(F)c2)nn1C[C@H]1CC[C@@H](COCC(=O)O)CC1] | 2-(((1s,4s)-4-((3-(3-fluorophenyl)-5-methyl-4-phenyl-1H-pyrazol-1-yl)methyl)cyclohexyl)methoxy)acetic acid |
| 69 | 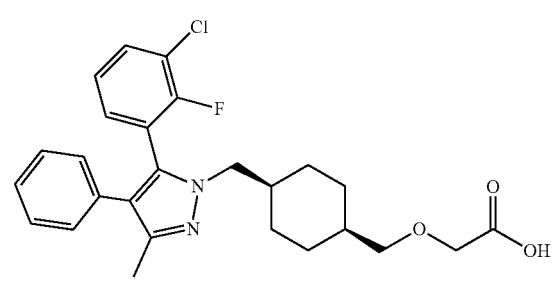 [SMILES: Cc1nn(C[C@H]2CC[C@@H](COCC(=O)O)CC2)c(-c2cccc(Cl)c2F)c1-c1ccccc1] | 2-(1s,4s)-4-((5-(3-chloro-2-fluorophenyl)-3-methyl-4-phenyl-1H-pyrazol-1-yl)methyl)cyclohexyl)methoxy)acetic acid |

TABLE A-continued

| Cpd No. | Chemical Structure | Chemical Name |
|---|---|---|
| 70 | 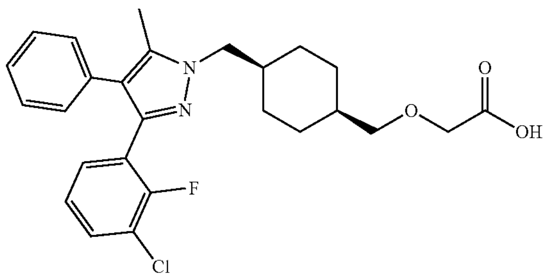 [SMILES: Cc1c(-c2ccccc2)c(-c2cccc(Cl)c2F)nn1C[C@H]1CC[C@@H](COCC(=O)O)CC1] | 2-(((1s,4s)-4-((3-(3-chloro-2-fluorophenyl)-5-methyl-4-phenyl-1H-pyrazol-1-yl)methyl)cyclohexyl)methoxy)acetic acid |
| 71 | 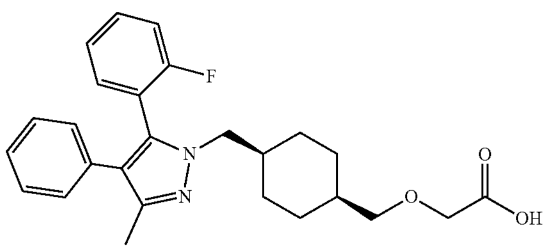 [SMILES: Cc1nn(C[C@H]2CC[C@@H](COCC(=O)O)CC2)c(-c2ccccc2F)c1-c1ccccc1] | 2-(((1s,4s)-4-((5-(2-fluorophenyl)-3-methyl-4-phenyl-1H-pyrazol-1-yl)methyl)cyclohexyl)methoxy)acetic acid |
| 72 | 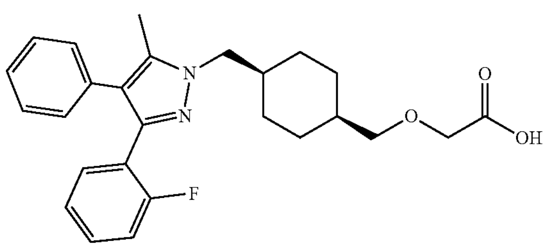 [SMILES: Cc1c(-c2ccccc2)c(-c2ccccc2F)nn1C[C@H]1CC[C@@H](COCC(=O)O)CC1] | 2-(((1s,4s)-4-((3-(2-fluorophenyl)-5-methyl-4-phenyl-1H-pyrazol-1-yl)methyl)cyclohexyl)methoxy)acetic acid |
| 73 | 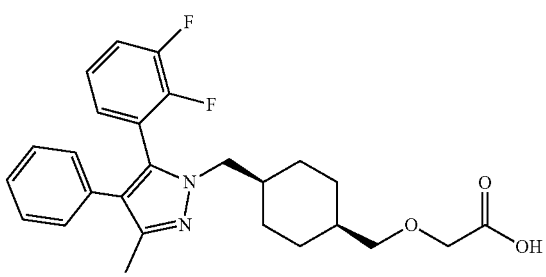 [SMILES: Cc1nn(C[C@H]2CC[C@@H](COCC(=O)O)CC2)c(-c2cccc(F)c2F)c1-c1ccccc1] | 2-(((1s,4s)-4-((5-(2,3-difluorophenyl)-3-methyl-4-phenyl-1H-pyrazol-1-yl)methyl)cyclohexyl)methoxy)acetic acid |
| 74 | 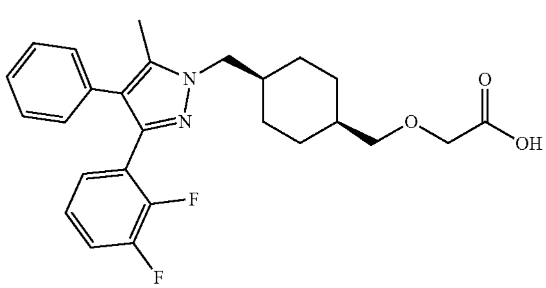 [SMILES: Cc1c(-c2ccccc2)c(-c2cccc(F)c2F)nn1C[C@H]1CC[C@@H](COCC(=O)O)CC1] | 2-(((1s,4s)-4-((3-(2,3-difluorophenyl)-5-methyl-4-phenyl-1H-pyrazol-1-yl)methyl)cyclohexyl)methoxy)acetic acid |

TABLE A-continued

| Cpd No. | Chemical Structure | Chemical Name |
|---|---|---|
| 75 | 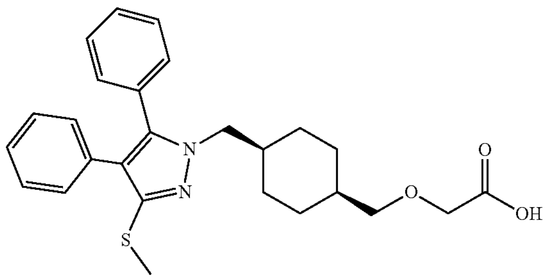 [SMILES: CSc1nn(C[C@H]2CC[C@@H](COCC(=O)O)CC2)c(-c2ccccc2)c1-c1ccccc1] | 2-(((1s,4s)-4-((3-(methylthio)-4,5-diphenyl-1H-pyrazol-1-yl)methyl)cyclohexyl)methoxy)acetic acid |
| 76 | 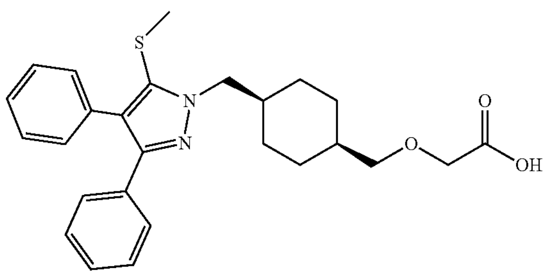 [SMILES: CSc1c(-c2ccccc2)c(-c2ccccc2)nn1C[C@H]1CC[C@@H](COCC(=O)O)CC1] | 2-(((1s,4s)-4-((5-(methylthio)-3,4-diphenyl-1H-pyrazol-1-yl)methyl)cyclohexyl)methoxy)acetic acid |
| 77 | 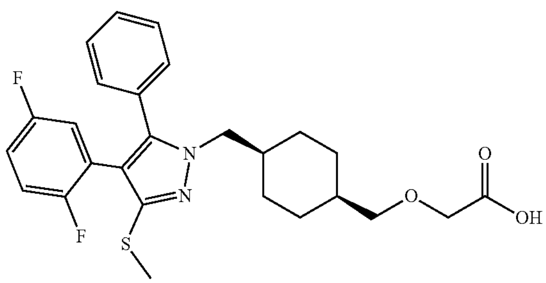 [SMILES: CSc1nn(C[C@H]2CC[C@@H](COCC(=O)O)CC2)c(-c2ccccc2)c1-c1cc(F)ccc1F] | 2-(((1s,4s)-4-((4-(2,5-difluorophenyl)-3-(methylthio)-5-phenyl-1H-pyrazol-1-yl)methyl)cyclohexyl)methoxy)acetic acid |
| 78 | 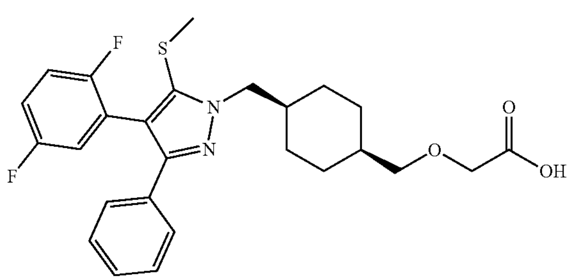 [SMILES: CSc1c(-c2cc(F)ccc2F)c(-c2ccccc2)nn1C[C@H]1CC[C@@H](COCC(=O)O)CC1] | 2-(((1s,4s)-4-((4-(2,5-difluorophenyl)-5-(methylthio)-3-phenyl-1H-pyrazol-1-yl)methyl)cyclohexyl)methoxy)acetic acid |
| 79 | 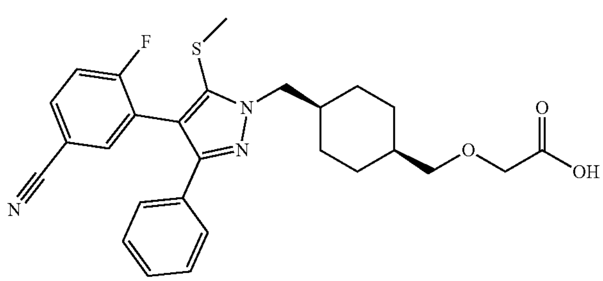 [SMILES: CSc1c(-c2cc(C#N)ccc2F)c(-c2ccccc2)nn1C[C@H]1CC[C@@H](COCC(=O)O)CC1] | 2-(((1s,4s)-4-((4-(5-cyano-2-fluorophenyl)-5-(methylthio)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 80 | 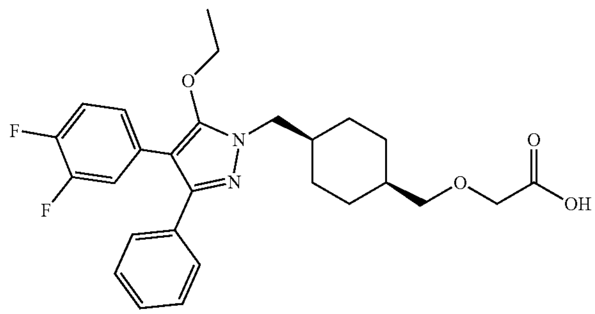 [SMILES: CCOc1c(-c2ccc(F)c(F)c2)c(-c2ccccc2)nn1C[C@H]1CC[C@@H](COCC(=O)O)CC1] | 2-(((1s,4s)-4-((4-(3,4-difluorophenyl)-5-ethoxy-3-phenyl-1H-pyrazol-1-yl)methyl)cyclohexyl)methoxy)acetic acid |
| 81 | 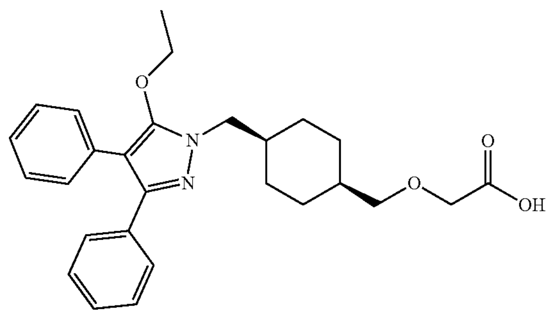 | 2-(((1s,4s)-4-((5-ethoxy-3,4-diphenyl-1H-pyrazol-1-yl)methyl)cyclohexyl)methoxy)acetic acid |
| 82 | 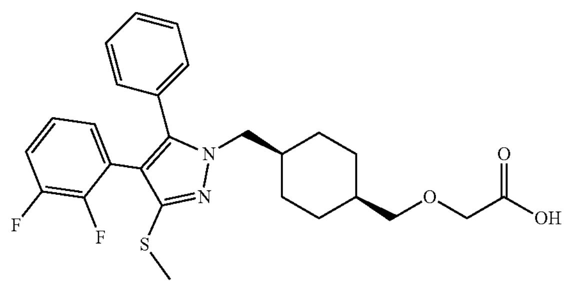 [SMILES: CSc1nn(C[C@H]2CC[C@@H](COCC(=O)O)CC2)c(-c2ccccc2)c1-c1cccc(F)c1F] | 2-(((1s,4s)-4-((4-(2,3-difluorophenyl)-3-(methylthio)-5-phenyl-1H-pyrazol-1-yl)methyl)cyclohexyl)methoxy)acetic acid |
| 83 | 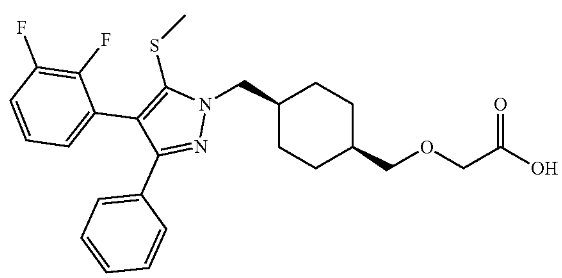 [SMILES: CSc1c(-c2cccc(F)c2F)c(-c2ccccc2)nn1C[C@H]1CC[C@@H](COCC(=O)O)CC1] | 2-(((1s,4s)-4-((4-(2,3-difluorophenyl)-5-(methylthio)-3-phenyl-1H-pyrazol-1-yl)methyl)cyclohexyl)methoxy)acetic acid |
| 84 | 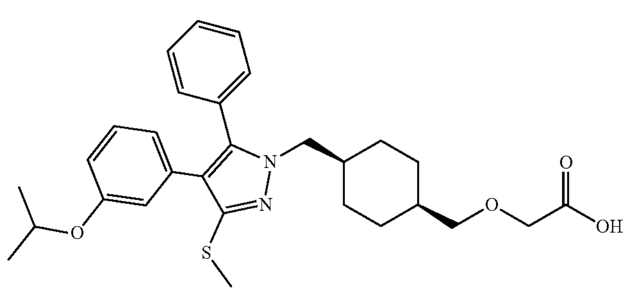 [SMILES: CSc1nn(C[C@H]2CC[C@@H](COCC(=O)O)CC2)c(-c2ccccc2)c1-c1cccc(OC(C)C)c1] | 2-(((1s,4s)-4-((4-(3-isopropoxyphenyl)-3-(methylthio)-5-phenyl-1H-pyrazol-1-yl)methyl)cyclohexyl)methoxy)acetic acid |

TABLE A-continued

| Cpd No. | Chemical Structure | Chemical Name |
|---|---|---|
| 85 | 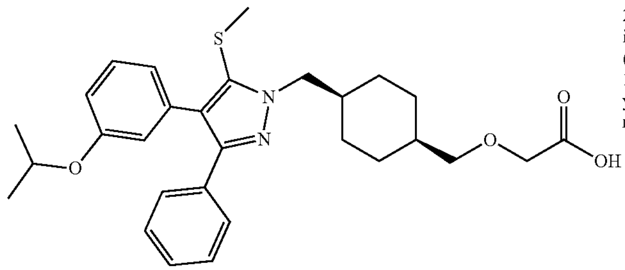 [SMILES: CSc1c(-c2cccc(OC(C)C)c2)c(-c2ccccc2)nn1C[C@H]1CC[C@@H](COCC(=O)O)CC1] | 2-(1s,4s)-4-((4-(3-isopropoxyphenyl)-5-(methylthio)-3-phenyl-1H-pyrazol-1-yl)methyl)cyclohexyl)methoxy)acetic acid |
| 86 | 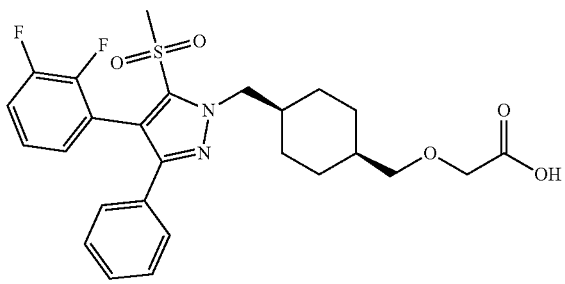 [SMILES: CS(=O)(=O)c1c(-c2cccc(F)c2F)c(-c2ccccc2)nn1C[C@H]1CC[C@@H](COCC(=O)O)CC1] | 2-(((1s,4s)-4-((4-(2,3-difluorophenyl)-5-(methylsulfonyl)-3-phenyl-1H-pyrazol-1-yl)methyl)cyclohexyl)methoxy)acetic acid |
| 87 | 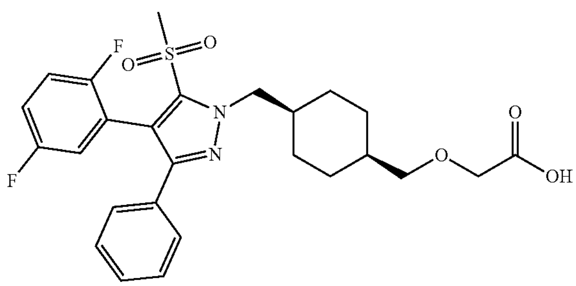 [SMILES: CS(=O)(=O)c1c(-c2cc(F)ccc2F)c(-c2ccccc2)nn1C[C@H]1CC[C@@H](COCC(=O)O)CC1] | 2-(1s,4s)4-((4-(2,5-difluorophenyl)-5-(methylsulfonyl)-3-phenyl-1H-pyrazol-1-yl)methyl)cyclohexyl)methoxy)acetic acid |
| 88 | 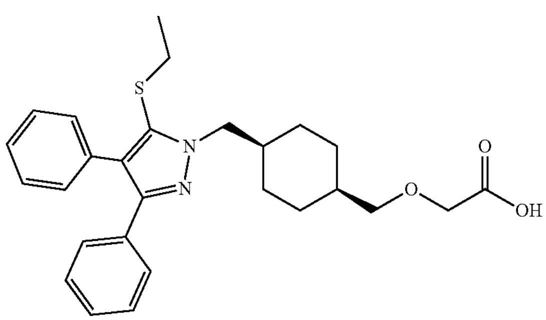 [SMILES: CCSc1c(-c2ccccc2)c(-c2ccccc2)nn1C[C@H]1CC[C@@H](COCC(=O)O)CC1] | 2-(((1s,4s)-4-((5-(ethylthio)-3,4-diphenyl-1H-pyrazol-1-yl)methyl)cyclohexyl)methoxy)acetic acid |
| 89 | 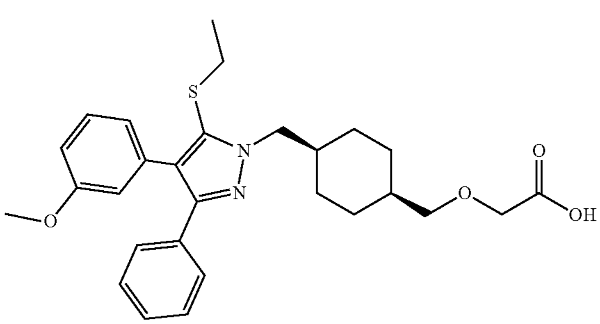 [SMILES: CCSc1c(-c2cccc(OC)c2)c(-c2ccccc2)nn1C[C@H]1CC[C@@H](COCC(=O)O)CC1] | 2-(((1s,4s)-4-((5-(ethylthio)-4-(3-methoxyphenyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 90 | 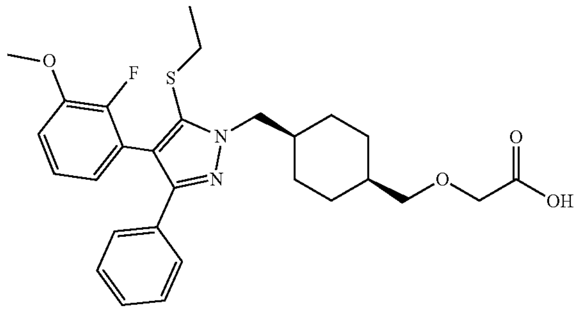 [SMILES: CCSc1c(-c2cccc(OC)c2F)c(-c2ccccc2)nn1C[C@H]1CC[C@@H](COCC(=O)O)CC1] | 2-(((1s,4s)-4-((5-(ethylthio)-4-(2-fluoro-3-methoxyphenyl)-3-phenyl-1H-pyrazol-1-yl)methyl)cyclohexyl)methoxy)acetic acid |
| 91 | 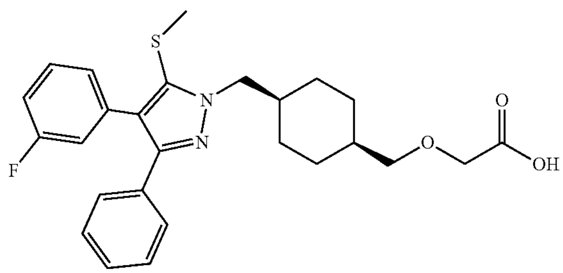 [SMILES: CSc1c(-c2cccc(F)c2)c(-c2ccccc2)nn1C[C@H]1CC[C@@H](COCC(=O)O)CC1] | 2-(((1s,4s)-4-((4-(3-fluorophenyl)-5-(methylthio)-3-phenyl-1H-pyrazol-1-yl)methyl)cyclohexyl)methoxy)acetic acid |
| 92 | 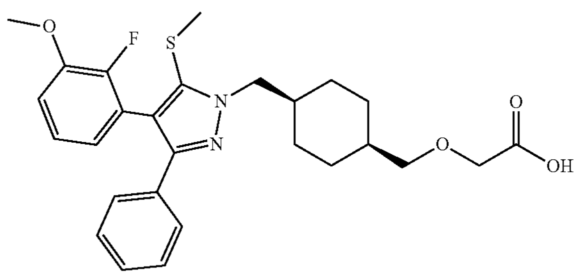 | 2-(((1s,4s)-4-((4-(2-fluoro-3-methoxyphenyl)-5-(methylthio)-3-phenyl-1H-pyrazol-1-yl)methyl)cyclohexyl)methoxy)acetic acid |
| 93 | 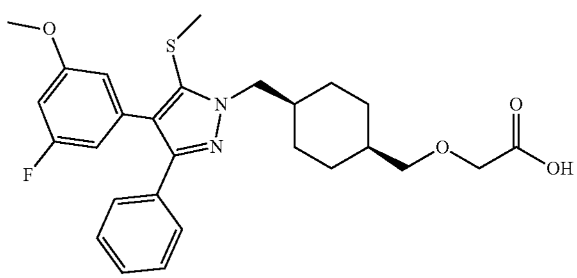 [SMILES: COc1cc(F)cc(-c2c(-c3ccccc3)nn(C[C@H]3CC[C@@H](COCC(=O)O)CC3)c2SC)c1] | 2-(((1s,4s)-4-((4-(3-fluoro-5-methoxyphenyl)-5-(methylthio)-3-phenyl-1H-pyrazol-1-yl)methyl)cyclohexyl)methoxy)acetic acid |
| 94 | 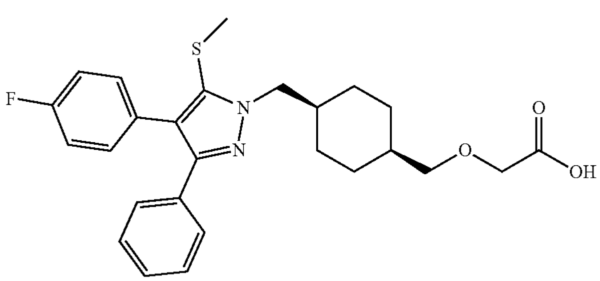 [SMILES: CSc1c(-c2ccc(F)cc2)c(-c2ccccc2)nn1C[C@H]1CC[C@@H](COCC(=O)O)CC1] | 2-(((1s,4s)-4-((4-(4-fluorophenyl)-5-methylthio-3-phenyl-1H-pyrazol-1-yl)methyl)cyclohexyl)methoxy)acetic acid |

TABLE A-continued

| Cpd No. | Chemical Structure | Chemical Name |
|---|---|---|
| 95 | 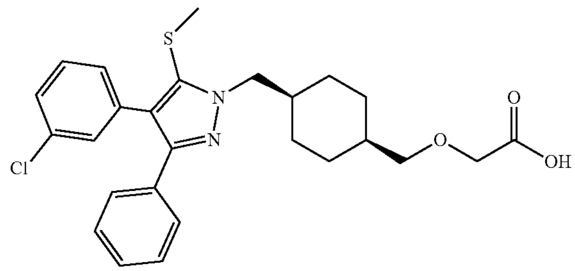 | 2-(((1s,4s)-4-((4-(3-chlorophenyl)-5-(methylthio)-3-phenyl-1H-pyrazol-1-yl)methyl)cyclohexyl)methoxy)acetic acid |
| 96 | 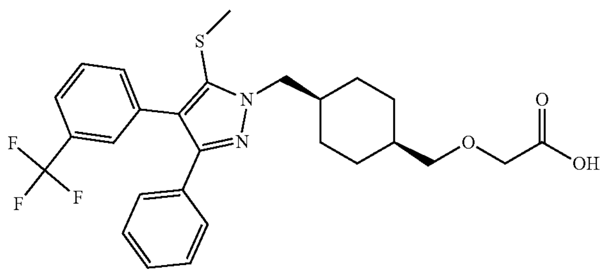 [SMILES: CSc1c(-c2cccc(C(F)(F)F)c2)c(-c2ccccc2)nn1C[C@H]1CC[C@@H](COCC(=O)O)CC1] | 2-(((1s,4s)-4-((5-(methylthio)-3-phenyl-4-(3-(trifluoromethyl)phenyl)1H-pyrazol-1-yl)methyl)cyclohexyl)methoxy)acetic acid |
| 97 | 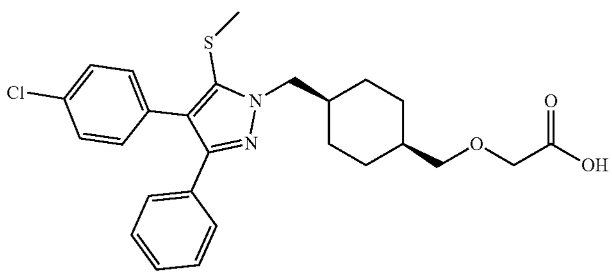 [SMILES: CSc1c(-c2ccc(Cl)cc2)c(-c2ccccc2)nn1C[C@H]1CC[C@@H](COCC(=O)O)CC1] | 2-(((1s,4s)-4-((4-(4-chlorophenyl)-5-(methylthio)-3-phenyl-1H-pyrazol-1-yl)methyl)cyclohexyl)methoxy)acetic acid |
| 98 | 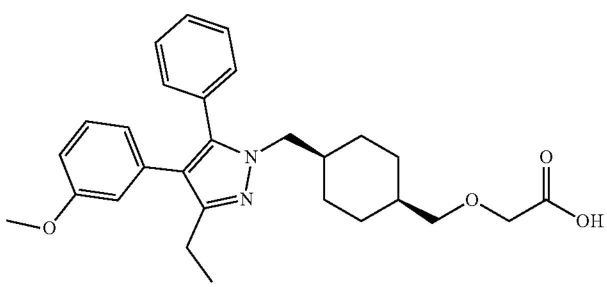 [SMILES: CCc1nn(C[C@H]2CC[C@@H](COCC(=O)O)CC2)c(-c2ccccc2)c1-c1cccc(OC)c1] | 2-(((1s,4s)-4-((3-ethyl-4-(3-methoxyphenyl)-5-phenyl-1H-pyrazol-1-yl)methyl)cyclohexyl)methoxy)acetic acid |
| 99 | 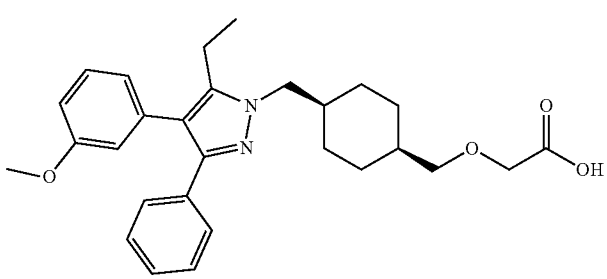 [SMILES: CCc1c(-c2cccc(OC)c2)c(-c2ccccc2)nn1C[C@H]1CC[C@@H](COCC(=O)O)CC1] | 2-(((1s,4s)-4-((5-ethyl-4-(3-methoxyphenyl)-3-phenyl-1H-pyrazol-1-yl)methyl)cyclohexyl)methoxy)acetic acid |

TABLE A-continued

| Cpd No. | Chemical Structure | Chemical Name |
| --- | --- | --- |
| 100 | 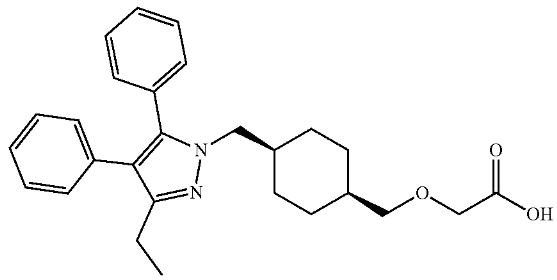 [SMILES: CCc1nn(C[C@H]2CC[C@@H](COCC(=O)O)CC2)c(-c2ccccc2)c1-c1ccccc1] | 2-(((1s,4s)-4-((3-ethyl-4,5-diphenyl-1H-pyrazol-1-yl)methyl)cyclohexyl)methoxy)acetic acid |
| 101 | 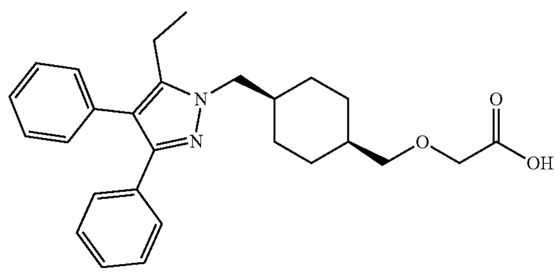 [SMILES: CCc1c(-c2ccccc2)c(-c2ccccc2)nn1C[C@H]1CC[C@@H](COCC(=O)O)CC1] | 2-(((1s,4s)-4-((5-ethyl-3,4-diphenyl-1H-pyrazol-1-yl)methyl)cyclohexyl)methoxy)acetic acid |
| 102 | 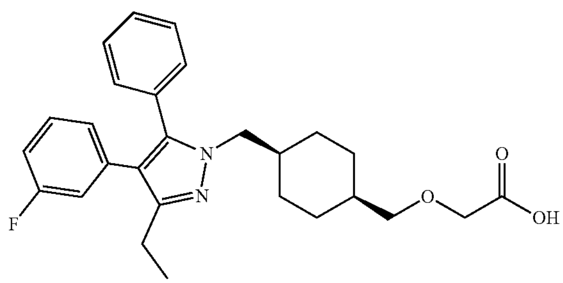 [SMILES: CCc1nn(C[C@H]2CC[C@@H](COCC(=O)O)CC2)c(-c2ccccc2)c1-c1cccc(F)c1] | 2-(((1s,4s)-4-((3-ethyl-4-(3-fluorophenyl)-5-phenyl-1H-pyrazol-1-yl)methyl)cyclohexyl)methoxy)acetic acid |
| 103 | 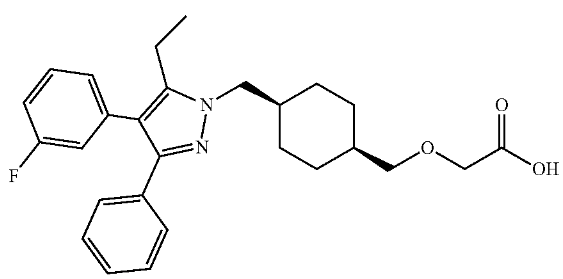 | 2-(((1s,4s)-4-((5-ethyl-4-(3-fluorophenyl)-3-phenyl-1H-pyrazol-1-yl)methyl)cyclohexyl)methoxy)acetic acid |
| 104 | 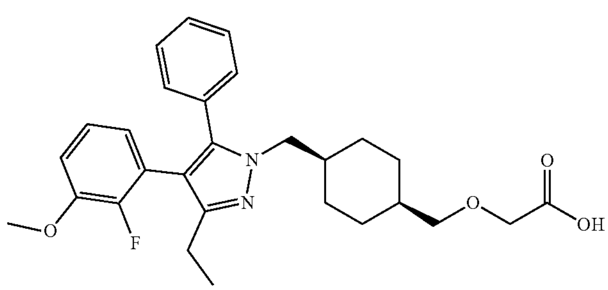 [SMILES: CCc1nn(C[C@H]2CC[C@@H](COCC(=O)O)CC2)c(-c2ccccc2)c1-c1cccc(OC)c1F] | 2-(((1s,4s)-4-((3-ethyl-4-(2-fluoro-3-methoxyphenyl)-5-phenyl-1H-pyrazol-1-yl)methyl)cyclohexyl)methoxy)acetic acid |

TABLE A-continued

| Cpd No. | Chemical Structure | Chemical Name |
|---|---|---|
| 105 | 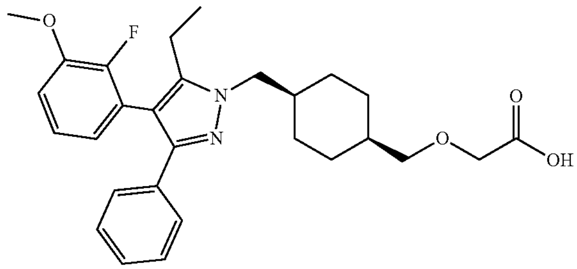 [SMILES: CCc1c(-c2cccc(OC)c2F)c(-c2ccccc2)nn1C[C@H]1CC[C@@H](COCC(=O)O)CC1] | 2-(((1s,4s)-4-((5-ethyl-4-(2-fluoro-3-methoxyphenyl)-3-phenyl-1H-pyrazol-1-yl)methyl)cyclohexyl)methoxy)acetic acid |
| 106 | 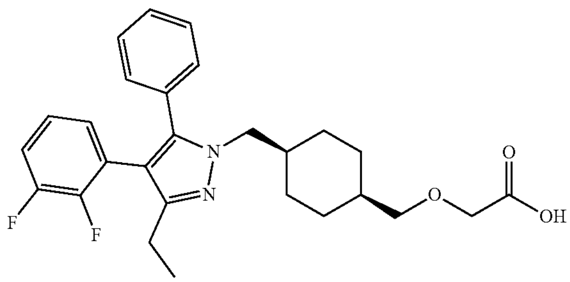 [SMILES: CCc1nn(C[C@H]2CC[C@@H](COCC(=O)O)CC2)c(-c2ccccc2)c1-c1cccc(F)c1F] | 2-(((1s,4s)-4-((4-(2,3-difluorophenyl)-3-ethyl-5-phenyl-1H-pyrazol-1-yl)methyl)cyclohexyl)methoxy)acetic acid |
| 107 | 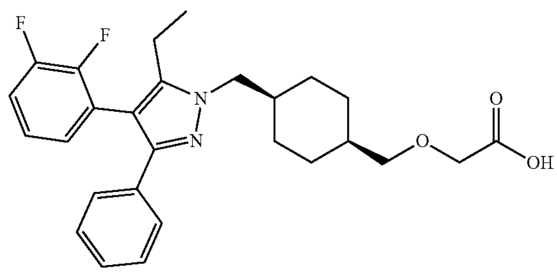 [SMILES: CCc1c(-c2cccc(F)c2F)c(-c2ccccc2)nn1C[C@H]1CC[C@@H](COCC(=O)O)CC1] | 2-(((1s,4s)-4-((4-(2,3-difluorophenyl)-5-ethyl-3-phenyl-1H-pyrazol-1-yl)methyl)cyclohexyl)methoxy)acetic acid |
| 108 | 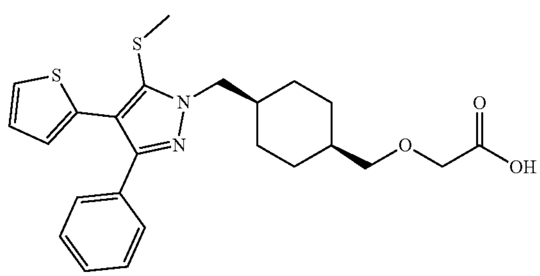 [SMILES: CSc1c(-c2cccs2)c(-c2ccccc2)nn1C[C@H]1CC[C@@H](COCC(=O)O)CC1] | 2-(((1s,4s)-4-((5-(methylthio)-3-phenyl-4-(thiophen-2-yl)-1H-pyrazol-1-yl)methyl)cyclohexyl)methoxy)acetic acid |
| 109 | 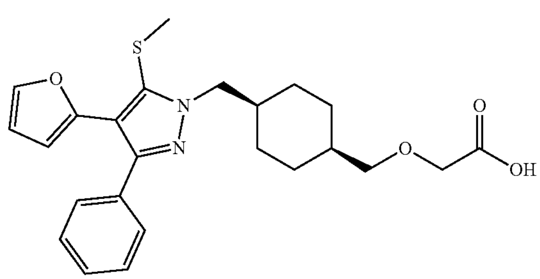 | 2-(((1s,4s)-4-((4-(furan-2-yl)-5-(methylthio)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 110 | 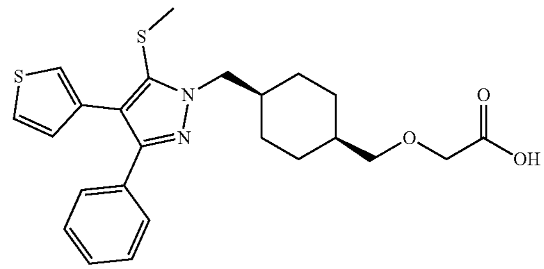 [SMILES: CSc1c(-c2ccsc2)c(-c2ccccc2)nn1C[C@H]1CC[C@@H](COCC(=O)O)CC1] | 2-(((1s,4s)-4-((5-(methylthio)-3-phenyl-4-(thiophen-3-yl)-1H-pyrazol-1-yl)methyl)cyclohexyl)methoxy)acetic acid |
| 111 | 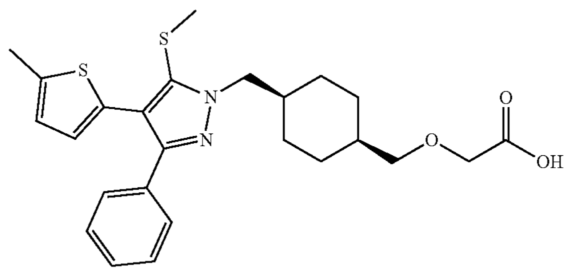 [SMILES: CSc1c(-c2ccc(C)s2)c(-c2ccccc2)nn1C[C@H]1CC[C@@H](COCC(=O)O)CC1] | 2-(((1s,4s)-4-((5-(methylthio)-4-(5-methylthiophen-2-yl)-3-phenyl-1H-pyrazol-1-yl)methyl)cyclohexyl)methoxy)acetic acid |
| 112 | 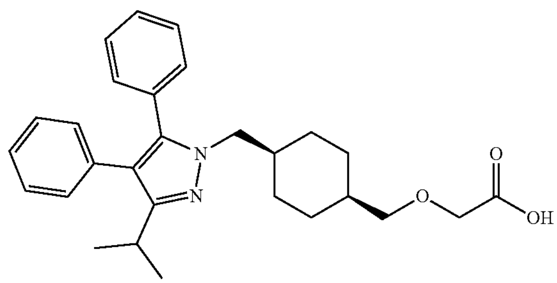 [SMILES: CC(C)c1nn(C[C@H]2CC[C@@H](COCC(=O)O)CC2)c(-c2ccccc2)c1-c1ccccc1] | 2-(1s,4s)-4-((3-isopropyl-4,5-diphenyl-1H-pyrazol-1-yl)methyl)cyclohexyl)methoxy)acetic acid |
| 113 | 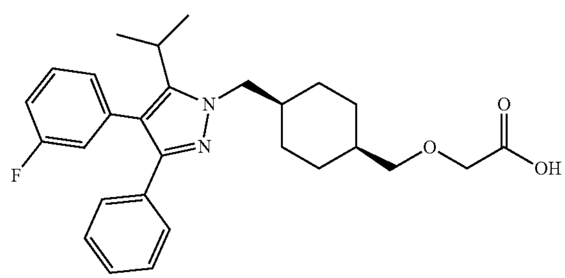 [SMILES: CC(C)c1c(-c2cccc(F)c2)c(-c2ccccc2)nn1C[C@H]1CC[C@@H](COCC(=O)O)CC1] | 2-(((1s,4s)-4-((4-(3-fluorophenyl)-5-isopropyl-3-phenyl-1H-pyrazol-1-yl)methyl)cyclohexyl)methoxy)acetic acid |
| 114 | 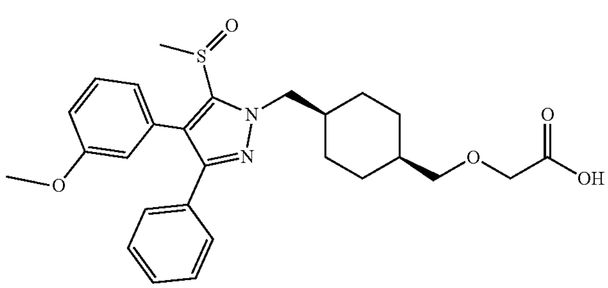 [SMILES: COc1cccc(-c2c(-c3ccccc3)nn(C[C@H]3CC[C@@H](COCC(=O)O)CC3)c2S(C)=O)c1] | 2-(((1s,4s)-4-((4-(3-methoxyphenyl)-5-(methylsulfinyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 115 | 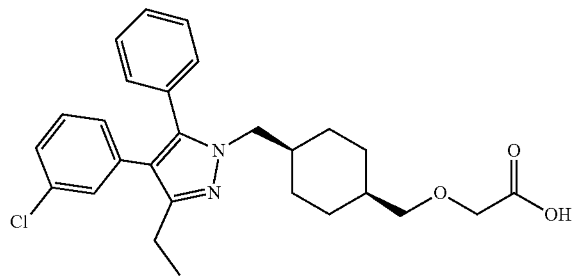 [SMILES: CCc1nn(C[C@H]2CC[C@@H](COCC(=O)O)CC2)c(-c2ccccc2)c1-c1cccc(Cl)c1] | 2-(((1s,4s)-4-((4-(3-chlorophenyl)-3-ethyl-5-phenyl-1H-pyrazol-1-yl)methyl)cyclohexyl)methoxy)acetic acid |
| 116 | 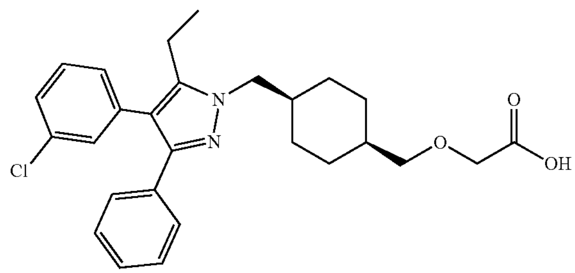 | 2-(((1s,4s)-4-((4-(3-chlorophenyl)-5-ethyl-3-phenyl-1H-pyrazol-1-yl)methyl)cyclohexyl)methoxy)acetic acid |
| 117 | 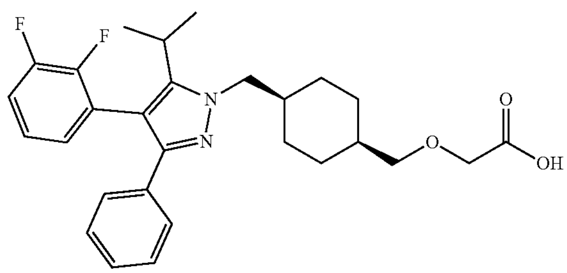 [SMILES: CC(C)c1c(-c2cccc(F)c2F)c(-c2ccccc2)nn1C[C@H]1CC[C@@H](COCC(=O)O)CC1] | 2-(((1s,4s)-4-((4-(2,3-difluorophenyl)-5-isopropyl-3-phenyl-1H-pyrazol-1-yl)methyl)cyclohexyl)methoxy)acetic acid |
| 118 | 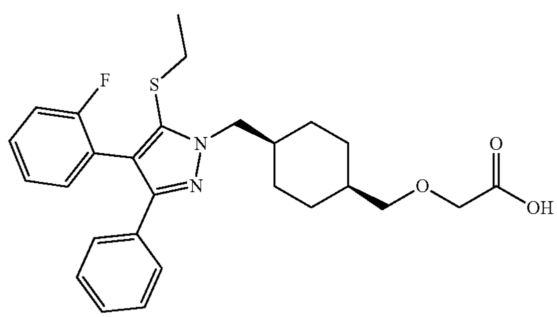 [SMILES: CCSc1c(-c2ccccc2F)c(-c2ccccc2)nn1C[C@H]1CC[C@@H](COCC(=O)O)CC1] | 2-(((1s,4s)-4-((5-(ethylthio)-4-(2-fluorophenyl)-3-phenyl-1H-pyrazol-1-yl)methyl)cyclohexyl)methoxy)acetic acid |
| 119 | 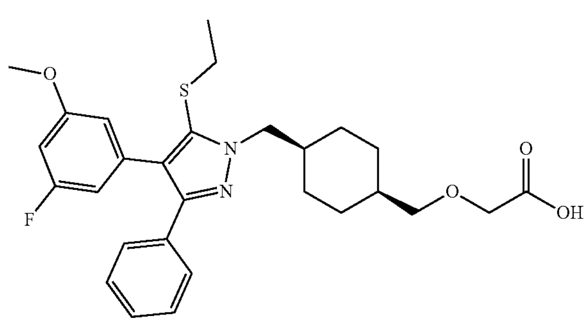 [SMILES: CCSc1c(-c2cc(F)cc(OC)c2)c(-c2ccccc2)nn1C[C@H]1CC[C@@H](COCC(=O)O)CC1] | 2-(((1s,4s)-4-((5-(ethylthio)-4-(3-fluoro-5-methoxyphenyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 120 | 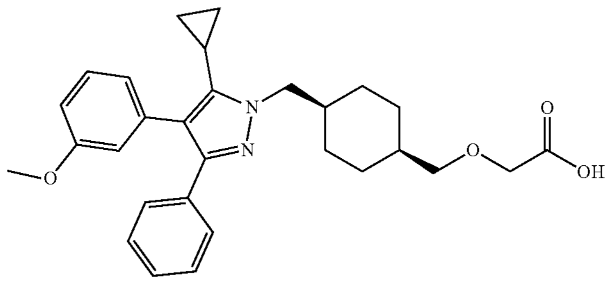 [SMILES: COc1cccc(-c2c(-c3ccccc3)nn(C[C@H]3CC[C@@H](COCC(=O)O)CC3)c2C2CC2)c1] | 2-(((1s,4s)-4-((5-cyclopropyl-4-(3-methoxyphenyl)-3-phenyl-1H-pyrazol-1-yl)methyl)cyclohexyl)methoxy)acetic acid |
| 121 | 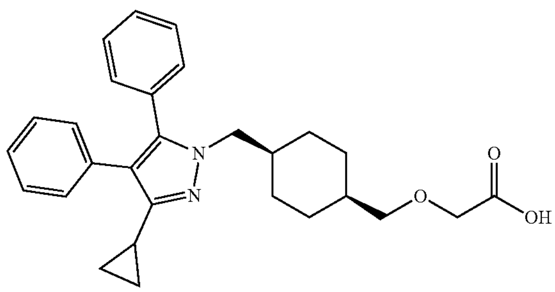 [SMILES: O=C(O)COC[C@H]1CC[C@@H](Cn2nc(C3CC3)c(-c3ccccc3)c2-c2ccccc2)CC1] | 2-(((1s,4s)-4-((3-cyclopropyl-4,5-diphenyl-1H-pyrazol-1-yl)methyl)cyclohexyl)methoxy)acetic acid |
| 122 | 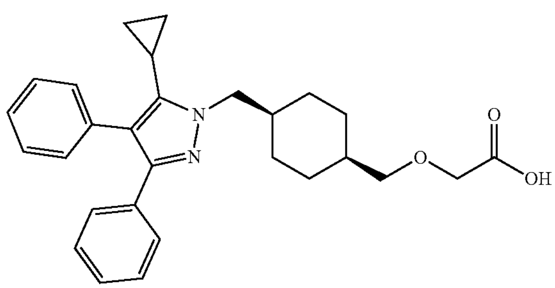 [SMILES: O=C(O)COC[C@H]1CC[C@@H](Cn2nc(-c3ccccc3)c(-c3ccccc3)c2C2CC2)CC1] | 2-(((1s,4s)-4-((5-cyclopropyl-3,4-diphenyl-1H-pyrazol-1-yl)methyl)cyclohexyl)methoxy)acetic acid |
| 123 | 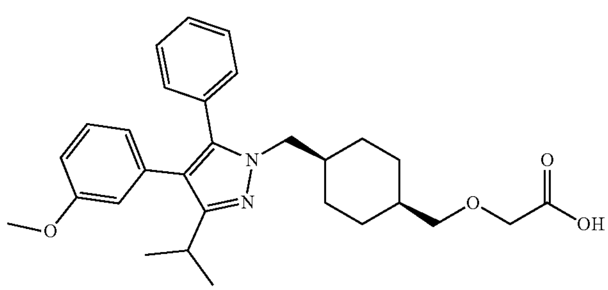 [SMILES: COc1cccc(-c2c(C(C)C)nn(C[C@H]3CC[C@@H](COCC(=O)O)CC3)c2-c2ccccc2)c1] | 2-(((1s,4s)-4-((3-isopropyl-4-(3-methoxyphenyl)-5-phenyl-1H-pyrazol-1-yl)methyl)cyclohexyl)methoxy)acetic acid |
| 124 | 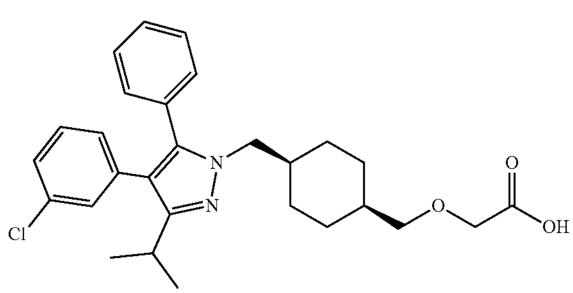 [SMILES: CC(C)c1nn(C[C@H]2CC[C@@H](COCC(=O)O)CC2)c(-c2ccccc2)c1-c1cccc(Cl)c1] | 2-(((1s,4s)-4-((4-(3-chlorophenyl)-3-isopropyl-5-phenyl-1H-pyrazol-1-yl)methyl)cyclohexyl)methoxy)acetic acid |

TABLE A-continued

| Cpd No. | Chemical Structure | Chemical Name |
|---|---|---|
| 125 | 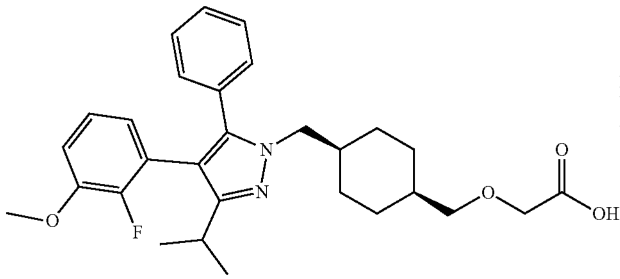 [SMILES: COc1cccc(-c2c(C(C)C)nn(C[C@H]3CC[C@@H](COCC(=O)O)CC3)c2-c2ccccc2)c1F] | 2-(((1s,4s)-4-((4-(2-fluoro-3-methoxyphenyl)-3-,isopropyl-5-phenyl-1H pyrazol-1-yl)methyl)cyclohexyl) methoxy)acetic acid |
| 126 | 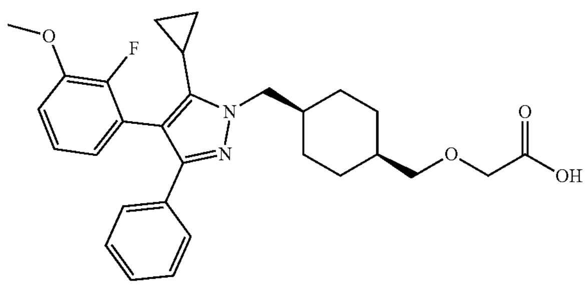 [SMILES: COc1cccc(-c2c(-c3ccccc3)nn(C[C@H]3CC[C@@H](COCC(=O)O)CC3)c2C2CC2)c1F] | 2-(((1s,4s)-4-((5-cyclopropyl-4-(2-fluoro-3-methoxyphenyl)-3-phenyl-1H-pyrazol-1-yl)methyl)cyclohexyl) methoxy)acetic acid |
| 127 | 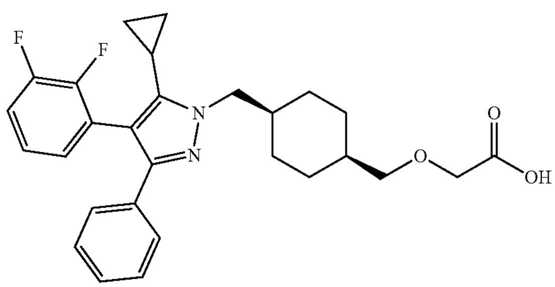 [SMILES: O=C(O)COC[C@H]1CC[C@@H](Cn2nc(-c3ccccc3)c(-c3cccc(F)c3F)c2C2CC2)CC1] | 2-(((1s,4s)-4-((5-cyclopropyl-4-(2,3-difluorophenyl)-3-phenyl-1H-pyrazol-1-yl) methyl)cyclohexyl) methoxy)acetic acid |
| 128 | 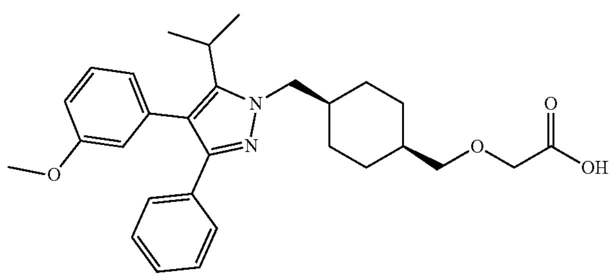 [SMILES: COc1cccc(-c2c(-c3ccccc3)nn(C[C@H]3CC[C@@H](COCC(=O)O)CC3)c2C(C)C)c1] | 2-(((1s,4s)-4-((5-isopropyl-4-(3-methoxyphenyl)-3-phenyl-1H-pyrazol-1-yl)methyl)cyclohexyl) methoxy)acetic acid |
| 129 | 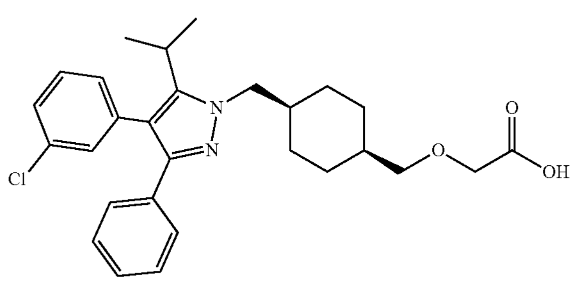 [SMILES: CC(C)c1c(-c2cccc(Cl)c2)c(-c2ccccc2)nn1C[C@H]1CC[C@@H](COCC(=O)O)CC1] | 2-(((1s,4s)-4-((4-(3-chlorophenyl)-5-isopropyl-3-phenyl-1H-pyrazol-1-yl)methyl) cyclohexyl) methoxy)acetic acid |

TABLE A-continued

| Cpd No. | Chemical Structure | Chemical Name |
|---|---|---|
| 130 | 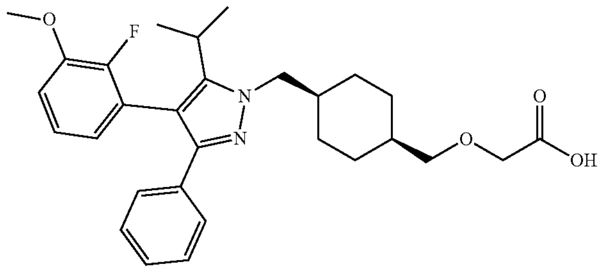 [SMILES: COc1cccc(-c2c(-c3ccccc3)nn(C[C@H]3CC[C@@H](COCC(=O)O)CC3)c2C(C)C)c1F] | 2-(((1s,4s)-4-((4-(2-fluoro-3-methoxyphenyl)-5-isopropyl-3-phenyl-1H-pyrazol-1-yl)methyl)cyclohexyl)methoxy)acetic acid |
| 131 | 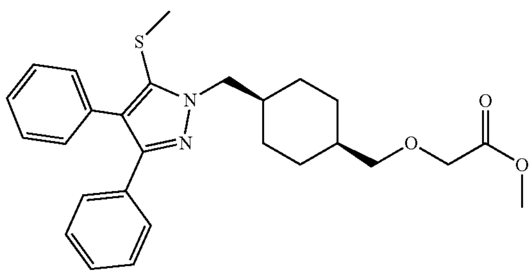 [SMILES: COC(=O)COC[C@H]1CC[C@@H](Cn2nc(-c3ccccc3)c(-c3ccccc3)c2SC)CC1] | methyl 2-(((1s,4s)-4-((5-(methylthio)-3,4-diphenyl-1H-pyrazol-1-yl)methyl)cyclohexyl)methoxy)acetate |
| 132 | 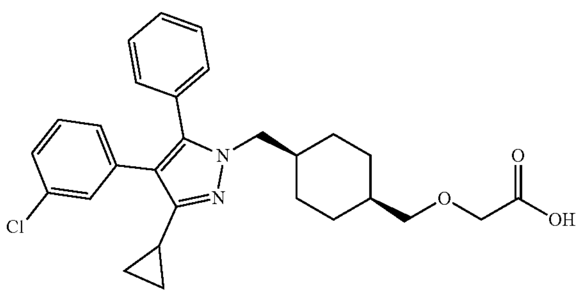 [SMILES: O=C(O)COC[C@H]1CC[C@@H](Cn2nc(C3CC3)c(-c3cccc(Cl)c3)c2-c2ccccc2)CC1] | 2-(((1s,4s)-4-((4-(3-chlorophenyl)-3-cyclopropyl-5-phenyl-1H-pyrazol-1-yl)methyl)cyclohexyl)methoxy)acetic acid |
| 133 | 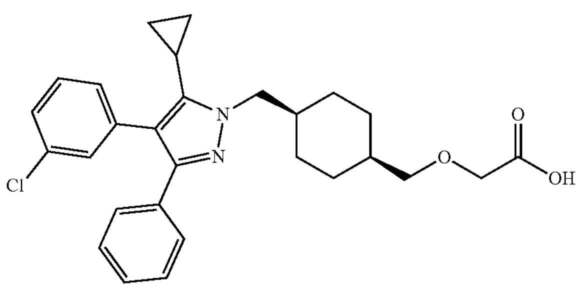 [SMILES: O=C(O)COC[C@H]1CC[C@@H](Cn2nc(-c3ccccc3)c(-c3cccc(Cl)c3)c2C2CC2)CC1] | 2-(((1s,4s)-4-((4-(3-chlorophenyl)-5-cyclopropyl-3-phenyl-1H-pyrazol-1-yl)methyl)cyclohexyl)methoxy)acetic acid |
| 134 | 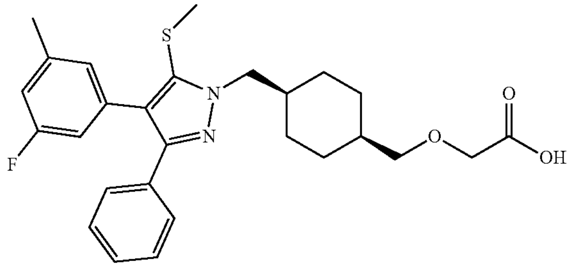 [SMILES: CSc1c(-c2cc(C)cc(F)c2)c(-c2ccccc2)nn1C[C@H]1CC[C@@H](COCC(=O)O)CC1] | 2-(((1s,4s)-4-((4-(3-fluoro-5-methylphenyl)-5-(methylthio)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 135 | 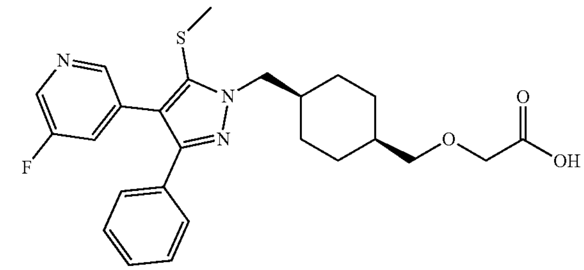 [SMILES: CSc1c(-c2cncc(F)c2)c(-c2ccccc2)nn1C[C@H]1CC[C@@H](COCC(=O)O)CC1] | 2-(((1s,4s)-4-((4-(5-fluoropyridin-3-yl)-5-(methylthio)-3-phenyl-1H-pyrazol-1-yl)methyl)cyclohexyl)methoxy)acetic acid |
| 136 | 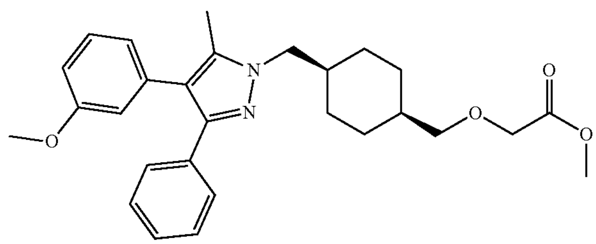 | methyl 2-(((1s,4s)-4-((4-(3-methoxyphenyl)-5-methyl-3-phenyl-1H-pyrazol-1-yl)methyl)cyclohexyl)methoxy)acetate |
| 137 | 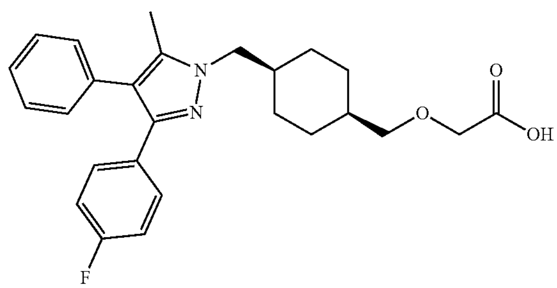 [SMILES: Cc1c(-c2ccccc2)c(-c2ccc(F)cc2)nn1C[C@H]1CC[C@@H](COCC(=O)O)CC1] | 2-(((1s,4s)-4-((3-(4-fluorophenyl)-5-methyl-4-phenyl-1H-pyrazol-1-yl)methyl)cyclohexyl)methoxy)acetic acid |
| 138 | 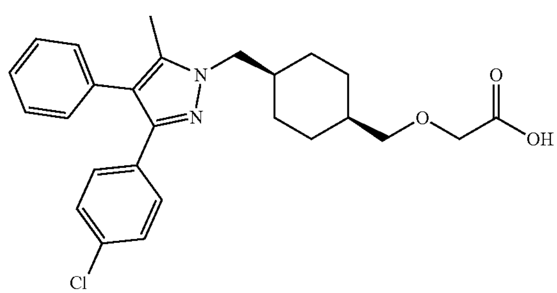 [SMILES: Cc1c(-c2ccccc2)c(-c2ccc(Cl)cc2)nn1C[C@H]1CC[C@@H](COCC(=O)O)CC1] | 2-(((1s,4s)-4-((3-(4-chlorophenyl)-5-methyl-4-phenyl-1H-pyrazol-1-yl)methyl)cyclohexyl)methoxy)acetic acid |
| 139 | 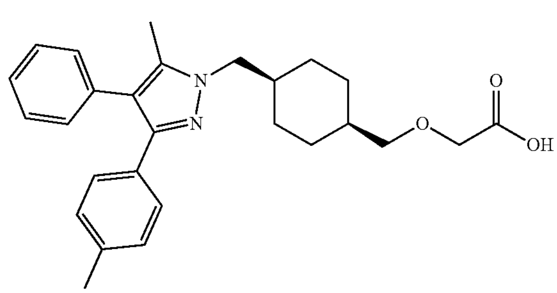 [SMILES: Cc1ccc(-c2nn(C[C@H]3CC[C@@H](COCC(=O)O)CC3)c(C)c2-c2ccccc2)cc1] | 2-(1s,4s)-4-((5-methyl-4-phenyl-3-p-tolyl-1H-pyrazol-1-yl)methyl)cyclohexyl)methoxy)acetic acid |

TABLE A-continued

| Cpd No. | Chemical Structure | Chemical Name |
|---|---|---|
| 140 | 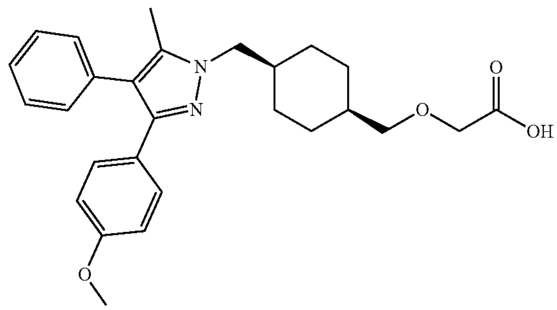 [SMILES: COc1ccc(-c2nn(C[C@H]3CC[C@@H](COCC(=O)O)CC3)c(C)c2-c2ccccc2)cc1] | 2-(((1s,4s)-4-((3-(4-methoxyphenyl)-5-methyl-4-phenyl-1H-pyrazol-1-yl)methyl)cyclohexyl)methoxy)acetic acid |
| 141 | 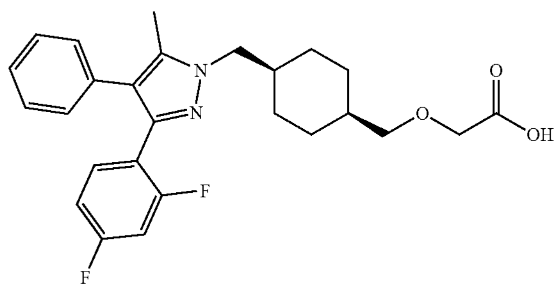 [SMILES: Cc1c(-c2ccccc2)c(-c2ccc(F)cc2F)nn1C[C@H]1CC[C@@H](COCC(=O)O)CC1] | 2-(((1s,4s)-4-((3-(2,4-difluorophenyl)-5-methyl-4-phenyl-1H-pyrazol-1-yl)methyl)cyclohexyl)methoxy)acetic acid |
| 142 | 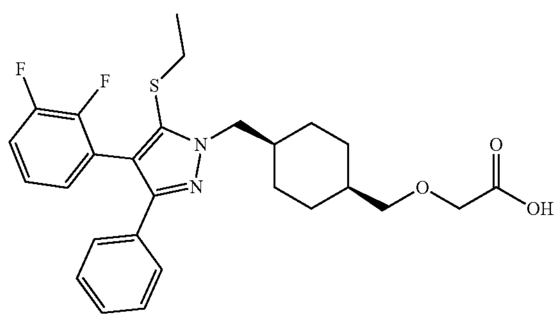 [SMILES: CCSc1c(-c2cccc(F)c2F)c(-c2ccccc2)nn1C[C@H]1CC[C@@H](COCC(=O)O)CC1] | 2-(((1s,4s)-4-((4-(2,3-difluorophenyl)-5-(ethylthio)-3-phenyl-1H-pyrazol-1-yl)methyl)cyclohexyl)methoxy)acetic acid |
| 143 | 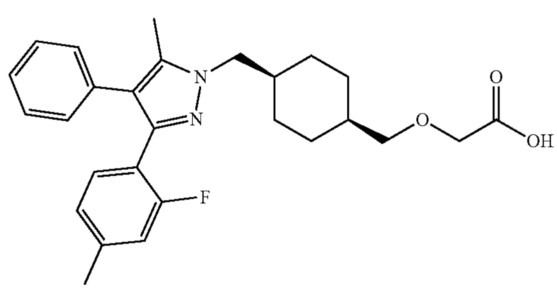 [SMILES: Cc1ccc(-c2nn(C[C@H]3CC[C@@H](COCC(=O)O)CC3)c(C)c2-c2ccccc2)c(F)c1] | 2-(((1s,4s)-4-((3-(2-fluoro-4-methylphenyl)-5-methyl-4-phenyl-1H-pyrazol-1-yl)methyl)cyclohexyl)methoxy)acetic acid |
| 144 | 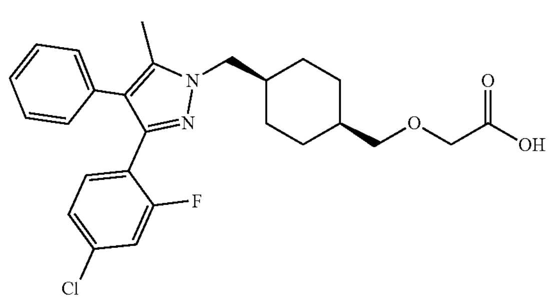 [SMILES: Cc1c(-c2ccccc2)c(-c2ccc(Cl)cc2F)nn1C[C@H]1CC[C@@H](COCC(=O)O)CC1] | 2-(((1s,4s)-4-((3-(4-chloro-2-fluorophenyl)-5-methyl-4-phenyl-1H-pyrazol-1-yl)methyl)cyclohexyl)methoxy)acetic acid |

TABLE A-continued

| Cpd No. | Chemical Structure | Chemical Name |
|---|---|---|
| 145 | 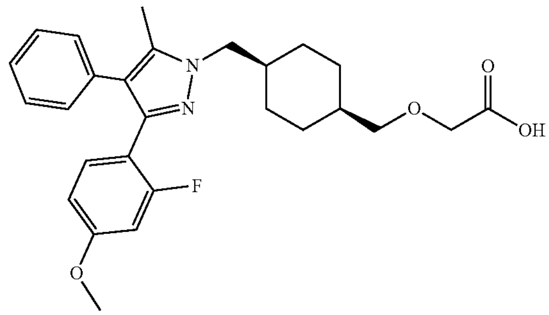 [SMILES: COc1ccc(-c2nn(C[C@H]3CC[C@@H](COCC(=O)O)CC3)c(C)c2-c2ccccc2)c(F)c1] | 2-(((1s,4s)-4-((3-(2-fluoro-4-methoxyphenyl)-5-methyl-4-phenyl-1H-pyrazol-1-yl)methyl)cyclohexyl)methoxy)acetic acid |
| 146 | 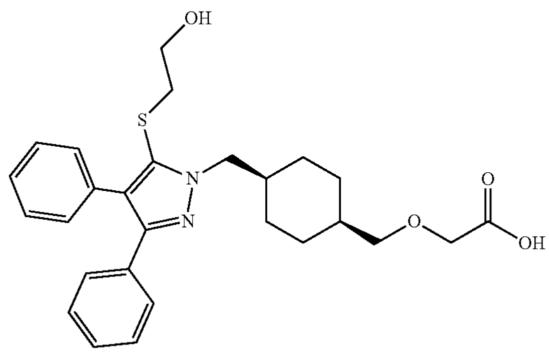 [SMILES: O=C(O)COC[C@H]1CC[C@@H](Cn2nc(-c3ccccc3)c(-c3ccccc3)c2SCCO)CC1] | 2-(((1s,4s)-4-((5-(2-hydroxyethylthio)-3,4-diphenyl-1H-pyrazol-1-yl)methyl)cyclohexyl)methoxy)acetic acid |
| 147 | 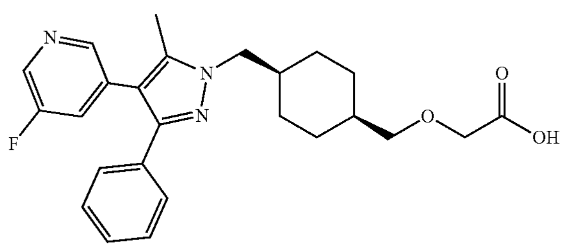 [SMILES: Cc1c(-c2cncc(F)c2)c(-c2ccccc2)nn1C[C@H]1CC[C@@H](COCC(=O)O)CC1] | 2-4(1s,4s)-4-((4-(5-fluoropyridin-3-yl)-5-methyl-3-phenyl-1H-pyrazol-1-yl)methyl)cyclohexyl)methoxy)acetic acid |
| 148 | 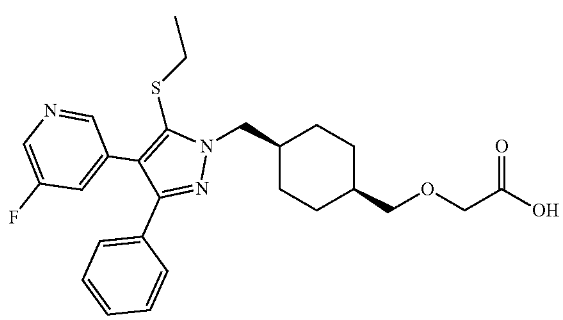 [SMILES: CCSc1c(-c2cncc(F)c2)c(-c2ccccc2)nn1C[C@H]1CC[C@@H](COCC(=O)O)CC1] | 2-(((1s,4s)-4-((5-(ethylthio)-4-(5-fluoropyridin-3-yl)-3-phenyl-1H-pyrazol-1-yl)methyl)cyclohexyl)methoxy)acetic acid |
| 149 | 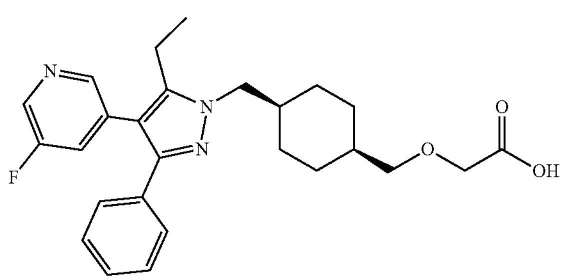 [SMILES: CCc1c(-c2cncc(F)c2)c(-c2ccccc2)nn1C[C@H]1CC[C@@H](COCC(=O)O)CC1] | 2-(((1s,4s)-4-((5-ethyl-4-(5-fluoropyridin-3-yl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 150 | 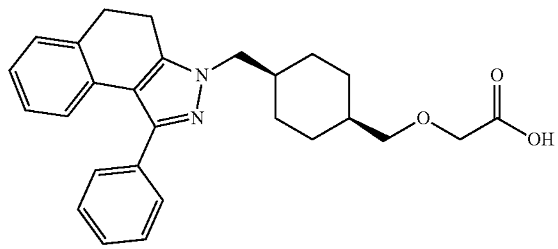 [SMILES: O=C(O)COC[C@H]1CC[C@@H](Cn2nc(-c3ccccc3)c3c2CCc2ccccc2-3)CC1] | 2-(((1s,4s)-4-((1-phenyl-4,5-dihydro-3H-benzo[e]indazol-3-yl)methyl)cyclohexyl)methoxy)acetic acid |
| 151 | 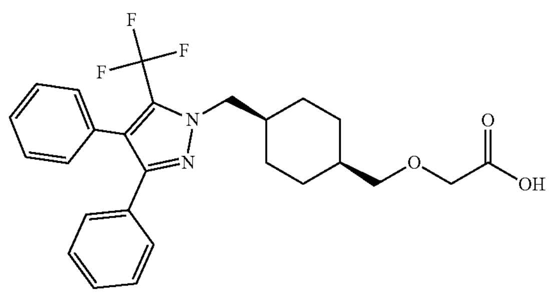 [SMILES: O=C(O)COC[C@H]1CC[C@@H](Cn2nc(-c3ccccc3)c(-c3ccccc3)c2C(F)(F)F)CC1] | 2-(((1s,4s)-4-((3,4-diphenyl-5-(trifluoromethyl)-1H-pyrazol-1-yl)methyl)cyclohexyl)methoxy)acetic acid |
| 152 | 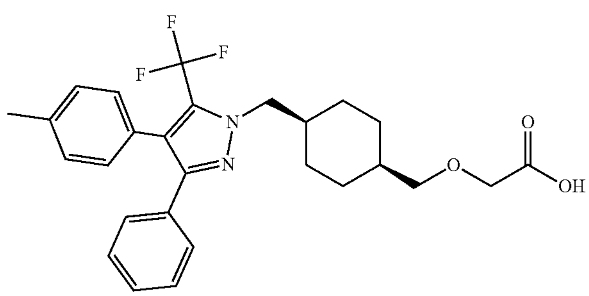 [SMILES: Cc1ccc(-c2c(-c3ccccc3)nn(C[C@H]3CC[C@@H](COCC(=O)O)CC3)c2C(F)(F)F)cc1] | 2-(((1s,4s)-4-((3-phenyl-4-p-tolyl-5-(trifluoromethyl)-1H-pyrazol-1-yl)methyl)cyclohexyl)methoxy)acetic acid |
| 153 | 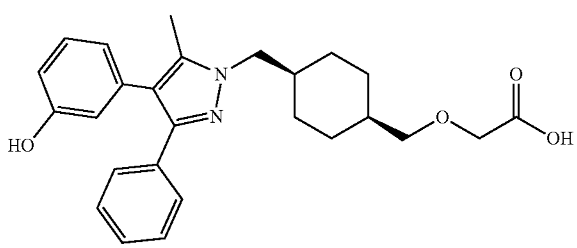 [SMILES: Cc1c(-c2cccc(O)c2)c(-c2ccccc2)nn1C[C@H]1CC[C@@H](COCC(=O)O)CC1] | 2-(1s,4s)-4-((4-(3-hydroxyphenyl)-5-methyl-3-phenyl-1H-pyrazol-1-yl)methyl)cyclohexyl)methoxy)acetic acid |
| 154 | 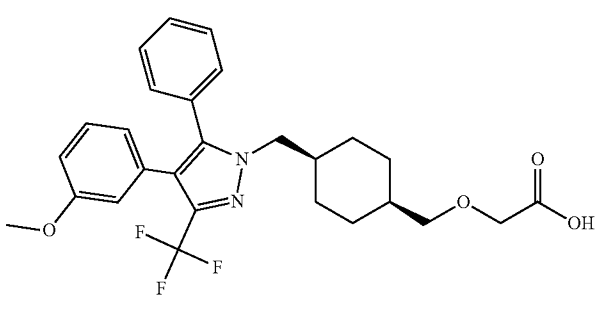 [SMILES: COc1cccc(-c2c(C(F)(F)F)nn(C[C@H]3CC[C@@H](COCC(=O)O)CC3)c2-c2ccccc2)c1] | 2-(((1s,4s)-4-((4-(3-methoxyphenyl)-5-phenyl-3-(trifluoromethyl)-1H-pyrazol-1-yl)methyl)cyclohexyl)methoxy)acetic acid |

TABLE A-continued

| Cpd No. | Chemical Structure | Chemical Name |
|---|---|---|
| 155 | 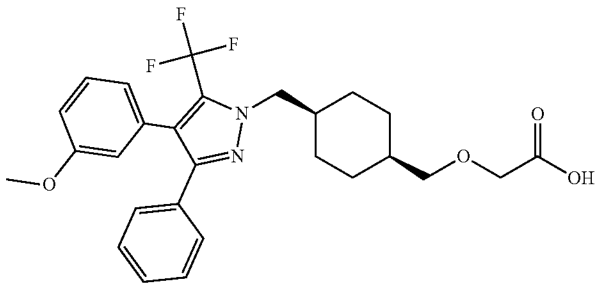 [SMILES: COc1cccc(-c2c(-c3ccccc3)nn(C[C@H]3CC[C@@H](COCC(=O)O)CC3)c2C(F)(F)F)c1] | 2-(((1s,4s)-4-((4-(3-methoxyphenyl)-3-phenyl-5-(trifluoromethyl)-1H-pyrazol-1-yl)methyl)cyclohexyl)methoxy)acetic acid |
| 156 | 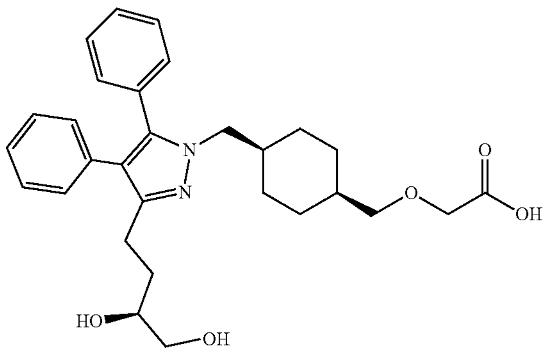 [SMILES: O=C(O)COC[C@H]1CC[C@@H](Cn2nc(CC[C@H](O)CO)c(-c3ccccc3)c2-c2ccccc2)CC1] | 2-(((1R,4s)-4-((3-((S)-3,4-dihydroxybutyl)-4,5-diphenyl-1H-pyrazol-1-yl)methyl)cyclohexyl)methoxy)acetic acid |
| 157 | 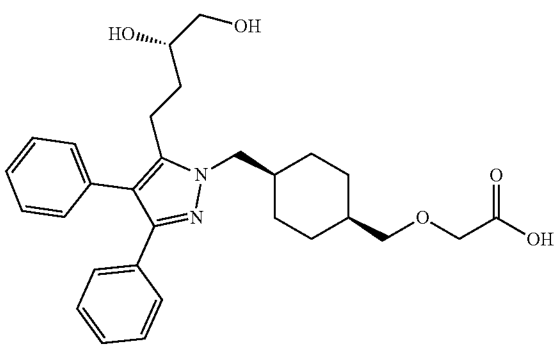 [SMILES: O=C(O)COC[C@H]1CC[C@@H](Cn2nc(-c3ccccc3)c(-c3ccccc3)c2CC[C@H](O)CO)CC1] | 2-(((1R,4s)-4-((5-((S)-3,4-dihydroxybutyl)-3,4-diphenyl-1H-pyrazol-1-yl)methyl)cyclohexyl)methoxy)acetic acid |
| 158 | 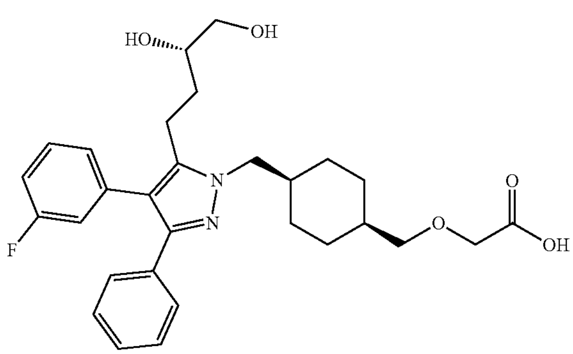 [SMILES: O=C(O)COC[C@H]1CC[C@@H](Cn2nc(-c3ccccc3)c(-c3cccc(F)c3)c2CC[C@H](O)CO)CC1] | 2-(((1R,4s)-4-((5-((S)-3,4-dihydroxybutyl)-4-(3-fluorophenyl)-3-phenyl-1H-pyrazol-1-yl)methyl)cyclohexyl)methoxy)acetic acid |

| Cpd No. | Chemical Structure | Chemical Name |
|---|---|---|
| 159 | 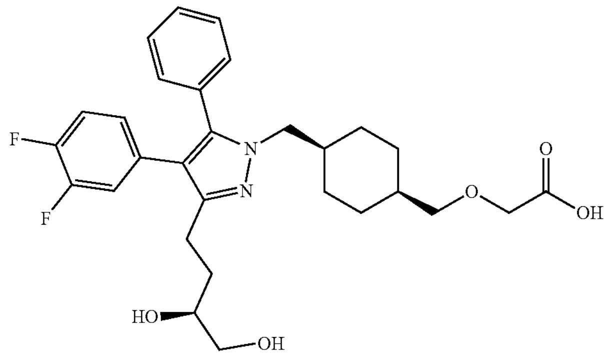 [SMILES: O=C(O)COC[C@H]1CC[C@@H](Cn2nc(CC[C@H](O)CO)c(-c3ccc(F)c(F)c3)c2-c2ccccc2)CC1] | 2-(((1R,4s)-4-((4-(3,4-difluorophenyl)-3-((S)-3,4-dihydroxybutyl)-5-phenyl-1H-pyrazol-1-yl)methyl)cyclohexyl)methoxy)acetic acid |
| 160 | 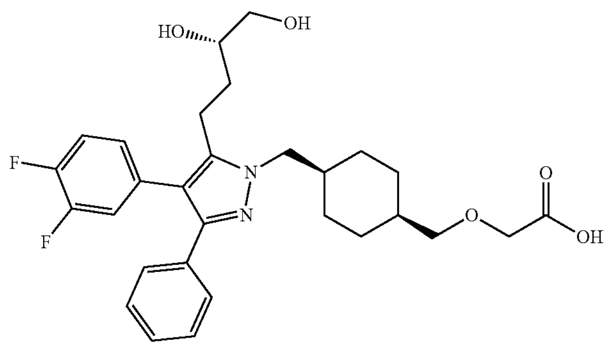 [SMILES: O=C(O)COC[C@H]1CC[C@@H](Cn2nc(-c3ccccc3)c(-c3ccc(F)c(F)c3)c2CC[C@H](O)CO)CC1] | 2-(((1R,4s)-4-((4-(3,4-difluorophenyl)-5-((S)-3,4-dihydroxybutyl)-3-phenyl-1H-pyrazol-1-yl)methyl)cyclohexyl)methoxy)acetic acid |
| 161 | 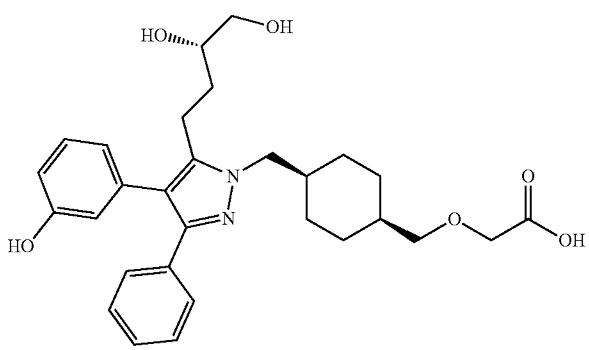 [SMILES: O=C(O)COC[C@H]1CC[C@@H](Cn2nc(-c3ccccc3)c(-c3cccc(O)c3)c2CC[C@H](O)CO)CC1] | 2-(((1R,4s)-4-((5-((S)-3,4-dihydroxybutyl)-4-(3-hydroxyphenyl)-3-phenyl-1H-pyrazol-1-yl)methyl)cyclohexyl)methoxy)acetic acid |
| 162 | 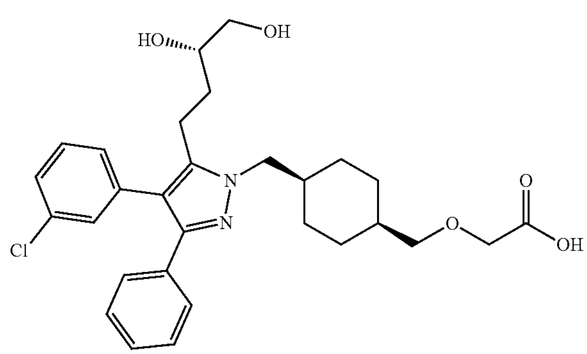 [SMILES: O=C(O)COC[C@H]1CC[C@@H](Cn2nc(-c3ccccc3)c(-c3cccc(Cl)c3)c2CC[C@H](O)CO)CC1] | 2-(((1R,4s)-4-((4-(3-chlorophenyl)-5-((S)-3,4-dihydroxybutyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 163 | 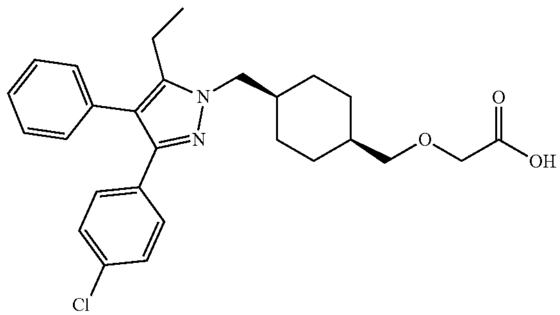 [SMILES: CCc1c(-c2ccccc2)c(-c2ccc(Cl)cc2)nn1C[C@H]1CC[C@@H](COCC(=O)O)CC1] | 2-(((1s,4s)-4-((3-(4-chlorophenyl)-5-ethyl-4-phenyl-1H-pyrazol-1-yl)methyl)cyclohexyl)methoxy)acetic acid |
| 164 | 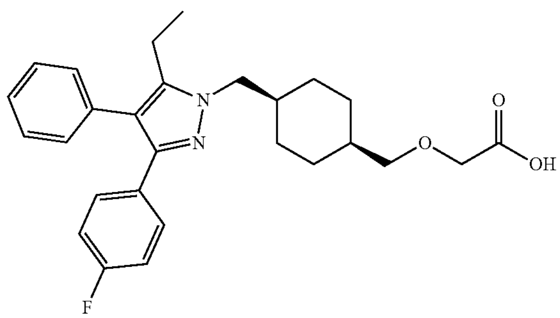 [SMILES: CCc1c(-c2ccccc2)c(-c2ccc(F)cc2)nn1C[C@H]1CC[C@@H](COCC(=O)O)CC1] | 2-(((1s,4s)-4-((5-ethyl-3-(4-fluorophenyl)-4-phenyl-1H-pyrazol-1-yl)methyl)cyclohexyl)methoxy)acetic acid |
| 165 | 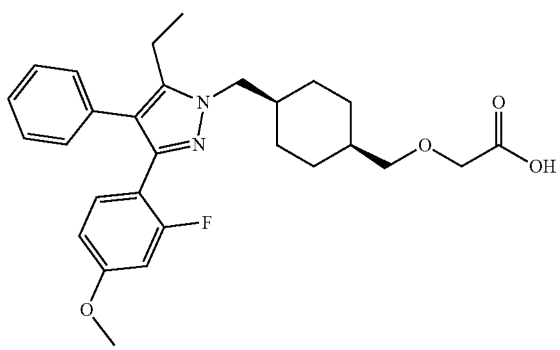 [SMILES: CCc1c(-c2ccccc2)c(-c2ccc(OC)cc2F)nn1C[C@H]1CC[C@@H](COCC(=O)O)CC1] | 2-(((1s,4s)-4-((5-ethyl-3-(2-fluoro-4-methoxyphenyl)-4-phenyl-1H-pyrazol-1-yl)methyl)cyclohexyl)methoxy)acetic acid |
| 166 | 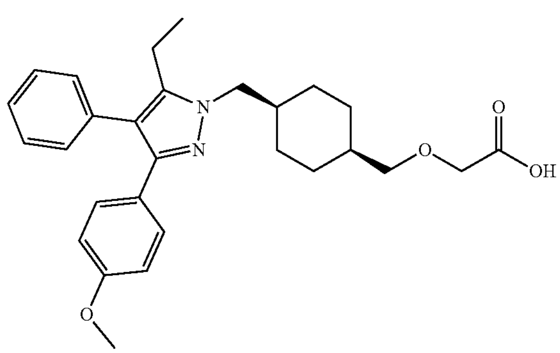 [SMILES: CCc1c(-c2ccccc2)c(-c2ccc(OC)cc2)nn1C[C@H]1CC[C@@H](COCC(=O)O)CC1] | 2-(((1s,4s)-4-((5-ethyl-3-(4-methoxyphenyl)-4-phenyl-1H-pyrazol-1-yl)methyl)cyclohexyl)methoxy)acetic acid |

TABLE A-continued

| Cpd No. | Chemical Structure | Chemical Name |
|---|---|---|
| 167 | 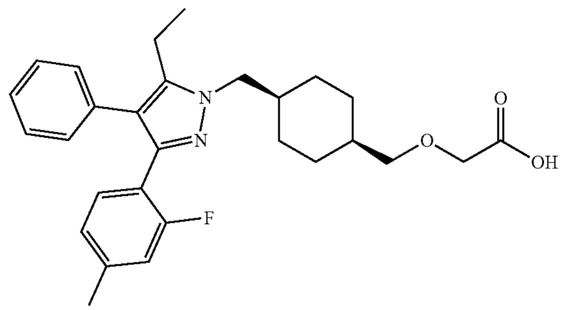 [SMILES: CCc1c(-c2ccccc2)c(-c2ccc(C)cc2F)nn1C[C@H]1CC[C@@H](COCC(=O)O)CC1] | 2-(((1s,4s)-4-((5-ethyl-3-(2-fluoro-4-methylphenyl)-4-phenyl-1H-pyrazol-1-yl)methyl)cyclohexyl)methoxy)acetic acid |
| 168 | 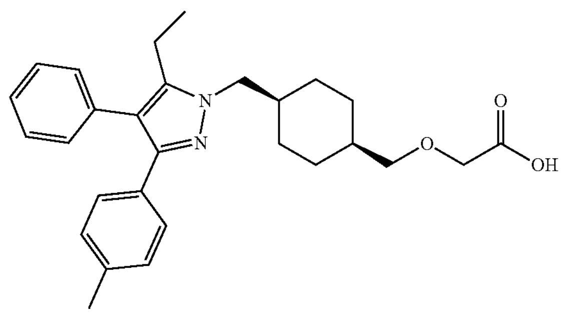 [SMILES: CCc1c(-c2ccccc2)c(-c2ccc(C)cc2)nn1C[C@H]1CC[C@@H](COCC(=O)O)CC1] | 2-(((1s,4s)-4-((5-ethyl-4-phenyl-3-p-tolyl-1H-pyrazol-1-yl)methyl)cyclohexyl)methoxy)acetic acid |
| 169 | 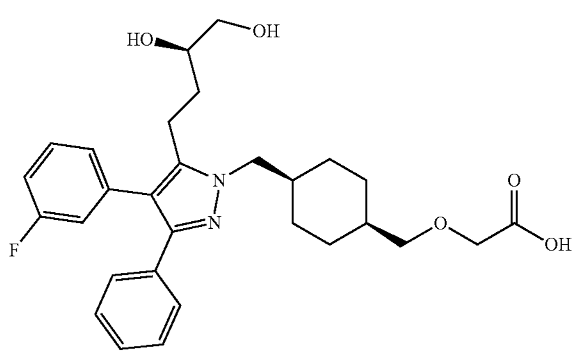 [SMILES: O=C(O)COC[C@H]1CC[C@@H](Cn2nc(-c3ccccc3)c(-c3cccc(F)c3)c2CC[C@@H](O)CO)CC1] | 2-(((1S,4s)-4-((5-((R)-3,4-dihydroxybutyl)-4-(3-fluorophenyl)-3-phenyl-1H-pyrazol-1-yl)methyl)cyclohexyl)methoxy)acetic acid |
| 170 | 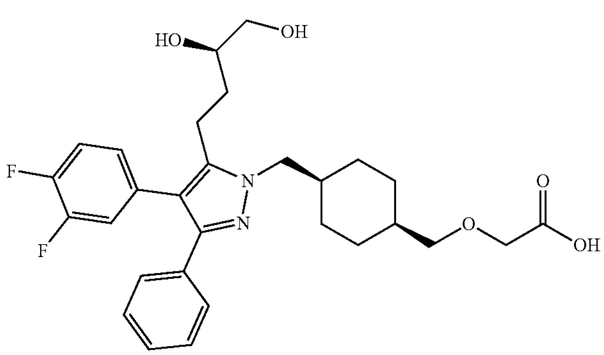 [SMILES: O=C(O)COC[C@H]1CC[C@@H](Cn2nc(-c3ccccc3)c(-c3ccc(F)c(F)c3)c2CC[C@@H](O)CO)CC1] | 2-(((1S,4s)-4-((4-(3,4-difluorophenyl)-5-((R)-3,4-dihydroxybutyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 171 | 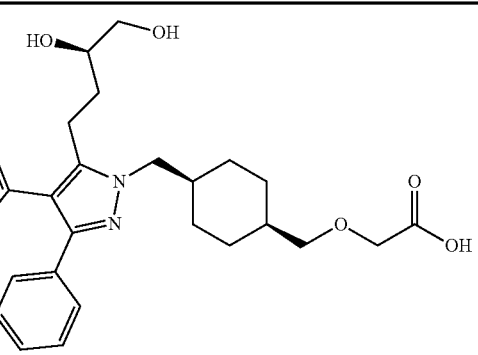 | 2-(((1S,4s)-4-((4-(3-chlorophenyl)-5-((R)-3,4-dihydroxybutyl)-3-phenyl-1H-pyrazol-1-yl)methyl)cyclohexyl)methoxy)acetic acid |
| 172 | 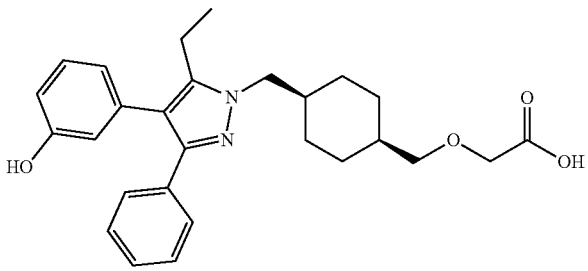 | 2-(((1s,4s)-4-((5-ethyl-4-(3-hydroxyphenyl)-3-phenyl-1H-pyrazol-1-yl)methyl)cyclohexyl)methoxy)acetic acid |
| 173 | 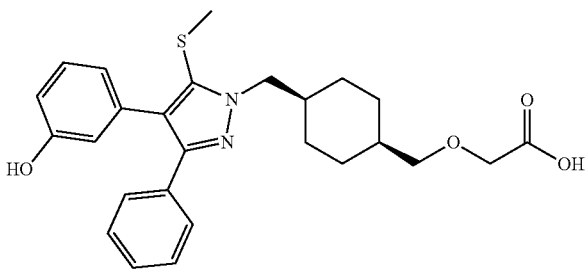 [SMILES: CSc1c(-c2cccc(O)c2)c(-c2ccccc2)nn1C[C@H]1CC[C@@H](COCC(=O)O)CC1] | 2-(((1s,4s)-4-((4-(3-hydroxyphenyl)-5-(methylthio)-3-phenyl-1H-pyrazol-1-yl)methyl)cyclohexyl)methoxy)acetic acid |
| 174 | 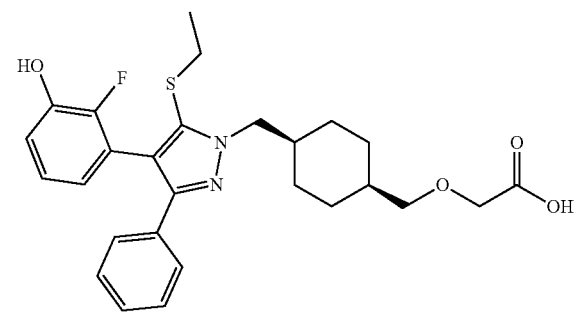 [SMILES: CCSc1c(-c2cccc(O)c2F)c(-c2ccccc2)nn1C[C@H]1CC[C@@H](COCC(=O)O)CC1] | 2-(((1s,4s)-4-((5-(ethylthio)-4-(2-fluoro-3-hydroxyphenyl)-3-phenyl-1H-pyrazol-1-yl)methyl)cyclohexyl)methoxy)acetic acid |
| 175 | 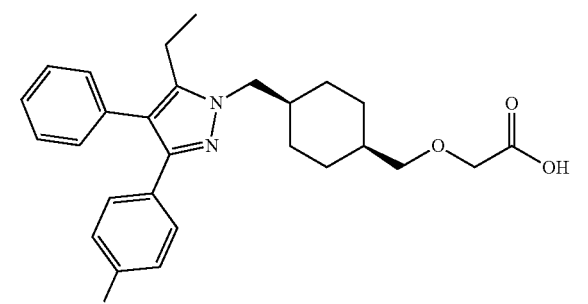 | 2-(((1s,4s)-4-((5-ethyl-3-(4-hydroxyphenyl)-4-phenyl-1H-pyrazol-1-yl)methyl)cyclohexyl)methoxy)acetic acid |

TABLE A-continued

| Cpd No. | Chemical Structure | Chemical Name |
|---|---|---|
| 176 | 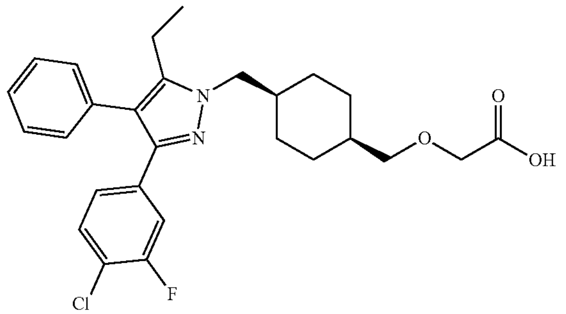 [SMILES: CCc1c(-c2ccccc2)c(-c2ccc(Cl)c(F)c2)nn1C[C@H]1CC[C@@H](COCC(=O)O)CC1] | 2-(((1s,4s)-4-((3-(4-chloro-3-fluorophenyl)-5-ethyl-4-phenyl-1H-pyrazol-1-yl)methyl)cyclohexyl)methoxy)acetic acid |
| 177 | 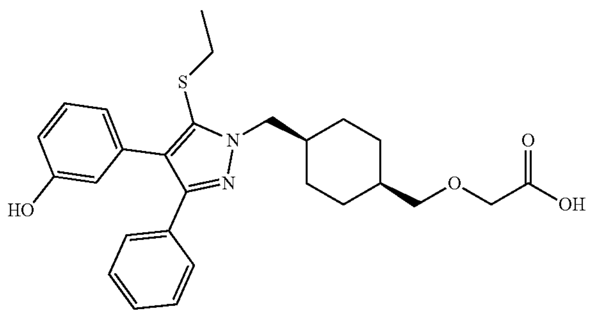 [SMILES: CCSc1c(-c2cccc(O)c2)c(-c2ccccc2)nn1C[C@H]1CC[C@@H](COCC(=O)O)CC1] | 2-(((1s,4s)4-((5-(ethylthio)-4-(3-hydroxyphenyl)-3-phenyl-1H-pyrazol-1-yl)methyl)cyclohexyl)methoxy)acetic acid |
| 178 | 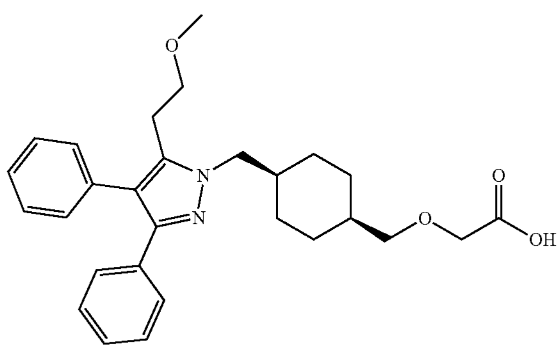 [SMILES: COCCc1c(-c2ccccc2)c(-c2ccccc2)nn1C[C@H]1CC[C@@H](COCC(=O)O)CC1] | 2-(((1s,4s)-4-((5-(2-methoxyethyl)-3,4-diphenyl-1H-pyrazol-1-yl)methyl)cyclohexyl)methoxy)acetic acid |
| 179 | 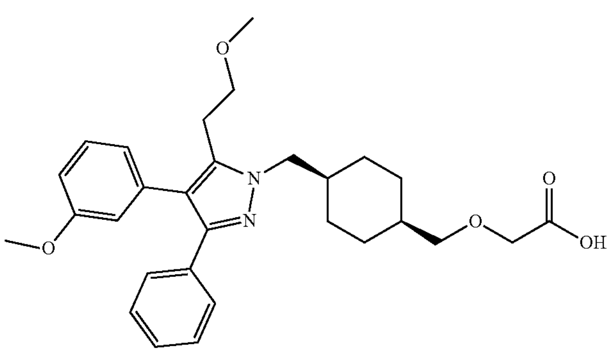 [SMILES: COCCc1c(-c2cccc(OC)c2)c(-c2ccccc2)nn1C[C@H]1CC[C@@H](COCC(=O)O)CC1] | 2-(((1s,4s)-4-((5-(2-methoxyethyl)-4-(3-methoxyphenyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 180 | 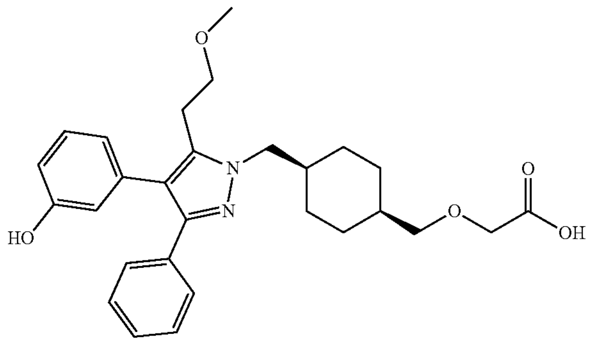 [SMILES: COCCc1c(-c2cccc(O)c2)c(-c2ccccc2)nn1C[C@H]1CC[C@@H](COCC(=O)O)CC1] | 2-(((1s,4s)-4-((4-(3-hydroxyphenyl)-5-(2-methoxyethyl)-3-phenyl-1H-pyrazol-1-yl)methyl)cyclohexyl)methoxy)acetic acid |
| 181 | 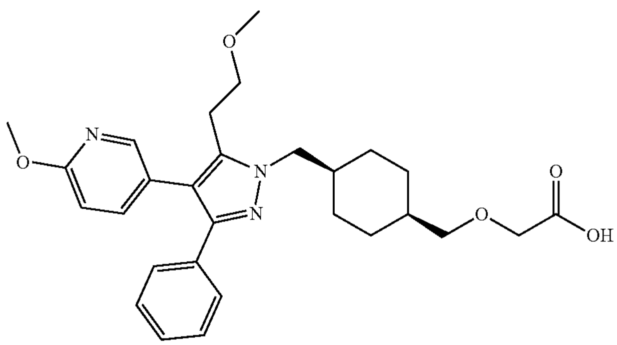 [SMILES: COCCc1c(-c2ccc(OC)nc2)c(-c2ccccc2)nn1C[C@H]1CC[C@@H](COCC(=O)O)CC1] | 2-(((1s,4s)-4-((5-(2-methoxyethyl)-4-(6-methoxypyridin-3-yl)-3-phenyl-1H-pyrazol-1-yl)methyl)cyclohexyl)methoxy)acetic acid |
| 182 | 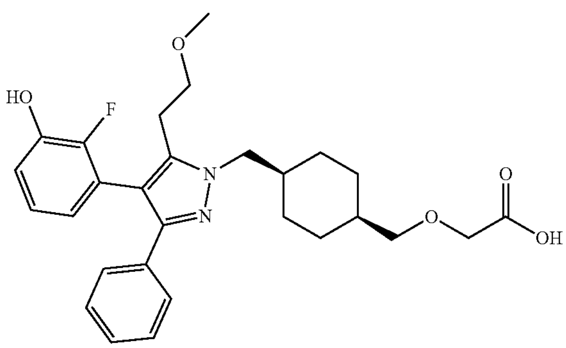 [SMILES: COCCc1c(-c2cccc(O)c2F)c(-c2ccccc2)nn1C[C@H]1CC[C@@H](COCC(=O)O)CC1] | 2-(((1s,4s)-4-((4-(2-fluoro-3-hydroxyphenyl)-5-(2-methoxyethyl)-3-phenyl-1H-pyrazol-1-yl)methyl)cyclohexyl)methoxy)acetic acid |
| 183 | 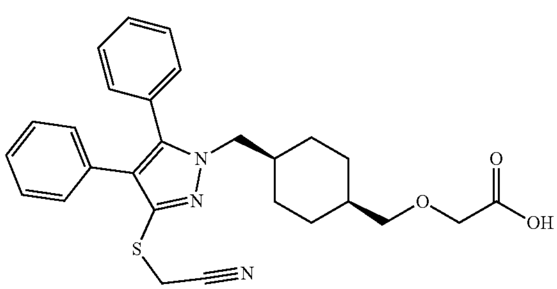 [SMILES: N#CCSc1nn(C[C@H]2CC[C@@H](COCC(=O)O)CC2)c(-c2ccccc2)c1-c1ccccc1] | 2-(((1s,4s)-4-((3-(cyanomethylthio)-4,5-diphenyl-1H-pyrazol-1-yl)methyl)cyclohexyl)methoxy)acetic acid |

TABLE A-continued

| Cpd No. | Chemical Structure | Chemical Name |
|---|---|---|
| 184 | 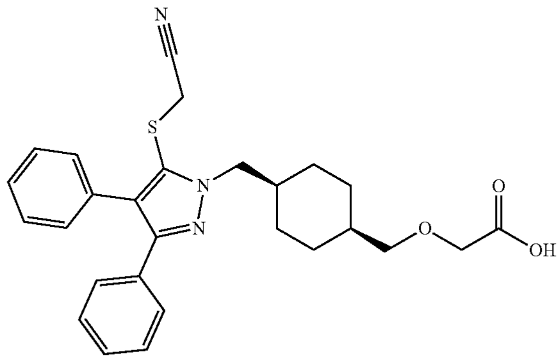 [SMILES: N#CCSc1c(-c2ccccc2)c(-c2ccccc2)nn1C[C@H]1CC[C@@H](COCC(=O)O)CC1] | 2-(((1s,4s)-4-((5-(cyanomethylthio)-3,4-diphenyl-1H-pyrazol-1-yl)methyl)cyclohexyl)methoxy)acetic acid |
| 185 | 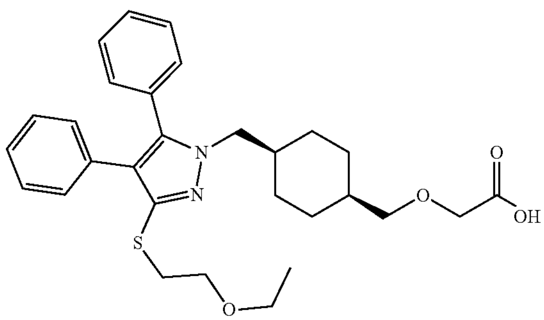 [SMILES: CCOCCSc1nn(C[C@H]2CC[C@@H](COCC(=O)O)CC2)c(-c2ccccc2)c1-c1ccccc1] | 2-(((1s,4s)-4-((3-(2-ethoxyethylthio)-4,5-diphenyl-1H-pyrazol-1-yl)methyl)cyclohexyl)methoxy)acetic acid |
| 186 | 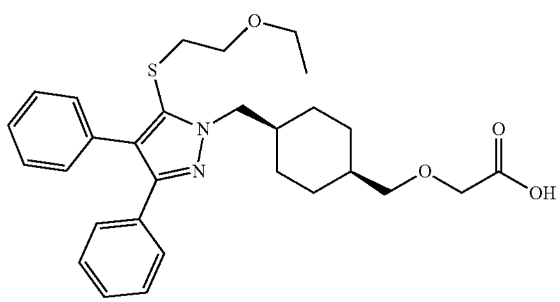 [SMILES: CCOCCSc1c(-c2ccccc2)c(-c2ccccc2)nn1C[C@H]1CC[C@@H](COCC(=O)O)CC1] | 2-(((1s,4s)-4-((5-(2-ethoxyethylthio)-3,4-diphenyl-1H-pyrazol-1-yl)methyl)cyclohexyl)methoxy)acetic acid |
| 187 | 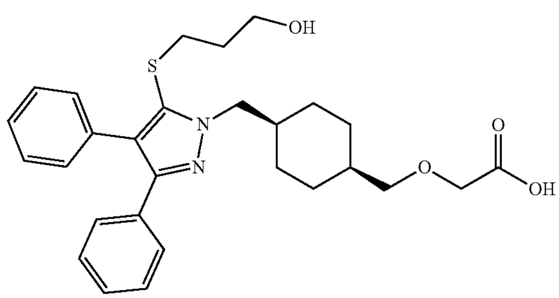 [SMILES: O=C(O)COC[C@H]1CC[C@@H](Cn2nc(-c3ccccc3)c(-c3ccccc3)c2SCCCO)CC1] | 2-(((1s,4s)-4-((5-(3-hydroxypropylthio)-3,4-diphenyl-1H-pyrazol-1-yl)methyl)cyclohexyl)methoxy)acetic acid |
| 188 | 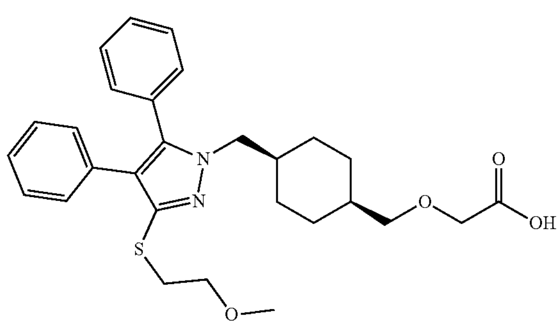 [SMILES: COCCSc1nn(C[C@H]2CC[C@@H](COCC(=O)O)CC2)c(-c2ccccc2)c1-c1ccccc1] | 2-(((1s,4s)-4-((3-(2-methoxyethylthio)-4,5-diphenyl-1H-pyrazol-1-yl)methyl)cyclohexyl)methoxy)acetic acid |

TABLE A-continued

| Cpd No. | Chemical Structure | Chemical Name |
|---|---|---|
| 189 | 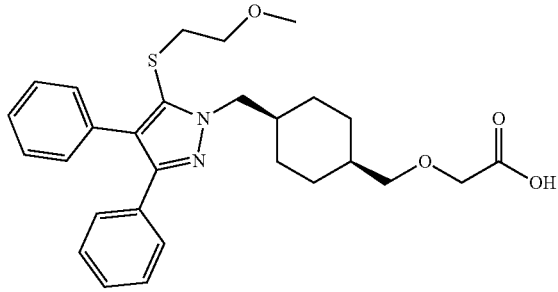 [SMILES: COCCSc1c(-c2ccccc2)c(-c2ccccc2)nn1C[C@H]1CC[C@@H](COCC(=O)O)CC1] | 2-(((1s,4s)-4-((5-(2-methoxyethylthio)-3,4-diphenyl-1H-pyrazol-1-yl)methyl)cyclohexyl)methoxy)acetic acid |
| 190 | 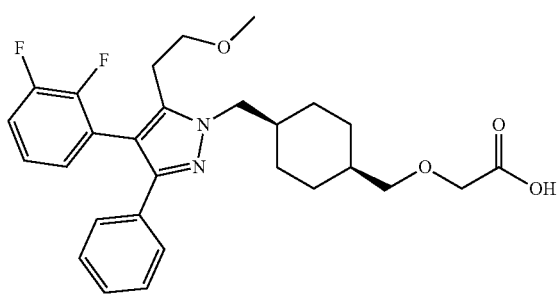 [SMILES: COCCc1c(-c2cccc(F)c2F)c(-c2ccccc2)nn1C[C@H]1CC[C@@H](COCC(=O)O)CC1] | 2-(((1s,4s)-4-((4-(2,3-difluorophenyl)-5-(2-methoxyethyl)-3-phenyl-1H-pyrazol-1-yl)methyl)cyclohexyl)methoxy)acetic acid |
| 191 | 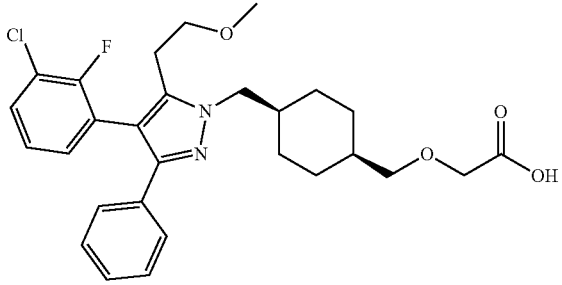 [SMILES: COCCc1c(-c2cccc(Cl)c2F)c(-c2ccccc2)nn1C[C@H]1CC[C@@H](COCC(=O)O)CC1] | 2-(((1s,4s)-4-((4-(3-chloro-2-fluorophenyl)-5-(2-methoxyethyl)-3-phenyl-1H-pyrazol-1-yl)methyl)cyclohexyl)methoxy)acetic acid |
| 192 | 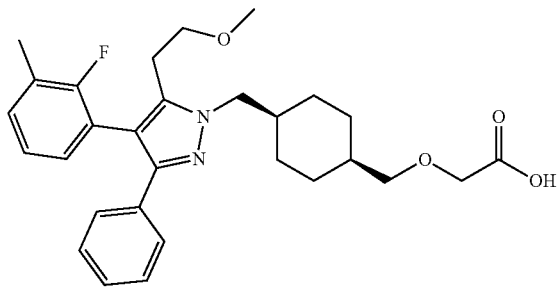 | 2-(((1s,4s)-4-((4-(2-fluoro-3-methylphenyl)-5-(2-methoxyethyl)-3-phenyl-1H-pyrazol-1-yl)methyl)cyclohexyl)methoxy)acetic acid |
| 193 | 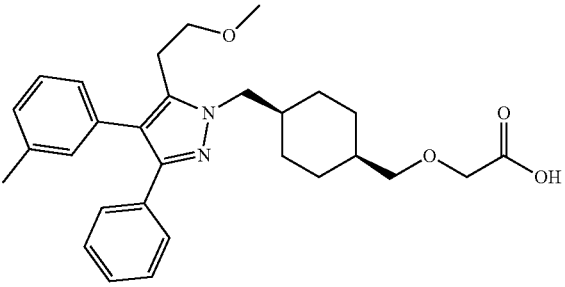 [SMILES: COCCc1c(-c2cccc(C)c2)c(-c2ccccc2)nn1C[C@H]1CC[C@@H](COCC(=O)O)CC1] | 2-(((1s,4s)-4-((5-(2-methoxyethyl)-3-phenyl-4-m-tolyl-1H-pyrazol-1-yl)methyl)cyclohexyl)methoxy)acetic acid |

TABLE A-continued

| Cpd No. | Chemical Structure | Chemical Name |
|---|---|---|
| 194 | 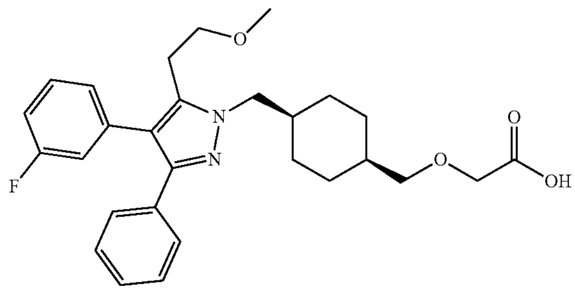 [SMILES: COCCc1c(-c2cccc(F)c2)c(-c2ccccc2)nn1C[C@H]1CC[C@@H](COCC(=O)O)CC1] | 2-(((1s,4s)-4-((4-(3-fluorophenyl)-5-(2-methoxyethyl)-3-phenyl-1H-pyrazol-1-yl)methyl)cyclohexyl)methoxy)acetic acid |
| 195 | 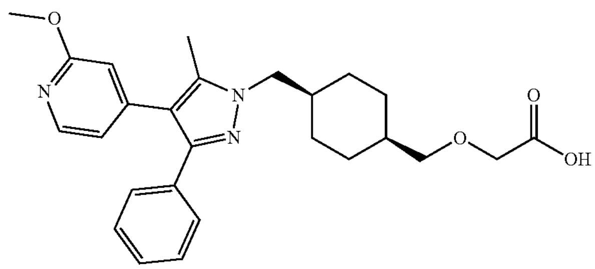 [SMILES: COc1cc(-c2c(-c3ccccc3)nn(C[C@H]3CC[C@@H](COCC(=O)O)CC3)c2C)ccn1] | 2-(((1s,4s)-4-((4-(2-methoxypyridin-4-yl)-5-methyl-3-phenyl-1H-pyrazol-1-yl)methyl)cyclohexyl)methoxy)acetic acid |
| 196 | 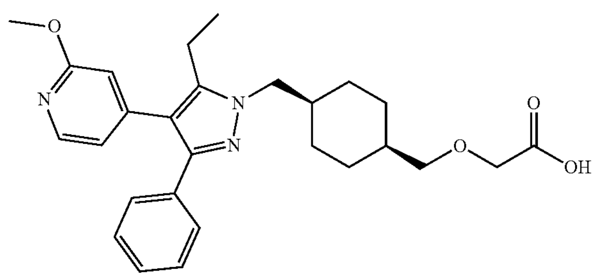 [SMILES: CCc1c(-c2ccnc(OC)c2)c(-c2ccccc2)nn1C[C@H]1CC[C@@H](COCC(=O)O)CC1] | 2-(((1s,4s)-4-((5-ethyl-4-(2-methoxypyridin-4-yl)-3-phenyl-1H-pyrazol-1-yl)methyl)cyclohexyl)methoxy)acetic acid |
| 197 | 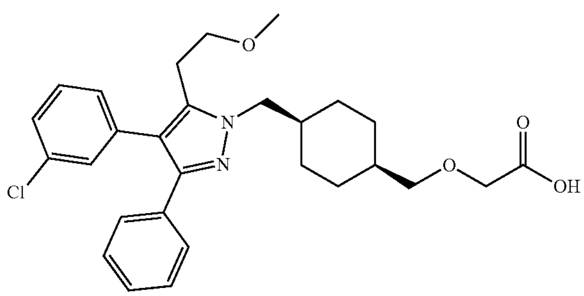 [SMILES: COCCc1c(-c2cccc(Cl)c2)c(-c2ccccc2)nn1C[C@H]1CC[C@@H](COCC(=O)O)CC1] | 2-(((1s,4s)-4-((4-(3-chlorophenyl)-5-(2-methoxyethyl)-3-phenyl-1H-pyrazol-1-yl)methyl)cyclohexyl)methoxy)acetic acid |
| 198 | 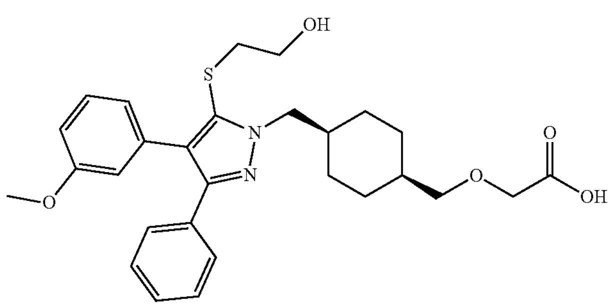 [SMILES: COc1cccc(-c2c(-c3ccccc3)nn(C[C@H]3CC[C@@H](COCC(=O)O)CC3)c2SCCO)c1] | 2-(((1s,4s)-4-((5-(2-hydroxyethylthio)-4-(3-methoxyphenyl)-3-phenyl-1H-pyrazol-1-yl)methyl)cyclohexyl)methoxy)acetic acid |

TABLE A-continued

| Cpd No. | Chemical Structure | Chemical Name |
| --- | --- | --- |
| 199 | 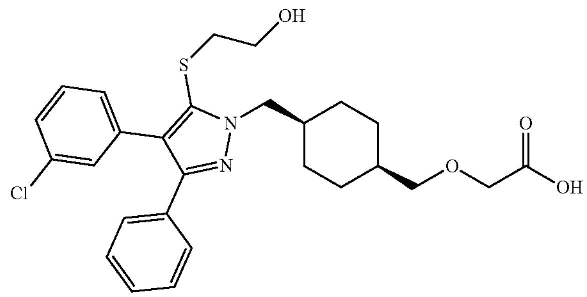 [SMILES: O=C(O)COC[C@H]1CC[C@@H](Cn2nc(-c3ccccc3)c(-c3cccc(Cl)c3)c2SCCO)CC1] | 2-(((1s,4s)-4-((4-(3-chlorophenyl)-5-(2-hydroxyethylthio)-3-phenyl-1H-pyrazol-1-yl)methyl)cyclohexyl)methoxy)acetic acid |
| 200 | 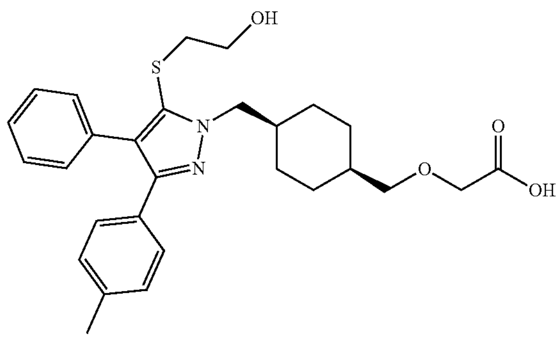 [SMILES: Cc1ccc(-c2nn(C[C@H]3CC[C@@H](COCC(=O)O)CC3)c(SCCO)c2-c2ccccc2)cc1] | 2-(((1s,4s)-4-((5-(2-hydroxyethylthio)-4-phenyl-3-p-tolyl-1H-pyrazol-1-yl)methyl)cyclohexyl)methoxy)acetic acid |
| 201 | 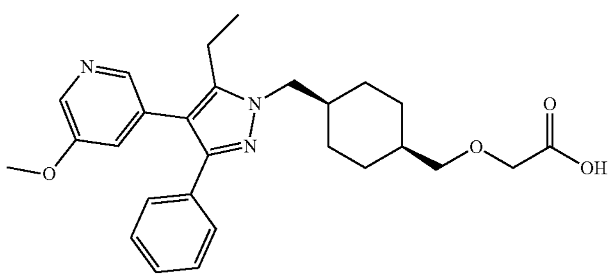 [SMILES: CCc1c(-c2cncc(OC)c2)c(-c2ccccc2)nn1C[C@H]1CC[C@@H](COCC(=O)O)CC1] | 2-(((1s,4s)-4-((5-ethyl-4-(5-methoxypyridin-3-yl)-3-phenyl-1H-pyrazol-1-yl)methyl)cyclohexyl)methoxy)acetic acid |
| 202 | 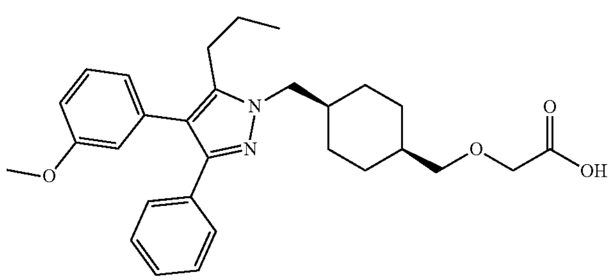 [SMILES: CCCc1c(-c2cccc(OC)c2)c(-c2ccccc2)nn1C[C@H]1CC[C@@H](COCC(=O)O)CC1] | 2-(((1s,4s)-4-((4-(3-methoxyphenyl)-3-phenyl-5-propyl-1H-pyrazol-1-yl)methyl)cyclohexyl)methoxy)acetic acid |
| 203 | 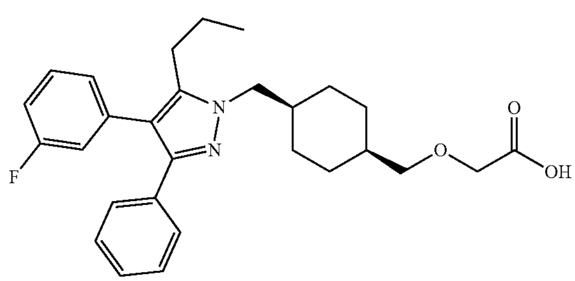 [SMILES: CCCc1c(-c2cccc(F)c2)c(-c2ccccc2)nn1C[C@H]1CC[C@@H](COCC(=O)O)CC1] | 2-(((1s,4s)-4-((4-(3-fluorophenyl)-3-phenyl-5-propyl-1H-pyrazol-1-yl)methyl)cyclohexyl)methoxy)acetic acid |

TABLE A-continued

| Cpd No. | Chemical Structure | Chemical Name |
|---|---|---|
| 204 | 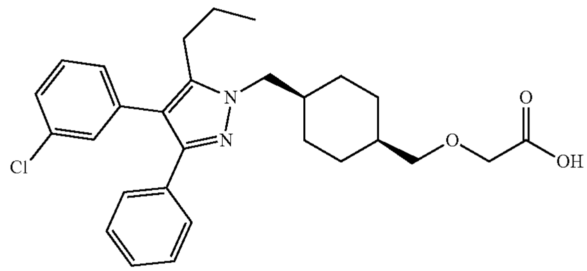 [SMILES: CCCc1c(-c2cccc(Cl)c2)c(-c2ccccc2)nn1C[C@H]1CC[C@@H](COCC(=O)O)CC1] | 2-(((1s,4s)-4-((4-(3-chlorophenyl)-3-phenyl-5-propyl-1H-pyrazol-1-yl)methyl)cyclohexyl)methoxy)acetic acid |
| 205 | 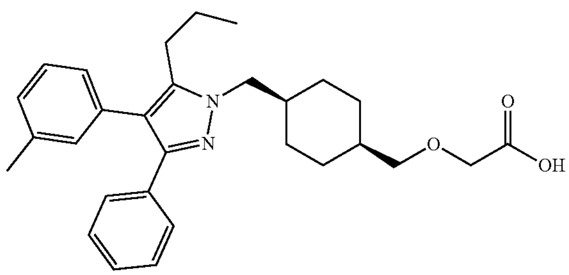 [SMILES: CCCc1c(-c2cccc(C)c2)c(-c2ccccc2)nn1C[C@H]1CC[C@@H](COCC(=O)O)CC1] | 2-(((1s,4s)-4-((3-phenyl-5-propyl-4-m-tolyl-1H-pyrazol-1-yl)methyl)cyclohexyl)methoxy)acetic acid |
| 206 | 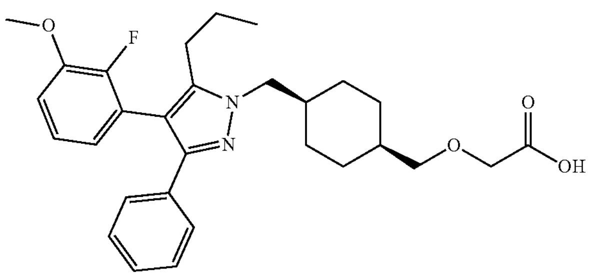 [SMILES: CCCc1c(-c2cccc(OC)c2F)c(-c2ccccc2)nn1C[C@H]1CC[C@@H](COCC(=O)O)CC1] | 2-(((1s,4s)-4-((4-(2-fluoro-3-methoxyphenyl)-3-phenyl-5-propyl-1H-pyrazol-1-yl)methyl)cyclohexyl)methoxy)acetic acid |
| 207 | 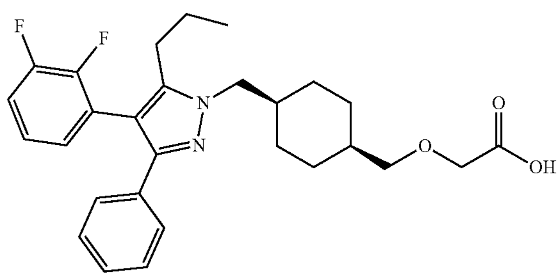 [SMILES: CCCc1c(-c2cccc(F)c2F)c(-c2ccccc2)nn1C[C@H]1CC[C@@H](COCC(=O)O)CC1] | 2-(((1s,4s)-4-((4-(2,3-difluorophenyl)-3-phenyl-5-propyl-1H-pyrazol-1-yl)methyl)cyclohexyl)methoxy)acetic acid |
| 208 | 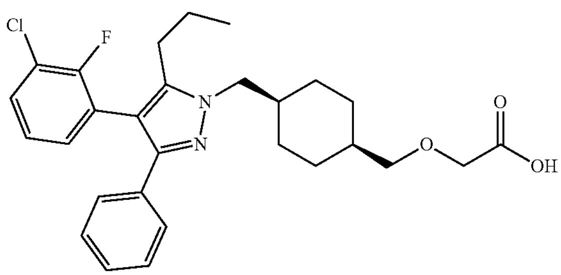 [SMILES: CCCc1c(-c2cccc(Cl)c2F)c(-c2ccccc2)nn1C[C@H]1CC[C@@H](COCC(=O)O)CC1] | 2-(((1s,4s)-4-((4-(3-chloro-2-fluorophenyl)-3-phenyl-5-propyl-1H-pyrazol-1-yl)methyl)cyclohexyl)methoxy)acetic acid |

TABLE A-continued

| Cpd No. | Chemical Structure | Chemical Name |
|---|---|---|
| 209 | 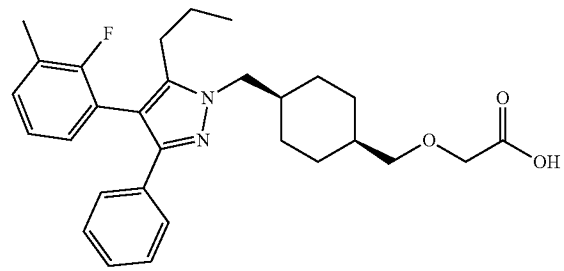 [SMILES: CCCc1c(-c2cccc(C)c2F)c(-c2ccccc2)nn1C[C@H]1CC[C@@H](COCC(=O)O)CC1] | 2-(1s,4s)-4-((4-(2-fluoro-3-methylphenyl)-3-phenyl-5-propyl-1H-pyrazol-1-yl)methyl)cyclohexyl)methoxy)acetic acid |
| 210 | 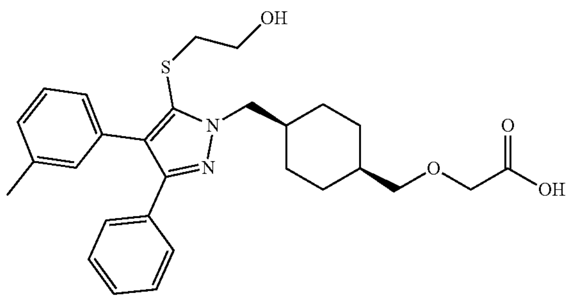 [SMILES: Cc1cccc(-c2c(-c3ccccc3)nn(C[C@H]3CC[C@@H](COCC(=O)O)CC3)c2SCCO)c1] | 2-(((1s,4s)-4-((5-(2-hydroxyethylthio)-3-phenyl-4-m-tolyl-1H-pyrazol-1-yl)methyl)cyclohexyl)methoxy)acetic acid |
| 211 | 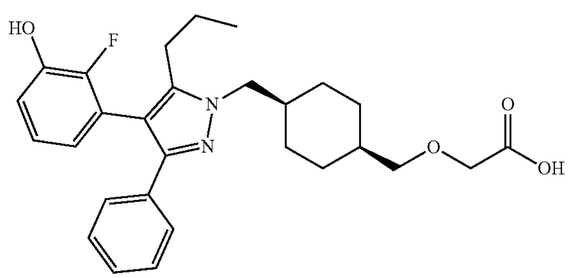 [SMILES: CCCc1c(-c2cccc(O)c2F)c(-c2ccccc2)nn1C[C@H]1CC[C@@H](COCC(=O)O)CC1] | 2-(((1s,4s)-4-((4-(2-fluoro-3-hydroxyphenyl)-3-phenyl-5-propyl-1H-pyrazol-1-yl)methyl)cyclohexyl)methoxy)acetic acid |
| 212 | 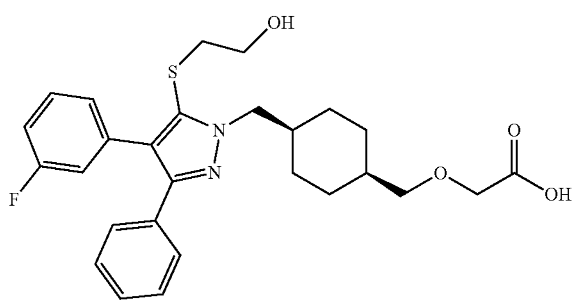 [SMILES: O=C(O)COC[C@H]1CC[C@@H](Cn2nc(-c3ccccc3)c(-c3cccc(F)c3)c2SCCO)CC1] | 2-(((1s,4s)-4-((4-(3-fluorophenyl)-5-(2-hydroxyethylthio)-3-phenyl-1H-pyrazol-1-yl)methyl)cyclohexyl)methoxy)acetic acid |
| 213 | 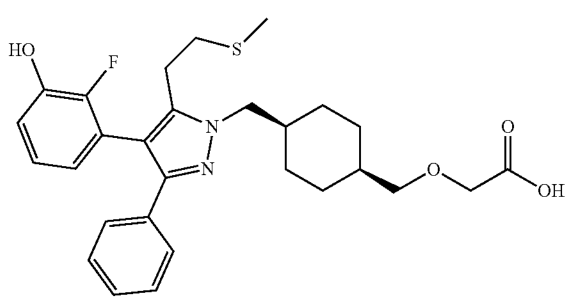 [SMILES: CSCCc1c(-c2cccc(O)c2F)c(-c2ccccc2)nn1C[C@H]1CC[C@@H](COCC(=O)O)CC1] | 2-(((1s,4s)-4-((4-(2-fluoro-3-hydroxyphenyl)-5-(2-(methylthio)ethyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 214 | 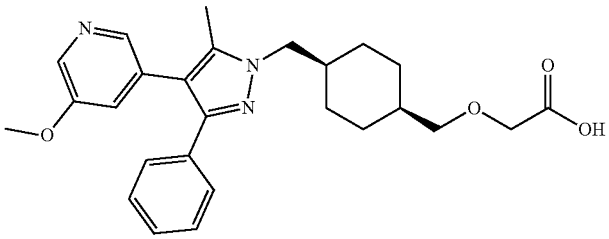 [SMILES: COc1cncc(-c2c(-c3ccccc3)nn(C[C@H]3CC[C@@H](COCC(=O)O)CC3)c2C)c1] | 2-(((1s,4s)-4-((4-(5-methoxypyridin-3-yl)-5-methyl-3-phenyl-1H-pyrazol-1-yl)methyl)cyclohexyl)methoxy)acetic acid |
| 215 | 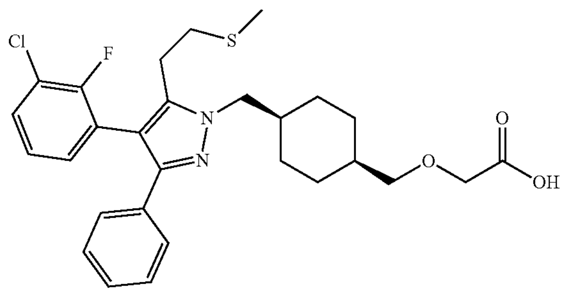 [SMILES: CSCCc1c(-c2cccc(Cl)c2F)c(-c2ccccc2)nn1C[C@H]1CC[C@@H](COCC(=O)O)CC1] | 2-(((1s,4s)-4-((4-(3-chloro-2-fluorophenyl)-5-(2-(methylthio)ethyl)-3-phenyl-1H-pyrazol-1-yl)methyl)cyclohexyl)methoxy)acetic acid |
| 216 | 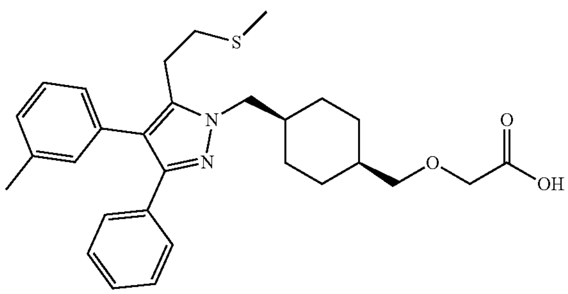 [SMILES: CSCCc1c(-c2cccc(C)c2)c(-c2ccccc2)nn1C[C@H]1CC[C@@H](COCC(=O)O)CC1] | 2-(((1s,4s)-4-((5-(2-(methylthio)ethyl)-3-phenyl-4-m-tolyl-1H-pyrazol-1-yl)methyl)cyclohexyl)methoxy)acetic acid |
| 217 | 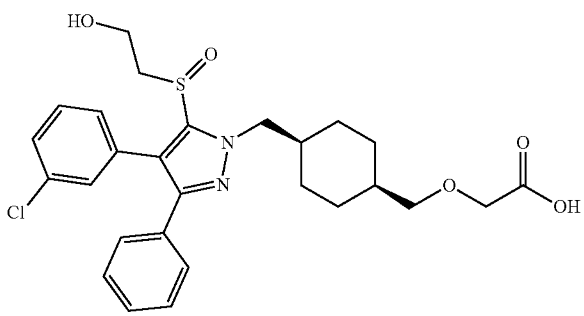 [SMILES: O=C(O)COC[C@H]1CC[C@@H](Cn2nc(-c3ccccc3)c(-c3cccc(Cl)c3)c2S(=O)CCO)CC1] | 2-(((1s,4s)-4-((4-(3-chlorophenyl)-5-(2-hydroxyethylsulfinyl)-3-phenyl-1H-pyrazol-1-yl)methyl)cyclohexyl)methoxy)acetic acid |
| 218 | 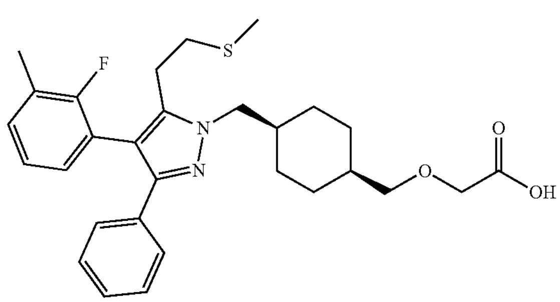 [SMILES: CSCCc1c(-c2cccc(C)c2F)c(-c2ccccc2)nn1C[C@H]1CC[C@@H](COCC(=O)O)CC1] | 2-(((1s,4s)-4-((4-(2-fluoro-3-methylphenyl)-5-(2-(methylthio)ethyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 219 | 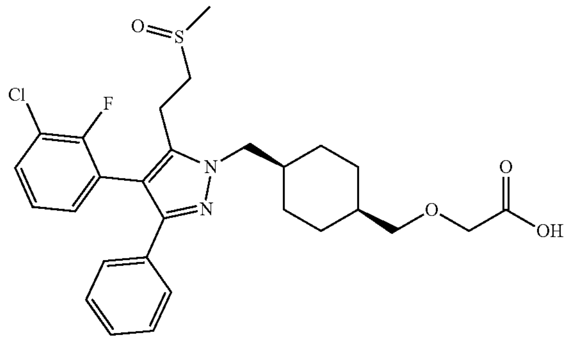 [SMILES: CS(=O)CCc1c(-c2cccc(Cl)c2F)c(-c2ccccc2)nn1C[C@H]1CC[C@@H](COCC(=O)O)CC1] | 2-(((1s,4s)-4-((4-(3-chloro-2-fluorophenyl)-5-(2-(methylsulfinyl)ethyl)-3-phenyl-1H-pyrazol-1-yl)methyl)cyclohexyl)methoxy)acetic acid |
| 220 | 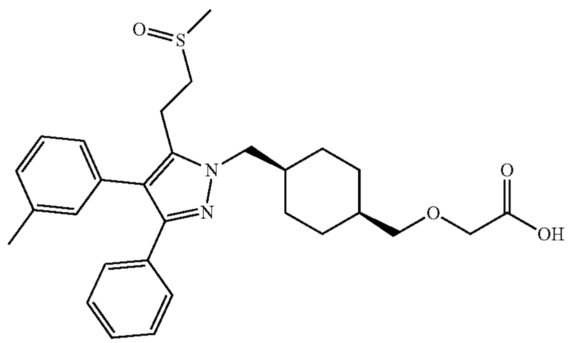 [SMILES: Cc1cccc(-c2c(-c3ccccc3)nn(C[C@H]3CC[C@@H](COCC(=O)O)CC3)c2CCS(C)=O)c1] | 2-(((1s,4s)-4-((5-(2-(methylsulfinyl)ethyl)-3-phenyl-4-m-tolyl-1H-pyrazol-1-yl)methyl)cyclohexyl)methoxy)acetic acid |
| 221 | 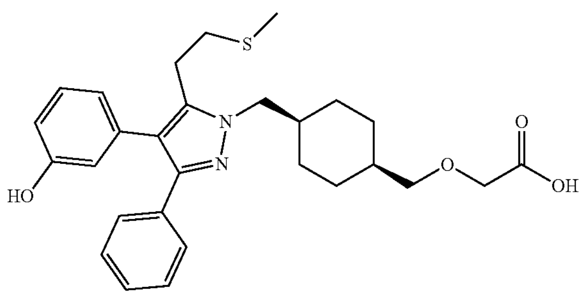 [SMILES: CSCCc1c(-c2cccc(O)c2)c(-c2ccccc2)nn1C[C@H]1CC[C@@H](COCC(=O)O)CC1] | 2-(((1s,4s)-4-((4-(3-hydroxyphenyl)-5-(2-(methylthio)ethyl)-3-phenyl-1H-pyrazol-1-yl)methyl)cyclohexyl)methoxy)acetic acid |
| 222 | 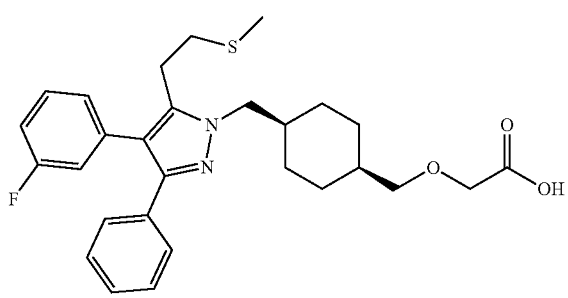 [SMILES: CSCCc1c(-c2cccc(F)c2)c(-c2ccccc2)nn1C[C@H]1CC[C@@H](COCC(=O)O)CC1] | 2-(((1s,4s)-4-((4-(3-fluorophenyl)-5-(2-(methylthio)ethyl)-3-phenyl-1H-pyrazol-1-yl)methyl)cyclohexyl)methoxy)acetic acid |
| 223 | 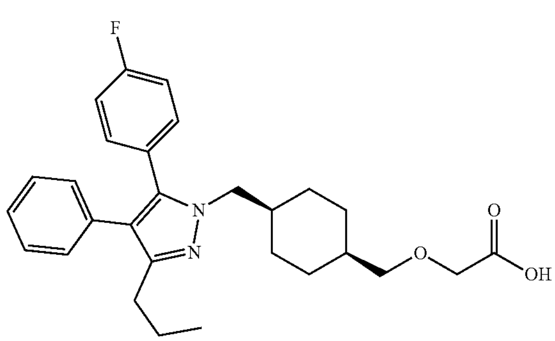 [SMILES: CCCc1nn(C[C@H]2CC[C@@H](COCC(=O)O)CC2)c(-c2ccc(F)cc2)c1-c1ccccc1] | 2-(((1s,4s)-4-((5-(4-fluorophenyl)-4-phenyl-3-propyl-1H-pyrazol-1-yl)methyl)cyclohexyl)methoxy)acetic acid |

TABLE A-continued

| Cpd No. | Chemical Structure | Chemical Name |
|---|---|---|
| 224 | 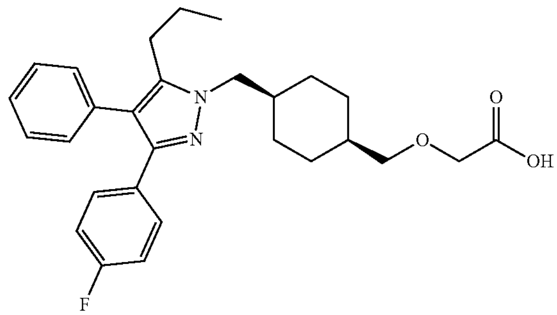 [SMILES: CCCc1c(-c2ccccc2)c(-c2ccc(F)cc2)nn1C[C@H]1CC[C@@H](COCC(=O)O)CC1] | 2-(((1s,4s)-4-((3-(4-fluorophenyl)-4-phenyl-5-propyl-1H-pyrazol-1-yl)methyl)cyclohexyl)methoxy)acetic acid |
| 225 | 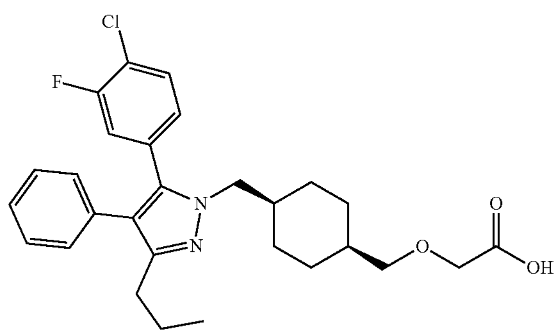 | 2-(((1s,4s)-4-((5-(4-chloro-3-fluorophenyl)-4-phenyl-3-propyl-1H-pyrazol-1-yl)methyl)cyclohexyl)methoxy)acetic acid |
| 226 | 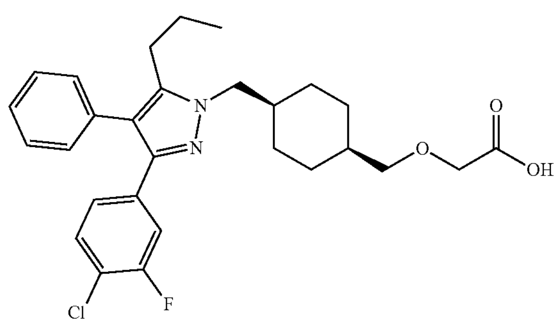 | 2-(((1s,4s)-4-((3-(4-chloro-3-fluorophenyl)-4-phenyl-5-propyl-1H-pyrazol-1-yl)methyl)cyclohexyl)methoxy)acetic acid |
| 227 | 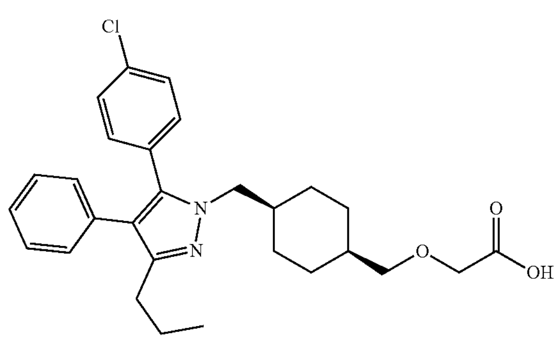 | 2-(((1s,4s)-4-((5-(4-chlorophenyl)-4-phenyl-3-propyl-1H-pyrazol-1-yl)methyl)cyclohexyl)methoxy)acetic acid |

TABLE A-continued

| Cpd No. | Chemical Structure | Chemical Name |
|---|---|---|
| 228 | 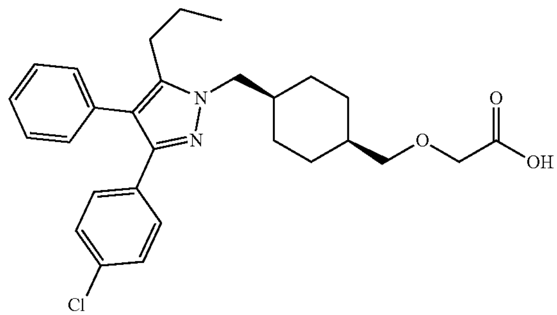 [SMILES: CCCc1c(-c2ccccc2)c(-c2ccc(Cl)cc2)nn1C[C@H]1CC[C@@H](COCC(=O)O)CC1] | 2-(((1s,4s)-4-((3-(4-chlorophenyl)-4-phenyl-5-propyl-1H-pyrazol-1-yl)methyl)cyclohexyl)methoxy)acetic acid |
| 229 | 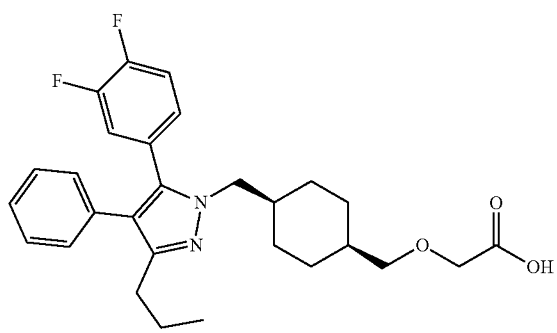 [SMILES: CCCc1nn(C[C@H]2CC[C@@H](COCC(=O)O)CC2)c(-c2ccc(F)c(F)c2)c1-c1ccccc1] | 2-(((1s,4s)-4-((5-(3,4-difluorophenyl)-4-phenyl-3-propyl-1H-pyrazol-1-yl)methyl)cyclohexyl)methoxy)acetic acid |
| 230 | 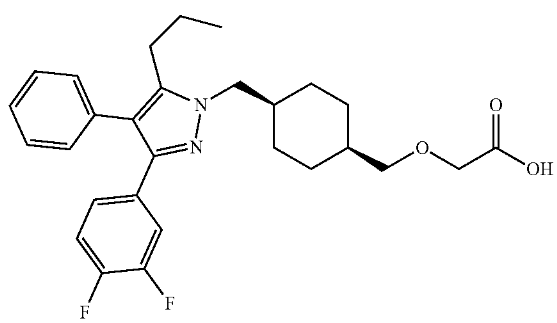 [SMILES: CCCc1c(-c2ccccc2)c(-c2ccc(F)c(F)c2)nn1C[C@H]1CC[C@@H](COCC(=O)O)CC1] | 2-(((1s,4s)-4-((3-(3,4-difluorophenyl)-4-phenyl-5-propyl-1H-pyrazol-1-yl)methyl)cyclohexyl)methoxy)acetic acid |
| 231 | 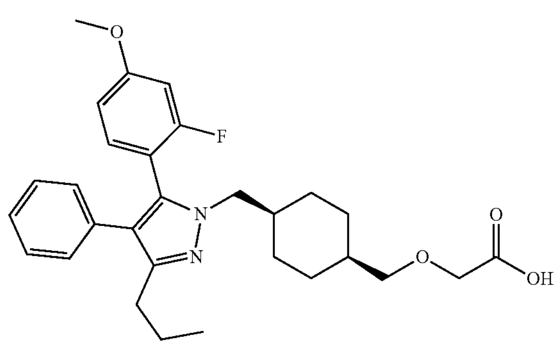 [SMILES: CCCc1nn(C[C@H]2CC[C@@H](COCC(=O)O)CC2)c(-c2ccc(OC)cc2F)c1-c1ccccc1] | 2-(((1s,4s)-4-((5-(2-fluoro-4-methoxyphenyl)-4-phenyl-3-propyl-1H-pyrazol-1-yl)methyl)cyclohexyl)methoxy)acetic acid |

TABLE A-continued

| Cpd No. | Chemical Structure | Chemical Name |
|---|---|---|
| 232 | 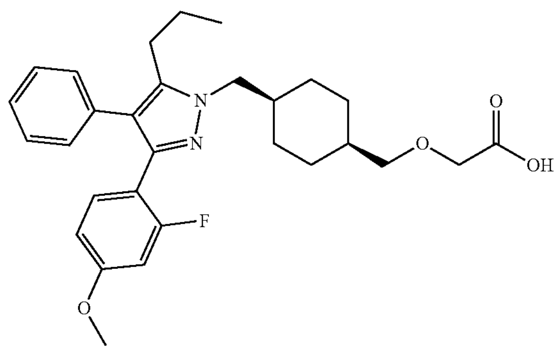 [SMILES: CCCc1c(-c2ccccc2)c(-c2ccc(OC)cc2F)nn1C[C@H]1CC[C@@H](COCC(=O)O)CC1] | 2-((1s,4s)-4-((3-(2-fluoro-4-methoxyphenyl)-4-phenyl-5-propyl-1H-pyrazol-1-yl)methyl)cyclohexyl)methoxy)acetic acid |
| 233 | 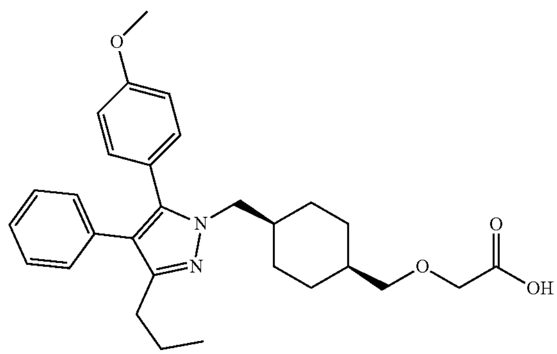 [SMILES: CCCc1nn(C[C@H]2CC[C@@H](COCC(=O)O)CC2)c(-c2ccc(OC)cc2)c1-c1ccccc1] | 2-(((1s,4s)-4-((5-(4-methoxyphenyl)-4-phenyl-3-propyl-1H-pyrazol-1-yl)methyl)cyclohexyl)methoxy)acetic acid |
| 234 | 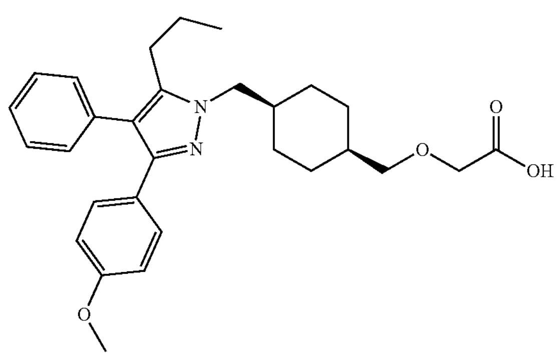 [SMILES: CCCc1c(-c2ccccc2)c(-c2ccc(OC)cc2)nn1C[C@H]1CC[C@@H](COCC(=O)O)CC1] | 2-(((1s,4s)-4-((3-(4-methoxyphenyl)-4-phenyl-5-propyl-1H-pyrazol-1-yl)methyl)cyclohexyl)methoxy)acetic acid |
| 235 | 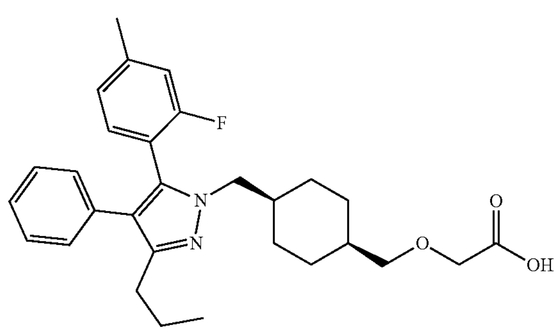 [SMILES: CCCc1nn(C[C@H]2CC[C@@H](COCC(=O)O)CC2)c(-c2ccc(C)cc2F)c1-c1ccccc1] | 2-(((1s,4s)-4-((5-(2-fluoro-4-methylphenyl)-4-phenyl-3-propyl-1H-pyrazol-1-yl)methyl)cyclohexyl)methoxy)acetic acid |

| Cpd No. | Chemical Structure | Chemical Name |
|---|---|---|
| 236 | 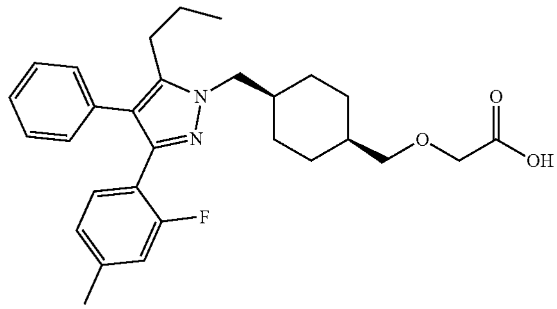 [SMILES: CCCc1c(-c2ccccc2)c(-c2ccc(C)cc2F)nn1C[C@H]1CC[C@@H](COCC(=O)O)CC1] | 2-(((1s,4s)-4-((3-(2-fluoro-4-methylphenyl)-4-phenyl-5-propyl-1H-pyrazol-1-yl)methyl)cyclohexyl)methoxy)acetic acid |
| 237 | 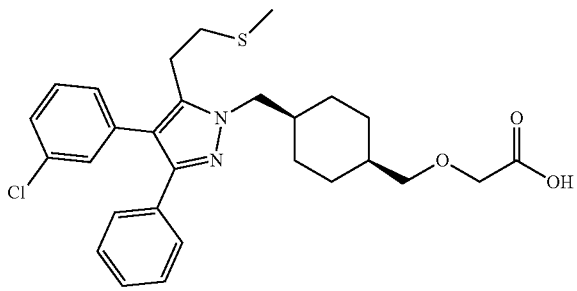 [SMILES: CSCCc1c(-c2cccc(Cl)c2)c(-c2ccccc2)nn1C[C@H]1CC[C@@H](COCC(=O)O)CC1] | 2-(((1s,4s)-4-((4-(3-chlorophenyl)-5-(2-(methylthio)ethyl)-3-phenyl-1H-pyrazol-1-yl)methyl)cyclohexyl)methoxy)acetic acid |
| 238 | 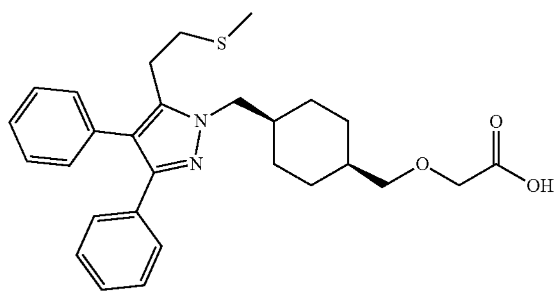 [SMILES: CSCCc1c(-c2ccccc2)c(-c2ccccc2)nn1C[C@H]1CC[C@@H](COCC(=O)O)CC1] | 2-(((1s,4s)-4-((5-(2-(methylthio)ethyl)-3,4-diphenyl-1H-pyrazol-1-yl)methyl)cyclohexyl)methoxy)acetic acid |
| 239 | 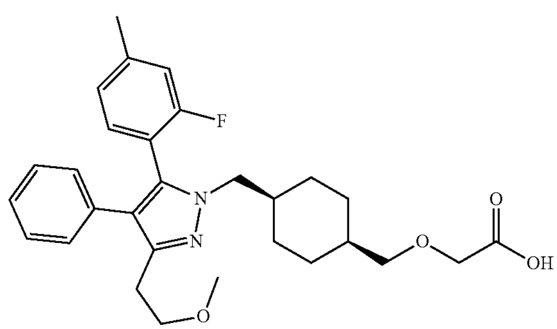 [SMILES: COCCc1nn(C[C@H]2CC[C@@H](COCC(=O)O)CC2)c(-c2ccc(C)cc2F)c1-c1ccccc1] | 2-(((1s,4s)-4-((5-(2-fluoro-4-methylphenyl)-3-(2-methoxyethyl)-4-phenyl-1H-pyrazol-1-yl)methyl)cyclohexyl)methoxy)acetic acid |
| 240 | 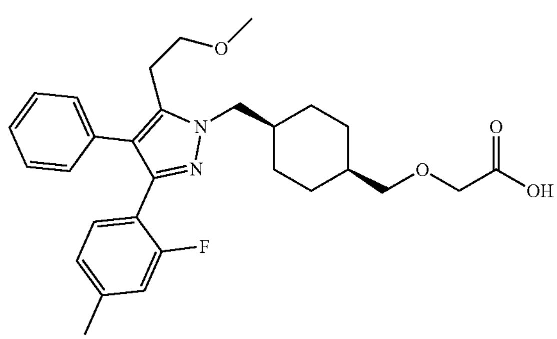 [SMILES: COCCc1c(-c2ccccc2)c(-c2ccc(C)cc2F)nn1C[C@H]1CC[C@@H](COCC(=O)O)CC1] | 2-(((1s,4s)-4-((3-(2-fluoro-4-methylphenyl)-5-(2-methoxyethyl)-4-phenyl-1H-pyrazol-1-yl)methyl)cyclohexyl)methoxy)acetic acid |

TABLE A-continued

| Cpd No. | Chemical Structure | Chemical Name |
|---|---|---|
| 241 | 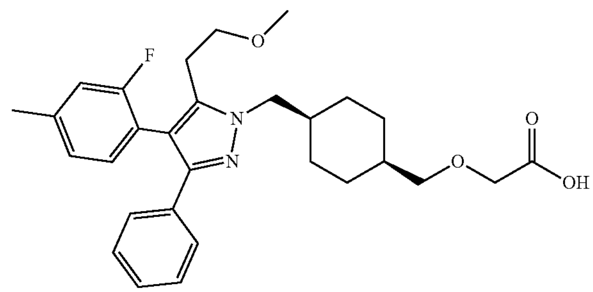 [SMILES: CSCCc1c(-c2ccc(C)cc2F)c(-c2ccccc2)nn1C[C@H]1CC[C@@H](COCC(=O)O)CC1] | 2-(((1s,4s)-4-((4-(2-fluoro-4-methylphenyl)-5-(2-methoxyethyl)-3-phenyl-1H-pyrazol-1-yl)methyl)cyclohexyl)methoxy)acetic acid |
| 242 | 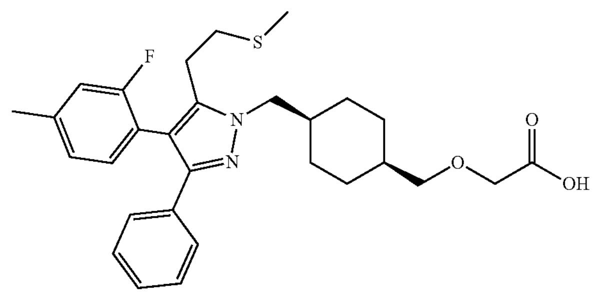 | 2-(((1s,4s)-4-((4-(2-fluoro-4-methylphenyl)-5-(2-(methylthio)ethyl)-3-phenyl-1H-pyrazol-1-yl)methyl)cyclohexyl)methoxy)acetic acid |
| 243 | 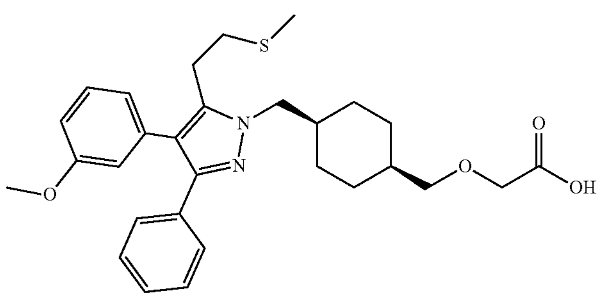 [SMILES: COc1cccc(-c2c(-c3ccccc3)nn(C[C@H]3CC[C@@H](COCC(=O)O)CC3)c2CCSC)c1] | 2-(((1s,4s)-4-((4-(3-methoxyphenyl)-5-(2-(methylthio)ethyl)-3-phenyl-1H-pyrazol-1-yl)methyl)cyclohexyl)methoxy)acetic acid |
| 244 | 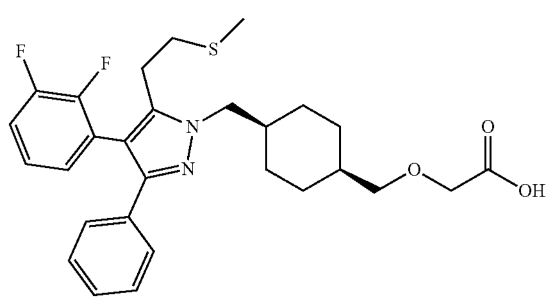 [SMILES: CSCCc1c(-c2cccc(F)c2F)c(-c2ccccc2)nn1C[C@H]1CC[C@@H](COCC(=O)O)CC1] | 2-(((1s,4s)-4-((4-(2,3-difluorophenyl)-5-(2-(methylthio)ethyl)-3-phenyl-1H-pyrazol-1-yl)methyl)cyclohexyl)methoxy)acetic acid |
| 245 | 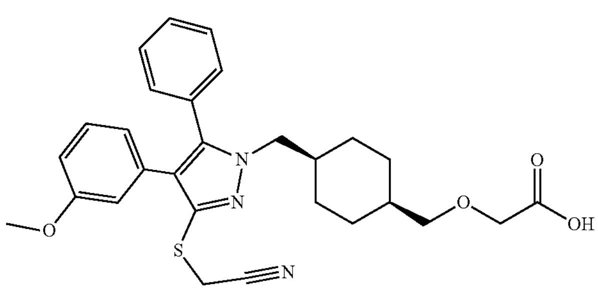 | 2-(((1r,4r)-4-((3-(cyanomethylthio)-4-(3-methoxyphenyl)-5-phenyl-1H-pyrazol-1-yl)methyl)cyclohexyl)methoxy)acetic acid |

TABLE A-continued

| Cpd No. | Chemical Structure | Chemical Name |
|---|---|---|
| 246 | 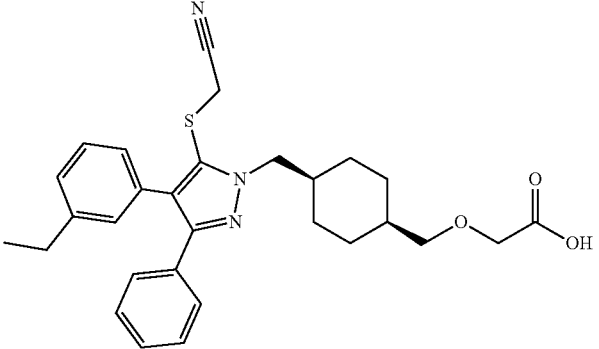 [SMILES: CCc1cccc(-c2c(-c3ccccc3)nn(C[C@H]3CC[C@@H](COCC(=O)O)CC3)c2SCC#N)c1] | 2-(((1s,4s)-4-((5-(cyanomethylthio)-4-(3-methoxyphenyl)-3-phenyl-1H-pyrazol-1-yl)methyl)cyclohexyl)methoxy)acetic acid |
| 247 | 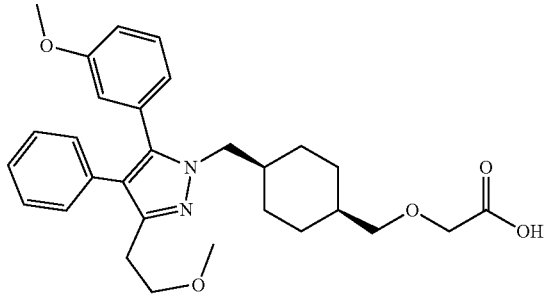 [SMILES: COCCc1nn(C[C@H]2CC[C@@H](COCC(=O)O)CC2)c(-c2cccc(OC)c2)c1-c1ccccc1] | 2-(((1s,4s)-4-((3-(2-methoxyethyl)-5-(3-methoxyphenyl)-4-phenyl-1H-pyrazol-1-yl)methyl)cyclohexyl)methoxy)acetic acid |
| 248 | 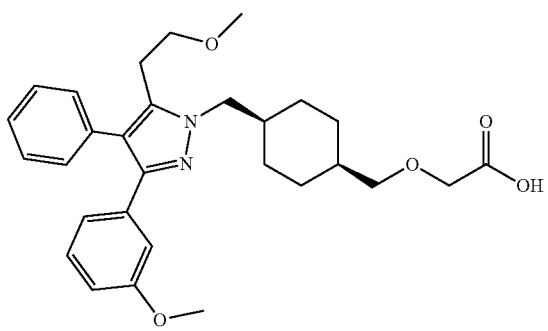 [SMILES: COCCc1c(-c2ccccc2)c(-c2cccc(OC)c2)nn1C[C@H]1CC[C@@H](COCC(=O)O)CC1] | 2-(((1s,4s)-4-((5-(2-methoxyethyl)-3-(3-methoxyphenyl)-4-phenyl-1H-pyrazol-1-yl)methyl)cyclohexyl)methoxy)acetic acid |
| 249 | 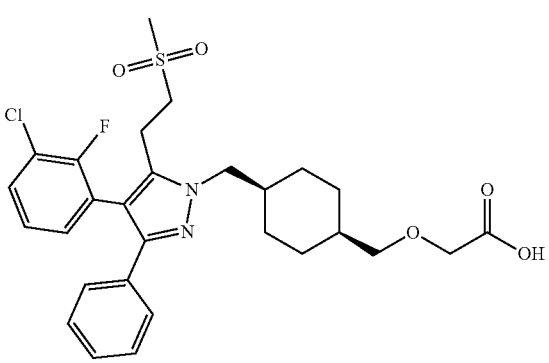 [SMILES: CS(=O)(=O)CCc1c(-c2cccc(Cl)c2F)c(-c2ccccc2)nn1C[C@H]1CC[C@@H](COCC(=O)O)CC1] | 2-(((1s,4s)-4-((4-(3-chloro-2-fluorophenyl)-5-(2-(methylsulfonyl)ethyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 250 | 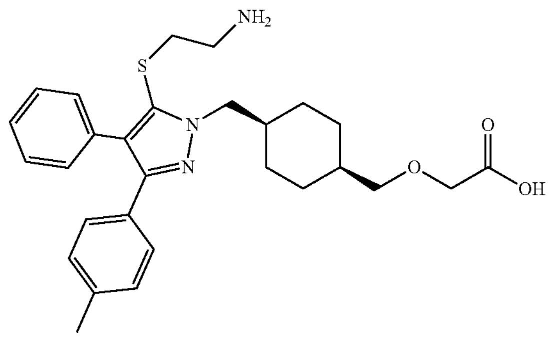 [SMILES: Cc1ccc(-c2nn(C[C@H]3CC[C@@H](COCC(=O)O)CC3)c(SCCN)c2-c2ccccc2)cc1] | 2-(((1s,4s)-4-((5-(2-aminoethylthio)-4-phenyl-3-p-tolyl-1H-pyrazol-1-yl)methyl)cyclohexyl)methoxy)acetic acid |
| 251 | 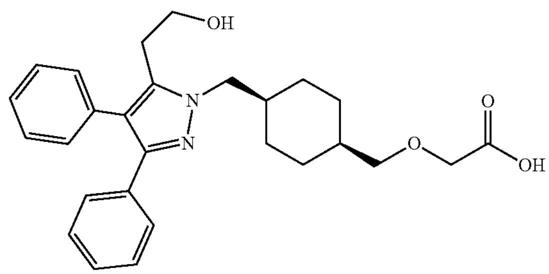 [SMILES: O=C(O)COC[C@H]1CC[C@@H](Cn2nc(-c3ccccc3)c(-c3ccccc3)c2CCO)CC1] | 2-(((1s,4s)-4-((5-(2-hydroxyethyl)-3,4-diphenyl-1H-pyrazol-1-yl)methyl)cyclohexyl)methoxy)acetic acid |
| 252 | 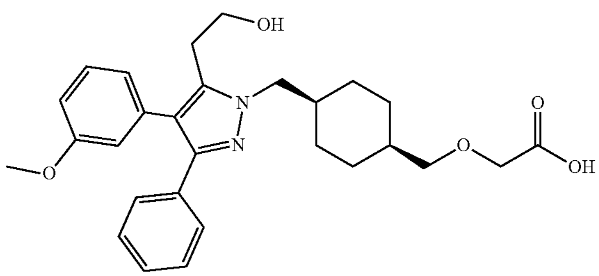 [SMILES: COc1cccc(-c2c(-c3ccccc3)nn(C[C@H]3CC[C@@H](COCC(=O)O)CC3)c2CCO)c1] | 2-(((1s,4s)-4-((5-(2-hydroxyethyl)-4-(3-methoxyphenyl)-3-phenyl-1H-pyrazol-1-yl)methyl)cyclohexyl)methoxy)acetic acid |
| 253 | 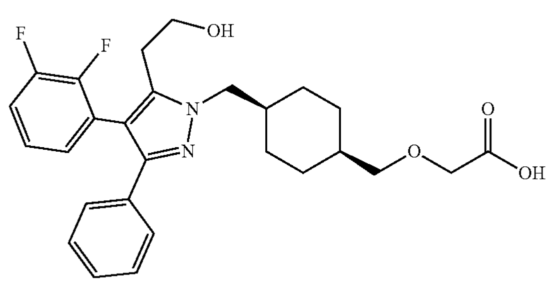 [SMILES: O=C(O)COC[C@H]1CC[C@@H](Cn2nc(-c3ccccc3)c(-c3cccc(F)c3F)c2CCO)CC1] | 2-(((1s,4s)-4-((4-(2,3-difluorophenyl)-5-(2-hydroxethyl)-3-phenyl-1H-pyrazol-1-yl)methyl)cyclohexyl)methoxy)acetic acid |
| 254 | 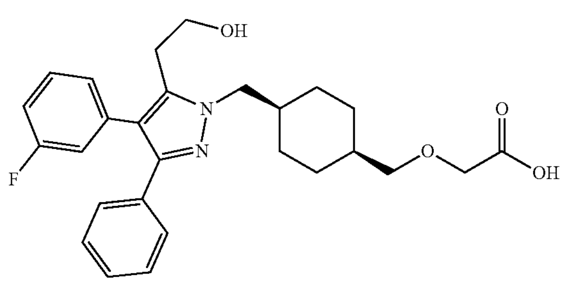 [SMILES: O=C(O)COC[C@H]1CC[C@@H](Cn2nc(-c3ccccc3)c(-c3cccc(F)c3)c2CCO)CC1] | 2-(((1s,4s)-4-((4-(3-fluorophenyl)-5-(2-hydroxyethyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 255 | 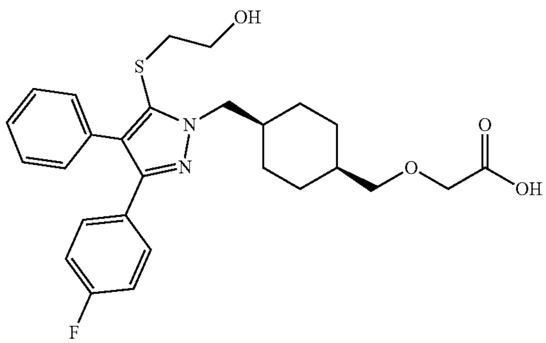 [SMILES: O=C(O)COC[C@H]1CC[C@@H](Cn2nc(-c3ccc(F)cc3)c(-c3ccccc3)c2SCCO)CC1] | 2-(((1s,4s)-4-((3-(4-fluorophenyl)-5-(2-hydroxyethylthio)-4-phenyl-1H-pyrazol-1-yl)methyl)cyclohexyl)methoxy)acetic acid |
| 256 | 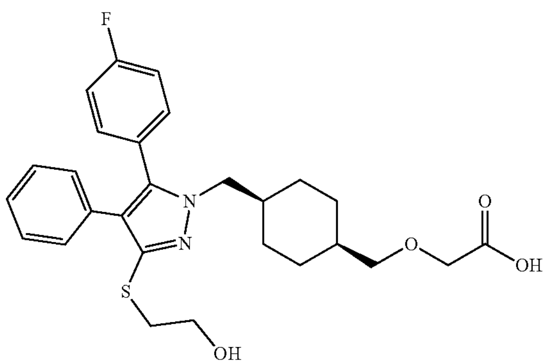 [SMILES: O=C(O)COC[C@H]1CC[C@@H](Cn2nc(SCCO)c(-c3ccccc3)c2-c2ccc(F)cc2)CC1] | 2-(((1s,4s)-4-((5-(4-fluorophenyl)-3-(2-hydroxyethylthio)-4-phenyl-1H-pyrazol-1-yl)methyl)cyclohexyl)methoxy)acetic acid |
| 257 | 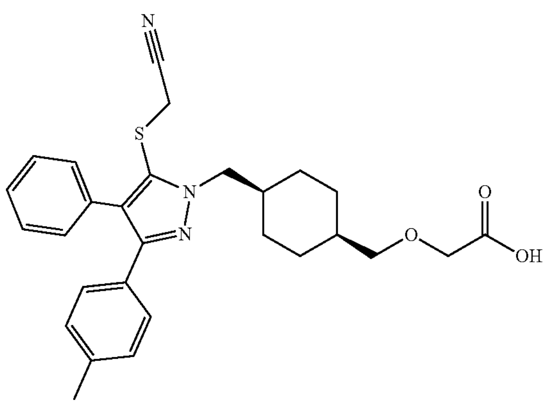 [SMILES: Cc1ccc(-c2nn(C[C@H]3CC[C@@H](COCC(=O)O)CC3)c(SCC#N)c2-c2ccccc2)cc1] | 2-(((1s,4s)-4-((5-(cyanomethylthio)-4-phenyl-3-p-tolyl-1H-pyrazol-1-yl)methyl)cyclohexyl)methoxy)acetic acid |
| 258 | 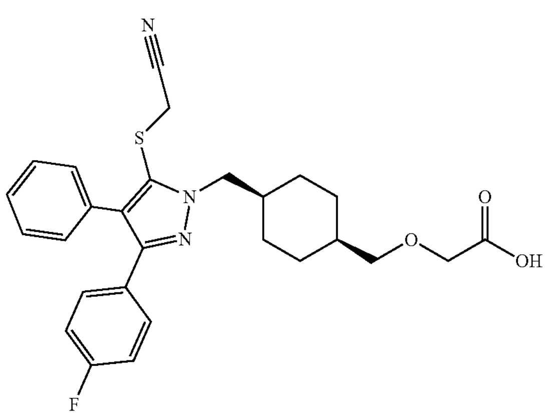 [SMILES: N#CCSc1c(-c2ccccc2)c(-c2ccc(F)cc2)nn1C[C@H]1CC[C@@H](COCC(=O)O)CC1] | 2-(((1s,4s)-4-((5-(cyanomethylthio)-3-(4-fluorophenyl)-4-phenyl-1H-pyrazol-1-yl)methyl)cyclohexyl)methoxy)acetic acid |

TABLE A-continued

| Cpd No. | Chemical Structure | Chemical Name |
|---|---|---|
| 259 | 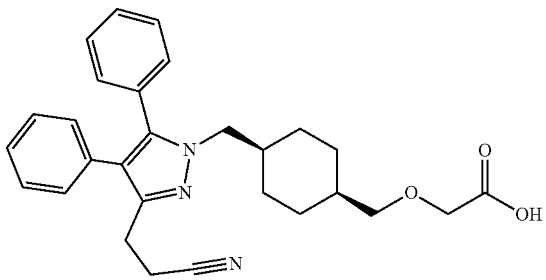 [SMILES: N#CCCc1nn(C[C@H]2CC[C@@H](COCC(=O)O)CC2)c(-c2ccccc2)c1-c1ccccc1] | 2-(((1s,4s)-4-((3-(2-cyanoethyl)-4,5-diphenyl-1H-pyrazol-1-yl)methyl)cyclohexyl)methoxy)acetic acid |
| 260 | 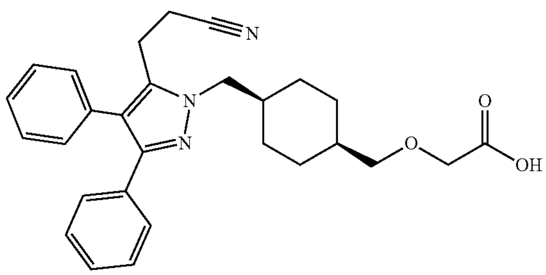 [SMILES: N#CCCc1c(-c2ccccc2)c(-c2ccccc2)nn1C[C@H]1CC[C@@H](COCC(=O)O)CC1] | 2-(((1s,4s)-4-((5-(2-cyanoethyl)-3,4-diphenyl-1H-pyrazol-1-yl)methyl)cyclohexyl)methoxy)acetic acid |
| 261 | 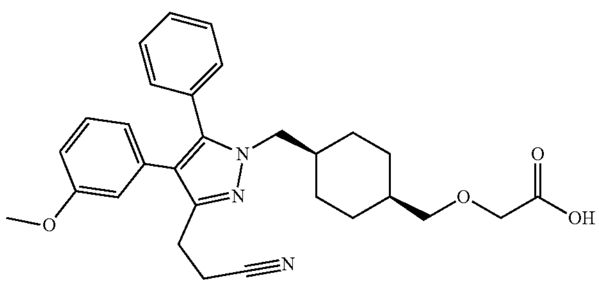 [SMILES: COc1cccc(-c2c(CCC#N)nn(C[C@H]3CC[C@@H](COCC(=O)O)CC3)c2-c2ccccc2)c1] | 2-(((1s,4s)-4-((3-(2-cyanoethyl)-4-(3-methoxyphenyl)-5-phenyl-1H-pyrazol-1-yl)methyl)cyclohexyl)methoxy)acetic acid |
| 262 | 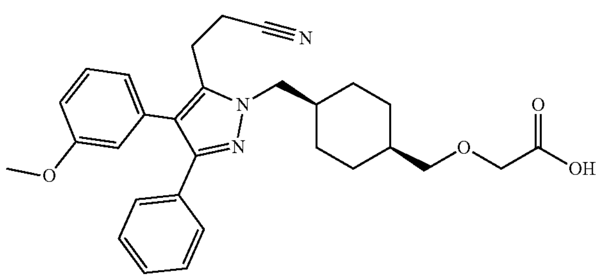 [SMILES: COc1cccc(-c2c(-c3ccccc3)nn(C[C@H]3CC[C@@H](COCC(=O)O)CC3)c2CCC#N)c1] | 2-(((1s,4s)-4-((5-(2-cyanoethyl)-4-(3-methoxyphenyl)-3-phenyl-1H-pyrazol-1-yl)methyl)cyclohexyl)methoxy)acetic acid |
| 263 | 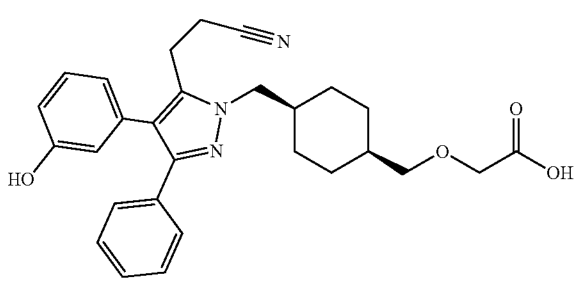 [SMILES: N#CCCc1c(-c2cccc(O)c2)c(-c2ccccc2)nn1C[C@H]1CC[C@@H](COCC(=O)O)CC1] | 2-(((1s,4s)-4-((5-(2-cyanoethyl)-4-(3-hydroxyphenyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 264 | 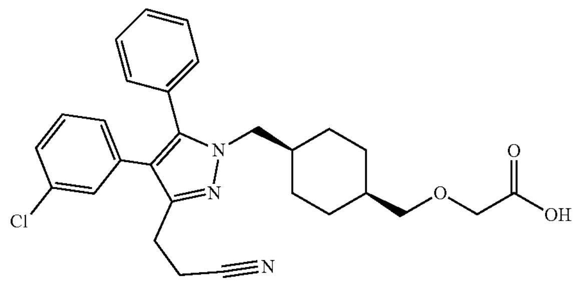 [SMILES: N#CCCc1nn(C[C@H]2CC[C@@H](COCC(=O)O)CC2)c(-c2ccccc2)c1-c1cccc(Cl)c1] | 2-(((1s,4s)-4-((4-(3-chlorophenyl)-3-(2-cyanoethyl)-5-phenyl-1H-pyrazol-1-yl)methyl)cyclohexyl)methoxy)acetic acid |
| 265 | 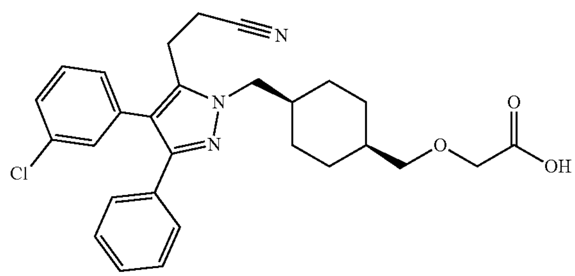 [SMILES: N#CCCc1c(-c2cccc(Cl)c2)c(-c2ccccc2)nn1C[C@H]1CC[C@@H](COCC(=O)O)CC1] | 2-(((1s,4s)-4-((4-(3-chlorophenyl)-5-(2-cyanoethyl)-3-phenyl-1H-pyrazol-1-yl)methyl)cyclohexyl)methoxy)acetic acid |
| 266 | 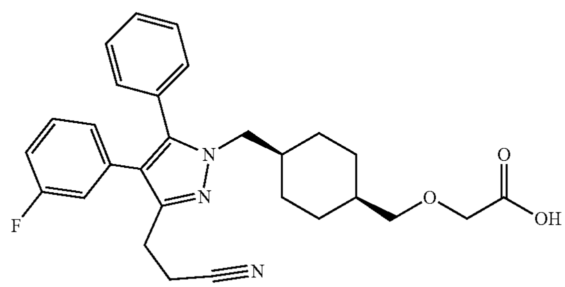 [SMILES: N#CCCc1nn(C[C@H]2CC[C@@H](COCC(=O)O)CC2)c(-c2ccccc2)c1-c1cccc(F)c1] | 2-(((1s,4s)-4-((3-(2-cyanoethyl)-4-(3-fluorophenyl)-5-phenyl-1H-pyrazol-1-yl)methyl)cyclohexyl)methoxy)acetic acid |
| 267 | 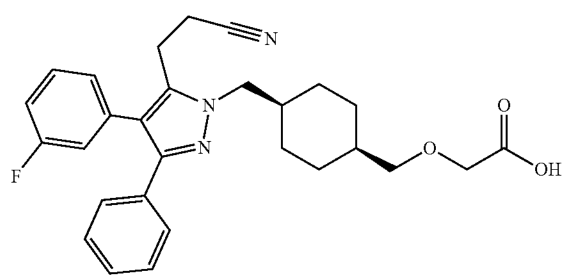 [SMILES: N#CCCc1c(-c2cccc(F)c2)c(-c2ccccc2)nn1C[C@H]1CC[C@@H](COCC(=O)O)CC1] | 2-(((1s,4s)-4-((5-(2-cyanoethyl)-4-(3-fluorophenyl)-3-phenyl-1H-pyrazol-1-yl)methyl)cyclohexyl)methoxy)acetic acid |
| 268 | 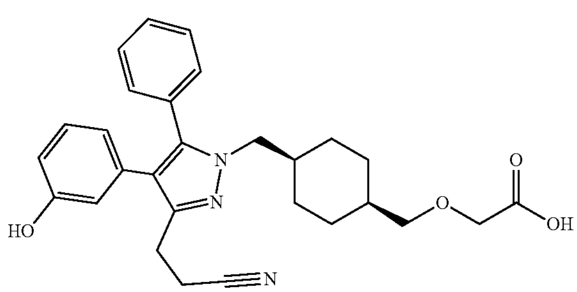 [SMILES: N#CCCc1nn(C[C@H]2CC[C@@H](COCC(=O)O)CC2)c(-c2ccccc2)c1-c1cccc(O)c1] | 2-(((1s,4s)-4-((3-(2-cyanoethyl)-4-(3-hydroxyphenyl)-5-phenyl-1H-pyrazol-1-yl)methyl)cyclohexyl)methoxy)acetic acid |

TABLE A-continued

| Cpd No. | Chemical Structure | Chemical Name |
| --- | --- | --- |
| 269 | 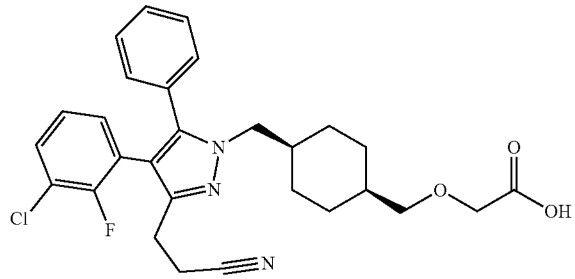 [SMILES: N#CCCc1nn(C[C@H]2CC[C@@H](COCC(=O)O)CC2)c(-c2ccccc2)c1-c1cccc(Cl)c1F] | 2-(((1s,4s)-4-((4-(3-chlor-2-fluorophenyl)-3-(2-cyanoethyl)-5-phenyl-1H-pyrazol-1-yl)methyl)cyclohexyl)methoxy)acetic acid |
| 270 | 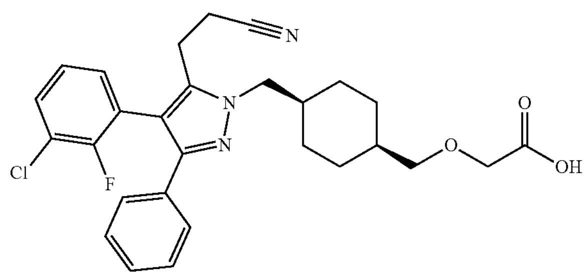 [SMILES: N#CCCc1c(-c2cccc(Cl)c2F)c(-c2ccccc2)nn1C[C@H]1CC[C@@H](COCC(=O)O)CC1] | 2-(((1s,4s)-4-((4-(3-chloro-2-fluorophenyl)-5-(2-cyanoethyl)-3-phenyl-1H-pyrazol-1-yl)methyl)cyclohexyl)methoxy)acetic acid |
| 271 | 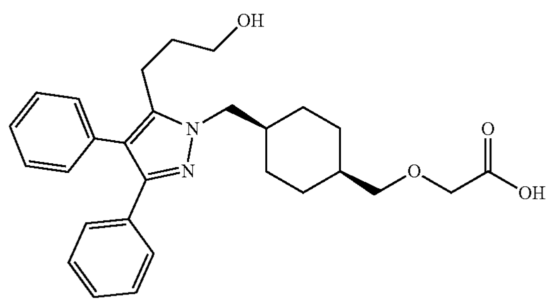 [SMILES: O=C(O)COC[C@H]1CC[C@@H](Cn2nc(-c3ccccc3)c(-c3ccccc3)c2CCCO)CC1] | 2-(((1s,4s)-4-((5-(3-hydroxypropyl)-3,4-diphenyl-1H-pyrazol-1-yl)methyl)cyclohexyl)methoxy)acetic acid |
| 272 | 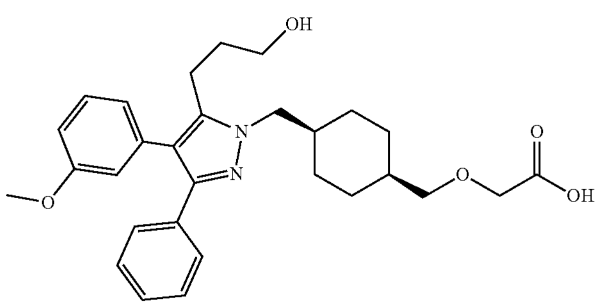 [SMILES: COc1cccc(-c2c(-c3ccccc3)nn(C[C@H]3CC[C@@H](COCC(=O)O)CC3)c2CCCO)c1] | 2-(((1s,4s)-4-((5-(3-hydroxypropyl)-4-(3-methoxyphenyl)-3-phenyl-1H-pyrazol-1-yl)methyl)cyclohexyl)methoxy)acetic acid |
| 273 | 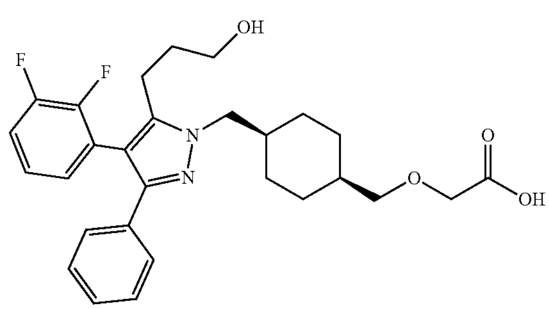 [SMILES: O=C(O)COC[C@H]1CC[C@@H](Cn2nc(-c3ccccc3)c(-c3cccc(F)c3F)c2CCCO)CC1] | 2-(((1s,4s)-4-((4-(2,3-difluorophenyl)-5-(3-hydroxypropyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 274 | 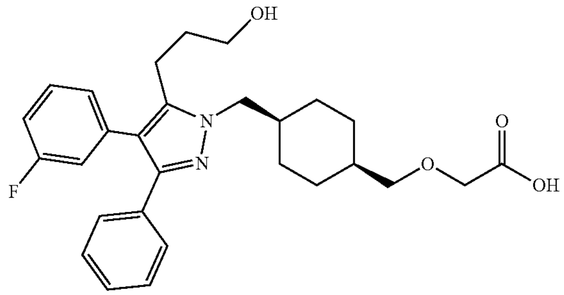 [SMILES: O=C(O)COC[C@H]1CC[C@@H](Cn2nc(-c3ccccc3)c(-c3cccc(F)c3)c2CCCO)CC1] | 2-(((1s,4s)-4-((4-(3-fluorophenyl)-5-(3-hydroxypropyl)-3-phenyl-1H-pyrazol-1-yl)methyl)cyclohexyl)methoxy)acetic acid |
| 275 | 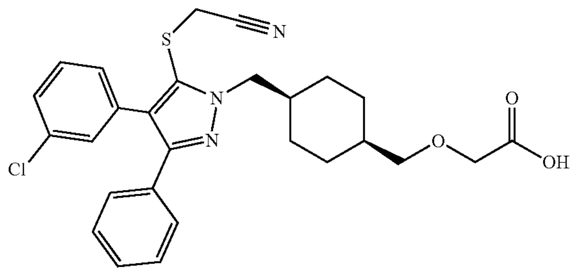 [SMILES: N#CCSc1c(-c2cccc(Cl)c2)c(-c2ccccc2)nn1C[C@H]1CC[C@@H](COCC(=O)O)CC1] | 2-(((1s,4s)-4-((4-(3-chlorophenyl)-5-(cyanomethylthio)-3-phenyl-1H-pyrazol-1-yl)methyl)cyclohexyl)methoxy)acetic acid |
| 276 | 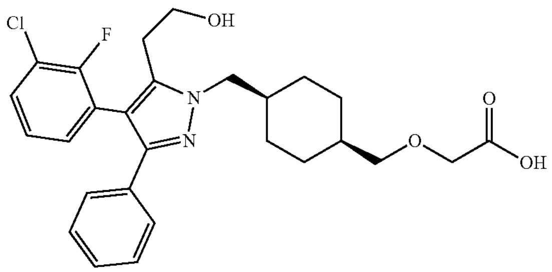 [SMILES: O=C(O)COC[C@H]1CC[C@@H](Cn2nc(-c3ccccc3)c(-c3cccc(Cl)c3F)c2CCO)CC1] | 2-(((1s,4s)-4-((4-(3-chloro-2-fluorophenyl)-5-(2-hydroxyethyl)-3-phenyl-1H-pyrazol-1-yl)methyl)cyclohexyl)methoxy)acetic acid |
| 277 | 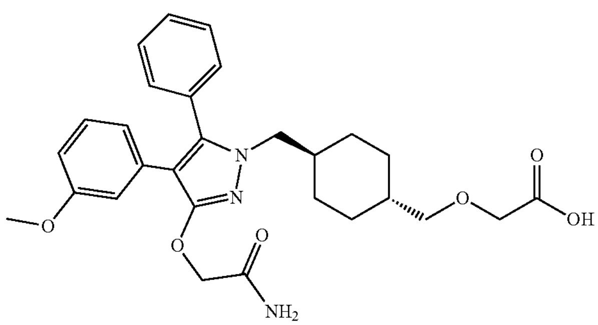 | 2-(((1r,4r)-4-((3-(2-amino-2-oxoethoxy)-4-(3-methoxyphenyl)-5-phenyl-1H-pyrazol-1-yl)methyl)cyclohexyl)methoxy)acetic acid |
| 278 | 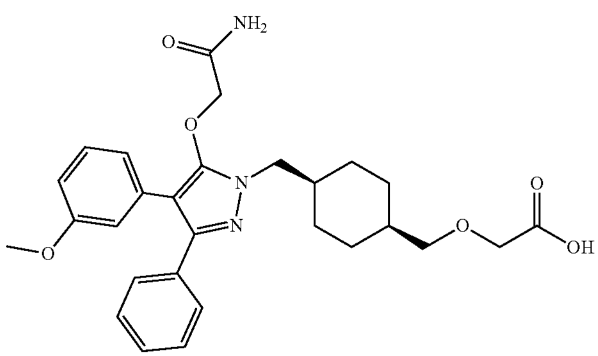 [SMILES: COc1cccc(-c2c(-c3ccccc3)nn(C[C@H]3CC[C@@H](COCC(=O)O)CC3)c2OCC(N)=O)c1] | 2-(((1s,4s)-4-((5-(2-amino-2-oxoethoxy)-4-(3-methoxyphenyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 279 | 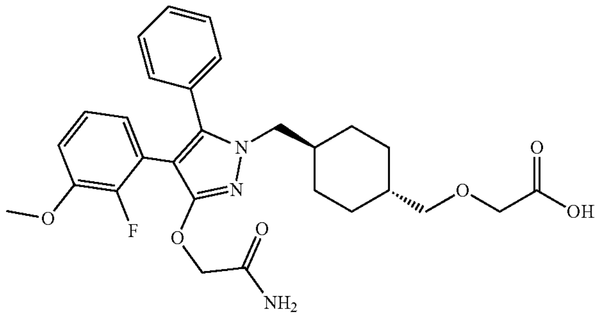 [SMILES: COc1cccc(-c2c(OCC(N)=O)nn(C[C@H]3CC[C@H](COCC(=O)O)CC3)c2-c2ccccc2)c1F] | 2-(((1r,4r)-4-((3-(2-amino-2-oxoethoxy)-4-(2-fluoro-3-methoxyphenyl)-5-phenyl-1H-pyrazol-1-yl)methyl)cyclohexyl)methoxy)acetic acid |
| 280 | 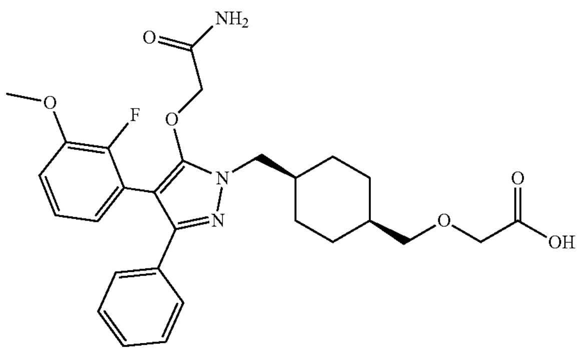 [SMILES: COc1cccc(-c2c(-c3ccccc3)nn(C[C@H]3CC[C@@H](COCC(=O)O)CC3)c2OCC(N)=O)c1F] | 2-(((1s,4s)-4-((5-(2-amino-2-oxoethoxy)-4-(2-fluoro-3-methoxyphenyl)-3-phenyl-1H-pyrazol-1-yl)methyl)cyclohexyl)methoxy)acetic acid |
| 281 | 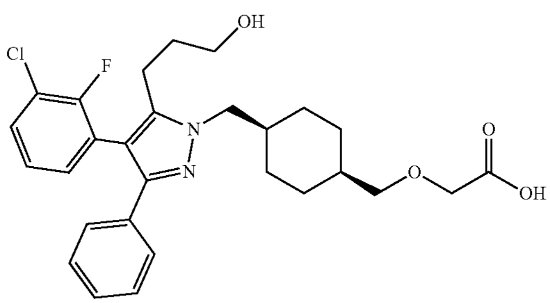 [SMILES: O=C(O)COC[C@H]1CC[C@@H](Cn2nc(-c3ccccc3)c(-c3cccc(Cl)c3F)c2CCCO)CC1] | 2-(((1s,4s)-4-((4-(3-chloro-2-fluorophenyl)-5-(3-hydroxypropyl)-3-phenyl-1H-pyrazol-1-yl)methyl)cyclohexyl)methoxy)acetic acid |
| 282 | 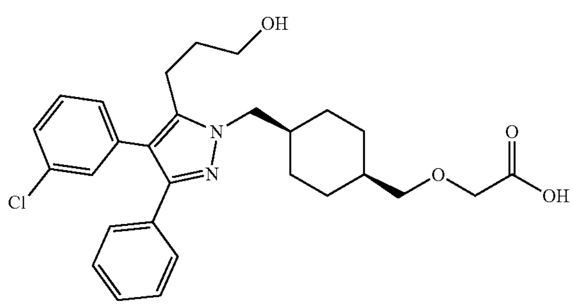 [SMILES: O=C(O)COC[C@H]1CC[C@@H](Cn2nc(-c3ccccc3)c(-c3cccc(Cl)c3)c2CCCO)CC1] | 2-(((1s,4s)-4-((4-(3-chlorophenyl)-5-(3-hydroxypropyl)-3-phenyl-1H-pyrazol-1-yl)methyl)cyclohexyl)methoxy)acetic acid |
| 283 | 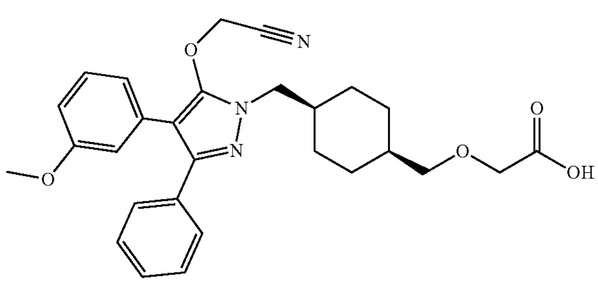 [SMILES: COc1cccc(-c2c(-c3ccccc3)nn(C[C@H]3CC[C@@H](COCC(=O)O)CC3)c2OCC#N)c1] | 2-(((1s,4s)-4-((5-(cyanomethoxy)-4-(3-methoxyphenyl)-3-phenyl-1H-pyrazol-1-yl)methyl)cyclohexyl)methoxy)acetic acid |

TABLE A-continued

| Cpd No. | Chemical Structure | Chemical Name |
|---|---|---|
| 284 | 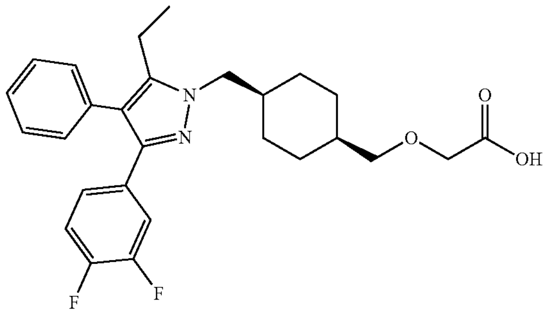 [SMILES: CCc1c(-c2ccccc2)c(-c2ccc(F)c(F)c2)nn1C[C@H]1CC[C@@H](COCC(=O)O)CC1] | 2-(((1s,4s)-4-((3-(3,4-difluorophenyl)-5-ethyl-4-phenyl-1H-pyrazol-1-yl)methyl)cyclohexyl)methoxy)acetic acid |
| 285 | 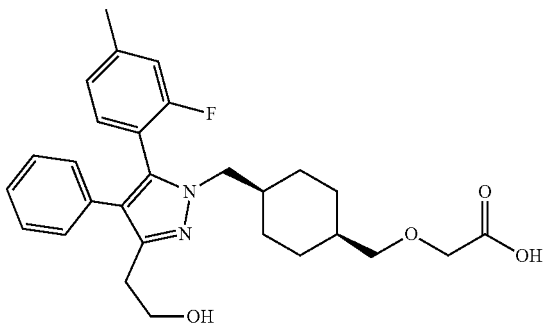 [SMILES: Cc1ccc(-c2c(-c3ccccc3)c(CCO)nn2C[C@H]2CC[C@@H](COCC(=O)O)CC2)c(F)c1] | 2-(((1s,4s)-4-((5-(2-fluoro-4-methylphenyl)-3-(2-hydroxyethyl)-4-phenyl-1H-pyrazol-1-yl)methyl)cyclohexyl)methoxy)acetic acid |
| 286 | 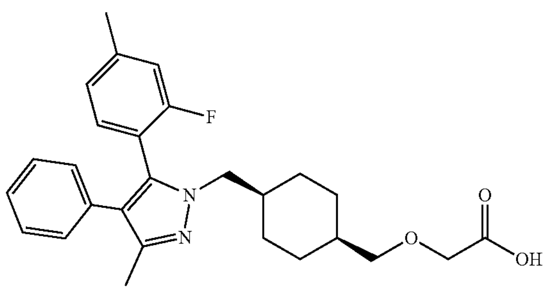 [SMILES: Cc1ccc(-c2c(-c3ccccc3)c(C)nn2C[C@H]2CC[C@@H](COCC(=O)O)CC2)c(F)c1] | 2-(((1s,4s)-4-((5-(2-fluoro-4-methylphenyl)-3-methyl-4-phenyl-1H-pyrazol-1-yl)methyl)cyclohexyl)methoxy)acetic acid |
| 287 | 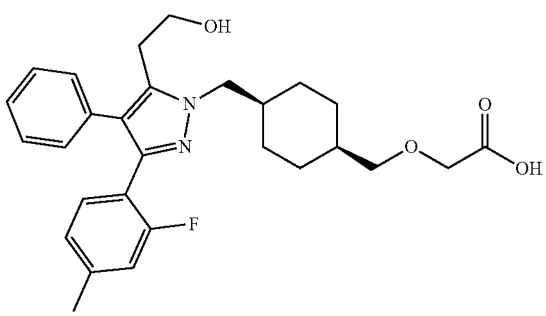 [SMILES: Cc1ccc(-c2nn(C[C@H]3CC[C@@H](COCC(=O)O)CC3)c(CCO)c2-c2ccccc2)c(F)c1] | 2-(1s,4s)-4-((3-(2-fluoro-4-methylphenyl)-5-(2-hydroxyethyl)-4-phenyl-1H-pyrazol-1-yl)methyl)cyclohexyl)methoxy)acetic acid |
| 288 | 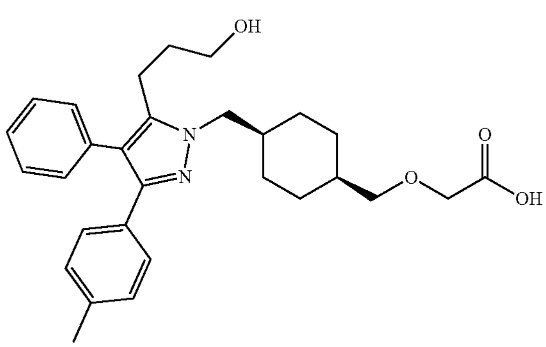 [SMILES: Cc1ccc(-c2nn(C[C@H]3CC[C@@H](COCC(=O)O)CC3)c(CCCO)c2-c2ccccc2)cc1] | 2-(((1s,4s)-4-((5-(3-hydroxypropyl)-4-phenyl-3-p-tolyl-1H-pyrazol-1-yl)methyl)cyclohexyl)methoxy)acetic acid |

TABLE A-continued

| Cpd No. | Chemical Structure | Chemical Name |
|---|---|---|
| 289 | 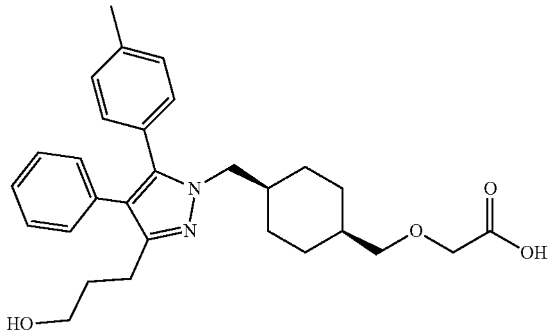 [SMILES: Cc1ccc(-c2c(-c3ccccc3)c(CCCO)nn2C[C@H]2CC[C@@H](COCC(=O)O)CC2)cc1] | 2-(((1s,4s)-4-((3-(3-hydroxypropyl)-4-phenyl-5-p-tolyl-1H-pyrazol-1-yl)methyl)cyclohexyl)methoxy)acetic acid |
| 290 | 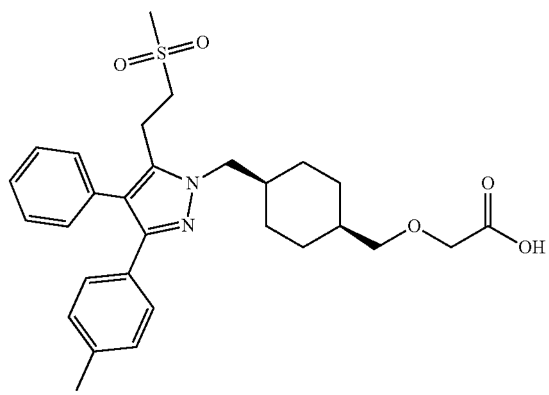 [SMILES: Cc1ccc(-c2nn(C[C@H]3CC[C@@H](COCC(=O)O)CC3)c(CCS(C)(=O)=O)c2-c2ccccc2)cc1] | 2-(((1s,4s)-4-((5-(2-(methylsulfonyl)ethyl)-4-phenyl-3-p-tolyl-1H-pyrazol-1-yl)methyl)cyclohexyl)methoxy)acetic acid |
| 291 | 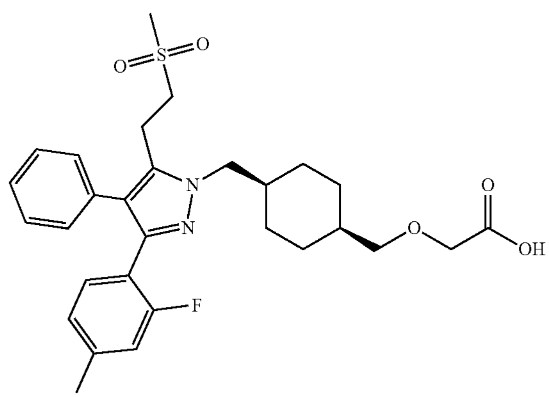 [SMILES: Cc1ccc(-c2nn(C[C@H]3CC[C@@H](COCC(=O)O)CC3)c(CCS(C)(=O)=O)c2-c2ccccc2)c(F)c1] | 2-(((1s,4s)-4-((3-(2-fluoro-4-methylphenyl)-5-(2-(methylsulfonyl)ethyl)-4-phenyl-1H-pyrazol-1-yl)methyl)cyclohexyl)methoxy)acetic acid |
| 292 | 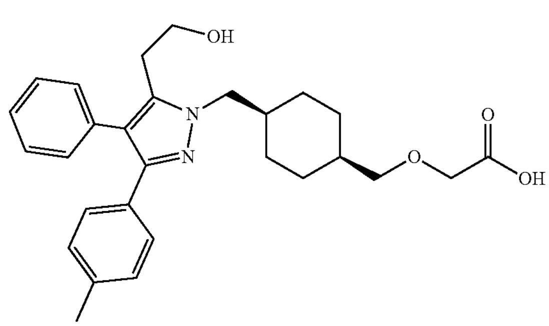 [SMILES: Cc1ccc(-c2nn(C[C@H]3CC[C@@H](COCC(=O)O)CC3)c(CCO)c2-c2ccccc2)cc1] | 2-(((1s,4s)-4-((5-(2-hydroxyethyl)-4-phenyl-3-p-tolyl-1H-pyrazol-1-yl)methyl)cyclohexyl)methoxy)acetic acid |

TABLE A-continued

| Cpd No. | Chemical Structure | Chemical Name |
|---|---|---|
| 293 | 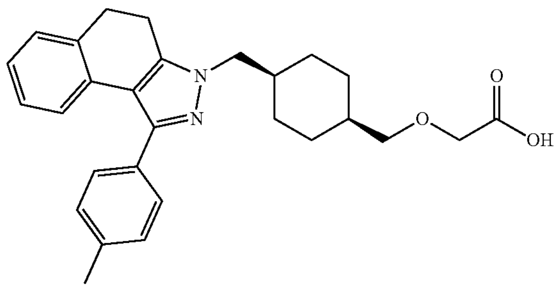 [SMILES: Cc1ccc(-c2nn(C[C@H]3CC[C@@H](COCC(=O)O)CC3)c3c2-c2ccccc2CC3)cc1] | 2-(((1s,4s)-4-((1-p-tolyl-4,5-dihydro-3H-benzo[e]indazol-3-yl)methyl)cyclohexyl)methoxy)acetic acid |

Additionally, individual compounds and chemical genera of the present invention, for example those compounds found in TABLE A including diastereoisomers and enantiomers thereof, encompass all pharmaceutically acceptable salts, solvates and particularly hydrates, thereof.

The compounds of the Formula Ia of the present invention may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]; incorporated herein by reference in its entirety).

It is understood that the present invention embraces each diastereoisomer, each enantiomer and mixtures thereof of each compound and generic formulae disclosed herein just as if they were each individually disclosed with the specific stereochemical designation for each chiral carbon. Separation of the individual isomers (such as, by chiral HPLC, recrystallization of diastereoisomeric mixtures and the like) or selective synthesis (such as, by enantiomeric selective syntheses and the like) of the individual isomers is accomplished by application of various methods which are well known to practitioners in the art.

Indications and Methods of Prophylaxis and/or Treatment

In addition to the foregoing beneficial uses for the modulators of PGI2 receptor activity disclosed herein, the compounds disclosed herein are useful in the treatment of several additional diseases and disorders, and in the amelioration of symptoms thereof. Without limitation, these include the following:

1. Pulmonary Arterial Hypertension (PAH)

Pulmonary arterial hypertension (PAH) has a multifactorial pathobiology. Vasoconstriction, remodeling of the pulmonary vessel wall, and thrombosis contribute to increased pulmonary vascular resistance in PAH (Humbert et al., J. Am. Coll, Cardiol., 2004, 43:13S-24S.)

The compounds of the present invention disclosed herein are useful in the treatment of pulmonary arterial hypertension (PAH) and symptoms thereof. PAH shall be understood to encompass the following forms of pulmonary arterial hypertension described in the 2003 World Health Organization (WHO) clinical classification of pulmonary arterial hypertension: idiopathic PAH (IPAH); familial PAH (FPAH); PAH associated with other conditions (APAH), such as PAH associated with collagen vascular disease, PAH associated with congenital systemic-to-pulmonary shunts, PAH associated with portal hypertension, PAH associated with HIV infection, PAH associated with drugs or toxins, or PAH associated with Other; and PAH associated with significant venous or capillary involvement.

Idiopathic PAH refers to PAH of undetermined cause.

Familial PAH refers to PAH for which hereditary transmission is suspected or documented.

PAH associated with collagen vascular disease shall be understood to encompass PAH associated with scleroderma, PAH associated with CREST (calcinosis cutis, Raynaud's phenomenon, esophageal dysfunction, sclerodactyly, and telangiectasias) syndrome, PAH associated with systemic lupus erythematosus (SLE), PAH associated with rheumatoid arthritis, PAH associated with Takayasu's arteritis, PAH associated with polymyositis, and PAH associated with dermatomyositis.

PAH associated with congenital systemic-to-pulmonary shunts shall be understood to encompass PAH associated with atrial septic defect (ASD), PAH associated with ventricular septic defect (VSD) and PAH associated with patent ductus arteriosus.

PAH associated with drugs or toxins shall be understood to encompass PAH associated with ingestion of aminorex, PAH associated with ingestion of a fenfluramine compound (e.g., PAH associated with ingestion of fenfluramine or PAH associated with ingestion of dexfenfluramine), PAH associated with ingestion of certain toxic oils (e.g., PAH associated with ingestion of rapeseed oil), PAH associated with ingestion of pyrrolizidine alkaloids (e.g., PAH associated with ingestion of bush tea) and PAH associated with ingestion of monocrotaline.

PAH associated with Other shall be understood to encompass PAH associated with a thyroid disorder, PAH associated with glycogen storage disease, PAH associated with Gaucher disease, PAH associated with hereditary hemorrhagic telangiectasia, PAH associated with a hemoglobinopathy, PAH associated with a myeloproliferative disorder, and PAH associated with splenectomy.

PAH associated with significant venous or capillary involvement shall be understood to encompass PAH associated with pulmonary veno-occlusive disease (PVOD) and PAH associated with pulmonary capillary hemangiomatosis (PCH).

(See, e.g., Simonneau et al., J. Am. Coll. Cardiol., 2004, 43:5S-12S; McGoon et a, Chest, 2004, 126:14S-34S; Rabinovitch, Annu. Rev. Pathol. Mech. Dis., 2007, 2:369-399; McLaughlin et al., Circulation, 2006, 114:1417-1431; Strauss et al., Clin. Chest. Med., 2007, 28:127-142; Taichman et al, Clin. Chest. Med., 2007, 28:1-22.)

Evidence for the association of PAH with scleroderma and the beneficial effect of an agonist of the PGI2 receptor on PAH is given by Badesch et al (Badesch et al, Ann. Intern.

Med., 2000, 132:425-434). Evidence for the association of PAH with the collagen vascular diseases mixed connective tissue disease (MCTD), systemic lupus erythematosus (SLE), Sjögren's syndrome and CREST syndrome and the beneficial effect of an agonist of the PGI2 receptor on PAH is given by Humbert et al (Eur. Respir. J., 1999, 13:1351-1356). Evidence for the association of PAH with CREST syndrome and the beneficial effect of an agonist of the PGI2 receptor on PAH is given by Miwa et al. (Int. Heart J., 2007, 48:417-422). Evidence for the association of PAH with SLE and the beneficial effect of an agonist of the PGI2 receptor on PAH is given by Robbins et al. (Chest, 2000, 117:14-18). Evidence for the association of PAH with HIV infection and the beneficial of an agonist of the PGI2 receptor on PAH is given by Aguilar et al. (Am. J. Respir. Crit. Care Med., 2000, 162:1846-1850). Evidence for the association of PAH with congenital heart defects (including ASD, VSD and patent ductus arteriosus) and the beneficial effect of an agonist of the PGI2 receptor on PAH is given by Rosenzweig et al. (Circulation, 1999, 99:1858-1865). Evidence for the association of PAH with fenfluramine and with dexfenfluramine, anorexigens, is given by Archer et al (Am. J. Respir. Crit. Care Med., 1998, 158:1061-1067). Evidence for the association of PAH with hereditary hemorrhagic telangiectasia is given by McGoon et al. (Chest, 2004, 126:14-34). Evidence for the association of PAH with splenectomy is given by Hoeper et a (Ann. Intern. Med., 1999, 130:506-509). Evidence for the association of PAH with portal hypertension and the beneficial effect of an agonist of the PGI2 receptor on PAH is given by Hoeper et al. (Eur. Respir. J., 2005, 25:502-508).

Symptoms of PAH include dyspnea, angina, syncope and edema (McLaughlin et al., Circulation, 2006, 114:1417-1431). The compounds of the present invention disclosed herein are useful in the treatment of symptoms of PAH.

Tawara et al have demonstrated that long-term inhibition of Rho-kinase, an effector of the small GTPase Rho, ameliorates monocrotaline-induced PAH in rats and hypoxia-induced PAH in mice. The same group also reported that prostacyclin and its oral analog, beraprost sodium (BPS), may lack direct inhibitory effect on Rho-kinase in vitro, suggesting that combination therapy with a Rho-kinase inhibitor and BPS is effective for the treatment of PAH. Thus, male Sprague-Dawley rats were given a s.c. injection of monocrotaline (60 mg/kg) and maintained with or without the treatment with a Rho-kinase inhibitor, fasudil (30 mg/kg/day), BPS (200 µg/kg/day), or a combination of both drugs for three weeks. The combination therapy, when compared with each monotherapy, showed significantly more improvement in PAH, right ventricular hypertrophy, and pulmonary medial thickness without any adverse effects. (See, Tawara et al., Journal of Cardiovascular Pharmacology (2007), 50(2), 195-200.)

The PGI2 receptor agonists disclosed herein, alone or in combination with a Rho-kinase inhibitor, are useful in the treatment of pulmonary arterial hypertension (PAH) and symptoms thereof.

The enzyme tryptophan hydroxylase (TPH), has two known isoforms: TPH1, which is expressed in the periphery, and TPH2, which is expressed primarily in the brain. Mice genetically deficient for the TPH1 gene ("knockout mice") have been reported. In one case, the mice reportedly expressed normal amounts of serotonin in classical serotonergic brain regions, but largely lacked serotonin in the periphery. Walther, D. J., et al., Science 299:76 (2003). In another, the knockout mice exhibited abnormal cardiac activity, which was attributed to a lack of peripheral serotonin. Cote, F., et al., PNAS 100(23):13525-13530 (2003).

Recently, TPH knockout mice were studied in a hypoxia-induced pulmonary arterial hypertension model. Morecroft, I., et al, Hypertension 49:232-236 (2007). The results of those studies suggest that TPH1 and peripheral serotonin play an essential role in the development of hypoxia-induced elevations in pulmonary pressures and hypoxia-induced pulmonary vascular remodeling.

The PGI2 receptor agonists disclosed herein, alone or in combination with a tryptophan hydroxylase inhibitor, are useful in the treatment of pulmonary arterial hypertension (PAH) and symptoms thereof.

2. Antiplatelet Therapies (Conditions Related to Platelet Aggregation)

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction ("MI" or "heart attack"), the heart muscle does not receive enough oxygen-rich blood as a result of a blockage in the coronary blood vessels. If taken while an attack is in progress or immediately afterward (preferably within 30 min), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes.

Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

There is evidence that a PGI2 receptor agonist will inhibit platelet aggregation and thus be a potential treatment as an antiplatelet therapy (see, e.g., Moncada et al., Lancet, 1977, 1:18-20). It has been shown that genetic deficiency of the PGI2 receptor in mice leads to an increased propensity towards thrombosis (Murata et al, Nature, 1997, 388:678-682).

PGI2 receptor agonists can be used to treat, for example, claudication or peripheral artery disease as well as cardiovascular complications, arterial thrombosis, atherosclerosis, vasoconstriction caused by serotonin, ischemia-reperfusion injury, and restenosis of arteries following angioplasty or stent placement. (See, e.g., Fetalvero et al., Prostaglandins Other Lipid Mediat., 2007, 82:109-118; Arehart et al., Curr. Med. Chem., 2007, 14:2161-2169; Davi et al., N. Engl. J. Med., 2007, 357:2482-2494; Fetalvero et al., Am. J. Physiol. Heart. Circ. Physiol., 2006, 290:H1337-H1346; Murata et al., Nature, 1997, 388:678-682; Wang et al., Proc. Natl. Acad. Sci. USA, 2006, 103:14507-14512; Xiao et al, Circulation, 2001, 104:2210-2215; McCormick et al., Biochem. Soc. Trans., 2007, 35:910-911; Arehart et al., Circ. Res., 2008, 102(8), 986-93.)

PGI2 receptor agonists can also be used alone or in combination with thrombolytic therapy, for example, tissue-type plasminogen activator (t-PA), to provide cardioprotection following MI or postischemic myocardial dysfunction or protection from ischemic injury during percutaneous coronary intervention, and the like, including complications resulting therefrom. PGI2 receptor agonists can also be used in antiplatelet therapies in combination with, for example, alpha-tocopherol (vitamin E), echistatin (a disintegrin) or, in states of hypercoagulability, heparin. (See, e.g., Chan., J. Nutr., 1998, 128:1593-1596; Mardla et al., Platelets, 2004, 15:319-324; Bernabei et al., Ann. Thorac. Surg., 1995, 59:149-153; Gainza et al., J. Nephrol., 2006, 19:648-655.)

The PGI2 receptor agonists disclosed herein provide beneficial improvement in microcirculation to patients in need of antiplatelet therapy by antagonizing the vasoconstrictive products of the aggregating platelets in, for example and not limited to the indications described above. Accordingly, in some embodiments, the present invention provides methods for reducing platelet aggregation in a patient in need thereof, comprising administering to the patient a composition comprising a PGI2 receptor agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising a PGI2 receptor agonist disclosed herein.

In further embodiments, the present invention provides methods for reducing risk of blood clot formation in an angioplasty or coronary bypass surgery patient, or a patient suffering from atrial fibrillation, comprising administering to the patient a composition comprising a PGI2 receptor agonist disclosed herein at a time where such risk exists.

3. Atherosclerosis

Atherosclerosis is a complex disease characterized by inflammation, lipid accumulation, cell death and fibrosis. It is the leading cause of mortality in many countries, including the United States. Atherosclerosis, as the term is used herein, shall be understood to encompass disorders of large and medium-sized arteries that result in the progressive accumulation within the intima of smooth muscle cells and lipids.

It has been shown that an agonist of the PGI2 receptor can confer protection from atherosclerosis, such as from atherothrombosis (Arehart et al., Curr. Med. Chem., 2007, 14:2161-2169; Stitham et al., Prostaglandins Other Lipid Mediat., 2007, 82:95-108; Fries et al., Hematology Am. Soc. Hematol. Educ. Program, 2005, 445-451; Egan et al., Science, 2004, 306:1954-1957; Kobayashi et al., J. Clin. Invest., 2004, 114:784-794; Arehart et al., Circ. Res., 2008, 102(8), 986-93).

It has been shown that defective PGI2 receptor signaling appears to accelerate atherothrombosis in humans, i.e. that an agonist of the PGI2 receptor can confer protection from atherothrombosis in humans (Arehart et al., Circ. Res., 2008, 102(8), 986-93).

The compounds of the present invention disclosed herein are useful in the treatment of atherosclerosis, and the treatment of the symptoms thereof. Accordingly, in some embodiments, the present invention provides methods for treating atherosclerosis in a patient in need of the treatment, comprising administering to the patient a composition comprising a PGI2 receptor agonist disclosed herein. In further embodiments, methods are provided for treating a symptom of atherosclerosis in a patient in need of the treatment, comprising administering to the patient a composition comprising a PGI2 receptor agonist disclosed herein.

4. Asthma

Asthma is a lymphocyte-mediated inflammatory airway disorder characterized by airway eosinophilia, increased mucus production by goblet cells, and structural remodeling of the airway wall. The prevalence of asthma has dramatically increased worldwide in recent decades. It has been shown that genetic deficiency of the PGI2 receptor in mice augments allergic airway inflammation (Takahashi et al., Br J Pharmacol, 2002, 137:315-322). It has been shown that an agonist of the PGI2 receptor can suppress not only the development of asthma when given during the sensitization phase, but also the cardinal features of experimental asthma when given during the challenge phase (Idzko et al., J. Clin. Invest., 2007, 117:464-472; Nagao et al., Am. J. Respir. Cell Mol. Biol., 2003, 29:314-320), at least in part through markedly interfering with the function of antigen-presenting dendritic cells within the airways (Idzko et al., J. Clin. Invest., 2007, 117:464-472; Zhou et al., J. Immunol., 2007, 178:702-710; Jaffar et al., J. Immunol., 2007, 179:6193-6203; Jozefowski et al., Int. Immunopharmacol., 2003, 3:865-878). These cells are crucial for both the initiation and the maintenance phases of allergic asthma, as depletion of airway dendritic cells during secondary challenge in sensitized mice abolished all characteristic features of asthma, an effect that could be completely restored by adoptive transfer of wild-type dendritic cells (van Rijt et al., J. Exp. Med., 2005, 201:981-991). It has also been shown that an agonist of the PGI2 receptor can inhibit proinflammatory cytokine secretion by human alveolar macrophages (Raychaudhuri et al., J. Biol. Chem., 2002, 277:33344-33348). The compounds of the present invention disclosed herein are useful in the treatment of asthma, and the treatment of the symptoms thereof. Accordingly, in some embodiments, the present invention provides methods for treating asthma in a patient in need of the treatment, comprising administering to the patient a composition comprising a PGI2 receptor agonist disclosed herein. In further embodiments, methods are provided for treating a symptom of asthma in a patient in need of the treatment, comprising administering to the patient a composition comprising a PGI2 receptor agonist disclosed herein.

5. Diabetic-Related Pathologies

Although hyperglycemia is the major cause for the pathogenesis of diabetic complications such as diabetic peripheral neuropathy (DPN), diabetic nephropathy (DN) and diabetic retinopathy (DR), enhanced vasoconstriction and platelet aggregation in diabetic patients has also been implicated to play a role in disease progression (Cameron et al., Naunyn Schmiedebergs Arch. Pharmacol., 2003, 367:607-614). Agonists of the PGI2 receptor promote vasodilation and inhibit platelet aggregation. Improving microvascular blood flow is able to benefit diabetic complications (Cameron, Diabetologia, 2001, 44:1973-1988).

It has been shown that an agonist of the PGI2 receptor can prevent and reverse motor and sensory peripheral nerve conduction abnormalities in streptozotocin-diabetic rats (Cotter et al., Naunyn Schmiedebergs Arch. Pharmacol., 1993, 347:534-540). Further evidence for the beneficial effect of an agonist of the PGI2 receptor in the treatment of diabetic peripheral neuropathy is given by Hotta et al. (Diabetes, 1996, 45:361-366), Ueno et al. (Jpn. J. Pharmacol., 1996, 70:177-182), Ueno et al. (Life Sci., 1996, 59:PL105-PLI10), Hotta et al. (Prostaglandins, 1995, 49:339-349), Shindo et al. (Prostaglandins, 1991, 41:85-96), Okuda et al. (Prostaglandins, 1996, 52:375-384), and Koike et al. (FASEB J., 2003, 17:779-781). Evidence for the beneficial effect of an agonist of the PGI2 receptor in the treatment of diabetic nephropathy is given by Owada et al. (Nephron, 2002, 92:788-796) and Yamashita et al. (Diabetes Res. Clin. Pract., 2002, 57:149-161). Evidence for the beneficial effect of an agonist of the PGI2 receptor in the treatment of diabetic retinopathy is given by Yamagishi et al. (Mol. Med., 2002, 8:546-550), Burnette et al. (Exp. Eye Res., 2006, 83:1359-1365), and Hotta et al. (Diabetes, 1996, 45:361-366). It has been shown that an agonist of the PGI2 receptor can reduce increased tumor necrosis factor-$\alpha$ (TNF-$\alpha$) levels in diabetic patients, implying that an agonist of the PGI2 receptor may contribute to the prevention of progression in diabetic complications (Fujiwara et al., Exp. Clin. Endocrinol. Diabetes, 2004, 112:390-394).

6. Glaucoma

Evidence that topical administration of an agonist of the PGI2 receptor can result in a decrease in intraocular pressure (IOP) in rabbits and dogs and thereby have beneficial effect in the treatment of glaucoma is given by Hoyng et al. (Hoyng et al., Invest. Ophthalmol. Vis. Sci., 1987, 28:470-476).

7. Hypertension

Agonists of the PGI2 receptor have been shown to have activity for regulation of vascular tone, for vasodilation, and for amelioration of pulmonary hypertension (see, e.g., Strauss et al., Clin Chest Med, 2007, 28:127-142; Driscoll et al., Expert Opin. Pharmacother., 2008, 9:65-81). Evidence for a beneficial effect of an agonist of the PGI2 receptor in the treatment of hypertension is given by Yamada et al. (Peptides, 2008, 29:412-418). Evidence that an agonist of the PGI2 receptor can protect against cerebral ischemia is given by Dogan et al. (Gen. Pharmacol., 1996, 27:1163-1166) and Fang et al. (J. Cereb. Blood Flow Metab., 2006, 26:491-501).

8. Anti-Inflammation Therapies

Anti-inflammation agents are prescribed for a variety of conditions. For example, in an inflammatory disease they are used to interfere with and thereby reduce an underlying deleterious There is evidence that a PGI2 receptor agonist can inhibit inflammation and thus be a potential treatment as an anti-inflammation therapy. It has been shown that an agonist of the PGI2 receptor can inhibit pro-inflammatory cytokine and chemokine (interleukin-12 (IL-12), tumor necrosis factor-$\alpha$ (TNF-$\alpha$), IL-1$\alpha$, IL-6, macrophage inflammatory protein-1alpha (MIP-1$\alpha$), monocyte chemoattractant protein-1 (MCP-1)) production and T cell stimulatory function of dendritic cells (Jozefowski et al., Int. Immunopharmacol., 2003, 865-878; Zhou et al., J. Immunol., 2007, 178:702-710; Nagao et al., Am. J. Respir. Cell Mol. Biol., 2003, 29:314-320; Idzko et al., J. Clin. Invest., 2007, 117:464-472). It has been shown that an agonist of the PGI2 receptor can inhibit pro-inflammatory cytokine (TNF-$\alpha$, IL-1$\beta$, IL-6, granulocyte macrophage stimulating factor (GM-CSF)) production by macrophages (Raychaudhuri et al., J. Biol. Chem., 2002, 277:33344-33348; Czeslick et al., Eur. J. Clin. Invest., 2003, 33:1013-1017; Di Renzo et al., Prostaglandin Leukot. Essent. Fatty Acids, 2005, 73:405-410; Shinomiya et al., Biochem. Pharmacol., 2001, 61:1153-1160). It has been shown that an agonist of the PGI2 receptor can stimulate anti-inflammatory cytokine (IL-10) production by dendritic cells (Jozefowski et al., Int. Immunopharmacol., 2003, 865-878; Zhou et al., J. Immunol., 2007, 178: 702-710). It has been shown that an agonist of the PGI2 receptor can stimulate anti-inflammatory cytokine (IL-10) production by macrophages (Shinomiya et al., Biochem. Pharmacol., 2001, 61:1153-1160). It has been shown that an agonist of the PGI2 receptor can inhibit a chemokine (CCL17)-induced chemotaxis of leukocytes (CD4$^+$ Th2 T cells) (Jaffar et al., J. Immunol., 2007, 179:6193-6203). It has been shown that an agonist of the PGI2 receptor can confer protection from atherosclerosis, such as from atherothrombosis (Arehart et al., Curr. Med. Chem., 2007, 14:2161-2169; Stitham et al., Prostaglandins Other Lipid Mediat., 2007, 82:95-108; Fries et al., Hematology Am. Soc. Hematol. Educ. Program, 2005, 445-451; Egan et al., Science, 2004, 306:1954-1957; Kobayashi et al., J. Clin. Invest., 2004, 114:784-794; Arehart et al, Circ. Res., 2008, 102(8), 986-93). It has been shown that an agonist of the PGI2 receptor can attenuate asthma (Idzko et al., J. Clin. Invest., 2007, 117:464-472; Jaffar et al., J. Immunol., 2007, 179:6193-6203; Nagao et al., Am. J. Respir. Cell. Mol. Biol., 2003, 29:314-320). It has been shown that an agonist of the PGI2 receptor can decrease TNF-$\alpha$ production in type 2 diabetes patients (Fujiwara et al., Exp. Clin. Endocrinol. Diabetes, 2004, 112:390-394; Goya et al., Metabolism, 2003, 52:192-198). It has been shown that an agonist of the PGI2 receptor can inhibit ischemia-reperfusion injury (Xiao et al., Circulation, 2001, 104:2210-2215). It has been shown that an agonist of the PGI2 receptor can inhibit restenosis (Cheng et a, Science, 2002, 296:539-541). It has been shown that an agonist of the PGI2 receptor can attenuate pulmonary vascular injury and shock in a rat model of septic shock (Harada et al., Shock, 2008, Feb. 21 Epub ahead of print). It has been shown that an agonist of the PGI2 receptor can reduce the serum levels of TNF-$\alpha$ in vivo in patients with rheumatoid arthritis, and this is associated with improvement in the clinical course of the disease (Gao et al., Rheumatol. Int., 2002, 22:45-51; Boehme et al., Rheumatol. Int., 2006, 26:340-347).

The compounds of the present invention disclosed herein provide beneficial reduction of inflammation. The compounds of the present invention disclosed herein provide beneficial reduction of a deleterious inflammatory response associated with an inflammatory disease. Accordingly, in some embodiments, the present invention provides methods for reducing inflammation in a patient in need thereof, comprising administering to the patient a composition comprising a PGI2 receptor agonist disclosed herein. In some embodiments, the present invention provides methods for decreasing IL-12, TNF-$\alpha$, IL-1a, IL-1$\beta$, IL-6, MIP-1$\alpha$ or MCP-1 production in a patient in need thereof, comprising administering to the patient a composition comprising a PGI2 receptor agonist disclosed herein. In some embodiments, the present invention provides methods for decreasing TNF-$\alpha$ production in a patient in need thereof, comprising administering to the patient a composition comprising a PGI2 receptor agonist disclosed herein. In some embodiments, the present invention provides methods for increasing IL-10 production in a patient in need thereof, comprising administering to the patient a composition comprising a PGI2 receptor agonist disclosed herein. In some embodiments, the present invention provides methods for reducing a deleterious inflammatory response associated with an inflammatory disease in a patient in need thereof, comprising administering to the patient a composition comprising a PGI2 receptor agonist disclosed herein. In some embodiments, the present invention provides methods for treating an inflammatory disease or a symptom thereof in a patient in need of the treatment comprising administering to the patient a composition comprising a PGI2 receptor agonist disclosed herein. In some embodiments, the present invention provides methods for treating an inflammatory disease or a symptom thereof in a patient in need of the treatment comprising administering to the patient a composition comprising a PGI2 receptor agonist disclosed herein. In some embodiments, the present invention provides methods for treating an inflammatory disease or a symptom thereof in a patient in need of the treatment comprising administering to the patient a composition comprising a PGI2 receptor agonist disclosed herein, wherein the inflammatory disease is selected from the group consisting of psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, diabetes (including type 1 diabetes and type 2 diabetes), sepsis, chronic obstructive pulmonary disease (COPD), and asthma.

9. Traumatic Brain Injury

Prostacyclin production is known to increase after brain trauma, and in a recent study, the importance of prostacyclin for posttraumatic hemodynamic alterations and neuron survival was investigated. Prostacyclin receptor-deficient ($IP^{-/-}$) mice were compared to mice with functional prostacyclin receptors ($IP^{+/+}$) after a controlled cortical injury. Contusion volume was increased in $IP^{-/-}$ mice compared with $IP^{+/+}$ mice. Three hours after trauma, cortical blood flow was decreased in the injured cortex of both groups and the reduction in blood flow in the cortex of the $IP^{-/-}$ mice persisted from 3 to 24 h, whereas blood flow approached normal values in the $IP^{+/+}$ mice after 24 h. (See, e.g., Lundblad et al. Journal of Cerebral Blood Flow & Metabolism (2008) 28, 367-376).

The PGI2 receptor agonists disclosed herein provide beneficial improvement in neuron survival after brain trauma. Accordingly, in some embodiments, the present invention provides methods for treating a traumatic brain injury in a patient in need thereof, comprising administering to the patient a composition comprising a PGI2 receptor agonist disclosed herein.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20<sup>th</sup> Edition, 2000, Lippincott Williams & Wilkins, (Editors: Gennaro et al.)

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate, hydrate or physiologically functional derivative thereof can be used as active ingredients in pharmaceutical compositions, specifically as PGI2 receptor modulators. By the term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt, solvate or hydrate of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents.

Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like. Certain compounds of the present invention which contain a carboxylic acid functional group may optionally exist as pharmaceutically acceptable salts containing non-toxic, pharmaceutically acceptable metal cations and cations derived from organic bases. Representative metals include, but are not limited to, aluminium, calcium, lithium, magnesium, potassium, sodium, zinc and the like. In some embodiments the pharmaceutically acceptable metal is sodium. Representative organic bases include, but are not limited to, benzathine (N,N-dibenzylethane-1,2-diamine), chloroprocaine (2-(diethylamino)ethyl 4-(chloroamino)benzoate), choline, diethanolamine, ethylenediamine, meglumine ((2R,3R,4R,5S)-6-(methylamino) hexane-1,2,3,4,5-pentaol), procaine (2-(diethylamino)ethyl 4-aminobenzoate), and the like. Certain pharmaceutically acceptable salts are listed in Berge, et al., *Journal of Pharmaceutical Sciences*, 66:1-19 (1977), incorporated herein by reference in its entirety.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the PGI2 receptor modulators are utilized as active ingredients in a pharmaceutical composition, these are not intended for use only in humans, but in other non-human mammals as well. Indeed, recent advances in the area of animal health-care mandate that consideration be given for the use of active agents, such as PGI2 receptor modulators, for the treatment of an PGI2-associated disease or disorder in companionship animals (e.g., cats, dogs, etc.) and in livestock animals (e.g., cows, chickens, fish, etc.) Those of ordinary skill in the art are readily credited with understanding the utility of such compounds in such settings.

Hydrates and Solvates

It is understood that when the phrase pharmaceutically acceptable salts, solvates and hydrates is used in referring to a particular formula herein, it is intended to embrace solvates and/or hydrates of compounds of the particular formula, pharmaceutically acceptable salts of compounds of the particular formula as well as solvates and/or hydrates of pharmaceutically acceptable salts of compounds of the particular formula.

The compounds of the present invention can be administrated in a wide variety of oral and parenteral dosage forms. It will be apparent to those skilled in the art that the following dosage forms may comprise, as the active component, either a compound of the invention or a pharmaceutically acceptable salt or as a solvate or hydrate thereof. Moreover, various hydrates and solvates of the compounds of the invention and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Poymorphs, Hydrates, Solvates, and Amorphous Solids," in: *Polymorphism in Pharmaceutical Solids*, ed. Harry G. Brittan, Vol. 95, Marcel Dekker, Inc., New York, 1999, incorporated herein by reference in its entirety. Accordingly, one aspect of the present invention pertains to hydrates and solvates of compounds of Formula Ia and/or their pharmaceutical acceptable salts, as described herein, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Other Utilities

Another object of the present invention relates to radio-labeled compounds of the present invention that would be useful not only in radio-imaging but also in assays, both in vitro and in vivo, for localizing and quantitating the PGI2 receptor in tissue samples, including human and for identifying PGI2 receptor ligands by inhibition binding of a radio-labeled compound. It is a further object of this invention to develop novel PGI2 receptor assays of which comprise such radio-labeled compounds.

The present invention embraces isotopically-labeled compounds of the present invention. Isotopically or radio-labeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{75}Br$, $^{76}Br$, $^{77}Br$, $^{82}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro PGI2 receptor labeling and competition assays, compounds that incorporate $^3$H, $^{14}$C, $^{82}$Br, $^{125}$I, $^{131}$I or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound of Formula La, Ic, Ie, Ig, or Ii that has incorporated at least one radionuclide; in some embodiments the radionuclide is selected from the group consisting of $^3$H, $^4$C, $^{125}$I, $^{35}$S and $^{82}$Br.

Certain isotopically-labeled compounds of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Drawings and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A represented procedure was reported by Zhu, G-D. and co-workers in *J. Org. Chem.*, 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.* 2001, 44, S280-S282.

A radiolabeled PGI2 receptor compound of Formula Ia can be used in a screening assay to identify/evaluate compounds. In general terms, a newly synthesized or identified compound (i.e., test compound) can be evaluated for its ability to reduce binding of the "radio-labeled compound of Formula Ia" to the PGI2 receptor. Accordingly, the ability of a test compound to compete with the "radio-labeled compound of Formula Ia" for the binding to the PGI2 receptor directly correlates to its binding affinity.

The labeled compounds of the present invention bind to the PGI2 receptor. In one embodiment the labeled compound has an IC$_{50}$ less than about 500 µM, in another embodiment the labeled compound has an IC$_{50}$ less than about 100 µM, in yet another embodiment the labeled compound has an IC$_{50}$ less than about 1 µM, in yet another embodiment the labeled compound has an IC$_{50}$ less than about 1 µM and in still yet another embodiment the labeled inhibitor has an IC$_{50}$ less than about 0.1 µM.

Other uses of the disclosed receptors and methods will become apparent to those skilled in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1: Syntheses of Compounds of the Present Invention

Illustrated syntheses for compounds of the present invention are shown in FIGS. 3 through 9 where the symbols have the same definitions as used throughout this disclosure.

The compounds of the invention and their syntheses are further illustrated by the following examples. The following examples are provided to further define the invention without, however, limiting the invention to the particulars of these examples. The compounds described herein, supra and infra, are named according to the CS ChemDraw Ultra Version 7.0.1, AutoNom version 2.2, or CS ChemDraw Ultra Version 9.0.7. In certain instances common names are used and it is understood that these common names would be recognized by those skilled in the art.

Chemistry: Proton nuclear magnetic resonance ($^1$H NMR) spectra were recorded on a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, ddd=doublet of doublet of doublets, dt=doublet of triplets, t=triplet, td=triplet of doublets, tt=triplet of triplets, q=quartet, m=multiplet, bs=broad singlet, bt=broad triplet. Microwave irradiations were carried out using a Smith Synthesizer™ or an Emrys Optimizer™ (Biotage). Thin-layer chromatography (TLC) was performed on silica gel 60 $F_{254}$ (Merck), preparatory thin-layer chromatography (prep TLC) was preformed on PK6F silica gel 60 A 1 mm plates (Whatman) and column chromatography was carried out on a silica gel column using Kieselgel 60, 0.063-0.200 mm (Merck). Evaporation was done under reduced pressure on a Büchi rotary evaporator.

LCMS spec: HPLC-pumps: LC-IOAD VP, Shimadzu Inc.; HPLC system controller: SCL-IOA VP, Shimadzu Inc; UV-Detector: SPD-IOA VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1.1: Preparation of t-Butyl 2-(((1s,4s)-4-(Tosyloxymethyl)cyclohexyl)methoxy)acetate Step A: Preparation of (1s,4s)-Diethyl Cyclohexane-1,4-dicarboxylate To a solution of (1s,4s)-cyclohexane-1,4-dicarboxylic acid (25 g, 145 mmol) in ethanol (150 mL) was added concentrated $H_2SO_4$ (1 mL). The reaction was refluxed for 16 h, cooled to room temperature and concentrated. The residue was extracted with EtOAc and saturated $NaHCO_3$, washed with brine, dried over $MgSO_4$, and filtered. The filtrate was concentrated to provide the title compound as a colorless oil (30.5 g). $^1$H NMR (400 MHz, $CDCl_3$) δ ppm 1.25 (t, J=7.14 Hz, 6H), 1.64-1.70 (m, 4H), 1.87-1.92 (m, 4H), 2.44-2.46 (m, 2H), 4.11-1.46 (quartet, J=7.12 Hz, 4H).

Step B: Preparation of (1s,4s)-Cyclohexane-1,4-diyldimethanol

To a solution of (1s,4s)-diethyl cyclohexane-1,4-dicarboxylate (13.0 g, 56.9 mmol) in THF (500 mL) was added lithium aluminum hydride (4.54 g, 120 mmol) in portions at 0° C. The mixture was stirred at that temperature for 2 h and quenched with cold water, filtered and concentrated to give the title compound as a colorless oil (8.2 g). $^1$H NMR (400 MHz, DMSO-$d_6$) δ ppm 1.27-1.42 (m, 8H), 1.46-1.54 (m, 2H), 3.26-3.31 (m, 4H), 4.27-4.30 (t, J=5.31 Hz, 2H).

Step C: Preparation of tert-Butyl 2-(((1s,4s)-4-(Hydroxymethyl)cyclohexyl)methoxy) acetate To a solution of (1s,4s)-cyclohexane-1,4-diyldimethanol (18.2 g, 126 mmol) in toluene (200 mL) was added NaOH (50% aqueous, 60 mL) and tetrabutylammonium iodide (2.331 g, 6.31 mmol), followed by tert-butyl-2-bromoacetate (20.50 mL, 139 mmol) at room temperature. The reaction mixture was stirred vigorously at room temperature for 2 h and diluted with ethyl acetate and water. After separation, the aqueous layer was extracted with EtOAc (3×30 mL). The combined organic layers were dried over $MgSO_4$, concentrated, and purified by silica gel column chromatography to give the title compound as a colorless oil (13.5 g). $^1$H NMR (400 MHz, $CDCl_3$) δ ppm 1.35-1.47 (m, 4H), 1.48 (s, 9H), 1.50-1.60 (m, 4H), 1.63-1.74 (m, 1H), 1.79-1.92 (m, 1H), 3.42 (d, J=6.95 Hz, 2H), 3.55 (d, J=6.82 Hz, 2H), 3.93 (s, 1H), 3.94 (s, 2H).

Step D: Preparation of tert-Butyl 2-(((1s,4s)-4-(Tosyloxymethyl)cyclohexyl)methoxy)acetate To a solution of tert-butyl 2-(((1s,4s)-4-(hydroxymethyl)cyclohexyl)methoxy)acetate (12.0 g, 46.4 mmol) in dichloromethane (150 mL) were added triethylamine (4.70 g, 46.4 mmol) and 4-(dimethylamino)pyridine (0.567 g, 4.64 mmol), followed by 4-methylbenzene-1-sulfonyl chloride (8.86 g, 46.4 mmol). The reaction was stirred at room temperature for 16 h. The solvent was removed and the residue was extracted with EtOAc/$H_2O$. The organic extracts were dried over $MgSO_4$, and concentrated. The residue was purified by silica gel column chromatography to give the title compound as a pale liquid (9.5 g). LCMS m/z=413.1 [M+H]$^+$; $^1$H NMR (400 MHz, $CDCl_3$) δ ppm 1.28-1.43 (m, 4H), 1.46-1.48 (m, 9H), 1.49-1.56 (m, 4H), 1.76-1.91 (m, 2H), 2.45 (s, 3H), 3.36 (d, J=6.95 Hz, 2H), 3.92 (d, J=7.05 Hz, 2H), 3.92 (s, 2H), 7.35 (d, J=8.46 Hz, 2H), 7.78 (d, J=8.34 Hz, 2H).

Example 1.2: Preparation of 2-(((1s,4s)-4-((4-(3-Chlorophenyl)-5-(methylthio)-3-phenyl-1H-pyrazol-1-yl)methyl)cyclohexyl)methoxy)acetic Acid (Compound 95)

Step A: Preparation of 4-(3-Chlorophenyl)-5-(methylthio)-3-phenyl-1H-pyrazole

To a solution of 2-(3-chlorophenyl)-1-phenylethanone (5 g, 21.67 mmol) in anhydrous THF (10 mL) was added a solution of 1.0 M KO-t-Bu in THF. The reaction was stirred for 15 min at room temperature, then $CS_2$ (1.782 g, 23.41 mmol) was added. After 10 min, iodomethane (6.77 g, 47.7 mmol) was added and the reaction was stirred for 4 h. The reaction was washed with saturated $NaHCO_3$ solution and dried over $MgSO_4$. The filtrate was concentrated under reduced pressure and the residue was triturated with 10% ethyl acetate. The solid was suspended in ethanol and hydrazine hydrate (5.43 g, 108 mmol) was added at room temperature. The reaction was refluxed for 4 h. The reaction mixture was concentrated under reduced pressure and the residue was triturated with ethyl acetate/hexane to give the title compound as a white solid (4.9 g). LCMS m/z=301.1 [M+H]$^+$.

Step B: Preparation of 2-(((1s,4s)-4-((4-(3-Chlorophenyl)-5-(methylthio)-3-phenyl-1H-pyrazol-1-yl)methyl)cyclohexyl)methoxy)acetic Acid To a solution of 4-(3-chlorophenyl)-5-(methylthio)-3-phenyl-1H-pyrazole (4.98 g, 16.62 mmol) in DMF (2 mL) was added sodium hydride (0.399 g, 16.62 mmol) at 0° C. After stirring for 10 min, tert-butyl 2-(((1s,4s)-4-(tosyloxymethyl)cyclohexyl)methoxy)acetate (6.86 g, 16.62 mmol) was added and warmed to 40° C. After stirring for 12 h, the mixture was extracted with ethyl acetate. The organic extract was concentrated under reduced pressure and the residue was treated with 4.0 M HCl for 8 h. The mixture was concentrated under reduced pressure and purified by HPLC to give the title compound (3.89 g). LCMS m/z=486.1 [M+H]$^+$; $^1$H NMR (400 MHz, DMSO-$d_6$) δ ppm 1.31-1.50 (m, 8H), 1.74 (m, 1H), 2.14 (m, 1H), 2.31 (s, 3H), 3.52 (d, J=7.0 Hz, 2H), 3.58 (s, 2H), 4.25 (d, J=7.5 Hz, 2H), 7.25-7.51 (m, 9H).

Example 1.3: Preparation of 2-(((1s,4s)-4-((4-(3,4-Difluorophenyl)-5-ethoxy-3-phenyl-1H-pyrazol-1-yl)methyl)cyclohexyl)methoxy)acetic Acid (Compound 80)

Step A: Preparation of 3-Phenyl-1H-pyrazol-5(4H)-one

To a solution of propyl 3-oxo-3-phenylpropanoate (10 g, 48.5 mmol) in ethanol (100 mL) was added hydrazine hydrate (9.71 g, 194 mmol) at room temperature. The reaction was heated to 80° C. for 2 h, cooled to room temperature and concentrated. The residue was crystallized from 20% ethyl acetate/hexane to give the title compound (6.58 g). LCMS m/z=161.08 [M+H]+; 1H NMR (400 MHz, DMSO-$d_6$) δ ppm, 2.32 (br, 2H), 7.32-7.78 (m, 5H), 12.1 (s, 1H).

Step B: Preparation of
5-Ethoxy-3-phenyl-1H-pyrazole

To a solution of 3-phenyl-1H-pyrazol-5(4H)-one (1.0 g, 6.24 mmol), ethanol (0.288 g, 6.24 mmol) and triphenylphosphine (1.638 g, 6.24 mmol) in N-methylmorpholine (7 mL) was added diethylazo dicarboxylate (0.988 mL, 6.24 mmol) dropwise at 0° C. The reaction was warmed to room temperature and stirred for 2 h. The reaction was poured into H$_2$O and extracted with ethyl acetate. The extract was dried over MgSO$_4$ and concentrated under reduced pressure. The residue was purified by silica gel column chromatography to give the title compound (0.89 g). LCMS m/z=189.19 [M+H]+; 1H NMR (400 MHz, DMSO-$d_6$) δ ppm 132 (t, J=4.2 Hz, 3H), 4.32 (q, J=4.2 Hz, 2H), 6.45 (s, 1H), 7.41-7.94 (m, 5H), 11.3 (s, 1H).

Step C: Preparation of
4-Bromo-5-ethoxy-3-phenyl-1H-pyrazole

To a solution of 5-ethoxy-3-phenyl-1H-pyrazole (1.0 g, 5.31 mmol) in dichloromethane (20 mL), was added bromine (0.849 g, 5.31 mmol) dropwise at room temperature. The reaction was stirred for 2 h, washed with saturated NaHCO$_3$ solution and concentrated under reduced pressure. The residue was triturated with 10% ethyl acetate/hexane to give the title compound as a yellowish solid (1.20 g). LCMS m/z=268.07 [M+H]+; 1H NMR (400 MHz, DMSO-$d_6$) δ ppm 1.38 (t, J=4.2 Hz, 3H), 4.39 (q, J=4.2 Hz, 21), 7.45-7.85 (m, 5H), 12.4 (s, 1H).

Step D: Preparation of tert-Butyl 2-(((1s,4s)-4-((4-Bromo-5-ethoxy-3-phenyl-1H-pyrazol-1-yl)methyl)cyclohexyl)methoxy)acetate To a solution of 4-bromo-5-ethoxy-3-phenyl-1H-pyrazole (1.5 g, 5.62 mmol) in DMF (5 mL) was added sodium hydride (0.135 g, 5.62 mmol) at room temperature. After stirring for 10 min, a solution of tert-butyl 2-(((1s,4s)-4-(tosyloxymethyl)cyclohexyl)methoxy)acetate (2.317 g, 5.62 mmol) in DMF (1 mL) was added at room temperature. The reaction was stirred at 45° C. for 8 h. The mixture was poured into H$_2$O and extracted with ethyl acetate. The organic extract was dried over MgSO$_4$ and concentrated under reduced pressure. The residue was purified by silica gel to give the title compound (1.45 g). LCMS m/z=508.35 [M+H]+.

Step E: Preparation of 2-(((1s,4s)-4-((4-(3,4-Difluorophenyl)-5-ethoxy-3-phenyl-1H-pyrazol-1-yl)methyl)cyclohexyl)methoxy)acetic Acid To a solution of tert-butyl 2-(((1s,4s)-4-((4-bromo-5-ethoxy-3-phenyl-1H-pyrazol-1-yl)methyl)cyclohexyl)methoxy)acetate (110 mg, 0.217 mmol) in dioxane (2 mL) were added 3,4-difluorophenylboronic acid (34.2 mg, 0.217 mmol), Pd(PPh$_3$)$_4$ (12.52 mg, 10.84 μmol), and K$_2$CO$_3$ (59.9 mg, 0.434 mmol) at room temperature. The reaction was irradiated under microwave for 1.5 h at 150° C. The mixture was filtered and the filtrate was concentrated under reduced pressure. The residue was treated with 4.0 M HCl (5 mL). After stirring for 10 h, the reaction was concentrated under reduced pressure and purified by HPLC to give the title compound (85 mg). LCMS m/z=485.3 [M+H]+; 1H NMR (400 MHz, DMSO-$d_6$) δ ppm 1.21 (t, J=4.1 Hz, 3H), 1.30-1.41 (m, 8H), 1.63-1.74 (m, 1H), 2.18-2.23 (m, 1H), 3.49 (d, J=7.1 Hz, 2H), 3.71 (s, 2H), 3.85 (q, J=4.1 Hz, 2H), 4.12 (d, J=7.4 Hz, 2H), 7.76-7.32 (m, 8H).

Example 1.4: Preparation of 2-(((1s,4s)-4-((4-(5-Cyano-2-fluorophenyl)-5-(methylthio)-3-phenyl-1H-pyrazol-1-yl)methyl)cyclohexyl)methoxy)acetic Acid (Compound 79)

Step A: Preparation of
5-(Methylthio)-3=phenyl-1H-pyrazole

To a solution of acetophenone (5.0 g, 41.6 mmol) and CS$_2$ (3.17 g, 41.6 mmol) in THF (150 mL) was added sodium hydride (1.997 g, 83 mmol) at 0° C. After 30 min at 0° C., the reaction was warmed to room temperature and stirred for 1 h, then refluxed for 4 h. The reaction was cooled to room temperature, added iodomethane (16.23 g, 104 mmol), and refluxed for another 12 h. The reaction was cooled and extracted with ethyl acetate. The organic extracts were concentrated under reduced pressure. The residue was diluted with ethanol (200 mL), added hydrazine (1.334 g, 41.6 mmol), and refluxed for 4 h. After cooling, the mixture was concentrated under reduced pressure and extracted with ethyl acetate. The organic extracts were dried over MgSO$_4$ and concentrated under reduced pressure. The residue was purified by silica gel column chromatography to give the title compound (6.02 g). LCMS m/z=191.37 [M+H]+; 1H NMR (400 MHz, DMSO-$d_6$) δ ppm 2.31 (s, 3H), 6.21 (s, 1H), 7.38-7.56 (m, 5H), 12.2 (s, 1H).

Step B: Preparation of
4-Iodo-5-(methylthio)-3-phenyl-1H-pyrazole

To a solution of 5-(methylthio)-3-phenyl-1H-pyrazole (1.5 g, 7.88 mmol) in THF (20 mL) and water (20 mL), were added sodium iodide (1.182 g, 7.88 mmol), iodine (3.00 g, 11.83 mmol), and K$_2$CO$_3$ (1.634 g, 11.83 mmol) at room temperature. The reaction was warmed to 100° C. and stirred for 2 h. The reaction was quenched with 2.0 M aqueous sodium thiosulfite and concentrated under reduced pressure. The mixture was extracted with ethyl acetate and washed with NaHCO$_3$ solution. The organic extracts were dried over MgSO$_4$ and concentrated under reduced pressure. The residue was purified by silica gel column chromatography to give the title compound (2.35 g). LCMS m/z=317.02 [M+H]+; 1H NMR (400 MHz, DMSO-$d_6$) δ ppm 2.43 (s, 3H), 7.43-7.79 (m, 5H), 13.5 (s, 1H).

Step C: Preparation of tert-Butyl 2-(((1s,4s)-4-((4-Iodo-5-(methylthio)-3-phenyl-1H-pyrazol-1-yl)methyl)cyclohexyl)methoxy)acetate To a solution of 5-(methylthio)-3,4-diphenyl-1H-pyrazole (100 mg, 0.375 mmol) in DMF (3 mL), was added sodium hydride (9.01 mg, 0.375 mmol) at room temperature. After stirring for 10 min, a solution of tert-butyl 2-(((1s,4s)-4-(tosyloxymethyl)cyclohexyl)methoxy)acetate (154 mg, 0.375 mmol) in DMF (1 mL) was added at room temperature. The reaction was heated to 45° C. and stirred for 8 h. The reaction was poured into H$_2$O and extracted with ethyl acetate. The organic extract was dried over MgSO$_4$ and concentrated under reduced pressure. The residue was purified by silica gel column chromatography to give the title compound (2.98 g). LCMS m/z=557.48 [M+H]$^+$.

Step D: Preparation of 2-(((1s,4s)-4-((4-(5-Cyano-2-fluorophenyl)-5-(methylthio)-3-phenyl-1H-pyrazol-1-yl)methyl)cyclohexyl)methoxy)acetic Acid To a solution of tert-butyl 2-(((1s,4s)-4-((4-iodo-5-(methylthio)-3-phenyl-1H-pyrazol-1-yl)methyl)cyclohexyl) methoxy)acetate (110 mg, 0.198 mmol) in dioxane (2 mL), were added 5-cyano-2-fluorophenylboronic acid (32.6 mg, 0.198 mmol), Pd(PPh$_3$)$_4$ (11.42 mg, 9.88 µmol), and K$_2$CO$_3$ (54.6 mg, 0.395 mmol) at room temperature. The reaction was heated under microwave irradiation for 1.5 h at 150° C. The mixture was filtered and concentrated under reduced pressure. The residue was treated with 4.0 M HCl (5 mL) for 10 h. The mixture was concentrated under reduced pressure and purified by HPLC to give the title compound (68 mg). LCMS m/z=494.5 [M+H]$^+$; $^1$H NMR (400 MHz, DMSO-d$_6$) δ ppm 1.31-1.40 (m, 8H), 1.60-1.78 (m, 1H), 2.18-2.20 (m, 1H), 2.38 (s, 3H), 3.51 (d, J=7.0 Hz, 2H), 3.79 (s, 2H), 4.19 (d, J=7.5 Hz, 2H), 7.21-7.34 (m, 5H), 7.80-7.41 (m, 3H).

Example 1.5: Preparation of 2-(((1s,4s)-4-((4-(Furan-2-yl)-5-(methylthio)-3-phenyl-1H-pyrazol-1-yl)methyl)cyclohexyl)methoxy)acetic Acid (Compound 109)

To a solution of tert-butyl 2-(((1s,4s)-4-((4-iodo-5-(methylthio)-3-phenyl-1H-pyrazol-1-yl)methyl)cyclohexyl) methoxy)acetate (150 mg, 0.270 mmol) in dioxane (1 mL), was added furan-2-yl boronic acid (31.23 mg, 0.270 mmol) followed by Pd(PPh$_3$)$_4$ (15.57 mg, 0.013 mmol) and K$_2$CO$_3$ (74.5 mg, 0.539 mmol) at room temperature. The reaction was heated under microwave at 120° C. for 1.5 h. The mixture was extracted with ethyl acetate and the organic extract was concentrated under reduced pressure. The residue was treated with 4.0 M HCl (3.37 mL, 13.48 mmol) for 5 h. The reaction was concentrated under reduced pressure and purified by HPLC to give the title compound (88 mg). LCMS m/z=441.3 [M+H]$^+$; $^1$H NMR (400 MHz, DMSO-d$_6$) δ ppm 1.24-1.39 (m, 8H), 1.64-1.80 (m, 1H), 2.12-2.17 (m, 1H), 2.34 (s, 3H), 3.49 (d, J=7.0 Hz, 2H), 3.78 (s, 2H), 4.19 (d, J=7.5 Hz, 2H), 7.31-7.45 (m, 8H).

Example 1.6: Preparation of 2-(((1s,4s)-4-((4-(5-Fluoropyridin-3-yl)-5-(methylthio)-3-phenyl-1H-pyrazol-1-yl)methyl)cyclohexyl)methoxy)acetic Acid (Compound 135)

To a solution of tert-butyl 2-(((1s,4s)-4-((4-iodo-5-(methylthio)-3-phenyl-1H-pyrazol-1-yl)methyl)cyclohexyl) methoxy)acetate (500 mg, 0.898 mmol) in dioxane (5 mL) was added 5-fluoropyridin-3-ylboronic acid (127 mg, 0.898 mmol) followed by Pd(PPh$_3$)$_4$ (51.9 mg, 0.045 mmol) and K$_2$CO$_3$ (248 mg, 1.797 mmol) at room temperature. The reaction was heated under microwave irradiation at 120° C. for 1.5 h. The reaction mixture was extracted with ethyl acetate and the organic extracts were concentrated under reduced pressure. The residue was treated with 4.0 M HC (11.23 mL, 44.9 mmol) in dioxane for 5 h. The mixture was concentrated under reduced pressure and the residue was purified by HPLC to give the title compound as a solid. The solid was dissolved in acetonitrile (1 mL) and water (2 mL) and added 1.0 eq. of NaOH in H$_2$O (1 mL). The mixture was concentrated under reduced pressure to give the sodium salt of the title compound (210 mg). LCMS m/z=470.2 [M+H]$^+$; $^1$H NMR (400 MHz, DMSO-d$_6$) δ ppm 1.39-1.58 (m, 8H), 174-1.80 (m, 1H), 2.20 (s, 3H), 2.21-2.31 (m, 1H), 3.31 (d, J=7.0 Hz, 2H), 3.73 (s, 2H), 4.32 (d, J=7.5 Hz, 2H), 6.65-7.40 (m, 5H), 7.76-7.70 (m, 1H), 8.34 (s, 1H), 8.55 (s, 1H).

Example 1.7: Preparation of 2-(((1s,4s)-4-((5-(Methylthio)-4-(5-methylthiophen-2-yl)-3-phenyl-1H-pyrazol-1-yl)methyl)cyclohexyl)methoxy)acetic Acid (Compound 111)

To a solution of tert-butyl 2-(((1s,4s)-4-((4-iodo-5-(methylthio)-3-phenyl-1H-pyrazol-1-yl)methyl)cyclohexyl) methoxy)acetate (500 mg, 0.981 mmol) in dioxane (5 mL) was added 5-methylthiophen-2-ylboronic acid (139 mg, 0.981 mmol) followed by Pd(PPh$_3$)$_4$ (56.7 mg, 0.049 mmol) and K$_2$CO$_3$ (271 mg, 1.963 mmol) at room temperature. The reaction was heated under microwave at 120° C. for 1.5 h. The mixture was extracted with ethyl acetate and concentrated under reduced pressure. The residue was treated with HCl (4.0 M in dioxane) for 5 h. The mixture was concentrated under reduced pressure and the residue was purified by HPLC to give the title compound as a solid. The solid was dissolved in acetonitrile (1 mL) and water (2 mL) and added 1.0 eq. of NaOH in H$_2$O (1 mL). The mixture was concentrated under reduced pressure to give the sodium salt of the title compound (158 mg). LCMS m/z=470.1 [M+H]$^+$; $^1$H NMR (400 MHz, DMSO-d$_6$) δ ppm 1.21-1.49 (m, 8H), 1.63-1.79 (m, 1H), 2.08-2.13 (m, 1H), 2.15 (s, 3H), 2.35 (s, 3H), 3.54 (d, J=7.0 Hz, 2H), 3.88 (s, 2H), 4.20 (d, J=7.5 Hz, 2H), 7.23-7.48 (m, 7H).

Example 1.8: Preparation of 2-(((1s,4s)-4-((4-(3-Methoxyphenyl)-5-methyl-3-phenyl-1H-pyrazol-1-yl)methyl)cyclohexyl)methoxy)acetic Acid (Compound 14)

To a solution of tert-butyl 2-(((1s,4s)-4-((4-bromo-5-methyl-3-phenyl-1H-pyrazol-1-yl)methyl)cyclohexyl) methoxy)acetate (1.5 g, 3.14 mmol) in dioxane (12 mL) was added 3-methoxyphenylboronic acid (0.477 g, 3.14 mmol) followed by Pd(PPh$_3$)$_4$ (0.182 g, 0.157 mmol) and K$_2$CO$_3$ (0.868 g, 6.28 mmol) at room temperature. The reaction was heated under microwave irradiation at 150° C. for 1 h. The reaction was extracted with ethyl acetate and the organic extracts were concentrated under reduced pressure. The residue was treated with HCl (4.0 M in dioxane) for 5 h. The mixture was concentrated under reduced pressure and the residue was purified by HPLC to give the title compound as the free acid. The free acid was treated with NaOH in 30% acetonitrile/H$_2$O and the mixture was concentrated under reduced pressure to give the sodium salt of the title compound (0.687 g). LCMS m/z=449.2 [M+H]$^+$; $^1$H NMR (400 MHz, DMSO-d$_6$) δ ppm 1.30-1.52 (m, 8H), 1.71-1.83 (m, 1H), 2.01-2.11 (m, 1H), 2.20 (s, 3H), 3.41 (d, J=7.0 Hz, 2H), 3.78 (s, 2H), 3.85 (s, 3H), 4.13 (d, J=7.5 Hz, 2H), 6.65-7.40 (m, 9H).

Example 1.9: Preparation of 2-(((1R,4s)-4-((5-((S)-3,4-Dihydroxybutyl)-4-(3-hydroxyphenyl)-3-phenyl-1H-pyrazol-1-yl)methyl)cyclohexyl)methoxy)acetic Acid (Compound 161)

Step A: Preparation of 1-Phenylhept-6-ene-1,3-dione

To a solution of 1-phenylbutane-1,3-dione (5 g, 30.8 mmol) in THF (50 mL) was added sodium hydride (0.740 g, 30.8 mmol) at 0° C. After warming and stirring at room temperature for 30 min, LDA, which was made by adding BuLi (1.975 g, 30.8 mmol) to a solution of diisopropylamine (4.39 mL, 30.8 mmol) in THF (50 mL) at −45° C., was added at 0° C. After stirring for 30 min at the same temperature, 3-bromoprop-1-ene (3.73 g, 30.8 mmol) was added at 0° C. After stirring for 1 h, the reaction was quenched with 1.0 M HCl and extracted with ethyl acetate. The organic extract was dried over $MgSO_4$ and concentrated under reduced pressure to give the title compound without further purification. LCMS m/z=203.19 [M+H]$^+$.

Step B: Preparation of 5-(But-3-enyl)-3-phenyl-1H-pyrazole

To a solution of 1-phenylhept-6-ene-1,3-dione (3 g, 14.83 mmol) in ethanol (50 mL) was added hydrazine hydrate (2.228 g, 44.5 mmol) at room temperature. The reaction was refluxed for 10 h, cooled to room temperature and concentrated under reduced pressure. The residue was extracted with ethyl acetate. The organic extract was dried over $MgSO_4$ and concentrated under reduced pressure to give the title compound without further purification. LCMS m/z=199.3 [M+H]$^+$; $^1$H NMR (400 MHz, DMSO-d$_6$) δ ppm 2.65-2.78 (m, 2H), 4.01-4.12 (m, 2H), 4.83-4.95 (m, 2H), 5.82-5.93 (m, 1H), 6.42 (s, 1H), 7.23-7.82 (in, 5H), 12.6 (s, 1H).

Step C: Preparation of (S)-4-(3-Phenyl-1H-pyrazol-5-yl)butane-1,2-diol

To a solution of 5-(but-3-enyl)-3-phenyl-1H-pyrazole (1 g, 5.04 mmol) in $H_2O$ (25 mL), and isopropanol (25 mL) was added AD-mix-$ (5 g, 5.04 mmol) at room temperature. The reaction was stirred for 48 h, quenched with $Na_2SO_3$ and extracted with ethyl acetate. The organic extract was dried over $MgSO_4$ and concentrated under reduced pressure to give the title compound (1.02 g) without further purification. LCMS m/z=232.9 [M+H]$^+$.

Step D: Preparation of (S)-5-(2-(2,2-Dimethyl-1,3-dioxolan-4-yl)ethyl)-3-phenyl-1H-pyrazole To a solution of (S)-4-(3-phenyl-1H-pyrazol-5-yl)butane-1,2-diol (2.5 g, 10.76 mmol) in acetone (50 mL) were added 2,2-dimethoxypropane (11.21 g, 108 mmol) and p-toluenesulfonic acid (0.185 g, 1.076 mmol) at room temperature. After stirring for 3 h, the reaction was concentrated under reduced pressure. The residue was extracted with ethyl acetate. The organic extract was dried over $MgSO_4$ and concentrated under reduced pressure to give the title compound (2.70 g) without further purification. LCMS m/z=273.0 [M+H]$^+$.

Step E: Preparation of (S)-4-Bromo-5-(2-(2,2-dimethyl-1,3-dioxolan-4-yl)ethyl)-3-phenyl-1H-pyrazole To a solution of (S)-5-(2-(2,2-dimethyl-1,3-dioxolan-4-yl)ethyl)-3-phenyl-1H-pyrazole (11 g, 4.04 mmol) and MP-carbonate in $CH_2Cl_2$ (50 mL) was added bromine (0.645 g, 4.04 mmol) dropwise at 0° C. After stirring for 1 h, MP-carbonate (12.4 g, 40.4 mmol) was filtered off and washed with $CH_2Cl_2$. The combined filtrate was poured into water, extracted with $CH_2Cl_2$, dried over $MgSO_4$, and concentrated under reduced pressure. The residue was purified by silica gel column chromatography to give the title compound as an oil (1.129 g). LCMS m/z=351.1 [M+H]$^+$.

Step F: Preparation of tert-Butyl 2-(((1R,4s)-4-((4-Bromo-5-(2-((S)-2,2-dimethyl-1,3-dioxolan-4-yl) ethyl)-3-phenyl-1H-pyrazol-1-yl)methyl)cyclohexyl) methoxy)acetate To a solution of (S)-4-bromo-5-(2-(2,2-dimethyl-1,3-dioxolan-4-yl)ethyl)-3-phenyl-1H-pyrazole (1.23 g, 3.50 mmol) in DMF (10 mL) was added sodium hydride (0.084 g, 3.50 mmol) at room temperature. After stirring for 30 min, tert-butyl 2-(((1s,4s)-4-(tosyloxymethyl)cyclohexyl) methoxy)acetate (1.44 g, 3.50 mmol) was added and the reaction was heated to 45° C. After stirring for 12 h at the same temperature, the reaction was poured into $H_2O$ and extracted with ethyl acetate. The organic extract was dried over $MgSO_4$ and concentrated under reduced pressure to give the title compound without further purification. LCMS m/z=592.1 [M+H]$^+$.

Step G: Preparation of 2-(((1R,4s)-4-((5-((S)-3,4-Dihydroxybutyl)-4-(3-hydroxyphenyl)-3-phenyl-1H-pyrazol-1-yl)methyl)cyclohexyl)methoxy)acetic Acid To a solution of tert-butyl 2-(((1s,4s)-4-((4-bromo-5-(2-((S)-2,2-dimethyl-1,3-dioxolan-4-yl)ethyl)-3-phenyl-1H-pyrazol-1-yl)methyl)cyclohexyl)methoxy)acetate (150 mg, 0.254 mmol) in dioxane (1 mL) was added 3-hydroxyphenylboronic acid (35.0 mg, 0.254 mmol) followed by Pd(PPh$_3$)$_4$ (14.65 mg, 0.013 mmol) and $K_2CO_3$ (70.1 mg, 0.507 mmol) at room temperature. The reaction was heated under microwave at 120° C. for 1.5 h. The reaction was extracted with ethyl acetate and concentrated under reduced pressure. The residue was treated with HCl (4.0 M in dioxane) for 5 h. The mixture was concentrated under reduced pressure and purified by HPLC to give the title compound (59 mg). LCMS m/z=509.3 [M+H]$^+$; $^1$H NMR (400 MHz, DMSO-d$_6$) δ ppm 1.20-1.62 (m, 12H), 1.75-1.80 (m, 1H), 2.10-2.15 (m, 1H), 2.45-2.70 (m, 1H), 3.14-3.20 (m, 2H), 3.39 (d, J=7.0 Hz, 2H), 3.83 (s, 2H), 4.05 (d, J=7.5 Hz, 2H), 6.50-7.35 (m, 9H).

Example 1.10: Preparation of 2-(((1s,4s)-4-((5-(Cyanomethylthio)-3,4-diphenyl-1H-pyrazol-1-yl) methyl)cyclohexyl)methoxy)acetic Acid (Compound 184)

Step A: Preparation of 3,4-Diphenyl-1H-pyrazole-5(4H)-thione

To a solution of 1,2-diphenylethanone (10 g, 51.0 mmol) in acetone (250 mL) were added $K_2CO_3$ (21.1 g, 153 mmol), $CS_2$ (11.62 g, 153 mmol), and dibromomethane (26.5 g, 153 mmol) at room temperature. The reaction was stirred for 48 h at 40° C. The reaction mixture was extracted with ethyl acetate, dried over $MgSO_4$, and concentrated under reduced pressure. The resulting residue was diluted with ethanol (125 mL) and hydrazine hydrate (2.55 g, 50.9 mmol) was added at room temperature. The reaction was refluxed for 4 h, cooled, and concentrated under reduced pressure. The residue was triturated with isopropanol and dried under reduced pressure to give the title compound as a white solid (8.25 g). LCMS m/z=253.1 [M+H]$^+$; $^1$H NMR (400 MHz, DMSO-d$_6$) δ ppm 3.14 (bs, 1H), 7.34-7.54 (m, 10H), 12.5 (s, 1H).

Step B: Preparation of 2-(3,4-Diphenyl-1H-pyrazol-5-ylthio)acetonitrile

To a solution of 3,4-diphenyl-1H-pyrazole-5(4H)-thione (0.5 g, 1.981 mmol) in DMF (5 mL), were added 2-bromoacetonitrile (0.238 g, 1.981 mmol) and $K_2CO_3$ (0.274 g, 1.981 mmol) at room temperature. After stirring at the same temperature for 1 h, the reaction was extracted with ethyl acetate; which was dried over $MgSO_4$ and concentrated under reduced pressure. The residue was purified by silica gel column chromatography to give the title compound (0.38 g). LCMS m/z=292.0 [M+H]$^+$; $^1$H NMR (400 MHz, DMSO-$d_6$) δ ppm 3.20 (s, 2H), 7.35-7.45 (m, 10H), 13.7 (s, 1H).

Step C: Preparation of 2-(((1s,4s)-4-((5-(Cyanomethylthio)-3,4-diphenyl-1H-pyrazol-1-yl)methyl)cyclohexyl)methoxy)acetic Acid To a solution of 2-(3,4-diphenyl-1H-pyrazol-5-ylthio)acetonitrile (330 mg, 1.133 mmol) in DMF (2 mL) was added sodium hydride (27.2 mg, 1.133 mmol) at 0° C. After stirring for 10 min, tert-butyl 2-(((1s,4s)-4-(tosyloxymethyl)cyclohexyl)methoxy)acetate (467 mg, 1.133 mmol) was added. The reaction was warmed to 40° C. and stirred for 12 h. The reaction mixture was extracted with ethyl acetate. The organic extract was concentrated under reduced pressure and the residue was treated with 4.0 M HCl for 8 h. The mixture was concentrated under reduced pressure and the residue was purified by HPLC to give the title compound (92 mg). LCMS m/z=476.3 [M+H]$^+$; $^1$H NMR (400 MHz, DMSO-$d_6$) δ ppm 1.31-1.53 (m, 8H), 1.63 (m, 1H), 2.15 (m, 1H), 3.32 (d, J=7.0 Hz, 2H), 3.63 (s, 2H), 3.73 (s, 2H), 4.25 (d, J=7.5 Hz, 2H), 7.21-7.35 (m, 10H).

Example 1.11: Preparation of 2-(((1s,4s)-4-((5-(Methylthio)-3,4-diphenyl-1H-pyrazol-1-yl)methyl)cyclohexyl)methoxy)acetic Acid (Compound 76)

Step A: Preparation 5-(Methylthio)-3,4-diphenyl-1H-pyrazole

To a solution of 1,2-diphenylethanone (5 g, 25.5 mmol) in anhydrous THF (10 mL) was added a solution of 1.0 M KO-t-Bu in THF (108 mL). The reaction was stirred for 15 min at room temperature, then $CS_2$ (2.09 g, 27.5 mmol) was added. After 10 min, iodomethane (7.96 g, 56.1 mmol) was added and the reaction was stirred for 4 h. The reaction was washed with saturated $NaHCO_3$ solution and dried over $MgSO_4$. The filtrate was concentrated under reduced pressure and the residue was triturated with 10% ethyl acetate. The solid was suspended in ethanol and hydrazine hydrate (5.10 g, 102 mmol) was added at room temperature. The reaction was refluxed for 4 h. The reaction mixture was concentrated under reduced pressure and the residue was triturated with ethyl acetate/hexane to give the title compound as a white solid (5.2 g). LCMS m/z=267.27 [M+H]$^+$.

Step B: Preparation of 2-(((1s,4s)-4-((5-(Methylthio)-3,4-diphenyl-1H-pyrazol-1-yl)methyl)cyclohexyl)methoxy)acetic Acid To a solution of 5-(methylthio)-3,4-diphenyl-1H-pyrazole (100 mg, 0.375 mmol) in DMF (3 mL) was added sodium hydride (9.01 mg, 0.375 mmol) at room temperature. After stirring for 10 min, a solution of tert-butyl 2-(((1s,4s)-4-(tosyloxymethyl)cyclohexyl)methoxy)acetate (155 mg, 0.375 mmol) in DMF (1 mL) was added. The reaction was heated to 45° C. and stirred for 8 h. The reaction mixture was poured into $H_2O$ and extracted with ethyl acetate. The organic extract was dried over $MgSO_4$ and concentrated under reduced pressure. The residue was treated with HCl (4.0 M in dioxane) overnight. The mixture was concentrated under reduced pressure and the residue was purified by HPLC to give the title compound (98 mg). LCMS m/z=451.47 [M+H]$^+$; $^1$H NMR (400 MHz, DMSO-$d_6$) δ ppm 1.33-1.55 (m, 8H), 2.12 (s, 3H) 1.69-1.81 (m, 1H), 2.14-2.26 (m, 1H), 3.39 (d, J=7.0 Hz, 2H), 3.80 (s, 2H), 4.28 (d, J=7.5 Hz, 2H), 7.21-7.43 (m, 10H).

Example 1.12: Preparation of 2-(((1s,4s)-4-((4-(4-Chlorophenyl)-3-methyl-5-phenyl-1H-pyrazol-1-yl)methyl)cyclohexyl)methoxy)acetic Acid (Compound 21)

Step A: Preparation of 5-Methyl-3-phenyl-1H-pyrazole

To a solution of acetophenone (10 g, 83 mmol) in anhydrous toluene (10 mL) was added LiHMDS (1.0 M in THF, 83 mL, 83 mmol) via syringe at 0° C. under argon. After 5 min, acetyl chloride (6.53 g, 83 mmol) was added in one portion via syringe. The ice bath was removed and glacial AcOH (5 mL), EtOH (50 mL), and hydrazine hydrate (12.50 g, 250 mmol) were added. The mixture was refluxed for 2 h. After cooled to room temperature, the reaction was neutralized to pH 7 by adding 1.0 M NaOH solution. The mixture was extracted with EtOAc, washed with brine, dried over $MgSO_4$, and concentrated. The residue was purified by silica gel column chromatography to give the title compound as a pale yellow oil (12.05 g). LCMS m/z=159.0 [M+H]$^+$; $^1$H NMR (400 MHz, DMSO-$d_6$) δ ppm 2.25 (s, 3H), 6.42 (s, 1H), 7.20-7.44 (m, 3H), 7.67-7.82 (m, 2H), 12.53 (bs, 1H).

Step B: Preparation of 4-Bromo-5-methyl-3-phenyl-1H-pyrazole

To a solution of 5-methyl-3-phenyl-1H-pyrazole (8.0 g, 50.6 mmol) in dichloromethane (150 mL) was added bromine (8.08 g, 50.6 mmol) dropwise at 0° C. The reaction was stirred at that temperature for 30 min and continued at room temperature for 2 h. After the reaction was quenched with an aqueous solution of $Na_2SO_3$ (10% w/w, 10 mL), the organic solvent was removed and the aqueous mixture was extracted with EtOAc, washed with brine, dried over $MgSO_4$, and concentrated. The residue was purified by silica gel column chromatography to give the title compound as a yellow oil (9.5 g). LCMS m/z=236.9 (M+H). $^1$H NMR (400 MHz, DMSO-$d_6$) δ ppm 2.26 (s, 3H), 7.30-7.57 (m, 5H), 13.12 (s, 1H).

Step C: Preparation of tert-Butyl 2-(((1s,4s)-4-((4-Bromo-5-methyl-3-phenyl-1H-pyrazol-1-yl)methyl)cyclohexyl)methoxy)acetate To a solution of 4-bromo-5-methyl-3-phenyl-1H-pyrazole (2.0 g, 8.44 mmol) in DMF (5 mL) was added sodium hydride (0.202 g, 8.44 mmol) in portions at 0° C. The reaction was stirred at 0° C. for 1 h and tert-butyl 2-(((1s,4s)-4-(tosyloxymethyl)cyclohexyl)methoxy)acetate (3.48 g, 8.44 mmol) was added. The reaction was heated to 42° C., stirred for 16 h, and quenched with $H_2O$ (2 mL). The mixture was extracted with ethyl acetate, dried over $MgSO_4$ and concentrated under reduced pressure. The residue was purified by silica gel column chromatography to give the title compound as a colorless liquid (3.05 g). LCMS m/z=477.3 [M+H]$^+$. $^1$H NMR (400 MHz, DMSO-d$_6$) δ ppm 1.26-1.50 (m, 8H), 1.43 (s, 9H), 1.66-1.78 (m, 1H), 1.97-2.09 (m, 1H), 2.30 (s, 3H), 3.39 (d, J=6.82 Hz, 2H), 3.94 (s, 2H), 4.06 (d, J=7.58 Hz, 2H), 7.30-7.50 (m, 3H), 7.74-7.85 (m, 2H).

Step D: Preparation of 2-(((1s,4s)-4-((4-(4-Chlorophenyl)-3-methyl-5-phenyl-1H-pyrazol-1-yl)methyl)cyclohexyl)methoxy)acetic Acid To a solution of tert-butyl 2-(((1s,4s)-4-((4-bromo-5-methyl-3-phenyl-1H-pyrazol-1-yl)methyl)cyclohexyl)methoxy)acetate (100 mg, 0.19 mmol) in dioxane (3 mL) were added 4-chlorophenylboronic acid (29.8 mg, 0.19 mmol), tetrakis(triphenylphosphine)palladium (22 mg, 0.019 mmol), and K$_2$CO$_3$ (2 M aqueous, 0.2 mL). The reaction was heated to 150° C. under microwave irradiation for 4 h. The reaction mixture was filtered and the filtrate was concentrated. The residue was treated with HCl (4 M in dioxane, 5 mL) at room temperature for 10 h. The mixture was concentrated and the residue was purified by HPLC to give the title compound (13.5 mg). LCMS m/z=453.4 [M+H]$^+$; $^1$H NMR (400 MHz, DMSO-d$_6$) δ ppm 1.01-1.19 (m, 4H), 1.21-1.36 (m, 4H), 1.54-1.66 (m, 1H), 1.86-1.98 (m, 1H), 2.22 (s, 3H), 3.19 (d, J=6.95 Hz, 2H), 3.89 (d, J=7.45 Hz, 2H), 3.91 (s, 2H), 7.04-7.11 (m, 2H), 7.21-7.31 (m, 5H), 7.39-7.47 (m, 2H).

Example 1.13: Preparation of 2-(((1s,4s)-4-((5-(Ethylthio)-4-(2-fluoro-3-methoxyphenyl)-3-phenyl-1H-pyrazol-1-yl)methyl)cyclohexyl)methoxy)acetic Acid (Compound 90)

From 5-(ethylthio)-3-phenyl-1H-pyrazole, using a similar method to the one described in Example 1.4, the title compound was obtained. LCMS m/z=513.1. $^1$H NMR (400 MHz, DMSO-d$_6$) δ ppm 0.96 (t, J=7.33 Hz, 3H), 1.30-1.52 (m, 8H), 1.68-1.80 (m, 1H), 2.14-2.26 (m, 1H), 2.53 (q, J=7.33 Hz, 2H), 3.37 (d, J=6.95 Hz, 2H), 3.68 (s, 2H), 3.84 (s, 3H), 4.28 (d, J=7.58 Hz, 2H), 6.76-6.94 (m, 2H), 7.13-7.40 (m, 6H).

Example 1.14: Preparation of 2-(((1s,4s)-4-((5-Ethyl-4-(3-methoxyphenyl)-3-phenyl-1H-pyrazol-1-yl)methyl)cyclohexyl)methoxy)acetic Acid (Compound 99)

Step A: Preparation of 5-Ethyl-3-phenyl-1H-pyrazole

To a solution of acetophenone (10 g, 83 mmol) in anhydrous toluene (10 mL) added LiHMDS (85.0 mL, 1.0 M in THF, 85.0 mmol) via syringe at 0° C. under argon. After 5 min, propionyl chloride (7.70 g, 83 mmol) was added in one portion via syringe. The ice bath was removed after 10 min and AcOH (2 mL), EtOH (50 mL), and hydrazine hydrate (8.35 g, 116 mmol) were added. The mixture was refluxed for 2 h. The resulting solution was added to 1.0 M NaOH solution, extracted with EtOAc, washed with brine, dried over MgSO$_4$, and concentrated. The residue was purified by silica gel column chromatography to give the title compound as a clear yellowish liquid (12.05 g). LCMS m/z=173.3 [M+H]$^+$; $^1$H NMR (400 MHz, DMSO-d$_6$) δ ppm 1.23 (t, J=7.58 Hz, 3H), 2.64 (q, J=7.07 Hz, 2H), 6.46 (s, 1H), 7.20-7.52 (m, 3H), 7.77 (d, J=6.32 Hz, 2H), 12.55 (s, 1H).

Step B: Preparation of 4-Bromo-5-ethyl-3-phenyl-1H-pyrazole

To a solution of 5-ethyl-3-phenyl-1H-pyrazole (10.0 g, 58.1 mmol) in DCM (150 mL) was added dropwise bromine (9.28 g, 58.1 mmol) at 0° C. The reaction was stirred at that temperature for 30 min and continued for 2 h at room temperature and then quenched with aqueous Na$_2$SO$_3$ solution (10% w/w, 10 mL). DCM was removed and the residue was extracted with EtOAc, washed with brine, dried over MgSO$_4$, and concentrated. The residue was purified by silica gel column chromatography to give the title compound as a yellow liquid (9.5 g). LCMS m/z=250.9 [M+H]$^+$; $^1$H NMR (400 MHz, DMSO-d$_6$) δ ppm 1.22 (t, J=7.58 Hz, 3H), 2.66 (q, J=7.58 Hz, 2H), 7.40-7.56 (m, 3H), 7.82 (d, J=7.58 Hz, 2H), 13.15 (s, 1H).

Step C: Preparation of tert-Butyl 2-(((1s,4s)-4-((4-Bromo-5-ethyl-3-phenyl-1H-pyrazol-1-yl)methyl)cyclohexyl)methoxy)acetate To a solution of 4-bromo-5-ethyl-3-phenyl-1H-pyrazole (3.0 g, 1195 mmol) in DMF (5 mL) was added sodium hydride (0.287 g, 11.95 mmol) followed by tert-butyl 2-(((1s,4s)-4-(tosyloxymethyl)cyclohexyl)methoxy)acetate (4.93 g, 1195 mmol). The reaction was heated at 45° C. overnight, quenched with water (2 mL), and the mixture was extracted with EtOAc. The organic phase was washed with brine, dried over MgSO$_4$, and concentrated. The residue was purified by silica gel column chromatography to give the title compound as a clear liquid (4.5 g). LCMS m/z=491.2 [M+H]$^+$; $^1$H NMR (400 MHz, CDCl$_3$) δ ppm 1.25 (t, J=7.20 Hz, 3H), 1.31-1.43 (m, 4H), 1.49 (s, 9H), 1.51-1.60 (m, 4H), 1.76-1.90 (m, 1H), 2.12-2.24 (m, 1H), 2.72 (q, J=7.75 Hz, 2H), 3.46 (d, J=6.82 Hz, 2H), 3.92 (s, 2H), 4.01 (d, J=7.58 Hz, 2H), 7.31-7.43 (m, 3H), 7.86 (d, J=7.33 Hz, 2H).

Step D: Preparation of 2-(((1s,4s)-4-((5-Ethyl-4-(3-methoxyphenyl)-3-phenyl-1H-pyrazol-1-yl)methyl)cyclohexyl)methoxy)acetic Acid A mixture of 3-methoxyphenylboronic acid (0.141 g, 0.929 mmol), tert-butyl 2-(((1s,4s)-4-((5-ethyl-4-iodo-3-phenyl-1H-pyrazol-1-yl)methyl)cyclohexyl)methoxy)acetate (0.5 g, 0.929 mmol), tetrakis(triphenylphosphine)palladium (0.107 g, 0.093 mmol), K$_2$CO$_3$ (2 M aqueous, 0.5 mL) and dioxane (10 mL) was heated to 150° C. under microwave irradiation for 4 h. The reaction mixture was filtered and the filtrate was concentrated. The residue was treated with HCl (4 M in dioxane, 5 mL) at room temperature for 10 h. The mixture was concentrated and the residue was purified by HPLC to give the title compound (0.135 g). LCMS m/z=463.2 [M+H]$^+$; $^1$H NMR (400 MHz, DMSO-d$_6$) δ ppm 1.04 (t, J=7.45 Hz, 3H), 1.35-1.55 (m, 8H), 1.71-1.83 (m, 1H), 2.06-2.18 (m, 1H), 2.60 (q, J=7.58 Hz, 2H), 3.40 (d, J=6.95 Hz, 2H), 3.70 (s, 3H), 3.72 (s, 2H), 4.02 (d, J=7.45 Hz, 2H), 6.69-6.78 (m, 2H), 6.85-6.91 (m, 1H), 7.15-7.36 (m, 6H).

Example 1.15: Preparation of 2-(((1s,4s)-4-((4-(3-Fluorophenyl)-5-isopropyl-3-phenyl-1H-pyrazol-1-yl)methyl)cyclohexyl)methoxy)acetic Acid (Compound 113)

Step A: Preparation of 5-Isopropyl-3-phenyl-1H-pyrazole

To a solution of acetophenone (1.21 g, 10.07 mmol) in dry toluene (5 mL) was added LiHMDS (11.0 mL, 1.0 M in THF, 11.0 mmol) via syringe at 0° C. under argon. After 5 min, isobutyryl chloride (1.073 g, 10.07 mmol) was added in one portion via syringe. The ice bath was removed and AcOH (2 mL), EtOH (50 mL) and THF (5 mL) were added to form a homogeneous mixture. Hydrazine hydrate (2 mL, 10.07 mmol) was added and the reaction was refluxed for 2 h. The reaction was cooled to room temperature and concentrated. The residue was extracted with EtOAc, washed with brine, dried over MgSO$_4$, and concentrated. The residue was purified by silica gel column chromatography to give the title compound as a colorless oil (0.70 g). LCMS m/z=187.3 [M+H]$^+$; $^1$H NMR (400 MHz, CDCl$_3$) δ ppm 1.33 (d, J=6.82 Hz, 6H), 2.94-3.13 (m, 1H), 6.38 (s, 1H), 7.17-7.45 (m, 5H), 10.14 (bs, 1H).

Step B: Preparation of 4-Iodo-5-isopropyl-3-phenyl-1H-pyrazole

To a solution of 5-isopropyl-3-phenyl-1H-pyrazole (0.64 g, 3.44 mmol) in THF (20 mL) and water (20.00 mL) were added sodium iodide (0.515 g, 3.44 mmol), iodine (1.308 g, 5.15 mmol), and potassium carbonate (0.712 g, 5.15 mmol) at room temperature. The reaction was refluxed for 2 h, cooled to room temperature and quenched with 10% aqueous Na$_2$SO$_3$. The organic solvent was removed under reduced pressure and the aqueous residue was extracted with EtOAc. The organic extract was washed with NaHCO$_3$ solution, brine, dried over MgSO$_4$, and concentrated. The residue was purified by silica gel column chromatography to give the title compound as a clear liquid (0.42 g). LCMS m/z=313.2 [M+H]$^+$; $^1$H NMR (400 MHz, CDCl$_3$) δ ppm 1.17 (d, J=7.07 Hz, 6H), 3.02 (septet, J=7.07 Hz, 1H), 7.23-7.32 (m, 3H), 7.60-7.67 (m, 2H), 11.81 (bs, 1H).

Step C: Preparation of tert-Butyl 2-(((1s,4s)-4-((4-Iodo-5-isopropyl-3-phenyl-1H-pyrazol-1-yl)methyl)cyclohexyl)methoxy)acetate To a solution of 4-iodo-5-isopropyl-3-phenyl-1H-pyrazole (0.35 g, 1.121 mmol) in DMF (5 mL) was added sodium hydride (0.027 g, 1.121 mmol) at room temperature. The reaction was stirred at room temperature for 1 h and tert-butyl 2-(((1s,4s)-4-(tosyloxymethyl)cyclohexyl)methoxy)acetate (0.463 g, 1.121 mmol) was added. The reaction was heated at 50° C. for 16 h, cooled to room temperature, and quenched with water (2 mL). The mixture was extracted with EtOAc. The organic extract was dried over MgSO$_4$ and concentrated. The residue was purified by silica gel column chromatography to give the title compound as a clear liquid (0.52 g). LCMS m/z=553.2 [M+H]$^+$; $^1$H NMR (400 MHz, CDCl$_3$) δ ppm 0.99-1.20 (m, 4H), 1.25-1.42 (m, 4H), 1.46 (d, J=7.20 Hz, 6H), 1.48 (s, 9H), 1.82-1.94 (m, 1H), 2.07-2.19 (m, 1H), 3.16-3.28 (m, 1H), 3.45 (d, J=7.07 Hz, 2H), 3.95 (s, 2H), 4.07 (d, J=7.71 Hz, 2H), 7.30-7.46 (m, 3H), 7.63-7.79 (m, 2H).

Step C: Preparation of 2-(((1s,4s)-4-((4-(3-Fluorophenyl)-5-isopropyl-3-phenyl-1H-pyrazol-1-yl)methyl)cyclohexyl)methoxy)acetic Acid A mixture of 3-fluorophenylboronic acid (25.3 mg, 0.181 mmol), tert-butyl 2-(((1s,4s)-4-((4-iodo-5-isopropyl-3-phenyl-1H-pyrazol-1-yl)methyl)cyclohexyl)methoxy)acetate (100 mg, 0.181 mmol), tetrakis(triphenylphosphine)palladium (10.0 mg, 0.009 mmol), K$_2$CO$_3$ (2 M aqueous, 0.2 mL) and dioxane (4 mL) was heated to 150° C. under microwave irradiation for 4 h. The mixture was filtered and the filtrate was concentrated. The residue was treated with HCl (4 M in dioxane, 5 mL) at room temperature for 10 h. The mixture was concentrated and the residue was purified by HPLC to give the title compound (15.5 mg). LCMS m/z=465.3 [M+H]$^+$; $^1$H NMR (400 MHz, DMSO-d$_6$) δ ppm 1.10 (d, J=7.07 Hz, 6H), 1.34-1.59 (m, 8H), 1.72-1.85 (m, 1H), 2.06-2.19 (m, 1H), 3.09-3.22 (m, 1H), 3.44 (d, J=7.07 Hz, 2H), 4.00 (s, 2H), 4.08 (d, J=7.58 Hz, 2H), 7.00-7.10 (m, 2H), 7.14-7.28 (m, 5H), 7.37-7.46 (m, 2H).

Example 1.16: Preparation of 2-(((1s,4s)-4-((3-Cyclopropyl-4,5-diphenyl-1H-pyrazol-1-yl)methyl)cyclohexyl)methoxy)acetic Acid (Compound 121)

Step A: Preparation of 5-Cyclopropyl-3-phenyl-1H-pyrazole

To a solution of acetophenone (5.0 g, 41.6 mmol) in dry toluene (5 mL) was added LiHMDS (42.0 mL, 1.0 M in THF, 42.0 mmol) via syringe at 0° C. under argon. After 5 min, cyclopropanecarbonyl chloride (4.35 g, 41.6 mmol) was added in one portion via syringe. The ice bath was removed and AcOH (2 mL), EtOH (50 mL), and hydrazine hydrate (10 mL, 64% aqueous, 127.8 mmol) was added. The mixture was refluxed for 30 min, cooled to room temperature, and concentrated. The residue was extracted with EtOAc, washed with brine, dried over MgSO$_4$, and purified by silica gel column chromatography to give the title compound as a colorless oil (4.5 g). LCMS m/z=184.7 [M+H]$^+$; $^1$H NMR (400 MHz, CDCl$_3$) δ ppm 0.71-0.80 (m, 2H), 0.89-1.00 (m, 2H), 1.81-1.98 (m, 1H), 6.22 (s, 1H), 7.11-7.56 (m, 5H), 10.50 (bs, 1H).

Step B: Preparation of 5-Cyclopropyl-4-iodo-3-phenyl-1H-pyrazole

To a solution of 5-cyclopropyl-3-phenyl-1H-pyrazole (3.0 g, 16.28 mmol) in THF (20 mL) and water (20 mL) were added sodium iodide (2.441 g, 16.28 mmol), iodine (6.20 g, 24.43 mmol), and potassium carbonate (3.38 g, 24.43 mmol) at room temperature. The reaction was refluxed for 2 h (100° C.). The reaction was cooled to room temperature and quenched with 10% aqueous Na$_2$SO$_3$. The organic solvent was removed under reduced pressure and the aqueous phase was extracted with EtOAc, washed with NaHCO$_3$ solution, brine, dried over MgSO$_4$, and concentrated. The residue was purified by silica gel column chromatography (2.7 g). LCMS m/z=310.8 [M+H]$^+$; $^1$H NMR (400 MHz, DMSO-d$_6$) δ ppm 0.75-0.81 (m, 2H), 0.83-0.88 (m, 2H), 2.46-2.56 (m, 1H), 7.33-7.47 (m, 3H), 7.62-7.71 (m, 2H), 12.91 (s, 1H).

Step C: Preparation of tert-Butyl 2-(((1s,4s)-4-((3-Cyclopropyl-4-iodo-5-phenyl-1H-pyrazol-1-yl)methyl)cyclohexyl)methoxy)acetate A solution of 5-cyclopropyl-4-iodo-3-phenyl-1H-pyrazole (3.5 g, 11.29 mmol) in DMF (5 mL) was treated with sodium hydride (0.271 g, 11.29 mmol) at room temperature for 1 h, then tert-butyl 2-(((1s,4s)-4-(tosyloxymethyl)cyclohexyl)methoxy)acetate (4.66 g, 11.29 mmol) was added. The reaction mixture was heated to 50° C. for 16 h and quenched with water (2 mL). The mixture was extracted by EtOAc, dried over MgSO$_4$, and concentrated. The residue was purified by silica gel column chromatography to give the title compound as a colorless oil (4.5 g). LCMS m/z=551.1 [M+H]$^+$; $^1$H NMR (400 MHz, CDCl$_3$) δ ppm 1.04-1.19 (m, 4H), 1.33-1.44 (m, 4H), 1.46 (s, 9H), 1.47 (d, J=8.08 Hz, 4H), 1.67-1.77 (in, 1H), 1.85-1.91 (m, 1H), 1.90-1.99 (m, 1H), 3.25 (d, J=7.07 Hz, 2H), 3.87 (s, 2H), 3.91 (d, J=7.58 Hz, 2H), 7.28-7.54 (m, 5H).

Step D: Preparation of 2-(((1s,4s)-4-((3-Cyclopropyl-4,5-diphenyl-1H-pyrazol-1-yl)methyl)cyclohexyl)methoxy)acetic Acid A mixture of phenylboronic acid (25.3 mg, 0.181 mmol), tert-butyl 2-(((1s,4s)-4-((3-cyclopropyl-4-iodo-5-phenyl-1H-pyrazol-1-yl)methyl)cyclohexyl)methoxy)acetate (100 mg, 0.181 mmol), tetrakis(triphenylphosphine)palladium (10.0 mg, 0.009 mmol), $K_2CO_3$ (2 M aqueous, 0.2 mL) and dioxane (4 mL) was heated to 150° C. under microwave irradiation for 4 h. The mixture was filtered and the filtrate was concentrated. The residue was treated with HC (4 M in dioxane, 5 mL) at room temperature for 10 h. The mixture was concentrated and the residue was purified by HPLC to give the title compound (23.5 mg). LCMS m/z=445.1 [M+H]$^+$; $^1$H NMR (400 MHz, DMSO-d$_6$) δ ppm 1.32-1.55 (m, 8H), 1.71-1.82 (m, 1H), 2.04-2.17 (m, 1H), 2.28 (s, 3H), 2.93 (t, J=6.82 Hz, 2H), 3.16 (s, 3H), 3.40 (t, J=6.63 Hz, 2H), 3.41 (d, J=6.69 Hz, 2H), 3.87 (s, 2H), 4.07 (d, J=7.45 Hz, 2H), 6.87-6.98 (m, 2H), 7.07-7.13 (m, 2H), 7.16-7.31 (m, 5H).

Example 1.17: Preparation of 2-(((1s,4s)-4-((3-(2-Fluoro-4-methylphenyl)-5-methyl-4-phenyl-1H-pyrazol-1-yl)methyl)cyclohexyl)methoxy)acetic Acid (Compound 143)

Step A: Preparation of 3-Iodo-5-methyl-4-phenyl-1H-pyrazole

To a solution of 5-methyl-4-phenyl-1H-pyrazole (5.0 g, 31.6 mmol) in THF (40 mL) and water (40 mL) were added sodium iodide (4.74 g, 31.6 mmol), iodine (12.03 g, 47.4 mmol), and $K_2CO_3$ (4.37 g, 31.6 mmol) at room temperature. The reaction was refluxed for 2 h and then quenched with aqueous $Na_2SO_3$ (10%). The mixture was extracted with ethyl acetate, dried over $MgSO_4$, and concentrated under reduced pressure. The residue was purified by silica gel column chromatography to give the title compound as a colorless oil (2.5 g). LCMS m/z=284.7 [M+H]$^+$; $^1$H NMR (400 MHz, DMSO-d$_6$) δ ppm 2.26 (s, 3H), 7.24-7.54 (m, 5H), 13.13 (s, 1H).

Step B: Preparation of tert-Butyl 2-(((1s,4s)-4-((3-Iodo-5-methyl-4-phenyl-1H-pyrazol-1-yl)methyl)cyclohexyl)methoxy)acetate A solution of 3-iodo-5-methyl-4-phenyl-1H-pyrazole (2.0 g, 7.04 mmol) in DMF (5 mL) was treated with sodium hydride (0.169 g, 7.04 mmol) at room temperature for 1 h, then tert-butyl 2-(((1s,4s)-4-(tosyloxymethyl)cyclohexyl)methoxy)acetate (2.9 g, 7.04 mmol) was added. The reaction mixture was heated to 50° C. for 16 h before it was quenched by addition of water (2 mL). The mixture was extracted with EtOAc, dried over $MgSO_4$ and concentrated. The residue was purified by silica gel column chromatography to give the title compound as a colorless oil (1.5 g). LCMS m/z=525.0 [M+H]$^+$; $^1$H NMR (400 MHz, DMSO-d$_6$) δ ppm 1.27-1.52 (m, 8H), 1.44 (s, 9H), 1.68-1.80 (m, 1H), 1.95-2.07 (m, 1H), 1.99 (s, 3H), 3.40 (d, J=6.82 Hz, 2H), 3.96 (s, 2H), 4.03 (d, J=7.33 Hz, 2H), 7.28-7.46 (m, 5H).

Step C: Preparation of 2-(((1s,4s)-4-((3-(2-Fluoro-4-methylphenyl)-5-methyl-4-phenyl-1H-pyrazol-1-yl)methyl)cyclohexyl)methoxy)acetic Acid A solution of 2-fluoro-4-methylphenylboronic acid (29.4 mg, 0.191 mmol), tert-butyl 2-(((1s,4s)-4-((3-iodo-5-methyl-4-phenyl-1H-pyrazol-1-yl)methyl)cyclohexyl)methoxy)acetate (100 mg, 0.191 mmol), tetrakis(triphenylphosphine)palladium (22.03 mg, 0.019 mmol), and $K_2CO_3$ (2 M aqueous, 0.5 mL) in dioxane (3 mL) was heated to 150° C. under microwave irradiation for 2 h. The mixture was filtered and the filtrate was concentrated. The residue was treated with HCl (4 M in dioxane, 3 mL) at room temperature for 16 h. The mixture was concentrated and the residue was purified by HPLC (Varian ProStar; Prep Column: Phenomenex 00G-4253-V0, Luna™ C18(2), 10 μm, 100 Å, 250×50 mm ID; Eluent: 40-65% ACN/$H_2O$ with 0.1% TFA over 15 min, and then 65% ACN/$H_2O$ with 0.1% FTA isocratic over 50 min) to give the title compound (retention time: 41 min, 25.0 mg). LCMS m/z=451.1 [M+H]$^+$; $^1$H NMR (400 MHz, DMSO-d$_6$) δ ppm 1.32-1.52 (m, 8H), 1.69-1.79 (m, 1H), 2.02-2.13 (m, 1H), 2.28 (s, 3H), 2.30 (s, 3H), 3.39 (d, J=6.95 Hz, 2H), 3.99 (s, 2H), 4.06 (d, J=7.45 Hz, 2H), 6.91 (d, J=11 Hz, 1H), 6.98 (d, J=7.8 Hz, 1H), 7.05 (m, 1H), 7.07 (m, 1H), 7.15-7.31 (m, 4H). A compound eluting at 37 min under the same HPLC conditions was collected and identified as the regioisomer of the title compound, 2-(((1s,4s)-4-((5-(2-fluoro-4-methylphenyl)-3-methyl-4-phenyl-1H-pyrazol-1-yl)methyl)cyclohexyl)methoxy)acetic acid (25.0 mg). $^1$H NMR (400 MHz, DMSO-d$_6$) δ ppm 1.07-1.20 (m, 4H), 1.21-1.39 (m, 4H), 1.60-1.75 (m, 1H), 1.90-1.99 (m, 1H), 2.23 (s, 3H), 2.35 (s, 3H), 3.21 (d, J=6.95 Hz, 2H), 3.80 (bs, 2H), 4.92 (s, 2H), 7.05-7.27 (m, 8H).

Example 1.18: Preparation of 2-(((1s,4s)-4-((3-(4-Chloro-2-fluorophenyl)-5-methyl-4-phenyl-1H-pyrazol-1-yl)methyl)cyclohexyl)methoxy)acetic Acid (Compound 144)

A solution of 4-chloro-2-fluorophenylboronic acid (33.2 mg, 0.191 mmol), tert-butyl 2-(((1s,4s)-4-((3-iodo-5-methyl-4-phenyl-1H-pyrazol-1-yl)methyl)cyclohexyl)methoxy)acetate (100 mg, 0.191 mmol), tetrakis(triphenylphosphine)palladium (22.03 mg, 0.019 mmol), and $K_2CO_3$ (2 M aqueous, 0.5 mL) in dioxane (3 mL) was heated to 150° C. under microwave irradiation for 2 h. The mixture was filtered and the filtrate was concentrated. The residue was treated with HCl (4 M in dioxane, 3 mL) at room temperature for 16 h. The mixture was concentrated and the residue was purified by HPLC to give the title compound (23.0 mg). LCMS m/z=471.1 [M+H]$^+$; $^1$H NMR (400 MHz, DMSO-d$_6$) δ ppm 1.32-1.53 (m, 8H), 1.70-1.80 (m, 1H), 2.02-2.12 (m, 1H), 2.29 (s, 3H), 3.39 (d, J=6.95 Hz, 2H), 3.82 (s, 2H), 4.07 (d, J=7.45 Hz, 2H), 7.03-7.10 (m, 2H), 7.18-7.41 (m, 6H).

Example 1.19: Preparation of 2-(((1s,4s)-4-((5-(2-Hydroxyethylthio)-3,4-diphenyl-1H-pyrazol-1-yl)methyl)cyclohexyl)methoxy)acetic Acid (Compound 146)

Step A: Preparation of 2-(1,3-Dithietan-2-ylidene)-1,2-diphenylethanone

To a solution of 1,2-diphenylethanone (10.0 g, 51.0 mmol) in anhydrous THF (100 mL) was added KOtBu (IM in THF, 51.0 mL, 51.0 mmol). The mixture was stirred for 30 min at room temperature, and carbon disulfide (7.76 g, 102 mmol) was added. After 10 min, dibromomethane (17.72 g, 102 mmol) was added and the reaction was stirred for 4 h at room temperature. The reaction was quenched with water (10 mL) and diluted with EtOAc. The organic layer was separated, dried over $MgSO_4$, and concentrated to give the title compound as a yellow solid (13.0 g). LCMS m/z=285.0 $[M+H]^+$.

Step B: Preparation of 3,4-Diphenyl-1H-pyrazole-5-thiol

To a suspension of 2-(1,3-dithietan-2-ylidene)-1,2-diphenylethanone (1.88 g, 6.61 mmol) in ethanol (50 mL) was added hydrazine hydrate (0.496 g, 9.92 mmol). The reaction was refluxed for 16 h, cooled to room temperature and concentrated. The residue was neutralized with HCl (1.0 M) to pH 6-7 and extracted with EtOAc/$H_2O$. The organic extract was dried over $MgSO_4$ and concentrated to give the title compound (1.5 g). LCMS m/z=253.4 $[M+H]^+$; $^1H$ NMR (400 MHz, $CDCl_3$) δ ppm 4.01-4.19 (m, 1H), 6.92-7.58 (m, 10H).

Step C: Preparation of 3,4-Diphenyl-5-(2-(tetrahydro-2H-pyran-2-yloxy)ethylthio)-1H-pyrazole To a solution of 3,4-diphenyl-1H-pyrazole-5-thiol (1.2 g, 4.76 mmol) and 2-(2-bromoethoxy)tetrahydro-2H-pyran (0.994 g, 4.76 mmol) in DMF (5 mL) was added $K_2CO_3$ (1.0 g, 7.23 mmol). The reaction was stirred at 60° C. for 2 h, cooled to room temperature, and quenched with $H_2O$ (5 mL). The mixture was extracted with EtOAc, dried over $MgSO_4$, and concentrated. The residue was purified by silica gel column chromatography to give the title compound as a colorless oil (1.7 g). LCMS m/z=381.2 $[M+H]^+$; $^1H$ NMR (400 MHz, DMSO-$d_6$) δ ppm 1.32-1.50 (m, 4H), 1.50-1.73 (m, 2H), 2.99-3.13 (m, 1H), 3.21-3.44 (m, 2H), 3.46-3.59 (m, 1H), 3.61-3.82 (m, 2H), 4.44-4.59 (m, 1H), 7.16-7.40 (m, 10H), 13.32 (bs, 1H).

Step D: Preparation of tert-Butyl 2-(((1s,4s)-4-((3,4-Diphenyl-5-(2-(tetrahydro-2H-pyran-2-yloxy)ethylthio)-1H-pyrazol-1-yl)methyl)cyclohexyl)methoxy)acetate To a solution of 3,4-diphenyl-5-(2-(tetrahydro-2H-pyran-2-yloxy)ethylthio)-1H-pyrazole (2.0 g, 5.26 mmol) in DMF (5 mL) was added sodium hydride (0.126 g, 5.26 mmol) slowly at room temperature. The reaction was stirred at room temperature for 30 min, and tert-butyl 2-(((1s,4s)-4-(tosyloxymethyl)cyclohexyl)methoxy)acetate (2.168 g, 5.26 mmol) was added. The reaction was gently heated to 60° C. for 16 h. After cooled to room temperature, the reaction was quenched with $H_2O$ (5 mL). The mixture was extracted with EtOAc, dried over $MgSO_4$, and concentrated. The residue was purified by silica gel column chromatography to give the title compound as a colorless oil (2.5 g). LCMS m/z=621.4 $[M+H]^+$; $^1H$ NMR (400 MHz, $CDCl_3$) δ ppm 1.26-1.43 (m, 4H), 1.44-1.54 (m, 4H), 1.47 (s, 9H), 1.54-1.62 (m, 2H), 1.76-1.92 (m, 4H), 2.23-2.36 (m, 2H), 2.63 (t, J=6.69 Hz, 2H), 3.21-3.32 (m, 1H), 3.36 (d, J=6.95 Hz, 2H), 3.38-3.44 (m, 1H), 3.56-3.64 (m, 1H), 3.73 (t, J=11.18 Hz, 1H), 3.91 (s, 2H), 3.93 (d, J=7.07 Hz, 2H), 4.33 (t, J=7.71 Hz, 1H), 7.20-7.43 (m, 6H), 7.75-7.81 (m, 4H).

Step E: Preparation of 2-(((1s,4s)-4-((5-(2-Hydroxyethylthio)-3,4-diphenyl-1H-pyrazol-1-yl)methyl)cyclohexyl)methoxy)acetic Acid A mixture of tert-butyl 2-(((1s,4s)-4-((3,4-diphenyl-5-(2-(tetrahydro-2H-pyran-2-yloxy)ethylthio)-1H-pyrazol-1-yl)methyl)cyclohexyl)methoxy)acetate (100 mg, 0.21 mmol) and HCl (4.0 M in dioxane, 4 mL) was stirred at room temperature for 16 h. The reaction mixture was concentrated and the residue was purified by HPLC to give the title compound. LCMS m/z=481.4 $[M+H]^+$; $^1H$ NMR (400 MHz, DMSO-$d_6$) δ ppm 1.02-1.20 (m, 4H), 1.22-1.37 (m, 4H), 1.55-1.64 (m, 1H), 1.88-1.99 (m, 1H), 3.03 (t, J=6.82 Hz, 2H), 3.20 (d, J=6.82 Hz, 2H), 3.61 (t, J=6.82 Hz, 2H), 3.91 (s, 2H), 3.93 (d, J=7.20 Hz, 2H), 7.06-7.32 (m, 10H), 12.51 (br. s., 1H).

Example 1.20: Preparation of 2-(((1s,4s)-4-((4-(3-Hydroxyphenyl)-5-methyl-3-phenyl-1H-pyrazol-1-yl)methyl)cyclohexyl)methoxy)acetic Acid (Compound 153)

Step A: Preparation of 5-Methyl-3-phenyl-1H-pyrazole

To a solution of acetophenone (10 g, 83 mmol) in anhydrous toluene (10 mL) was added LiHMDS (1.0 M in THF, 83 mL, 83 mmol) via syringe at 0° C. under argon. After 5 min, acetyl chloride (6.53 g, 83 mmol) was added via syringe in one portion. The ice bath was removed and AcOH (5 mL, glacial), EtOH (50 mL), and hydrazine hydrate (12.50 g, 250 mmol) were added. The mixture was refluxed for 2 h, cooled to room temperature, and neutralized to pH 7 by adding 1.0 M NaOH solution. The mixture was extracted with EtOAc, washed with brine, dried over $MgSO_4$, and concentrated. The residue was purified by silica gel column chromatography to give the title compound as a pale yellow oil (12.05 g). LCMS m/z=159.0 $[M+H]^+$; $^1H$ NMR (400 MHz, DMSO-$d_6$) δ ppm 2.25 (s, 3H), 6.42 (s, 1H), 7.20-7.44 (m, 3H), 7.67-7.82 (m, 2H), 12.53 (bs, 1H).

Step B: Preparation of 4-Bromo-5-methyl-3-phenyl-1H-pyrazole

To a solution of 5-methyl-3-phenyl-1H-pyrazole (8.0 g, 50.6 mmol) in dichloromethane (150 mL) was added bromine (8.08 g, 50.6 mmol) dropwise at 0° C. The reaction was stirred at 0° C. for 30 min and then at room temperature for 2 h before quenching with aqueous $Na_2SO_3$ (10% w/w, 10 mL). The organic solvent was removed and the aqueous phase was extracted with EtOAc, washed with brine, dried over $MgSO_4$, and concentrated. The residue was purified by silica gel column chromatography to give the title compound as a yellow oil (9.5 g). LCMS m/z=236.9 $[M+H]^+$; $^1H$ NMR (400 MHz, DMSO-$d_6$) δ ppm 2.26 (s, 3H), 7.30-7.57 (m, 5H), 13.12 (s, 1H).

Step C: Preparation of tert-Butyl 2-(((1s,4s)-4-((4-Bromo-5-methyl-3-phenyl-1H-pyrazol-1-yl)methyl)cyclohexyl)methoxy)acetate To a solution of 4-bromo-5-methyl-3-phenyl-1H-pyrazole (2.0 g, 8.44 mmol) in DMF (5 mL) were added sodium hydride (0.202 g, 8.44 mmol) in portions at 0° C. The reaction was stirred at that temperature for 1 h and tert-butyl 2-(((1s,4s)-4-(tosyloxymethyl)cyclohexyl)methoxy)acetate (3.48 g, 8.44 mmol) was added. The reaction was gently heated to 42° C. for 16 h, cooled to room temperature, and quenched with H₂O (2 mL). The mixture was extracted with ethyl acetate, dried over MgSO₄ and concentrated under reduced pressure. The residue was purified by silica gel column chromatography to give the title compound as a colorless liquid (3.05 g). LCMS m/z=477.3 [M+H]⁺; ¹H NMR (400 MHz, DMSO-d₆) δ ppm 1.26-1.50 (m, 8H), 1.43 (s, 9H), 1.66-1.78 (m, 1H), 1.97-2.09 (m, 1H), 2.30 (s, 3H), 3.39 (d, J=6.82 Hz, 2H), 3.94 (s, 2H), 4.06 (d, J=7.58 Hz, 2H), 7.30-7.50 (m, 3H), 7.74-7.85 (m, 2H).

Step D: Preparation of 2-(((1s,4s)-4-((4-(3-Hydroxyphenyl)-5-methyl-3-phenyl-1H-pyrazol-1-yl)methyl)cyclohexyl)methoxy)acetic Acid To a solution of tert-butyl 2-(((1s,4s)-4-((4-iodo-5-methyl-3-phenyl-1H-pyrazol-1-yl)methyl)cyclohexyl)methoxy)acetate (100 mg, 0.191 mmol) in dioxane (3 mL) was added 3-hydroxyphenylboronic acid (26.3 mg, 0.191 mmol), tetrakis(triphenylphosphine)palladium (22.03 mg, 0.019 mmol), and K₂CO₃ (2 M aqueous, 0.2 mL, 0.4 mmol). The mixture was heated to 150° C. under microwave irradiation for 4 h, filtered through a plug of silica gel, and concentrated. The residue was treated with HCl (4 M in dioxane, 3 mL) for 10 h. The mixture was concentrated and the residue was purified by HPLC to give the title compound (25.6 mg). LCMS m/z=435.2 [M+H]⁺; ¹H NMR (400 MHz, DMSO-d₆) δ ppm 1.31-1.54 (m, 8H), 1.70-1.81 (m, 1H), 2.03-2.13 (m, 1H), 2.19 (s, 3H), 3.42 (d, J=7.07 Hz, 2H), 3.99 (s, 2H), 4.03 (d, J=7.45 Hz, 2H), 6.52-6.73 (m, 4H), 7.11-7.39 (m, 5H), 9.44 (bs, 1H).

Example 1.21: Preparation of 2-(((1s,4s)-4-((5-(2-Methoxyethyl)-3,4-diphenyl-1H-pyrazol-1-yl)methyl)cyclohexyl)methoxy)acetic Acid (Compound 178)

Step A: Preparation of 5-(2-Methoxyethyl)-3-phenyl-1H-pyrazole

To a solution of acetophenone (3.5 g, 29.1 mmol) in dry toluene (10 mL) was added LiHMDS (1.0 M in toluene) via syringe at 0° C. under argon. After 5 min, 3-methoxypropanoyl chloride (3.57 g, 29.1 mmol) was added in one portion via syringe. The ice bath was removed and AcOH (2 mL), EtOH (100 mL), and hydrazine hydrate (4.37 g, 87 mmol) were added. The reaction was refluxed for 2 h, cooled to room temperature, and concentrated. The residue was extracted with EtOAc/H₂O, washed with brine, dried over MgSO₄, and concentrated. The resulting residue was purified by silica gel column chromatography to give the title compound as a pale yellow oil (2.0 g). LCMS m/z=203.1 [M+H]⁺; ¹H NMR (400 MHz, DMSO-d₆) δ ppm 2.85 (bs, 2H), 3.27 (s, 3H), 3.59 (t, J=6.82 Hz, 2H), 6.49 (s, 1H), 7.21-7.46 (m, 3H), 7.74 (m, 2H), 12.56 (s, 1H).

Step B: Preparation of 4-Bromo-5-(2-methoxyethyl)-3-phenyl-1H-pyrazole

To a solution of 5-(2-methoxyethyl)-3-phenyl-1H-pyrazole (2.0 g, 9.89 mmol) in DCM (100 mL) was added bromine (4.74 g, 29.7 mmol) dropwise at 0° C. The reaction was stirred at 0° C. for 1 h and then at room temperature for 2 h before quenching with Na₂SO₃ (10% aqueous). The organic phase was removed and the aqueous layer was extracted with DCM (2×50 mL). The organic layers were combined, washed with brine, dried over MgSO₄, and concentrated to give the title compound (2.5 g). LCMS m/z=281.1 [M+H]⁺; ¹H NMR (400 MHz, DMSO-d₆) δ ppm 2.87 (t, J=6.82 Hz, 2H), 3.27 (s, 3H), 3.62 (t, J=6.82 Hz, 2H), 5.75 (s, 1H), 7.35-7.51 (m, 3H), 7.75-7.82 (m, 2H).

Step C: Preparation of tert-Butyl 2-(((1s,4s)-4-((4-Bromo-5-(2-methoxyethyl)-3-phenyl-1H-pyrazol-1-yl)methyl)cyclohexyl)methoxy)acetate To a solution of 4-bromo-5-(2-methoxyethyl)-3-phenyl-1H-pyrazole (3.0 g, 10.67 mmol) in DMF (5 mL) was added sodium hydride (0.256 g, 10.67 mmol), followed by tert-butyl 2-(((1s,4s)-4-(tosyloxymethyl)cyclohexyl)methoxy)acetate (4.40 g, 10.67 mmol). The reaction was gently heated to 45° C. overnight. After quenching with water (5 mL), the mixture was extracted with EtOAc, washed with brine, dried over MgSO₄, and concentrated. The residue was purified by silica gel column chromatography to give the title compound (4.5 g). LCMS m/z=523.4 [M+H]⁺; ¹H NMR (400 MHz, DMSO-d₆) δ ppm 1.69-1.80 (m, 4H), 1.81-1.89 (m, 4H), 1.91 (s, 9H), 2.19-2.30 (m, 2H), 2.90 (s, 3H), 3.46 (t, J=6.63 Hz, 2H), 3.89 (d, J=6.95 Hz, 2H), 4.02 (t, J=6.32 Hz, 2H), 4.43 (s, 2H), 4.56 (d, J=7.45 Hz, 2H), 7.81-7.99 (m, 3H), 8.24-8.32 (m, 2H).

Step D: Preparation of 2-(((1s,4s)-4-((5-(2-Methoxyethyl)-3,4-diphenyl-1H-pyrazol-1-yl)methyl)cyclohexyl)methoxy)acetic Acid To a solution of tert-butyl 2-(((1s,4s)-4-((4-bromo-5-(2-methoxyethyl)-3-phenyl-1H-pyrazol-1-yl)methyl)cyclohexyl)methoxy)acetate (100 mg, 0.192 mmol) in dioxane (3 mL) was added phenylboronic acid (23.4 mg, 0.192 mmol), tetrakis(triphenylphosphine)palladium (22.03 mg, 0.019 mmol), and K₂CO₃ (2 M aqueous, 0.5 mL). The reaction was heated under microwave irradiation at 150° C. for 4 h, filtered through a plug of silica gel and concentrated. The residue was treated with HCl (4M in dioxane, 3 mL) for 10 h, and the mixture was purified by HPLC to give the title compound (23.5 mg). LCMS m/z=463.3 [M+H]⁺; ¹H NMR (400 MHz, DMSO-d₆) δ ppm 133-1.56 (m, 8H), 1.71-1.84 (m, 1H), 2.05-2.20 (m, 1H), 2.84 (t, J=6.82 Hz, 2H), 3.13 (s, 3H), 3.35 (t, J=6.82 Hz, 2H), 3.39 (d, J=7.07 Hz, 2H), 3.67 (s, 2H), 4.06 (d, J=7.33 Hz, 2H), 7.15-7.42 (m, 10H).

Example 1.22: Preparation of 2-(((1s,4s)-4-((5-(2-Methoxyethyl)-4-(3-methoxyphenyl)-3-phenyl-1H-pyrazol-1-yl)methyl)cyclohexyl)methoxy)acetic Acid (Compound 179)

To a solution of tert-butyl 2-(((1s,4s)-4-((4-bromo-5-(2-methoxyethyl)-3-phenyl-1H-pyrazol-1-yl)methyl)cyclohexyl)methoxy)acetate (100 mg, 0.192 mmol) in dioxane (3 mL) was added 3-methoxyphenylboronic acid (23.4 mg, 0.192 mmol), tetrakis(triphenylphosphine)palladium (22.03 mg, 0.019 mmol), and K₂CO₃ (2 M aqueous, 0.5 mL). The reaction was heated under microwave irradiation at 150° C. for 4 h, filtered through a plug of silica gel and concentrated. The residue was treated with HCl (4M in dioxane, 3 mL) for 10 h. The mixture was purified by HPLC to give the title compound (23.5 mg). LCMS m/z=493.4 [M+H]⁺; ¹H NMR (400 MHz, DMSO-d₆) δ ppm 1.32-1.56 (m, 8H), 1.72-1.85 (m, 1H), 2.06-2.18 (m, 1H), 2.85 (t, J=6.69 Hz, 2H), 3.16 (s, 3H), 3.36-3.38 (m, 2H), 3.40 (d, J=3.03 Hz, 2H), 3.66 (s, 2H), 3.70 (s, 3H), 4.05 (d, J=7.33 Hz, 2H), 6.71-6.80 (m, 2H), 6.85-6.91 (m, 1H), 7.16-7.35 (m, 6H).

Example 1.23: Preparation of 2-(((1s,4s)-4-((4-(3-Chloro-2-fluorophenyl)-5-(2-(methylthio)ethyl)-3-phenyl-1H-pyrazol-1-yl)methyl)cyclohexyl)methoxy)acetic Acid (Compound 215)

Step A: Preparation of 5-(2-(Methylthio)ethyl)-3-phenyl-1H-pyrazole

To a solution of acetophenone (5.0 g, 41.6 mmol) in dry toluene (10 mL) was added LiHMDS (1.0 M in toluene, 42 mL, 42 mmol) via syringe at 0° C. under argon. After 5 min, 3-(methylthio)propanoyl chloride (5.77 g, 41.6 mmol) was added in one portion via syringe. The ice bath was removed and AcOH (5 mL), EtOH (100 mL), and hydrazine hydrate (6.25 g, 125 mmol) were added. The mixture was refluxed for 2 h, cooled to room temperature, and concentrated. The residue was partitioned between EtOAc and water, and the organic phase was washed with brine, dried over $MgSO_4$, and concentrated. The resulting residue was purified by silica gel column chromatography to give the title compound as a pale yellow oil (6.5 g). LCMS m/z=219.2 [M+H]$^+$; $^1$H NMR (400 MHz, DMSO-$d_6$) δ ppm 2.09 (s, 3H), 2.77 (t, J=7.71 Hz, 2H), 2.84-2.95 (m, 2H), 6.53 (s, 1H), 7.18-7.50 (m, 3H), 7.63-7.84 (m, 2H), 12.60 (bs, 1H).

Step B: Preparation of 4-Bromo-5-(2-(methylthio)ethyl)-3-phenyl-1H-pyrazole To a solution of 5-(2-(methylthio)ethyl)-3-phenyl-1H-pyrazole (4.0 g, 18.32 mmol) in methanol (20 mL) was added N-bromosuccinimide (3.26 g, 18.32 mmol) slowly at 0° C. The reaction was stirred at 0° C. for 2 h. The mixture was concentrated and purified by silica gel column chromatography to give the title compound (3.4 g). LCMS m/z=297.0 [M+H]$^+$; $^1$H NMR (400 MHz, DMSO-$d_6$) δ ppm 2.11 (s, 3H), 2.79 (t, J=7.83 Hz, 2H), 2.83-2.97 (m, 2H), 7.32-7.56 (m, 3H), 7.67-7.88 (m, 2H), 13.20 (bs, 1H).

Step C: Preparation of tert-Butyl 2-(((1s,4s)-4-((4-Bromo-5-(2-(methylthio)ethyl)-3-phenyl-1H-pyrazol-1-yl)methyl)cyclohexyl)methoxy)acetate To a solution of 4-bromo-5-(2-(methylthio)ethyl)-3-phenyl-1H-pyrazole (3.4 g, 11.44 mmol) in DMF (5 mL) was added sodium hydride (0.275 g, 11.44 mmol) at room temperature, followed by tert-butyl 2-(((1s,4s)-4-(tosyloxymethyl)cyclohexyl)methoxy)acetate (4.72 g, 11.44 mmol). The reaction was heated to 45° C. overnight, cooled to room temperature, and quenched with water (5 mL). The mixture was extracted with EtOAc, washed with brine, dried over $MgSO_4$, and concentrated. The residue was purified by silica gel column chromatography to give the title compound (3.5 g). LCMS m/z=539.1 [M+H]$^+$; $^1$H NMR (400 MHz, DMSO-$d_6$) δ ppm 1.30-1.40 (m, 4H), 1.43 (s, 9H), 1.44-1.52 (m, 4H), 1.70-1.80 (m, 1H), 2.03-2.11 (m, 1H), 2.14 (s, 3H), 2.72 (t, J=7.07 Hz, 2H), 3.00 (t, J=7.20 Hz, 2H), 3.40 (d, J=6.95 Hz, 2H), 3.94 (s, 2H), 4.09 (d, J=7.45 Hz, 2H), 7.32-7.51 (m, 3H), 7.75-7.84 (m, 2H).

Step D: Preparation of 2-(((1s,4s)-4-((4-(3-Chloro-2-fluorophenyl)-5-(2-(methylthio)ethyl)-3-phenyl-1H-pyrazol-1-yl)methyl)cyclohexyl)methoxy)acetic Acid To a solution of tert-butyl 2-(((1s,4s)-4-((4-bromo-5-(2-(methylthio)ethyl)-3-phenyl-1H-pyrazol-1-yl)methyl)cyclohexyl)methoxy)acetate (100 mg, 0.19 mmol) in dioxane (3 mL) were added 2-fluoro-3-chlorophenylboronic acid (32.4 mg, 0.19 mmol), tetrakis(triphenylphosphine)palladium (22 mg, 0.019 mmol), and $K_2CO_3$ (2 M aqueous, 0.2 mL). The reaction mixture was heated to 150° C. under microwave irradiation for 4 h. The mixture was then filtered through a plug of silica gel and concentrated, and the residue was treated with HCl (4 M in dioxane, 5 mL) at room temperature for 10 h. The mixture was concentrated and the residue was purified by HPLC to give the title compound (24.5 mg). LCMS m/z=531.2 [M+H]$^+$; $^1$H NMR (400 MHz, DMSO-$d_6$) δ ppm 1.32-1.55 (m, 8H), 1.71-1.83 (m, 1H), 1.86 (s, 3H), 2.06-2.19 (m, 1H), 2.50 (t, J=7.83 Hz, 2H), 2.85 (t, J=7.39 Hz, 2H), 3.40 (d, J=6.95 Hz, 2H), 3.71 (s, 2H), 4.09 (d, J=7.33 Hz, 2H), 7.15-7.38 (m, 6H), 7.54-7.65 (m, 2H).

Example 1.24: Preparation of 2-(((1s,4s)-4-((4-(3-Methoxyphenyl)-5-(methylthio)-3-phenyl-1H-pyrazol-1-yl)methyl)cyclohexyl)methoxy)acetic Acid (Compound 31)

Step A: Preparation of 2-(3-Methoxyphenyl)-3,3-bis(methylthio)-1-phenylprop-2-en-1-one To a solution of 2-(3-methoxyphenyl)-1-phenylethanone (5.0 g, 22.10 mmol) in anhydrous THF (44.0 mL) was added a solution of potassium tert-butoxide (1 M in THF, 46.0 mL, 46.0 mmol). The reaction mixture was stirred for 15 min at room temperature, and then $CS_2$ (1.45 mL, 24.05 mmol) was added. After several minutes, MeI (3.40 mL, 54.4 mmol) was added and the reaction was stirred for 5 h. Upon completion, the reaction mixture was diluted with saturated $NaHCO_3$ and extracted with EtOAc. The combined organic layers were washed with $H_2O$, brine, dried over $MgSO_4$ and concentrated to give the title compound as an orange oil.

Step B: Preparation of 4-(3-Methoxyphenyl)-5-(methylthio)-3-phenyl-1H-pyrazole To a solution of 2-(3-methoxyphenyl)-3,3-bis(methylthio)-1-phenylprop-2-en-1-one in EtOH (100 mL) was added hydrazine hydrate (5.36 mL, 110 mmol). The reaction mixture was refluxed overnight, additional hydrazine hydrate (1.00 mL, 20.6 mmol) was added, and the mixture was refluxed until the reaction was complete. The mixture was concentrated under reduced pressure, washed with $H_2O$ and extracted with $CH_2Cl_2$. The combined organic layers were washed with $H_2O$, brine, dried over $MgSO_4$ and concentrated to give the title compound (6.67 g). LCMS m/z=397 [M+H]$^+$.

Step C: Preparation of tert-Butyl 2-(((1s,4s)-4-((4-(3-Methoxyphenyl)-5-(methylthio)-3-phenyl-1H-pyrazol-1-yl)methyl)cyclohexyl)methoxy)acetate In a reaction vial was placed 4-(3-methoxyphenyl)-5-(methylthio)-3-phenyl-1H-pyrazole (2.241 g, 7.56 mmol) and NaH (357.4 mg, 8.94 mmol) in DMF (36.0 mL). The mixture was stirred at room temperature for 15 min then a solution of tert-butyl 2-(((1s,4s)-4-(tosyloxymethyl)cyclohexyl)methoxy)acetate (3.0415 g, 7.37 mmol) in DMF (10.0 mL) was added. The reaction was heated at 45° C. for 15 h. Upon completion, the reaction mixture was quenched with $H_2O$ and extracted with EtOAc. The combined organic layers were washed with brine, dried over $MgSO_4$, and concentrated. The residue was purified by silica gel column chromatography to give the title compound.

Step D: Preparation of 2-(((1s,4s)-4-((4-(3-Methoxyphenyl)-5-(methylthio)-3-phenyl-1H-pyrazol-1-yl)methyl)cyclohexyl)methoxy)acetic Acid To tert-butyl 2-(((1s,4s)-4-((4-(3-methoxyphenyl)-5-(methylthio)-3-phenyl-1H-pyrazol-1-yl)methyl)cyclohexyl)methoxy)acetate obtained above was added 4 M HCl in dioxane. The reaction was stirred at room temperature overnight. Upon completion, the reaction was basified with 10% NaOH and organic impurities were extracted out with MTBE. The aqueous layer was then acidified with 1 M HCl and extracted with MTBE. The combined organic layers were dried over $MgSO_4$ and concentrated. The residue obtained was dissolved in ACN and 1 N NaOH solution (2.45 mL, 2.45 mmol) was added. The mixture was lyophilized to give a solid which was recrystallized from isopropyl alcohol to give the sodium salt of the title compound as an off-white solid (897.6 mg). LCMS m/z=481 $[M+H]^+$; $^1H$ NMR (400 MHz, DMSO-$d_6$) δ 1.17-1.80 (m, 1H), 2.14 (s, 3H), 3.34 (d, J=7.0 Hz, 2H), 3.50 (s, 2H), 3.71 (s, 3H), 4.27 (d, J=7.5 Hz, 2H), 6.80-6.85 (m, 2H), 6.89-6.94 (m, 1H), 7.21-7.37 (m, 6H).

Example 1.25: Preparation of 2-(((1s,4s)-4-((5-(2-Hydroxyethylthio)-4-(3-methoxyphenyl)-3-phenyl-1H-pyrazol-1-yl)methyl)cyclohexyl)methoxy)acetic Acid (Compound 198)

Step A: Preparation of 4-(3-Methoxyphenyl)-3-phenyl-5-(2-(tetrahydro-2H-pyran-2-yloxy)ethylthio)-1H-pyrazole To a stirred solution of 2-(3-methoxyphenyl)-1-phenylethanone (1.25 g, 5.52 mmol) in THF (11.05 mL) was added potassium tert-butoxide (11.49 mL, 11.49 mmol). After 30 min, $CS_2$ (0.363 mL, 6.02 mmol) was added and the mixture was stirred for 10 min before 2-(2-bromoethoxy)tetrahydro-2H-pyran (2.086 mL, 13.81 mmol) was added and the reaction was stirred overnight. The mixture was diluted with ethanol (11.05 mL). Acetic acid (1.898 mL, 33.1 mmol) was added followed by hydrazine hydrate (2.71 mL, 55.2 mmol). The reaction was stirred at 85° C. overnight and concentrated under reduced pressure. The residue was extracted with EtOAc/$H_2O$ (twice). The organic phases were combined and washed with brine, dried over $MgSO_4$ and concentrated. The residue was purified by silica gel column chromatography to give the title compound as a white solid (1.681 g). $^1H$ NMR (400 MHz, $CDCl_3$) δ ppm 1.52-1.64 (m, 3H), 1.65-1.93 (m, 3H), 3.06 (t, J=5.94 Hz, 2H), 3.49-3.57 (m, 1H), 3.65-3.71 (m, 1H), 3.72 (s, 3H), 3.88-3.95 (m, 1H), 3.97-4.05 (m, 1H), 4.66-4.69 (m, 1H), 6.79-6.90 (m, 3H), 7.19-7.26 (m, 1H), 7.26-7.33 (m, 3H), 7.37-7.45 (m, 2H), 10.91 (bs, 1H).

Step B: Preparation of tert-Butyl 2-(((1s,4s)-4-((4-(3-Methoxyphenyl)-3-phenyl-5-(2-(tetrahydro-2H-pyran-2-yloxy)ethylthio)-1H-pyrazol-1-yl)methyl)cyclohexyl)methoxy)acetate and tert-Butyl 2-(((1s,4s)-4-((4-(3-Methoxyphenyl)-5-phenyl-3-(2-(tetrahydro-2H-pyran-2-yloxy)ethylthio)-1H-pyrazol-1-yl)methyl)cyclohexyl)methoxy)acetate To a stirred solution of 4-(3-methoxyphenyl)-3-phenyl-5-(2-(tetrahydro-2H-pyran-2-yloxy)ethylthio)-1H-pyrazole (0.123 g, 0.3 mmol) was added 60% NaH (0.012 g, 0.300 mmol). After 20 min, tert-butyl 2-(((1s,4s)-4-(tosyloxymethyl)cyclohexyl)methoxy)acetate (0.124 g, 0.300 mmol) was added. The reaction was heated to 70° C. for 18 h, cooled to room temperature, and diluted with water. The mixture was extracted three times with EtOAc. The combined extracts were washed with brine, dried over $MgSO_4$ and concentrated. The residue was purified by silica gel column chromatography to give the title compound as a mixture of regioisomers (46 mg). LCMS m/z=651.7 $[M+H]^+$.

Step C: Preparation of 2-(((1s,4s)-4-((5-(2-Hydroxyethylthio)-4-(3-methoxyphenyl)-3-phenyl-1H-pyrazol-1-yl)methyl)cyclohexyl)methoxy)acetic Acid To a stirred solution of tert-butyl 2-(((1s,4s)-4-((4-(3-methoxyphenyl)-3-phenyl-5-(2-(tetrahydro-2H-pyran-2-yloxy)ethylthio)-1H-pyrazol-1-yl)methyl)cyclohexyl)methoxy)acetate (46 mg, 0.071 mmol) and tert-butyl 2-(((1s,4s)-4-((4-(3-methoxyphenyl)-5-phenyl-3-(2-(tetrahydro-2-pyran-2-yloxy)ethylthio)-1H-pyrazol-1-yl)methyl)cyclohexyl)methoxy)acetate (a mixture of regioisomers) in DCM (214 μL) was added water (21.42 μL), triethylsilane (113 μl, 0.707 mmol), and TFA (109 μL, 1.413 mmol). The reaction was stirred overnight, further TFA (0.5 mL) was added and the reaction was stirred for an additional 1 h. The solvent was evaporated. The residue was taken up in 70% acetonitrile/water and purified by HPLC (50% acetonitrile/water; isocratic) to give the title compound as a solid. LCMS m/z=511.5 $[M+H]^+$; 1H NMR (400 MHz, DMSO-$d_6$) δ ppm 1.31-1.45 (m, 4H), 1.45-1.54 (m, 4H), 1.69-1.80 (m, J=4.55 Hz, 1H), 2.18 (bs, 1H), 2.51-2.56 (m, 2H), 2.60 (t, J=6.69 Hz, 2H), 2.60 (t, J=6.69 Hz, 1H), 3.41 (d, J=7.07 Hz, 2H), 3.71 (s, 3H), 3.96-4.01 (m, 2H), 4.29 (d, J=7.58 Hz, 2H), 6.79-6.84 (m, 2H), 6.88-6.95 (m, 1H), 7.23-7.30 (m, 4H), 7.30-7.37 (m, 2H).

Example 1.26: Preparation of 2-(((1s,4s)-4-((5-(2-Hydroxyethylthio)-4-phenyl-3-p-tolyl-1H-pyrazol-1-yl)methyl)cyclohexyl)methoxy)acetic Acid (Compound 200)

Step A: Preparation of 4-Phenyl-5-(2-(tetrahydro-2H-pyran-2-yloxy)ethylthio)-3-p-tolyl-1H-pyrazole From 2-phenyl-1-p-tolylethanone, using a similar method to the one described in Example 1.25, step A, the title compound was obtained as a white solid. $^1H$ NMR (400 MHz, $CDCl_3$) δ ppm 1.54-1.64 (m, 3H), 1.66-1.90 (m, 3H), 2.33 (s, 3H), 3.05 (t, J=5.43 Hz, 2H), 3.47-3.56 (m, 1H), 3.64-3.72 (m, 1H), 3.86-3.94 (m, 1H), 3.95-4.01 (m, 1H), 4.63-4.67 (m, 1H), 7.10 (d, J=8.08 Hz, 2H), 7.25-7.30 (m, 5H), 7.30-7.39 (m, 2H).

Step B: Preparation of tert-Butyl 2-(((1s,4s)-4-((4-Phenyl-5-(2-(tetrahydro-2H-pyran-2-yloxy)ethylthio)-3-p-tolyl-1H-pyrazol-1-yl)methyl)cyclohexyl)methoxy)acetate From 4-phenyl-5-(2-(tetrahydro-2H-pyran-2-yloxy)ethylthio)-3-p-tolyl-1H-pyrazole, using a similar method to the one described in Example 1.25, step B, the title compound was obtained as a clear solid. LCMS m/z=635.6 $[M+H]^+$.

Step C: Preparation of 2-(((1s,4s)-4-((5-(2-Hydroxyethylthio)-4-phenyl-3-p-tolyl-1H-pyrazol-1-yl)methyl)cyclohexyl)methoxy)acetic Acid From tert-butyl 2-(((1s,4s)-4-((4-phenyl-5-(2-(tetrahydro-2H-pyran-2-yloxy)ethylthio)-3-p-tolyl-1H-pyrazol-1-yl)

methyl)cyclohexyl)methoxy)acetate, using a method similar to the one described in Example 1.25, Step C, the title compound was obtained as a white solid. LCMS m/z=495.3 [M+H]$^+$; $^1$H NMR (400 MHz, DMSO-d$_6$) δ ppm 1.32-1.45 (m, 4H), 1.45-1.52 (m, 4H), 1.68-1.80 (m, 1H), 2.13-2.22 (m, 1H), 2.25 (s, 3H), 2.56 (t, J=6.69 Hz, 2H), 3.23-3.29 (m, 2H), 3.41 (d, J=6.82 Hz, 2H), 3.98-4.01 (m, 2H), 4.28 (d, J=7.58 Hz, 2H), 4.75 (bs, 1H), 7.06 (d, J=7.83 Hz, 2H), 7.20 (d, J=8.08 Hz. 2H), 7.23-7.28 (m, 2H), 7.30-7.43 (m, 3H), 12.52 (bs, 1H).

Example 1.27: Preparation of 2-(((1r,4r)-4-((3,4-Diphenyl-1H-pyrazol-1-yl)methyl)cyclohexyl) methoxy)acetic Acid (Compound 8) and 2-(((1r,4r)-4-((4,5-Diphenyl-1H-pyrazol-1-yl)methyl) cyclohexyl)methoxy)acetic Acid (Compound 9)

Step A: Preparation of 3,4-Diphenyl-1H-pyrazole

Phenyl(3-phenyloxiran-2-yl)methanone (5.0 g, 22.3 mmol) was suspended in dry Et$_2$O (40 mL) under an argon balloon. Boron trifluoride diethyl etherate (3.00 mL, 23.7 mmol) was added slowly via syringe. The reaction was refluxed at 50° C. for an hour, then cooled and extracted with 60 mL each of H$_2$O and Et$_2$O/EtOAc. The aqueous layer was extracted again with EtOAc (60 mL). The combined organic layer was dried and concentrated to give 3-oxo-2,3-diphenylpropanal.

3-Oxo-2,3-diphenylpropanal (5.00 g, 22.3 mmol) was dissolved in EtOH (40 mL). Hydrazine monohydrate (2.0 mL, 38.7 mmol) was added slowly via syringe. The reaction was stirred at room temperature for an hour. The solvent was evaporated and the residue was purified by silica gel column chromatography to yield the title compound as a light purple solid (2.75 g). LCMS m/z=221.1 [M+H]$^+$; $^1$H NMR (400 MHz, DMSO-d$_6$) δ ppm 6.99-7.57 (in, 10H), 7.66-8.09 (bs, 1H), 13.15 (bs, 1H).

Step B: Preparation of 2-(((1r,4r)-4-((3,4-Diphenyl-1H-pyrazol-1-yl)methyl)cyclohexyl)methoxy)acetic Acid and 2-(((1r,4r)-4-((4,5-Diphenyl-1H-pyrazol-1-yl)methyl)cyclohexyl)methoxy)acetic Acid 3,4-Diphenyl-1H-pyrazole (16.02 mg, 0.073 mmol) was dissolved in DMF (0.4 mL). NaH (1.745 mg, 0.073 mmol) was added and the reaction was stirred at room temperature for 15 min. tert-Butyl-2-(((1r,4r)-4-(tosyloxymethyl)cyclohexyl)methoxy)acetate (prepared in a similar manner to Example 1.1) (30.0 mg, 0.073 mmol) was added and the reaction was stirred at room temperature for an hour. After this time, the reaction was partitioned between with H$_2$O (2 mL) and EtOAc (2 mL). The aqueous layer was extracted with EtOAc (2 mL). The organic layers were combined, dried and concentrated. The resulting oil was redissolved in HCl (4 M in dioxane) (400 μL, 1.600 mmol) and stirred overnight. The solvent was evaporated and the residue was purified by preparative LC/MS (50% acetonitrile/water; isocratic) to yield Compound 8 as a white solid (6.5 mg); LCMS m/z=405.5 [M+H]$^+$; $^1$H NMR (400 MHz, DMSO-d$_6$) δ ppm 0.86-1.12 (m, 4H), 1.44-1.58 (m, 1H), 1.61-1.71 (m, 2H), 1.73-1.80 (m, 2H), 1.80-1.91 (m, 1H), 3.26 (d, J=6.32 Hz, 2H), 3.95 (s, 2H), 4.00 (d, J=7.07 Hz, 2H), 7.20-7.27 (m, 3H), 7.27-7.36 (m, 5H), 7.36-7.44 (m, 2H), 7.92 (s, 1H); and Compound 9 as a white solid (1.0 mg); LCMS m/z=405.6 [M+H]$^+$; $^1$H NMR (400 MHz, DMSO-d$_6$) δ ppm 0.68-0.88 (m, 4H), 1.33-1.50 (m, J=9.98 Hz, 3H), 1.57-1.78 (m, 3H), 3.20 (d, J=6.32 Hz, 2H), 3.78 (d, J=7.20 Hz, 2H), 3.92 (s, 2H), 7.07-7.16 (m, 3H), 7.16-7.22 (m, 2H), 7.30-7.36 (m, 2H), 7.47-7.56 (m, 3H), 7.83 (s, 1H).

Example 1.28: Preparation of 2-(((1s,4s)-4-((1-Phenyl-4,5-dihydro-3H-benzo[e]indazol-3-yl)methyl) cyclohexyl)methoxy)acetic Acid (Compound 150)

Step A: Preparation of 1-Phenyl-4,5-dihydro-3H-benzo[e]indazole 3,4-Dihydronaphthalen-2(1H)-one (2.080 g, 14.23 mmol) was dissolved in toluene (15 mL) and the solution was cooled on an ice bath. LiHMDS (7.470 mL, 7.470 mmol) was added with vigorous stirring. One minute later benzoyl chloride (0.8258 mL, 7.114 mmol) was added. The reaction was removed from the ice bath and stirred for another minute. AcOH (4 mL) was added with stirring, followed by EtOH (10 mL), THF (5 mL), and hydrazine monohydrate (5 mL, 96.8 mmol). After 10 min, the solution was poured into a seperatory funnel loaded with IM NaOH (30 mL) and extracted with additional H$_2$O (70 mL) and EtOAc (100 mL). The aqueous layer was extracted again with EtOAc (100 mL). The combined organic layer was dried and concentrated. The residue was purified by silica gel column chromatography to yield the title compound as a light-purple colored solid. LCMS m/z=247.2 [M+H]$^+$; $^1$H NMR (400 MHz, DMSO-d$_6$) δ ppm 2.72-2.86 (m, 2H), 2.90-3.00 (m, 2H), 6.99-7.09 (m, 2H), 7.11-7.21 (m, 1H), 7.23-7.29 (m, 1H), 7.37-7.61 (m, 5H), 12.75 (s, 0.7H), 12.97 (s, 0.3H).

Step B: Preparation of 2-(((1s,4s)-4-((1-Phenyl-4,5-dihydro-3H-benzo[e]indazol-3-yl)methyl)cyclohexyl)methoxy)acetic Acid 1-Phenyl-4,5-dihydro-3H-benzo[e]indazole (100 mg, 0.406 mmol) was dissolved in DMF (0.4 mL). Sodium hydride (9.74 mg, 0.406 mmol) was added. The reaction was stirred at room temperature for 10 min and then tert-butyl 2-(((1s,4s)-4-(tosyloxymethyl)cyclohexyl) methoxy)acetate (167 mg, 0.406 mmol), pre-dissolved in DMF (0.2 mL) was added. The reaction was stirred for 1 h at 50° C. After this time, more NaH (10 mg) was added. The reaction was again stirred for 1 h at 50° C. The mixture was extracted with 15 mL each of H$_2$O and EtOAc. The aqueous layer was extracted again with EtOAc (15 mL). The combined organic layer was dried and concentrated. The residue was redissolved in HCl (4 M in dioxane) (507 μL, 2.030 mmol) and stirred overnight at room temperature. The solvent was evaporated and the residue was purified by preparative LC/MS to give the title compound as a light-tan solid (35 mg). LCMS m/z=431.4 [M+H]$^+$; $^1$H NMR (400 MHz, DMSO-d$_6$) δ ppm 1.28-1.54 (m, 8H), 1.69-1.80 (m, 1H), 2.00-2.10 (m, 1H), 2.85 (d, J=7.83 Hz, 2H), 2.97 (t, J=7.33 Hz, 2H), 3.41 (d, J=6.95 Hz, 2H), 3.99 (s, 2H), 4.04 (d, J=7.58 Hz, 2H), 6.98-7.08 (m, 2H), 7.10-7.18 (m, 1H), 7.22-7.30 (m, 1H), 7.35-7.50 (m, 3H), 7.54-7.60 (m, 2H).

Example 1.29: Preparation of 2-(((1s,4s)-4-((3-(2-Fluoro-4-methylphenyl)-5-methyl-4-phenyl-1H-pyrazol-1-yl)methyl)cyclohexyl)methoxy)acetic Acid (Compound 143)

Step A: Preparation of (1s,4s)-Ethyl 4-(Hydroxymethyl)cyclohexanecarboxylate

To a solution of (1s,4s)-4-(hydroxymethyl)cyclohexanecarboxylic acid (10 g, 63.2 mmol) in ethanol (100 mL), was added sulfuric acid (0.31 g, 3.16 mmol) at room temperature. After heating for 10 h at 85° C., the reaction was cooled to room temperature and concentrated under reduced pressure. The residue was extracted with ethyl acetate, dried over MgSO$_4$, and then concentrated under reduced pressure to give the title compound (4.98 g). H NMR (400 MHz, DMSO-d$_6$) δ ppm 1.15 (t, J=7.1 Hz, 3H), 1.40-1.54 (m, 7H), 2.55 (m, 1H), 1.82 (m, 2H), 3.21 (d, J=6.4 Hz, 2H), 4.01 (q, J=7.1 Hz, 2H).

Step B: Preparation of ((1s,4s)-4-(Benzyloxymethyl)cyclohexyl)methanol

To a solution of (1s,4s)-ethyl 4-(hydroxymethyl)cyclohexanecarboxylate (5 g, 26.8 mmol) in DMF (50 mL) was added (bromomethyl)benzene (4.59 g, 26.8 mmol) followed by NaH (0.644 g, 26.8 mmol) at 0° C. After stirring for 4 h at room temperature, the mixture was poured into water and extracted with ethyl acetate. The extract was dried over MgSO$_4$ and concentrated under reduced pressure. The residue was purified by silica gel column chromatography to give (1s,4s)-ethyl 4-(benzyloxymethyl)cyclohexanecarboxylate (3.2 g, 13.66 mmol). The above material was dissolved in THF (50 mL) and lithium aluminum hydride (1.02 g, 26.8 mmol) was added at 0° C. After stirring for 1 h at room temperature, the reaction was quenched with H$_2$O (5 mL) at 0° C. After stirring at room temperature for 1 h, the resulting precipitate was filtered off. The filtrate was dried over MgSO$_4$ and concentrated under reduced pressure to give the title compound (3.2 g). $^1$H NMR (400 MHz, DMSO-d$_6$) δ ppm 0.84-0.99 (m, 7H), 1.35 (m, 1H), 1.46 (m, 1H), 1.52 (m, 1H), 3.23 (d, J=7.0 Hz, 2H), 3.25 (d, J=5.7 Hz, 2H), 4.45 (s, 2H), 7.21-7.40 (m, 5H).

Step C: Preparation of (1s,4s)-4-(Benzyloxymethyl)cyclohexanecarbaldehyde

To a solution of DMSO (1.32 mL, 18.78 mmol) in CH$_2$Cl$_2$ (50 mL) was added oxalyl dichloride (1.19 g, 9.39 mmol) dropwise at −50° C. After stirring for 10 min, ((1s,4s)-4-(benzyloxymethyl)cyclohexyl)methanol (2.0 g, 8.53 mmol) and triethylamine (4.32 g, 42.7 mmol) were added at the same temperature. After stirring for 1 h at room temperature, the reaction was extracted with CH$_2$Cl$_2$ and dried over MgSO$_4$. The organic layer was concentrated under reduced pressure to give the title compound (1.9 g). $^1$H NMR (400 MHz, DMSO-d$_6$) δ ppm 0.91-1.21 (m, 6H), 1.45 (m, 1H), 1.75-1.95 (m, 2H), 2.25 (m, 1H), 3.25 (d, J=7.1 Hz, 2H), 4.42 (s, 2H), 7.25-7.42 (m, 5H), 9.52 (s, 1H).

Step D: Preparation of tert-Butyl 2-(((1s,4s)-4-(Benzyloxymethyl)cyclohexyl)methyl)hydrazinecarboxylate To a solution of (1s,4s)-4-(benzyloxymethyl)cyclohexanecarbaldehyde (1.2 g, 5.17 mmol) in MeOH (50 mL) was added tert-butyl hydrazinecarboxylate (0.68 g, 5.17 mmol) at room temperature. After stirring for 1 h, the reaction was concentrated under reduced pressure. The residue was dissolved in MeOH (25 mL) and acetic acid (25 mL). NaCNBH$_3$ (0.33 g, 5.17 mmol) was added at 0° C. After stirring for 30 min, the reaction was concentrated under reduced pressure. The residue was dissolved in ethyl acetate and washed with 0.1 M NaOH. The extract was dried over MgSO$_4$ and concentrated under reduced pressure. The residue was purified by silica gel column chromatography to give the title compound (0.85 g). LCMS m/z=349.4 [M+H]$^+$.

Step E: Preparation of 1-(((1s,4s)-4-(Benzyloxymethyl)cyclohexyl)methyl)-2-(2-fluoro-4-methylbenzylidene)hydrazine To a solution of tert-butyl 1-(((1s,4s)-4-(benzyloxymethyl)cyclohexyl)methyl)hydrazinecarboxylate (1.0 g, 2.87 mmol) in CH$_2$Cl$_2$ (5 mL), was added TFA (5.0 mL) at room temperature. After stirring for 3 h at the same temperature, the reaction was concentrated under reduced pressure. The residue was dissolved in THF (10 mL) and 2-fluoro-4-methylbenzaldehyde (0.40 g, 2.87 mmol) was added. After stirring for 30 min, the reaction was washed with saturated NaHCO$_3$. The organics were dried over MgSO$_4$ and concentrated under reduced pressure to give the title compound (0.96 g). LCMS m/z=369.3 [M+H]$^+$.

Step F: Preparation of 1-(((1s,4s)-4-(Benzyloxymethyl)cyclohexyl)methyl)-3-(2-fluoro-4-methylphenyl)-5-methyl-4-phenyl-1H-pyrazole To a solution of 1-(((1s,4s)-4-(benzyloxymethyl)cyclohexyl)methyl)-2-(2-fluoro-4-methylbenzylidene)hydrazine (0.5 g, 1.357 mmol) and (2-nitroprop-1-enyl)benzene (0.22 g, 1.36 mmol) in THE (5 mL) at −78° C., was added potassium butan-1-olate (0.152 g, 1.357 mmol) dropwise. After 10 min, TFA (0.21 mL, 2.71 mmol) was added at the same temperature and maintained for 2 h. After warming to room temperature, the reaction was extracted with ethyl acetate, dried over MgSO$_4$, and then concentrated under reduced pressure. The residue was purified by silica gel column chromatography to give the title compound (0.49 g). LCMS m/z=483.3 [M+H]$^+$; $^1$H NMR (400 MHz, DMSO-d$_6$) δ ppm 1.34-1.52 (m, 8H), 1.85 (m, 1H), 2.15 (m, 1H), 2.25 (s, 3H), 2.31 (s, 3H), 3.34 (d, J=7.0 Hz, 2H), 4.25 (d, J=7.4 Hz, 2H), 4.51 (s, 2H), 6.92-7.38 (m, 4H), 7.39-7.45 (m, 9H).

Step G: Preparation of ((1s,4s)-4-((3-(2-Fluoro-4-methylphenyl)-5-methyl-4-phenyl-1H-pyrazol-1-yl)methyl)cyclohexyl)methanol To a solution of 1-(((1s,4s)-4-(benzyloxymethyl)cycloexyl)methyl)-3-(2-fluoro-4-methylphenyl)-5-methy-4-phenyl-1H-pyrazole (100 mg, 0.21 mmol) in MeOH (5 mL), was added ammonium formate (261 mg, 4.14 mmol) followed by 10% Pd/C (5 mg). The reaction was heated to 80° C. for 10 h. After filtration of insoluble material, the reaction was concentrated under reduced pressure to give the title compound as a colorless oil (78 mg). LCMS m/z=393.3 [M+H]$^+$.

Step H: Preparation of tert-Butyl 2-(((1s,4s)-4-((3-(2-Fluoro-4-methylphenyl)-5-methyl-4-phenyl-1H-pyrazol-1-yl)methyl)cyclohexyl)methoxy)acetate To a solution of ((1s,4s)-4-((3-(2-fluoro-4-methylphenyl)-5-methyl-4-phenyl-1H-pyrazol-1-yl)methyl)cyclohexyl)methanol (20 mg, 0.051 mmol) and (Rh(OAc)$_2$)$_2$ (2.25 mg, 5.10 µmol) in CH$_2$Cl$_2$ (2 mL), was added a solution of tert-butyl 2-diazoacetate (7.24 mg, 0.051 mmol) in CH$_2$Cl$_2$ (0.5 mL) dropwise for 10 min at −10° C. The reaction was stirred for 1 h at the same temperature. The solid material was filtered off and the filtrate was concentrated under reduced pressure. The residue was purified by silica gel column chromatography to give the title compound (20 mg). LCMS m/z=507.5 [M+H]$^+$; $^1$H NMR (400 MHz, DMSO-d$_6$) δ ppm 1.30-1.45 (m, 17H), 1.75 (m, 1H), 2.11 (m, 1H), 2.28 (s, 3H), 2.30 (s, 3H), 3.52 (d, J=7.0 Hz, 2H), 3.95 (s, 2H), 4.05 (d, J=7.3 Hz, 2H), 6.90 (d, J=11.5 Hz, 1H), 6.95 (d, J=7.7 Hz, 1H), 7.05-7.33 (m, 6H).

Step I: Preparation of 2-(((1s,4s)-4-((3-(2-Fluoro-4-methylphenyl)-5-methyl-4-phenyl-1H-pyrazol-1-yl)methyl)cyclohexyl)methoxy)acetic Acid tert-Butyl 2-(((1s,4s)-4-((3-(2-fluoro-4-methylphenyl)-5-methyl-4-phenyl-1H-pyrazol-1-yl)methyl)cyclohexyl)methoxy)acetate (250 mg, 0.49 mmol) was treated with HCl (4.0 M in dioxane, 10 mL) at room temperature. After stirring for 12 h, the reaction was concentrated in vacuo and purified by HPLC. The free acid was dissolved in acetonitrile (5 mL) and H$_2$O (2 mL), added into a solution of sodium hydroxide (19.74 mg, 0.49 mmol) in H$_2$O (10 mL), and dried under reduced pressure to give the sodium salt of the title compound (149 mg). LCMS m/z=451.2 [M+H]$^+$; $^1$H NMR (400 MHz, DMSO-d$_6$) δ ppm 1.32-1.52 (m, 8H), 1.71-1.81 (m, 1H), 2.02-2.13 (m, 1H), 2.28 (s, 3H), 2.30 (s, 3H), 3.37 (d, J=6.7 Hz, 2H), 3.61 (s, 2H), 4.05 (d, J=7.3 Hz, 2H), 6.91 (d, J=11.2 Hz, 1H), 6.98 (d, J=7.9 Hz, 1H), 7.05 (s, 1H), 7.07 (s, 1H), 7.16-7.32 (m, 4H).

Example 1.30: Preparation of 2-(((1s,4s)-4-((4-(3-Chlorophenyl)-5-(2-hydroxyethylthio)-3-phenyl-1H-pyrazol-1-yl)methyl)cyclohexyl)methoxy)acetic Acid (Compound 199)

Step A: Preparation of 4-(3-Chlorophenyl)-3-phenyl-5-(2-(tetrahydro-2H-pyran-2-yloxy)ethylthio)-1H-pyrazole From 2-(3-chlorophenyl)-1-phenethanone, using a similar method to the one described in Example 1.25, Step A, the title compound was obtained as a yellow solid. $^1$H NMR (400 MHz, CDCl$_3$) δ ppm 1.51-1.65 (m, 3H), 1.66-1.92 (m, 3H), 3.07 (t, J=5.81 Hz, 2H), 3.49-3.59 (m, 1H), 3.66-3.75 (m, 1H), 3.87-3.96 (m, 1H), 3.97-4.04 (m, 1H), 4.68 (dd, J=4.29, 3.03 Hz, 1H), 7.09-7.15 (m, 1H), 7.23-7.27 (m, 2H), 7.28-7.33 (m, 4H), 7.34-7.42 (m, 2H), 10.95 (bs, 1H).

Step B: Preparation of tert-Butyl 2-(((1s,4s)-4-((4-(3-Chlorophenyl)-3-phenyl-5-(2-(tetrahydro-2H-pyran-2-yloxy)ethylthio)-1H-pyrazol-1-yl)methyl)cyclohexyl)methoxy)acetate and tert-Butyl 2-(((1s,4s)-4-((4-(3-Chlorophenyl)-5-phenyl-3-(2-(tetrahydro-2H-pyran-2-yloxy)ethylthio)-1H-pyrazol-1-yl)methyl)cyclohexyl)methoxy)acetate as a Mixture of Regioisomers From 4-(3-chlorophenyl)-3-phenyl-5-(2-(tetrahydro-2H-pyran-2-yloxy)ethylthio)-1H-pyrazole, using a similar method to the one described in Example 1.25, Step B, the title compound was obtained as a clear oil (a mixture of regioisomers). LCMS m/z=655.4 [M+H]$^+$.

Step C: Preparation of 2-(((1s,4s)-4-((4-(3-Chlorophenyl)-5-(2-hydroxyethylthio)-3-phenyl-1H-pyrazol-1-yl)methyl)cyclohexyl)methoxy)acetic Acid From tert-butyl 2-(((1s,4s)-4-((4-(3-chlorophenyl)-3-phenyl-5-(2-(tetrahydro-2H-pyran-2-yloxy)ethylthio)-1H-pyrazol-1-yl)methyl)cyclohexyl)methoxy)acetate and tert-butyl 2-(((1s,4s)-4-((4-(3-chlorophenyl)-5-phenyl-3-(2-(tetrahydro-2H-pyran-2-yloxy)ethylthio)-1H-pyrazol-1-yl)methyl)cyclohexyl)methoxy)acetate as a mixture of regioisomers, using a similar method to the one described in Example 1.25, Step C, the title compound was obtained as a clear solid. LCMS m/z=515.5 [M+H]$^+$; $^1$H NMR (400 MHz, DMSO-d$_6$) δ ppm 1.32-1.54 (m, 8H), 1.71-1.79 (m, 1H), 2.11-2.23 (m, 1H), 2.51-2.55 (m, 2H), 2.61 (t, J=6.57 Hz, 2H), 3.30 (t, J=6.57 Hz, 1H), 3.41 (d, J=6.82 Hz, 2H), 3.98 (s, 2H), 4.30 (d, J=7.58 Hz, 2H), 7.18-7.23 (m, 1H), 7.25-7.34 (m, 6H), 7.38-7.44 (m, 2H).

Example 1.31: Preparation of 2-(((1s,4s)-4-((5-(2-Hydroxyethylthio)-3-phenyl-4-m-tolyl-1H-pyrazol-1-yl)methyl)cyclohexyl)methoxy)acetic Acid (Compound 210)

Step A: Preparation of 3-Phenyl-5-(2-(tetrahydro-2H-pyran-2-yloxy)ethylthio)-4-m-tolyl-1H-pyrazole From 1-phenyl-2-m-tolylethanone, using a similar method to the one described in Example 1.25, Step A, the title compound was obtained as a white solid. $^1$H NMR (400 MHz, DMSO-d$_6$) δ ppm 1.30-1.51 (m, 4H), 1.52-1.73 (m, 2H), 2.26 (s, 3H), 3.10 (t, J=6.82 Hz, 2H), 3.32-3.45 (m, 1H), 3.53-3.67 (m, 1H), 3.68-3.76 (m, 1H), 3.76-3.84 (m, 1H), 4.55 (t, J=3.16 Hz, 1H), 6.97 (d, J=7.33 Hz, 1H), 7.04 (s, 1H), 7.08-7.14 (m, 1H), 7.20-7.27 (m, 2H), 7.29-7.37 (m, 4H), 13.30 (s, 1H).

Step B: Preparation of tert-Butyl 2-(((1s,4s)-4-((3-Phenyl-5-(2-(tetrahydro-2H-pyran-2-yloxy)ethylthio)-4-m-tolyl-1H-pyrazol-1-yl)methyl)cyclohexyl)methoxy)acetate and tert-Butyl 2-(((1s,4s)-4-((5-Phenyl-3-(2-(tetrahydro-2H-pyran-2-yloxy)ethylthio)-4-m-tolyl-1H-pyrazol-1-yl)methyl)cyclohexyl)methoxy)acetate as a Mixture of Regioisomers From 3-phenyl-5-(2-(tetrahydro-2H-pyran-2-yloxy)ethylthio)-4-m-tolyl-1H-pyrazole, using a similar method to the one described in Example 1.25, Step B, the title compound was obtained as a clear oil (a mixture of regioisomers). LCMS m/z=635.7 [M+H]$^+$.

Step C: Preparation of 2-(((1s,4s)-4-((5-(2-Hydroxyethylthio)-3-phenyl-4-m-tolyl-1H-pyrazol-1-yl)methyl)cyclohexyl)methoxy)acetic Acid From tert-butyl 2-(((1s,4s)-4-((3-phenyl-5-(2-(tetrahydro-2H-pyran-2-yloxy)ethylthio)-4-m-tolyl-1H-pyrazol-1-yl)methyl)cyclohexyl)methoxy)acetate and tert-butyl 2-(((1s,4s)-4-((5-phenyl-3-(2-(tetrahydro-2H-pyran-2-yloxy)ethylthio)-4-m-tolyl-1H-pyrazol-1-yl)methyl)cyclohexyl)methoxy)acetate as a mixture of regioisomers, using a similar method to the one described in Example 1.25, Step C, the title compound was obtained as a yellow oily solid. LCMS m/z=495.4 [M+H]$^+$; $^1$H NMR (400 MHz, DMSO-d$_6$) δ ppm 1.33-1.44 (m, 4H), 1.44-1.53 (m, 4H), 1.68-1.80 (m, 1H), 2.13-2.23 (m, 1H), 2.30 (s, 3H), 2.58 (t, J=6.69 Hz, 2H), 3.17 (d, J=5.05 Hz, 1H), 3.26-3.35 (m, 2H), 3.41 (d, J=7.07 Hz, 2H), 3.99 (s, 2H), 4.29 (d, J=7.58 Hz, 2H), 7.02 (d, J=7.58 Hz, 1H), 7.10 (s, 1H), 7.16 (d, J=7.83 Hz, 1H), 7.22-7.29 (m, 4H), 7.30-7.35 (m, 2H).

Example 1.32: Preparation of 2-(((1s,4s)-4-((4-(3-Fluorophenyl)-5-(2-hydroxyethylthio)-3-phenyl-1H-pyrazol-1-yl)methyl)cyclohexyl)methoxy)acetic Acid (Compound 212)

Step A: Preparation of 4-(3-Fluoorophenyl)-3-phenyl-5-(2-(tetrahydro-2H-pyran-2-yloxy)ethylthio)-1H-pyrazole From 2-(3-fluorophenyl)-1-phenethanone, using a similar method to the one described in Example 1.25, Step A, the title compound was obtained as a white solid. $^1$H NMR (400 MHz, DMSO-$d_6$) δ ppm 1.31-1.51 (m, 4H), 1.50-1.75 (m, 2H), 3.12 (t, J=6.69 Hz, 2H), 3.33-3.43 (m, 1H), 3.52-3.66 (m, 1H), 3.67-3.76 (m, 1H), 3.76-3.84 (m, 1H), 4.55 (t, J=3.28 Hz, 1H), 6.96-7.05 (m, 2H), 7.08-7.15 (m, 1H), 7.23-7.44 (m, 6H), 13.41 (s, 1H).

Step B: Preparation of tert-Butyl 2-(((1s,4s)-4-((4-(3-Fluoorophenyl)-3-phenyl-5-(2-(tetrahydro-2H-pyran-2-yloxy)ethylthio)-1H-pyrazol-1-yl)methyl)cyclohexyl)methoxy)acetate and tert-Butyl 2-(((1s,4s)-4-((4-(3-Fluoorophenyl)-5-phenyl-3-(2-(tetrahydro-2H-pyran-2-yloxy)ethylthio)-1H-pyrazol-1-yl)methyl)cyclohexyl)methoxy)acetate as a Mixture of Regioisomers From 4-(3-fluorophenyl)-3-phenyl-5-(2-(tetrahydro-2H-pyran-2-yloxy)ethylthio)-1H-pyrazole, using a similar method to the one described in Example 1.25, Step B, the title compound was obtained as a clear oil (a mixture of regioisomers). LCMS m/z=639.5 [M+H]$^+$.

Step C: Preparation of 2-(((1s,4s)-4-((4-(3-Fluorophenyl)-5-(2-hydroxyethylthio)-3-phenyl-1H-pyrazol-1-yl)methyl)cyclohexyl)methoxy)acetic Acid From tert-butyl 2-(((1s,4s)-4-((4-(3-fluoorophenyl)-3-phenyl-5-(2-(tetrahydro-2H-pyran-2-yloxy)ethylthio)-1H-pyrazol-1-yl)methyl)cyclohexyl)methoxy)acetate and tert-butyl 2-(((1s,4s)-4-((4-(3-fluoorophenyl)-5-phenyl-3-(2-(tetrahydro-2H-pyran-2-yloxy)ethylthio)-1H-pyrazol-1-yl)methyl)cyclohexyl)methoxy)acetate as a mixture of regioisomers, using a similar method to the one described in Example 1.25, Step C, the title compound was obtained as a clear oily solid. LCMS m/z=499.6 [M+H]$^+$; $^1$H NMR (400 MHz, DMSO-$d_6$) δ ppm 1.34-1.45 (m, 4H), 1.45-1.53 (m, 4H), 1.69-1.81 (m, 1H), 2.11-2.22 (m, 1H), 2.43-2.56 (m, 2H), 2.60 (t, J=6.69 Hz, 1H), 3.21-3.33 (m, 2H), 3.41 (d, J=7.07 Hz, 2H), 3.99-4.00 (m, 2H), 4.30 (d, J=7.58 Hz, 2H), 7.05-7.12 (m, 2H), 7.13-7.22 (m, 1H), 7.23-7.34 (m, 5H), 7.38-7.46 (m, 1H), 12.52 (s, 1H).

Example 1.33: Preparation of 2-(((1s,4s)-4-((4-(3-Chlorophenyl)-5-(2-hydroxyethylsulfinyl)-3-phenyl-1H-pyrazol-1-yl)methyl)cyclohexyl)methoxy)acetic Acid (Compound 217)

To a solution of 2-(((1s,4s)-4-((4-(3-chlorophenyl)-5-(2-hydroxyethylthio)-3-phenyl-1H-pyrazol-1-yl)methyl)cyclohexyl)methoxy)acetic acid (18.3 mg, 0.036 mmol) in DCM (178 μL) was added mCPBA (5.82 mg, 0.034 mmol). The reaction was stirred for 20 min and concentrated under reduced pressure. The residue was taken up in ACN/H$_2$O and purified via preparative HPLC to give the title compound (9.7 mg) as a white solid. LCMS m/z=531.3 [M+H]$^+$; $^1$H NMR (400 MHz, DMSO-$d_6$) δ ppm 1.33-1.55 (m, J=4.29 Hz, 8H), 1.72-1.80 (m, 1H), 2.26 (bs, 1H), 2.98-3.10 (m, 1H), 3.25-3.28 (m, 2H), 3.40 (d, J=7.20 Hz, 1H), 3.57-3.66 (m, 1H), 3.68-3.77 (m, 1H), 3.99 (s, 2H), 4.28-4.50 (m, 2H), 5.08 (bs, 1H), 7.21-7.27 (m, 1H), 7.27-7.33 (m, 5H), 7.38-7.46 (m, 3H), 12.51 (s, 1H).

Example 1.34: Preparation of 2-(((1s,4s)-4-((5-(2-Aminoethylthio)-4-phenyl-3-p-tolyl-1H-pyrazol-1-yl)methyl)cyclohexyl)methoxy)acetic Acid (Compound 250)

Step A: Preparation of tert-Butyl 2-(4-Phenyl-3-p-tolyl-1H-pyrazol-5-ylthio)ethylcarbamate From 2-phenyl-1-p-tolylethanone and tert-butyl 2-bromoethylcarbamate, using a similar method to the one described in Example 1.25, Step A, the title compound was obtained as a light yellow solid. $^1$H NMR (400 MHz, DMSO-$d_6$) δ ppm 1.36 (s, 9H), 2.28 (s, 3H), 2.71-2.78 (m, 1H), 2.94 (t, J=7.07 Hz, 2H), 3.13-3.21 (m, 2H), 6.88 (t, J=5.68 Hz, 1H), 7.13-7.23 (m, 6H), 7.32-7.37 (m, 2H), 13.26 (s, 1H).

Step B: Preparation of tert-Butyl 2-(((1s,4s)-4-((5-(2-(tert-Butoxycarbonylamino)ethylthio)-4-phenyl-3-p-tolyl-1H-pyrazol-1-yl)methyl)cyclohexyl)methoxy)acetate and tert-Butyl 2-(((1s,4s)-4-((3-(2-(tert-Butoxycarbonylamino)ethylthio)-4-phenyl-5-p-tolyl-1H-pyrazol-1-yl)methyl)cyclohexyl)methoxy)acetate as a Mixture of Regioisomers From tert-butyl 2-(4-phenyl-3-p-tolyl-1H-pyrazol-5-ylthio)ethylcarbamate, using a similar method to the one described in Example 1.25, Step B, the title compound was obtained as a clear oil (a mixture of regioisomers). LCMS m/z=650.7 [M+H]$^+$; $^1$H NMR (400 MHz, DMSO-$d_6$) δ ppm 1.34 (s, 9H), 1.36-1.46 (m, 3H), 1.43 (s, 9H), 1.45-1.52 (m, 3H), 1.68-1.80 (m, 1H), 2.12-2.21 (m, 1H), 2.25 (s, 3H), 2.51-2.55 (m, 2H), 2.83 (q, J=6.61 Hz, 2H), 3.14-3.19 (m, 2H), 3.40 (d, J=6.82 Hz, 2H), 3.95 (s, 2H), 4.26 (d, J=7.58 Hz, 2H), 6.64-6.75 (m, 1H), 7.05 (d, J=7.96 Hz, 2H), 7.20 (d, J=8.08 Hz, 2H), 7.23-7.27 (m, 2H), 7.30-7.42 (m, 3H).

Step C: Preparation of 2-(((1s,4s)-4-((5-(2-Aminoethylthio)-4-phenyl-3-p-tolyl-1H-pyrazol-1-yl)methyl)cyclohexyl)methoxy)acetic Acid From tert-butyl 2-(((1s,4s)-4-((5-(2-(tert-butoxycarbonylamino)ethylthio)-4-phenyl-3-p-tolyl-1H-pyrazol-1-yl)methyl)cyclohexyl)methoxy)acetate and tert-butyl 2-(((1s,4s)-4-((3-(2-(tert-butoxycarbonylamino)ethylthio)-4-phenyl-5-p-tolyl-1H-pyrazol-1-yl)methyl)cyclohexyl)methoxy)acetate as a mixture of regioisomers, using a similar method to the one described in Example 1.25, Step C, the title compound was obtained as a white solid. LCMS m/z=494.5 [M+H]$^+$; $^1$H NMR (400 MHz, DMSO-$d_6$) δ ppm 1.30-1.46 (m, J=23.31, 5.62 Hz, 4H), 1.46-1.54 (m, 4H), 1.70-1.85 (m, 1H), 2.14-2.23 (m, 1H), 2.26 (s, 3H), 2.57-2.74 (m, 4H), 3.42 (d, J=7.07 Hz, 2H), 4.00 (s, 2H), 4.28 (d, J=7.45 Hz, 2H), 7.07 (d, J=7.96 Hz, 2H), 7.20 (d, J=8.08 Hz, 2H), 7.24-7.29 (m, 2H), 7.31-7.45 (m, 3H), 7.64 (bs, 2H), 12.54 (s, 1H).

Example 1.35: Preparation of 2-(((1s,4s)-4-((3-(4-Fluorophenyl)-5-(2-hydroxyethylthio)-4-phenyl-1H-pyrazol-1-yl)methyl)cyclohexyl)methoxy)acetic Acid (Compound 255)

Step A: Preparation of 3-(4-Fluorophenyl)-4-phenyl-5-(2-(tetrahydro-2H-pyran-2-yloxy)ethylthio)-1H-pyrazole From 1-(4-fluorophenyl)-2-phenethanone, using a similar method to the one described in Example 1.25, Step A, the title compound was obtained as a white solid. $^1$H NMR (400 MHz, DMSO-d$_6$) δ ppm 1.32-1.51 (m, 3H), 1.52-1.75 (m, 3H), 3.10 (t, J=6.63 Hz, 2H), 3.33-3.44 (m, 1H), 3.53-3.66 (m, 1H), 3.68-3.83 (m, 2H), 4.52-4.57 (m, 1H), 7.11 (t, J=8.27 Hz, 1H), 7.21 (t, J=8.97 Hz, 3H), 7.24-7.43 (m, 5H), 13.34 (s, 1H).

Step B: Preparation of tert-butyl 2-(((1s,4s)-4-((3-(4-Fluorophenyl)-4-phenyl-5-(2-(tetrahydro-2H-pyran-2-yloxy)ethylthio)-1H-pyrazol-1-yl)methyl)cyclohexyl)methoxy)acetate and tert-Butyl 2-(((1s,4s)-4-((5-(4-Fluorophenyl)-4-phenyl-3-(2-(tetrahydro-2H-pyran-2-yloxy)ethylthio)-1H-pyrazol-1-yl)methyl)cyclohexyl)methoxy)acetate as a Mixture of Regioisomers From 4-(3-fluorophenyl)-3-phenyl-5-(2-(tetrahydro-2H-pyran-2-yloxy)ethylthio)-1H-pyrazole, using a similar method to the one described in Example 1.25, Step B, the title compound was obtained as a clear oil (a mixture of regioisomers). LCMS m/z=639.6 [M+H]$^+$; $^1$H NMR (400 MHz, DMSO-d$_6$) δ ppm 1.30-1.42 (m, 4H), 1.43 (s, 9H), 1.45-1.54 (m, 7H), 1.56-1.79 (m, 3H), 2.14-2.24 (m, 1H), 2.65-2.72 (m, 2H), 3.20-3.28 (m, 2H), 3.31-3.37 (m, 1H), 3.39 (d, J=6.82 Hz, 2H), 3.47-3.56 (m, 1H), 3.58-3.66 (m, 1H), 3.95 (s, 2H), 4.30 (dd, J=7.39, 3.09 Hz, 2H), 4.34-4.36 (m, 1H), 7.06-7.13 (m, 2H), 7.24-7.28 (m, 2H), 7.29-7.44 (m, 5H).

Step C: Preparation of 2-(((1s,4s)-4-((3-(4-Fluorophenyl)-5-(2-hydroxyethylthio)-4-phenyl-1H-pyrazol-1-yl)methyl)cyclohexyl)methoxy)acetic Acid From tert-butyl 2-(((1s,4s)-4-((3-(4-fluorophenyl)-4-phenyl-5-(2-(tetrahydro-2H-pyran-2-yloxy)ethylthio)-1H-pyrazol-1-yl)methyl)cyclohexyl)methoxy)acetate and tert-butyl 2-(((1s,4s)-4-((5-(4-fluorophenyl)-4-phenyl-3-(2-(tetrahydro-2H-pyran-2-yloxy)ethylthio)-1H-pyrazol-1-yl)methyl)cyclohexyl)methoxy)acetate, using a similar method to the one described in Example 1.25, Step C, the title compounds were obtained as clear oily solids. LCMS m/z=499.7 [M+H]$^+$; $^1$H NMR (400 MHz, DMSO-d$_6$) δ ppm 1.29-1.45 (m, 4H), 1.45-1.53 (m, 4H), 1.69-1.80 (m, 1H), 2.14-2.22 (m, 1H), 2.57 (t, J=6.69 Hz, 2H), 3.25-3.29 (m, 2H), 3.28-3.32 (m, 1H), 3.40 (d, J=6.95 Hz, 2H), 3.97 (s, 2H), 4.29 (d, J=7.45 Hz, 2H), 7.06-7.14 (m, 2H), 7.23-7.28 (m, 2H), 7.30-7.43 (m, 5H).

Example 1.36: Preparation of 2-(((1s,4s)-4-((5-(4-Fluorophenyl)-3-(2-hydroxyethylthio)-4-phenyl-1H-pyrazol-1-yl)methyl)cyclohexyl)methoxy)acetic Acid (Compound 256)

From tert-butyl 2-(((1s,4s)-4-((3-(4-fluorophenyl)-4-phenyl-5-(2-(tetrahydro-2H-pyran-2-yloxy)ethylthio)-1H-pyrazol-1-yl)methyl)cyclohexyl)methoxy)acetate and tert-butyl 2-(((1s,4s)-4-((5-(4-fluorophenyl)-4-phenyl-3-(2-(tetrahydro-2H-pyran-2-yloxy)ethylthio)-1H-pyrazol-1-yl)methyl)cyclohexyl)methoxy)acetate, using a similar method to the one described in Example 1.25, Step C, the title compound was obtained as clear oil solid. LCMS m/z=499.7 [M+H]$^+$; $^1$H NMR (400 MHz, DMSO-d$_6$) δ ppm 0.81-0.99 (m, 2H), 1.01-1.14 (m, 2H), 1.46-1.59 (m, 1H), 1.65 (dd, J=13.20, 2.08 Hz, 2H), 1.76 (dd, J=12.44, 2.08 Hz, 2H), 1.86-1.97 (m, 1H), 2.56 (t, J=6.63 Hz, 2H), 3.27 (dd, J=13.52, 6.69 Hz, 4H), 3.91 (s, 2H), 4.20 (d, J=7.20 Hz, 2H), 4.76 (bs, 1H), 7.07-7.14 (m, 2H), 7.25-7.28 (m, 2H), 7.31-7.43 (m, 5H).

Example 1.37: Preparation of 2-(((1s,4s)-4-((5-(2-Hydroxyethyl)-3,4-diphenyl-1H-pyrazol-1-yl)methyl)cyclohexyl)methoxy)acetic Acid (Compound 251)

Step A: Preparation of 2-(3-Phenyl-1H-pyrazol-5-yl)ethanol 5-(2-(Benzyloxy)ethyl-3-phenyl-1H-pyrazole (2.1 g, 7.54 mmol) was dissolved in acetic acid (10 mL) and THF (10 mL). Palladium on carbon (0.080 g, 0.754 mmol) was added and the reaction was stirred for 4 days under hydrogen atmosphere on the Parr shaker at 55 psi. After this time, the reaction was filtered through celite and washed with EtOAc. The solvents were evaporated. The reaction progress was checked by TLC and shown to be ~50-60% complete. The reaction was set up on the Parr shaker again. After three more days on the Parr shaker, the reaction was stopped. The reaction was filtered through celite and the solvents removed. The reaction was extracted (70 mL each of H$_2$O and EtOAc). The aqueous layer was extracted again with EtOAc (70 mL). The combined organic layer was dried and concentrated, and the residue was purified by column chromatography to give the title compound (665 mg) as a white solid. LCMS m/z=189.4 [M+H]$^+$; $^1$H NMR (400 MHz, DMSO-d$_6$) δ ppm 2.68-2.82 (m, 2H), 3.60-3.71 (m, 2H), 4.73-4.81 (m, 1H), 6.48 (s, 1H), 7.20-7.49 (m, 3H), 7.55-7.96 (m, 2H), 12.53 (s, 1H).

Step B: Preparation of 2-(4-Bromo-3-phenyl-1H-pyrazol-5-yl)ethanol 2-(3-Phenyl-1H-pyrazol-5-yl)ethanol (664 mg, 3.53 mmol) was dissolved in dry DCM (40 mL) and THF (10 mL). The reaction was cooled in an ice bath and Br$_2$(363 μL, 7.06 mmol), pre-dissolved in DCM (3 mL), was added slowly dropwise via addition funnel. The reaction was stirred for 2 h in an ice bath, then the reaction was quenched by the addition of Na$_2$SO$_3$ (20 mL of 10% solution; the reaction went from reddish-brown to clear and some bubbling was observed). The reaction was extracted (100 mL each of H$_2$O and DCM). The aqueous layer was extracted again with DCM (100 mL). The combined organic layer was back extracted again with H$_2$O (200 mL). The organic layer was dried and concentrated to yield the title compound (880 mg) as a light yellow solid. LCMS m/z=267.1 [M+H]$^+$; $^1$H NMR (400 MHz, DMSO-d$_6$) δ ppm 2.78 (t, J=7.14 Hz, 2H), 3.66 (t, J=7.14 Hz, 2H), 7.35-7.42 (m, 1H), 7.43-7.51 (m, 2H), 7.72-7.84 (m, 2H).

Step C: Preparation of tert-Butyl 2-(((1s,4s)-4-((4-Bromo-5-(2-hydroxyethyl)-3-phenyl-1H-pyrazol-1-yl)methyl)cyclohexyl)methoxy)acetate 2-(4-Bromo-3-phenyl-1H-pyrazol-5-yl)ethanol (880 mg, 3.29 mmol), tert-butyl 2-(((1s,4s)-4-(tosyloxymethyl)cyclohexyl)methoxy)acetate (1359 mg, 3.29 mmol), and cesium carbonate (2147 mg, 6.59 mmol) were added to DMF (15 mL). The reaction was heated to 80° C. and stirred at this temperature for 1 h. The reaction was cooled and extracted (50 mL each of $H_2O$ and EtOAc). The aqueous layer was extracted again with EtOAc (50 mL). The combined organic layer was back extracted with $H_2O$ (100 mL). The organic layer was dried, concentrated, and the residue was purified by chromatography to yield the title compound (640 mg) as a light yellow oil. LCMS m/z=507.4 [M+H]$^+$; $^1$H NMR (400 MHz, DMSO-d$_6$) δ ppm 1.28-1.53 (m, 17H), 1.69-1.81 (m, J=5.31 Hz, 1H), 2.02-2.14 (m, 1H), 2.87 (t, J=6.76 Hz, 2H), 3.39 (d, J=6.95 Hz, 2H), 3.56-3.66 (m, 2H), 3.94 (s, 2H), 4.10 (d, J=7.45 Hz, 2H), 4.92 (t, J=5.43 Hz, 1H), 7.33-7.40 (m, 1H), 7.40-7.49 (m, 2H), 7.75-7.85 (m, 2H).

Step D: Preparation of 2-(((1s,4s)-4-((5-(2-Hydroxyethyl)-3,4-diphenyl-1H-pyrazol-1-yl)methyl)cyclohexyl)methoxy)acetic Acid tert-Butyl 2-(((1s,4s)-4-((4-bromo-5-(2-hydroxyethyl)-3-phenyl-1H-pyrazol-1-yl)methyl)cyclohexyl)methoxy)acetate (30 mg, 0.059 mmol), phenyl boronic acid (1.1 eq), tetrakistriphenylphospinepalladium (3.42 mg, 2.96 μmol), and $K_2CO_3$ (16.34 mg, 0.118 mmol) were added to a vial with dioxane (300 μL). The reaction was heated in a microwave at 150° C. for 1 h. After this time, the reaction was filtered through a plug of $MgSO_4$. The solvent was removed and the resulting oil (t-butyl ester intermediate) was re-dissolved in HCl (500 μL, 2.000 mmol). The reaction was stirred overnight at room temperature. The next day, the solvent was removed and the product was purified by preparative LC/MS to give the title compound (4.2 mg) as a white solid. LCMS m/z=449.3 [M+H]$^+$; $^1$H NMR (400 MHz, DMSO-d$_6$) δ ppm 1.33-1.59 (m, 8H), 1.73-1.82 (m, 1H), 2.09-2.21 (m, 1H), 2.75 (t, J=7.14 Hz, 2H), 3.40-3.46 (m, 4H), 3.98-4.00 (m, 2H), 4.06-4.09 (m, 2H), 7.15-7.25 (m, 5H), 7.26-7.34 (m, 3H), 7.34-7.42 (m, 22H).

Example 1.38: Preparation of 2-(((1s,4s)-4-((5-(2-Hydroxyethyl)-4-(3-methoxyphenyl)-3-phenyl-1H-pyrazol-1-yl)methyl)cyclohexyl)methoxy)acetic Acid (Compound 252)

From tert-butyl 2-(((1s,4s)-4-((4-bromo-5-(2-hydroxyethyl)-3-phenyl-1H-pyrazol-1-yl)methyl)cyclohexyl)methoxy)acetate and 3-methoxyphenylboronic acid, using a similar method to the one described in Example 1.37, the title compound was obtained as a white solid. LCMS m/z=479.6 [M+H]$^+$; $^1$H NMR (400 MHz, DMSO-d$_6$) δ ppm 1.32-159 (m, 8H), 1.71-1.86 (m, 1H), 2.06-2.22 (m, 1H), 2.76 (t, J=6.19 Hz, 2H), 3.41-3.50 (m, 4H), 3.70 (s, 3H), 4.00 (s, 2H), 4.07 (d, J=6.32 Hz, 2H), 6.73-6.80 (m, 2H), 6.85-6.92 (m, 1H), 7.14-7.36 (m, 6H).

Example 1.39: Preparation of Sodium 2-(((1s,4s)-4-((5-(2-Hydroxyethyl)-4-(3-methoxyphenyl)-3-phenyl-1H-pyrazol-1-yl)methyl)cyclohexyl)methoxy)acetate 2-(((1s,4s)-4-((5-(2-Hydroxyethyl)-4-(3-methoxyphenyl)-3-phenyl-1H-pyrazol-1-yl)methyl)cyclohexyl)methoxy)acetic acid (8.2 mg, 0.017 mmol) was dissolved in ACN (0.2 mL). NaOH (5.71 μL, 0.017 mmol) was added, followed by $H_2O$ (0.2 mL), and the reaction was stirred for an hour. After this time, the reaction was frozen and lyophilized to give the title compound (8.5 mg) as a white solid. LCMS m/z=479.4 [M-Na+H]$^+$.

Example 1.40: Preparation of 2-(((1s,4s)-4-((4-(2,3-Difluorophenyl)-5-(2-hydroxyethyl)-3-phenyl-1H-pyrazol-1-yl)methyl)cyclohexyl)methoxy)acetic Acid (Compound 253)

From tert-butyl 2-(((1s,4s)-4-((4-bromo-5-(2-hydroxyethyl)-3-phenyl-1H-pyrazol-1-yl)methyl)cyclohexyl)methoxy)acetate and 2,3-difluorophenylboronic acid, using a similar method to the one described in Example 1.37, the title compound was obtained as a white solid. LCMS m/z=485.4 [M+H]$^+$; $^1$H NMR (400 MHz, DMSO-d$_6$) δ ppm 1.31-1.55 (m, 8H), 1.73-1.83 (m, 1H), 2.09-2.19 (m, 1H), 2.73 (t, J=7.01 Hz, 2H), 3.37-3.45 (m, 4H), 4.00 (s, 2H), 4.10 (d, J=7.45 Hz, 2H), 7.10-7.17 (m, 1H), 7.19-7.32 (m, 6H), 7.38-7.49 (m, 1H).

Example 1.41: Preparation of 2-(((1s,4s)-4-((4-(3-Fluorophenyl)-5-(2-hydroxyethyl)-3-phenyl-1H-pyrazol-1-yl)methyl)cyclohexyl)methoxy)acetic Acid (Compound 254)

From tert-butyl 2-(((1s,4s)-4-((4-bromo-5-(2-hydroxyethyl)-3-phenyl-1H-pyrazol-1-yl)methyl)cyclohexyl)methoxy)acetate and 3-fluorophenylboronic acid, using a similar method to the one described in Example 1.37, the title compound was obtained as a white solid. LCMS m/z=467.6 [M+H]$^+$; $^1$H NMR (400 MHz, DMSO-d$_6$) δ ppm 1.32-1.59 (m, 8H), 1.77 (dd, J=9.92, 4.48 Hz, 1H), 2.09-2.19 (m, 1H), 2.77 (t, J=7.01 Hz, 2H), 3.41-3.48 (m, 4H), 4.00 (s, 2H), 4.08 (d, J=7.45 Hz, 2H), 6.99-7.08 (m, 2H), 7.10-7.18 (m, 1H), 7.18-7.32 (m, 5H), 7.35-7.45 (m, 1H).

Example 1.42: Preparation of 2-(((1s,4s)-4-((4-(3-Chloro-2-fluorophenyl)-5-(2-hydroxyethyl)-3-phenyl-1H-pyrazol-1-yl)methyl)cyclohexyl)methoxy)acetic Acid (Compound 276)

From tert-butyl 2-(((1s,4s)-4-((4-bromo-5-(2-hydroxyethyl)-3-phenyl-1H-pyrazol-1-yl)methyl)cyclohexyl)methoxy)acetate and 3-chloro-2-fluorophenylboronic acid, using a similar method to the one described in Example 1.37, the title compound was obtained as a white solid. LCMS m/z=−501.5 [M+H]$^+$.

Example 1.43: Preparation of 2-(((1s,4s)-4-((5-(3-Hydroxypropyl)-3,4-diphenyl-1H-pyrazol-1-yl)methyl)cyclohexyl)methoxy)acetic Acid (Compound 271)

Step A: Preparation of 5-(But-3-enyl)-3-phenyl-1H-pyrazole

Acetophenone (4.92 mL, 42.2 mmol) was dissolved in toluene (50 mL). The reaction was cooled on an ice bath. LiHMDS (42.2 mL, 42.2 mmol) was added via syringe and the reaction was stirred for 2 min. Pent-4-enoyl chloride (4.66 mL, 42.2 mmol) was added and then the reaction was stirred for 2 more min. Hydrazine hydrate (8.18 mL, 169 mmol) was then added, along with AcOH (2 mL) and EtOH (2 mL). The reaction was warmed to room temperature and then heated in an oil bath to 80° C. for 1 h. After this time, the reaction was cooled and an extraction was performed (200 mL each of $H_2O$ and EtOAc). The aqueous layer was extracted again with EtOAc (200 mL). The combined organic layer was dried, concentrated, and the residue was purified by column chromatography to give the title compound (5.4 g) as a yellow oil. LCMS m/z=199.3 [M+H]$^+$; $^1$H NMR (400 MHz, DMSO-d$_6$) δ ppm 2.39 (q, J=7.28 Hz, 2H), 2.61-2.76 (m, 2H), 5.00 (d, J=9.98 Hz, 1H), 5.04-5.13 (m, 1H), 5.78-5.95 (m, 1H), 6.47 (s, 1H), 7.21-7.33 (m, 1H), 7.33-7.48 (m, 2H), 7.65-7.81 (m, 2H), 12.56 (s, 1H).

Step B: Preparation of 3-(3-Phenyl-1H-pyrazol-5-yl)propan-1-ol 5-(But-3-enyl)-3-phenyl-1H-pyrazole (5.4 g, 27.2 mmol) was dissolved in MeOH (40 mL) and DCM (10 mL). The reaction was cooled on a dry-ice/acetone bath and ozone was bubbled through the solution for ~2 h. The reaction was transferred into an ice bath and NaBH$_4$ (1.546 g, 40.9 mmol) was added slowly portion-wise (bubbling was observed). Upon complete addition, the reaction was removed from the ice bath and stirred at room temperature for 1 h. Excess solvent was evaporated and the reaction was extracted (100 mL each of H$_2$O and EtOAc). The aqueous layer was extracted again with EtOAc (100 mL). The combined organic layer was dried, concentrated, and the residue was purified by column chromatography to yield the title compound (3.0 g) as a white solid. LCMS m/z=203.3 [M+H]$^+$; $^1$H NMR (400 MHz, DMSO-d$_6$) δ ppm 1.72-1.82 (m, 2H), 2.54-2.69 (m, 2H), 3.46 (q, J=6.11 Hz, 2H), 4.40-4.54 (m, 1H), 6.45 (s, 1H), 7.21-7.45 (m, 3H), 7.66-7.79 (m, J=7.45 Hz, 2H), 12.53 (s, 1H).

Step C: Preparation of 3-(4-Bromo-3-phenyl-1H-pyrazol-5-yl)propan-1-ol 3-(3-Phenyl-1H-pyrazol-5-yl)propan-1-ol (3.0 g, 14.83 mmol) was dissolved in dry DCM (40 mL) and THF (15 mL). The reaction was cooled in an ice bath and Br$_2$ (1.146 mL, 22.25 mmol) pre-dissolved in DCM (10 mL) was added slowly dropwise via addition funnel. The reaction was stirred for 2 h in an ice bath. The reaction was quenched by the addition of Na$_2$SO$_3$ (20 mL of 10% solution; the reaction went from reddish-brown to clear and some bubbling was observed). The reaction was extracted (100 mL each of H$_2$O and DCM). The aqueous layer was extracted again with DCM (100 mL). The combined organic layer was back extracted again with H$_2$O (200 mL). The organic layer was dried and concentrated to give the title compound (4.08 g) as a yellow solid. LCMS m/z=281.3 [M+H]$^+$; $^1$H NMR (400 MHz, DMSO-d$_6$) δ ppm 1.72-1.83 (m, 2H), 2.61-2.68 (m, 2H), 3.47 (t, J=6.44 Hz, 2H), 7.39 (t, J=7.33 Hz, 1H), 7.47 (t, J=7.45 Hz, 2H), 7.78 (d, J=7.07 Hz, 2H).

Step D: Preparation of tert-Butyl 2-(((1s,4s)-4-((4-Bromo-5-(3-hydroxypropyl)-3-phenyl-1H-pyrazol-1-yl)methyl)cyclohexyl)methoxy)acetate 3-(4-Bromo-3-phenyl-1H-pyrazol-5-yl)propan-1-ol, tert-butyl 2-(((1s,4s)-4-(tosyloxymethyl)cyclohexyl)methoxy)acetate (2.93 g, 7.11 mmol), and cesium carbonate (4.64 g, 14.23 mmol) were dissolved in DMF (35 mL). The reaction was heated to 80° C. in an oil bath and stirred at this temperature for an hour. The reaction was cooled and extracted (100 mL each of H$_2$O and EtOAc). The aqueous layer was extracted again with EtOAc (100 mL). The combined organic layer was back extracted once with H$_2$O (200 mL). The organic layer was dried, concentrated, and the residue was purified by column chromatography to give the title compound (1.54 g) as a light yellow oil. LCMS m/z=521.7 [M+H]$^+$; $^1$H NMR (400 MHz, DMSO-d$_6$) δ ppm 0.97-1.05 (m, 4H), 1.26-1.55 (m, 13H), 1.65-1.79 (m, 3H), 2.01-2.12 (m, 1H), 2.71-2.77 (m, 2H), 3.39 (d, J=6.95 Hz, 2H), 3.46 (t, J=6.19 Hz, 2H), 3.94 (s, 2H), 4.06 (d, J=7.45 Hz, 2H), 7.32-7.39 (m, 1H), 7.40-7.48 (m, 2H), 7.77-7.82 (m, J=8.34, 1.14 Hz, 2H).

Step E: Preparation of 2-(((1s,4s)-4-((5-(3-Hydroxypropy)-3,4-diphenyl-1H-pyrazol-1-yl)methyl)cyclohexyl)methoxy)acetic Acid tert-Butyl 2-(((1s,4s)-4-((4-bromo-5-(3-hydroxypropyl)-3-phenyl-1H-pyrazol-1-yl)methyl)cyclohexyl)methoxy)acetate (50 mg, 0.096 mmol), phenylboronic acid (1.1 eq), tetrakis(triphenylphosphine)palladium(O) (11.08 mg, 9.59 μmol), and K$_2$CO$_3$ (26.5 mg, 0.192 mmol) were added to a vial with dioxane (0.4 mL). The reaction was heated in a microwave at 150° C. for 2 h. After this time, the reaction was filtered through a plug of MgSO$_4$. The solvent was removed and the ester intermediate obtained was re-dissolved in HC (4M in dioxane) (503 μL, 2.013 mmol). The reaction was stirred overnight at room temperature. The next day, the solvent was removed and the residue was purified by preparative LC/MS. After lyophilizing the reaction, there was observed the side-product formation of the TFA-ester off of the side chain alcohol. Therefore, the product was dissolved in THF (0.3 mL). Then 3M LiOH (50 μL) was added. The reactions were stirred at room temperature overnight. The next day, 1 M HCl (200 L) was added to make the reaction acidic. The reactions were extracted (2 mL each of HCl/H$_2$O and EtOAc). The aqueous layer was extracted again with EtOAc (2 mL). The combined organic layer was dried and concentrated. The resulting oil was re-dissolved in ACN (0.3 mL) and H$_2$O (0.2 mL). The mixture was frozen and lyophilized to give the title compound (8.9 mg) as a white solid. LCMS m/z=463.5 [M+H]$^+$; $^1$H NMR (400 MHz, DMSO-d$_6$) δ ppm 1.32-1.60 (m, 10H), 1.71-1.84 (m, 1H), 2.08-2.19 (m, 1H), 2.59-2.65 (m, 2H), 3.31 (t, J=6.19 Hz, 2H), 3.43-3.44 (m, 2H), 3.99 (s, 2H), 4.05 (d, J=7.33 Hz, 2H), 7.14-7.25 (m, 5H), 7.26-7.40 (m, 5H).

Example 1.44: Preparation of 2-(((1s,4s)-4-((5-(3-Hydroxypropyl)-4-(3-methoxyphenyl)-3-phenyl-1H-pyrazol-1-yl)methyl)cyclohexyl)methoxy)acetic Acid (Compound 272)

From tert-butyl 2-(((1s,4s)-4-((4-bromo-5-(3-hydroxypropyl)-3-phenyl-1H-pyrazol-1-yl)methyl)cyclohexyl)methoxy)acetate and 3-methoxyphenylboronic acid, using a similar method to the one described in Example 1.43, the title compound was obtained as a white solid. LCMS m/z=493.6 [M+H]$^+$; $^1$H NMR (400 MHz, DMSO-d$_6$) δ ppm 1.32-1.61 (m, 10H), 1.72-1.83 (m, 1H), 2.08-2.18 (m, 1H), 2.60-2.66 (m, 2H), 3.33 (t, J=6.19 Hz, 2H), 3.42 (d, J=6.82 Hz, 2H), 3.70 (s, 3H), 3.99 (s, 2H), 4.04 (d, J=7.33 Hz, 2H), 6.70-6.75 (m, 2H), 6.87 (dd, J=7.96, 2.15 Hz, 1H), 7.16-7.37 (m, 6H).

Example 1.45: Preparation of 2-(((1s,4s)-4-((4-(2,3-Difluorophenyl)-5-(3-hydroxypropyl)-3-phenyl-1H-pyrazol-1-yl)methyl)cyclohexyl)methoxy)acetic Acid (Compound 273)

From tert-butyl 2-(((1s,4s)-4-((4-bromo-5-(3-hydroxypropyl)-3-phenyl-1H-pyrazol-1-yl)methyl)cyclohexyl)methoxy)acetate and 2,3-difluorophenylboronic acid, using a similar method to the one described in Example 1.43, the title compound was obtained as a white solid. LCMS m/z=499.7 [M+H]$^+$.

Example 1.46: Preparation of 2-(((1s,4s)-4-((4-(3-Fluorophenyl)-5-(3-hydroxypropyl)-3-phenyl-1H-pyrazol-1-yl)methyl)cyclohexyl)methoxy)acetic Acid (Compound 274)

From tert-butyl 2-(((1s,4s)-4-((4-bromo-5-(3-hydroxypropyl)-3-phenyl-1H-pyrazol-1-yl)methyl)cyclohexyl)methoxy)acetate and 3-fluorophenylboronic acid, using a similar method to the one described in Example 1.43, the title compound was obtained as a white solid. LCMS m/z=481.3 [M+H]$^+$.

Example 1.47: Preparation of 2-(((1s,4s)-4-((4-(3-Chloro-2-fluorophenyl)-5-(3-hydroxypropyl)-3-phenyl-1H-pyrazol-1-yl)methyl)cyclohexyl)methoxy)acetic Acid (Compound 281)

From tert-butyl 2-(((1s,4s)-4-((4-bromo-5-(3-hydroxypropyl)-3-phenyl-1H-pyrazol-1-yl)methyl)cyclohexyl)methoxy)acetate and 3-chloro-2-fluorophenylboronic acid, using a similar method to the one described in Example 1.43, the title compound was obtained as a white solid. LCMS m/z=515.5 [M+H]$^+$.

Example 1.48: Preparation of 2-(((1s,4s)-4-((4-(3-Chlorophenyl)-5-(3-hydroxypropyl)-3-phenyl-1H-pyrazol-1-yl)methyl)cyclohexyl)methoxy)acetic Acid (Compound 282)

From tert-butyl 2-(((1s,4s)-4-((4-bromo-5-(3-hydroxypropyl)-3-phenyl-1H-pyrazol-1-yl)methyl)cyclohexyl)methoxy)acetate and 3-chlorophenylboronic acid, using a similar method to the one described in Example 1.43, the title compound was obtained as a white solid. LCMS m/z=497.5 [M+H]$^+$.

Example 1.49: Preparation of 2-(((1s,4s)-4-((5-(3-hydroxypropyl)-4-phenyl-3-p-tolyl-1H-pyrazol-1-yl)methyl)cyclohexyl)methoxy)acetic Acid (Compound 288)

Step A: Preparation of 5-(But-3-enyl)-4-phenyl-3-p-tolyl-1H-pyrazole

2-Phenyl-1-p-tolylethanone (1.0 g, 4.76 mmol) was dissolved in Toluene (20 mL). The reaction was cooled in an ice bath and then LiHMDS (4.76 mL, 4.76 mmol) was added slowly via syringe. The reaction was stirred at this temperature for 5 min and then pent-4-enoyl chloride (0.564 g, 4.76 mmol) was added. The reaction was warmed to room temperature and stirred at this temperature for 20 min. After this time EtOH (10 mL), AcOH (2 mL), and hydrazine hydrate (0.231 mL, 4.76 mmol) were added to the reaction. The reaction was heated to 80° C. and stirred at this temperature for an hour. After this time, the reaction was cooled and extracted (50 mL each of EtOAc and IM NaOH). The aqueous layer was extracted again with EtOAc (50 mL). The combined organic layer was dried, concentrated, and the residue was purified by silica gel column chromatography to give the title compound (355 mg) as a colorless oil. LCMS m/z=289.0 [M+H]$^+$; $^1$H NMR (400 MHz, DMSO-d$_6$) δ ppm 2.22-2.32 (m, 5H), 2.55-2.69 (m, 2H), 4.86-5.02 (m, 2H), 5.75 (s, 1H), 6.99-7.24 (m, 6H), 7.25-7.31 (m, 1H), 7.33-7.39 (m, 2H), 12.74 (s, 1H).

Step B: Preparation of 3-(4-Phenyl-3-p-tolyl-1H-pyrazol-5-yl)propan-1-ol 5-(But-3-enyl)-4-phenyl-3-p-tolyl-1H-pyrazole (360 mg, 1.248 mmol) was dissolved in MeOH (20 mL) and DCM (5 mL). The reaction was cooled to −78° C. and ozone was bubbled through the solution. After the starting material was consumed, the reaction was cooled in an ice bath. Sodium borohydride (70.8 mg, 1.872 mmol) was added to the reaction. The reaction was warmed to room temperature and stirred for an hour. The solvent was removed under reduced pressure and the reaction was extracted (50 mL each of H$_2$O and EtOAc). The aqueous layer was extracted again with EtOAc (50 mL). The combined organic layer was dried, concentrated, and the residue was purified by silica gel column chromatography to give the title compound (130 mg) as a white solid. LCMS m/z=293.1 [M+H]$^+$; $^1$H NMR (400 MHz, DMSO-d$_6$) δ ppm 1.60-1.74 (m, 2H), 2.25 (s, 3H), 2.54-2.62 (m, 2H), 3.33-3.44 (m, 2H), 4.44 (br. s., 1H), 7.16 (t, J=6.44 Hz, 6H), 7.24-7.30 (m, 1H), 7.32-7.38 (m, 2H), 12.71 (s, 1H).

Step C: Preparation of 2-(((1s,4s)-4-((5-(3-Hydroxypropyl)-4-phenyl-3-p-tolyl-1H-pyrazol-1-yl)methyl)cyclohexyl)methoxy)acetic Acid 3-(4-Phenyl-3-p-tolyl-1H-pyrazol-5-yl)propan-1-ol (50 mg, 0.171 mmol), tert-butyl 2-(((1s,4s)-4-(tosyloxymethyl)cyclohexyl)methoxy)acetate (70.5 mg, 0.171 mmol), and Cs$_2$CO$_3$ (111 mg, 0.342 mmol) were suspended in DMF (0.5 mL). The reaction was heated at 80° C. for an hour. The mixture was cooled and extracted (2 mL each of H$_2$O and EtOAc). The aqueous layer was extracted again with EtOAc (2 mL). The combined organic layer was filtered through a plug of MgSO$_4$. The solvents were removed, then the resulting oil was re-dissolved in HCl (4M in dioxane) (0.5 mL, 2.000 mmol). The reaction was stirred at room temperature overnight. The mixture was purified by preparative LC/MS. After lyophilization, the product was re-dissolved in THE (0.3 mL) and stirred with IM NaOH (100 μL) overnight. The reaction was then made acidic by addition of IM HCl (200 μL). The reaction was extracted (2 mL each of H$_2$O and EtOAc). The aqueous layer was extracted again with EtOAc (2 mL). The combined organic layer was filtered through a plug of MgSO$_4$ and concentrated to give the title compound (3.5 mg), one of the two regioisomers, as a colorless oil. LCMS m/z=477.4 [M+H]$^+$.

Example 1.50: Preparation of 2-(((1s,4s)-4-((3-(3-Hydroxypropyl)-4-phenyl-5-p-tolyl-1H-pyrazol-1-yl)methyl)cyclohexyl)methoxy)acetic Acid (Compound 289)

The title compound was isolated as one of the two regioisomers from Example 1.49, Step C, to give an oil. LCMS m/z=477.5 [M+H]$^+$.

Example 1.51: Preparation of 2-(((1s,4s)-4-((5-(2-fluoro-4-methylphenyl)-3-methyl-4-phenyl-1H-pyrazol-1-yl)methyl)cyclohexyl)methoxy)acetic Acid (Compound 286)

Step A: Preparation of tert-Butyl 2-(((1s,4s)-4-((5-(2-Fluoro-4-methylphenyl)-3-methyl-4-phenyl-1H-pyrazol-1-yl)methyl)cyclohexyl)methoxy)acetate 3-(2-Fluoro-4-methylphenyl)-5-methyl-4-phenyl-1H-pyrazole (2.82 g, 10.59 mmol) was dissolved in dry DMF (40 mL). Cs₂CO₃ (6.90 g, 21.18 mmol) and tert-butyl 2-(((1s,4s)-4-(tosyloxymethyl)cyclohexyl)methoxy)acetate (4.37 g, 10.59 mmol) were added. The reaction was heated to 80° C. and stirred at this temperature for 1 h. The reaction was cooled and extracted (100 mL each of H₂O and EtOAc). The aqueous layer was extracted again with EtOAc (100 mL). The combined organic layer was back extracted once with H₂O/Brine (200 mL). The organic layer was dried, concentrated, and the residue was purified by chromatography to give the title compound (3.2 g), a mixture of regioisomers, as a colorless oil. LCMS m/z=507.2 [M+H]⁺.

Step B: Preparation of 2-(((1s,4s)-4-((5-(2-Fluoro-4-methylphenyl)-3-methyl-4-phenyl-1H-pyrazol-1-yl)methyl)cyclohexyl)methoxy)acetic Acid tert-Butyl 2-(((1s,4s)-4-((3-(2-fluoro-4-methylphenyl)-5-methyl-4-phenyl-1H-pyrazol-1-yl)methyl)cyclohexyl) methoxy)acetate (3.2 g, 6.32 mmol) was dissolved in HCl (4M in dioxane) (50.0 mL, 200 mmol). The reaction was stirred overnight at room temperature. The solvent was removed and the residue was purified by HPLC to give the title compound as a colorless oil (746 mg). LCMS m/z=451.3 [M+H]⁺; ¹H NMR (400 MHz, DMSO-d6) δ ppm 1.08-1.20 (m, 4H), 1.22-1.37 (m, 4H), 1.57-1.69 (m, 1H), 1.90-1.97 (m, 1H), 2.23 (s, 3H), 2.35 (s, 3H), 3.22 (d, J=6.82 Hz, 2H), 3.71-3.87 (m, 2H), 3.92 (s, 2H), 7.04-7.11 (m, 4H), 7.11-7.20 (m, 2H), 7.24 (t, J=7.33 Hz, 2H).

Example 1.52: Preparation of 2-(((1s,4s)-4-((3-(4-Chlorophenyl)-5-ethyl-4-phenyl-1H-pyrazol-1-yl) methyl)cyclohexyl)methoxy)acetic Acid (Compound 163)

Step A: Preparation of 1-(Dimethylamino)-2-phenylpent-1-en-3-one

To a solution of 1-phenylbutan-2-one (5.00 g, 33.7 mmol) in DMF (80.0 mL) was added 1,1-dimethoxy-N,N-dimethylmethanamine (6.03 g, 50.6 mmol). The resulting mixture was stirred at 90° C. for 16 h. Upon completion, the reaction mixture was quenched with water (40.0 mL), extracted with EtOAc (4×50.0 mL), and washed with brine. The combined organics were dried over MgSO₄, filtered, and concentrated to give a brown oil. This brown oil was purified by flash chromatography to give the title compound as a yellow oil (3.32 g). ¹H NMR (400 MHz, CDCl₃) δ ppm 0.97 (t, J=7.32 Hz, 3H), 2.19 (q, J=7.49 Hz, 2H), 2.67 (s, 6H), 7.14-7.41 (m, 5H), 7.61 (s, 1H).

Step B: Preparation of 5-Ethyl-4-phenyl-1H-pyrazole

To a mixture of 1-(dimethylamino)-2-phenylpent-1-en-3-one (3.32 g, 16.33 mmol) in EtOH (80.0 mL) was added hydrazine hydrate (1.58 mL, 32.66 mmol). The resulting mixture was stirred at 80° C. for 3 h. The reaction mixture was cooled to room temperature and concentrated to give a solid. The solid was re-crystallized, using 20% ethanol in water to give the title compound as a white solid (2.81 g). LCMS m/z=173 [M+H]⁺; ¹H NMR (400 MHz, CDCl₃) δ ppm 1.31 (t, J=7.58 Hz, 3H), 2.88 (q, J=7.58 Hz, 2H), 7.22-7.30 (m, 1H), 7.35-7.42 (m, 4H).

Step C: Preparation of 3-Bromo-5-ethyl-4-phenyl-1H-pyrazole

To a solution of 5-ethyl-4-phenyl-1H-pyrazole (3.34 g, 19.39 mmol) in dichloromethane (111.0 mL), was added bromine (1.49 mL, 29.09 mmol) at 25° C. The reaction was stirred at room temperature for 72 h and quenched with NaOH (aq.) to pH 12. The organics were separated. The aqueous layer was extracted again with DCM (3×). The combined organics were washed with brine, dried (MgSO₄), filtered and concentrated to give a red oil. This oil was purified by flash chromatography to give the title compound as a yellow oil (2.84 g). LCMS m/z=251.2 [M+H]⁺.

Step D: Preparation of tert-Butyl 2-(((1s,4s)-4-((3-Bromo-5-ethyl-4-phenyl-1H-pyrazol-1-yl)methyl) cyclohexyl)methoxy)acetate To a solution of 3-bromo-5-ethyl-4-phenyl-1H-pyrazole (0.364 g, 1.451 mmol) in DMF (5.0 mL), was slowly added 60% sodium hydride (0.070 g, 1.740 mmol). The solution was allowed to stir for a total of 20 min, before a mixture of tert-butyl 2-(((1s,4s)-4-(tosyloxymethyl)cyclohexyl) methoxy)acetate (0.598 g, 1.450 mmol) in DMF (1.0 mL) was added. The reaction mixture was then stirred at 45° C. for 12 h. Upon completion, the reaction mixture was quenched with water and extracted with EtOAc (4×). The combined organics were dried over MgSO₄, filtered, and concentrated to give a brown oil. This brown oil was purified by flash chromatography to give the title compound as a yellow oil (0.213 g). LCMS m/z=491.4, 493.5 [M+H]⁺; ¹H NMR (400 MHz, CDCl₃) δ ppm 1.13-1.29 (m, 4H), 1.27-1.41 (m, 2H), 1.43-1.62 (m, 13H), 1.79-1.93 (m, 2H), 2.09-2.25 (m, 1H), 2.76 (q, J=7.58 Hz, 2H), 3.39-3.50 (m, 2H), 3.84-4.05 (m, 4H), 7.20-7.28 (m, 2H), 7.33-7.39 (m, 1H), 7.45-7.54 (m, 2H)

Step E: Preparation of tert-Butyl 2-(((1s,4s)-4-((3-(4-Chlorophenyl)-5-ethyl-4-phenyl-1H-pyrazol-1-yl) methyl)cyclohexyl)methoxy)acetate To a solution of 4-chlorophenylboronic acid (0.019 g, 0.122 mmol), tert-butyl 2-(((1s,4s)-4-((3-bromo-5-ethyl-4-phenyl-1H-pyrazol-1-yl)methyl)cyclohexyl)methoxy)acetate (0.060 g, 0.122 mmol), tetrakis(triphenylphosphine) palladium (0) (0.004 g, 0.004 mmol) in benzene (3.0 mL) and EtOH (1.0 mL) was added sodium carbonate (0.122 mL, 0.244 mmol). The reaction mixture was then heated in a microwave at 130° C. for 1 h. Upon completion, the reaction mixture was diluted with water and extracted with EtOAc (3×). The combined organics were dried over MgSO₄, filtered, and concentrated to give a yellow oil. This yellow oil was re-suspended in ACN/H₂O and purified by HPLC to give the title compound as a white solid (0.032 g). LCMS m/z=523.4, 525.8 [M+H]⁺.

Step F: Preparation of 2-(((1s,4s)-4-((3-(4-Chlorophenyl)-5-ethyl-4-phenyl-1H-pyrazol-1-yl)methyl) cyclohexyl)methoxy)acetic Acid To a solution of tert-butyl 2-(((1s,4s)-4-((3-(4-chlorophenyl)-5-ethyl-4-phenyl-1H-pyrazol-1-yl)methyl)cyclohexyl) methoxy)acetate (0.032 g, 0.060 mmol) in DCM (2.0 mL) was added 4M HCl in dioxane (0.151 mL, 0.602 mmol). The resulting reaction mixture was stirred at 25° C. for 16 h. The reaction was concentrated to give a yellow oil. This yellow oil was then re-suspended in ACN/H₂O and purified by HPLC to give the title compound as a white solid (0.004 g). LCMS m/z=467.5 [M+H]⁺.

Example 1.53: Preparation of 2-(((1s,4s)-4-((3-(3,4-difluorophenyl)-5-ethyl-4-phenyl-1H-pyrazol-1-yl)methyl)cyclohexyl)methoxy)acetic Acid (Compound 284)

Step A: Preparation of tert-Butyl 2-(((1s,4s)-4-((3-(3,4-Difluorophenyl)-5-ethyl-4-phenyl-1H-pyrazol-1-yl)methyl)cyclohexyl)methoxy)acetate From 3,4-difluorophenylboronic acid and tert-butyl 2-(((1s,4s)-4-((3-bromo-5-ethyl-4-phenyl-1H-pyrazol-1-yl)methyl)cyclohexyl)methoxy)acetate, using a similar method to the one described in Example 1.52, Step E, the title compound was obtained as a white solid. LCMS m/z=525.5 [M+H]$^+$.

Step B: 2-(((1s,4s)-4-((3-(3,4-Difluorophenyl)-5-ethyl-4-phenyl-1H-pyrazol-1-yl)methyl)cyclohexyl)methoxy)acetic Acid From tert-butyl 2-(((1s,4s)-4-((3-(3,4-difluorophenyl)-5-ethyl-4-phenyl-1H-pyrazol-1-yl)methyl)cyclohexyl)methoxy)acetate, using a similar method to the one described in Example 1.52, Step F, the title compound was obtained as a white solid. LCMS m/z=469.5 [M+H]$^+$.

Example 1.54: Preparation of 2-(((1s,4s)-4-((5-Ethyl-3-(4-fluorophenyl)-4-phenyl-1H-pyrazol-1-yl)methyl)cyclohexyl)methoxy)acetic Acid (Compound 164)

Step A: Preparation of tert-Butyl 2-(((1s,4s)-4-((5-Ethyl-3-(4-fluorophenyl)-4-phenyl-1H-pyrazol-1-yl)methyl)cyclohexyl)methoxy)acetate From 4-difluorophenylboronic acid and tert-butyl 2-(((1s,4s)-4-((3-bromo-5-ethyl-4-phenyl-1H-pyrazol-1-yl)methyl)cyclohexyl)methoxy)acetate, using a similar method to the one described in Example 1.52, Step E, the title compound was obtained as a white solid. LCMS m/z=507.4 [M+H]$^+$.

Step B: Preparation of 2-(((1s,4s)-4-((5-Ethyl-3-(4-fluorophenyl)-4-phenyl-1H-pyrazol-1-yl)methyl)cyclohexyl)methoxy)acetic Acid From tert-butyl 2-(((1s,4s)-4-((5-ethyl-3-(4-fluorophenyl)-4-phenyl-1H-pyrazol-1-yl)methyl)cyclohexyl)methoxy)acetate, using a similar method to the one described in Example 1.52, Step F, the title compound was obtained as a white solid. LCMS m/z=4513 [M+H]$^+$.

Example 1.55: Preparation of 2-(((1s,4s)-4-((5-Ethyl-3-(2-fluoro-4-methoxyphenyl)-4-phenyl-1H-pyrazol-1-yl)methyl)cyclohexyl)methoxy)acetic Acid (Compound 165)

Step A: Preparation of tert-Butyl 2-(((1s,4s)-4-((5-Ethyl-3-(2-fluoro-4-methoxyphenyl)-4-phenyl-1H-pyrazol-1-yl)methyl)cyclohexyl)methoxy)acetate To a solution of 2-fluoro-4-methoxyphenylboronic acid (0.021 g, 0.122 mmol), tert-butyl 2-(((1s,4s)-4-((3-bromo-5-ethyl-4-phenyl-1H-pyrazol-1-yl)methyl)cyclohexyl)methoxy)acetate (0.060 g, 0.122 mmol), aq. Na$_2$CO$_3$ (2 M solution, 0.122 mL, 0.244 mmol), and Pd(PPh$_3$)$_4$ (0.004 g, 0.004 mmol) in EtOH (1.0 mL) and benzene (3.0 mL). The reaction mixture was then heated in a microwave at 130° C. for 1 h. Upon completion, the reaction mixture was quenched with H$_2$O and extracted with EtOAc (2×). The combined organics layers were dried over MgSO$_4$, filtered and concentrated to give the title compound as a yellow oil without further purification. LCMS m/z=537.5 [M+H]$^+$.

Step B: Preparation of 2-(((1s,4s)-4-((5-Ethyl-3-(2-fluoro-4-methoxyphenyl)-4-phenyl-1H-pyrazol-1-yl)methyl)cyclohexyl)methoxy)acetic Acid To tert-butyl 2-(((1s,4s)-4-((5-ethyl-3-(2-fluoro-4-methoxyphenyl)-4-phenyl-1H-pyrazol-1-yl)methyl)cyclohexyl)methoxy)acetate obtained was added 4 M HCl (0.610 mL, 2.44 mmol) in 1,4-dioxane. The reaction mixture was stirred at 40° C. for 6 h. The reaction mixture was concentrated and the residue was purified by HPLC to give the title compound (0.005 g) as a white solid. LCMS m/z=481.2 [M+H]$^+$.

Example 1.56: Preparation of 2-(((1s,4s)-4-((5-Ethyl-3-(4-methoxyphenyl)-4-phenyl-1H-pyrazol-1-yl)methyl)cyclohexyl)methoxy)acetic Acid (Compound 166)

From 4-methoxyphenylboronic acid and tert-butyl 2-(((1s,4s)-4-((3-bromo-5-ethyl-4-phenyl-1H-pyrazol-1-yl)methyl)cyclohexyl)methoxy)acetate, using a similar method to the one described in Example 1.55, the title compound was obtained as a white solid. LCMS m/z=463.4 [M+H]$^+$.

Example 1.57: Preparation of 2-(((1s,4s)-4-((5-Ethyl-3-(2-fluoro-4-methylphenyl)-4-phenyl-1H-pyrazol-1-yl)methyl)cyclohexyl)methoxy)acetic Acid (Compound 167)

From 2-fluoro-4-methylphenylboronic acid and tert-butyl 2-(((1s,4s)-4-((3-bromo-5-ethyl-4-phenyl-1H-pyrazol-1-yl)methyl)cyclohexyl)methoxy)acetate, using a similar method to the one described in Example 1.55, the title compound was obtained as a white solid. LCMS m/z=465.2 [M+H]$^+$.

Example 1.58: Preparation of 2-(((1s,4s)-4-((5-Ethyl-4-phenyl-3-p-tolyl-1H-pyrazol-1-yl)methyl)cyclohexyl)methoxy)acetic Acid (Compound 168)

From p-tolylboronic acid and tert-butyl 2-(((1s,4s)-4-((3-bromo-5-ethyl-4-phenyl-1H-pyrazol-1-yl)methyl)cyclohexyl)methoxy)acetate, using a similar method to the one described in Example 1.55, the title compound was obtained as a white solid. LCMS m/z=447.5 [M+H]$^+$.

Example 1.59: Preparation of 2-(((1s,4s)-4-((5-Ethyl-3-(4-hydroxyphenyl)-4-phenyl-1H-pyrazol-1-yl)methyl)cyclohexyl)methoxy)acetic Acid (Compound 175)

From 4-hydroxyphenylboronic acid and tert-butyl 2-(((1s,4s)-4-((3-bromo-5-ethyl-4-phenyl-1H-pyrazol-1-yl)methyl)cyclohexyl)methoxy)acetate, using a similar method to the one described in Example 1.55, The title compound was obtained as a white solid. LCMS m/z=449.3 [M+H]$^+$.

Example 1.60: Preparation of 2-(((1s,4s)-4-((3-(4-Chloro-3-fluorophenyl)-5-ethyl-4-phenyl-1H-pyrazol-1-yl)methyl)cyclohexyl)methoxy)acetic Acid (Compound 176)

From 4-chloro-3-fluorophenylboronic acid and tert-butyl 2-(((1s,4s)-4-((3-bromo-5-ethyl-4-phenyl-1H-pyrazol-1-yl)

methyl)cyclohexyl)methoxy)acetate, using a similar method to the one described in Example 1.55, The title compound was obtained as a white solid. LCMS m/z=485.4 [M+H]⁺.

Example 1.61: Preparation of 2-(((1s,4s)-4-((4-(3-Methoxyphenyl)-3-phenyl-5-propyl-1H-pyrazol-1-yl)methyl)cyclohexyl)methoxy)acetic Acid (Compound 202)

Step A: Preparation of 3-Phenyl-5-propyl-1H-pyrazole

To a solution of acetophenone (4.87 mL, 41.6 mmol) in dry toluene (5.0 mL) cooled to 0° C. was added LiHMDS (41.6 mL, 41.6 mmol). The resulting mixture was stirred at 0° C. for 5 min before butyryl chloride (4.36 mL, 41.6 mmol) was added in portions. After the addition of the butyryl chloride, the ice bath was then removed before AcOH (2.0 mL) and EtOH (10.0 mL) were added to form a homogenous mixture, then hydrazine hydrate (3.03 mL, 62.4 mmol) was added. The resulting mixture was heated to reflux. After 30 min, the reaction mixture was quenched with 1.0 M NaOH solution, extracted with EtOAc and washed with brine. The combined organics were dried over MgSO₄, filtered, and concentrated to give an orange oil. This orange oil was purified by silica gel flash chromatography to give the title compound as a yellow oil (3.83 g). LCMS m/z=187.2 [M+H]⁺; ¹H NMR (400 MHz, CDCl₃) δ ppm 0.92 (t, J=7.33 Hz, 3H), 1.58-1.71 (m, 2H), 2.57 (t, J=7.58 Hz, 2H), 6.34 (s, 1H), 7.22-7.39 (m, 3H), 7.72 (d, J=7.83 Hz, 2H).

Step B: Preparation of 4-Bromo-3-phenyl-5-propyl-1H-pyrazole

To a solution of 3-phenyl-5-propyl-1H-pyrazole (3.83 g, 20.56 mmol) in dichloromethane (118.0 mL) was added bromine (1.05 mL, 20.56 mmol) at 25° C. The reaction mixture was stirred at room temperature for 16 h. The reaction mixture was then quenched with 2 M Na₂CO₃ (aq.) to pH 12 and the organics were separated. The aqueous layer was extracted with DCM (thrice). The combined organics were washed with brine, dried over MgSO₄, filtered and concentrated to give a red oil. This oil was purified by silica gel flash chromatography to give the title compound as a yellow oil (3.44 g). LCMS m/z=265.1, 267.1 [M+H]⁺; ¹H NMR (400 MHz, CDCl₃) δ ppm 0.97 (t, J=7.33 Hz, 3H), 1.63-1.74 (m, 2H), 2.57 (t, J=7.58 Hz, 2H), 7.37-7.48 (m, 3H), 7.77-7.82 (m, 2H).

Step C: Preparation of tert-Butyl 2-(((1s,4s)-4-((4-Bromo-3-phenyl-5-propyl-1H-pyrazol-1-yl)methyl)cyclohexyl)methoxy)acetate To a solution of 4-bromo-3-phenyl-5-propyl-1H-pyrazole (1.00 g, 3.77 mmol) in DMF (13.0 mL) was slowly added 60% sodium hydride (0.181 g, 4.53 mmol). The solution was allowed to stir for a total of 20 min, before a mixture of tert-butyl 2-(((1s,4s)-4-(tosyloxymethyl)cyclohexyl)methoxy)acetate (1.556 g, 3.77 mmol) in DMF (2.0 mL) was added. The reaction mixture was then stirred at 45° C. for 12 h, quenched with water and extracted with EtOAc (4 times). The combined organics were dried over MgSO₄, filtered, and concentrated to give a brown oil. This brown oil was purified by silica gel flash chromatography to give the title compound as a yellow oil (1.501 g). LCMS m/z=505.4, 507.4 [M+H]⁺; ¹H NMR (400 MHz, CDCl₃) δ ppm 1.02 (t, J=7.45 Hz, 3H), 1.29-1.41 (m, 2H), 1.43-1.59 (m, 15H), 1.65 (d, J=7.83 Hz, 2H), 1.82-1.94 (m, 1H), 2.13-2.24 (m, 1H), 2.66 (t, J=7.83 Hz, 2H), 3.46 (d, J=7.07 Hz, 2H), 3.95 (s, 2H), 4.00 (d, J=7.58 Hz, 2H), 7.33 (d, J=7.58 Hz, 1H), 7.40 (t, J=7.45 Hz, 2H), 7.84-7.89 (m, 2H).

Step D: Preparation of tert-Butyl 2-(((1s,4s)-4-((4-(3-Methoxyphenyl)-3-phenyl-5-propyl-1H-pyrazol-1-yl)methyl)cyclohexyl)methoxy)acetate To a solution of 3-methoxyphenylboronic acid (0.029 g, 0.194 mmol), tert-butyl 2-(((1s,4s)-4-((4-bromo-3-phenyl-5-propyl-1H-pyrazol-1-yl)methyl)cyclohexyl)methoxy)acetate (0.098 g, 0.194 mmol), aq. Na₂CO₃ (2 M solution, 0.194 mL, 0.388 mmol), and Pd(PPh₃)₄ (0.004 g, 0.007 mmol) in EtOH (1.0 mL) and benzene (3.0 mL). The reaction mixture was then heated in a microwave at 130° C. for 1 h, quenched with H₂O and extracted with EtOAc (2×). The combined organics layers were dried over MgSO₄, filtered and concentrated to give the title compound as a yellow oil without purification. LCMS m/z=533.4 [M+H]⁺.

Step E: Preparation of 2-(((1s,4s)-4-((4-(3-Methoxyphenyl)-3-phenyl-5-propyl-1H-pyrazol-1-yl)methyl)cyclohexyl)methoxy)acetic Acid To tert-butyl 2-(((1s,4s)-4-((4-(3-methoxyphenyl)-3-phenyl-5-propyl-1H-pyrazol-1-yl)methyl)cyclohexyl)methoxy)acetate obtained was added 4 M HCl (0.969 mL, 3.88 mmol) in 1,4-dioxane. The resulting reaction mixture was stirred at 25° C. for 4 h. The reaction was concentrated to give a yellow oil. This yellow oil was purified by HPLC to give the title compound (0.026 g) as a white solid. LCMS m/z=477.4 [M+H]⁺; ¹H NMR (400 MHz, CDCl₃) δ ppm 0.87 (t, J=7.33 Hz, 3H), 1.33-1.62 (m, 9H), 1.86-1.97 (m, 1H), 2.17-2.29 (m, 1H), 2.54-2.62 (m, 2H), 3.50-3.55 (m, 2H), 3.72 (s, 3H), 3.86 (s, 1H), 4.02-4.13 (m, 4H), 6.70-6.86 (m, 3H), 7.15-7.27 (m, 4H), 7.34-7.43 (m, 2H).

Example 1.62: Preparation of 2-(((1s,4s)-4-((4-(3-Fluorophenyl)-3-phenyl-5-propyl-1H-pyrazol-1-yl)methyl)cyclohexyl)methoxy)acetic Acid (Compound 203)

From 3-fluorophenylboronic acid tert-butyl 2-(((1s,4s)-4-((4-bromo-3-phenyl-5-propyl-1H-pyrazol-1-yl)methyl)cyclohexyl)methoxy)acetate, using a similar method to the one described in Example 1.61, Step D & E, the title compound was obtained as a white solid. LCMS m/z=465.2 [M+H]⁺.

Example 1.63: Preparation of 2-(((1s,4s)-4-((4-(3-Chlorophenyl)-3-phenyl-5-propyl-1H-pyrazol-1-yl)methyl)cyclohexyl)methoxy)acetic Acid (Compound 204)

From 3-chlorophenylboronic acid and tert-butyl 2-(((1s,4s)-4-((4-bromo-3-phenyl-5-propyl-1H-pyrazol-1-yl)methyl)cyclohexyl)methoxy)acetate, using a similar method to the one described in Example 1.62, the title compound was obtained as a white solid. LCMS m/z=481.3 [M+H]⁺.

Example 1.64: Preparation of 2-(((1s,4s)-4-((3-Phenyl-5-propyl-4-m-tolyl-1H-pyrazol-1-yl)methyl)cyclohexyl)methoxy)acetic Acid (Compound 205)

From m-tolylboronic acid and tert-butyl 2-(((1s,4s)-4-((4-bromo-3-phenyl-5-propyl-1H-pyrazol-1-yl)methyl)cyclo-

Example 1.65: Preparation of 2-(((1s,4s)-4-((4-(2-Fluoro-3-methoxyphenyl)-3-phenyl-5-propyl-1H-pyrazol-1-yl)methyl)cyclohexyl)methoxy)acetic Acid (Compound 206)

From 2-fluoro-3-methoxyphenylboronic acid and tert-butyl 2-(((1s,4s)-4-((4-bromo-3-phenyl-5-propyl-1H-pyrazol-1-yl)methyl)cyclohexyl)methoxy)acetate, using a similar method to the one described in Example 1.62, the title compound was obtained as a white solid. LCMS m/z=495.5 [M+H]$^+$.

Example 1.66: Preparation of 2-(((1s,4s)-4-((4-(2,3-Difluorophenyl)-3-phenyl-5-propyl-1H-pyrazol-1-yl)methyl)cyclohexyl)methoxy)acetic Acid (Compound 207)

From 2,3-difluorophenylboronic acid and tert-butyl 2-(((1s,4s)-4-((4-bromo-3-phenyl-5-propyl-1H-pyrazol-1-yl)methyl)cyclohexyl)methoxy)acetate, using a similar method to the one described in Example 1.62, the title compound was obtained as a white solid. LCMS m/z=483.4 [M+H]$^+$.

Example 1.67: Preparation of 2-(((1s,4s)-4-((4-(3-Chloro-2-fluorophenyl)-3-phenyl-5-propyl-1H-pyrazol-1-yl)methyl)cyclohexyl)methoxy)acetic Acid (Compound 208)

From 3-chloro-2-fluorophenylboronic acid and tert-butyl 2-(((1s,4s)-4-((4-bromo-3-phenyl-5-propyl-1H-pyrazol-1-yl)methyl)cyclohexyl)methoxy)acetate, using a similar method to the one described in Example 1.62, the title compound was obtained as a white solid. LCMS m/z=499.7 [M+H]$^+$.

Example 1.68: Preparation of 2-(((1s,4s)-4-((4-(2-Fluoro-3-methylphenyl)-3-phenyl-5-propyl-1H-pyrazol-1-yl)methyl)cyclohexyl)methoxy)acetic Acid (Compound 209)

From 2-fluoro-3-methylphenylboronic acid and tert-butyl 2-(((1s,4s)-4-((4-bromo-3-phenyl-5-propyl-1H-pyrazol-1-yl)methyl)cyclohexyl)methoxy)acetate, using a similar method to the one described in Example 1.62, the title compound was obtained as a white solid. LCMS m/z=479.6 [M+H]$^+$.

Example 1.69: Preparation of 2-(((1s,4s)-4-((4-(2-Fluoro-3-hydroxyphenyl)-3-phenyl-5-propyl-1H-pyrazol-1-yl)methyl)cyclohexyl)methoxy)acetic Acid (Compound 211)

From 2-fluoro-3-hydroxyphenylboronic acid and tert-butyl 2-(((1s,4s)-4-((4-bromo-3-phenyl-5-propyl-1H-pyrazol-1-yl)methyl)cyclohexyl)methoxy)acetate, using a similar method to the one described in Example 1.62, the title compound was obtained as a white solid. LCMS m/z=481.3 [M+H]$^+$.

Example 1.70: Preparation of 2-(((1s,4s)-4-((5-(4-Fluorophenyl)-4-phenyl-3-propyl-1H-pyrazol-1-yl)methyl)cyclohexyl)methoxy)acetic Acid (Compound 223)

Step A: Preparation of 1-(Dimethylamino)-2-phenylhex-1-en-3-one

To a solution of 1-phenylpentan-2-one (5.00 g, 30.8 mmol) in dry DMF (80.0 mL) was added 1,1-dimethoxy-N,N-dimethylmethanamine (6.16 mL, 46.2 mmol). The resulting mixture was heated at 90° C. After 16 h, the reaction mixture was quenched with water, extracted with EtOAc (3×) and washed with brine. The combined organics were dried over MgSO$_4$, filtered, and concentrated to give a yellow oil. This yellow oil was purified by silica gel flash chromatography to give the title compound as a yellow oil (3.51 g). $^1$H NMR (400 MHz, CDCl$_3$) δ ppm 0.76-0.83 (m, 3H), 0.83-0.89 (m, 2H), 2.11-2.19 (m, 2H), 2.62-2.71 (m, 6H), 7.15-7.42 (m, 5H), 7.61 (s, 1H).

Step B: Preparation of 4-Phenyl-5-propyl-1H-pyrazole

To a solution of 1-(dimethylamino)-2-phenylhex-1-en-3-one (3.51 g, 16.2 mmol) in ethanol (80.0 mL), was added hydrazine hydrate (1.57 mL, 32.4 mmol). The reaction mixture was stirred at 80° C. After 3 h, the reaction mixture was cooled to room temperature, concentrated under reduced pressure and crystallized in 20% ethanol/H$_2$O to give the title compound as a white solid (3.01 g). LCMS m/z=187.1 [M+H]$^+$; $^1$H NMR (400 MHz, CDCl$_3$) δ ppm 0.92-1.00 (m, 3H), 1.64-1.76 (m, 2H), 2.75-2.84 (m, 2H), 7.36-7.41 (m, 5H), 7.65 (s, 1H).

Step C: Preparation of 3-Bromo-4-phenyl-5-propyl-1H-pyrazole

To a solution of 4-phenyl-5-propyl-1H-pyrazole (1.43 g, 7.68 mmol) in acetonitrile (38.0 mL), was added N-bromosuccinimide (1.50 g, 8.45 mmol). The reaction mixture was stirred at 82° C. After 16 h, the reaction mixture was quenched with 2 M Na$_2$CO$_3$ (aq.) to pH 12 and the organics were separated. The aqueous layer was extracted with EtOAc (3×). The combined organics were dried over MgSO$_4$, filtered and concentrated to give a dark oil. This oil was purified by silica gel flash chromatography to give the title compound as a yellow oil (0.310 g). LCMS m/z=265.1, 267.1 [M+H]$^+$.

Step D: Preparation of tert-Butyl 2-(((1s,4s)-4-((3-Bromo-4-phenyl-5-propyl-1H-pyrazol-1-yl)methyl)cyclohexyl)methoxy)acetate and tert-Butyl 2-(((1s,4s)-4-((5-Bromo-4-phenyl-3-propyl-1H-pyrazol-1-yl)methyl)cyclohexyl)methoxy)acetate To a solution of 3-bromo-4-phenyl-5-propyl-1H-pyrazole (0.940 g, 3.55 mmol) in DMF (12.0 mL), was slowly added 60% sodium hydride (0.170 g, 4.25 mmol). The solution was stirred for a total of 20 min, before a mixture of tert-butyl 2-(((1s,4s)-4-(tosyloxymethyl)cyclohexyl)methoxy)acetate (1.463 g, 3.55 mmol) in DMF (2.0 mL) was added. The reaction mixture was then stirred at 45° C. for 12 h, quenched with water and extracted with EtOAc (4×). The combined organics were dried over MgSO$_4$, filtered, and concentrated to give a brown oil. This brown oil was purified by silica gel flash chromatography to give a mixture of regioisomers, the title compounds as a yellow oil (1.219 g). LCMS m/z=505.4 [M+H]⁺; ¹H NMR (400 MHz, CDCl₃) δ ppm 0.85 (t, J=7.33 Hz, 3H), 1.32-1.63 (m, 18H), 1.76-1.93 (m, 2H), 2.17-2.29 (m, 1H), 2.56-2.64 (m, 2H), 3.45 (d, J=6.82 Hz, 2H), 3.95 (s, 2H), 4.05-4.14 (m, 2H), 7.28-7.35 (m, 3H), 7.36-7.43 (m, 2H).

Step E: Preparation of tert-Butyl 2-(((1s,4s)-4-((5-(4-Fluorophenyl)-4-phenyl-3-propyl-1H-pyrazol-1-yl)methyl)cyclohexyl)methoxy)acetate and tert-Butyl 2-(((1s,4s)-4-((3-(4-Fluorophenyl)-4-phenyl-5-propyl-1H-pyrazol-1-yl)methyl)cyclohexyl)methoxy)acetate To a solution of 4-fluorophenylboronic acid (0.032 g, 0.231 mmol), a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate (0.117 g, 0.231 mmol), aq. Na₂CO₃ (2 M solution, 0.231 mL, 0.463 mmol), and Pd(PPh₃)₄ (0.008 g, 0.007 mmol) in EtOH (1.0 mL) and benzene (3.0 mL). The reaction mixture was then heated under microwave at 130° C. for 1 h, quenched with H₂O and extracted with EtOAc (2×). The combined organics layers were dried over MgSO₄, filtered and concentrated to give a mixture of regioisomers, the title compounds as a yellow oil without further purification. LCMS m/z=521.7 [M+H]⁺.

Step F: Preparation of 2-(((1s,4s)-4-((5-(4-Fluorophenyl)-4-phenyl-3-propyl-1H-pyrazol-1-yl)methyl)cyclohexyl)methoxy)acetic Acid To a mixture of regioisomers, tert-Butyl 2-(((1s,4s)-4-((5-(4-Fluorophenyl)-4-phenyl-3-propyl-1H-pyrazol-1-yl)methyl)cyclohexyl)methoxy)acetate and tert-Butyl 2-(((1s,4s)-4-((3-(4-Fluorophenyl)-4-phenyl-5-propyl-1H-pyrazol-1-yl)methyl)cyclohexyl)methoxy)acetate obtained was added 4 M HCl (1.16 mL, 4.63 mmol) in 1,4-dioxane. The resulting reaction mixture was stirred at 25°. After 4 h, the reaction mixture concentrated to give a yellow oil. This yellow oil was purified by HPLC to give the title compound (0.019 g) as a white solid. LCMS m/z=465.3 [M+H]⁺.

Example 1.71: Preparation of 2-(((1s,4s)-4-((3-(4-Fluorophenyl)-4-phenyl-5-propyl-1H-pyrazol-1-yl)methyl)cyclohexyl)methoxy)acetic Acid (Compound 224)

From a mixture of regioisomers, tert-butyl 2-(((1s,4s)-4-((5-(4-fluorophenyl)-4-phenyl-3-propyl-1H-pyrazol-1-yl)methyl)cyclohexyl)methoxy)acetate and tert-butyl 2-(((1s,4s)-4-((3-(4-fluorophenyl)-4-phenyl-5-propyl-1H-pyrazol-1-yl)methyl)cyclohexyl)methoxy)acetate, using a similar method to the one described in Example 1.70, Step F, the title compound was obtained as a second isomer. LCMS m/z=465.3 [M+H]⁺; ¹H NMR (400 MHz, CDCl₃) δ ppm 0.87 (t, J=7.26 Hz, 3H), 1.16-1.30 (m, 1H), 1.33-1.68 (m, 8H), 1.94 (s, 2H), 2.21 (s, 1H), 2.52-2.64 (m, 2H), 3.53 (d, J=6.95 Hz, 2H), 3.97-4.19 (m, 4H), 6.91 (t, J=8.72 Hz, 2H), 7.13-7.19 (m, 2H), 7.28-7.39 (m, 5H).

Example 1.72: Preparation of 2-(((1s,4s)-4-((5-(4-Chloro-3-fluorophenyl)-4-phenyl-3-propyl-1H-pyrazol-1-yl)methyl)cyclohexyl)methoxy)acetic Acid (Compound 225)

From 4-chloro-3-fluorophenylboronic acid and a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.70, Step E & F, the title compound was obtained as a white solid. LCMS m/z=499.6 [M+H]⁺.

Example 1.73: Preparation of 2-(((1s,4s)-4-((3-(4-Chloro-3-fluorophenyl)-4-phenyl-5-propyl-1H-pyrazol-1-yl)methyl)cyclohexyl)methoxy)acetic Acid (Compound 226)

From 4-chloro-3-fluorophenylboronic acid and a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.72, the title compound was obtained as an isomer. LCMS m/z=499.7 [M+H]⁺.

Example 1.74: Preparation of 2-(((1s,4s)-4-((5-(4-Chlorophenyl)-4-phenyl-3-propyl-1H-pyrazol-1-yl)methyl)cyclohexyl)methoxy)acetic Acid (Compound 227)

From 4-chlorophenylboronic acid and a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.72, the title compound was obtained as a white solid. LCMS m/z=481.2 [M+H]⁺.

Example 1.75: Preparation of 2-(((1s,4s)-4-((3-(4-Chlorophenyl)-4-phenyl-5-propyl-1H-pyrazol-1-yl)methyl)cyclohexyl)methoxy)acetic Acid (Compound 228)

From 4-chlorophenylboronic acid and a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.72, the title compound was obtained as a white solid. LCMS m/z=481.4 [M+H]⁺.

Example 1.76: Preparation of 2-(((1s,4s)-4-((5-(3,4-Difluorophenyl)-4-phenyl-3-propyl-1H-pyrazol-1-yl)methyl)cyclohexyl)methoxy)acetic Acid (Compound 229)

From 3,4-difluorophenylboronic acid and a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.72, the title compound was obtained as a white solid. LCMS m/z=483.4 [M+H]⁺.

Example 1.77: Preparation of 2-(((1s,4s)-4-((3-(3,4-Difluorophenyl)-4-phenyl-5-propyl-1H-pyrazol-1-yl)methyl)cyclohexyl)methoxy)acetic Acid (Compound 230)

From 3,4-difluorophenylboronic acid and a mixture of regioisomers, tert-butyl 2-(((1s,4s)-4-((3-bromo-4-phenyl- 5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.72, the title compound was obtained as a white solid. LCMS m/z=483.4 [M+H]$^+$.

Example 1.78: Preparation of 2-(((1s,4s)-4-((5-(2-Fluoro-4-methoxyphenyl)-4-phenyl-3-propyl-1H-pyrazol-1-yl)methyl)cyclohexyl)methoxy)acetic Acid (Compound 231)

From 2-fluoro-4-methoxyphenylboronic acid and a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.72, the title compound was obtained as a white solid. LCMS m/z=495.6 [M+H]$^+$.

Example 1.79: Preparation of 2-(((1s,4s)-4-((3-(2-Fluoro-4-methoxyphenyl)-4-phenyl-5-propyl-1H-pyrazol-1-yl)methyl)cyclohexyl)methoxy)acetic Acid (Compound 232)

From 2-fluoro-4-methoxyphenylboronic acid and a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.72, the title compound was obtained as a white solid. LCMS m/z=495.5 [M+H]$^+$.

Example 1.80: Preparation of 2-(((1s,4s)-4-((5-(4-Methoxyphenyl)-4-phenyl-3-propyl-1H-pyrazol-1-yl)methyl)cyclohexyl)methoxy)acetic Acid (Compound 233)

From 4-methoxyphenylboronic acid and a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.72, the title compound was obtained as a white solid. LCMS m/z=477.4 [M+H]$^+$.

Example 1.81: Preparation of 2-(((1s,4s)-4-((3-(4-Methoxyphenyl)-4-phenyl-5-propyl-1H-pyrazol-1-yl)methyl)cyclohexyl)methoxy)acetic Acid (Compound 234)

From 4-methoxyphenylboronic acid and a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.72, the title compound was obtained as a white solid. LCMS m/z=477.5 [M+H]$^+$.

Example 1.82: Preparation of 2-(((1s,4s)-4-((5-(2-Fluoro-4-methylphenyl)-4-phenyl-3-propyl-1H-pyrazol-1-yl)methyl)cyclohexyl)methoxy)acetic Acid (Compound 235)

From 2-fluoro-4-methylphenylboronic acid and a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.72, the title compound was obtained as a white solid. LCMS m/z=479.5 [M+H]$^+$.

Example 1.83: Preparation of 2-(((1s,4s)-4-((3-(2-Fluoro-4-methylphenyl)-4-phenyl-5-propyl-1H-pyrazol-1-yl)methyl)cyclohexyl)methoxy)acetic Acid (Compound 236)

From 2-fluoro-4-methylphenylboronic acid and a mixture of regioisomers, tert-butyl 2-(((1s,4s)-4-((3-bromo-4-phenyl-5-propyl-1H-pyrazol-1-yl)methyl)cyclohexyl)methoxy)acetate and tert-butyl 2-(((1s,4s)-4-((5-bromo-4-phenyl-3-propyl-1H-pyrazol-1-yl)methyl)cyclohexyl)methoxy)acetate, using a similar method to the one described in Example 1.72, the title compound was obtained as a white solid. LCMS m/z=479.4 [M+H]$^+$.

Example 1.84: Preparation of 2-(((1s,4s)-4-((5-(Cyanomethylthio)-4-phenyl-3-p-tolyl-1H-pyrazol-1-yl)methyl)cyclohexyl)methoxy)acetic Acid (Compound 257)

Step A: Preparation of 2-(1,3-Dithietan-2-ylidene)-2-phenyl-1-p-tolylethanone

To a solution of 2-phenyl-1-p-tolylethanone (3.00 g, 14.27 mmol) in THF (50.0 mL) was added KOtBu (30.0 mL, 30.0 mmol), CS$_2$ (0.862 mL, 14.27 mmol) and dibromomethane (0.994 mL, 14.27 mmol). The reaction was stirred at 25° C. for 12 h, quenched with water (40.0 mL) and extracted with EtOAc (3×50.0 mL). The combined organics were dried over MgSO$_4$, filtered, and concentrated to give the title compound as a brown oil without further purification. LCMS m/z=299.2 [M+H]$^+$.

Step B: Preparation of A Mixture of 4-Phenyl-3-p-tolyl-1H-pyrazole-5(4H)-thione and 1,2-Bis(4-phenyl-3-p-tolyl-1H-pyrazol-5-yl)disulfane To a solution of 2-(1,3-dithietan-2-ylidene)-2-phenyl-1-p-tolylethanone dissolved in isopropanol (25.0 mL) was added hydrazine (7.00 mL, 143.0 mmol). The reaction was stirred at 100° C. for 16 h. After cooling to room temperature, a precipitate was formed. The precipitate was filtered and washed with isopropanol and dried under reduced pressure to give the title compounds as a mixture of 4-phenyl-3-p-tolyl-1H-pyrazole-5(4H)-thione and 1,2-bis(4-phenyl-3-p-tolyl-1H-pyrazol-5-yl)disulfane as a white solid (2.24 g). LCMS m/z=267.2 [M+H]$^+$; 531.3 [M+H]$^+$; $^1$H NMR (400 MHz, CD$_3$OD) δ ppm 2.31 (s, 3H), 7.04 (d, J=7.58 Hz, 2H), 7.10-7.16 (m, 1H), 7.17-7.27 (m, 5H), 7.39 (d, J=7.33 Hz, 2H).

Step C: Preparation of 2-(4-Phenyl-3-p-tolyl-1H-pyrazol-5-ylthio)acetonitrile

To a mixture of 4-phenyl-3-p-tolyl-1H-pyrazole-5(4H)-thione and 1,2-bis(4-phenyl-3-p-tolyl-1H-pyrazol-5-yl)disulfane (0.500 g, 1.88 mmol) in DMF (12.5 mL) was added 2-bromoacetonitrile (0.125 mL, 1.88 mmol) and K$_2$CO$_3$ (0.259 g, 1.88 mmol). The reaction was stirred at 25° C. for 72 h, quenched with water (40.0 mL) and extracted with EtOAc (4×50.0 mL) and washed with brine. The combined organics were dried over MgSO$_4$, filtered, and concentrated to give the title compound as a yellow oil (0.547 g). LCMS m/z=306.2 [M+H]$^+$.

Step C: Preparation of tert-Butyl 2-(((1s,4s)-4-((5-(Cyanomethylthio)-4-phenyl-3-p-tolyl-1H-pyrazol-1-yl)methyl)cyclohexyl)methoxy)acetate To a solution of 2-(4-phenyl-3-p-tolyl-1H-pyrazol-5-ylthio)acetonitrile (0.250 g, 0.819 mmol) in anhydrous DMF (4.0 mL) was added cesium carbonate (0.533 g, 1.64 mmol) and tert-butyl 2-(((1s,4s)-4-(tosyloxymethyl)cyclohexyl)methoxy)acetate (0.338 g, 0.819 mmol) in DMF (1.0 mL). The reaction was heated at 80° C. for 1 h, quenched with water and extracted with EtOAc (2x). The combined organics were dried over MgSO$_4$, filtered, and concentrated to give the title compound as a yellow oil without further purification. LCMS m/z=546.4 [M+H]$^+$.

Step D: Preparation of 2-(((1s,4s)-4-((5-(Cyanomethylthio)-4-phenyl-3-p-tolyl-1H-pyrazol-1-yl)methyl)cyclohexyl)methoxy)acetic Acid To tert-butyl 2-(((1s,4s)-4-((5-(cyanomethylthio)-4-phenyl-3-p-tolyl-1H-pyrazol-1-yl)methyl)cyclohexyl)methoxy)acetate obtained above was added 4 M HCl (4.09 mL, 16.37 mmol) in 1,4-dioxane. The reaction was stirred at 25° C. for 16 h and concentrated to give a yellow oil. This yellow oil was purified by HPLC to give the title compound as a white solid (0.013 g). LCMS m/z=490.5 [M+H]$^+$.

Example 1.85: Preparation of 2-(((1r,4r)-4-((3-(Cyanomethylthio)-4-(3-methoxyphenyl)-5-phenyl-1H-pyrazol-1-yl)methyl)cyclohexyl)methoxy)acetic Acid (Compound 245)

Step A: Preparation of 2-(4-(3-Methoxyphenyl)-3-phenyl-1H-pyrazol-5-ylthio)acetonitrile To a solution of 4-(3-methoxyphenyl)-3-phenyl-1H-pyrazole-5(4H)-thione (0.200 g, 0.708 mmol) in DMF (5.0 mL) was added 2-bromoacetonitrile (0.047 mL, 0.708 mmol) and K$_2$CO$_3$ (0.098 g, 0.708 mmol). The mixture was stirred at 25° C. for 72 h, quenched with water (40.0 mL), extracted with EtOAc (4x50.0 mL) and washed with brine. The combined organics were dried over MgSO$_4$, filtered, and concentrated to give a brown oil. This brown oil was purified by silica gel flash chromatography to give the title compound as a white solid (0.158 g). LCMS m/z=332.3 [M+H]$^+$; $^1$H NMR (400 MHz, CDCl$_3$) δ ppm 3.67 (s, 2H), 3.74 (s, 3H), 6.82-6.89 (m, 3H), 7.23-7.29 (m, 1H), 7.34 (s, 5H).

Step B: Preparation of tert-Butyl 2-(((1r,4r)-4-((3-(Cyanomethylthio)-4-(3-methoxyphenyl)-5-phenyl-1H-pyrazol-1-yl)methyl)cyclohexyl)methoxy)acetate and tert-Butyl 2-(((1s,4s)-4-((5-(Cyanomethylthio)-4-(3-methoxyphenyl)-3-phenyl-1H-pyrazol-1-yl)methyl)cyclohexyl)methoxy)acetate To a solution of 2-(4-(3-methoxyphenyl)-3-phenyl-1H-pyrazol-5-ylthio)acetonitrile (0.158 g, 0.492 mmol) in DMF (2.0 mL) at 0° C. was slowly added 60% sodium hydride (0.022 g, 0.541 mmol). The solution was allowed to stir for a total of 20 min, before a mixture of tert-butyl 2-(((1s,4s)-4-(tosyloxymethyl)cyclohexyl)methoxy)acetate (0.203 g, 0.492 mmol) in DMF (1.0 mL) was added. The reaction mixture was then stirred at 40° C. for 16 h, quenched with water and extracted with EtOAc (2x). The combined organics were dried over MgSO$_4$, filtered, and concentrated to give a mixture of tert-butyl 2-(((1r,4r)-4-((3-(cyanomethylthio)-4-(3-methoxyphenyl)-5-phenyl-1H-pyrazol-1-yl)methyl)cyclohexyl)methoxy)acetate and tert-butyl 2-(((1s,4s)-4-((5-(cyanomethylthio)-4-(3-methoxyphenyl)-3-phenyl-1H-pyrazol-1-yl)methyl)cyclohexyl)methoxy)acetate without further purification. LCMS m/z=562.4 [M+H]$^+$.

Step C: Preparation of 2-(((1r,4r)-4-((3-(Cyanomethylthio)-4-(3-methoxyphenyl)-5-phenyl-1H-pyrazol-1-yl)methyl)cyclohexyl)methoxy)acetic Acid To the mixture of tert-butyl 2-(((1r,4r)-4-((3-(cyanomethylthio)-4-(3-methoxyphenyl)-5-phenyl-1H-pyrazol-1-yl)methyl)cyclohexyl)methoxy)acetate and tert-butyl 2-(((1s,4s)-4-((5-(cyanomethylthio)-4-(3-methoxyphenyl)-3-phenyl-1H-pyrazol-1-yl)methyl)cyclohexyl)methoxy)acetate obtained above was added 4 M HCl (2.46 mL, 9.83 mmol) in 1,4-dioxane. The reaction was stirred at 25° C. for 16 h and concentrated to give a yellow oil. This yellow oil was purified by HPLC to give the title compound (0.042 g) as a white solid. LCMS m/z=506.5 [M+H]$^+$.

Example 1.86: Preparation of 2-(((1s,4s)-4-((5-(Cyanomethylthio)-4-(3-methoxyphenyl)-3-phenyl-1H-pyrazol-1-yl)methyl)cyclohexyl)methoxy)acetic Acid (Compound 246)

From a mixture of regioisomers tert-butyl 2-(((1r,4r)-4-((3-(cyanomethylthio)-4-(3-methoxyphenyl)-5-phenyl-1H-pyrazol-1-yl)methyl)cyclohexyl)methoxy)acetate and tert-butyl 2-(((1s,4s)-4-((5-(cyanomethylthio)-4-(3-methoxyphenyl)-3-phenyl-1H-pyrazol-1-yl)methyl)cyclohexyl)methoxy)acetate, using a similar method to the one described in Example 1.85, Step C, the title compound was also isolated as a white solid. LCMS m/z=506.4 [M+H]$^+$.

Example 1.87: Preparation of 2-(((1s,4s)-4-((5-(Cyanomethylthio)-3-(4-fluorophenyl)-4-phenyl-1H-pyrazol-1-yl)methyl)cyclohexyl)methoxy)acetic Acid (Compound 258)

From 1-(4-fluorophenyl)-2-phenylethanone, using a similar method to the one described in Example 1.85, the title compound was obtained as a white solid. LCMS m/z=494.5 [M+H]$^+$.

Example 1.88: Preparation of 2-(((1s,4s)-4-((4-(3-Chlorophenyl)-5-(cyanomethylthio)-3-phenyl-1H-pyrazol-1-yl)methyl)cyclohexyl)methoxy)acetic Acid (Compound 275)

From 2-(3-chlorophenyl)-1-phenylethanone, using a similar method to the one described in Example 1.85, the title compound was obtained as a white solid. LCMS m/z=510.3 [M+H]$^+$.

Example 1.89: Preparation of 2-(((1r,4r)-4-((3-(2-Amino-2-oxoethoxy)-4-(3-methoxyphenyl)-5-phenyl-1H-pyrazol-1-yl)methyl)cyclohexyl)methoxy)acetic Acid (Compound 277)

Step A: Preparation of 2-(3-Phenyl-1H-pyrazol-5-yloxy)acetonitrile

To a solution of 3-phenyl-1H-pyrazol-5(4H)-one (1.00 g, 6.24 mmol) in DMF (5.0 mL) was added 2-bromoacetonitrile (0.520 mL, 7.80 mmol) and K$_2$CO$_3$ (0.863 g, 6.24 mmol). The reaction was stirred at 25° C. for 12 h, quenched with water (40.0 mL), extracted with EtOAc (3×50.0 mL) and washed with brine. The combined organics were dried over MgSO$_4$, filtered, and concentrated to give the title compound as a yellow oil. This yellow oil was purified by silica gel flash chromatography to give the title compound as a clear oil (0.990 g). LCMS m/z=200.3 [M+H]$^+$.

Step B: Preparation of 2-(4-Bromo-3-phenyl-1H-pyrazol-5-yloxy)acetonitrile

To a solution of 2-(3-phenyl-1H-pyrazol-5-yloxy)acetonitrile (0.500 g, 2.51 mmol) in dichloromethane (15.0 mL), was added bromine (0.129 mL, 2.51 mmol) at 25° C. The reaction was stirred at room temperature for 1 h and quenched with 2 M Na$_2$CO$_3$ (aq.) to pH 12. The organics were separated. The aqueous layer was extracted with DCM (3×). The combined organics were washed with brine, dried (MgSO$_4$), filtered and concentrated to give a red oil. This oil was purified by silica gel flash chromatography to give the title compound as a yellow solid (0.360 g). LCMS m/z=278.1, 280.2 [M+H]$^+$; $^1$H NMR (400 MHz, DMSO-d$_6$) δ ppm 5.21 (s, 2H), 7.39-7.61 (m, 3H), 7.70-7.77 (m, 2H), 13.04 (s, 1H).

Step C: Preparation of tert-Butyl 2-(((1s,4s)-4-((4-Bromo-5-(cyanomethoxy)-3-phenyl-1H-pyrazol-1-yl)methyl)cyclohexyl)methoxy)acetate and tert-Butyl 2-(((1s,4s)-4-((4-Bromo-3-(cyanomethoxy)-5-phenyl-1H-pyrazol-1-yl)methyl)cyclohexyl)methoxy)acetate To a solution of 2-(4-bromo-3-phenyl-1H-pyrazol-5-yloxy)acetonitrile (0.570 g, 2.50 mmol) in anhydrous DMF (18.0 mL) was added cesium carbonate (1.34 g, 4.10 mmol) and a mixture of tert-butyl 2-(((1s,4s)-4-(tosyloxymethyl)cyclohexyl)methoxy)acetate (0.846 g, 2.50 mmol) in DMF (2.0 mL). The reaction was heated at 80° C. for 1 h, quenched with water and extracted with EtOAc (3×). The combined organics were dried over MgSO$_4$, filtered, and concentrated to give a yellow oil. This oil was purified by silica gel flash chromatography to give the title compound as a clear oil (0.386 g). LCMS m/z=518.4, 520.5 [M+H]$^+$; $^1$H NMR (400 MHz, CDCl$_3$) δ ppm 1.09-1.22 (m, 1H), 1.28-1.57 (m, 13H), 1.61 (s, 1H), 1.69-1.91 (m, 2H), 1.95-2.08 (m, 1H), 2.45 (s, 2H), 3.26 (d, J=6.82 Hz, 1H), 3.36 (d, J=6.82 Hz, 1H), 3.83-3.97 (m, 3H), 4.97 (d, 2H), 7.31-7.38 (m, 2H), 7.45-7.51 (m, 1H), 7.78 (d, J=8.34 Hz, 2H).

Step D: Preparation of tert-Butyl 2-(((1s,4s)-4-((3-(Cyanomethoxy)-4-(3-methoxyphenyl)-5-phenyl-1H-pyrazol-1-yl)methyl)cyclohexyl)methoxy)acetate and tert-Butyl 2-(((1s,4s)-4-((5-(Cyanomethoxy)-4-(3-methoxyphenyl)-3-phenyl-1H-pyrazol-1-yl)methyl)cyclohexyl)methoxy)acetate To a solution of 3-methoxyphenylboronic acid (0.019 g, 0.123 mmol), tert-butyl 2-(((1s,4s)-4-((4-bromo-5-(cyanomethoxy)-3-phenyl-1H-pyrazol-1-yl)methyl)cyclohexyl)methoxy)acetate (0.064 g, 0.123 mmol), aq. Na$_2$CO$_3$ (2 M solution, 0.123 mL, 0.247 mmol), and Pd(PPh$_3$)$_4$ (0.004 g, 0.004 mmol) in EtOH (1.0 mL) and benzene (3.0 mL). The reaction mixture was then heated in a microwave at 130° C. for 1 h, quenched with H$_2$O and extracted with EtOAc (2×). The combined organics layers were dried over MgSO$_4$, filtered and concentrated to give the title compounds as a dark solid mixture without further purification. LCMS m/z=546.5 [M+H]$^+$.

Step E: Preparation of 2-(((1s,4s)-4-((3-(2-Amino-2-oxoethoxy)-4-(3-methoxyphenyl)-5-phenyl-1H-pyrazol-1-yl)methyl)cyclohexyl)methoxy)acetic Acid To tert-butyl 2-(((1r,4r)-4-((3-(2-Amino-2-oxoethoxy)-4-(3-methoxyphenyl)-5-phenyl-1H-pyrazol-1-yl)methyl)cyclohexyl)methoxy)acetate and tert-butyl 2-(((1s,4s)-4-((5-(2-Amino-2-oxoethoxy)-4-(3-methoxyphenyl)-3-phenyl-1H-pyrazol-1-yl)methyl)cyclohexyl)methoxy)acetate obtained was added 4 M HCl (0.309 mL, 1.23 mmol) in 1,4-dioxane. The reaction was stirred at 25° C. for 16 h, and concentrated to give a yellow oil. This yellow oil was purified by HPLC to give the title compound (0.004 g) as a white solid. LCMS m/z=508.3 [M+H]$^+$.

Example 1.90: Preparation of 2-(((1s,4s)-4-((5-(2-Amino-2-oxoethoxy)-4-(3-methoxyphenyl)-3-phenyl-1H-pyrazol-1-yl)methyl)cyclohexyl)methoxy)acetic Acid (Compound 278)

From the same mixture of tert-butyl 2-(((1s,4s)-4-((3-(cyanomethoxy)-4-(3-methoxyphenyl)-5-phenyl-1H-pyrazol-1-yl)methyl)cyclohexyl)methoxy)acetate and tert-butyl 2-(((1s,4s)-4-((5-(cyanomethoxy)-4-(3-methoxyphenyl)-3-phenyl-1H-pyrazol-1-yl)methyl)cyclohexyl)methoxy)acetate obtained, using a similar method to the one described in Example 1.89, Step E, the title compound was also isolated as a white solid. LCMS m/z=509.4 [M+H]$^+$.

Example 1.91: Preparation of 2-(((1r,4r)-4-((3-(2-Amino-2-oxoethoxy)-4-(2-fluoro-3-methoxyphenyl)-5-phenyl-1H-pyrazol-1-yl)methyl)cyclohexyl)methoxy)acetic Acid (Compound 279)

From 2-fluoro-3-methoxyphenylboronic acid and a mixture of tert-Butyl 2-(((1s,4s)-4-((4-Bromo-5-(cyanomethoxy)-3-phenyl-1H-pyrazol-1-yl)methyl)cyclohexyl)methoxy)acetate and tert-Butyl 2-(((1s,4s)-4-((4-Bromo-3-(cyanomethoxy)-5-phenyl-1H-pyrazol-1-yl)methyl)cyclohexyl)methoxy)acetate, using a similar method to the one described in Example 1.89, Step D&E, the title compound was obtained as a white solid. LCMS m/z=526.8 [M+H]$^+$.

Example 1.92: Preparation of 2-(((1s,4s)-4-((5-(2-Amino-2-oxoethoxy)-4-(2-fluoro-3-methoxyphenyl)-3-phenyl-1H-pyrazol-1-yl)methyl)cyclohexyl)methoxy)acetic Acid (Compound 280)

From 2-fluoro-3-methoxyphenylboronic acid and a mixture of tert-butyl 2-(((1s,4s)-4-((4-Bromo-5-(cyanomethoxy)-3-phenyl-1H-pyrazol-1-yl)methyl)cyclohexyl)methoxy)acetate and tert-butyl 2-(((1s,4s)-4-((4-Bromo-3-(cyanomethoxy)-5-phenyl-1H-pyrazol-1-yl)methyl)cyclohexyl)methoxy)acetate, using a similar method to the one described in Example 1.89, Step D&E, the title compound was obtained as a white solid. LCMS m/z=527.6 [M+H]$^+$.

Example 1.93: Preparation of 2-(((1s,4s)-4-((5-(Cyanomethoxy)-4-(3-methoxyphenyl)-3-phenyl-1H-pyrazol-1-yl)methyl)cyclohexyl)methoxy)acetic Acid (Compound 283)

From 3-methoxyphenylboronic acid, using a similar method to the one described in Example 1.89, Step D&E, the title compound was obtained as a white solid. LCMS m/z=490.5 [M+H]$^+$.

Example 1.94: Preparation of 2-(((1s,4s)-4-((4-Benzhydryl-1H-pyrazol-1-yl)methyl)cyclohexyl)methoxy)acetic Acid (Compound 17)

A mixture of 4-benzhydryl-1H-pyrazole (30 mg, 0.128 mmol), tert-butyl 2-(((1s,4s)-4-((methylsulfonyloxy)methyl)cyclohexyl)methoxy)acetate (43.1 mg, 0.128 mmol), potassium tert-butoxide (28.7 mg, 0.256 mmol) and 18-Crown-6 (6.77 mg, 0.026 mmol) was stirred at room temperature overnight. The mixture was purified by preparative LCMS to give the title compound (one of the two regioisomers separated). LCMS m/z=419.3 [M+H]$^+$; $^1$H NMR (400 MHz, CDCl$_3$) δ ppm 7.36-7.27 (m, 5H), 7.23 (m, 2H), 7.17 (m, 4H), 7.03 (s, 1H), 5.34 (s, 1H), 4.07 (m, 4H), 3.46 (d, 2H, J=5.6 Hz), 2.06 (m, 1H), 1.85 (m, 1H), 1.58-1.44 (m, 6H), 1.28 (m, 2H).

Example 195: Preparation of 2-(((1r,4r)-4-((4-Benzhydryl-1H-pyrazol-1-yl)methyl)cyclohexyl)methoxy)acetic Acid (Compound 18)

A mixture of 4-benzhydryl-1H-pyrazole (30 mg, 0.128 mmol), tert-butyl 2-(((1s,4s)-4-((methylsulfonyloxy)methyl)cyclohexyl)methoxy)acetate (43.1 mg, 0.128 mmol), potassium tert-butoxide (28.7 mg, 0.256 mmol) and 18-Crown-6 (6.77 mg, 0.026 mmol) was stirred at room temperature overnight. The mixture was purified by preparative LCMS to give the title compound (one of the two regioisomers separated). LCMS m/z=419.3 [M+H]$^+$; $^1$H NMR (400 MHz, CDCl$_3$) δ ppm 7.31-7.27 (m, 5H), 7.23 (d, 2H, J=7 Hz), 7.17 (m, 4H), 6.97 (s, 1H), 5.34 (s, 1H), 4.08 (s, 2H), 3.93 (d, 2H, J=6.8 Hz), 3.36 (d, 2H, J=6.3 Hz), 1.83 (m, 3H), 1.63 (m, 3H), 0.99 (m, 4H).

Example 1.96: Preparation of 2-(((1s,4s)-4-((3,4-Diphenyl-1H-pyrazol-1-yl)methyl)cyclohexyl)methoxy)acetic Acid (Compound 3)

A mixture of 3,4-diphenyl-1H-pyrazole (50 mg, 0.227 mmol), tert-butyl 2-(((1s,4s)-4-((methylsulfonyloxy)methyl)cyclohexyl)methoxy)acetate (76 mg, 0.227 mmol), potassium tert-butoxide (76 mg, 0.681 mmol) and 18-Crown-6 (12.00 mg, 0.045 mmol) in DMF (2 mL) was stirred at 25° C. for 18 h. The mixture was purified by HPLC to give the title compound. LCMS m/z=405.3 [M+H]$^+$; $^1$H NMR (400 MHz, CDCl$_3$) δ ppm 7.47 (m, 3H), 7.30 (m, 4H), 7.26 (m, 4H), 4.16 (d, 2H, J=7.6 Hz), 4.11 (s, 2H), 3.50 (d, 2H, J=6.8 Hz), 2.22 (m, 1H), 1.90 (m, 1H), 1.58 (m, 6H), 1.40 (m, 2H).

Example 1.97: Preparation of 2-(((1s,4s)-4-((3-Methyl-5-phenyl-4-m-tolyl-1H-pyrazol-1-yl)methyl)cyclohexyl)methoxy)acetic Acid (Compound 19)

Step A: Preparation of (1s,4s)-Diethyl Cyclohexane-1,4-dicarboxylate

To a solution of (1s,4s)-cyclohexane-1,4-dicarboxylic acid (25 g, 145 mmol) in ethanol (150 mL) was added concentrated H2SO$_4$ (1 mL). The reaction was refluxed for 16 h, cooled to room temperature and concentrated. The residue was extracted with EtOAc and saturated NaHCO$_3$, washed with brine, dried over MgSO$_4$, and filtered. The filtrate was concentrated to provide the title compound as a colorless oil (30.5 g). $^1$H NMR (400 MHz, CDCl$_3$) δ ppm 1.25 (t, J=7.14 Hz, 6H), 1.64-1.70 (m, 4H), 1.87-1.92 (m, 4H), 2.44-2.46 (m, 2H), 4.11-1.46 (quartet, J=7.12 Hz, 4H).

Step B: Preparation of (1s,4s)-Cyclohexane-1,4-diyldimethanol

To a solution of (1s,4s)-diethyl cyclohexane-1,4-dicarboxylate (13.0 g, 56.9 mmol) in THF (500 mL) was added lithium aluminum hydride (4.54 g, 120 mmol) in portions at 0° C. The mixture was stirred at that temperature for 2 h and quenched with cold water, filtered and concentrated to give the title compound as colorless oil (8.2 g). $^1$H NMR (400 MHz, DMSO-d$_6$) δ ppm 1.27-1.42 (m, 8H), 1.46-1.54 (m, 2H), 3.26-3.31 (m, 4H), 4.27-4.30 (t, J=5.31 Hz, 2H).

Step C: Preparation of tert-Butyl 2-(((1s,4s)-4-(Hydroxymethyl)cyclohexyl)methoxy)acetate To a solution of (1s,4s)-cyclohexane-1,4-diyldimethanol (18.2 g, 126 mmol) in toluene (200 mL) was added NaOH (50% aq., 60 mL) and tetrabutylammonium iodide (2.331 g, 6.31 mmol), followed by tert-butyl-2-bromoacetate (20.50 mL, 139 mmol) at room temperature. The reaction mixture was stirred violently at room temperature for 2 h and diluted with ethyl acetate and water. After separation, the aqueous layer was extracted with EtOAc (3×30 mL). The combined organic layers were dried over MgSO$_4$, concentrated, and purified by silica gel column chromatography to give the title compound as colorless oil (13.5 g). $^1$H NMR (400 MHz, CDCl$_3$) δ ppm 1.35-1.47 (m, 4H), 1.48 (s, 9H), 1.50-1.60 (m, 4H), 1.63-1.74 (m, 1H), 1.79-1.92 (m, 1H), 3.42 (d, J=6.95 Hz, 2H), 3.55 (d, J=6.82 Hz, 2H), 3.93 (s, 1H), 3.94 (s, 2H).

Step D: Preparation of tert-Butyl 2-(((1s,4s)-4-(Tosyloxymethyl)cyclohexyl)methoxy)acetate To a solution of tert-butyl 2-(((1s,4s)-4-(hydroxymethyl)cyclohexyl)methoxy)acetate (12.0 g, 46.4 mmol) in dichloromethane (150 mL) were added triethylamine (4.70 g, 46.4 mmol) and 4-(dimethylamino)pyridine (0.567 g, 4.64 mmol), followed by 4-methylbenzene-1-sulfonyl chloride (8.86 g, 46.4 mmol). The reaction was stirred at room temperature for 16 h. The solvent was removed and the residue was extracted with EtOAc/H$_2$O. The organic extracts were dried over MgSO$_4$, and concentrated. The residue was purified by silica gel column chromatography to give the title compound as pale liquid (9.5 g). LCMS m/z=413.1 [M+H]$^+$; $^1$H NMR (400 MHz, CDCl$_3$) δ ppm 1.28-1.43 (m, 4H), 1.46-1.48 (m, 9H), 1.49-1.56 (m, 4H), 1.76-1.91 (m, 2H), 2.45 (s, 3H), 3.36 (d, J=6.95 Hz, 2H), 3.92 (d, J=7.05 Hz, 2H), 3.92 (s, 2H), 7.35 (d, J=8.46 Hz, 2H), 7.78 (d, J=8.34 Hz, 2H).

Step E: Preparation of 5-Methyl-3-phenyl-1H-pyrazole

To a solution of acetophenone (10 g, 83 mmol) in anhydrous toluene (10 mL) was added LiHMDS (1.0 M in THF, 83 mL, 83 mmol) via syringe at 0° C. under argon. After 5 min, acetyl chloride (6.53 g, 83 mmol) was added in one portion via syringe. The ice bath was removed and glacial AcOH (5 mL), EtOH (50 mL), and hydrazine hydrate (12.50 g, 250 mmol) were added. The mixture was refluxed for 2 h. After cooled to room temperature, the reaction was neutralized to pH 7 by adding 1.0 M NaOH solution. The mixture was extracted with EtOAc, washed with brine, dried over MgSO$_4$, and concentrated. The residue was purified by silica gel column chromatography to give the title compound as pale yellow oil (12.05 g). LCMS m/z=159.0 [M+H]$^+$; $^1$H NMR (400 MHz, DMSO-d$_6$) δ ppm 2.25 (s, 3H), 6.42 (s, 1H), 7.20-7.44 (m, 3H), 7.67-7.82 (m, 2H), 12.53 (bs, 1H).

Step F: Preparation of 4-Bromo-5-methyl-3-phenyl-1H-pyrazole

To a solution of 5-methyl-3-phenyl-1H-pyrazole (8.0 g, 50.6 mmol) in dichloromethane (150 mL) was added bromine (8.08 g, 50.6 mmol) dropwise at 0° C. The reaction was stirred at that temperature for 30 min and continued at room temperature for 2 h. After quenched with aqueous solution of Na$_2$SO$_3$ (10% wt aq., 10 mL), the organic solvent was removed and the aqueous mixture was extracted with EtOAc, washed with brine, dried over MgSO$_4$, and concentrated. The residue was purified by silica gel column chromatography to give the title compound as yellow oil (9.5 g). LCMS m/z=236.9 [M+H]$^+$; $^1$H NMR (400 MHz, DMSO-d$_6$) δ ppm 2.26 (s, 3H), 7.30-7.57 (m, 5H), 13.12 (s, 1H).

Step G: Preparation of tert-Butyl 2-(((1s,4s)-4-((4-Bromo-3-methyl-5-phenyl-1H-pyrazol-1-yl)methyl)cyclohexyl)methoxy)acetate and tert-Butyl 2-(((1s,4s)-4-((4-Bromo-5-methyl-3-phenyl-1H-pyrazol-1-yl)methyl)cyclohexyl)methoxy)acetate as a Mixture of Regioisomers To a solution of 4-bromo-5-methyl-3-phenyl-1H-pyrazole (2.0 g, 8.44 mmol) in DMF (5 mL) were added sodium hydride (0.202 g, 8.44 mmol) in portions at 0° C. The reaction was stirred at that temperature for 1 h and tert-butyl 2-(((1s,4s)-4-(tosyloxymethyl)cyclohexyl)methoxy)acetate (3.48 g, 8.44 mmol) was added. The reaction was heated to 42° C., stirred for 16 h, and quenched with H$_2$O (2 mL). The mixture was extracted with ethyl acetate, dried over MgSO$_4$ and concentrated under reduced pressure. The residue was purified by silica gel column chromatography to give the title compound as a colorless liquid (3.05 g) (mixture of two isomers). LCMS m/z=477.3 [M+H]$^+$.

Step H: Preparation of 2-(((1s,4s)-4-((3-Methyl-5-phenyl-4-m-tolyl-1H-pyrazol-1-yl)methyl)cyclohexyl)methoxy)acetic Acid To a solution of tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers (100 mg, 0.19 mmol) in dioxane (3 mL) were added m-tolylboronic acid (25.8 mg, 0.19 mmol), tetrakis(triphenylphosphine)palladium (22 mg, 0.019 mmol), and K$_2$CO$_3$ (2 M aq., 0.2 mL). The reaction was heated to 150° C. under microwave irradiation for 4 h. The reaction mixture was filtered and concentrated. The residue was treated with HCl (4 M in dioxane, 5 mL) at room temperature for 10 h. The mixture was concentrated and purified by HPLC to give the title compound (13.5 mg) as a white solid. LCMS m/z=433.2 [M+H]$^+$; $^1$H NMR (400 MHz, DMSO-d$_6$) δ ppm 1.01-1.19 (m, 4H), 1.21-1.36 (m, 4H), 1.54-1.66 (m, 1H), 1.86-1.98 (m, 1H), 2.22 (s, 3H), 3.19 (d, J=6.95 Hz, 2H), 3.89 (d, J=7.45 Hz, 2H), 3.91 (s, 2H), 7.04-7.11 (m, 2H), 7.21-7.31 (m, 5H), 7.39-7.47 (m, 2H).

Example 1.98: Preparation of 2-(((1s,4s)-4-((4-(2,5-Difluorophenyl)-5-methyl-3-phenyl-1H-pyrazol-1-yl)methyl)cyclohexyl)methoxy)acetic Acid (Compound 20)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers, and 2,5-difluorophenylboronic acid, the title compound was obtained using a similar method to the one described in Example 1.97. LCMS m/z=455.2 [M+H]$^+$; $^1$H NMR (400 MHz, DMSO-d$_6$) δ ppm 0.99-1.21 (m, 4H), 1.21-1.38 (m, 4H), 1.54-1.66 (m, 1H), 1.88-2.02 (m, 1H), 2.13 (s, 3H), 3.20 (d, J=7.07 Hz, 2H), 3.91 (s, 2H), 3.93 (d, J=7.07 Hz, 2H), 6.93-7.00 (m, 1H), 7.05-7.27 (m, 5H), 7.38-7.43 (m, 2H).

Example 1.99: Preparation of 2-(((1s,4s)-4-((4-(4-Fluorophenyl)-5-methyl-3-phenyl-1H-pyrazol-1-yl)methyl)cyclohexyl)methoxy)acetic Acid (Compound 22)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 4-fluorophenylboronic, the title compound was obtained using a similar method to the one described in Example 1.97. LCMS m/z=437.2 [M+H]$^+$; $^1$H NMR (400 MHz, DMSO-d$_6$) δ ppm 1.33-1.54 (m, 8H), 1.71-1.82 (m, 1H), 2.05-2.15 (m, 1H), 2.20 (s, 3H), 3.43 (d, J=7.07 Hz, 2H), 4.00 (s, 2H), 4.05 (d, J=7.58 Hz, 2H), 7.17-7.21 (m, 3H), 7.21-7.28 (m, 3H), 7.29-7.34 (m, 3H).

Example 1.100: Preparation of 2-(((1s,4s)-4-((4-(3-Chlorophenyl)-5-methyl-3-phenyl-1H-pyrazol-1-yl)methyl)cyclohexyl)methoxy)acetic Acid (Compound 23)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 3-chlorophenylboronic acid, the title compound was obtained using a similar method to the one described in Example 1.97. LCMS m/z=453.3 [M+H]$^+$; $^1$H NMR (400 MHz, DMSO-d$_6$) δ ppm 1.34-1.55 (m, 8H), 1.73-1.82 (m, 1H), 2.04-2.16 (m, 1H), 2.23 (s, 3H), 3.43 (d, J=7.07 Hz, 2H), 4.01 (s, 2H), 4.06 (d, J=7.58 Hz, 2H), 7.09-7.14 (m, 1H), 7.18-7.41 (m, 8H).

Example 1.101: Preparation of 2-(((1s,4s)-4-((5-Methyl-3-phenyl-4-m-tolyl-1H-pyrazol-1-yl)methyl)cyclohexyl)methoxy)acetic Acid (Compound 24)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and m-tolylboronic acid, the title compound was obtained using a similar method to the one described in Example 1.97. LCMS m/z=433.2 [M+H]$^+$; $^1$H NMR (400 MHz, DMSO-d$_6$) δ ppm 1.33-1.55 (m, 8H), 1.72-1.82 (m, 1H), 2.07-2.15 (m, 1H), 2.19 (s, 3H), 2.28 (s, 3H), 3.43 (d, J=6.82 Hz, 2H), 4.00 (s, 2H), 4.05 (d, J=7.58 Hz, 2H), 6.88-7.14 (m, 3H), 7.15-7.29 (m, 3H), 7.29-7.39 (m, 3H).

Example 1.102: Preparation of 2-(((1s,4s)-4-((4-(4-Fluorophenyl)-3-methyl-5-phenyl-1H-pyrazol-1-yl)methyl)cyclohexyl)methoxy)acetic Acid (Compound 25)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 4-fluorophenylboronic acid, the title compound was obtained using a similar method to the one described in Example 1.97. LCMS m/z=437.2 [M+H]$^+$; $^1$H NMR (400 MHz, DMSO-d$_6$) δ ppm 1.01-1.20 (m, 4H), 1.21-1.36 (m, 4H), 1.52-1.67 (m, 1H), 1.86-2.00 (m, 1H), 2.20 (s, 3H), 3.19 (d, J=6.82 Hz, 2H), 3.88 (d, J=7.58 Hz, 2H), 3.91 (s, 2H), 6.96-7.17 (m, 4H), 7.18-7.31 (m, 2H), 7.34-7.48 (m, 3H).

Example 1.103: Preparation of 2-(((1s,4s)-4-((4-(2,3-Difluorophenyl)-3-methyl-5-phenyl-1H-pyrazol-1-yl)methyl)cyclohexyl)methoxy)acetic Acid (Compound 26)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 2,3-difluorophenylboronic acid, the title compound was obtained using a similar method to the one described in Example 1.97. LCMS m/z=455.2 [M+H]$^+$; $^1$H NMR (400 MHz, DMSO-d$_6$) δ ppm 0.98-1.20 (m, 4H), 1.21-1.38 (m, 4H), 1.53-1.69 (m, 1H), 1.88-2.02 (m, 1H), 2.13 (s, 3H), 3.19 (d, J=7.07 Hz, 2H), 3.91 (s, 21H), 3.94 (d, J=7.33 Hz, 2H), 6.91-6.97 (m, 1H), 7.05-7.12 (m, 1H), 7.20-7.25 (m, 3H), 7.37-7.42 (m, 3H).

Example 1.104: Preparation of 2-(((1s,4s)-4-((4-(2,3-Difluorophenyl)-5-methyl-3-phenyl-1H-pyrazol-1-yl)methyl)cyclohexyl)methoxy)acetic Acid (Compound 27)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 23-difluorophenylboronic acid, the title compound was obtained using a similar method to the one described in Example 1.97. LCMS m/z=455.2 [M+H]$^+$; $^1$H NMR (400 MHz, DMSO-d$_6$) δ ppm 1.31-1.54 (m, 8H), 1.71-1.81 (m, 1H), 2.05-2.15 (m, 1H), 2.17 (s, 3H), 3.42 (d, J=7.07 Hz, 2H), 3.99 (s, 2H), 4.07 (d, J=7.58 Hz, 2H), 7.02-7.09 (m, 2H), 7.19-7.32 (m, 4H), 7.34-7.46 (m, 2H).

Example 1.105: Preparation of 2-(((1s,4s)-4-((4-(4-Chlorophenyl)-5-methyl-3-phenyl-1H-pyrazol-1-yl)methyl)cyclohexyl)methoxy)acetic Acid (Compound 28)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 4-chlorophenylboronic acid, the title compound was obtained using a similar method to the one described in Example 1.97. LCMS m/z=453.2 [M+H]$^+$; $^1$H NMR (400 MHz, DMSO-d$_6$) δ ppm 1.31-1.57 (m, 8H), 1.70-1.83 (m, 1H), 2.03-2.14 (m, 1H), 2.21 (s, 3H), 3.42 (d, J=6.95 Hz, 2H), 4.00 (s, 2H), 4.05 (d, J=7.58 Hz, 2H), 7.14-7.20 (m, 2H), 7.22-7.34 (m, 5H), 7.38-7.44 (m, 2H).

Example 1.106: Preparation of 2-(((1s,4s)-4-((4-(2,5-Difluorophenyl)-3-methyl-5-phenyl-1H-pyrazol-1-yl)methyl)cyclohexyl)methoxy)acetic Acid (Compound 29)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 2,5-difluorophenylboronic acid, the title compound was obtained using a similar method to the one described in Example 1.97. LCMS m/z=455.2 [M+H]$^+$; $^1$H NMR (400 MHz, DMSO-d$_6$) δ ppm 0.99-1.21 (m, 4H), 1.21-1.38 (m, 4H), 1.54-1.66 (m, 1H), 1.88-2.02 (m, 1H), 2.13 (s, 3H), 3.20 (d, J=7.07 Hz, 2H), 3.91 (s, 2H), 3.93 (d, J=7.07 Hz, 2H), 6.93-7.00 (m, 1H), 7.05-7.27 (m, 5H), 7.38-7.43 (m, 2H).

Example 1.107: Preparation of 2-(((1s,4s)-4-((5-(3-Methoxyphenyl)-3-methyl-4-phenyl-1H-pyrazol-1-yl)methyl)cyclohexyl)methoxy)acetic Acid (Compound 32)

Step A: Preparation of 3-Bromo-5-methyl-4-phenyl-1H-pyrazole

To a solution of 5-methyl-4-phenyl-1H-pyrazole (3.0 g, 18.96 mmol) in acetic acid (glacial, 100 mL) was added bromine (1.457 mL, 28.4 mmol) at room temperature. The reaction was stirred at room temperature for 2 h. After quenched with aqueous solution of Na$_2$SO$_3$ (10% wt aq., 10 mL), the reaction was concentrated and extracted with EtOAc, washed with brine, dried over MgSO$_4$, and purified by silica gel column chromatography to give the title compound as yellow oil (2.8 g). LCMS m/z=236.9 [M+H]$^+$; $^1$H NMR (400 MHz, DMSO-d$_6$) δ ppm 2.26 (s, 3H), 7.24-7.54 (m, 5H), 13.13 (s, 1H).

Step B: Preparation of tert-Butyl 2-(((1s,4s)-4-((5-Bromo-3-methyl-4-phenyl-1H-pyrazol-1-yl)methyl)cyclohexyl)methoxy)acetate and tert-Butyl 2-(((1s,4s)-4-((3-Bromo-5-methyl-4-phenyl-1H-pyrazol-1-yl)methyl)cyclohexyl)methoxy)acetate as a Mixture of Regioisomers A solution of 3-bromo-5-methyl-4-phenyl-1H-pyrazole (2.0 g, 7.04 mmol) in DMF (10 mL) was treated with sodium hydride (0.169 g, 7.04 mmol) at 0° C. for 1 h, then a solution of tert-butyl 2-(((1s,4s)-4-(tosyloxymethyl)cyclohexyl)methoxy)acetate (2.90 g, 7.04 mmol) in DMF (5 mL) was added. The reaction mixture was gently warmed to 60° C. for 16 h and quenched by water (2 mL). The mixture was extracted by EtOAc, dried over MgSO$_4$, and purified by silica gel column chromatography to give the title compound (2.25 g) (mixture of two regioisomers). LCMS m/z=477.3 [M+H]$^+$.

Step C: Preparation of 2-(((1s,4s)-4-((5-(3-Methoxyphenyl)-3-methyl-4-phenyl-1H-pyrazol-1-yl)methyl)cyclohexyl)methoxy)acetic Acid To a solution of tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers (100 mg, 0.19 mmol) in dioxane (3 mL) were added 3-methoxyphenylboronic acid (28.9 mg, 0.19 mmol), tetrakis(triphenylphosphine)palladium (22 mg, 0.019 mmol), and $K_2CO_3$ (2 M aq., 0.2 mL). The reaction was heated to 150° C. under microwave irradiation for 4 h. The reaction mixture was filtered and concentrated. The residue was treated with HCl (4.0 M in dioxane, 5 mL) at room temperature for 10 h. The mixture was concentrated and purified by HPLC to give the title compound (one of the two regioisomers separated) as a white solid. LCMS m/z=449.2 [M+H]$^+$; $^1$H NMR (400 MHz, DMSO-d$_6$) δ ppm 1.09-1.20 (m, 4H), 1.22-1.38 (m, 4H), 1.57-1.69 (m, 1H), 1.89-1.99 (m, 1H), 2.21 (s, 3H), 3.23 (d, J=6.82 Hz, 2H), 3.77 (s, 3H), 3.86 (d, J=7.33 Hz, 2H), 3.92 (s, 2H), 6.94-6.99 (m, 2H), 7.04-7.10 (m, 2H), 7.11-7.19 (m, 3H), 7.20-7.26 (m, 2H).

Example 1.108: Preparation of 2-(((1s,4s)-4-((3-(3-Methoxyphenyl)-5-methyl-4-phenyl-1H-pyrazol-1-yl)methyl)cyclohexyl)methoxy)acetic Acid (Compound 33)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 3-methoxyphenylboronic acid, the title compound (one of the two regioisomers separated) was obtained using a similar method to the one described in Example 1.107. LCMS m/z=449.2 [M+H]$^+$; $^1$H NMR (400 MHz, DMSO-d$_6$) δ ppm 1.32-1.54 (m, 8H), 1.71-1.80 (m, 1H), 2.04-2.14 (m, 1H), 2.19 (s, 3H), 3.42 (d, J=6.82 Hz, 2H), 3.71 (s, 3H), 3.99 (s, 2H), 4.03 (d, J=7.58 Hz, 2H), 6.77-6.84 (m, 2H), 7.12-7.19 (m, 2H), 7.20-7.31 (m, 3H), 7.32-7.39 (m, 2H).

Example 1.109: Preparation of 2-(((1s,4s)-4-((5-(3-Fluoro-5-methoxyphenyl)-3-methyl-4-phenyl-1H-pyrazol-1-yl)methyl)cyclohexyl)methoxy)acetic Acid (Compound 34)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 3-fluoro-5-methoxyphenylboronic acid, the title compound (one of the two regioisomers separated) was obtained using a similar method to the one described in Example 1.107. LCMS m/z=467.3 [M+H]$^+$; $^1$H NMR (400 MHz, DMSO-d$_6$) δ ppm 1.09-1.22 (m, 4H), 1.23-1.39 (m, 4H), 1.56-1.69 (m, 1H), 1.88-2.00 (m, 1H), 2.20 (s, 3H), 3.24 (d, J=6.32 Hz, 2H), 3.72 (s, 3H), 3.79 (d, J=7.57 Hz, 2H), 3.93 (s, 2H), 6.60-6.92 (m, 3H), 7.05-7.35 (m, 51).

Example 1.110: Preparation of 2-(((1s,4s)-4-((3-(3-Fluoro-5-methoxyphenyl)-5-methyl-4-phenyl-1H-pyrazol-1-yl)methyl)cyclohexyl)methoxy)acetic Acid (Compound 35)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 3-fluoro-5-methoxyphenylboronic acid, the title compound (one of the two regioisomers separated) was obtained using a similar method to the one described in Example 1.107. LCMS m/z=467.3 [M+H]$^+$; $^1$H NMR (400 MHz, DMSO-d$_6$) δ ppm 1.33-1.54 (m, 8H), 1.71-1.81 (m, 1H), 2.05-2.14 (m, 1H), 2.18 (s, 3H), 3.42 (d, J=6.82 Hz, 2H), 3.59 (s, 3H), 3.99 (s, 2H), 4.05 (d, J=7.58 Hz, 2H), 6.62-6.71 (m, 4H), 7.17-7.23 (m, 1H), 7.29-7.44 (m, 3H).

Example 1.111: Preparation of 2-(((1s,4s)-4-((4-(4-Methoxyphenyl)-5-methyl-3-phenyl-1H-pyrazol-1-yl)methyl)cyclohexyl)methoxy)acetic Acid (Compound 38)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 4-methoxyphenylboronic acid (26.6 mg, 0.19 mmol), the title compound (one of the two regioisomers separated) was obtained using a similar method to the one described in Example 1.97. LCMS m/z=449.2 [M+H]$^+$; $^1$H NMR (400 MHz, DMSO-d$_6$) δ ppm 131-1.54 (m, 8H), 1.71-1.81 (m, 1H), 2.04-2.14 (m, 1H), 2.17 (s, 3H), 3.42 (d, J=6.82 Hz, 2H), 3.77 (s, 3H), 4.00 (s, 2H), 4.04 (d, J=7.58 Hz, 2H), 6.90-6.96 (m, 2H), 7.04-7.11 (m, 2H), 7.16-7.27 (m, 3H), 7.30-7.37 (m, 2H).

Example 1.112: Preparation of 2-(((1s,4s)-4-((4-(3-Fluoro-5-methoxyphenyl)-5-methyl-3-phenyl-1H-pyrazol-1-yl)methyl)cyclohexyl)methoxy)acetic Acid (Compound 39)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 3-fluoro-5-methoxyphenylboronic acid, the title compound (one of the two regioisomers separated) was obtained using a similar method to the one described in Example 1.97. LCMS m/z=467.2 [M+H]$^+$; H NMR (400 MHz, DMSO-d$_6$) δ ppm 1.31-1.55 (m, 8H), 1.70-1.82 (m, 1H), 2.03-2.14 (m, 1H), 2.23 (s, 3H), 3.42 (d, J=7.07 Hz, 2H), 3.70 (s, 3H), 3.99 (s, 2H), 4.04 (d, J=7.58 Hz, 2H), 6.39-6.81 (m, 3H), 7.19-7.36 (m, 5H).

Example 1.113: Preparation of 2-(((1s,4s)-4-((4-(3-Fluorophenyl)-5-methyl-3-phenyl-1H-pyrazol-1-yl)methyl)cyclohexyl)methoxy)acetic Acid (Compound 40)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 3-fluorophenylboronic acid, the title compound (one of the two regioisomers separated) was obtained using a similar method to the one described in Example 1.97. LCMS m/z=437.2 [M+H]$^+$; $^1$H NMR (400 MHz, DMSO-d$_6$) δ ppm 1.34-1.53 (m, 8H), 1.72-1.81 (m, 1H), 2.04-2.15 (m, 1H), 2.23 (s, 3H), 3.43 (d, J=7.07 Hz, 2H), 4.00 (s, 2H), 4.06 (d, J=7.58 Hz, 2H), 6.93-7.01 (m, 2H), 7.08-7.15 (m, 1H), 7.20-7.35 (m, 5H), 7.35-7.44 (m, 1H).

Example 1.114: Preparation of 2-(((1s,4s)-4-((4-(3-Chlorophenyl)-3-methyl-5-phenyl-1H-pyrazol-1-yl)methyl)cyclohexyl)methoxy)acetic Acid (Compound 41)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 3-chlorophenylboronic acid, the title compound (one of the two regioisomers separated) was obtained using a similar method to the one described in Example 1.97. LCMS m/z=453.3 [M+H]$^+$; $^1$H NMR (400 MHz, DMSO-d$_6$) δ ppm 1.02-1.20 (m, 4H), 1.21-1.35 (m, 4H), 1.54-1.65 (m, 1H), 1.88-1.98 (m, 1H), 2.24 (s, 3H), 3.20 (d, J=6.82 Hz, 2H), 3.89 (d, J=7.58 Hz, 2H), 3.91 (s, 2H), 7.00-7.08 (m, 2H), 7.17-7.30 (m, 5H), 7.40-7.48 (m, 2H).

Example 1.115: Preparation of 2-(((1s,4s)-4-((4-(4-Methoxyphenyl)-3-methyl-5-phenyl-1-pyrazol-1-yl)methyl)cyclohexyl)methoxy)acetic Acid (Compound 42)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 4-methoxyphenylboronic acid, the title compound (one of the two regioisomers separated) was obtained using a similar method to the one described in Example 1.97. LCMS m/z=449.2 [M+H]$^+$; H NMR (400 MHz, DMSO-d$_6$) δ ppm 1.01-1.19 (m, 4H), 1.20-1.35 (m, 4H), 1.54-1.64 (m, 1H), 1.86-1.97 (m, 11-), 2.19 (s, 3H), 3.19 (d, J=6.82 Hz, 2H), 3.69 (s, 3H), 3.87 (d, J=7.33 Hz, 2H), 3.91 (s, 2H), 6.76-6.82 (m, 2H), 6.95-7.02 (m, 2H), 7.19-7.26 (m, 2H), 7.35-7.45 (m, 3H).

Example 1.116: Preparation of 2-(((1s,4s)-4-((4-(3-Fluoro-5-methoxyphenyl)-3-methyl-5-phenyl-1H-pyrazol-1-yl)methyl)cyclohexyl)methoxy)acetic Acid (Compound 43)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 3-fluoro-5-methoxyphenylboronic acid, the title compound (one of the two regioisomers separated) was obtained using a similar method to the one described in Example 1.97. LCMS m/z=467.2 [M+H]$^+$; $^1$H NMR (400 MHz, DMSO-d$_6$) δ ppm 1.01-1.20 (m, 4H), 1.21-1.36 (m, 4H), 1.56-1.64 (m, 1H), 1.88-1.97 (m, 1H), 2.25 (s, 3H), 3.20 (d, J=7.07 Hz, 2H), 3.60 (s, 3H), 3.87 (d, J=7.33 Hz, 2H), 3.91 (s, 2H), 6.36-6.65 (m, 4H), 7.20-7.52 (m, 4H).

Example 1.117: Preparation of 2-(((1s,4s)-4-((4-(2-Chlorophenyl)-5-methyl-3-phenyl-1H-pyrazol-1-yl)methyl)cyclohexyl)methoxy)acetic Acid (Compound 44)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methy-3-phenyl-1H-pyrazol-1-yl)methyl)cyclohexyl)methoxy)acetate as a mixture of regioisomers and 2-chlorophenylboronic acid, the title compound (one of the two regioisomers separated) was obtained using a similar method to the one described in Example 1.97. LCMS m/z=453.2 [M+H]$^+$; $^1$H NMR (400 MHz, DMSO-d$_6$) δ ppm 1.32-1.53 (m, 8H), 1.71-1.82 (m, 1H), 2.08 (s, 3H), 2.08-2.17 (m, 1H), 3.42 (d, J=6.82 Hz, 2H), 3.99 (s, 2H), 4.06 (d, J=7.58 Hz, 2H), 7.16-7.30 (m, 4H), 7.33-7.44 (m, 3H), 7.52-7.59 (m, 2H).

Example 1.118: Preparation of 2-(((1s,4s)-4-((4-(2-Chlorophenyl)-3-methyl-5-phenyl-1H-pyrazol-1-yl)methyl)cyclohexyl)methoxy)acetic Acid (Compound 45)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 2-chlorophenylboronic acid, the title compound (one of the two regioisomers separated) was obtained using a similar method to the one described in Example 1.97. LCMS m/z=453.2 [M+H]$^+$; $^1$H NMR (400 MHz, DMSO-d$_6$) δ ppm 1.00-1.20 (m, 4H), 1.20-1.37 (m, 4H), 1.55-1.64 (m, 1H), 1.91-2.00 (m, 1H), 2.03 (s, 3H), 3.18 (d, J=6.82 Hz, 2H), 3.90 (s, 2H), 3.95 (d, J=7.58 Hz, 2H), 7.14-7.29 (m, 4H), 7.31-7.39 (m, 3H), 7.41-7.45 (m, 2H).

Example 1.119: Preparation of 2-(((1s,4s)-4-((4-(3-Fluorophenyl)-3-methyl-5-phenyl-1H-pyrazol-1-yl)methyl)cyclohexyl)methoxy)acetic Acid (Compound 46)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 3-fluorophenylboronic acid, the title compound (one of the two regioisomers separated) was obtained using a similar method to the one described in Example 1.97. LCMS m/z=437.2 [M+H]$^+$; $^1$H NMR (400 MHz, DMSO-d$_6$) δ ppm 1.02-1.19 (m, 4H), 1.21-1.36 (m, 4H), 1.55-1.66 (m, 1H), 1.87-1.98 (m, 1H), 2.24 (s, 3H), 3.20 (d, J=7.07 Hz, 2H), 3.88 (d, J=7.33 Hz, 2H), 3.91 (s, 2H), 6.79-7.01 (m, 3H), 7.22-7.30 (m, 3H), 7.40-7.47 (m, 3H).

Example 1.120: Preparation of 2-(((1s,4s)-4-((5-Methyl-3-phenyl-4-p-tolyl-1H-pyrazol-1-yl)methyl)cyclohexyl)methoxy)acetic Acid (Compound 47)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and p-tolylboronic acid, the title compound (one of the two regioisomers separated) was obtained using a similar method to the one described in Example 1.97. LCMS m/z=433.2 [M+H]$^+$; $^1$H NMR (400 MHz, DMSO-d$_6$) δ ppm 1.34-1.53 (m, 8H), 1.71-1.80 (m, 1H), 2.04-2.14 (m, 1H), 2.18 (s, 3H), 2.32 (s, 3H), 3.42 (d, J=7.07 Hz, 2H), 3.99 (s, 2H), 4.04 (d, J=7.58 Hz, 2H), 7.02-7.07 (m, 2H), 7.14-7.27 (m, 5H), 7.30-7.35 (m, 2H).

Example 1.121: Preparation of 2-(((1s,4s)-4-((4-(2,4-Difluorophenyl)-5-methyl-3-phenyl-1H-pyrazol-1-yl)methyl)cyclohexyl)methoxy)acetic Acid (Compound 48)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 2,4-difluorophenylboronic acid, the title compound (one of the two regioisomers separated) was obtained using a similar method to the one described in Example 1.97. LCMS m/z=455.2 [M+H]$^+$; $^1$H NMR (400 MHz, DMSO-d$_6$) δ ppm 1.33-1.53 (m, 8H), 1.72-1.81 (m, 1H), 2.06-2.13 (m, 1H), 2.14 (s, 3H), 3.43 (d, J=7.07 Hz, 2H), 4.00 (s, 2H), 4.07 (d, J=7.58 Hz, 2H), 7.07-7.15 (m, 2H), 7.19-7.34 (m, 6H).

Example 1.122: Preparation of 2-(((1s,4s)-4-((4-(4-Chlorophenyl)-3-phenyl-1H-pyrazol-1-yl)methyl)cyclohexyl)methoxy)acetic Acid (Compound 49)

Step A: Preparation of 4-Bromo-3-phenyl-1H-pyrazole

To a solution of 3-phenyl-1H-pyrazole-4-carbaldehyde (10.0 g, 58.1 mmol) in acetic acid (100 mL, 58.1 mmol) was added bromine (10 mL, 195 mmol) dropwise at room temperature. The reaction was stirred at room temperature for 2 h. After quenched with aqueous solution of Na$_2$SO$_3$ (10% wt aq., 10 mL), the reaction was concentrated and extracted with EtOAc, washed with brine, dried over MgSO$_4$, and purified by silica gel column chromatography to give the title compound as yellow oil (10.2 g). LCMS m/z=223.0 [M+H]$^+$; $^1$H NMR (400 MHz, DMSO-d$_6$) δ ppm 7.37-7.53 (m, 3H), 7.76-7.84 (m, 2H), 7.91 (s, 1H).

Step B: Preparation of tert-Butyl 2-(((1s,4s)-4-((4-Bromo-3-phenyl-1H-pyrazol-1-yl)methyl)cyclohexyl)methoxy)acetate and tert-Butyl 2-(((1s,4s)-4-((4-Bromo-5-phenyl-1H-pyrazol-1-yl)methyl)cyclohexyl)methoxy)acetate as a Mixture of Regioisomers A solution of 3-bromo-5-methyl-4-phenyl-1H-pyrazole (2.0 g, 7.04 mmol) in DMF (10 mL) was treated with sodium hydride (0.169 g, 7.04 mmol) at 0° C. for 1 h, then a solution of tert-butyl 2-(((1s,4s)-4-(tosyloxymethyl)cyclohexyl)methoxy)acetate (2.90 g, 7.04 mmol) in DMF (5 mL) was added. The reaction mixture was gently warmed to 60° C. for 16 h and quenched by water (2 mL). The mixture was extracted by EtOAc, dried over MgSO$_4$, and concentrated. The residue was purified by column chromatography to give the title compound as a mixture of regioisomers (2.25 g). LCMS m/z=462.2 [M+H]$^+$; $^1$H NMR (400 MHz, DMSO-d$_6$) δ ppm 1.22-133 (m, 4H), 1.35-1.48 (m, 4H), 1.43 (s, 9H), 1.65-1.79 (m, 1H), 2.02-2.15 (m, 1H), 3.37 (d, J=6.82 Hz, 2H), 3.95 (s, 2H), 4.09 (d, J=7.58 Hz, 2H), 7.34-7.51 (m, 3H), 7.76-7.84 (m, 2H), 8.08 (s, 1H).

Step C: Preparation of 2-(((1s,4s)-4-((4-(4-Chlorophenyl)-3-phenyl-1H-pyrazol-1-yl)methyl)cyclohexyl)methoxy)acetic Acid To a solution of tert-butyl 2-(((1s,4s)-4-((4-bromo-3-phenyl-1H-pyrazol-1-yl)methyl)cyclohexyl)methoxy)acetate and tert-butyl 2-(((1s,4s)-4-((4-bromo-5-phenyl-1H-pyrazol-1-yl)methyl)cyclohexyl)methoxy)acetate as a mixture of regioisomers (100 mg, 0.22 mmol) in dioxane (3 mL) were added 4-chlorophenylboronic acid (34.4 mg, 0.22 mmol), tetrakis(triphenylphosphine)palladium (25 mg, 0.022 mmol), and K$_2$CO$_3$ (2 M aq., 0.2 mL). The reaction was heated to 150° C. under microwave irradiation for 4 h. The reaction mixture was filtered and concentrated. The residue was treated with HCl (4.0 M in dioxane, 5 mL) at room temperature for 10 h. The mixture was concentrated and purified by HPLC to give the title compound (one of the two regioisomers separated) as a white solid. LCMS m/z=438.2 [M+H]$^+$; $^1$H NMR (400 MHz, DMSO-d$_6$) δ ppm 1.29-1.52 (m, 8H), 1.71-1.79 (m, 1H), 2.07-2.19 (m, 1H), 3.40 (d, J=6.82 Hz, 2H), 3.99 (s, 2H), 4.09 (d, J=7.83 Hz, 2H), 7.21-7.27 (m, 2H), 7.29-7.42 (m, 7H), 7.98 (s, 1H).

Example 1.123: Preparation of 2-(((1s,4s)-4-((4-(3-Fluorophenyl)-3-phenyl-1H-pyrazol-1-yl)methyl)cyclohexyl)methoxy)acetic Acid (Compound 50)

From tert-butyl 2-(((1s,4s)-4-((4-bromo-3-phenyl-1H-pyrazol-1-yl)methyl)cyclohexyl)methoxy)acetate and tert-butyl 2-(((1s,4s)-4-((4-bromo-5-phenyl-1H-pyrazol-1-yl)methyl)cyclohexyl)methoxy)acetate as a mixture of regioisomers and 3-fluorophenylboronic acid, the title compound (one of the two regioisomers separated) was obtained using a similar method to the one described in Example 1.122. LCMS m/z=423.2 [M+H]$^+$; $^1$H NMR (400 MHz, DMSO-d$_6$) δ ppm 1.27-1.55 (m, 8H), 1.67-1.84 (m, 1H), 2.07-2.22 (m, 1H), 3.41 (d, J=6.82 Hz, 2H), 4.00 (s, 2H), 4.10 (d, J=7.58 Hz, 2H), 6.99-7.10 (m, 3H), 7.29-7.43 (m, 6H), 8.04 (s, 1H).

Example 1.124: Preparation of 2-(((1s,4s)-4-((4-(4-Fluorophenyl)-3-phenyl-1H-pyrazol-1-yl)methyl)cyclohexyl)methoxy)acetic Acid (Compound 51)

From tert-butyl 2-(((1s,4s)-4-((4-bromo-3-phenyl-1H-pyrazol-1-yl)methyl)cyclohexyl)methoxy)acetate and tert-butyl 2-(((1s,4s)-4-((4-bromo-5-phenyl-1H-pyrazol-1-yl)methyl)cyclohexyl)methoxy)acetate as a mixture of regioisomers and 4-fluorophenylboronic acid, the title compound (one of the two regioisomers separated) was obtained using a similar method to the one described in Example 1.122. LCMS m/z=423.2 [M+H]$^+$; $^1$H NMR (400 MHz, DMSO-d$_6$) δ ppm 1.28-1.53 (m, 8H), 1.70-1.80 (m, 1H), 2.08-2.18 (m, 1H), 3.40 (d, J=6.82 Hz, 2H), 3.99 (s, 2H), 4.09 (d, J=7.58 Hz, 2H), 7.10-7.17 (m, 2H), 7.22-7.36 (m, 5H), 7.36-7.41 (m, 2H), 7.93 (s, 1H).

Example 1.125: Preparation of 2-(((1s,4s)-4-((4-(3-Chloro-2-fluorophenyl)-5-methyl-3-phenyl-1H-pyrazol-1-yl)methyl)cyclohexyl)methoxy)acetic Acid (Compound 52)

From tert-butyl 2-(((1s,4s)-4-((4-bromo-5-methyl-3-phenyl-1H-pyrazol-1-yl)methyl)cyclohexyl)methoxy)acetate and tert-butyl 2-(((1s,4s)-4-((4-bromo-3-methyl-5-phenyl-1H-pyrazol-1-yl)methyl)cyclohexyl)methoxy)acetate as a mixture of regioisomers and 3-chloro-2-fluorophenylboronic acid, the title compound (one of the two regioisomers separated) was obtained using a similar method to the one described in Example 1.97. LCMS m/z=470.1 [M+H]$^+$; $^1$H NMR (400 MHz, DMSO-d$_6$) δ ppm 1.30-1.54 (m, 8H), 1.71-1.82 (m, 1H), 2.05-2.14 (m, 1H), 2.16 (s, 3H), 3.43 (d, J=7.07 Hz, 2H), 4.00 (s, 2H), 4.07 (d, J=7.58 Hz, 2H), 7.16-7.36 (m, 6H), 7.50-7.63 (m, 2H).

Example 1.126: Preparation of 2-(((1s,4s)-4-((4-(2,4-Difluorophenyl)-3-methyl-5-phenyl-1H-pyrazol-1-yl)methyl)cyclohexyl)methoxy)acetic Acid (Compound 53)

From tert-butyl 2-(((1s,4s)-4-((4-bromo-5-methyl-3-phenyl-1H-pyrazol-1-yl)methyl)cyclohexyl)methoxy)acetate and tert-butyl 2-(((1s,4s)-4-((4-bromo-3-methyl-5-phenyl-1H-pyrazol-1-yl)methyl)cyclohexyl)methoxy)acetate as a mixture of regioisomers and 2,4-difluorophenylboronic acid, the title compound was obtained using a similar method to the one described in Example 1.97. LCMS m/z=455.2 [M+H]⁺; ¹H NMR (400 MHz, DMSO-d₆) δ ppm 1.02-1.18 (m, 4H), 1.21-1.35 (m, 4H), 1.55-1.64 (m, 1H), 1.89-1.99 (m, 1H), 2.10 (s, 3H), 3.19 (d, J=7.07 Hz, 2H), 3.91 (s, 2H), 3.93 (d, J=7.33 Hz, 2H), 6.94-7.02 (m, 2H), 7.11-7.24 (m, 3H), 7.34-7.43 (m, 3H).

Example 1.127: Preparation of 2-(((1s,4s)-4-((4-(3-Chloro-2-fluorophenyl)-3-methyl-5-phenyl-1H-pyrazol-1-yl)methyl)cyclohexyl)methoxy)acetic Acid (Compound 54)

From tert-butyl 2-(((1s,4s)-4-((4-bromo-5-methyl-3-phenyl-1H-pyrazol-1-yl)methyl)cyclohexyl)methoxy)acetate and tert-butyl 2-(((1s,4s)-4-((4-bromo-3-methyl-5-phenyl-1H-pyrazol-1-yl)methyl)cyclohexyl)methoxy)acetate as a mixture of regioisomers and 3-chloro-2-fluorophenylboronic acid, the title compound (one of the two regioisomers separated) was obtained using a similar method to the one described in Example 1.97. LCMS m/z=470.1 [M+H]⁺; ¹H NMR (400 MHz, DMSO-d₆) δ ppm 1.01-1.20 (m, 4H), 1.21-1.39 (m, 4H), 1.54-1.66 (m, 1H), 1.90-2.00 (m, 1H), 2.12 (s, 3H), 3.20 (d, J=6.82 Hz, 2H), 3.91 (s, 2H), 3.94 (d, J=7.58 Hz, 2H), 7.05-7.30 (m, 4H), 7.34-7.53 (m, 4H).

Example 1.128: Preparation of 2-(((1s,4s)-4-((3-Methyl-5-phenyl-4-p-tolyl-1H-pyrazol-1-yl)methyl)cyclohexyl)methoxy)acetic Acid (Compound 55)

From tert-butyl 2-(((1s,4s)-4-((4-bromo-5-methyl-3-phenyl-1H-pyrazol-1-yl)methyl)cyclohexyl)methoxy)acetate and tert-butyl 2-(((1s,4s)-4-((4-bromo-3-methyl-5-phenyl-1H-pyrazol-1-yl)methyl)cyclohexyl)methoxy)acetate as a mixture of regioisomers and p-tolylboronic acid, the title compound (one of the two regioisomers separated) was obtained using a similar method to the one described in Example 1.97. LCMS m/z=433.2 [M+H]⁺; ¹H NMR (400 MHz, DMSO-d₆) δ ppm 1.25-1.50 (m, 8H), 1.68-1.79 (m, 1H), 1.98-2.08 (m, 1H), 2.07 (s, 3H), 2.31 (s, 3H), 3.40 (d, J=7.07 Hz, 2H), 3.98 (s, 2H), 4.06 (d, J=7.58 Hz, 2H), 7.33-7.39 (m, 2H), 7.40-7.47 (m, 4H), 7.77-7.82 (m, 3H).

Example 1.129: Preparation of 2-(((1s,4s)-4-((4-(3-Chloro-4-fluorophenyl)-3-methyl-5-phenyl-1H-pyrazol-1-yl)methyl)cyclohexyl)methoxy)acetic Acid (Compound 56)

From tert-butyl 2-(((1s,4s)-4-((4-bromo-5-methyl-3-phenyl-1H-pyrazol-1-yl)methyl)cyclohexyl)methoxy)acetate and tert-butyl 2-(((1s,4s)-4-((4-bromo-3-methyl-5-phenyl-1H-pyrazol-1-yl)methyl)cyclohexyl)methoxy)acetate as a mixture of regioisomers and 3-chloro-4-fluorophenylboronic acid, the title compound (one of the two regioisomers separated) was obtained using a similar method to the one described in Example 1.97. LCMS m/z=471.1 [M+H]⁺; ¹H NMR (400 MHz, DMSO-d₆) δ ppm 1.02-1.18 (m, 4H), 1.21-1.36 (m, 4H), 1.55-1.65 (m, 1H), 1.87-1.98 (m, 1H), 2.23 (s, 3H), 3.20 (d, J=6.82 Hz, 2H), 3.89 (d, J=7.58 Hz, 2H), 3.91 (s, 2H), 7.01-7.08 (m, 1H), 7.18-7.29 (m, 4H), 7.41-7.48 (m, 3H).

Example 1.130: Preparation of 2-(((1s,4s)-4-((4-(3-Chloro-4-fluorophenyl)-5-methyl-3-phenyl-1H-pyrazol-1-yl)methyl)cyclohexyl)methoxy)acetic Acid (Compound 57)

From tert-butyl 2-(((1s,4s)-4-((4-bromo-5-methyl-3-phenyl-1H-pyrazol-1-yl)methyl)cyclohexyl)methoxy)acetate and tert-butyl 2-(((1s,4s)-4-((4-bromo-3-methyl-5-phenyl-1H-pyrazol-1-yl)methyl)cyclohexyl)methoxy)acetate as a mixture of regioisomers and 3-chloro-4-fluorophenylboronic acid, the title compound was obtained using a similar method to the one described in Example 1.97. LCMS m/z=471.1 [M+H]⁺; ¹H NMR (400 MHz, DMSO-d₆) δ ppm 1.33-1.55 (m, 8H), 1.72-1.83 (m, 1H), 2.05-2.15 (m, 1H), 2.22 (s, 3H), 3.44 (d, J=7.07 Hz, 2H), 4.01 (s, 2H), 4.06 (d, J=7.58 Hz, 2H), 7.10-7.17 (m, 1H), 7.21-7.42 (m, 7H).

Example 1.131: Preparation of 2-(((1s,4s)-4-((4-(4-Methoxyphenyl)-3-phenyl-1H-pyrazol-1-yl)methyl)cyclohexyl)methoxy)acetic Acid (Compound 58)

From tert-butyl 2-(((1s,4s)-4-((4-bromo-3-phenyl-1H-pyrazol-1-yl)methyl)cyclohexyl)methoxy)acetate and tert-butyl 2-(((1s,4s)-4-((4-bromo-5-phenyl-1H-pyrazol-1-yl)methyl)cyclohexyl)methoxy)acetate as a mixture of regioisomers (100 mg, 0.22 mmol) and 4-methoxyphenylboronic acid, the title compound (one of the two regioisomers separated) was obtained using a similar method to the one described in Example 1.122. LCMS m/z=435.3 [M+H]⁺; ¹H NMR (400 MHz, DMSO-d₆) δ ppm 1.26-1.54 (m, 8H), 1.65-1.81 (m, 1H), 2.03-2.19 (m, 1H), 3.40 (d, J=6.82 Hz, 2H), 3.75 (s, 3H), 3.99 (s, 2H), 4.07 (d, J=7.58 Hz, 2H), 6.85-6.92 (m, 2H), 7.11-7.18 (m, 2H), 7.23-7.34 (m, 3H), 7.37-7.43 (m, 2H), 7.84 (s, 1H).

Example 1.132: Preparation of 2-(((1s,4s)-4-((4-(2-Methoxyphenyl)-3-phenyl-1H-pyrazol-1-yl)methyl)cyclohexyl)methoxy)acetic Acid (Compound 59)

From tert-butyl 2-(((1s,4s)-4-((4-bromo-3-phenyl-1H-pyrazol-1-yl)methyl)cyclohexyl)methoxy)acetate and tert-butyl 2-(((1s,4s)-4-((4-bromo-5-phenyl-1H-pyrazol-1-yl)methyl)cyclohexyl)methoxy)acetate as a mixture of regioisomers and 2-methoxyphenylboronic acid, the title compound (one of the two regioisomers separated) was obtained using a similar method to the one described in Example 1.122. LCMS m/z=435.3 [M+H]⁺; ¹H NMR (400 MHz, DMSO-d₆) δ ppm 1.29-1.52 (m, 8H), 1.69-1.80 (m, 1H), 2.13 (dd, J=6.57, 3.79 Hz, 1H), 3.40 (d, J=6.82 Hz, 2H), 3.52 (s, 3H), 3.99 (s, 2H), 4.09 (d, J=7.58 Hz, 2H), 6.85-6.93 (m, 2H), 7.08-7.13 (m, 2H), 7.18-7.31 (m, 3H), 7.32-7.38 (m, 2H), 7.77 (s, 1H).

Example 1.133: Preparation of 2-(((1s,4s)-4-((3-Phenyl-4-m-tolyl-1H-pyrazol-1-yl)methyl)cyclohexyl)methoxy)acetic Acid (Compound 60)

From tert-butyl 2-(((1s,4s)-4-((4-bromo-3-phenyl-1H-pyrazol-1-yl)methyl)cyclohexyl)methoxy)acetate and tert-butyl 2-(((1s,4s)-4-((4-bromo-5-phenyl-1H-pyrazol-1-yl)methyl)cyclohexyl)methoxy)acetate as a mixture of regioisomers and m-tolylboronic acid, the title compound (one of the two regioisomers separated) was obtained using a similar method to the one described in Example 1.122. LCMS m/z=419.3 [M+H]⁺; ¹H NMR (400 MHz, DMSO-d₆) δ ppm 1.29-1.53 (m, 8H), 1.70-1.81 (m, 1H), 2.07-2.18 (m, 1H), 2.25 (s, 3H), 3.40 (d, J=7.07 Hz, 2H), 3.99 (s, 2H), 4.09 (d, J=7.58 Hz, 2H), 6.96-7.08 (m, 2H), 7.09-7.21 (m, 2H), 7.25-7.35 (m, 3H), 7.38-7.44 (m, 2H), 7.90 (s, 1H).

Example 1.134: Preparation of 2-(((1s,4s)-4-((3-Phenyl-4-p-tolyl-1H-pyrazol-1-yl)methyl)cyclohexyl)methoxy)acetic Acid (Compound 61)

From tert-butyl 2-(((1s,4s)-4-((4-bromo-3-phenyl-1H-pyrazol-1-yl)methyl)cyclohexyl)methoxy)acetate and tert-butyl 2-(((1s,4s)-4-((4-bromo-5-phenyl-1H-pyrazol-1-yl)methyl)cyclohexyl)methoxy)acetate as a mixture of regioisomers and p-tolylboronic acid, the title compound (one of the two regioisomers separated) was obtained using a similar method to the one described in Example 1.122. LCMS m/z=419.3 [M+H]⁺; ¹H NMR (400 MHz, DMSO-d₆) δ ppm 1.28-1.51 (m, 8H), 1.70-1.80 (m, 1H), 2.08-2.18 (m, 1H), 2.29 (s, 3H), 3.40 (d, J=7.07 Hz, 2H), 3.99 (s, 2H), 4.08 (d, J=7.58 Hz, 2H), 7.10-7.16 (m, 3H), 7.26-7.36 (m, 3H), 7.37-7.44 (m, 3H), 7.88 (s, 1H).

Example 1.135: Preparation of 2-(((1s,4s)-4-((4-(3-Chlorophenyl)-3-phenyl-1H-pyrazol-1-yl)methyl)cyclohexyl)methoxy)acetic Acid (Compound 62)

From tert-butyl 2-(((1s,4s)-4-((4-bromo-3-phenyl-1H-pyrazol-1-yl)methyl)cyclohexyl)methoxy)acetate and tert-butyl 2-(((1s,4s)-4-((4-bromo-5-phenyl-1H-pyrazol-1-yl)methyl)cyclohexyl)methoxy)acetate as a mixture of regioisomers and 3-chlorophenylboronic acid, the title compound (one of the two regioisomers separated) was obtained using a similar method to the one described in Example 1.122. LCMS m/z=439.2 [M+H]⁺; ¹H NMR (400 MHz, DMSO-d₆) δ ppm 1.29-1.53 (m, 8H), 1.70-1.79 (m, 1H), 2.08-2.19 (m, 1H), 3.40 (d, J=7.07 Hz, 2H), 4.00 (s, 2H), 4.10 (d, J=7.58 Hz, 2H), 7.15-7.19 (m, 1H), 7.25-7.42 (m, 8H), 8.05 (s, 1H).

Example 1.136: Preparation of 2-(((1s,4s)-4-((4-(2-Fluorophenyl)-3-phenyl-1H-pyrazol-1-yl)methyl)cyclohexyl)methoxy)acetic Acid (Compound 63)

From tert-butyl 2-(((1s,4s)-4-((4-bromo-3-phenyl-1H-pyrazol-1-yl)methyl)cyclohexyl)methoxy)acetate and tert-butyl 2-(((1s,4s)-4-((4-bromo-5-phenyl-1H-pyrazol-1-yl)methyl)cyclohexyl)methoxy)acetate as a mixture of regioisomers and 2-fluorophenylboronic acid, the title compound (one of the two regioisomers separated) was obtained using a similar method to the one described in Example 1.122. LCMS m/z=423.2 [M+H]⁺; ¹H NMR (400 MHz, DMSO-d₆) δ ppm 1.29-1.53 (m, 8H), 1.71-1.81 (m, 1H), 2.09-2.20 (m, 1H), 3.41 (d, J=7.07 Hz, 2H), 4.00 (s, 2H), 4.12 (d, J=7.83 Hz, 2H), 7.13-7.40 (m, 9H), 7.92 (s, 1H).

Example 1.137: Preparation of 2-(((1s,4s)-4-((3-Methyl-4-phenyl-5-m-tolyl-1H-pyrazol-1-yl)methyl)cyclohexyl)methoxy)acetic Acid (Compound 64)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and m-tolylboronic acid, the title compound (one of the two regioisomers separated) was obtained using a similar method to the one described in Example 1.107. LCMS m/z=433.2 [M+H]⁺; ¹H NMR (400 MHz, CDCl₃) δ ppm 1.29-1.44 (m, 4H), 1.48 (s, 9H), 1.49-1.60 (m, 4H), 1.81-1.91 (m, 1H), 2.04 (s, 3H), 2.12-2.20 (m, 1H), 3.25 (d, J=6.95 Hz, 2H), 3.87 (s, 2H), 4.02 (d, J=7.58 Hz, 2H), 7.30-7.37 (m, 1H), 7.37-7.49 (m, 3H), 7.84-7.89 (m, 1H).

Example 1.138: Preparation of 2-(((1s,4s)-4-((5-Methyl-4-phenyl-3-m-tolyl-1H-pyrazol-1-yl)methyl)cyclohexyl)methoxy)acetic Acid (Compound 65)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and m-tolylboronic acid, the title compound was obtained using a similar method to the one described in Example 1.107. LCMS m/z=433.3 [M+H]⁺; ¹H NMR (400 MHz, DMSO-d₆) δ ppm 1.26-1.50 (m, 8H), 1.43 (s, 9H), 1.66-1.78 (m, 1H), 1.97-2.09 (m, 1H), 2.30 (s, 3H), 3.39 (d, J=6.82 Hz, 2H), 3.94 (s, 2H), 4.06 (d, J=7.58 Hz, 2H), 7.30-7.50 (m, 3H), 7.74-7.85 (m, 2H).

Example 1.139: Preparation of 2-(((1s,4s)-4-((3-(3-Chlorophenyl)-5-methyl-4-phenyl-1H-pyrazol-1-yl)methyl)cyclohexyl)methoxy)acetic Acid (Compound 66)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 3-chlorophenylboronic acid, the title compound (one of the two regioisomers separated) was obtained using a similar method to the one described in Example 1.107. LCMS m/z=453.3 [M+H]⁺; ¹H NMR (400 MHz, DMSO-d₆) δ ppm 1.33-1.54 (m, 8H), 1.73-1.81 (m, 1H), 2.06-2.15 (m, 1H), 2.20 (s, 3H), 3.43 (d, J=6.82 Hz, 2H), 4.00 (s, 2H), 4.06 (d, J=7.58 Hz, 2H), 7.16-7.29 (m, 5H), 7.31-7.43 (m, 4H).

Example 1.140: Preparation of 2-(((1s,4s)-4-((5-(3-Fluorophenyl)-3-methyl-4-phenyl-1H-pyrazol-1-yl)methyl)cyclohexyl)methoxy)acetic Acid (Compound 67)

From tert-butyl 2-(((1s,4s)-4-((5-bromo-3-methy-4-phenyl-1H-pyrazol-1-yl)methyl)cyclohexyl)methoxy)acetate and tert-butyl 2-(((1s,4s)-4-((3-bromo-5-methy-4-phenyl-1H-pyrazol-1-yl)methyl)cyclohexyl)methoxy)acetate as a mixture of regioisomers and 3-fluorophenylboronic acid, the title compound (one of the two regioisomers separated) was obtained using a similar method to the one described in Example 1.107. LCMS m/z=437.2 [M+H]⁺; ¹H NMR (400 MHz, DMSO-d₆) δ ppm 1.04-1.20 (m, 4H), 1.22-1.37 (m, 4H), 1.56-1.64 (m, 1H), 1.86-1.96 (m, 1H), 2.21 (s, 3H), 3.22 (d, J=6.82 Hz, 2H), 3.91 (d, J=7.53 Hz, 2H), 3.91 (s, 2H), 7.04-7.29 (m, 7H), 7.41-7.50 (m, 2H).

Example 1.141: Preparation of 2-(((1s,4s)-4-((3-(3-Fluorophenyl)-5-methy-4-phenyl-1H-pyrazol-1-yl)methyl)cyclohexyl)methoxy)acetic Acid (Compound 68)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 3-fluorophenylboronic acid, the title compound (one of the two regioisomers separated) was obtained using a similar method to the one described in Example 1.107. LCMS m/z=437.2 [M+H]⁺; ¹H NMR (400 MHz, DMSO-d₆) δ ppm 1.33-1.54 (m, 8H), 1.71-1.81 (m, 1H), 2.05-2.15 (m, 1H), 2.19 (s, 3H), 3.42 (d, J=7.07 Hz, 2H), 4.00 (s, 2H), 4.06 (d, J=7.58 Hz, 2H), 6.99-7.08 (m, 2H), 7.12-7.21 (m, 3H), 7.23-7.44 (m, 4H).

Example 1.142: Preparation of 2-(((1s,4s)-4-((5-(3-Chloro-2-fluorophenyl)-3-methyl-4-phenyl-1H-pyrazol-1-yl)methyl)cyclohexyl)methoxy)acetic Acid (Compound 69)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 3-chloro-2-fluorophenylboronic acid, the title compound (one of the two regioisomers separated) was obtained using a similar method to the one described in Example 1.107. LCMS m/z=470.1 [M+H]$^+$; $^1$H NMR (400 MHz, DMSO-d$_6$) δ ppm 1.00-1.21 (m, 4H), 1.22-1.37 (m, 4H), 1.55-1.72 (m, 1H), 1.89-2.00 (m, 1H), 2.24 (s, 3H), 3.21 (d, J=6.82 Hz, 2H), 3.67 (d, J=7.58 Hz, 2H), 3.91 (s, 2H), 7.03-7.11 (m, 2H), 7.14-7.39 (m, 6H).

Example 1.143: Preparation of 2-(((1s,4s)-4-((3-(3-Chloro-2-fluorophenyl)-5-methyl-4-phenyl-1H-pyrazol-1-yl)methyl)cyclohexyl)methoxy)acetic Acid (Compound 70)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 3-chloro-2-fluorophenylboronic acid, the title compound (one of the two regioisomers separated) was obtained using a similar method to the one described in Example 1.107. LCMS m/z=470.1 [M+H]$^+$; $^1$H NMR (400 MHz, DMSO-d$_6$) δ ppm 1.32-1.54 (m, 8H), 1.70-1.81 (m, 1H), 2.04-2.14 (m, 1H), 2.30 (s, 3H), 3.42 (d, J=6.82 Hz, 2H), 3.99 (s, 2H), 4.08 (d, J=7.58 Hz, 2H), 7.05-7.11 (m, 2H), 7.16-7.34 (m, 4H), 7.48-7.56 (m, 2H).

Example 1.144: Preparation of 2-(((1s,4s)-4-((5-(2-Fluorophenyl)-3-methyl-4-phenyl-1H-pyrazol-1-yl)methyl)cyclohexyl)methoxy)acetic Acid (Compound 71)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 2-fluorophenylboronic acid, the title compound (one of the two regioisomers separated) was obtained using a similar method to the one described in Example 1.107. LCMS m/z=437.3 [M+H]$^+$; $^1$H NMR (400 MHz, DMSO-d$_6$) δ ppm 1.02-1.19 (m, 4H), 1.22-1.35 (m, 4H), 1.88-1.98 (m, 1H), 2.05-2.14 (m, 1H), 2.24 (s, 3H), 3.42 (d, J=7.07 Hz, 2H), 3.99 (s, 2H), 4.07 (d, J=7.58 Hz, 2H), 7.03-7.10 (m, 2H), 7.12-7.39 (m, 6H), 7.43-7.54 (m, 1H).

Example 1.145: Preparation of 2-(((1s,4s)-4-((3-(2-Fluorophenyl)-5-methyl-4-phenyl-1H-pyrazol-1-yl)methyl)cyclohexyl)methoxy)acetic Acid (Compound 72)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 2-fluorophenylboronic acid, the title compound (one of the two regioisomers separated) was obtained using a similar method to the one described in Example 1.107. LCMS m/z=437.3 [M+H]$^+$; $^1$H NMR (400 MHz, DMSO-d$_6$) δ ppm 1.35-1.53 (m, 8H), 1.72-1.80 (m, 1H), 2.04-2.14 (m, 1H), 2.30 (s, 3H), 3.41 (d, J=7.07 Hz, 2H), 3.99 (s, 2H), 4.07 (d, J=7.58 Hz, 2H), 7.03-7.10 (m, 3H), 7.12-7.38 (m, 6H).

Example 1.146: Preparation of 2-(((1s,4s)-4-((5-(2,3-Difluorophenyl)-3-methyl-4-phenyl-1H-pyrazol-1-yl)methyl)cyclohexyl)methoxy)acetic Acid (Compound 73)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 2,3-difluorophenylboronic acid, the title compound (one of the two regioisomers separated) was obtained using a similar method to the one described in Example 1.107. LCMS m/z=455.2 [M+H]$^+$; $^1$H NMR (400 MHz, DMSO-d$_6$) δ ppm 1.04-1.22 (m, 4H), 1.24-1.38 (m, 4H), 1.58-1.70 (m, 1H), 1.88-1.98 (m, 1H), 2.24 (s, 3H), 3.23 (d, J=6.82 Hz, 2H), 3.92 (s, 2H), 3.98 (d, J=7.58 Hz, 2H), 7.05-7.39 (m, 8H).

Example 1.147: Preparation of 2-(((1s,4s)-4-((3-(2,3-Difluorophenyl)-5-methyl-4-phenyl-1H-pyrazol-1-yl)methyl)cyclohexyl)methoxy)acetic Acid (Compound 74)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 2,3-difluorophenylboronic acid, the title compound (one of the two regioisomers separated) was obtained using a similar method to the one described in Example 1.107. LCMS m/z=455.2 [M+H]$^+$; $^1$H NMR (400 MHz, DMSO-d$_6$) δ ppm 1.33-1.53 (m, 8H), 1.72-1.81 (m, 1H), 2.04-2.14 (m, 1H), 2.29 (s, 3H), 3.42 (d, J=6.82 Hz, 2H), 3.99 (s, 2H), 4.08 (d, J=7.58 Hz, 2H), 7.01-7.35 (m, 8H).

Example 1.148: Preparation of 2-(((1s,4s)-4-((5-Ethoxy-3,4-diphenyl-1H-pyrazol-1-yl)methyl)cyclohexyl)methoxy)acetic Acid (Compound 81)

To a solution of tert-butyl 2-(((1s,4s)-4-((5-ethoxy-3,4-diphenyl-1H-pyrazol-1-yl)methyl)cyclohexyl)methoxy)acetate (100 mg, 0.20 mmol) in dioxane (4 mL) were added phenylboronic acid (24.0 mg, 0.20 mmol), tetrakis(triphenylphosphine)palladium (22.8 mg, 0.20 mmol), and K$_2$CO$_3$ (2 M aq., 0.2 mL). The reaction mixture was heated to 150° C. under microwave for 4 h. The reaction mixture was filtered and concentrated. The residue was treated with HCl (4 M in dioxane, 5 mL) at room temperature for 16 h. The mixture was concentrated and purified by HPLC to give the title compound (one of the two regioisomers separated) as a white solid. LCMS m/z=449.3 [M+H]$^+$; $^1$H NMR (400 MHz, DMSO-d$_6$) δ ppm 1.15-1.42 (m, 8H), 1.35 (t, J=7.35 Hz, 3H), 1.66-1.75 (m, 1H), 1.87-1.95 (m, 1H), 3.02 (q, J=7.35 Hz, 2H), 3.35 (d, J=6.82 Hz, 2H), 3.99 (s, 2H), 4.08 (d, J=7.58 Hz, 2H), 7.08-7.32 (m, 8H), 7.40-7.48 (m, 2H).

Example 1.149: Preparation of 2-(((1s,4s)-4-((5-(Ethylthio)-3,4-diphenyl-1H-pyrazol-1-yl)methyl)cyclohexyl)methoxy)acetic Acid (Compound 88)

To a solution of tert-butyl 2-(((1s,4s)-4-((5-(ethylthio)-4-iodo-3-phenyl-1H-pyrazol-1-yl)methyl)cyclohexyl)methoxy)acetate and tert-butyl 2-(((1s,4s)-4-((3-(ethylthio)-4-iodo-5-phenyl-1H-pyrazol-1-yl)methyl)cyclohexyl)methoxy)acetate as a mixture of regioisomers (100 mg, 0.18 mmol) in dioxane (4 mL) were added phenylboronic acid (21.9 mg, 0.18 mmol), tetrakis(triphenylphosphine)palladium (22.8 mg, 0.20 mmol), and K$_2$CO$_3$ (2 M aq., 0.2 mL). The reaction mixture was heated to 150° C. under microwave for 4 h. The reaction mixture was filtered and concentrated. The residue was treated with HCl (4 M in dioxane, 5 mL) at room temperature for 16 h. The mixture was concentrated and purified by HPLC to give the title compound (one of the two regioisomers separated) as white solid. LCMS m/z=465.2 [M+H]$^+$; $^1$H NMR (400 MHz, DMSO-d$_6$) δ ppm 1.05-1.36 (m, 8H), 1.24 (t, J=7.33 Hz, 3H), 1.56-1.65 (m, 1H), 1.87-1.99 (m, 1H), 2.92 (q, J=7.33 Hz, 2H), 3.20 (d, J=6.82 Hz, 2H), 3.91 (s, 2H), 3.94 (d, J=7.58 Hz, 2H), 7.07-7.31 (m, 8H), 7.38-7.45 (m, 2H).

Example 1.150: Preparation of 2-(((1s,4s)-4-((5-(Ethylthio)-4-(3-methoxyphenyl)-3-phenyl-1H-pyrazol-1-yl)methyl)cyclohexyl)methoxy)acetic Acid (Compound 89)

From tert-butyl 2-(((1s,4s)-4-((5-(ethylthio)-4-iodo-3-phenyl-1H-pyrazol-1-yl)methyl)cyclohexyl)methoxy)acetate and tert-butyl 2-(((1s,4s)-4-((3-(ethylthio)-4-iodo-5-phenyl-1H-pyrazol-1-yl)methyl)cyclohexyl)methoxy) acetate as a mixture of regioisomers and 3-methoxyphenylboronic acid, the title compound (one of the two regioisomers separated) was obtained using a similar method to the one described in Example 1.149. LCMS m/z=495.3 [M+H]$^+$; $^1$H NMR (400 MHz, DMSO-d$_6$) δ ppm 0.96 (t, J=7.33 Hz, 3H), 1.32-1.55 (m, 8H), 1.70-1.81 (m, 1H), 2.15-2.25 (m, 1H), 2.53 (q, J=7.58 Hz, 2H), 3.42 (d, J=7.07 Hz, 2H), 3.70 (s, 3H), 4.00 (s, 2H), 4.28 (d, J=7.58 Hz, 2H), 6.79-6.95 (m, 4H), 7.21-7.32 (m, 3H), 7.33-7.40 (m, 2H).

Example 1.151: Preparation of 2-(((1s,4s)-4-((4-(3-Fluoro-5-methoxyphenyl)-5-(methylthio)-3-phenyl-1H-pyrazol-1-yl)methyl)cyclohexyl)methoxy)acetic Acid (Compound 93)

To a solution of tert-butyl 2-(((1s,4s)-4-((4-iodo-5-(methylthio)-3-phenyl-1H-pyrazol-1-yl)methyl)cyclohexyl) methoxy)acetate and tert-butyl 2-(((1s,4s)-4-((4-iodo-3-(methylthio)-5-phenyl-1H-pyrazol-1-yl)methyl)cyclohexyl) methoxy)acetate as a mixture of regioisomers (100 mg, 0.18 mmol) in dioxane (3 mL) were added 3-fluoro-5-methoxyphenylboronic acid (30.6 mg, 0.18 mmol), tetrakis(triphenylphosphine)palladium (20.8 mg, 0.20 mmol), and K$_2$CO$_3$ (2 M aq., 0.2 mL). The reaction mixture was heated to 150° C. under microwave for 4 h. The reaction mixture was filtered and concentrated. The residue was treated with HCl (4 M in dioxane, 5 mL) at room temperature for 16 h. The mixture was concentrated and purified by HPLC to give the title compound (one of the two regioisomers separated) as a white solid. LCMS m/z=499.2 [M+H]$^+$; $^1$H NMR (400 MHz, DMSO-d$_6$) δ ppm 1.31-1.56 (m, 8H), 1.62-1.82 (m, 1H), 2.12-2.24 (m, 1H), 2.17 (s, 3H), 3.35 (d, J=6.95 Hz, 2H), 3.54 (s, 2H), 3.72 (s, 3H), 4.27 (d, J=7.58 Hz, 2H), 6.60-6.70 (m, 2H), 6.75-6.87 (m, 2H), 7.19-7.41 (m, 4H).

Example 1.152: Preparation of 2-(((1s,4s)-4-((3-Ethyl-4-(3-methoxyphenyl)-5-phenyl-1H-pyrazol-1-yl)methyl)cyclohexyl)methoxy)acetic Acid (Compound 98)

Step A: Preparation of 5-Ethyl-3-phenyl-1H-pyrazole

To a solution of acetophenone (10 g, 83 mmol) in anhydrous toluene (10 mL) was added LiHMDS (85.0 mL, 1.0 M in THF, 85.0 mmol) via syringe at 0° C. under argon. After 5 min, propionyl chloride (7.70 g, 83 mmol) was added in one portion via syringe. The ice bath was removed after 10 min and AcOH (2 mL), EtOH (50 mL), and hydrazine hydrate (8.35 g, 116 mmol) was added. The mixture was refluxed for 2 h. The resulting solution was added to 1.0 M NaOH solution, extracted with EtOAc, washed with brine, dried over MgSO$_4$, and concentrated. The residue was purified by silica gel column chromatography to give the title compound as a clear yellowish liquid (12.05 g). LCMS m/z=173.3 [M+H]$^+$; $^1$H NMR (400 MHz, DMSO-d$_6$) δ ppm 1.23 (t, J=7.58 Hz, 3H), 2.64 (q, J=7.07 Hz, 2H), 6.46 (s, 1H), 7.20-7.52 (m, 3H), 7.77 (d, J=6.32 Hz, 2H), 12.55 (s, 1H).

Step B: Preparation of 4-Bromo-5-ethyl-3-phenyl-1H-pyrazole

To a solution of 5-ethyl-3-phenyl-1H-pyrazole (10.0 g, 58.1 mmol) in DCM (150 mL) was added dropwise bromine (9.28 g, 58.1 mmol) at 0° C. The reaction was stirred at that temperature for 30 min and continued for 2 h at room temperature before quenched with aqueous Na$_2$SO$_3$ solution (10% wt, 10 mL). DCM was removed and the residue was extracted with EtOAc, washed with brine, dried over MgSO$_4$, and concentrated. The residue was purified by silica gel column chromatography to give the title compound as a yellow liquid (9.5 g). LCMS m/z=250.9 [M+H]$^+$; $^1$H NMR (400 MHz, DMSO-d$_6$) δ ppm 1.22 (t, J=7.58 Hz, 3H), 2.66 (q, J=7.58 Hz, 2H), 7.40-7.56 (m, 3H), 7.82 (d, J=7.58 Hz, 2H), 13.15 (s, 1H).

Step C: Preparation of tert-Butyl 2-(((1s,4s)-4-((4-Bromo-3-ethyl-5-phenyl-1H-pyrazol-1-yl)methyl) cyclohexyl)methoxy)acetate and tert-Butyl 2-(((1s, 4s)-4-((4-Bromo-5-ethyl-3-phenyl-1H-pyrazol-1-yl) methyl)cyclohexyl)methoxy)acetate as a Mixture of Regioisomers To a solution of 4-bromo-5-ethyl-3-phenyl-1H-pyrazole (3.0 g, 11.95 mmol) in DMF (5 mL) was added sodium hydride (0.287 g, 11.95 mmol) followed by tert-butyl 2-(((1s,4s)-4-(tosyloxymethyl)cyclohexyl)methoxy)acetate (4.93 g, 11.95 mmol). The reaction was heated at 45° C. overnight. After quenched with water (2 mL), the mixture was extracted with EtOAc, washed with brine, dried over MgSO$_4$, and concentrated. The residue was purified by silica gel column chromatography to give the title compound (a mixture of regioisomers) as a clear liquid (4.5 g). LCMS m/z=491.2 [M+H]$^+$; $^1$H NMR (400 MHz, CDCl$_3$) δ ppm 1.25 (t, J=7.20 Hz, 3H), 1.31-1.43 (m, 4H), 1.49 (s, 9H), 1.51-1.60 (m, 4H), 1.76-1.90 (m, 1H), 2.12-2.24 (m, 1H), 2.72 (q, J=7.75 Hz, 2H), 3.46 (d, J=6.82 Hz, 2H), 3.92 (s, 2H), 4.01 (d, J=7.58 Hz, 2H), 7.31-7.43 (m, 3H), 7.86 (d, J=7.33 Hz, 2H).

Step D: Preparation of 2-(((1s,4s)-4-((3-Ethyl-4-(3-methoxyphenyl)-5-phenyl-1H-pyrazol-1-yl)methyl) cyclohexyl)methoxy)acetic Acid To a solution of tert-butyl 2-(((1s,4s)-4-((4-bromo-3-ethyl-5-phenyl-1H-pyrazol-1-yl)methyl)cyclohexyl) methoxy)acetate and tert-butyl 2-(((1s,4s)-4-((4-bromo-5-ethyl-3-phenyl-1H-pyrazol-1-yl)methyl)cyclohexyl) methoxy)acetate as a mixture of regioisomers (100 mg, 0.20 mmol) were added 3-methoxyphenylboronic acid (30.2 mg, 0.20 mmol), tetrakis(triphenylphosphine)palladium (23.1 mg, 0.20 mmol), K₂CO₃ (2 M aq., 0.5 mL) and dioxane (3 mL) was heated to 150° C. under microwave for 4 h. The reaction mixture was filtered and concentrated. The residue was treated with HCl (4 M in dioxane, 5 mL) at room temperature for 10 h. The mixture was concentrated and purified by HPLC to give the title compound (one of the two regioisomers separated) as a white solid (13.5 mg). LCMS m/z=463.3 [M+H]⁺; ¹H NMR (400 MHz, DMSO-d₆) δ ppm 1.01-1.18 (m, 4H), 1.12 (t, J=7.58 Hz, 3H), 1.22-1.35 (m, 4H), 1.54-1.68 (m, 1H), 1.87-1.98 (m, 1H), 2.63 (q, J=7.58 Hz, 2H), 3.20 (d, J=6.82 Hz, 2H), 3.58 (s, 3H), 3.90 (d, J=7.32 Hz, 2H), 3.91 (s, 2H), 6.55-6.74 (m, 3H), 7.10-7.17 (m, 2H), 7.22-7.28 (m, 2H), 7.36-7.44 (m, 2H).

Example 1.153: Preparation of 2-(((1s,4s)-4-((3-Ethyl-4,5-diphenyl-1H-pyrazol-1-yl)methyl)cyclohexyl)methoxy)acetic Acid (Compound 100)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and phenylboronic acid, the title compound (one of the two regioisomers separated) was obtained using a similar method to the one described in Example 1.152. LCMS m/z=433.3 [M+H]⁺; ¹H NMR (400 MHz, DMSO-d₆) δ ppm 1.01-1.16 (m, 4H), 1.11 (t, J=7.58 Hz, 3H), 1.22-1.34 (m, 4H), 1.55-1.66 (m, 1H), 1.83-1.96 (m, 1H), 2.60 (q, J=7.83 Hz, 2H), 3.20 (d, J=6.82 Hz, 2H), 3.90 (s, 2H), 3.94 (d, J=7.33 Hz, 2H), 7.04-7.26 (m, 5H), 7.35-7.57 (m, 5H).

Example 1.154: Preparation of 2-(((1s,4s)-4-((5-Ethyl-3,4-diphenyl-1H-pyrazol-1-yl)methyl)cyclohexyl)methoxy)acetic Acid (Compound 101)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and phenylboronic acid, the title compound was obtained using a similar method to the one described in Example 1.152. LCMS m/z=433.3 [M+H]⁺; ¹H NMR (400 MHz, DMSO-d₆) δ ppm 1.02 (t, J=7.58 Hz, 3H), 1.30-1.57 (m, 8H), 1.72-1.83 (m, 1H), 2.08-2.18 (m, 1H), 2.59 (q, J=7.49 Hz, 2H), 3.44 (d, J=7.07 Hz, 2H), 4.00 (s, 2H), 4.03 (d, J=7.33 Hz, 2H), 7.15-7.25 (m, 4H), 7.28-7.47 (m, 6H).

Example 1.155: Preparation of 2-(((1s,4s)-4-((3-Ethyl-4-(3-fluorophenyl)-5-phenyl-1H-pyrazol-1-yl)methyl)cyclohexyl)methoxy)acetic Acid (Compound 102)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and 3-fluorophenylboronic acid, the title compound (one of the two regioisomers separated) was obtained using a similar method to the one described in Example 1.152. LCMS m/z=4513 [M+H]⁺; ¹H NMR (400 MHz, DMSO-d₆) δ ppm 1.00-1.19 (m, 4H), 1.12 (t, J=7.45 Hz, 3H), 1.21-1.35 (m, 4H), 1.53-1.64 (m, 1H), 1.88-1.98 (m, 1H), 2.64 (q, J=7.58 Hz, 2H), 3.20 (d, J=7.07 Hz, 2H), 3.91 (d, J=7.33 Hz, 2H), 3.91 (s, 2H), 6.80-7.02 (m, 3H), 7.22-7.46 (m, 6H).

Example 1.156: Preparation of 2-(((1s,4s)-4-((5-Ethyl-4-(3-fluorophenyl)-3-phenyl-1H-pyrazol-1-yl)methyl)cyclohexyl)methoxy)acetic Acid (Compound 103)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and 3-fluorophenylboronic acid, the title compound (one of the two regioisomers separated) was obtained using a similar method to the one described in Example 1.152. LCMS m/z=451.3 [M+H]⁺; ¹H NMR (400 MHz, DMSO-d₆) δ ppm 1.03 (t, J=7.58 Hz, 3H), 1.34-1.56 (m, 8H), 1.74-1.82 (m, 1H), 2.09-2.18 (m, 1H), 2.63 (q, J=7.58 Hz, 2H), 3.44 (d, J=7.07 Hz, 2H), 4.00 (s, 2H), 4.04 (d, J=7.33 Hz, 2H), 6.95-7.04 (m, 2H), 7.10-7.18 (m, 1H), 7.18-7.33 (m, 5H), 7.37-7.45 (m, 1H).

Example 1.157: Preparation of 2-(((1s,4s)-4-((3-Ethyl-4-(2-fluoro-3-methoxyphenyl)-5-phenyl-1H-pyrazol-1-yl)methyl)cyclohexyl)methoxy)acetic Acid (Compound 104)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and 2-fluoro-3-methoxyphenylboronic acid, the title compound (one of the two regioisomers separated) was obtained using a similar method to the one described in Example 1.152. LCMS m/z=481.3 [M+H]⁺; ¹H NMR (400 MHz, DMSO-d₆) δ ppm 1.06 (t, J=7.58 Hz, 3H), 1.06-1.19 (m, 4H), 1.26-1.39 (m, 4H), 1.54-1.63 (m, 1H), 1.88-1.98 (m, 1H), 2.64 (q, J=7.41 Hz, 2H), 3.19 (d, J=6.82 Hz, 2H), 3.77 (s, 3H), 3.96 (d, J=7.58 Hz, 2H), 3.99 (s, 2H), 6.95-7.04 (m, 2H), 7.18-7.29 (m, 3H), 7.32-7.42 (m, 3H).

Example 1.158: Preparation of 2-(((1s,4s)-4-((5-Ethyl-4-(2-fluoro-3-methoxyphenyl)-3-phenyl-1H-pyrazol-1-yl)methyl)cyclohexyl)methoxy)acetic Acid (Compound 105)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and 2-fluoro-3-methoxyphenylboronic acid, the title compound (one of the two regioisomers separated) was obtained using a similar method to the one described in Example 1.152. LCMS m/z=481.3 [M+H]⁺; ¹H NMR (400 MHz, CD₃OD) δ ppm 1.24 (t, J=7.58 Hz, 3H), 1.32-1.70 (m, 8H), 1.85-1.99 (m, 1H), 2.15-2.27 (m, 1H), 2.65 (q, J=7.45 Hz, 2H), 3.53 (d, J=7.07 Hz, 2H), 3.87 (s, 3H), 4.07 (s, 2H), 4.10 (d, J=7.71 Hz, 2H), 6.68-6.74 (m, 1H), 7.04-7.10 (m, 1H), 7.18-7.24 (m, 2H), 7.29-7.38 (m, 2H), 7.45-7.55 (m, 2H).

Example 1.159: Preparation of 2-(((1s,4s)-4-(4-(2,3-Difluorophenyl)-3-ethyl-5-phenyl-1H-pyrazol-1-yl)methyl)cyclohexyl)methoxy)acetic Acid (Compound 106)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and 2,3-difluorophenylboronic acid, the title compound (one of the two regioisomers separated) was obtained using a similar method to the one described in Example 1.152. LCMS m/z=469.3 [M+H]$^+$; $^1$H NMR (400 MHz, DMSO-d$_6$) δ ppm 1.00 (t, J=7.45 Hz, 3H), 1.03-1.13 (m, 4H), 1.22-1.32 (m, 4H), 1.54-1.65 (m, 1H), 1.81-1.90 (m, 1H), 2.58 (q, J=7.58 Hz, 2H), 3.18 (d, J=6.82 Hz, 2H), 3.90 (s, 2H), 3.95 (d, J=7.83 Hz, 2H), 7.07-7.14 (m, 1H), 7.19-7.32 (m, 3H), 7.36-7.58 (m, 4H).

Example 1.160: Preparation of 2-(((1s,4s)-4-((4-(2,3-Difluorophenyl)-5-ethyl-3-phenyl-1H-pyrazol-1-yl)methyl)cyclohexyl)methoxy)acetic Acid (Compound 107)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and 2,3-difluorophenylboronic acid, the title compound (one of the two regioisomers separated) was obtained using a similar method to the one described in Example 1.152. LCMS m/z=469.3 [M+H]$^+$; $^1$H NMR (400 MHz, CD$_3$OD) δ ppm 1.08 (t, J=7.58 Hz, 3H), 1.38-1.68 (m, 8H), 1.85-1.95 (m, 1H), 2.17-2.27 (m, 1H), 2.66 (q, J=7.58 Hz, 2H), 3.53 (d, J=7.07 Hz, 2H), 4.08 (s, 2H), 4.12 (d, J=7.58 Hz, 2H), 6.96-7.02 (m, 1H), 7.11-7.18 (m, 1H), 7.20-7.26 (m, 3H), 7.28-7.33 (m, 3H).

Example 1.161: Preparation of 2-(((1s,4s)-4-((3-Isopropyl-4,5-diphenyl-1H-pyrazol-1-yl)methyl)cyclohexyl)methoxy)acetic Acid (Compound 112)

Step A: Preparation of 5-Isopropyl-3-phenyl-1H-pyrazole (15)

To a solution of acetophenone (1.21 g, 10.07 mmol) in dry toluene (5 mL) was added LiHMDS (11.0 mL, 1.0 M in THF, 11.0 mmol) via syringe at 0° C. under argon. After 5 min, isobutyryl chloride (1.073 g, 10.07 mmol) was added in one portion via syringe. The ice bath was removed and AcOH (2 mL), EtOH (50 mL) and THF (5 mL) were added to form a homogeneous mixture. Hydrazine hydrate (2 mL, 10.07 mmol) was added and the reaction was refluxed for 2 h. After cooled to room temperature, the reaction was concentrated and extracted with EtOAc, washed with brine, dried over MgSO$_4$, and concentrated. The residue was purified by silica gel column chromatography to give the title compound as colorless oil (0.70 g). LCMS m/z=187.3 [M+H]$^+$; $^1$H NMR (400 MHz, CDCl$_3$) δ ppm 1.33 (d, J=6.82 Hz, 6H), 2.94-3.13 (m, 1H), 6.38 (s, 1H), 7.17-7.45 (m, 5H), 10.14 (bs, 1H).

Step B: Preparation of 4-Iodo-5-isopropyl-3-phenyl-1H-pyrazole

To a solution of 5-isopropyl-3-phenyl-1H-pyrazole (0.64 g, 3.44 mmol) in THF (20 mL) and water (20.00 mL) were added sodium iodide (0.515 g, 3.44 mmol), iodine (1.308 g, 5.15 mmol), and potassium carbonate (0.712 g, 5.15 mmol) at room temperature. The reaction was refluxed for 2 h, cooled to room temperature and quenched with 10% aq. Na$_2$SO$_3$. The organic solvent was removed under reduced pressure and the aqueous residue was extracted with EtOAc. The organic extract was washed with NaHCO$_3$ solution, brine, dried over MgSO$_4$, and concentrated. The residue was purified by silica gel column chromatography to give the title compound as a clear liquid (0.42 g). LCMS m/z=313.2 [M+H]$^+$; $^1$H NMR (400 MHz, CDCl$_3$) δ ppm 1.17 (d, J=7.07 Hz, 6H), 3.02 (septet, J=7.07 Hz, 1H), 7.23-7.32 (m, 3H), 7.60-7.67 (m, 2H), 11.81 (bs, 1H).

Step C: Preparation of tert-Butyl 2-(((1s,4s)-4-((4-Iodo-5-isopropyl-3-phenyl-1H-pyrazol-1-yl)methyl)cyclohexyl)methoxy)acetate and tert-Butyl 2-(((1s,4s)-4-((4-Iodo-3-isopropyl-5-phenyl-1H-pyrazol-1-yl)methyl)cyclohexyl)methoxy)acetate as a Mixture of Regioisomers To a solution of 4-iodo-5-isopropyl-3-phenyl-1H-pyrazole (0.35 g, 1.121 mmol) in DMF (5 mL) was added sodium hydride (0.027 g, 1.121 mmol) at room temperature. The reaction was stirred at room temperature for 1 h and tert-butyl 2-(((1s,4s)-4-(tosyloxymethyl)cyclohexyl)methoxy)acetate (0.463 g, 1.121 mmol) was added. The reaction was heated at 50° C. for 16 h, cooled to room temperature, and quenched with water (2 mL). The mixture was extracted with EtOAc. The organic extract was dried over MgSO$_4$ and concentrated. The residue was purified by silica gel column chromatography to give the title compound (a mixture of two regioisomers) as a clear liquid (0.52 g). LCMS m/z=553.2 [M+H]$^+$; $^1$H NMR (400 MHz, CDCl$_3$) δ ppm 0.99-1.20 (m, 4H), 1.25-1.42 (m, 4H), 1.46 (d, J=7.20 Hz, 6H), 1.48 (s, 9H), 1.82-1.94 (m, 1H), 2.07-2.19 (m, 1H), 3.16-3.28 (m, 1H), 3.45 (d, J=7.07 Hz, 2H), 3.95 (s, 2H), 4.07 (d, J=7.71 Hz, 2H), 7.30-7.46 (m, 3H), 7.63-7.79 (m, 2H).

Step D: Preparation of 2-(((1s,4s)-4-((3-Isopropyl-4,5-diphenyl-1H-pyrazol-1-yl)methyl)cyclohexyl)methoxy)acetic Acid A mixture of phenylboronic acid (21.9 mg, 0.18 mmol), tert-butyl 2-(((1s,4s)-4-((4-iodo-5-isopropyl-3-phenyl-1H-pyrazol-1-yl)methyl)cyclohexyl)methoxy)acetate and tert-butyl 2-(((1s,4s)-4-((4-iodo-3-isopropyl-5-phenyl-1H-pyrazol-1-yl)methyl)cyclohexyl)methoxy)acetate as a mixture of regioisomers (100 mg, 0.18 mmol), tetrakis(triphenylphosphine)palladium (10.0 mg, 0.009 mmol), K$_2$CO$_3$ (2 M aq., 0.2 mL) and dioxane (4 mL) was heated to 150° C. under microwave irradiation for 4 h. The mixture was filtered and concentrated. The residue was treated with HCl (4 M in dioxane, 5 mL) at room temperature for 10 h. The mixture was concentrated and purified by HPLC to give the title compound (one of the two regioisomers separated) as a white solid (15.5 mg). LCMS m/z=447.3 [M+H]$^+$; $^1$H NMR (400 MHz, DMSO-d$_6$) δ ppm 1.05-1.15 (m, 4H), 1.17 (d, J=6.82 Hz, 6H), 1.21-1.35 (m, 4H), 1.55-1.63 (m, 1H), 1.84-1.95 (m, 1H), 2.96-3.04 (m, 1H), 3.20 (d, J=6.82 Hz, 2H), 3.91 (s, 2H), 3.93 (d, J=7.58 Hz, 2H), 7.05-7.10 (m, 2H), 7.12-7.19 (m, 2H), 7.19-7.27 (m, 3H), 7.32-7.40 (m, 3H).

Example 1.162: Preparation of 2-(((1s,4s)-4-((4-(3-Chlorophenyl)-3-ethyl-5-phenyl-1H-pyrazol-1-yl)methyl)cyclohexyl)methoxy)acetic Acid (Compound 115)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and 3-chlorophenylboronic acid, the title compound (one of the two regioisomers separated) was obtained using a similar method to the one described in Example 1.152. LCMS m/z=467.2 [M+H]$^+$; $^1$H NMR (400 MHz, CDCl$_3$) δ ppm 1.08-1.23 (m, 4H), 1.21 (t, J=7.58 Hz, 3H), 1.27-1.45 (m, 4H), 1.68-1.79 (m, 1H), 1.94-2.04 (m, 1H), 2.77 (q, J=7.54 Hz, 2H), 3.31 (d, J=6.57 Hz, 2H), 4.02 (s, 2H), 4.12 (d, J=7.58 Hz, 2H), 6.88-6.95 (m, 2H), 7.06-7.23 (m, 5H), 7.35-7.44 (m, 2H).

Example 1.163: Preparation of 2-(((1s,4s)-4-((4-(3-Chlorophenyl)-5-ethyl-3-phenyl-1H-pyrazol-1-yl)methyl)cyclohexyl)methoxy)acetic Acid (Compound 116)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and 3-chlorophenylboronic acid, the title compound (one of the two regioisomers separated) was obtained using a similar method to the one described in Example 1.152. LCMS m/z=467.2 [M+H]$^+$; $^1$H NMR (400 MHz, CDCl$_3$) δ ppm 1.13 (t, J=7.52 Hz, 3H), 1.32-1.46 (m, 4H), 1.48-1.66 (m, 4H), 1.87-1.99 (m, 1H), 2.13-2.26 (m, 1H), 2.66 (q, J=7.58 Hz, 2H), 3.52 (d, J=6.69 Hz, 2H), 4.10 (s, 2H), 4.17 (d, J=7.45 Hz, 2H), 7.02-7.08 (m, 2H), 7.18-7.38 (m, 7H).

Example 1.164: Preparation of 2-(((1s,4s)-4-((4-(2,3-Difluorophenyl)-5-isopropyl-3-phenyl-1H-pyrazol-1-yl)methyl)cyclohexyl)methoxy)acetic Acid (Compound 117)

From tert-butyl 2-(((1s,4s)-4-((4-iodo-5-isopropyl-3-phenyl-1H-pyrazol-1-yl)methyl)cyclohexyl)methoxy)acetate and tert-butyl 2-(((1s,4s)-4-((4-iodo-3-isopropyl-5-phenyl-1H-pyrazol-1-yl)methyl)cyclohexyl)methoxy)acetate as a mixture of regioisomers and 2,3-difluorophenylboronic acid, the title compound (one of the two regioisomers separated) was obtained using a similar method to the one described in Example 1.161. LCMS m/z=483.3 [M+H]$^+$; $^1$H NMR (400 MHz, DMSO-d$_6$) δ ppm 1.14 (d, J=7.07 Hz, 6H), 1.20-1.36 (m, 8H), 1.56-1.64 (m, 1H), 1.87-1.97 (m, 1H), 2.78-2.88 (m, 1H), 3.20 (d, J=7.07 Hz, 2H), 3.91 (s, 2H), 3.98 (d, J=7.58 Hz, 2H), 6.96-7.14 (m, 2H), 7.19-7.26 (m, 3H), 7.32-7.41 (m, 3H).

Example 1.165: Preparation of 2-(((1s,4s)-4-((5-(Ethylthio)-4-(2-fluorophenyl)-3-phenyl-1H-pyrazol-1-yl)methyl)cyclohexyl)methoxy)acetic Acid (Compound 118)

From tert-butyl 2-(((1s,4s)-4-((5-(ethylthio)-4-iodo-3-phenyl-1H-pyrazol-1-yl)methyl)cyclohexyl)methoxy)acetate and tert-butyl 2-(((1s,4s)-4-((3-(ethylthio)-4-iodo-5-phenyl-1H-pyrazol-1-yl)methyl)cyclohexyl)methoxy)acetate as a mixture of regioisomers and 3-fluorophenylboronic acid, the title compound (one of the two regioisomers separated) was obtained using a similar method to the one described in Example 1.149. LCMS m/z=483.2 [M+H]$^+$; $^1$H NMR (400 MHz, DMSO-d$_6$) δ ppm 0.95 (t, J=7.33 Hz, 3H), 1.32-1.56 (m, 8H), 1.72-1.82 (m, 1H), 2.17-2.28 (m, 1H), 2.53 (q, J=7.33 Hz, 2H), 3.42 (d, J=6.82 Hz, 2H), 4.01 (s, 2H), 4.30 (d, J=7.58 Hz, 2H), 7.20-7.30 (m, 5H), 7.32-7.39 (m, 2H), 7.40-7.49 (m, 2H).

Example 1.166: Preparation of 2-(((1s,4s)-4-((5-(Ethylthio)-4-(3-fluoro-5-methoxyphenyl)-3-phenyl-1H-pyrazol-1-yl)methyl)cyclohexyl)methoxy)acetic Acid (Compound 119)

From tert-butyl 2-(((1s,4s)-4-((5-(ethylthio)-4-iodo-3-phenyl-1H-pyrazol-1-yl)methyl)cyclohexyl)methoxy)acetate and tert-butyl 2-(((1s,4s)-4-((3-(ethylthio)-4-iodo-5-phenyl-1H-pyrazol-1-yl)methyl)cyclohexyl)methoxy)acetate as a mixture of regioisomers and 3-fluoro-5-methoxyphenylboronic acid, the title compound (one of the two regioisomers separated) was obtained using a similar method to the one described in Example 1.149. LCMS m/z=513.3 [M+H]$^+$; $^1$H NMR (400 MHz, DMSO-d$_6$) δ ppm 0.99 (t, J=7.33 Hz, 3H), 1.33-1.56 (m, 8H), 1.72-1.82 (m, 1H), 2.17-2.27 (m, 1H), 2.57 (q, J=7.33 Hz, 2H), 3.42 (d, J=6.82 Hz, 2H), 3.731 (s, 3H), 4.01 (s, 2H), 4.28 (d, J=7.58 Hz, 2H), 6.62-6.70 (m, 2H), 6.76-6.83 (m, 1H), 7.23-7.41 (m, 5H).

Example 1.167: Preparation of 2-(((1s,4s)-4-((5-Cyclopropyl-4-(3-methoxyphenyl)-3-phenyl-1H-pyrazol-1-yl)methyl)cyclohexyl)methoxy)acetic Acid (Compound 120)

Step A: Preparation of 5-Cyclopropyl-3-phenyl-1H-pyrazole

To a solution of acetophenone (5.0 g, 41.6 mmol) in dry toluene (5 mL) was added LiHMDS (42.0 mL, 1.0 M in THF, 42.0 mmol) via syringe at 0° C. under argon. After 5 min, cyclopropanecarbonyl chloride (4.35 g, 41.6 mmol) was added in one portion via syringe. The ice bath was removed and AcOH (2 mL), EtOH (50 mL), and hydrazine hydrate (10 mL, 64% aq., 127.8 mmol) was added. The mixture was refluxed for 30 min, cooled to room temperature, and concentrated. The residue was extracted with EtOAc, washed with brine, dried over MgSO$_4$, and purified by silica gel column chromatography to give the title compound as colorless oil (4.5 g). LCMS m/z=184.7 [M+H]$^+$; $^1$H NMR (400 MHz, CDCl$_3$) δ ppm 0.71-0.80 (m, 2H), 0.89-1.00 (m, 2H), 1.81-1.98 (m, 1H), 6.22 (s, 1H), 7.11-7.56 (m, 5H), 10.50 (bs, 1H).

Step B: Preparation of 5-Cyclopropyl-4-iodo-3-phenyl-1H-pyrazole

To a solution of 5-cyclopropyl-3-phenyl-1H-pyrazole (3.0 g, 16.28 mmol) in THF (20 mL) and water (20 mL) were added sodium iodide (2.441 g, 16.28 mmol), iodine (6.20 g, 24.43 mmol), and potassium carbonate (3.38 g, 24.43 mmol) at room temperature. The reaction was brought to reflux for 2 h at 100° C. The reaction was cooled to room temperature and quenched with 10% aq. Na$_2$SO$_3$. The organic solvent was removed under reduced pressure and the aqueous was extracted with EtOAc, washed with NaHCO$_3$ solution, brine, dried over MgSO$_4$, and concentrated. The residue was purified by silica gel column chromatography to give the title compound (2.7 g). LCMS m/z=310.8 [M+H]$^+$; $^1$H NMR (400 MHz, DMSO-d$_6$) δ ppm 0.75-0.81 (m, 2H), 0.83-0.88 (m, 2H), 2.46-2.56 (m, 1H), 7.33-7.47 (m, 3H), 7.62-7.71 (m, 2H), 12.91 (s, 1H).

Step C: Preparation of tert-Butyl 2-(((1s,4s)-4-((3-Cyclopropyl-4-iodo-5-phenyl-1H-pyrazol-1-yl)methyl)cyclohexyl)methoxy)acetate and tert-Butyl 2-(((1s,4s)-4-((5-Cyclopropyl-4-iodo-3-phenyl-1H-pyrazol-1-yl)methyl)cyclohexyl)methoxy)acetate as a Mixture of Regioisomers A solution of 5-cyclopropyl-4-iodo-3-phenyl-1H-pyrazole (3.5 g, 11.29 mmol) in DMF (5 mL) was treated with sodium hydride (0.271 g, 11.29 mmol) at room temperature for 1 h, then tert-butyl 2-(((1s,4s)-4-(tosyloxymethyl)cyclohexyl)methoxy)acetate (4.66 g, 11.29 mmol) was added. The reaction mixture was heated to 50° C. for 16 h and quenched by water (2 mL). The mixture was extracted by EtOAc, dried over MgSO$_4$, and concentrated. The residue was purified by silica gel column chromatography to give the title compound (a mixture of two regioisomers) as colorless oil (4.5 g). LCMS m/z=551.1 [M+H]$^+$; $^1$H NMR (400 MHz, CDCl$_3$) δ ppm 1.04-1.19 (m, 4H), 1.33-1.44 (m, 4H), 1.46 (s, 9H), 1.47 (d, J=8.08 Hz, 4H), 1.67-1.77 (m, 1H), 1.85-1.91 (m, 1H), 1.90-1.99 (m, 1H), 3.25 (d, J=7.07 Hz, 2H), 3.87 (s, 2H), 3.91 (d, J=7.58 Hz, 2H), 7.28-7.54 (m, 5H).

Step D: Preparation of 2-(((1s,4s)-4-((5-Cyclopropyl-4-(3-methoxyphenyl)-3-phenyl-1H-pyrazol-1-yl)methyl)cyclohexyl)methoxy)acetic Acid A mixture of 3-methoxyphenylboronic acid (27.4 mg, 0.18 mmol), tert-butyl 2-(((1s,4s)-4-((3-cyclopropyl-4-iodo-5-phenyl-1H-pyrazol-1-yl)methyl)cyclohexyl)methoxy)acetate and tert-butyl 2-(((1s,4s)-4-((5-cyclopropyl-4-iodo-3-phenyl-1H-pyrazol-1-yl)methyl)cyclohexyl)methoxy)acetate as a mixture of regioisomers (100 mg, 0.18 mmol), tetrakis(triphenylphosphine)palladium (10.0 mg, 0.009 mmol), K$_2$CO$_3$ (2 M aq., 0.2 mL) and dioxane (4 mL) was heated to 150° C. under microwave irradiation for 4 h. The mixture was filtered and concentrated. The residue was treated with HCl (4 M in dioxane, 5 mL) at room temperature for 10 h. The mixture was concentrated and purified by HPLC to give the title compound (one of the two regioisomers separated) as white solid (23.5 mg). LCMS m/z=475.3 [M+H]$^+$; $^1$H NMR (400 MHz, CD$_3$OD) δ ppm 0.35-0.48 (m, 2H), 0.86-0.99 (m, 2H), 1.44-1.80 (m, 8H), 1.83-2.01 (m, 1H), 2.29-2.41 (m, 1H), 2.67-2.76 (m, 1H), 3.57 (d, J=6.95 Hz, 2H), 3.74 (s, 3H), 4.13 (s, 2H), 4.30 (d, J=7.33 Hz, 2H), 6.70-7.00 (m, 4H), 7.17-7.55 (m, 5H).

Example 1.168: Preparation of 2-(((1s,4s)-4-((5-Cyclopropyl-3,4-diphenyl-1H-pyrazol-1-yl)methyl)cyclohexyl)methoxy)acetic Acid (Compound 122)

From tert-butyl 2-(((1s,4s)-4-((3-cyclopropyl-4-iodo-5-phenyl-1H-pyrazol-1-yl)methyl)cyclohexyl)methoxy)acetate and tert-butyl 2-(((1s,4s)-4-((5-cyclopropyl-4-iodo-3-phenyl-1H-pyrazol-1-yl)methyl)cyclohexyl)methoxy)acetate as a mixture of regioisomers and phenylboronic acid, the title compound (one of the two regioisomers separated) was obtained using a similar method to the one described in Example 1.167. LCMS m/z=445.4 [M+H]$^+$; $^1$H NMR (400 MHz, DMSO-d$_6$) δ ppm 0.20-0.27 (m, 2H), 0.74-0.81 (m, 2H), 1.36-1.56 (m, 8H), 1.70-1.81 (m, 1H), 1.81-1.91 (m, 1H), 2.13-2.28 (m, 1H), 3.42 (d, J=6.95 Hz, 2H), 4.00 (s, 2H), 4.17 (d, J=7.45 Hz, 2H), 7.16-7.25 (m, 5H), 7.25-7.37 (m, 5H).

Example 1.169: Preparation of 2-(((1s,4s)-4-((3-Isopropyl-4-(3-methoxyphenyl)-5-phenyl-1H-pyrazol-1-yl)methyl)cyclohexyl)methoxy)acetic Acid (Compound 123)

From tert-butyl 2-(((1s,4s)-4-((4-iodo-5-isopropyl-3-phenyl-1H-pyrazol-1-yl)methyl)cyclohexyl)methoxy)acetate and tert-butyl 2-(((1s,4s)-4-((4-iodo-3-isopropyl-5-phenyl-1H-pyrazol-1-yl)methyl)cyclohexyl)methoxy)acetate as a mixture of regioisomers, and 3-methoxyphenylboronic acid, the title compound (one of the two regioisomers separated) was obtained using a similar method to the one described in Example 1.161. LCMS m/z=477.3 [M+H]$^+$; $^1$H NMR (400 MHz, CD$_3$OD) δ ppm 1.10-1.26 (m, 4H), 1.29 (d, J=6.95 Hz, 6H), 1.30-1.45 (m, 4H), 1.66-1.76 (m, 1H), 1.95-2.06 (m, 1H), 3.10-3.22 (m, 1f), 3.29 (d, J=6.95 Hz, 2H), 3.66 (s, 3H), 4.00 (s, 2H), 4.10 (d, J=7.71 Hz, 2H), 6.60-6.81 (m, 3H), 7.13-7.31 (m, 3H), 7.33-7.46 (m, 3H).

Example 1.170: Preparation of 2-(((1s,4s)-4-((4-(3-Chlorophenyl)-3-isopropyl-5-phenyl-1H-pyrazol-1-yl)methyl)cyclohexyl)methoxy)acetic Acid (Compound 124)

From tert-butyl 2-(((1s,4s)-4-((4-iodo-5-isopropyl-3-phenyl-1H-pyrazol-1-yl)methyl)cyclohexyl)methoxy)acetate and tert-butyl 2-(((1s,4s)-4-((4-iodo-3-isopropyl-5-phenyl-1H-pyrazol-1-yl)methyl)cyclohexyl)methoxy)acetate as a mixture of regioisomers and 3-chlorophenylboronic acid, the title compound (one of the two regioisomers separated) was obtained using a similar method to the one described in Example 1.161. LCMS m/z=481.3 [M+H]$^+$; $^1$H NMR (400 MHz, DMSO-d$_6$) δ ppm 1.18 (d, J=6.82 Hz, 6f), 1.21-1.35 (m, 4H), 1.37-1.56 (m, 4H), 1.83-195 (m, 1H), 2.06-2.17 (m, 1H), 2.96-3.06 (m, 1H), 3.20 (d, J=7.07 Hz, 2H), 3.91 (s, 2H), 3.93 (d, J=7.83 Hz, 2H), 7.01-7.09 (m, 1H), 7.15-7.31 (m, 5H), 7.35-7.44 (m, 3H).

Example 1.171: Preparation of 2-(((1s,4s)-4-((4-(2-Fluoro-3-methoxyphenyl)-3-isopropyl-5-phenyl-1H-pyrazol-1-yl)methyl)cyclohexyl)methoxy)acetic Acid (Compound 125)

From tert-butyl 2-(((1s,4s)-4-((4-iodo-5-isopropyl-3-phenyl-1H-pyrazol-1-yl)methyl)cyclohexyl)methoxy)acetate and tert-butyl 2-(((1s,4s)-4-((4-iodo-3-isopropyl-5-phenyl-1H-pyrazol-1-yl)methyl)cyclohexyl)methoxy)acetate as a mixture of regioisomers and 2-fluoro-3-methoxyphenylboronic acid, the title compound (one of the two regioisomers separated) was obtained using a similar method to the one described in Example 1.161. LCMS m/z=495.3 [M+H]$^+$; $^1$H NMR (400 MHz, DMSO-d$_6$) δ ppm 1.24 (d, J=6.82 Hz, 6H), 1.25-1.33 (m, 4H), 1.34-1.43 (m, 4H), 1.72-1.82 (m, 1H), 2.07-2.15 (m, 1H), 2.98-3.08 (m, 1H), 3.42 (d, J=6.82 Hz, 2H), 3.77 (s, 3H), 3.99 (s, 2H), 4.01 (d, J=7.59 Hz, 2H), 6.81-6.88 (m, 1H), 6.96-7.04 (m, 2H), 7.22-7.30 (m, 2H), 7.32-7.40 (m, 3H).

Example 1.172: Preparation of 2-(((1s,4s)-4-((5-Cyclopropyl-4-(2-fluoro-3-methoxyphenyl)-3-phenyl-1H-pyrazol-1-yl)methyl)cyclohexyl)methoxy)acetic Acid (Compound 126)

From tert-butyl 2-(((1s,4s)-4-((3-cyclopropyl-4-iodo-5-phenyl-1H-pyrazol-1-yl)methyl)cyclohexyl)methoxy)acetate and tert-butyl 2-(((1s,4s)-4-((5-cyclopropyl-4-iodo-3-phenyl-1H-pyrazol-1-yl)methyl)cyclohexyl)methoxy)acetate as a mixture of regioisomers and 2-fluoro-3-methoxyphenylboronic acid, the title compound was obtained using a similar method to the one described in Example 1.167. LCMS m/z=493.3 [M+H]$^+$; $^1$H NMR (400 MHz, CD$_3$OD) δ ppm 0.38-0.45 (m, 2H), 0.82-0.90 (m, 2H), 1.49-1.71 (m, 8H), 1.82-1.90 (m, 1H), 1.90-2.00 (m, 1H), 2.29-2.40 (m, 1H), 3.57 (d, J=6.95 Hz, 2H), 3.93 (s, 3H), 4.13 (s, 2H), 4.31 (d, J=7.58 Hz, 2H), 6.66-6.77 (m, 2H), 7.01-7.15 (m, 3H), 7.22-7.39 (m, 3H).

Example 1.173: Preparation of 2-(((1s,4s)-4-((5-Cyclopropyl-4-(2,3-difluorophenyl)-3-phenyl-1H-pyrazol-1-yl)methyl)cyclohexyl)methoxy)acetic Acid (Compound 127)

From tert-butyl 2-(((1s,4s)-4-((3-cyclopropyl-4-iodo-5-phenyl-1H-pyrazol-1-yl)methyl)cyclohexyl)methoxy)acetate and tert-butyl 2-(((1s,4s)-4-((5-cyclopropyl-4-iodo-3-phenyl-1H-pyrazol-1-yl)methyl)cyclohexyl)methoxy)acetate as a mixture of regioisomers and 2,3-difluorophenylboronic acid, the title compound was obtained using a similar method to the one described in Example 1.167. LCMS m/z=481.2 [M+H]+; 1H NMR (400 MHz, CD3OD) δ ppm 0.36-0.42 (m, 2H), 0.85-0.94 (m, 2H), 1.48-1.72 (m, 8H), 1.84-1.91 (m, 1H), 1.89-1.97 (m, 1H), 2.29-2.40 (m, 1H), 3.56 (d, J=6.95 Hz, 2H), 4.12 (s, 2H), 4.31 (d, J=7.70 Hz, 2H), 6.92-7.04 (m, 2H), 7.09-7.19 (m, 2H), 7.19-7.40 (m, 4H).

Example 1.174: Preparation of 2-(((1s,4s)-4-((5-Isopropyl-4-(3-methoxyphenyl)-3-phenyl-1H-pyrazol-1-yl)methyl)cyclohexyl)methoxy)acetic Acid (Compound 128)

From tert-butyl 2-(((1s,4s)-4-((4-iodo-5-isopropyl-3-phenyl-1H-pyrazol-1-yl)methyl)cyclohexyl)methoxy)acetate and tert-butyl 2-(((1s,4s)-4-((4-iodo-3-isopropyl-5-phenyl-1H-pyrazol-1-yl)methyl)cyclohexyl)methoxy)acetate as a mixture of regioisomers and 3-methoxyphenylboronic acid, the title compound (one of the two regioisomers separated) was obtained using a similar method to the one described in Example 1.161. LCMS m/z=477.3 [M+H]+; 1H NMR (400 MHz, CD3OD) δ ppm 1.23 (d, J=7.07 Hz, 6H), 1.44-1.75 (m, 8H), 1.90-2.00 (m, 1H), 2.17-2.27 (m, 1H), 3.19-3.30 (m, 1H), 3.58 (d, J=7.07 Hz, 2H), 3.78 (s, 3H), 4.13 (s, 2H), 4.17 (d, J=7.58 Hz, 2H), 6.78-6.97 (m, 3H), 7.20-7.25 (m, 3H), 7.27-7.37 (m, 3H).

Example 1.175: Preparation of 2-(((1s,4s)-4-((4-(3-Chlorophenyl)-5-isopropyl-3-phenyl-1H-pyrazol-1-yl)methyl)cyclohexyl)methoxy)acetic Acid (Compound 129)

From tert-butyl 2-(((1s,4s)-4-((4-iodo-5-isopropyl-3-phenyl-1H-pyrazol-1-yl)methyl)cyclohexyl)methoxy)acetate and tert-butyl 2-(((1s,4s)-4-((4-iodo-3-isopropyl-5-phenyl-1H-pyrazol-1-yl)methyl)cyclohexyl)methoxy)acetate as a mixture of regioisomers and 3-chlorophenylboronic acid, the title compound (one of the two regioisomers separated) was obtained using a similar method to the one described in Example 1161. LCMS m/z=481.3 [M+H]+; 1H NMR (400 MHz, DMSO-d6) δ ppm 1.09 (d, J=7.07 Hz, 6H), 1.34-1.57 (m, 8H), 1.74-1.83 (m, 1H), 2.06-2.17 (m, 1H), 2.95-3.05 (m, 1H), 3.43 (d, J=7.07 Hz, 2H), 3.99 (s, 2H), 4.07 (d, J=7.33 Hz, 2H), 7.01-7.08 (m, 1H), 7.12-7.27 (m, 4H), 7.32-7.54 (m, 4H).

Example 1.176: Preparation of 2-(((1s,4s)-4-((4-(2-Fluoro-3-methoxyphenyl)-5-isopropyl-3-phenyl-1H-pyrazol-1-yl)methyl)cyclohexyl)methoxy)acetic Acid (Compound 130)

From tert-butyl 2-(((1s,4s)-4-((4-iodo-5-isopropyl-3-phenyl-1H-pyrazol-1-yl)methyl)cyclohexyl)methoxy)acetate and tert-butyl 2-(((1s,4s)-4-((4-iodo-3-isopropyl-5-phenyl-1H-pyrazol-1-yl)methyl)cyclohexyl)methoxy)acetate as a mixture of regioisomers and 2-fluoro-3-methoxyphenylboronic acid, the title compound (one of the two regioisomers separated) was obtained using a similar method to the one described in Example 1.161. LCMS m/z=495.3 [M+H]+; 1H NMR (400 MHz, DMSO-d6) δ ppm 1.12 (d, J=7.07 Hz, 6H), 1.39-1.55 (m, 8H), 1.70-1.82 (m, 1H), 1.86-1.97 (m, 1H), 2.75-2.85 (m, 1H), 3.20 (d, J=7.07 Hz, 2H), 3.77 (s, 3H), 3.91 (s, 2H), 3.96 (d, J=7.83 Hz, 2H), 6.97-7.05 (m, 1H), 7.13-7.30 (m, 4H), 7.31-7.40 (m, 3H).

Example 1.177: Preparation of Methyl 2-(((1s,4s)-4-((5-(Methylthio)-3,4-diphenyl-1H-pyrazol-1-yl) methyl)cyclohexyl) Methoxy)acetate (Compound 131)

From tert-butyl 2-(((1s,4s)-4-((4-iodo-5-(methylthio)-3-phenyl-1H-pyrazol-1-yl)methyl)cyclohexyl)methoxy)acetate and phenylboronic acid, the title compound (one of the two regioisomers separated) was obtained using a similar method to the one described in Example 1.151. LCMS m/z=451.2 [M+H]+; 1H NMR (400 MHz, DMSO-d6) δ ppm 1.32-1.53 (m, 8H), 1.70-1.80 (m, 1H), 2.12 (s, 3H), 2.15-2.25 (m, 1H), 3.39 (d, J=6.95 Hz, 2H), 3.80 (s, 2H), 4.28 (d, J=7.45 Hz, 2H), 7.22-7.29 (m, 5H), 7.30-7.43 (m, 5H).

Example 1.178: Preparation of 2-(((1s,4s)-4-((4-(3-Chlorophenyl)-3-cyclopropyl-5-phenyl-1H-pyrazol-1-yl)methyl)cyclohexyl)methoxy)acetic Acid (Compound 132)

From tert-butyl 2-(((1s,4s)-4-((3-cyclopropyl-4-iodo-5-phenyl-1H-pyrazol-1-yl)methyl)cyclohexyl)methoxy)acetate and tert-butyl 2-(((1s,4s)-4-((5-cyclopropyl-4-iodo-3-phenyl-1H-pyrazol-1-yl)methyl)cyclohexyl)methoxy) acetate as a mixture of regioisomers and 3-chlorophenylboronic acid, the title compound (one of the two regioisomers separated) was obtained using a similar method to the one described in Example 1.167. LCMS m/z=479.3 [M+H]+; 1H NMR (400 MHz, DMSO-d6) δ ppm 0.54-0.62 (m, 4H), 0.76-0.92 (m, 4H), 0.95-1.10 (m, 4H), 1.30-1.41 (m, 1H), 1.53-1.60 (m, 1H), 1.60-1.69 (m, 1H), 2.95 (d, J=6.82 Hz, 2H), 3.61 (d, J=7.33 Hz, 2H), 3.67 (s, 2H), 6.85-6.93 (m, 2H), 6.95-7.07 (m, 4H), 7.08-7.23 (m, 3H).

Example 1.179: Preparation of 2-(((1s,4s)-4-((4-(3-Chlorophenyl)-5-cyclopropyl-3-phenyl-1H-pyrazol-1-yl)methyl)cyclohexyl)methoxy)acetic Acid (Compound 133)

From tert-butyl 2-(((1s,4s)-4-((3-cyclopropyl-4-iodo-5-phenyl-1H-pyrazol-1-yl)methyl)cyclohexyl)methoxy)acetate and tert-butyl 2-(((1s,4s)-4-((5-cyclopropyl-4-iodo-3-phenyl-1H-pyrazol-1-yl)methyl)cyclohexyl)methoxy) acetate as a mixture of regioisomers and 3-chlorophenylboronic acid, the title compound (one of the two regioisomers separated) was obtained using a similar method to the one described in Example 1.167. LCMS m/z=479.3 [M+H]+; 1H NMR (400 MHz, CDCl3) δ ppm 0.34-0.41 (m, 2H), 0.87-0.95 (m, 2H), 1.37-1.65 (m, 8H), 1.71-1.80 (m, 1H), 1.88-1.97 (m, 1H), 2.23-2.33 (m, 1H), 3.53 (d, J=6.95 Hz, 2H), 4.11 (s, 2H), 4.31 (d, J=7.58 Hz, 2H), 7.00-7.05 (m, 1H), 7.19-7.30 (m, 6H), 7.30-7.36 (m, 2H).

Example 1.180: Preparation of Methyl 2-(((1s,4s)-4-((4-(3-Methoxyphenyl)-5-methyl-3-phenyl-1H-pyrazol-1-yl)methyl)cyclohexyl) Methoxy)acetate (Compound 136)

To a solution of tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers (100 mg, 0.19 mmol) in dioxane (3 mL) were added 3-methoxyphenylboronic acid (28.9 mg, 0.19 mmol), tetrakis(triphenylphosphine)palladium (22 mg, 0.019 mmol), and $K_2CO_3$ (2 M aq., 0.2 mL). The reaction was heated to 150° C. under microwave irradiation for 4 h. The reaction mixture was filtered and concentrated. The residue was treated with HCl (4.0 M in dioxane, 5 mL) at room temperature for 10 h. The mixture was concentrated and purified by HPLC to give 2-(((1s,4s)-4-((4-(3-methoxyphenyl)-5-methyl-3-phenyl-1H-pyrazol-1-yl)methyl)cyclohexyl)methoxy)acetic acid. The title compound (15.4 mg) was obtained by treating the above acid with anhydrous methanol for 1 h. LCMS m/z=463.3 [M+H]$^+$; $^1$H NMR (400 MHz, DMSO-d$_6$) δ ppm 1.31-1.53 (m, 8H), 1.69-1.80 (m, 1H), 2.03-2.13 (m, 1H), 2.21 (s, 3H), 3.36 (d, J=7.07 Hz, 2H), 3.56 (s, 3H), 3.68 (s, 3H), 3.82 (s, 2H), 4.04 (d, J=7.45 Hz, 2H), 6.67-6.75 (m, 2H), 6.83-6.88 (m, 1H), 7.20-7.30 (m, 4H), 7.30-7.35 (m, 2H).

Example 1.181: Preparation of 2-(((1s,4s)-4-((3-(4-Fluorophenyl)-5-methyl-4-phenyl-1H-pyrazol-1-yl)methyl)cyclohexyl)methoxy)acetic Acid (Compound 137)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 4-fluorophenylboronic acid, the title compound (one of the two regioisomers separated) was obtained using a similar method to the one described in Example 1.107. LCMS m/z=437.2 [M+H]$^+$; $^1$H NMR (400 MHz, DMSO-d$_6$) δ ppm 1.35-1.53 (m, 8H), 1.72-1.81 (m, 1H), 2.05-2.13 (m, 1H), 2.20 (s, 3H), 3.42 (d, J=6.95 Hz, 2H), 3.99 (s, 2H), 4.05 (d, J=7.58 Hz, 2H), 7.03-7.18 (m, 4H), 7.25-7.42 (m, 5H).

Example 1.182: Preparation of 2-(((1s,4s)-4-((3-(4-Chlorophenyl)-5-methyl-4-phenyl-1H-pyrazol-1-yl)methyl)cyclohexyl)methoxy)acetic Acid (Compound 138)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 4-chlorophenylboronic acid, the title compound (one of the two regioisomers separated) was obtained using a similar method to the one described in Example 1.107. LCMS m/z=453.2 [M+H]$^+$; $^1$H NMR (400 MHz, DMSO-d$_6$) δ ppm 1.33-1.53 (m, 8H), 1.71-1.82 (m, 1H), 2.03-2.14 (m, 1H), 2.20 (s, 3H), 3.42 (d, J=6.95 Hz, 2H), 3.99 (s, 2H), 4.05 (d, J=7.45 Hz, 2H), 7.13-7.19 (m, 3H), 7.28-7.34 (m, 3H), 7.35-7.41 (m, 3H).

Example 1.183: Preparation of 2-(((1s,4s)-4-((5-Methyl-4-phenyl-3-p-tolyl-1H-pyrazol-1-yl)methyl)cyclohexyl)methoxy)acetic Acid (Compound 139)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and p-tolylboronic acid, the title compound (one of the two regioisomers separated) was obtained using a similar method to the one described in Example 1.107. LCMS m/z=433.3[M+H]$^+$; $^1$H NMR (400 MHz, DMSO-d$_6$) δ ppm 1.35-1.53 (m, 8H), 1.72-1.80 (m, 1H), 2.04-2.13 (m, 1H), 2.19 (s, 3H), 2.25 (s, 3H), 3.42 (d, J=6.95 Hz, 2H), 3.99 (s, 2H), 4.03 (d, J=7.45 Hz, 2H), 7.00-7.07 (m, 2H), 7.11-7.22 (m, 4H), 7.24-7.40 (m, 3H).

Example 1.184: Preparation of 2-(((1s,4s)-4-((3-(4-Methoxyphenyl)-5-methyl-4-phenyl-1H-pyrazol-1-yl)methyl)cyclohexyl)methoxy)acetic Acid (Compound 140)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 4-methoxyphenylboronic acid, the title compound (one of the two regioisomers separated) was obtained using a similar method to the one described in Example 1.107. LCMS m/z=449.3 [M+H]$^+$; $^1$H NMR (400 MHz, DMSO-d$_6$) δ ppm 1.34-1.53 (m, 8H), 1.71-1.80 (m, 1H), 2.04-2.14 (m, 1H), 2.19 (s, 3H), 3.42 (d, J=7.07 Hz, 2H), 3.71 (s, 3H), 3.99 (s, 2H), 4.02 (d, J=7.45 Hz, 2H), 6.77-6.85 (m, 2H), 7.12-7.19 (m, 2H), 7.18-7.41 (m, 5H).

Example 1.185: Preparation of 2-(((1s,4s)-4-((3-(2,4-Difluorophenyl)-5-methyl-4-phenyl-1H-pyrazol-1-yl)methyl)cyclohexyl)methoxy)acetic Acid (Compound 141)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 2,4-difluorophenylboronic acid, the title compound (one of the two regioisomers separated) was obtained using a similar method to the one described in Example 1.107. LCMS m/z=454.2 [M+H]$^+$; $^1$H NMR (400 MHz, DMSO-d$_6$) δ ppm 1.31-1.53 (m, 8H), 1.70-1.81 (m, 1H), 2.03-2.14 (m, 1H), 2.29 (s, 3H), 3.41 (d, J=6.95 Hz, 2H), 3.99 (s, 2H), 4.07 (d, J=7.45 Hz, 2H), 7.04-7.08 (m, 2H), 7.08-7.24 (m, 3H), 7.25-7.43 (m, 3H).

Example 1.186: Preparation of 2-(((1s,4s)-4-((4-(2,3-Difluorophenyl)-5-(ethylthio)-3-phenyl-1H-pyrazol-1-yl)methyl)cyclohexyl)methoxy)acetic Acid (Compound 142)

From tert-butyl 2-(((1s,4s)-4-((5-(ethylthio)-4-iodo-3-phenyl-1H-pyrazol-1-yl)methyl)cyclohexyl)methoxy)acetate and 2,3-difluoro-methoxyphenylboronic acid, the title compound (one of the two regioisomers separated) was obtained using a similar method to the one described in Example 1.149. LCMS m/z=501.2 [M+H]$^+$; $^1$H NMR (400 MHz, DMSO-d$_6$) δ ppm 0.95 (t, J=7.33 Hz, 3H), 1.30-1.53 (m, 8H), 1.69-1.81 (m, 1H), 2.15-2.27 (m, 1H), 2.56 (q, J=7.33 Hz, 2H), 3.38 (d, J=6.95 Hz, 2H), 3.75 (s, 2H), 4.29 (d, J=7.45 Hz, 2H), 7.14-7.21 (m, 1H), 7.23-7.37 (m, 6H), 7.42-7.52 (m, 1H).

Example 1.187: Preparation of 2-(((1s,4s)-4-((3-(2-Fluoro-4-methoxyphenyl)-5-methyl-4-phenyl-1H-pyrazol-1-yl)methyl)cyclohexyl)methoxy)acetic Acid (Compound 145)

From tert-butyl 2-(((1s,4s)-4-((5-bromo-3-methyl-4-phenyl-1H-pyrazol-1-yl)methyl)cyclohexyl)methoxy)acetate and tert-butyl 2-(((1s,4s)-4-((3-bromo-5-methyl-4-phenyl-1H-pyrazol-1-yl)methyl)cyclohexyl)methoxy)acetate as a mixture of regioisomers and 2-fluoro-4-methoxyphenylboronic acid, the title compound (one of the two regioisomers separated) was obtained using a similar method to the one described in Example 1.107. LCMS m/z=467.2 [M+H]$^+$; $^1$H NMR (400 MHz, DMSO-d$_6$) δ ppm 1.34-1.53 (m, 8H), 1.70-1.80 (m, 1H), 2.05-2.14 (m, 1H), 2.29 (s, 3H), 3.42 (d, J=6.82 Hz, 2H), 3.66 (s, 3H), 3.99 (s, 2H), 4.07 (d, J=7.58 Hz, 2H), 6.79-6.91 (m, 2H), 6.97-7.12 (m, 3H), 7.15-7.33 (m, 3H).

Example 1.188: Preparation of 2-(((1s,4s)-4-((4 (5-Fluoropyridin-3-yl)-5-methyl-3-phenyl-1H-pyrazol-1-yl)methyl)cyclohexyl)methoxy)acetic Acid (Compound 147)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 5-fluoropyridin-3-ylboronic acid, the title compound (one of the two regioisomers separated) was obtained using a similar method to the one described in Example 1.97. LCMS m/z=438.2 [M+H]$^+$; $^1$H NMR (400 MHz, DMSO-d$_6$) δ ppm 1.30-1.54 (m, 8H), 1.70-1.81 (m, 1H), 2.02-2.14 (m, 1H), 2.27 (s, 3H), 3.42 (d, J=6.95 Hz, 2H), 3.99 (s, 2H), 4.08 (d, J=7.58 Hz, 2H), 7.22-7.32 (m, 3H), 7.33-7.40 (m, 1H), 7.54-7.61 (m, 1H), 7.69-7.74 (m, 1H), 8.18-8.23 (m, 1H), 8.50 (d, J=2.78 Hz, 1H).

Example 1.189: Preparation of 2-(((1s,4s)-4-((5-(Ethylthio)-4-(5-fluoropyridin-3-yl)-3-phenyl-1H-pyrazol-1-yl)methyl)cyclohexyl)methoxy)acetic Acid (Compound 148)

From tert-butyl 2-(((1s,4s)-4-((5-(ethylthio)-4-iodo-3-phenyl-1H-pyrazol-1-yl)methyl)cyclohexyl)methoxy)acetate and 5-fluoropyridin-3-ylboronic acid, the title compound (one of the two regioisomers separated) was obtained using a similar method to the one described in Example 1.149. LCMS m/z=484.2 [M+H]$^+$; $^1$H NMR (400 MHz, DMSO-d$_6$) δ ppm 0.95 (t, J=7.33 Hz, 3H), 1.34-1.54 (m, 8H), 1.70-1.81 (m, 1H), 2.16-2.26 (m, 1H), 2.58 (q, J=7.33 Hz, 2H), 3.41 (d, J=6.95 Hz, 2H), 4.00 (s, 2H), 4.30 (d, J=7.58 Hz, 2H), 7.27-7.35 (m, 5H), 7.65-7.71 (m, 1H), 8.29 (t, J=1.64 Hz, 1H), 8.55 (d, J=2.78 Hz, 1H).

Example 1.190: Preparation of 2-(((1s,4s)-4-((5-Ethyl-4-(5-fluoropyridin-3-yl)-3-phenyl-1H-pyrazol-1-yl)methyl)cyclohexyl)methoxy)acetic Acid (Compound 149)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and 5-fluoropyridin-3-ylboronic acid, the title compound (one of the two regioisomers separated) was obtained using a similar method to the one described in Example 1.152. LCMS m/z=452.2 [M+H]$^+$; $^1$H NMR (400 MHz, DMSO-d$_6$) δ ppm 1.00-1.07 (m, 3H), 1.35-1.57 (m, 8H), 1.73-1.83 (m, 1H), 2.07-2.19 (m, 1H), 2.66 (q, J=7.49 Hz, 2H), 3.44 (d, J=7.07 Hz, 2H), 4.00 (s, 2H), 4.06 (d, J=7.45 Hz, 2H), 7.23-7.31 (m, 5H), 7.57-7.62 (m, 1H), 8.23 (t, J=1.71 Hz, 1H), 8.53 (d, J=2.78 Hz, 1H).

Example 1.191: Preparation of 2-(((1s,4s)-4-((3,4-Diphenyl-5-(trifluoromethyl)-1H-pyrazol-1-yl) methyl)cyclohexyl)methoxy)acetic Acid (Compound 151)

Step A: Preparation of 3-Phenyl-5-(trifluoromethyl)-1H-pyrazole

To a stirred mixture of 4,4,4-trifluoro-1-phenylbutane-1,3-dione (5.0 g, 23.13 mmol) in dry ethanol (100 mL) was added hydrazine hydrate (1.737 g, 34.7 mmol) dropwise. The resulting solution was refluxed for 16 h. The reaction was cooled to room temperature and concentrated. The oil was diluted with saturated NaHCO$_3$ solution and extracted with EtOAc, washed with brine, dried over MgSO$_4$ and concentrated. The residue was purified by silica gel column chromatography to give the title compound as a clear liquid which was crystallized in hexanes/ethyl acetate (3.25 g). LCMS m/z=213.1 [M+H]$^+$; $^1$H NMR (400 MHz, CDCl$_3$) δ ppm 6.77 (s, 1H), 7.36-7.51 (m, 3H), 7.53-7.64 (m, 2H), 11.59 (s, 1H).

Step B: Preparation of 4-Iodo-3-phenyl-5-(trifluoromethyl)-1H-pyrazole

To a mixture of 3-phenyl-5-(trifluoromethyl)-1H-pyrazole (4.0 g, 18.85 mmol) in THF (50 mL) and water (50 mL) were added sodium iodide (2.83 g, 18.85 mmol), iodine (7.18 g, 28.3 mmol), and K$_2$CO$_3$ (2.61 g, 18.85 mmol) at room temperature. The reaction was refluxed for 16 h, quenched with sodium thiosulfite (2.0 M aq. 10 mL) and concentrated under reduced pressure. The reaction was extracted with ethyl acetate and washed with NaHCO$_3$, brine, dried over MgSO$_4$ and concentrated under reduced pressure. The residue was purified by silica gel column chromatography to give the title compound as white solid (4.0 g). LCMS m/z=338.8 [M+H]$^+$; $^1$H NMR (400 MHz, DMSO-d$_6$) δ ppm 7.39-7.62 (m, 3H), 7.70-7.75 (m, 1H), 7.82-7.88 (m, 1H), 14.11 (s, 1H).

Step C: Preparation of tert-Butyl 2-(((1s,4s)-4-((4-Iodo-5-phenyl-3-(trifluoromethyl)-1H-pyrazol-1-yl) methyl)cyclohexyl)methoxy)acetate and tert-Butyl 2-(((1s,4s)-4-((4-Iodo-3-phenyl-5-(trifluoromethyl)-1H-pyrazol-1-yl)methyl)cyclohexyl)methoxy)acetate as a Mixture of Regioisomers To a solution of 4-iodo-3-phenyl-5-(trifluoromethyl)-1H-pyrazole (2.0 g, 5.92 mmol) in DMF (6 mL) was added sodium hydride (0.14 g, 5.92 mmol) in portions at 0° C. The reaction was stirred at that temperature for 1 h and tert-butyl 2-(((1s,4s)-4-(tosyloxymethyl)cyclohexyl)methoxy)acetate (2.44 g, 5.92 mmol) was added. The reaction was gently heated to 60° C. for 16 h, quenched with water (2 mL), extracted with ethyl acetate, dried over MgSO$_4$, and concentrated. The residue was purified by silica gel column chromatography to give the title compound (a mixture of two regioisomers) as a colorless liquid (2.7 g). LCMS m/z=579.1 [M+H]$^+$.

Step D: Preparation of 2-(((1s,4s)-4-((3,4-Diphenyl-5-(trifluoromethyl)-1H-pyrazol-1-yl)methyl)cyclohexyl)methoxy)acetic Acid In a solution of tert-butyl 2-(((1s,4s)-4-((4-iodo-5-phenyl-3-(trifluoromethyl)-1H-pyrazol-1-yl)methyl)cyclohexyl)

methoxy)acetate and tert-butyl 2-(((1s,4s)-4-((4-iodo-3-phenyl-5-(trifluoromethyl)-1H-pyrazol-1-yl)methyl)cyclohexyl)methoxy)acetate as a mixture of regioisomers (100 mg, 0.17 mmol) in dioxane (3 mL) were added phenylboronic acid (21.0 mg, 0.17 mmol), tetrakis(triphenylphosphine)palladium (22 mg, 0.019 mmol), and $K_2CO_3$ (2 M aq., 0.2 mL). The reaction was heated to 150° C. under microwave irradiation for 4 h. The reaction mixture was filtered and concentrated. The residue was treated with HCl (4.0 M in dioxane, 4 mL) at room temperature for 10 h. The mixture was concentrated and purified by HPLC to give the title compound as a white solid (16.4 mg). LCMS m/z=473.2 [M+H]$^+$; $^1$H NMR (400 MHz, DMSO-d$_6$) δ ppm 1.35-1.54 (m, 8H), 1.73-1.82 (m, 1H), 2.13-2.21 (m, 1H), 3.42 (d, J=7.07 Hz, 2H), 3.99 (s, 2H), 4.27 (d, J=7.45 Hz, 2H), 7.23-7.29 (m, 5H), 7.37-7.43 (m, 5H), 12.30-12.76 (m, 1H).

Example 1.192: Preparation of 2-(((1s,4s)-4-((3-Phenyl-4-p-tolyl-5-(trifluoromethyl)-1H-pyrazol-1-yl)methyl)cyclohexyl)methoxy)acetic Acid (Compound 152)

From tert-butyl 2-(((1s,4s)-4-((4-iodo-5-phenyl-3-(trifluoromethyl)-1H-pyrazol-1-yl)methyl)cyclohexyl)methoxy)acetate and tert-butyl 2-(((1s,4s)-4-((4-iodo-3-phenyl-5-(trifluoromethyl)-1H-pyrazol-1-yl)methyl)cyclohexyl)methoxy)acetate as a mixture of regioisomers and p-tolylboronic acid, the title compound (one of the two regioisomers separated) was obtained using a similar method to the one described in Example 1.191. LCMS m/z=487.2 [M+H]$^+$; $^1$H NMR (400 MHz, DMSO-d$_6$) δ ppm 1.34-1.54 (m, 8H), 1.73-1.83 (m, 1H), 2.12-2.21 (m, 1H), 2.34 (s, 3H), 3.42 (d, J=7.07 Hz, 2H), 3.99 (s, 2H), 4.26 (d, J=7.45 Hz, 2H), 7.09-7.15 (m, 2H), 7.18-7.23 (m, 2H), 7.23-7.30 (m, 5H), 12.47 (s, 1H).

Example 1.193: Preparation of 2-(((1s,4s)-4-((4-(3-Methoxyphenyl)-5-phenyl-3-(trifluoromethyl)-1H-pyrazol-1-yl)methyl)cyclohexyl)methoxy)acetic Acid (Compound 154)

From tert-butyl 2-(((1s,4s)-4-((4-iodo-5-phenyl-3-(trifluoromethyl)-1H-pyrazol-1-yl)methyl)cyclohexyl)methoxy)acetate and tert-butyl 2-(((1s,4s)-4-((4-iodo-3-phenyl-5-(trifluoromethyl)-1H-pyrazol-1-yl)methyl)cyclohexyl)methoxy)acetate as a mixture of regioisomers and 3-methoxyphenylboronic acid, the title compound (one of the two regioisomers separated) was obtained using a similar method to the one described in Example 1.191. LCMS m/z=503.2 [M+H]$^+$; $^1$H NMR (400 MHz, DMSO-d$_6$) δ ppm 1.01-1.22 (m, 4H), 1.23-1.41 (m, 4H), 1.54-1.70 (m, 1H), 1.86-2.02 (m, 1H), 3.15 (d, J=6.82 Hz, 2H), 3.49 (s, 2H), 3.62 (s, 3H), 4.03 (d, J=7.07 Hz, 2H), 6.63-6.87 (m, 4H), 7.13-7.24 (m, 2H), 7.29-7.53 (m, 3H).

Example 1.194: Preparation of 2-(((1s,4s)-4-((4-(3-Methoxyphenyl)-3-phenyl-5-(trifluoromethyl)-1H-pyrazol-1-yl)methyl)cyclohexyl)methoxy)acetic Acid (Compound 155)

From tert-butyl 2-(((1s,4s)-4-((4-iodo-5-phenyl-3-(trifluoromethyl)-1H-pyrazol-1-yl)methyl)cyclohexyl)methoxy)acetate and tert-butyl 2-(((1s,4s)-4-((4-iodo-3-phenyl-5-(trifluoromethyl)-1H-pyrazol-1-yl)methyl)cyclohexyl)methoxy)acetate as a mixture of regioisomers and 3-methoxyphenylboronic acid, the title compound (one of the two regioisomers separated) was obtained using a similar method to the one described in Example 1.191. LCMS m/z=503.2 [M+H]$^+$; $^1$H NMR (400 MHz, DMSO-d$_6$) δ ppm 1.34-1.53 (m, 8H), 1.69-1.82 (m, 1H), 2.11-2.19 (m, 1H), 3.35 (d, J=7.58 Hz, 2H), 3.53 (s, 2H), 3.71 (s, 3H), 4.26 (d, J=7.96 Hz, 2H), 6.77-6.83 (m, 2H), 6.94-7.01 (m, 2H), 7.22-7.35 (m, 5H).

Example 1.195: Preparation of 2-(((1s,4s)-4-((5-Ethyl-4-(3-hydroxyphenyl)-3-phenyl-1H-pyrazol-1-yl)methyl)cyclohexyl)methoxy)acetic Acid (Compound 172)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and 3-hydroxyphenylboronic acid, the title compound (one of the two regioisomers separated) was obtained using a similar method to the one described in Example 1.152. LCMS m/z=449.2 [M+H]$^+$; $^1$H NMR (400 MHz, DMSO-d$_6$) δ ppm 1.03 (t, J=7.45 Hz, 3H), 1.31-1.56 (m, 8H), 1.69-1.83 (m, 1H), 2.03-2.19 (m, 1H), 2.58 (q, J=7.41 Hz, 2H), 3.40 (d, J=7.07 Hz, 2H), 3.79 (s, 2H), 4.01 (d, J=7.58 Hz, 2H), 6.54-6.63 (m, 2H), 6.67-6.75 (m, 1H), 7.09-7.38 (m, 6H).

Example 1.196: Preparation of 2-(((1s,4s)-4-((4-(3-Hydroxyphenyl)-5-(methylthio)-3-phenyl-1H-pyrazol-1-yl)methyl)cyclohexyl)methoxy)acetic Acid (Compound 173)

From tert-butyl 2-(((1s,4s)-4-((4-iodo-5-(methylthio)-3-phenyl-1H-pyrazol-1-yl)methyl)cyclohexyl)methoxy)acetate and phenylboronic acid, the title compound (one of the two regioisomers separated) was obtained using a similar method to the one described in Example 1151. LCMS m/z=467.2 [M+H]$^+$; $^1$H NMR (400 MHz, DMSO-d$_6$) δ ppm 1.31-1.53 (m, 8H), 1.70-1.80 (m, 1H), 2.13 (s, 3H), 2.15-2.25 (m, 1H), 3.38 (d, J=7.07 Hz, 2H), 3.80 (s, 2H), 4.26 (d, J=7.33 Hz, 2H), 6.63-6.78 (m, 3H), 7.13-7.20 (m, 1H), 7.21-7.30 (m, 3H), 7.33-7.38 (m, 2H).

Example 1.197: Preparation of 2-(((1s,4s)-4-((5-(Ethylthio)-4-(2-fluoro-3-hydroxyphenyl)-3-phenyl-1H-pyrazol-1-yl)methyl)cyclohexyl)methoxy)acetic Acid (Compound 174)

From tert-butyl 2-(((1s,4s)-4-((5-(ethylthio)-4-iodo-3-phenyl-1H-pyrazol-1-yl)methyl)cyclohexyl)methoxy)acetate and 2-fluoro-3-hydroxyphenylboronic acid, the title compound (one of the two regioisomers separated) was obtained using a similar method to the one described in Example 1.149. LCMS m/z=499.2 [M+H]$^+$; $^1$H NMR (400 MHz, DMSO-d$_6$) δ ppm 0.97 (t, J=7.33 Hz, 3H), 1.31-1.53 (m, 8H), 1.68-1.81 (m, 1H), 2.14-2.25 (m, 1H), 2.54 (q, J=7.33 Hz, 2H), 3.38 (d, J=6.82 Hz, 2H), 3.74 (s, 2H), 4.27 (d, J=7.33 Hz, 2H), 6.64-6.73 (m, 1H), 6.95-7.06 (m, 2H), 7.19-7.30 (m, 2H), 7.34-7.40 (m, 2H), 7.41-7.53 (m, 1H).

Example 1.198: Preparation of 2-(((1s,4s)-4-((5-(Ethylthio)-4-(3-hydroxyphenyl)-3-phenyl-1H-pyrazol-1-yl)methyl)cyclohexyl)methoxy)acetic Acid (Compound 177)

From tert-butyl 2-(((1s,4s)-4-((5-(ethylthio)-4-iodo-3-phenyl-1H-pyrazol-1-yl)methyl)cyclohexyl)methoxy)acetate and 3-hydroxyphenylboronic acid, the title compound (one of the two regioisomers separated) was obtained using a similar method to the one described in Example 1.149. LCMS m/z=489.2 [M+H]+; 1H NMR (400 MHz, DMSO-d6) δ ppm 0.97 (t, J=7.33 Hz, 3H), 1.31-1.53 (m, 8H), 1.70-1.81 (m, 1H), 2.14-2.25 (m, 1H), 2.53 (q, J=7.33 Hz, 2H), 3.41 (d, J=7.07 Hz, 2H), 4.00 (s, 2H), 4.26 (d, J=7.58 Hz, 2H), 6.63-6.76 (m, 2H), 7.14-7.21 (m, 2H), 7.21-7.30 (m, 3H), 7.32-7.39 (m, 2H).

Example 1.199: Preparation of 2-(((1s,4s)-4-((4-(3-Hydroxyphenyl)-5-(2-methoxyethyl)-3-phenyl-1H-pyrazol-1-yl)methyl)cyclohexyl)methoxy)acetic Acid (Compound 180)

Step A: Preparation of 5-(2-Methoxyethyl)-3-phenyl-1H-pyrazole

To a solution of acetophenone (3.5 g, 29.1 mmol) in dry toluene (10 mL) was added LiHMDS (1.0 M in toluene) via syringe at 0° C. under argon. After 5 min, 3-methoxypropanoyl chloride (3.57 g, 29.1 mmol) was added in one portion via syringe. The ice bath was removed and AcOH (2 mL), EtOH (100 mL), and hydrazine hydrate (4.37 g, 87 mmol) were added. The reaction was refluxed for 2 h, cooled to room temperature, and concentrated. The residue was extracted with EtOAc/H2, washed with brine, dried over MgSO4, and concentrated. The resulting residue was purified by silica gel column chromatography to give the title compound as pale yellow oil (2.0 g). LCMS m/z=203.1 [M+H]+; 1H NMR (400 MHz, DMSO-d6) δ ppm 2.85 (bs, 2H), 3.27 (s, 3H), 3.59 (t, J=6.82 Hz, 2H), 6.49 (s, 1H), 7.21-7.46 (m, 3H), 7.74 (m, 2H), 12.56 (s, 1H).

Step B: Preparation of 4-Bromo-5-(2-methoxyethyl)-3-phenyl-1H-pyrazole

To a solution of 5-(2-methoxyethyl)-3-phenyl-1H-pyrazole (2.0 g, 9.89 mmol) in DCM (100 mL) was added bromine (4.74 g, 29.7 mmol) dropwise at 0° C. The reaction was stirred at that temperature for 1 h and continued at room temperature for 2 h before quenched with Na2SO3 (10% aq.). The organics were separated, and the aqueous layer was extracted with DCM (2×50 mL). The combined organics were washed with brine, dried over MgSO4, and concentrated to give the title compound (2.5 g). LCMS m/z=281.1 [M+H]+; 1H NMR (400 MHz, DMSO-d6) δ ppm 2.87 (t, J=6.82 Hz, 21), 3.27 (s, 3H), 3.62 (t, J=6.82 Hz, 2H), 5.75 (s, 1H), 7.35-7.51 (m, 3H), 7.75-7.82 (m, 2H).

Step C: Preparation of tert-Butyl 2-(((1s,4s)-4-((4-Bromo-5-(2-methoxyethyl)-3-phenyl-1H-pyrazol-1-yl)methyl)cyclohexyl)methoxy)acetate and tert-Butyl 2-(((1s,4s)-4-((4-Bromo-3-(2-methoxyethyl)-5-phenyl-1H-pyrazol-1-yl)methyl)cyclohexyl)methoxy)acetate as a Mixture of Regioisomers To a solution of 4-bromo-5-(2-methoxyethyl)-3-phenyl-1H-pyrazole (3.0 g, 10.67 mmol) in DMF (5 mL) was added sodium hydride (0.256 g, 10.67 mmol), followed by tert-butyl 2-(((1s,4s)-4-(tosyloxymethyl)cyclohexyl)methoxy)acetate (4.40 g, 10.67 mmol). The reaction was gently heated to 45° C. overnight. After quenched with water (5 mL), the mixture was extracted with EtOAc, washed with brine, dried over MgSO4, and concentrated. The residue was purified by silica gel column chromatography to give the title compound (a mixture of two regioisomers, 4.5 g). LCMS m/z=523.4 [M+H]+; 1H NMR (400 MHz, DMSO-d6) δ ppm 1.69-1.80 (m, 4H), 1.81-1.89 (m, 4H), 1.91 (s, 9H), 2.19-2.30 (m, 2H), 2.90 (s, 3H), 3.46 (t, J=6.63 Hz, 2H), 3.89 (d, J=6.95 Hz, 2H), 4.02 (t, J=6.32 Hz, 2H), 4.43 (s, 2H), 4.56 (d, J=7.45 Hz, 2H), 7.81-7.99 (m, 3H), 8.24-8.32 (m, 2H).

Step D: Preparation of 2-(((1s,4s)-4-((4-(3-Hydroxyphenyl)-5-(2-methoxyethyl)-3-phenyl-1H-pyrazol-1-yl)methyl)cyclohexyl)methoxy)acetic Acid To a solution of tert-butyl 2-(((1s,4s)-4-((4-bromo-5-(2-methoxyethyl)-3-phenyl-1H-pyrazol-1-yl)methyl)cyclohexyl)methoxy)acetate and tert-butyl 2-(((1s,4s)-4-((4-bromo-3-(2-methoxyethyl)-5-phenyl-1H-pyrazol-1-yl)methyl)cyclohexyl)methoxy)acetate as a mixture of regioisomers (100 mg, 0.192 mmol) in dioxane (3 mL) were added 3-hydroxyphenylboronic acid (26.5 mg, 0.192 mmol), tetrakis(triphenylphosphine)palladium (22 mg, 0.019 mmol), and K2CO3 (2 M aq., 0.2 mL). The reaction was heated to 150° C. under microwave irradiation for 4 h. The reaction mixture was filtered and concentrated. The residue was treated with HCl (4.0 M in dioxane, 5 mL) at room temperature for 10 h. The mixture was concentrated and purified by HPLC to give the title compound (one of the two regioisomers separated) as a white solid (12.8 mg). LCMS m/z=479.3 [M+H]+; 1H NMR (400 MHz, DMSO-d6) δ ppm 1.32-1.57 (m, 8H), 1.73-1.82 (m, 1H), 2.07-2.18 (m, 1H), 2.83 (t, J=6.95 Hz, 2H), 3.15 (s, 3H), 3.35 (t, J=6.95 Hz, 2H), 3.43 (d, J=7.07 Hz, 2H), 4.00 (s, 2H), 4.05 (d, J=7.58 Hz, 2H), 6.56-6.75 (m, 3H), 7.14-7.26 (m, 4H), 7.30-7.37 (m, 2H).

Example 1.200: Preparation of 2-(((1s,4s)-4-((5-(2-Methoxyethyl)-4-(6-methoxypyridin-3-yl)-3-phenyl-1H-pyrazol-1-yl)methyl)cyclohexyl)methoxy)acetic Acid (Compound 181)

From tert-butyl 2-(((1s,4s)-4-((4-bromo-5-(2-methoxyethyl)-3-phenyl-1H-pyrazol-1-yl)methyl)cyclohexyl)methoxy)acetate and tert-butyl 2-(((1s,4s)-4-((4-bromo-3-(2-methoxyethyl)-5-phenyl-1H-pyrazol-1-yl)methyl)cyclohexyl)methoxy)acetate as a mixture of regioisomers and 6-methoxypyridin-3-ylboronic acid, the title compound (one of the two regioisomers separated) was obtained using a similar method to the one described in Example 1.199. LCMS m/z=494.3 [M+H]+; 1H NMR (400 MHz, DMSO-d6) δ ppm 1.33-1.57 (m, 8H), 1.74-1.84 (m, 1H), 2.09-2.18 (m, 1H), 2.83 (t, J=6.69 Hz, 2H), 3.16 (s, 3H), 3.38 (t, J=6.69 Hz, 2H), 3.43 (d, J=7.07 Hz, 2H), 3.87 (s, 3H), 4.00 (s, 2H), 4.06 (d, J=7.33 Hz, 2H), 6.83 (d, J=8.59 Hz, 1H), 7.19-7.33 (m, 5H), 7.51 (dd, J=8.46, 2.40 Hz, 1H), 8.01 (d, J=2.02 Hz, 1H).

Example 1.201: Preparation of 2-(((1s,4s)-4-((4-(2-Fluoro-3-hydroxyphenyl)-5-(2-methoxyethyl)-3-phenyl-1H-pyrazol-1-yl)methyl)cyclohexyl)methoxy)acetic Acid (Compound 182)

From tert-butyl 2-(((1s,4s)-4-((4-bromo-5-(2-methoxyethyl)-3-phenyl-1H-pyrazol-1-yl)methyl)cyclohexyl)methoxy)acetate and tert-butyl 2-(((1s,4s)-4-((4-bromo-3-(2-methoxyethyl)-5-phenyl-1H-pyrazol-1-yl)methyl)cyclohexyl)methoxy)acetate as a mixture of regioisomers and 2-fluoro-3-hydroxyphenylboronic acid, the title compound (one of the two regioisomers separated) was obtained using a similar method to the one described in Example 1.199. LCMS m/z=497.2 [M+H]+; 1H NMR (400 MHz, DMSO-d$_6$) δ ppm 1.31-1.54 (m, 8H), 1.72-1.84 (m, 1H), 2.06-2.19 (m, 1H), 2.79 (t, J=6.32 Hz, 2H), 3.12 (s, 3H), 3.31 (t, J=6.95 Hz, 2H), 3.40 (d, J=6.82 Hz, 2H), 3.68 (s, 2H), 4.07 (d, J=7.07 Hz, 2H), 6.59-6.65 (m, 1H), 6.94-7.04 (m, 2H), 7.16-7.27 (m, 3H), 7.31-7.37 (m, 2H).

Example 1.202: Preparation of 2-(((1s,4s)-4-((4-(2,3-Difluorophenyl)-5-(2-methoxyethyl)-3-phenyl-1H-pyrazol-1-yl)methyl)cyclohexyl)methoxy)acetic Acid (Compound 190)

From tert-butyl 2-(((1s,4s)-4-((4-bromo-5-(2-methoxyethyl)-3-phenyl-1H-pyrazol-1-yl)methyl)cyclohexyl)methoxy)acetate and tert-butyl 2-(((1s,4s)-4-((4-bromo-3-(2-methoxyethyl)-5-phenyl-1H-pyrazol-1-yl)methyl)cyclohexyl)methoxy)acetate as a mixture of regioisomers and 2,3-difluoro-phenylboronic acid, the title compound (one of the two regioisomers separated) was obtained using a similar method to the one described in Example 1.199. LCMS m/z=499.2 [M+H]$^+$; $^1$H NMR (400 MHz, DMSO-d$_6$) δ ppm 1.31-1.56 (m, 8H), 1.71-1.83 (m, 1H), 2.07-2.19 (m, 1H), 2.83 (t, J=6.32 Hz, 2H), 3.11 (s, 3H), 3.33 (t, J=6.57 Hz, 2H), 3.39 (d, J=6.82 Hz, 2H), 3.67 (s, 2H), 4.09 (d, J=7.33 Hz, 2H), 7.10-7.18 (m, 1H), 7.19-7.33 (m, 6H), 7.38-7.48 (m, 1H).

Example 1.203: Preparation of 2-(((1s,4s)-4-((4-(3-Chloro-2-fluorophenyl)-5-(2-methoxyethyl)-3-phenyl-1H-pyrazol-1-yl)methyl)cyclohexyl)methoxy)acetic Acid (Compound 191)

From tert-butyl 2-(((1s,4s)-4-((4-bromo-5-(2-methoxyethyl)-3-phenyl-1H-pyrazol-1-yl)methyl)cyclohexyl)methoxy)acetate and tert-butyl 2-(((1s,4s)-4-((4-bromo-3-(2-methoxyethyl)-5-phenyl-1H-pyrazol-1-yl)methyl)cyclohexyl)methoxy)acetate as a mixture of regioisomers and 3-chloro-2-fluorophenylboronic acid, the title compound (one of the two regioisomers separated) was obtained using a similar method to the one described in Example 1.199. LCMS m/z=515.2 [M+H]$^+$; $^1$H NMR (400 MHz, DMSO-d$_b$) δ ppm 1.28-1.55 (m, 8H), 1.71-1.85 (m, 1H), 2.07-2.19 (m, 1H), 2.81 (t, J=5.68 Hz, 2H), 3.11 (s, 3H), 3.32 (t, J=6.44 Hz, 2H), 3.40 (d, J=6.82 Hz, 2H), 3.68 (s, 2H), 4.09 (d, J=7.33 Hz, 2H), 7.18-7.34 (m, 6H), 7.55-7.63 (m, 2H).

Example 1.204: Preparation of 2-(((1s,4s)-4-((4-(2-Fluoro-3-methylphenyl)-5-(2-methoxyethyl)-3-phenyl-1H-pyrazol-1-yl)methyl)cyclohexyl)methoxy)acetic Acid (Compound 192)

From tert-butyl 2-(((1s,4s)-4-((4-bromo-5-(2-methoxyethyl)-3-phenyl-1H-pyrazol-1-yl)methyl)cyclohexyl)methoxy)acetate and tert-butyl 2-(((1s,4s)-4-((4-bromo-3-(2-methoxyethyl)-5-phenyl-1H-pyrazol-1-yl)methyl)cyclohexyl)methoxy)acetate as a mixture of regioisomers and 2-fluoro-3-methylphenylboronic acid, the title compound (one of the two regioisomers separated) was obtained using a similar method to the one described in Example 1.199. LCMS m/z=495.3 [M+H]$^+$; $^1$H NMR (400 MHz, DMSO-d$_6$) δ ppm 1.32-1.56 (m, 8H), 1.72-1.83 (m, 1H), 2.06-2.17 (m, 1H), 2.23 (s, 3H), 2.78 (t, J=5.94 Hz, 2H), 3.11 (s, 3H), 3.30 (t, J=6.06 Hz, 2H), 3.40 (d, J=6.57 Hz, 2H), 3.71 (s, 2H), 4.07 (d, J=6.82 Hz, 2H), 7.05-7.16 (m, 3H), 7.16-7.34 (m, 5H).

Example 1.205: Preparation of 2-(((1s,4s)-4-((5-(2-Methoxyethyl)-3-phenyl-4-m-tolyl-1H-pyrazol-1-yl)methyl)cyclohexyl)methoxy)acetic Acid (Compound 193)

From tert-butyl 2-(((1s,4s)-4-((4-bromo-5-(2-methoxyethyl)-3-phenyl-1H-pyrazol-1-yl)methyl)cyclohexyl)methoxy)acetate and tert-butyl 2-(((1s,4s)-4-((4-bromo-3-(2-methoxyethyl)-5-phenyl-1H-pyrazol-1-yl)methyl)cyclohexyl)methoxy)acetate as a mixture of regioisomers and m-tolylboronic acid, the title compound (one of the two regioisomers separated) was obtained using a similar method to the one described in Example 1.199. LCMS m/z=477.3 [M+H]$^+$; $^1$H NMR (400 MHz, DMSO-d$_6$) δ ppm 1.32-1.54 (m, 8H), 1.72-1.84 (m, 1H), 2.06-2.18 (m, 1H), 2.28 (s, 3H), 2.82 (t, J=6.82 Hz, 2H), 3.14 (s, 3H), 3.35 (t, J=6.82 Hz, 2H), 3.40 (d, J=7.07 Hz, 2H), 3.69 (s, 2H), 4.06 (d, J=7.33 Hz, 2H), 6.97 (d, J=7.58 Hz, 1H), 7.04 (s, 1H), 7.13 (d, J=7.58 Hz, 1H), 7.17-7.35 (m, 6H).

Example 1.206: Preparation of 2-(((1s,4s)-4-((4-(3-Fluorophenyl)-5-(2-methoxyethyl)-3-phenyl-1H-pyrazol-1-yl)methyl)cyclohexyl)methoxy)acetic Acid (Compound 194)

From tert-butyl 2-(((1s,4s)-4-((4-bromo-5-(2-methoxyethyl)-3-phenyl-1H-pyrazol-1-yl)methyl)cyclohexyl)methoxy)acetate and tert-butyl 2-(((1s,4s)-4-((4-bromo-3-(2-methoxyethyl)-5-phenyl-1H-pyrazol-1-yl)methyl)cyclohexyl)methoxy)acetate as a mixture of regioisomers and 3-fluorophenylboronic acid, the title compound (one of the two regioisomers separated) was obtained using a similar method to the one described in Example 1.199. LCMS m/z=481.3 [M+H]$^+$; $^1$H NMR (400 MHz, DMSO-d$_6$) δ ppm 1.32-1.56 (m, 8H), 1.73-1.83 (m, 1H), 2.07-2.18 (m, 1H), 2.87 (t, J=6.69 Hz, 2H), 3.15 (s, 3H), 3.37 (t, J=6.69 Hz, 2H), 3.41 (d, J=7.07 Hz, 2H), 3.83 (s, 2H), 4.07 (d, J=7.33 Hz, 2H), 7.01-7.06 (m, 2H), 7.11-7.18 (m, 1H), 7.19-7.33 (m, 4H), 7.37-7.45 (m, 2H).

Example 1.207: Preparation of 2-(((1s,4s)-4-((4-(2-Methoxypyridin-4-yl)-5-methyl-3-phenyl-1H-pyrazol-1-yl)methyl)cyclohexyl)methoxy)acetic Acid (Compound 195)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers and 2-methoxypyridin-4-ylboronic acid, the title compound (one of the two regioisomers separated) was obtained using a similar method to the one described in Example 1.97. LCMS m/z=450.2 [M+H]$^+$; $^1$H NMR (400 MHz, DMSO-d$_6$) δ ppm 1.32-1.54 (m, 8H), 1.71-1.80 (m, 1H), 2.04-2.13 (m, 1H), 2.28 (s, 3H), 3.42 (d, J=7.07 Hz, 2H), 3.85 (s, 3H), 3.99 (s, 2H), 4.06 (d, J=7.33 Hz, 2H), 6.62 (s, 1H), 6.74 (dd, J=5.31, 1.26 Hz, 1H), 7.26-7.35 (m, 5H), 8.10 (d, J=5.31 Hz, 1H).

Example 1.208: Preparation of 2-(((1s,4s)-4-((5-Ethyl-4-(2-methoxypyridin-4-yl)-3-phenyl-1H-pyrazol-1-yl)methyl)cyclohexyl)methoxy)acetic Acid (Compound 196)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H- pyrazol-1-yl)methyl)cyclohexyl)methoxy)acetate as a mixture of regioisomers and 2-methoxypyridin-4-ylboronic acid, the title compound (one of the two regioisomers separated) was obtained using a similar method to the one described in Example 1.152. LCMS m/z=464.3 [M+H]$^+$; $^1$H NMR (400 MHz, DMSO-d$_6$) δ ppm 1.06 (t, J=7.58 Hz, 3H), 1.32-1.57 (m, 8H), 1.71-1.83 (m, 1H), 2.07-2.18 (m, 1H), 2.67 (q, J=7.49 Hz, 2H), 3.43 (d, J=6.82 Hz, 2H), 3.85 (s, 3H), 4.00 (s, 2H), 4.04 (d, J=7.33 Hz, 2H), 6.61 (s, 1H), 6.76 (dd, J=5.31, 1.26 Hz, 1H), 7.22-7.34 (m, 5H), 8.12 (d, J=5.31 Hz, 1H).

Example 1.209: Preparation of 2-(((1s,4s)-4-((4-(3-Chlorophenyl)-5-(2-methoxyethyl)-3-phenyl-1H-pyrazol-1-yl)methyl)cyclohexyl)methoxy)acetic Acid (Compound 197)

From tert-butyl 2-(((1s,4s)-4-((4-bromo-5-(2-methoxyethyl)-3-phenyl-1H-pyrazol-1-yl)methyl)cyclohexyl)methoxy)acetate and tert-butyl 2-(((1s,4s)-4-((4-bromo-3-(2-methoxyethyl)-5-phenyl-1H-pyrazol-1-yl)methyl)cyclohexyl)methoxy)acetate as a mixture of regioisomers and 3-chlorophenylboronic acid, the title compound (one of the two regioisomers separated) was obtained using a similar method to the one described in Example 1.199. LCMS m/z=497.2 [M+H]$^+$; $^1$H NMR (400 MHz, DMSO-d$_6$) δ ppm 1.33-1.56 (m, 8H), 1.73-1.84 (m, 1H), 2.06-2.18 (m, 1H), 2.86 (t, J=6.69 Hz, 2H), 3.15 (s, 3H), 3.37 (d, J=6.82 Hz, 2H), 3.39 (t, J=7.07 Hz, 2H), 3.75 (s, 2H), 4.06 (d, J=7.58 Hz, 2H), 7.14-7.19 (m, 1H), 7.20-7.31 (m, 6H), 7.35-7.43 (m, 2H).

Example 1.210: Preparation of 2-(((1s,4s)-4-((5-Ethyl-4-(5-methoxypyridin-3-yl)-3-phenyl-1H-pyrazol-1-yl)methyl)cyclohexyl)methoxy)acetic Acid (Compound 201)

From tert-butyl 2-(((1s,4s)-4-((4-bromo-3-ethyl-5-phenyl-1H-pyrazol-1-yl)methyl)cyclohexyl)methoxy)acetate and tert-butyl 2-(((1s,4s)-4-((4-bromo-5-ethyl-3-phenyl-1H-pyrazol-1-yl)methyl)cyclohexyl)methoxy)acetate as a mixture of regioisomers and 5-methoxypyridin-3-ylboronic acid, the title compound (one of the two regioisomers separated) was obtained using a similar method to the one described in Example 1152. LCMS m/z=464.3 [M+H]$^+$; $^1$H NMR (400 MHz, DMSO-d$_6$) δ ppm 1.05 (t, J=7.52 Hz, 3H), 1.36-1.58 (m, 8H), 1.74-1.83 (m, 1H), 2.10-2.19 (m, 1H), 2.67 (q, J=7.45 Hz, 2H), 3.44 (d, J=7.07 Hz, 2H), 3.84 (s, 3H), 4.00 (s, 2H), 4.07 (d, J=7.45 Hz, 2H), 7.23-7.33 (m, 5H), 7.47 (dd, J=2.65, 1.64 Hz, 1H), 8.09 (d, J=1.64 Hz, 1H), 8.38 (d, J=2.78 Hz, 1H).

Example 1.211: Preparation of 2-(((1s,4s)-4-((4-(2-Fluoro-3-hydroxyphenyl)-5-(2-(methylthio)ethyl)-3-phenyl-1H-pyrazol-1-yl)methyl)cyclohexyl)methoxy)acetic Acid (Compound 213)

Step A: Preparation of 5-(2-(Methylthio)ethyl)-3-phenyl-1H-pyrazole

To a solution of acetophenone (5.0 g, 41.6 mmol) in dry toluene (10 mL) was added LiHMDS (1.0 M in toluene, 42 mL, 42 mmol) via syringe at 0° C. under argon. After 5 min, 3-(methylthio)propanoyl chloride (5.77 g, 41.6 mmol) was added in one portion via syringe. The ice bath was removed and AcOH (5 mL), EtOH (100 mL), and hydrazine hydrate (6.25 g, 125 mmol) were added. The mixture was refluxed for 2 h, cooled to room temperature, and concentrated. The residue was extracted with EtOAc/H$_2$O, washed with brine, dried over MgSO$_4$, and concentrated. The resulting residue was purified by silica gel column chromatography to give the title compound as a pale yellow oil (6.5 g). LCMS m/z=219.2 [M+H]$^+$; $^1$H NMR (400 MHz, DMSO-d$_6$) δ ppm 2.09 (s, 3H), 2.77 (t, J=7.71 Hz, 2H), 2.84-2.95 (m, 2H), 6.53 (s, 1H), 7.18-7.50 (m, 3H), 7.63-7.84 (m, 2H), 12.60 (bs, 1H).

Step B: Preparation of 4-Bromo-5-(2-(methylthio)ethyl)-3-phenyl-1H-pyrazole

To a solution of 5-(2-(methylthio)ethyl)-3-phenyl-1H-pyrazole (4.0 g, 18.32 mmol) in methanol (20 mL) was added N-bromosuccinimide (3.26 g, 18.32 mmol) slowly at 0° C. The reaction was stirred at 0° C. for 2 h. The mixture was concentrated and purified by silica gel column chromatography to give the title compound (3.4 g). LCMS m/z=297.0 [M+H]$^+$; $^1$H NMR (400 MHz, DMSO-d$_6$) δ ppm 2.11 (s, 3H), 2.79 (t, J=7.83 Hz, 2H), 2.83-2.97 (m, 2H), 7.32-7.56 (m, 3H), 7.67-7.88 (m, 2H), 13.20 (bs, 1H).

Step C: Preparation of tert-Butyl 2-(((1s,4s)-4-((4-Bromo-5-(2-(methylthio)ethyl)-3-phenyl-1H-pyrazol-1-yl)methyl)cyclohexyl)methoxy)acetate and tert-Butyl 2-(((1s,4s)-4-((4-Bromo-3-(2-(methylthio)ethyl)-5-phenyl-1H-pyrazol-1-yl)methyl)cyclohexyl)methoxy)acetate as a Mixture of Regioisomers To a solution of 4-bromo-5-(2-(methylthio)ethyl)-3-phenyl-1H-pyrazole (3.4 g, 11.44 mmol) in DMF (5 mL) was added sodium hydride (0.275 g, 11.44 mmol) at room temperature, followed by tert-butyl 2-(((1s,4s)-4-(tosyloxymethyl)cyclohexyl)methoxy)acetate (4.72 g, 11.44 mmol). The reaction was heated to 45° C. overnight, cooled to room temperature, and quenched with water (5 mL). The mixture was extracted with EtOAc, washed with brine, dried over MgSO$_4$, and concentrated. The residue was purified by silica gel column chromatography to give the title compound (a mixture of two regioisomers, 3.5 g). LCMS m/z=539.1 [M+H]$^+$; $^1$H NMR (400 MHz, DMSO-d$_6$) δ ppm 1.30-1.40 (m, 4H), 1.43 (s, 9H), 1.44-1.52 (m, 4H), 1.70-1.80 (m, 1H), 2.03-2.11 (m, 1H), 2.14 (s, 3H), 2.72 (t, J=7.07 Hz, 2H), 3.00 (t, J=7.20 Hz, 2H), 3.40 (d, J=6.95 Hz, 2H), 3.94 (s, 2H), 4.09 (d, J=7.45 Hz, 2H), 7.32-7.51 (m, 3H), 7.75-7.84 (m, 2H).

Step D: Preparation of 2-(((1s,4s)-4-((4-(2-Fluoro-3-hydroxyphenyl)-5-(2-(methylthio)ethyl)-3-phenyl-1H-pyrazol-1-yl)methyl)cyclohexyl)methoxy)acetic Acid To a solution of tert-butyl 2-(((1s,4s)-4-((4-bromo-5-(2-(methylthio)ethyl)-3-phenyl-1H-pyrazol-1-yl)methyl)cyclohexyl)methoxy)acetate and tert-butyl 2-(((1s,4s)-4-((4-bromo-3-(2-(methylthio)ethyl)-5-phenyl-1H-pyrazol-1-yl)methyl)cyclohexyl)methoxy)acetate as a mixture of regioisomers (100 mg, 0.19 mmol) in dioxane were added 2-fluoro-3-hydroxyphenylboronic acid (29.6 mg, 0.19 mmol), tetrakis(triphenylphosphine)palladium (22 mg, 0.019 mmol), and K$_2$CO$_3$ (2 M aq., 0.2 mL). The reaction was heated to 150° C. under microwave irradiation for 4 h. The reaction mixture was filtered and concentrated. The residue was treated with HCl (4.0 M in dioxane, 5 mL) at room temperature for 10 h. The mixture was concentrated and purified by HPLC to give the title compound (one of the two regioisomers separated) as a white solid (15.5 mg). LCMS m/z=513.2 [M+H]⁺; ¹H NMR (400 MHz, DMSO-d₆) δ ppm 1.32-1.57 (m, 8H), 1.74-1.82 (m, 1H), 1.88 (s, 3H), 2.08-2.18 (m, 1H), 2.46 (t, J=7.71 Hz, 2H), 2.82 (t, J=7.20 Hz, 2H), 3.43 (d, J=7.07 Hz, 2H), 4.00 (s, 2H), 4.08 (d, J=7.45 Hz, 2H), 6.65-6.72 (m, 1H), 6.91-7.04 (m, 3H), 7.17-7.28 (m, 3H), 7.31-7.37 (m, 1H).

Example 1.212: Preparation of 2-(((1s,4s)-4-((4-(5-Methoxypyridin-3-yl)-5-methyl-3-phenyl-1H-pyrazol-1-yl)methyl)cyclohexyl)methoxy)acetic Acid (Compound 214)

From tert-butyl 2-(((1s,4s)-4-((4-bromo-3-methyl-5-phenyl-1H-pyrazol-1-yl)methyl)cyclohexyl)methoxy)acetate and tert-butyl 2-(((1s,4s)-4-((4-bromo-5-methyl-3-phenyl-1H-pyrazol-1-yl)methyl)cyclohexyl)methoxy)acetate as a mixture of regioisomers, and 5-methoxypyridin-3-ylboronic acid, the title compound (one of the two regioisomers separated) was obtained using a similar method to the one described in Example 1.97. LCMS m/z=450.2 [M+H]⁺; ¹H NMR (400 MHz, DMSO-d₆) δ ppm 1.35-1.55 (m, 8H), 1.72-1.82 (m, 114), 2.05-2.15 (m, 1H), 2.27 (s, 3H), 3.42 (d, J=7.07 Hz, 2H), 3.81 (s, 3H), 4.00 (s, 2H), 4.08 (d, J=7.45 Hz, 2H), 7.23-7.33 (m, 5H), 7.39 (dd, J=2.65, 1.64 Hz, 1H), 8.04 (d, J=1.52 Hz, 1H), 8.32 (d, J=2.78 Hz, 1H).

Example 1.213: Preparation of 2-(((1s,4s)-4-((5-(2-(Methylthio)ethyl)-3-phenyl-4-m-tolyl-1H-pyrazol-1-yl)methyl)cyclohexyl)methoxy)acetic Acid (Compound 216)

From tert-butyl 2-(((1s,4s)-4-((4-bromo-5-(2-(methylthio)ethyl)-3-phenyl-1H-pyrazol-1-yl)methyl)cyclohexyl)methoxy)acetate and tert-butyl 2-(((1s,4s)-4-((4-bromo-3-(2-(methylthio)ethyl)-5-phenyl-1H-pyrazol-1-yl)methyl)cyclohexyl)methoxy)acetate as a mixture of regioisomers and m-tolylboronic acid, the title compound (one of the two regioisomers separated) was obtained using a similar method to the one described in Example 1.211. LCMS m/z=493.3 [M+H]⁺; ¹H NMR (400 MHz, DMSO-d₆) δ ppm 1.33-1.56 (m, 8H), 1.70-1.82 (m, 1H), 1.89 (s, 3H), 2.07-2.16 (m, 1H), 2.29 (s, 3H), 2.50 (t, J=7.06 Hz, 2H), 2.86 (t, J=7.33 Hz, 2H), 3.40 (d, J=6.80 Hz, 2H), 3.77 (s, 2H), 4.06 (d, J=7.45 Hz, 2H), 6.98 (d, J=7.71 Hz, 1H), 7.07 (s, 1H), 7.13 (d, J=7.58 Hz, 1H), 7.17-7.28 (m, 4H), 7.29-7.35 (m, 2H).

Example 1.214: Preparation of 2-(((1s,4s)-4-((4-(2-Fluoro-3-methylphenyl)-5-(2-(methylthio)ethyl)-3-phenyl-1H-pyrazol-1-yl)methyl)cyclohexyl)methoxy)acetic Acid (Compound 218)

From tert-butyl 2-(((1s,4s)-4-((4-bromo-5-(2-(methylthio)ethyl)-3-phenyl-1H-pyrazol-1-yl)methyl)cyclohexyl)methoxy)acetate and tert-butyl 2-(((1s,4s)-4-((4-bromo-3-(2-(methylthio)ethyl)-5-phenyl-1H-pyrazol-1-yl)methyl)cyclohexyl)methoxy)acetate as a mixture of regioisomers and 2-fluoro-3-methylphenylboronic acid, the title compound (one of the two regioisomers separated) was obtained using a similar method to the one described in Example 1.211. LCMS m/z=511.2 [M+H]⁺; ¹H NMR (400 MHz, DMSO-d₆) δ ppm 1.33-1.56 (m, 8H), 1.73-1.81 (m, 1H), 1.85 (s, 3H), 2.09-2.17 (m, 1H), 2.23 (s, 3H), 2.46 (t, J=7.71 Hz, 2H), 2.81 (t, J=7.07 Hz, 2H), 3.41 (d, J=6.95 Hz, 2H), 3.81 (s, 2H), 4.08 (d, J=7.45 Hz, 2H), 7.07-7.14 (m, 2H), 7.18-7.26 (m, 3H), 7.26-7.35 (m, 3H).

Example 1.215: Preparation of 2-(((1s,4s)-4-((4-(3-Chloro-2-fluorophenyl)-5-(2-(methylsulfinyl)ethyl)-3-phenyl-1H-pyrazol-1-yl)methyl)cyclohexyl)methoxy)acetic Acid (Compound 219)

2-(((1s,4s)-4-((4-(3-Chloro-2-fluorophenyl)-5-(2-(methylthio)ethyl)-3-phenyl-1H-pyrazol-1-yl)methyl)cyclohexyl)methoxy)acetic acid (16.4 mg, 0.031 mmol) was dissolved in DCM (2 mL) and 3-chloroperbenzoic acid (5.33 mg, 0.031 mmol) was added. After stirred at room temperature for 30 min, the reaction mixture was concentrated and purified by HPLC to give the title compound as a white solid (10.8 mg). LCMS m/z=547.2 [M+H]⁺; ¹H NMR (400 MHz, DMSO-d₆) δ ppm 1.33-1.56 (m, 8H), 1.74-1.82 (m, 1H), 2.10-2.20 (m, 1H), 2.46 (s, 3H), 2.66-2.77 (m, 2H), 2.83-3.00 (m, 2H), 3.43 (d, J=7.07 Hz, 2H), 3.99 (s, 2H), 4.08-4.14 (m, 2H), 7.20-7.30 (m, 6H), 7.30-7.36 (m, 1H), 7.56-7.64 (m, 1H).

Example 1.216: Preparation of 2-(((1s,4s)-4-((5-(2-(Methylsulfinyl)ethyl)-3-phenyl-4-m-tolyl-1H-pyrazol-1-yl)methyl)cyclohexyl)methoxy)acetic Acid (Compound 220)

To a solution of 2-(((1s,4s)-4-((5-(2-(methylthio)ethyl)-3-phenyl-4-m-tolyl-1H-pyrazol-1-yl)methyl)cyclohexyl)methoxy)acetic acid (19.7 mg, 0.040 mmol) in DCM (2 mL) was added 3-chloroperbenzoic acid (6.9 mg, 0.040 mmol). After stirred at room temperature for 30 min, the reaction mixture was concentrated and purified by HPLC to give the title compound as a white solid (14.2 mg). LCMS m/z=509.2 [M+H]⁺; ¹H NMR (400 MHz, DMSO-d₆) δ ppm 1.31-1.55 (m, 8H), 1.71-.81 (m, 1H), 2.08-2.18 (m, 1H), 2.27 (s, 3H), 2.44 (s, 3H), 2.68-2.79 (m, 2H), 2.82-2.99 (m, 2H), 3.43 (d, J=7.07 Hz, 2H), 3.98 (s, 2H), 4.04-4.10 (m, 2H), 6.97 (d, J=7.58 Hz, 1H), 7.05 (s, 1H), 7.13 (d, J=7.58 Hz, 1H), 7.17-7.27 (m, 4H), 7.28-7.33 (m, 2H).

Example 1.217: Preparation of 2-(((1s,4s)-4-((4-(3-Hydroxyphenyl)-5-(2-(methylthio)ethyl)-3-phenyl-1H-pyrazol-1-yl)methyl)cyclohexyl)methoxy)acetic Acid (Compound 221)

From tert-butyl 2-(((1s,4s)-4-((4-bromo-5-(2-(methylthio)ethyl)-3-phenyl-1H-pyrazol-1-yl)methyl)cyclohexyl)methoxy)acetate and tert-butyl 2-(((1s,4s)-4-((4-bromo-3-(2-(methylthio)ethyl)-5-phenyl-1H-pyrazol-1-yl)methyl)cyclohexyl)methoxy)acetate as a mixture of regioisomers and 3-hydroxyphenylboronic acid, the title compound (one of the two regioisomers separated) was obtained using a similar method to the one described in Example 1.211. LCMS m/z=495.2 [M+H]⁺; ¹H NMR (400 MHz, DMSO-d₆) δ ppm 1.34-1.55 (m, 8H), 1.74-1.82 (m, 1H), 1.91 (s, 3H), 2.09-2.16 (m, 1H), 2.51 (t, J=6.82 Hz, 2H), 2.86 (t, J=7.33 Hz, 2H), 3.43 (d, J=7.07 Hz, 2H), 4.00 (s, 2H), 4.06 (d, J=7.45 Hz, 2H), 6.57-6.75 (m, 3H), 7.15-7.27 (m, 4H), 7.32-7.37 (m, 2H).

Example 1.218: Preparation of 2-(((1s,4s)-4-((4-(3-Fluorophenyl)-5-(2-(methylthio)ethyl)-3-phenyl-1H-pyrazol-1-yl)methyl)cyclohexyl)methoxy)acetic Acid (Compound 222)

From tert-butyl 2-(((1s,4s)-4-((4-bromo-5-(2-(methylthio)ethyl)-3-phenyl-1H-pyrazol-1-yl)methyl)cyclohexyl)

methoxy)acetate and tert-butyl 2-(((1s,4s)-4-((4-bromo-3-(2-(methylthio)ethyl)-5-phenyl-1H-pyrazol-1-yl)methyl)cyclohexyl)methoxy)acetate as a mixture of regioisomers and 3-fluorophenylboronic acid, the title compound was obtained using a similar method to the one described in Example 1.211. LCMS m/z=497.2 [M+H]⁺; ¹H NMR (400 MHz, DMSO-d₆) δ ppm 1.34-1.59 (m, 8I), 1.74-1.82 (m, 1H), 1.90 (s, 3H), 2.09-2.18 (m, 1H), 2.52 (t, J=6.82 Hz, 2H), 2.91 (t, J=7.33 Hz, 2H), 3.44 (d, J=6.95 Hz, 2H), 4.00 (s, 2H), 4.08 (d, J=7.45 Hz, 2H), 7.02-7.09 (m, 2H), 7.12-7.19 (m, 1H), 7.19-7.33 (m, 5H), 7.38-7.47 (m, 1H).

Example 1.219: Preparation of 2-(((1s,4s)-4-((4-(3-Chlorophenyl)-5-(2-(methylthio)ethyl)-3-phenyl-1H-pyrazol-1-yl)methyl)cyclohexyl)methoxy)acetic Acid (Compound 237)

From tert-butyl 2-(((1s,4s)-4-((4-bromo-5-(2-(methylthio)ethyl)-3-phenyl-1H-pyrazol-1-yl)methyl)cyclohexyl)methoxy)acetate and tert-butyl 2-(((1s,4s)-4-((4-bromo-3-(2-(methylthio)ethyl)-5-phenyl-1H-pyrazol-1-yl)methyl)cyclohexyl)methoxy)acetate as a mixture of regioisomers and 3-chlorophenylboronic acid, the title compound (one of the two regioisomers separated) was obtained using a similar method to the one described in Example 1.211. LCMS m/z=513.2 [M+H]⁺; ¹H NMR (400 MHz, DMSO-d₆) δ ppm 1.35-1.55 (m, 8H), 1.74-1.82 (m, 1H), 1.90 (s, 3H), 2.09-2.17 (m, 1H), 2.53 (t, J=7.20 Hz, 2H), 2.90 (t, J=7.45 Hz, 2H), 3.43 (d, J=7.07 Hz, 2H), 3.96 (s, 2H), 4.07 (d, J=7.45 Hz, 2H), 7.15-7.19 (m, 2H), 7.22-7.32 (m, 5H), 7.37-7.41 (m, 2H).

Example 1.220: Preparation of 2-(((1s,4s)-4-((5-(2-(Methylthio)ethyl)-3,4-diphenyl-1H-pyrazol-1-yl)methyl)cyclohexyl)methoxy)acetic Acid (Compound 238)

From tert-butyl 2-(((1s,4s)-4-((4-bromo-5-(2-(methylthio)ethyl)-3-phenyl-1H-pyrazol-1-yl)methyl)cyclohexyl)methoxy)acetate and tert-butyl 2-(((1s,4s)-4-((4-bromo-3-(2-(methylthio)ethyl)-5-phenyl-1H-pyrazol-1-yl)methyl)cyclohexyl)methoxy)acetate as a mixture of regioisomers and phenylboronic acid, the title compound (one of the two regioisomers separated) was obtained using a similar method to the one described in Example 1.211. LCMS m/z=479.2 [M+H]⁺; ¹H NMR (400 MHz, DMSO-d₆) δ ppm 1.34-1.56 (m, 8H), 1.73-1.81 (m, 1H), 1.88 (s, 3H), 2.08-2.18 (m, 1H), 2.50 (t, J=7.33 Hz, 2H), 2.87 (t, J=7.33 Hz, 2H), 3.42 (d, J=7.07 Hz, 2H), 3.88 (s, 2H), 4.07 (d, J=7.45 Hz, 2H), 7.16-7.25 (m, 5H), 7.28-7.41 (m, 5H).

Example 1.221: Preparation of 2-(((1s,4s)-4-((5-(2-Fluoro-4-methylphenyl)-3-(2-methoxyethyl)-4-phenyl-1H-pyrazol-1-yl)methyl)cyclohexyl)methoxy)acetic Acid (Compound 239)

Step A: Preparation of 5-(2-Methoxyethyl)-4-phenyl-1H-pyrazole

To a solution of 2-phenylacetaldehyde (4.0 g, 33.3 mmol) in toluene (10 mL), were added LiHMDS (33.3 mL, 33.3 mmol) at 0° C. After stirring for 10 min, 3-methoxypropanoyl chloride (4.08 g, 33.3 mmol) was added and continued stirring for 30 min at 0° C. The reaction was quenched with acetic acid (glacial, 2 mL), diluted with ethanol (75 mL), and hydrazine hydrate (5.00 g, 100 mmol) was added. The reaction was brought to reflux for 4 hrs. After cooling to room temperature, the reaction was concentrated and extracted with EtOAc, dried over MgSO₄, and purified by column chromatography to give the title compound as yellowish oil (2.5 g). LCMS m/z=203.1 [M+H]⁺; ¹H NMR (400 MHz, DMSO-d₆) δ ppm 2.85 (t, J=6.69 Hz, 2H), 3.17 (s, 3H), 3.48 (t, J=6.63 Hz, 2H), 5.75 (s, 1H), 7.31-7.38 (m, 3H), 7.41-7.47 (m, 2H), 13.08 (s, 1H).

Step B: Preparation of 3-Bromo-5-(2-methoxyethyl)-4-phenyl-1H-pyrazole

To a solution of 5-(2-methoxyethyl)-4-phenyl-1H-pyrazole (1.0 g, 4.94 mmol) in methanol (20 mL) was added N-bromosuccinimide (0.880 g, 4.94 mmol) in portions at room temperature. After stirred at room temperature for 16 h, the reaction was concentrated and extracted with EtOAc/H₂O, purified by column chromatography to give the title compound as yellow oil (1.0 g). LCMS m/z=281.3 [M+H]⁺; ¹H NMR (400 MHz, DMSO-d₆) δ ppm 2.97 (t, J=6.63 Hz, 2H), 3.22 (s, 3H), 3.57 (t, J=7.07 Hz, 2H), 7.20-7.27 (m, 2H), 7.35-7.45 (m, 3H), 12.67 (bs, 1H).

Step C: Preparation of tert-Butyl 2-(((1s,4s)-4-((3-Bromo-5-(2-methoxyethyl)-4-phenyl-1H-pyrazol-1-yl)methyl)cyclohexyl)methoxy)acetate and tert-Butyl 2-(((1s,4s)-4-((5-Bromo-3-(2-methoxyethyl)-4-phenyl-1H-pyrazol-1-yl)methyl)cyclohexyl)methoxy)acetate as a Mixture of Regioisomers To a solution of 3-bromo-5-(2-methoxyethyl)-4-phenyl-1H-pyrazole (1.0 g, 3.6 mmol) in DMF (5 mL) were added cesium carbonate (1.16 g, 3.6 mmol), followed by tert-butyl 2-(((1s,4s)-4-(tosyloxymethyl)cyclohexyl)methoxy)acetate (1.47 g, 3.6 mmol). The reaction was gently heated to 80° C. for 10 h. After cooled to room temperature, the reaction was quenched with water (2 mL), extracted with EtOAc, dried over MgSO₄, and purified by column chromatography to give the title compound as clear oil. LCMS m/z=521.5 [M+H]⁺; ¹H NMR (400 MHz, DMSO-d₆) δ ppm 1.33-1.42 (m, 4H), 1.43 (s, 9H), 1.44-1.52 (m, 4H), 1.70-1.81 (m, 1H), 2.04-2.14 (m, 1H), 2.91 (t, J=6.57 Hz, 2H), 3.14 (s, 3H), 3.41 (d, J=6.95 Hz, 2H), 3.47 (t, J=7.20 Hz, 2H), 3.95 (s, 2H), 4.04 (d, J=7.07 Hz, 2H), 7.32-7.39 (m, 3H), 7.40-7.50 (m, 2H).

Step D: Preparation of 2-(((1s,4s)-4-((5-(2-Fluoro-4-methylphenyl)-3-(2-methoxyethyl)-4-phenyl-1H-pyrazol-1-yl)methyl)cyclohexyl)methoxy)acetic Acid To a solution of tert-butyl 2-(((1s,4s)-4-((3-bromo-5-(2-methoxyethyl)-4-phenyl-1H-pyrazol-1-yl)methyl)cyclohexyl)methoxy)acetate and tert-butyl 2-(((1s,4s)-4-((5-bromo-3-(2-methoxyethyl)-4-phenyl-1H-pyrazol-1-yl)methyl)cyclohexyl)methoxy)acetate as a mixture of regioisomers (100 mg, 0.19 mmol) in dioxane (3 mL) were added 2-fluoro-4-methylphenylboronic acid (29.3 mg, 0.19 mmol), tetrakis(triphenylphosphine)palladium (22 mg, 0.019 mmol), and K₂CO₃ (2 M aq., 0.2 mL). The reaction was heated to 150° C. under microwave irradiation for 4 h. After filtered and concentrated, the residue was treated with HCl (4.0 M in dioxane, 5 mL) at room temperature for 10 h. The mixture was concentrated and purified by HPLC to give the title compound as white solid (15.6 mg). LCMS m/z=495.4 [M+H]⁺; ¹H NMR (400 MHz, DMSO-d₆) δ ppm 1.05-1.18 (m, 4H), 1.21-1.36 (m, 4H), 1.56-1.67 (m, 1H), 1.85-1.97 (m, 1H), 2.33 (s, 3H), 2.84 (t, J=7.45 Hz, 2H), 3.18 (s, 3H), 3.19 (d, J=7.07 Hz, 2H), 3.53 (t, J=7.39 Hz, 2H), 3.74 (s, 2H), 3.81 (d, J=7.83 Hz, 2H), 7.03-7.13 (m, 5H), 7.13-7.20 (m, 2H), 7.22-7.28 (m, 2H).

Example 1.222: Preparation of 2-(((1s,4s)-4-((3-(2-Fluoro-4-methylphenyl)-5-(2-methoxyethyl)-4-phenyl-1H-pyrazol-1-yl)methyl)cyclohexyl)methoxy) acetic Acid (Compound 240)

From tert-butyl 2-(((1s,4s)-4-((3-bromo-5-(2-methoxyethyl)-4-phenyl-1H-pyrazol-1-yl)methyl)cyclohexyl)methoxy)acetate and tert-butyl 2-(((1s,4s)-4-((5-bromo-3-(2-methoxyethyl)-4-phenyl-1H-pyrazol-1-yl)methyl)cyclohexyl)methoxy)acetate as a mixture of regioisomers and 2-fluoro-4-methylphenylboronic acid, the title compound (one of the two regioisomers separated) was obtained using a similar method to the one described in Example 1.221. LCMS m/z=495.4 [M+H]$^+$; $^1$H NMR (400 MHz, DMSO-$d_6$) δ ppm 1.32-1.55 (m, 8H), 1.71-1.82 (m, 1H), 2.04-2.17 (m, 1H), 2.28 (s, 3H), 2.93 (t, J=6.82 Hz, 2H), 3.16 (s, 3H), 3.40 (t, J=6.63 Hz, 2H), 3.41 (d, J=6.69 Hz, 2H), 3.87 (s, 2H), 4.07 (d, J=7.45 Hz, 2H), 6.87-6.98 (m, 2H), 7.07-7.13 (m, 2H), 7.16-7.31 (m, 5H).

Example 1.223: Preparation of 2-(((1s,4s)-4-((4-(2-Fluoro-4-methylphenyl)-5-(2-methoxyethyl)-3-phenyl-1H-pyrazol-1-yl)methyl)cyclohexyl)methoxy) acetic Acid (Compound 241)

From tert-butyl 2-(((1s,4s)-4-((4-bromo-5-(2-methoxyethyl)-3-phenyl-1H-pyrazol-1-yl)methyl)cyclohexyl)methoxy)acetate and tert-butyl 2-(((1s,4s)-4-((4-bromo-3-(2-methoxyethyl)-5-phenyl-1H-pyrazol-1-yl)methyl)cyclohexyl)methoxy)acetate as a mixture of regioisomers and 2-fluoro-4-methylphenylboronic acid, the title compound (one of the two regioisomers separated) was obtained using a similar method to the one described in Example 1.199. LCMS m/z=495.2 [M+H]$^+$; $^1$H NMR (400 MHz, DMSO-$d_6$) δ ppm 1.31-1.57 (m, 8H), 1.73-1.83 (m, 1H), 2.08-2.18 (m, 1H), 2.36 (s, 3H), 2.78 (t, J=6.76 Hz, 2H), 3.12 (s, 3H), 3.30 (t, J=6.82 Hz, 2H), 3.42 (d, J=7.07 Hz, 2H), 3.92 (s, 2H), 4.07 (d, J=7.45 Hz, 2H), 7.03-7.10 (m, 2H), 7.13-7.27 (m, 4H), 7.30-7.34 (m, 2H).

Example 1.224: Preparation of 2-(((1s,4s)-4-((4-(2-Fluoro-4-methylphenyl)-5-(2-(methylthio)ethyl)-3-phenyl-1H-pyrazol-1-yl)methyl)cyclohexyl) methoxy)acetic Acid (Compound 242)

From tert-butyl 2-(((1s,4s)-4-((4-bromo-5-(2-(methylthio)ethyl)-3-phenyl-1H-pyrazol-1-yl)methyl)cyclohexyl)methoxy)acetate and tert-butyl 2-(((1s,4s)-4-((4-bromo-3-(2-(methylthio)ethyl)-5-phenyl-1H-pyrazol-1-yl)methyl)cyclohexyl)methoxy)acetate as a mixture of regioisomers and 2-fluoro-4-methylphenylboronic acid, the title compound (one of the two regioisomers separated) was obtained using a similar method to the one described in Example 1.211. LCMS m/z=511.1 [M+H]$^+$; $^1$H NMR (400 MHz, DMSO-$d_6$) δ ppm 1.34-1.55 (m, 8H), 1.73-1.82 (m, 1H), 1.88 (s, 3H), 2.08-2.18 (m, 1H), 2.36 (s, 3H), 2.48 (t, J=7.58 Hz, 2H), 2.82 (t, J=7.20 Hz, 2H), 3.43 (d, J=7.07 Hz, 2H), 3.95 (s, 2H), 4.08 (d, J=7.45 Hz, 2H), 7.03-7.11 (m, 2H), 7.15-7.27 (m, 4H), 7.30-7.35 (m, 2H).

Example 1.225: Preparation of 2-(((1s,4s)-4-((4-(3-Methoxyphenyl)-5-(2-(methylthio)ethyl)-3-phenyl-1H-pyrazol-1-yl)methyl)cyclohexyl)methoxy)acetic Acid (Compound 243)

From tert-butyl 2-(((1s,4s)-4-((4-bromo-5-(2-(methylthio)ethyl)-3-phenyl-1H-pyrazol-1-yl)methyl)cyclohexyl)methoxy)acetate and tert-butyl 2-(((1s,4s)-4-((4-bromo-3-(2-(methylthio)ethyl)-5-phenyl-1H-pyrazol-1-yl)methyl)cyclohexyl)methoxy)acetate as a mixture of regioisomers and 3-methoxyphenylboronic acid, the title compound (one of the two regioisomers separated) was obtained using a similar method to the one described in Example 1.211. LCMS m/z=509.7 [M+H]$^+$; $^1$H NMR (400 MHz, DMSO-$d_6$) δ ppm 1.34-1.56 (m, 8H), 1.74-1.82 (m, 1H), 191 (s, 3H), 2.09-2.18 (m, 1H), 2.52 (t, J=8.46 Hz, 2H), 2.89 (t, J=8.21 Hz, 2H), 3.43 (d, J=6.95 Hz, 2H), 3.70 (s, 3H), 3.98 (s, 2H), 4.06 (d, J=7.33 Hz, 2H), 6.74-6.80 (m, 2H), 6.87-6.92 (m, 1H), 7.17-7.36 (m, 6H).

Example 1.226: Preparation of 2-(((1s,4s)-4-((4-(2,3-Difluorophenyl)-5-(2-(methylthio)ethyl)-3-phenyl-1H-pyrazol-1-yl)methyl)cyclohexyl)methoxy)acetic Acid (Compound 244)

From tert-butyl 2-(((1s,4s)-4-((4-bromo-5-(2-(methylthio)ethyl)-3-phenyl-1H-pyrazol-1-yl)methyl)cyclohexyl)methoxy)acetate and tert-butyl 2-(((1s,4s)-4-((4-bromo-3-(2-(methylthio)ethyl)-5-phenyl-1H-pyrazol-1-yl)methyl)cyclohexyl)methoxy)acetate as a mixture of regioisomers (100 mg, 0.19 mmol) and 2,3-difluorophenylboronic acid (30.0 mg, 0.19 mmol), the title compound was obtained using a similar method to the one described in Example 1.211. LCMS m/z=515.4 [M+H]$^+$; $^1$H NMR (400 MHz, DMSO-$d_6$) δ ppm 1.34-1.58 (m, 8H), 1.73-1.82 (m, 1H), 1.86 (s, 3H), 2.09-2.19 (m, 1H), 2.50 (t, J=7.20 Hz, 2H), 2.86 (t, J=7.20 Hz, 2H), 3.42 (d, J=7.07 Hz, 2H), 3.90 (s, 2H), 4.09 (d, J=7.45 Hz, 2H), 7.13-7.20 (m, 1H), 7.20-7.34 (m, 6H), 7.39-7.49 (m, 1H).

Example 1.227: Preparation of 2-(((1s,4s)-4-((3-(2-Methoxyethyl)-5-(3-methoxyphenyl)-4-phenyl-1H-pyrazol-1-yl)methyl)cyclohexyl)methoxy)acetic Acid (Compound 247)

From tert-butyl 2-(((1s,4s)-4-((3-bromo-5-(2-methoxyethyl)-4-phenyl-1H-pyrazol-1-yl)methyl)cyclohexyl)methoxy)acetate and tert-butyl 2-(((1s,4s)-4-((5-bromo-3-(2-methoxyethyl)-4-phenyl-1H-pyrazol-1-yl)methyl)cyclohexyl)methoxy)acetate as a mixture of regioisomers and 3-methoxyphenylboronic acid, the title compound (one of the two regioisomers separated) was obtained using a similar method to the one described in Example 1.221. LCMS m/z=493.1 [M+H]$^+$; $^1$H NMR (400 MHz, DMSO-$d_6$) δ ppm 1.06-1.20 (m, 4H), 1.22-1.37 (m, 4H), 1.55-169 (m, 1H), 1.86-1.99 (m, 1H), 2.82 (t, J=7.39 Hz, 2H), 3.17 (s, 3H), 3.21 (d, J=6.69 Hz, 2H), 3.51 (t, J=7.33 Hz, 2H), 3.68 (s, 3H), 3.84 (s, 2H), 3.94 (d, J=7.45 Hz, 2H), 6.74-6.82 (m, 2H), 6.91-6.97 (m, 1H), 7.06-7.34 (m, 6H).

Example 1.228: Preparation of 2-(((1s,4s)-4-((5-(2-Methoxyethyl)-3-(3-methoxyphenyl)-4-phenyl-1H-pyrazol-1-yl)methyl)cyclohexyl)methoxy)acetic Acid (Compound 248)

From tert-butyl 2-(((1s,4s)-4-((3-bromo-5-(2-methoxyethyl)-4-phenyl-1H-pyrazol-1-yl)methyl)cyclohexyl)methoxy)acetate and tert-butyl 2-(((1s,4s)-4-((5-bromo-3-(2-methoxyethyl)-4-phenyl-1H-pyrazol-1-yl)methyl)cyclohexyl)methoxy)acetate as a mixture of regioisomers and 3-methoxyphenylboronic acid, the title compound (one of the two regioisomers separated) was obtained using a similar method to the one described in Example 1.221. LCMS m/z=493.1 [M+H]$^+$; $^1$H NMR (400 MHz, DMSO-$d_6$)

δ ppm 1.32-1.57 (m, 8H), 1.73-1.83 (m, 1H), 2.05-2.19 (m, 1H), 2.83 (t, J=6.76 Hz, 2H), 3.13 (s, 3H), 3.34 (t, J=6.76 Hz, 2H), 3.43 (d, J=6.95 Hz, 2H), 3.55 (s, 3H), 3.93 (s, 2H), 4.06 (d, J=7.45 Hz, 2H), 6.72-6.81 (m, 2H), 6.90-6.97 (m, 1H), 7.09-7.25 (m, 3H), 7.29-7.42 (in, 3H).

Example 1.229: Preparation of 2-(((1s,4s)-4-((4-(3-Chloro-2-fluorophenyl)-5-(2-(methylsulfonyl)ethyl)-3-phenyl-1H-pyrazol-1-yl)methyl)cyclohexyl)methoxy)acetic Acid (Compound 249)

To a solution of 2-(((1s,4s)-4-((4-(3-chloro-2-fluorophenyl)-5-(2-(methylthio)ethyl)-3-phenyl-1H-pyrazol-1-yl)methyl)cyclohexyl)methoxy)acetic acid (16.4 mg, 0.031 mmol) in DCM (2 ML) was added 3-chloroperbenzoic acid (16.0 mg, 0.093 mmol) was added. After stirred at room temperature for 30 min, the reaction mixture was concentrated and purified on prep HPLC to give the title compound as white solid (12.3 mg). LCMS m/z=563.3 [M+H]$^+$; $^1$H NMR (400 MHz, DMSO-d$_6$) δ ppm 1.34-1.58 (m, 8H), 1.73-1.84 (m, 1H), 2.11-2.23 (m, 1H), 2.95 (s, 3H), 3.01 (t, J=8.02 Hz, 2H), 3.24 (t, J=8.02 Hz, 2H), 3.43 (d, J=6.95 Hz, 2H), 4.00 (s, 2H), 4.12 (d, J=7.33 Hz, 2H), 7.21-7.32 (m, 6H), 7.32-7.39 (m, 1H), 7.58-7.65 (m, 1H).

Example 1.230: Preparation of 2-(((1s,4s)-4-((3-(2-Cyanoethyl)-4,5-diphenyl-1H-pyrazol-1-yl)methyl)cyclohexyl)methoxy)acetic Acid (Compound 259)

Step A: Preparation of 3-(3-Phenyl-1H-pyrazol-5-yl)propanenitrile

To a solution of acetophenone (5.0 g, 41.6 mmol) in dry toluene (10 mL) was added LiHMDS (1.0 M in toluene) via syringe at 0° C. under argon. The reaction was allowed to stir at that temperature for 5 min and 3-cyanopropanoyl chloride (4.89 g, 41.6 mmol) was added via syringe in one portion. The ice bath was removed and AcOH (glacial, 5 mL), EtOH (100 mL), and hydrazine hydrate (6.25 g, 125 mmol) were added. The mixture was brought to reflux for 16 h. After cooled to room temperature, the reaction was concentrated, extracted with EtOAc, dried over MgSO$_4$, and purified by column chromatography to give the title compound as yellowish oil (2.5 g). LCMS m/z=198.1 [M+H]$^+$; $^1$H NMR (400 MHz, DMSO-d$_6$) δ ppm 2.87 (t, J=4.42 Hz, 2H), 2.92 (t, J=4.04 Hz, 2H), 6.59 (s, 1H), 7.25-7.48 (m, 3H), 7.63-7.81 (m, 2H), 13.06 (bs, 1H).

Step B: Preparation of 3-(4-Bromo-3-phenyl-1H-pyrazol-5-yl)propanenitrile

To a solution of 3-(3-phenyl-1H-pyrazol-5-yl)propanenitrile (2.0 g, 10.14 mmol) in methanol (20 mL) was added N-bromosuccinimide (1.80 g, 10.14 mmol) in portions at room temperature. After stirred at room temperature for 16 h, the reaction was concentrated and extracted with EtOAc/H$_2$O, purified by column chromatography to give the title compound as yellow oil (2.4 g). LCMS m/z=276.0 [M+H]$^+$; $^1$H NMR (400 MHz, DMSO-d$_6$) δ ppm 2.90 (t, J=4.80 Hz, 2H), 2.92 (t, J=4.29 Hz, 2H), 7.33-7.59 (m, 3H), 7.76 (d, J=7.07 Hz, 2H), 13.45 (bs, 1H).

Step C: Preparation of tert-Butyl 2-(((1s,4s)-4-((4-Bromo-3-(2-cyanoethyl)-5-phenyl-1H-pyrazol-1-yl)methyl)cyclohexyl)methoxy)acetate and tert-Butyl 2-(((1s,4s)-4-((4-Bromo-5-(2-cyanoethyl)-3-phenyl-1H-pyrazol-1-yl)methyl)cyclohexyl)methoxy)acetate as a Mixture of Regioisomers To a solution of 3-(4-bromo-3-phenyl-1H-pyrazol-5-yl)propanenitrile (2.0 g, 7.24 mmol) in DMF (5 mL) were added cesium carbonate (1.16 g, 3.6 mmol), followed by tert-butyl 2-(((1s,4s)-4-(tosyloxymethyl)cyclohexyl)methoxy)acetate (2.36 g, 7.24 mmol). The reaction was gently heated to 80° C. for 10 h. After cooled to room temperature, the reaction was quenched with water (2 mL), extracted with EtOAc, dried over MgSO$_4$, and purified by column chromatography to give the title compound as clear oil (2.4 g) (mixture of two isomers). LCMS m/z=516.2 [M+H]$^+$.

Step D: Preparation of 2-(((1s,4s)-4-((3-(2-Cyanoethyl)-4,5-diphenyl-1H-pyrazol-1-yl)methyl)cyclohexyl)methoxy)acetic Acid To a solution of tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)cyclohexyl)methoxy)acetate as a mixture of regioisomers (100 mg, 0.19 mmol) in dioxane (3 mL) were added phenylboronic acid (29.3 mg, 0.19 mmol), tetrakis(triphenylphosphine)palladium (22 mg, 0.019 mmol), and K$_2$CO$_3$ (2 M aq., 0.2 mL). The reaction was heated to 150° C. under microwave irradiation for 4 h. After filtered and concentrated, the residue was treated with HCl (4.0 M in dioxane, 5 mL) at room temperature for 10 h. The mixture was concentrated and purified by HPLC to give the title compound as white solid (13.5 mg). LCMS m/z=458.3 [M+H]$^+$; $^1$H NMR (400 MHz, DMSO-d$_6$) δ ppm 1.03-1.19 (m, 4H), 1.22-1.36 (m, 4H), 1.55-1.66 (m, 1H), 1.88-1.99 (m, 1H), 2.79 (t, J=6.95 Hz, 2H), 2.93 (t, J=7.07 Hz, 2H), 3.20 (d, J=6.95 Hz, 2H), 3.91 (s, 2H), 3.95 (d, J=7.45 Hz, 2H), 7.06-7.13 (m, 2H), 7.15-7.30 (m, 5H), 7.36-7.45 (m, 3H).

Example 1.231: Preparation of 2-(((1s,4s)-4-((5-(2-Cyanoethyl)-3,4-diphenyl-1H-pyrazol-1-yl)methyl)cyclohexyl)methoxy)acetic Acid (Compound 260)

From tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)cyclohexyl)methoxy)acetate as a mixture of regioisomers and phenylboronic acid, the title compound (one of the two regioisomers separated) was obtained using a similar method to the one described in Example 1.230. LCMS m/z=458.3 [M+H]$^+$; $^1$H NMR (400 MHz, DMSO-d$_6$) δ ppm 1.33-1.59 (m, 8H), 1.74-1.84 (m, 1H), 2.06-2.18 (m, 1H), 2.58 (t, J=7.39 Hz, 2H), 2.97 (t, J=7.39 Hz, 2H), 3.45 (d, J=7.07 Hz, 2H), 4.00 (s, 2H), 4.10 (d, J=7.45 Hz, 2H), 7.19-7.27 (m, 5H), 7.28-7.32 (m, 2H), 7.34-7.44 (m, 3H).

Example 1.232: Preparation of 2-(((1s,4s)-4-((3-(2-Cyanoethyl)-4-(3-methoxyphenyl)-5-phenyl-1H-pyrazol-1-yl)methyl)cyclohexyl)methoxy)acetic Acid (Compound 261)

From tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)cyclohexyl)methoxy)acetate as a mixture of regioisomers and 3-methoxyphenylboronic acid, the title compound (one of the two regioisomers separated) was obtained using a similar method to the one described in Example 1.230. LCMS m/z=488.3 [M+H]$^+$; $^1$H NMR (400 MHz, DMSO-d$_6$) δ ppm 1.05-1.20 (m, 4H), 1.22-136 (m, 4H), 1.56-1.66 (m, 1H), 1.89-2.01 (m, 1H), 2.80 (t, J=7.20 Hz, 2H), 2.95 (t, J=7.07 Hz, 2H), 3.21 (d, J=6.95 Hz, 2H), 3.60 (s, 3H), 3.91 (s, 2H), 3.94 (d, J=7.45 Hz, 2H), 6.59-6.64 (m, 1H), 6.69 (d, J=7.71 Hz, 1H), 6.75 (dd, J=8.02, 2.21 Hz, 1H), 7.17 (t, J=7.96 Hz, 1H), 7.23-7.30 (m, 2H), 7.38-7.46 (m, 3H).

Example 1.233: Preparation of 2-(((1s,4s)-4-((5-(2-Cyanoethyl)-4-(3-methoxyphenyl)-3-phenyl-1H-pyrazol-1-yl)methyl)cyclohexyl)methoxy)acetic Acid (Compound 262)

From tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)cyclohexyl)methoxy)acetate as a mixture of regioisomers and 3-methoxyphenylboronic acid, the title compound (one of the two regioisomers separated) was obtained using a similar method to the one described in Example 1.230. LCMS m/z=488.3 [M+H]$^+$; $^1$H NMR (400 MHz, DMSO-d$_6$) δ ppm 1.33-1.59 (m, 8H), 1.76-1.84 (m, 1H), 2.08-2.18 (m, 1H), 2.61 (t, J=7.33 Hz, 2H), 2.99 (t, J=7.33 Hz, 2H), 3.45 (d, J=7.20 Hz, 2H), 3.72 (s, 3H), 4.00 (s, 2H), 4.10 (d, J=7.45 Hz, 2H), 6.79 (s, 1H), 6.80 (d, J=1.64 Hz, 1H), 6.90-6.94 (m, 1H), 7.19-7.27 (m, 3H), 7.28-7.37 (m, 3H).

Example 1.234: Preparation of 2-(((1s,4s)-4-((5-(2-Cyanoethyl)-4-(3-hydroxyphenyl)-3-phenyl-1H-pyrazol-1-yl)methyl)cyclohexyl)methoxy)acetic Acid (Compound 263)

From tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)cyclohexyl)methoxy)acetate as a mixture of regioisomers and 3-hydroxyphenylboronic acid, the title compound (one of the two regioisomers separated) was obtained using a similar method to the one described in Example 1.230. LCMS m/z=474.2 [M+H]$^+$; $^1$H NMR (400 MHz, DMSO-d$_6$) δ ppm 1.31-1.59 (m, 8H), 1.73-1.84 (m, 1H), 2.07-2.17 (m, 1H), 2.58 (t, J=7.39 Hz, 2H), 2.97 (t, J=7.39 Hz, 2H), 3.45 (d, J=7.07 Hz, 2H), 4.00 (s, 2H), 4.09 (d, J=7.45 Hz, 2H), 6.59-6.62 (m, 1H), 6.68 (d, J=7.58 Hz, 1H), 6.73-6.78 (m, 1H), 7.17-7.28 (m, 5H), 7.31-7.37 (m, 1H).

Example 1.235: Preparation of 2-(((1s,4s)-4-((4-(3-Chlorophenyl)-3-(2-cyanoethyl)-5-phenyl-1H-pyrazol-1-yl)methyl)cyclohexyl)methoxy)acetic Acid (Compound 264)

From tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)cyclohexyl)methoxy)acetate as a mixture of regioisomers and 3-chlorophenylboronic acid, the title compound (one of the two regioisomers separated) was obtained using a similar method to the one described in Example 1.230. LCMS m/z=492.2 [M+H]$^+$; $^1$H NMR (400 MHz, DMSO-d$_6$) δ ppm 1.04-1.20 (m, 4H), 1.22-1.36 (m, 4H), 1.55-1.66 (m, 1H), 1.90-2.01 (m, 1H), 2.82 (t, J=6.95 Hz, 2H), 2.95 (t, J=6.95 Hz, 2H), 3.21 (d, J=6.95 Hz, 2H), 3.92 (s, 2H), 3.95 (d, J=7.45 Hz, 2H), 7.04-7.09 (m, 2H), 7.11-7.14 (m, 1H), 7.21-7.32 (m, 4H), 7.40-7.47 (m, 2H).

Example 1.236: Preparation of 2-(((1s,4s)-4-((4-(3-Chlorophenyl)-5-(2-cyanoethyl)-3-phenyl-1H-pyrazol-1-yl)methyl)cyclohexyl)methoxy)acetic Acid (Compound 265)

From tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)cyclohexyl)methoxy)acetate as a mixture of regioisomers and 3-chlorophenylboronic acid, the title compound was obtained using a similar method to the one described in Example 1.230. LCMS m/z=492.2 [M+M]$^+$; $^1$H NMR (400 MHz, DMSO-d$_6$) δ ppm 1.32-1.60 (m, 8H), 1.76-1.84 (m, 1H), 2.09-2.18 (m, 1H), 2.63 (t, J=7.26 Hz, 2H), 3.00 (t, J=7.33 Hz, 2H), 3.45 (d, J=7.07 Hz, 2H), 4.01 (s, 2H), 4.10 (d, J=7.45 Hz, 2H), 7.19-7.33 (m, 7H), 7.40-7.44 (m, 2H).

Example 1.237: Preparation of 2-(((1s,4s)-4-((3-(2-Cyanoethyl)-4-(3-fluorophenyl)-5-phenyl-1H-pyrazol-1-yl)methyl)cyclohexyl)methoxy)acetic Acid (Compound 266)

From tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)cyclohexyl)methoxy)acetate as a mixture of regioisomers and 3-fluorophenylboronic acid, the title compound (one of the two regioisomers separated) was obtained using a similar method to the one described in Example 1.230. LCMS m/z=476.2 [M+H]$^+$; $^1$H NMR (400 MHz, DMSO-d$_6$) δ ppm 1.04-1.22 (m, 4H), 1.23-1.36 (m, 4H), 1.57-1.67 (m, 1H), 1.91-2.00 (m, 1H), 2.82 (t, J=7.20 Hz, 2H), 2.97 (t, J=7.07 Hz, 2H), 3.22 (d, J=6.82 Hz, 2H), 3.92 (s, 2H), 3.96 (d, J=7.58 Hz, 2H), 6.86-6.96 (m, 2H), 6.97-7.05 (m, 1H), 7.24-7.33 (m, 3H), 7.40-7.46 (m, 3H).

Example 1.238: Preparation of 2-(((1s,4s)-4-((5-(2-Cyanoethyl)-4-(3-fluorophenyl)-3-phenyl-1H-pyrazol-1-yl)methyl)cyclohexyl)methoxy)acetic Acid (Compound 267)

From tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)cyclohexyl)methoxy)acetate as a mixture of regioisomers and 3-fluorophenylboronic acid, the title compound (one of the two regioisomers separated) was obtained using a similar method to the one described in Example 1.230. LCMS m/z=476.2 [M+H]$^+$; $^1$H NMR (400 MHz, DMSO-d$_b$) δ ppm 1.33-1.61 (m, 8H), 1.75-1.86 (m, 1H), 2.09-2.19 (m, 1H), 2.62 (t, J=7.33 Hz, 2H), 3.01 (t, J=7.33 Hz, 2H), 3.46 (d, J=7.07 Hz, 2H), 4.01 (s, 2H), 4.11 (d, J=7.58 Hz, 2H), 7.05-7.11 (m, 2H), 7.14-7.21 (m, 1H), 7.21-7.34 (m, 5H), 7.40-7.48 (m, 1H).

Example 1.239: Preparation of 2-((1s,4s)-4-((3-(2-Cyanoethyl)-4-(3-hydroxyphenyl)-5-phenyl-1H-pyrazol-1-yl)methyl)cyclohexyl)methoxy)acetic Acid (Compound 268)

From tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)

cyclohexyl)methoxy)acetate as a mixture of regioisomers and 3-hydroxyphenylboronic acid, the title compound (one of the two regioisomers separated) was obtained using a similar method to the one described in Example 1.230. LCMS m/z=474.2 [M+H]$^+$; $^1$H NMR (400 MHz, DMSO-d$_6$) δ ppm 1.03-1.19 (m, 4H), 1.20-1.36 (m, 4H), 1.54-1.67 (m, 1H), 1.87-1.97 (m, 1H), 2.78 (t, J=7.01 Hz, 2H), 2.91 (t, J=7.01 Hz, 2H), 3.20 (d, J=6.82 Hz, 2H), 3.91 (s, 2H), 3.93 (d, J=8.08 Hz, 2H), 6.46-6.54 (m, 2H), 6.59 (dd, J=8.15, 1.58 Hz, 1H), 7.04 (t, J=7.83 Hz, 2H), 7.22-7.28 (m, 2H), 7.38-7.46 (m, 2H).

Example 1.240: Preparation of 2-(((1s,4s)-4-((4-(3-Chloro-2-fluorophenyl)-3-(2-cyanoethyl)-5-phenyl-1H-pyrazol-1-yl)methyl)cyclohexyl)methoxy)acetic Acid (Compound 269)

From tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)cyclohexyl)methoxy)acetate as a mixture of regioisomers and 3-chloro-2-fluorophenylboronic acid, the title compound (one of the two regioisomers separated) was obtained using a similar method to the one described in Example 1.230. LCMS m/z=510.2 [M+H]$^+$; $^1$H NMR (400 MHz, DMSO-d$_6$) δ ppm 0.99-1.15 (m, 4H), 1.16-1.34 (m, 4H), 1.55-1.67 (m, 1H), 1.81-1.93 (m, 1H), 2.82-2.94 (m, 4H), 3.16 (d, J=6.95 Hz, 2H), 3.68 (s, 2H), 3.98 (d, J=7.45 Hz, 2H), 7.39-7.46 (m, 3H), 7.48-7.60 (m, 5H).

Example 1.241: Preparation of 2-(((1s,4s)-4-((4-(3-Chloro-2-fluorophenyl)-5-(2-cyanoethyl)-3-phenyl-1H-pyrazol-1-yl)methyl)cyclohexyl)methoxy)acetic Acid (Compound 270)

From tert-butyl 2-(((1s,4s)-4-((4-bromo-3-(2-cyanoethyl)-5-phenyl-1H-pyrazol-1-yl)methyl)cyclohexyl)methoxy)acetate and tert-butyl 2-(((1s,4s)-4-((4-bromo-5-(2-cyanoethyl)-3-phenyl-1H-pyrazol-1-yl)methyl)cyclohexyl)methoxy)acetate as a mixture of regioisomers and 3-chloro-2-fluorophenylboronic acid, the title compound (one of the two regioisomers separated) was obtained using a similar method to the one described in Example 1.230. LCMS m/z=510.2 [M+H]$^+$; $^1$H NMR (400 MHz, DMSO-d$_6$) δ ppm 1.27-1.56 (m, 8H), 1.71-1.83 (m, 1H), 2.00-2.11 (m, 1H), 2.83 (t, J=7.20 Hz, 2H), 3.11 (t, J=7.26 Hz, 2H), 3.41 (d, J=7.20 Hz, 2H), 3.81 (s, 2H), 4.11 (d, J=7.58 Hz, 2H), 7.35-7.42 (m, 2H), 7.42-7.49 (m, 3H), 7.79-7.85 (m, 3H).

Example 1.242: Preparation of 2-(((1s,4s)-4-((3-(2-Fluoro-4-methylphenyl)-5-(2-hydroxyethyl)-4-phenyl-1H-pyrazol-1-yl)methyl)cyclohexyl)methoxy) acetic Acid (Compound 287)

Step A: Preparation of Ethyl 3-(2-Fluoro-4-methylphenyl)-3-oxo-2-phenylpropanoate 2-Fluoro-4-methylbenzoyl chloride was made 2 h before the reaction by adding oxalyl chloride (3.20 mL, 36.5 mmol) to a solution of 2-fluoro-4-methylbenzoic acid (4.69 g, 30.5 mmol) in DCM (5 mL) at room temperature. After stirring for 2 h, the resulting solution was concentrated to dryness and dissolved in THF (10 mL), used as it was without further purification.

The solution of ethyl 2-phenylacetate (5 g, 30.5 mmol) in THF (20 mL) was cooled to −78° C. and LiHMDS (30.5 mL, 30.5 mmol) was added, followed by prior made solution of 2-fluoro-4-methylbenzoyl chloride in THF (10 mL). The reaction was allowed to warm to room temperature slowly and stirred for 4 h. Quenched with AcOH (2 mL), extracted with EtOAc, washed with brine, dried over MgSO$_4$, and purified by column chromatography to give the title compound as clear liquid (7.10 g). LCMS m/z=301.2 [M+H]$^+$; $^1$H NMR (400 MHz, DMSO-d$_6$) δ ppm 1.14 (t, J=7.07 Hz, 3H), 2.32 (s, 3H), 4.22 (q, J=7.07 Hz, 2H), 5.77 (s, 1H), 7.03-7.17 (m, 3H), 7.24-7.40 (m, 4H), 7.82 (t, J=8.21 Hz, 1H).

Step B: Preparation of 1-(2-Fluoro-4-methylphenyl)-2-phenylethanone

Ethyl 3-(2-fluoro-4-methylphenyl)-3-oxo-2-phenylpropanoate (8.0 g, 26.6 mmol) was dissolved in THF (20 mL) and hydrogen chloride (37% wt., 32.0 mL, 400 mmol) was added. The reaction was brought to reflux overnight. After cooled to room temperature, the reaction was diluted with H2 (100 mL) and neutralized to pH 8 with NaOH (4.0 M aq.). The mixture was extracted with EtOAc (3×75 mL), dried over MgSO$_4$, and purified by column chromatography to give the title compound as a clear oil (4.81 g). LCMS m/z=229.1 [M+H]$^+$; $^1$H NMR (400 MHz, DMSO-d$_6$) δ ppm 2.36 (s, 3H), 4.28 (s, 2H), 7.11-7.18 (m, 2H), 7.19-7.26 (m, 3H), 7.27-7.34 (m, 2H), 7.77 (t, J=8.21 Hz, 1H).

Step C: Preparation of 1-(1H-Benzo[d][1,2,3]triazol-1-yl)but-3-en-1-one

Sulfurous dichloride (6.91 g, 58.1 mmol) was added to a stirred solution of 1H-benzo[d][1,2,3]triazole (27.7 g, 232 mmol) in anhydrous dichloromethane (100 mL) at room temperature under argon atmosphere. The mixture was stirred for 30 min and but-3-enoic acid (5.0 g, 58.1 mmol) was added in one portion and stirring was continued for 2 h. The resulting suspension was filtered off and washed with 2.0 M NaOH (3×50 mL), dried over MgSO$_4$, and purified by column chromatography to give the title compound as white solid (5.12 g). LCMS m/z=188.1 [M+H]$^+$; $^1$H NMR (400 MHz, DMSO-d$_6$) δ ppm 4.24 (d, J=6.57 Hz, 2H), 528-5.42 (m, 2H), 6.04-6.19 (m, 1H), 7.61 (t, J=7.71 Hz, 1H), 7.78 (t, J=7.71 Hz, 1H), 8.24 (dd, J=10.61, 8.34 Hz, 2H).

Step D: Preparation of 5-Allyl-3-(2-fluoro-4-methylphenyl)-4-phenyl-1H-pyrazole

To a solution of 1-(2-fluoro-4-methylphenyl)-2-phenylethanone (1.0 g, 4.38 mmol) in THF (10 mL) was added LiHMDS (1.0 M in THF) (8.76 mL, 8.76 mmol) slowly via syringe at 0° C. After stirring for 10 min, 1-(1H-benzo[d][1,2,3]triazol-1-yl)but-3-en-1-one (0.984 g, 5.26 mmol) was added in one portion. The reaction was stirred at 0° C. for 30 min before quenched with AcOH (2 mL). To the reaction were added EtOH (30 mL), hydrazine hydrate (0.658 g, 13.14 mmol), and heated to reflux for 1 h. After cooled to room temperature, the reaction was concentrated and extracted with EtOAc/H$_2$O, washed with brine, dried over MgSO$_4$, and purified by column chromatography to give the title compound as clear oil (0.50 g). LCMS m/z=293.2 [M+H]$^+$; $^1$H NMR (400 MHz, DMSO-d$_6$) δ ppm 2.31 (s, 3H), 3.40 (d, J=5.94 Hz, 2H), 4.94-5.08 (m, 2H), 5.88-6.00 (m, 1H), 6.92-7.31 (m, 8H).

Step E: Preparation of 2-(3-(2-Fluoro-4-methylphenyl)-4-phenyl-1H-pyrazol-5-yl)ethanol 5-Allyl-3-(2-fluoro-4-methylphenyl)-4-phenyl-1H-pyrazole (1.0 g, 3.42 mmol) was dissolved in methanol (40 mL) and dichloromethane (10 mL) and cooled to −78° C. on a dry-ice/acetone bath. Ozone was bubbled through the solution for ~2 h, until the solution appeared light blue. To the reaction added sodium borohydride (0.129 g, 3.42 mmol) slowly. Upon complete addition, the reaction was removed from the dry-ice bath and stirred at room temperature for 1 h. Excess solvent was removed under reduced pressure and the reaction was extracted with EtOAc/H$_2$O, dried over MgSO$_4$, and purified by column chromatography to give the title compound as clear oil (0.70 g). LCMS m/z=297.2 [M+H]$^+$; $^1$H NMR (400 MHz, DMSO-d$_6$) δ ppm 2.30 (s, 3H), 2.79 (t, J=7.20 Hz, 2H), 3.62 (t, J=7.33 Hz, 2H), 6.93-7.00 (m, 1H), 7.09-7.14 (m, 2H), 7.15-7.23 (m, 3H), 7.25-7.31 (m, 2H), 12.86 (bs, 1H).

Step F: Preparation of tert-Butyl 2-(((1s,4s)-4-((3-(2-Fluoro-4-methylphenyl)-5-(2-hydroxyethyl)-4-phenyl-1H-pyrazol-1-yl)methyl)cyclohexyl)methoxy)acetate To a solution of 2-(3-(2-fluoro-4-methylphenyl)-4-phenyl-1H-pyrazol-5-yl)ethanol (0.7 g, 2.362 mmol) in DMF (10 mL) were added cesium carbonate (0.770 g, 2.362 mmol) and tert-butyl 2-(((1s,4s)-4-(tosyloxymethyl)cyclohexyl)methoxy)acetate (0.974 g, 2.362 mmol). The reaction was gently heated to 60° C. for 2 h. After cooled to room temperature, the reaction mixture was extracted with EtOAC/H$_2$, dried over MgSO$_4$, and purified by column chromatography to give the title compound as a clear oil (0.75 g). LCMS m/z=537.5 [M+H]$^+$; $^1$H NMR (400 MHz, CDCl$_3$) δ ppm 1.14-1.29 (m, 4H), 1.33-1.46 (m, 4H), 1.47 (s, 9H), 1.72-1.81 (m, 1H), 2.00-2.09 (m, 1H), 2.37 (s, 3H), 2.91 (t, J=5.56 Hz, 2H), 3.30 (d, J=7.07 Hz, 2H), 3.89 (s, 2H), 3.90 (d, J=7.33 Hz, 2H), 3.91 (t, J=5.81 Hz, 2H), 4.68 (s, 1H), 6.89-7.01 (m, 2H), 7.04-7.10 (m, 1H), 7.13-7.27 (m, 5H).

Step G: Preparation of 2-(((1s,4s)-4-((3-(2-Fluoro-4-methylphenyl)-5-(2-hydroxyethyl)-4-phenyl-1H-pyrazol-1-yl)methyl)cyclohexyl)methoxy)acetic Acid (Compound 287)

tert-Butyl 2-(((1s,4s)-4-((3-(2-fluoro-4-methylphenyl)-5-(2-hydroxyethyl)-4-phenyl-1H-pyrazol-1-yl)methyl)cyclohexyl)methoxy)acetate (0.50 g, 0.932 mmol) was dissolved in hydrogen chloride (4.0 M in dioxane) (4.66 mL, 18.63 mmol) and stirred at room temperature for 16 h. The reaction was concentrated and purified by HPLC to give the title compound. LCMS m/z=481.6 [M+H]$^+$; $^1$H NMR (400 MHz, DMSO-d$_6$) δ ppm 1.07-1.19 (m, 4H), 1.21-1.41 (m, 4H), 1.55-1.72 (m, 1H), 1.86-1.97 (m, 1H), 2.33 (s, 3H), 3.22 (d, J=6.82 Hz, 2H), 3.59 (t, J=5.81 Hz, 2H), 3.82 (t, J=5.85 Hz, 2H), 3.91 (s, 2H), 3.93 (d, J=7.54 Hz, 2H), 4.55 (s, 1H), 7.03-7.12 (m, 4H), 7.13-7.19 (m, 2H), 7.22-7.27 (m, 2H).

Example 1.243: Preparation of 2-(((1s,4s)-4-((5-(2-fluoro-4-methylphenyl)-3-(2-hydroxyethyl)-4-phenyl-1H-pyrazol-1-yl)methyl)cyclohexyl)methoxy)acetic Acid (Compound 285)

The title compound was obtained using a similar method to the one described in Example 1.242. LCMS m/z=481.6 [M+H]$^+$; $^1$H NMR (400 MHz, DMSO-d$_6$) δ ppm 1.32-1.53 (m, 8H), 1.71-1.81 (m, 1H), 2.08-2.17 (m, 1H), 2.28 (s, 3H), 2.84 (t, J=7.07 Hz, 2H), 3.41 (d, J=7.07 Hz, 2H), 3.49 (t, J=7.20 Hz, 2H), 3.93 (s, 2H), 4.08 (d, J=7.58 Hz, 2H), 4.45 (s, 1H), 6.86-6.98 (m, 1H), 7.08-7.13 (m, 2H), 7.16-7.31 (m, 5H).

Example 1.244: Preparation of 2-(((1s,4s)-4-((5-(2-(Methylsulfonyl)ethyl)-4-phenyl-3-p-tolyl-1H-pyrazol-1-yl)methyl)cyclohexyl)methoxy)acetic Acid (Compound 290)

Step A: Preparation of 1-(1H-benzo[d][1,2,3]triazol-1-yl)-3-(methylthio)propan-1-one Sulfurous dichloride (4.95 g, 41.6 mmol) was added to a stirred solution of 1H-benzo[d][1,2,3]triazole (19.83 g, 166 mmol) in anhydrous dichloromethane (300 mL) at room temperature under argon. The mixture was stirred for 30 min and 3-(methylthio)propanoic acid (5.0 g, 41.6 mmol) was added in one portion and stirring was continued for 2 h. The resulting suspension was filtered off and the filtrated was washed with 2 M NaOH (3×50 mL), dried over MgSO$_4$ and purified by column chromatography to give the title compound as clear oil (5.12 g). LCMS m/z=222.1 [M+H]$^+$; $^1$H NMR (400 MHz, CDCl$_3$) δ ppm 2.21 (s, 3H), 3.05 (t, J=7.07 Hz, 2H), 3.74 (t, J=7.07 Hz, 2H), 7.42-7.54 (m, 1H), 7.56-7.69 (m, 1H), 8.08 (d, J=8.34 Hz, 1H), 8.24 (d, J=8.08 Hz, 1H).

Step B: Preparation of 5-(2-(Methylthio)ethyl)-4-phenyl-3-p-tolyl-1H-pyrazole To a solution of 2-phenyl-1-p-tolylethanone (2.0 g, 9.51 mmol) in THF (10 mL) was added LiHMDS (1.0 M in THF) (19.02 mL, 19.02 mmol) slowly via syringe at 0° C. After stirring for 10 min, 1-(1H-benzo[d][1,2,3]triazol-1-yl)-3-(methylthio)propan-1-one (2.53 g, 11.41 mmol) was added in one portion. The reaction was stirred at 0° C. for 30 min before quenched with AcOH (2 mL). To the reaction were added EtOH (30 mL), hydrazine hydrate (1.428 g, 28.5 mmol), and brought to reflux for 2 h. After cooled to room temperature, the reaction was concentrated and extracted with EtOAc/H$_2$O, washed with brine, dried over MgSO$_4$, and purified by column chromatography to give the title compound a as clear oil (1.50 g). LCMS m/z=309.3 [M+H]$^+$; $^1$H NMR (400 MHz, CDCl$_3$) δ ppm 1.96 (s, 3H), 2.29 (s, 3H), 2.66 (t, J=7.71 Hz, 2H), 2.90 (t, J=7.58 Hz, 2H), 7.01-7.06 (m, 2H), 7.18-7.25 (m, 3H), 7.26-7.37 (m, 3H).

Step C: Preparation of tert-butyl 2-(((1s,4s)-4-((5-(2-(Methylthio)ethyl)-4-phenyl-3-p-tolyl-1H-pyrazol-1-yl)methyl)cyclohexyl)methoxy)acetate To a solution of 5-(2-(methylthio)ethyl)-4-phenyl-3-p-tolyl-1H-pyrazole (0.5 g, 1.621 mmol) in DMF (10 mL) were added cesium carbonate (0.528 g, 1.621 mmol) and tert-butyl 2-(((1s,4s)-4-(tosyloxymethyl)cyclohexyl)methoxy)acetate (0.669 g, 1.621 mmol). The reaction was gently heated to 60° C. for 2 h. After cooled to room temperature, the mixture was extracted with EtOAc/H$_2$O, dried over MgSO$_4$, and purified by column chromatography to give the title compound as a clear oil. LCMS m/z=549.5 [M+H]$^+$; $^1$H NMR (400 MHz, CDCl$_3$) δ ppm 1.10-1.27 (m, 4H), 1.29-1.45 (m, 4H), 1.46 (s, 9H), 1.53-1.61 (m, 1H), 1.73-1.81 (m, 1H), 2.04 (s, 3H), 2.35 (s, 3H), 2.73 (t, J=7.58 Hz, 2H), 2.99 (t, J=7.58 Hz, 2H), 3.28 (d, J=6.82 Hz, 2H), 3.88 (s, 2H), 3.96 (d, J=7.58 Hz, 2H), 7.04-7.10 (m, 4H), 7.11-7.18 (m, 3H), 7.18-7.24 (m, 2H).

Step D: Preparation of 2-(((1s,4s)-4-((5-(2-(Methylsulfonyl)ethyl)-4-phenyl-3-p-tolyl-1H-pyrazol-1-yl)methyl)cyclohexyl)methoxy)acetic Acid (Compound 290)

tert-Butyl 2-(((1s,4s)-4-((5-(2-(methylthio)ethyl)-4-phenyl-3-p-tolyl-1H-pyrazol-1-yl)methyl)cyclohexyl)methoxy)acetate (0.50 g, 0.911 mmol) was dissolved in hydrogen chloride (4.0 M in dioxane) (4.56 mL, 18.22 mmol) and stirred at room temperature for 16 h. The reaction was concentrated to dryness and dissolved in dichloromethane (5 mL) and 3-chloroperoxybenzoic acid (0.550 g, 3.19 mmol) was added. After stirred at room temperature for 1 h, the reaction was concentrated and purified on HPLC. LCMS m/z=525.4 [M+H]+; 1H NMR (400 MHz, DMSO-d6) δ ppm 1.08-1.20 (m, 4H), 1.23-1.36 (m, 4H), 1.57-1.68 (m, 1H), 1.90-2.00 (m, 1H), 2.32 (s, 3H), 2.97 (s, 3H), 3.04 (t, J=8.59 Hz, 2H), 3.22 (d, J=6.82 Hz, 2H), 3.41 (t, J=8.08 Hz, 2H), 3.92 (d, J=7.38 Hz, 2H), 3.92 (s, 2H), 7.08-7.15 (m, 3H), 7.16-7.31 (m, 6H).

Example 1.245: Preparation of 2-(((1s,4s)-4-((3-(2-Fluoro-4-methylphenyl)-5-(2-(methylsulfonyl)ethyl)-4-phenyl-1H-pyrazol-1-yl)methyl)cyclohexyl)methoxy)acetic Acid (Compound 291)

Step A: Preparation of 3-(2-Fluoro-4-methylphenyl)-5-(2-(methylthio)ethyl)-4-phenyl-1H-pyrazole To a solution of 1-(2-fluoro-4-methylphenyl)-2-phenylethanone (2.0 g, 8.76 mmol) in THF (10 mL) was added LiHMDS (1.0 M in THF) (17.52 mL, 17.52 mmol) slowly via syringe at 0° C. After stirring for 10 min, 1-(1H-benzo[d][1,2,3]triazol-1-yl)-3-(methylthio)propan-1-one (2.327 g, 10.51 mmol) was added in one portion. The reaction was stirred at 0° C. for 30 min before quenched with AcOH (2 mL). To the reaction were added EtOH (30 mL), hydrazine hydrate (1.316 g, 26.3 mmol), and brought to reflux for 2 h. After cooled to room temperature, the reaction was concentrated and extracted with EtOAc/H2O, washed with brine, dried over MgSO4, and purified by column chromatography to give the title compound as a clear oil (1.40 g). LCMS m/z=327.2 [M+H]+; 1H NMR (400 MHz, CDCl3) δ ppm 1.94 (s, 3H), 2.22 (s, 3H), 2.65 (t, J=7.33 Hz, 2H), 2.88 (t, J=7.58 Hz, 2H), 6.71 (d, J=7.83 Hz, 1H), 6.80 (d, J=11.87 Hz, 1H), 6.97 (t, J=7.96 Hz, 1H), 7.09-7.29 (m, 5H), 9.64 (bs, 1H).

Step B: Preparation of tert-Butyl 2-(((1s,4s)-4-((3-(2-Fluoro-4-methylphenyl)-5-(2-(methylthio)ethyl)-4-phenyl-1H-pyrazol-1-yl)methyl)cyclohexyl)methoxy)acetate To a solution of 3-(2-fluoro-4-methylphenyl)-5-(2-(methylthio)ethyl)-4-phenyl-1H-pyrazole (0.5 g, 1.532 mmol) in DMF (10 mL) were added cesium carbonate (0.499 g, 1.532 mmol) and tert-butyl 2-(((1s,4s)-4-(tosyloxymethyl)cyclohexyl)methoxy)acetate (0.632 g, 1.532 mmol). The reaction was gently heated to 60° C. for 2 h. After cooled to room temperature, the mixture was extracted with EtOAc/H2O, dried over MgSO4, and purified by column chromatography to give the title compound as a clear oil. LCMS m/z=567.5 [M+H]+; 1H NMR (400 MHz, CDCl3) δ ppm 1.31-1.44 (m, 4H), 1.46 (s, 9H), 1.52-1.65 (m, 4H), 1.69-1.81 (m, 1H), 1.84-1.92 (m, 1H), 2.04 (s, 3H), 2.35 (s, 3H), 2.55 (t, J=7.83 Hz, 2H), 2.74 (t, J=7.58 Hz, 2H), 3.47 (d, J=7.07 Hz, 2H), 3.96 (s, 2H), 4.08 (d, J=7.33 Hz, 2H), 6.84-7.01 (m, 2H), 7.06-7.18 (m, 3H), 7.19-7.32 (m, 3H).

Step C: Preparation of 2-(((1s,4s)-4-((3-(2-Fluoro-4-methylphenyl)-5-(2-(methylsulfonyl)ethyl)-4-phenyl-1H-pyrazol-1-yl)methyl)cyclohexyl)methoxy)acetic Acid (Compound 291)

tert-Butyl 2-(((1s,4s)-4-((3-(2-fluoro-4-methylphenyl)-5-(2-(methylthio)ethyl)-4-phenyl-1H-pyrazol-1-yl)methyl)cyclohexyl)methoxy)acetate (0.50 g, 0.882 mmol) was dissolved in hydrogen chloride (4.0 M in dioxane) (4.41 mL, 17.64 mmol) and stirred at room temperature for 16 h. The reaction was concentrated and dissolved in DCM (5 mL). 3-Chloroperoxybenzoic acid (0.533 g, 3.09 mmol) was added. After stirred at room temperature for 1 h, the reaction was concentrated and the residue was purified by HPLC to give the title compound. LCMS m/z=543.4 [M+H]+; 1H NMR (400 MHz, DMSO-d6) δ ppm 1.05-1.20 (m, 4H), 1.23-1.37 (m, 4H), 1.57-1.69 (m, 1H), 1.89-1.99 (m, 1H), 2.34 (s, 3H), 2.97 (s, 3H), 3.06 (t, J=8.21 Hz, 2H), 3.22 (d, J=6.82 Hz, 2H), 3.43 (t, J=8.21 Hz, 2H), 3.92 (d, J=7.33 Hz, 2H), 3.91 (s, 2H), 7.05-7.14 (m, 3H), 7.15-7.23 (m, 3H), 7.24-7.31 (m, 2H).

Example 1.246: Preparation of 2-(((1s,4s)-4-((5-(2-Hydroxyethyl)-4-phenyl-3-p-tolyl-1H-pyrazol-1-yl)methyl)cyclohexyl)methoxy)acetic Acid (Compound 292)

Step A: Preparation of 5-Allyl-4-phenyl-3-p-tolyl-1H-pyrazole

To a solution of 2-phenyl-1-p-tolylethanone (1.0 g, 4.76 mmol) in THF (10 mL) added LiHMDS (1.0 M in THF) (9.51 mL, 9.51 mmol) slowly via syringe at 0° C. After stirring for 10 min, 1-(1H-benzo[d][1,2,3]triazol-1-yl)but-3-en-1-one (1.068 g, 5.71 mmol) was added in one portion. The reaction was stirred at 0° C. for 30 min and then quenched with AcOH (2 mL). EtOH (30 mL) and hydrazine hydrate (0.714 g, 14.27 mmol) were added, and the reaction was heated to reflux for 30 min. The reaction was cooled to room temperature, concentrated and the residue was extracted with EtOAc/H2O, washed with brine, dried over MgSO4, and purified by column chromatography to give the title compound as clear oil (0.47 g). LCMS m/z=275.0 [M+H]+; 1H NMR (400 MHz, CDCl3) δ ppm 2.31 (s, 3H), 3.38-3.43 (m, 2H), 5.07-5.14 (m, 2H), 5.90-6.01 (m, 1H), 7.03-7.09 (m, 2H), 7.19-7.30 (m, 5H), 7.30-7.36 (m, 2H).

Step B: Preparation of 2-(4-Phenyl-3-p-tolyl-1H-pyrazol-5-yl)ethanol

5-Allyl-4-phenyl-3-p-tolyl-1H-pyrazole (1.0 g, 3.64 mmol) was dissolved in methanol (40 mL) and dichloromethane (10 mL) and cooled to −78° C. on a dry-ice/acetone bath. Ozone was bubbled through the solution for 2 h, until the solution appeared light blue. To the reaction was added sodium borohydride (0.138 g, 3.64 mmol) and the reaction was removed from the dry-ice bath and stirred at room temperature for 1 h. Excess solvent was removed under reduced pressure and the reaction was extracted with EtOAc/H2O, dried over MgSO4, and purified by column chromatography to give the title compound as white solid (0.54 g). LCMS m/z=279.2 [M+H]+; 1H NMR (400 MHz, DMSO-$d_6$) δ ppm 2.25 (s, 3H), 2.71 (t, J=7.33 Hz, 2H), 3.57 (t, J=7.33 Hz, 2H), 4.65 (bs, 1H), 7.03-7.09 (m, 2H), 7.16-7.23 (m, 3H), 7.24-7.31 (m, 2H), 7.32-7.40 (m, 2H).

Step C: Preparation of tert-Butyl 2-(((1s,4s)-4-((5-(2-Hydroxyethyl)-4-phenyl-3-p-tolyl-1H-pyrazol-1-yl)methyl)cyclohexyl)methoxy)acetate To a solution of 2-(4-phenyl-3-p-tolyl-1H-pyrazol-5-yl)ethanol (0.7 g, 2.51 mmol) in DMF (10 mL) were added cesium carbonate (0.819 g, 2.51 mmol) and tert-butyl 2-(((1s,4s)-4-(tosyloxymethyl)cyclohexyl)methoxy)acetate (1.037 g, 2.51 mmol). The reaction was gently heated to 60° C. for 2 h. The reaction was cooled to room temperature and extracted with EtOAc/$H_2O$. The organic layer was dried over $MgSO_4$ and purified by column chromatography to give the title compound as clear oil (0.75 g). LCMS m/z=519.5 [M+H]$^+$; $^1$H NMR (400 MHz, $CDCl_3$) δ ppm 1.34-1.45 (m, 4H), 1.49 (s, 9H), 1.55-1.63 (m, 4H), 1.72-1.80 (m, 1H), 1.85-1.93 (m, 1H), 2.28 (s, 3H), 2.90 (t, J=6.95 Hz, 2H), 3.47 (d, J=7.07 Hz, 2H), 3.66 (t, J=6.44 Hz, 2H), 3.96 (s, 2H), 4.09 (d, J=7.58 Hz, 2H), 6.98-7.10 (m, 2H), 7.12-7.24 (m, 2H), 7.24-7.37 (m, 5H).

Step D: Preparation of 2-(((1s,4s)-4-((5-(2-Hydroxyethyl)-4-phenyl-3-p-tolyl-1H-pyrazol-1-yl)methyl)cyclohexyl)methoxy)acetic Acid (Compound 292)

tert-Butyl 2-(((1s,4s)-4-((5-(2-hydroxyethyl)-4-phenyl-3-p-tolyl-1H-pyrazol-1-yl)methyl)cyclohexyl)methoxy)acetate (0.50 g, 0.964 mmol) was dissolved in hydrogen chloride (4.0 M in dioxane) (4.82 mL, 19.28 mmol) and stirred at room temperature for 16 h. The reaction was concentrated and purified by HPLC to give the title compound. LCMS m/z=463.4 [M+H]$^+$; $^1$H NMR (400 MHz, DMSO-$d_6$) δ ppm 1.31-1.57 (m, 8H), 1.73-1.83 (m, 1H), 2.09-2.19 (m, 1H), 2.24 (s, 3H), 2.75 (t, J=7.20 Hz, 2H), 3.44 (t, J=7.20 Hz, 2H), 3.44 (d, J=6.82 Hz, 2H), 4.00 (s, 2H), 4.07 (d, J=7.33 Hz, 2H), 7.00-7.05 (m, 2H), 7.16-7.22 (m, 4H), 7.27-7.40 (m, 3H).

Example 1.247: Preparation of 2-(((1r,4r)-4-((5-(4-Fluorophenyl)-3-(methylthio)-4-phenyl-1H-pyrazol-1-yl)methyl)cyclohexyl)methoxy)acetic Acid (Compound 1)

Step A: Preparation of 3-(4-Fluorophenyl)-5-(methylthio)-4-phenyl-1H-pyrazole To a solution of 1-(4-fluorophenyl)-2-phenylethanone (1.0 g, 4.67 mmol) in anhydrous THF (10 mL), was added a solution of 1.0 M KO-t-Bu in THF (2 mL). The reaction was stirred for 15 min at room temperature, and then quenched with $CS_2$ (0.38 g, 5.04 mmol). After stirring for 30 min, iodomethane (1.45 g, 10.22 mmol) was added to the reaction over 5 min. The reaction was maintained at the same temperature for 4 h. The reaction was poured into water and extracted with ethyl acetate. The extract was dried over $MgSO_4$ and concentrated under reduced pressure to give a yellow solid (1.02 g). To the suspension of the above-mentioned yellow solid in ethanol (10 mL), hydrazine hydrate (0.70 g, 14.0 mmol) was added at room temperature. The reaction was refluxed for 4 h. After cooling to room temperature, the mixture was concentrated under reduced pressure and extracted with ethyl acetate. The organic extract was dried over $MgSO_4$ and concentrated under reduced pressure. The residue was poured into 10% ethyl acetate in hexane and the precipitate was filtered and dried in air to give the title compound (0.69 g) as a white solid. LCMS m/z=285.4 [M+H]$^+$.

Step B: Preparation of (2-(((1r,4r)-4-((5-(4-Fluorophenyl)-3-(methylthio)-4-phenyl-1H-pyrazol-1-yl)methyl)cyclohexyl)methoxy)acetic Acid To a solution of 3-(4-fluorophenyl)-5-(methylthio)-4-phenyl-1H-pyrazole (150 mg, 0.528 mmol) and tert-butyl 2-(((1r,4r)-4-(tosyloxymethyl)cyclohexyl)methoxy)acetate (218 mg, 0.528 mmol) in DMF (3 mL) was added sodium hydride (12.66 mg, 0.528 mmol) at room temperature. The reaction was heated at 60° C. overnight. After cooling to room temperature, the reaction was poured into water and extracted with ethyl acetate. The organic extract was concentrated under reduced pressure and the resulting residue was purified by HPLC to give the title compound (29 mg). LCMS m/z=469.8 [M+H]$^+$.

Example 1.248: Preparation of 2-(((1r,4r)-4-((3-(4-Fluorophenyl)-5-(methylthio)-4-phenyl-1H-pyrazol-1-yl)methyl)cyclohexyl)methoxy)acetic Acid (Compound 2)

From 3-(4-fluorophenyl)-5-(methylthio)-4-phenyl-1H-pyrazole and tert-butyl 2-(((1r,4r)-4-(tosyloxymethyl)cyclohexyl)methoxy)acetate, the title compound was obtained using a similar method to the one described in Example 1.247, Step B. LCMS m/z=469.5 [M+H]$^+$; $^1$H NMR (400 MHz, DMSO-$d_6$) δ ppm 0.95 (m, 2H), 1.15 (m, 2H), 1.56 (m, 1H), 1.74 (m, 2H), 181 (m, 2H), 1.89 (m, 1H), 2.10 (s, 3H), 3.25 (d, J=6.4 Hz, 2H), 3.89 (s, 2H), 4.20 (d, J=7.2 Hz, 2H), 7.12-7.20 (m, 2H), 7.23-7.49 (m, 7H).

Example 1.249: Preparation of 2-(((1r,4r)-4-((4-(3-Methoxyphenyl)-3-methyl-5-phenyl-1H-pyrazol-1-yl)methyl)cyclohexyl)methoxy)acetic Acid (Compound 6)

Step A: Preparation of 3-Methyl-5-phenyl-1H-pyrazole

To a solution of 1-phenylbutane-1,3-dione (5.0 g, 30.8 mmol) in ethanol (50 mL), was added hydrazine hydrate (1.54 g, 30.8 mmol) at ambient temperature. The reaction was refluxed for 5 h. After cooling, the reaction was concentrated under reduced pressure and extracted with ethyl acetate. The extract was dried over $MgSO_4$ and concentrated under reduced pressure. The residue was added 10% ethyl acetate in hexane. The precipitate was filtered and washed with hexane. The white solid was dried in air to give the title compound (3.9 g). LCMS m/z=159.3 [M+H]$^+$; $^1$H NMR (400 MHz, DMSO-$d_6$) δ ppm 2.25 (s, 3H), 6.65 (s, 1H), 7.34 (m, 1H), 7.42 (m, 2H), 7.82 (m, 2H).

Step B: Preparation of 4-Iodo-3-methyl-5-phenyl-1H-pyrazole

To a solution of 5-methyl-3-phenyl-1H-pyrazole (1.5 g, 9.48 mmol) in THF (20 mL) and water (20 mL), were added sodium iodide (1.42 g, 9.48 mmol), iodine (3.61 g, 14.22 mmol), and $K_2CO_3$ (1.96 g, 14.22 mmol) at room temperature. The reaction was warmed to 100° C. and stirred for 10 h. After cooling to room temperature, the reaction was poured into water and extracted with ethyl acetate, which was washed with 2.0 M aq. sodium thiosulfite and saturated. NaHCO₃ successively. The extract was dried over MgSO₄ and concentrated under reduced pressure to give a semi-solid, which was recrystallized from 10% ethyl acetate in hexane to give the title compound (1.9 g). LCMS m/z=285.5 [M+H]⁺.

Step C: Preparation of tert-Butyl 2-(((1r,4r)-4-((4-Iodo-3-methyl-5-phenyl-1H-pyrazol-1-yl)methyl) cyclohexyl)methoxy)acetate and tert-Butyl 2-(((1r, 4r)-4-((4-Iodo-5-methyl-3-phenyl-1H-pyrazol-1-yl) methyl)cyclohexyl)methoxy)acetate as a Mixture of Regioisomers To a solution of 4-iodo-5-methyl-3-phenyl-1H-pyrazole (1.0 g, 3.52 mmol) in DMF (10 mL), was added sodium hydride (0.084 g, 3.52 mmol) at ambient temperature. After stirring for 10 min, a solution of tert-butyl 2-(((1r,4r)-4-(tosyloxymethyl)cyclohexyl)methoxy)acetate (1.45 g, 3.52 mmol) in DMF (1 mL) was added at room temperature. The reaction was heated to 45° C. and stirred for 8 h. After cooling to room temperature, the reaction was poured into H₂O and extracted with ethyl acetate, which was dried over MgSO₄ and concentrated under reduced pressure. The resulting residue was purified by silica gel column chromatography to give the title compound (1.25 g) as a colorless oil. LCMS m/z=525.4 [M+H]⁺.

Step D: Preparation of (2-(((1r,4r)-4-((4-(3-Methoxyphenyl)-3-methyl-5-phenyl-1H-pyrazol-1-yl)methyl)cyclohexyl)methoxy)acetic Acid To a solution of regioisomers, tert-butyl 2-(((1r,4r)-4-((4-iodo-3-methyl-5-phenyl-1H-pyrazol-1-yl)methyl)cyclohexyl)methoxy)acetate and tert-butyl 2-(((1r,4r)-4-((4-iodo-5-methyl-3-phenyl-1H-pyrazol-1-yl)methyl)cyclohexyl) methoxy)acetate (200 mg, 0.381 mmol), in dioxane (2 mL), were added 3-methoxyphenylboronic acid (58.0 mg, 0.381 mmol), Pd(PPh₃)₄ (22.03 mg, 0.019 mmol), and a 2.0 M aqueous solution of K₂CO₃ (105 mg, 0.763 mmol) at ambient temperature. The reaction was irradiated under microwave for 1.5 h at 150° C. After cooling to room temperature, the reaction was poured into water, extracted with ethyl acetate, and then dried over MgSO₄. The extract was concentrated under reduced pressure and the residue was treated with 4.0 M HCl (5 mL) at room temperature. After stirring for 10 h, the reaction was concentrated under reduced pressure and purified by HPLC to give the title compound (25 mg). LCMS m/z=449.3 [M+H]⁺.

Example 1.250: Preparation of 2-(((1r,4r)-4-((4-(3-Methoxyphenyl)-5-methyl-3-phenyl-1H-pyrazol-1-yl)methyl)cyclohexyl)methoxy)acetic Acid (Compound 7)

From a mixture of regioisomers, tert-butyl 2-(((1r,4r)-4-((4-iodo-3-methyl-5-phenyl-1H-pyrazol-1-yl)methyl)cyclohexyl)methoxy)acetate and tert-butyl 2-(((1r,4r)-4-((4-iodo-5-methyl-3-phenyl-1H-pyrazol-1-yl)methyl)cyclohexyl) methoxy)acetate, and 3-methoxyphenylboronic acid, the title compound was obtained using a similar method to the one described in Example 1.250, Step D. LCMS m/z=449.5 [M+H]⁺; ¹H NMR (400 MHz, DMSO-d₆) δ ppm 0.91 (m, 2H), 1.15 (m, 2H), 1.59 (m, 1H), 1.75 (m, 2H), 1.82 (m, 2H), 1.95 (m, 1H), 2.25 (s, 3H), 2.51 (s, 3H), 3.24 (d, J=6.8 Hz, 2H), 3.75 (s, 2H), 4.01 (d, J=7.4 Hz, 2H), 6.65-6.89 (m, 3H), 7.26-7.49 (m, 6H).

Example 1.251: Preparation of 2-(((1r,4r)-4-((5-Methyl-3,4-diphenyl-1H-pyrazol-1-yl)methyl)cyclohexyl)methoxy)acetic Acid (Compound 11)

To a solution of regioisomers, tert-butyl 2-(((1r,4r)-4-((4-iodo-3-methyl-5-phenyl-1H-pyrazol-1-yl)methyl)cyclohexyl)methoxy)acetate and tert-butyl 2-(((1r,4r)-4-((4-iodo-5-methyl-3-phenyl-1H-pyrazol-1-yl)methyl)cyclohexyl) methoxy)acetate (200 mg, 0.381 mmol), in dioxane (2 mL), were added phenylboronic acid (0.046 g, 0.381 mmol), Pd(PPh₃)₄ (0.022 g, 0.019 mmol), and a 2.0 M aqueous solution of K₂CO₃ (0.105 g, 0.763 mmol) at ambient temperature. The reaction was irradiated under microwave for 4 h at 150° C. After cooling to room temperature, the reaction was poured into water, extracted with ethyl acetate, and then dried over MgSO₄. The extract was concentrated under reduced pressure and the residue was treated with 4.0 M HC (5 mL). After stirring for 10 h, the reaction was concentrated under reduced pressure and purified by HPLC to give the title compound (0.104 g). LCMS m/z=419.3 [M+H]⁺.

Example 1.252: Preparation of 2-(((1s,4s)-4-((5-(4-Fluorophenyl)-3-(methylthio)-4-phenyl-1H-pyrazol-1-yl)methyl)cyclohexyl)methoxy)acetic Acid (Compound 12)

To a solution of 3-(4-fliorophenyl)-5-(methylthio)-4-phenyl-1H-pyrazole (150.0 mg, 0.502 mmol) in DMF (5 mL), was added sodium hydride (12.66 mg, 0.528 mmol) at room temperature. After stirring for 30 min, a solution of tert-butyl 2-(((1r,4r)-4-(tosyloxymethyl)cyclohexyl)methoxy)acetate (218 mg, 0.528 mmol) in DMF (I mL) was added into the reaction at room temperature. The reaction was heated at 60° C. overnight. After cooling to room temperature, the reaction was poured into water and extracted with ethyl acetate. The extract was concentrated under reduced pressure and the residue was treated with 4.0 M HCl in dioxane (5 mL). After standing for 10 h, the reaction was concentrated under reduced pressure and purified by HPLC to give the title compound (21.0 mg). LCMS m/z=469.5 [M+H]⁺.

Example 1.253: Preparation of 2-(((1s,4s)-4-((3-(4-Fluorophenyl)-5-(methylthio)-4-phenyl-1H-pyrazol-1-yl)methyl)cyclohexyl)methoxy)acetic Acid (Compound 10)

From 3-(4-fliorophenyl)-5-(methylthio)-4-phenyl-1H-pyrazole and tert-butyl 2-(((1r,4r)-4-(tosyloxymethyl)cyclohexyl)methoxy), the title compound was obtained using a similar method to the one described in Example 1.252. LCMS m/z=496.4 [M+H]⁺.

Example 1.254: Preparation of 2-(((1s,4s)-4-((4-(3-Methoxyphenyl)-3-methyl-5-phenyl-1H-pyrazol-1-yl)methyl)cyclohexyl)methoxy)acetic Acid (Compound 13)

Step A: Preparation of tert-Buty 2-(((1r,4s)-4-((4-Iodo-3-methyl-5-phenyl-1H-pyrazol-1-yl)methyl) cyclohexyl)methoxy)acetate and tert-Butyl 2-(((1r, 4s)-4-((4-Iodo-5-methyl-3-phenyl-1H-pyrazol-1-yl) methyl)cyclohexyl)methoxy)acetate as a Mixture of Regioisomers To a solution of 4-Iodo-5-methyl-3-phenyl-1H-pyrazole (1.0 g, 3.52 mmol) in DMF (5 mL), was added sodium hydride (0.084 g, 3.52 mmol) at room temperature. After stirring for 30 min, the reaction was treated with tert-butyl 2-(((1r,4r)-4-(tosyloxymethyl)cyclohexyl)methoxy)acetate (132 g, 0.528 mmol) in DMF (5 mL) at ambient temperature. The reaction was stirred at 60° C. for 12 h. The reaction was poured into H$_2$O and extracted with ethyl acetate. The organic extract was dried over MgSO$_4$ and concentrated under reduced pressure. The residue was purified by column chromatography to give the titled compounds (1.2 g) as a mixture of regioisomers. LCMS m/z=525.7 [M+H]$^+$.

Step B: Preparation of (2-(((1s,4s)-4-((4-(3-Methoxyphenyl)-3-methyl-5-phenyl-1H-pyrazol-1-yl)methyl)cyclohexyl)methoxy)acetic Acid To a solution of regioisomers, tert-butyl 2-(((1r,4s)-4-((4-iodo-3-methyl-5-phenyl-1H-pyrazol-1-yl)methyl)cyclohexyl)methoxy)acetate and tert-butyl 2-(((1r,4s)-4-((4-iodo-5-methyl-3-phenyl-1H-pyrazol-1-yl)methyl)cyclohexyl)methoxy)acetate (0.2 g, 0.381 mmol), in dioxane (5 mL), were added 3-methoxyphenylboronic acid (0.058 g, 0.381 mmol), Pd(PPh$_3$)$_4$ (0.022 g, 0.019 mmol), and a 2.0 M aqueous solution of K$_2$CO$_3$ (0.131 g, 0.952 mmol) at ambient temperature. The reaction was irradiated under microwave for 4 h at 150° C. After cooling to room temperature, the mixture was poured into water and extracted with ethyl acetate. The extract was concentrated under reduced pressure and the residue was treated with 4.0 M HCl in dioxane (5 mL). After standing for 10 h, the reaction was concentrated under reduced pressure and purified by HPLC to give the title compound (0.032 g). LCMS m/z=449.2 [M+H]$^+$.

Example 1.255: Preparation of ((1s,4s)-4-((5-Methyl-3,4-diphenyl-1H-pyrazol-1-yl)methyl)cyclohexyl)methanol Step A: Preparation of (E)-1-Benzylidene-2-(((1s,4s)-4-(benzyloxymethyl)cyclohexyl)methyl)hydrazine To a solution of tert-butyl 2-(((1s,4s)-4-(benzyloxymethyl)cyclohexyl)methyl)hydrazinecarboxylate (1.0 g, 2.87 mmol) in dichloromethane (5 mL), was added TFA (5.0 mL) at room temperature. After stirring for 3 h at the same temperature, the mixture was concentrated under reduced pressure. The resulting residue was dissolved in THF (10.0 mL) and benzaldehyde (0.31 g, 2.87 mmol) was added at room temperature. After stirring for 30 min, the reaction was poured into water and extracted with ethyl acetate. The organic layer was washed with sat.NaHCO$_3$, dried over MgSO$_4$, and concentrated under reduced pressure to give the titled compound (0.96 g) without further purification. LCMS m/z=337.4 [M+H]$^+$; $^1$H NMR (400 MHz, DMSO-d$_6$) δ ppm 1.32-1.55 (m, 8H), 1.75-1.85 (m, 2H), 3.11 (m, 2H), 3.31 (d, J=2.5 Hz, 2H), 4.45 (s, 2H), 7.21-7.54 (m, 11H).

Step B: Preparation of 1-(((1s,4s)-4-(Benzyloxymethyl)cyclohexyl)methyl)-5-methyl-3,4-diphenyl-1H-pyrazole To a solution of (E)-1-benzylidene-2-(((1s,4s)-4-(benzyloxymethyl)cyclohexyl)methyl)hydrazine (0.77 g, 2.28 mmol) and (E)-(2-nitroprop-1-enyl)benzene (0.37 g, 2.28 mmol) in THF (5 mL) at −78° C., was added potassium butan-1-olate (0.25 g, 2.28 mmol) dropwise. After stirring for 10 min, TFA (0.35 mL, 4.58 mmol) was added at the same temperature and maintained for 2 h. After warmed to room temperature, the reaction was poured into water and extracted with ethyl acetate. The organic layer was dried over MgSO$_4$, and concentrated under reduced pressure. The residue was purified by silica gel to give the title compound (0.45 g). LCMS m/z=451.3 [M+H]$^+$; $^1$H NMR (400 MHz, DMSO-d$_6$) δ ppm 1.29-1.52 (m, 8H), 1.75-1.80 (m, 1H), 2.11-2.15 (m, 1H), 2.22 (s, 3H), 3.30 (s, 2H), 3.42 (d, J=2.5 Hz, 2H), 4.14 (d, J=2.4 Hz, 2H), 7.23-7.42 (m, 15H).

Step C: Preparation of ((1s,4s)-4-((5-Methyl-3,4-diphenyl-1H-pyrazol-1-yl)methyl)cyclohexyl)methanol To a solution of 1-(((1s,4s)-4-(benzyloxymethyl)cyclohexyl)methyl)-5-methyl-3,4-diphenyl-1H-pyrazole (100 mg, 0.22 mmol) in MeOH (5 mL), was added ammonium formate (280 mg, 4.44 mmol) followed by 10% Pd/C (5 mg). The reaction was heated to 80° C. for 10 h. The mixture was filtered. The filtrate was concentrated under reduced pressure to give the titled compound (78 mg) as a colorless oil. LCMS m/z=361.2 [M+H]$^+$; $^1$H NMR (400 MHz, DMSO-d$_6$) δ ppm 1.34-1.55 (m, 8H), 1.56-1.60 (m, 1H), 2.10-2.15 (m, 1H), 2.21 (s, 3H), 3.31 (d, J=2.5 Hz, 2H), 4.20 (d, J=2.4 Hz, 2H), 7.31-7.54 (m, 10H).

Example 1.256: Preparation of 2-(((1s,4s)-4-((3-Methyl-4,5-diphenyl-1H-pyrazol-1-yl)methyl)cyclohexyl)methoxy)acetic Acid (Compound 15)

To a solution of regioisomers, tert-butyl 2-(((1r,4s)-4-((4-iodo-3-methyl-5-phenyl-1H-pyrazol-1-yl)methyl)cyclohexyl)methoxy)acetate and tert-butyl 2-(((1r,4s)-4-((4-iodo-5-methyl-3-phenyl-1H-pyrazol-1-yl)methyl)cyclohexyl)methoxy)acetate (0.2 g, 0.381 mmol), in dioxane (5 mL), were added phenylboronic acid (0.183 g, 1.5 mmol), Pd(PPh$_3$)$_4$ (86.6 mg, 0.0075 mmol) and a 2.0 M aqueous solution of K$_2$CO$_3$ (0.513 g, 3.5 mmol) at ambient temperature. The reaction was irradiated under microwave for 1.5 h at 150° C. After cooling to room temperature, the reaction was poured into water and extracted with ethyl acetate. The organic extract was concentrated under reduced pressure and the residue was treated with 4.0 M HCl in dioxane (5 mL). After standing for 10 h, the reaction was concentrated under reduced pressure and purified by HPLC to give the title compound (0.075 g). LCMS m/z=419.3 [M+H]$^+$.

Example 1.257: Preparation of 2-(((1s,4s)-4-((5-Methyl-3,4-diphenyl-1H-pyrazol-1-yl)methyl)cyclohexyl)methoxy)acetic Acid (Compound 16)

From a mixture of regioisomers, tert-butyl 2-(((1r,4s)-4-((4-iodo-3-methyl-5-phenyl-1H-pyrazol-1-yl)methyl)cyclohexyl)methoxy)acetate and tert-butyl 2-(((1r,4s)-4-((4-iodo-5-methyl-3-phenyl-1H-pyrazol-1-yl)methyl)cyclohexyl)methoxy)acetate, and phenylboronic acid, the title compound was obtained using a similar method to the one described in Example 1.256. LCMS m/z=419.4 [M+H]$^+$; $^1$H NMR (400 MHz, DMSO-d$_6$) δ ppm 1.25-1.64 (m, 8H), 1.75 (m, 1H), 2.11 (m, 1H), 2.20 (s, 3H), 3.45 (d, J=7.1 Hz, 2H), 4.05 (s, 2H), 4.12 (d, J=7.3 Hz, 2H), 7.23-7.46 (m, 10H).

Example 1.258: Preparation of 2-(((1s,4s)-4-((4-(3-Methoxyphenyl)-3-(methylthio)-5-phenyl-1H-pyrazol-1-yl)methyl)cyclohexyl)methoxy)acetic Acid (Compound 30)

Step A: Preparation of 4-(3-Methoxyphenyl)-5-(methylthio)-3-phenyl-1H-pyrazole

To a solution of 2-(3-methoxyphenyl)-1-phenylethanone (3.0 g, 13.26 mmol) in anhydrous THF (10 mL), was added a solution of 1.0 M KO-t-Bu in THF (13.26 mL, 13.26 mmol). The reaction was stirred for 15 min at room temperature, and carbon disulfide (1.01 g, 13.26 mmol) was added at 0° C. After 15 min, iodomethane (4.12 g, 29.0 mmol) was added dropwise and the reaction was maintained at the same temperature for 4 h. The reaction was poured into water and extracted with ethyl acetate. The organic extract was dried over MgSO$_4$ and concentrated under reduced pressure. The residue was suspended in ethanol (10 mL) and added hydrazine hydrate (1.99 g, 39.8 mmol) at room temperature. The reaction was refluxed for 4 h. After cooling to room temperature, the reaction was concentrated under reduced pressure and extracted with ethyl acetate. The organic extract was dried over MgSO$_4$ and concentrated under reduced pressure to give a semi-solid, which was recrystallized from 10% ethyl acetate in hexane to give the title compound (2.15 g). LCMS m/z=297.5 [M+H]$^+$.

Step B: Preparation of (2-(((1s,4s)-4-((4-(3-Methoxyphenyl)-3-(methylthio)-5-phenyl-1H-pyrazol-1-yl)methyl)cyclohexyl)methoxy)acetic Acid To a solution of 4-(3-methoxyphenyl)-5-(methylthio)-3-phenyl-1H-pyrazole (100 mg, 0.337 mmol) in DMF (2 mL), was added sodium hydride (8.10 mg, 0.337 mmol) at ambient temperature. After stirring for 10 min, a solution of tert-butyl 2-(((1s,4s)-4-(tosyloxymethyl)cyclohexyl)methoxy)acetate (139 mg, 0.337 mmol) in DMF (I mL) was added at room temperature. The reaction was heated to 45° C. and stirred for 8 h. After cooling to room temperature, the reaction was poured into H$_2$O and extracted with ethyl acetate, which was dried over MgSO$_4$ and concentrated under reduced pressure. The resulting residue was treated with 4.0 M HCl in dioxane and stirred for overnight. The reaction was concentrated under reduced pressure and the residue was purified by HPLC to give the title compound (21 mg). LCMS m/z=481.6 [M+H]$^+$.

Example 1.259: Preparation of 1-((1s,4s)-4-(Benzyloxymethyl)cyclohexyl)methyl)-3-(4-fluorophenyl)-5-methyl-4-phenyl-1H-pyrazole Step A: Preparation of (E)-1-(((1s,4s)-4-(benzyloxymethyl)cyclohexyl)methyl)-2-(4-fluorobenzylidene)hydrazine To a solution of tert-butyl 2-(((1s,4s)-4-(benzyloxymethyl)cyclohexyl)methyl)hydrazinecarboxylate (1.0 g, 2.87 mmol) in dichloromethane (5 mL), was added TFA (5.0 mL) at room temperature. After stirring for 3 h at the same temperature, the reaction was concentrated under reduced pressure. The resulting residue was dissolved in THF (10 mL) and 4-fluorobenzaldehyde (0.36 g, 2.87 mmol) was added at room temperature. After stirring for 30 min, the reaction was poured into water and extracted with ethyl acetate. The organic layer was washed with saturated NaHCO$_3$, dried over MgSO$_4$ and then concentrated under reduced pressure to give the title compound (0.96 g) without further purification. LCMS m/z=355.3 [M+H]$^+$.

Step B: Preparation of 1-(((1s,4s)-4-(Benzyloxymethyl)cyclohexyl)methyl)-3-(4-fluorophenyl)-5-methyl-4-phenyl-1H-pyrazole To a solution of (E)-1-(((1s,4s)-4-(benzyloxymethyl)cyclohexyl)methyl)-2-(4-fluorobenzylidene)hydrazine (0.97 g, 2.73 mmol) and (E)-(2-nitroprop-1-enyl)benzene (0.445 g, 2.73 mmol) in THF (5 mL) at −78° C., was added potassium butan-1-olate (0.31 g, 2.73 mmol) dropwise. After stirring for 10 min, TFA (0.42 mL, 5.45 mmol) was added and the reaction maintained at −78° C. for 2 h. After warmed to room temperature, the reaction was poured into water and extracted with ethyl acetate. The organic layer was dried over MgSO$_4$ and concentrated under reduced pressure. The resulting residue was purified by silica gel column chromatography to give the title compound (0.2 g). LCMS m/z=469.3.

Example 1.260: Preparation of 2-(((1s,4s)-4-((5-(4-Methoxyphenyl)-3-(methylthio)-4-phenyl-1H-pyrazol-1-yl)methyl)cyclohexyl)methoxy)acetic Acid (Compound 36)

Step A: Preparation of 3-(4-Methoxyphenyl)-5-(methylthio)-4-phenyl-1H-pyrazole

To a solution of 1-(4-methoxyphenyl)-2-phenylethanone (3.7 g, 16.35 mmol) in anhydrous THF (10 mL), was added a solution of 1.0 M KO-t-Bu in THF at ambient temperature. The reaction was stirred for 15 min at room temperature, then CS$_2$ (1.345 g, 17.66 mmol) was added. After 5 min, iodomethane (5.08 g, 35.8 mmol) was added and the reaction was stirred for 4 h. The reaction was poured into water and extracted with ethyl acetate. The extract was dried over MgSO$_4$ and concentrated under reduced pressure. The residue was dissolved in ethanol (10 mL) and added hydrazine hydrate (2.45 g, 49.1 mmol) at room temperature. The reaction was refluxed for 4 h. After cooling, the reaction was poured into water and extracted with ethyl acetate. The organic layer was dried over MgSO$_4$ and concentrated under reduced pressure. The residue was purified by column chromatography to give the title compound (3.95 g) as a solid. LCMS m/z=297.4 [M+H]$^+$; $^1$H NMR (400 MHz, DMSO-d$_6$) δ ppm 2.41 (s, 3H), 3.72 (s, 3H), 6.72-6.90 (m, 2H), 7.10-7.43 (m, 7H).

Step B: Preparation of (2-(((1s,4s)-4-((5-(4-Methoxyphenyl)-3-(methylthio)-4-phenyl-1H-pyrazol-1-yl)methyl)cyclohexyl)methoxy)acetic Acid To a solution of 3-(4-methoxyphenyl)-5-(methylthio)-4-phenyl-1H-pyrazole (100 mg, 0.337 mmol) in DMF (2 mL), was added sodium hydride (8.10 mg, 0.337 mmol) at ambient temperature. After stirring for 10 min, a solution of tert-butyl 2-(((1s,4s)-4-(tosyloxymethyl)cyclohexyl)methoxy)acetate (139 mg, 0.337 mmol) in DMF (1 mL) was added at room temperature. The reaction was heated to 45° C. and stirred for 8 h. After cooling to room temperature, the reaction was poured into H$_2$O and extracted with ethyl acetate, which was dried over MgSO$_4$ and concentrated under reduced pressure. The resulting residue was treated with 4.0 M HCl in dioxane and stirred for overnight. The reaction was concentrated under reduced pressure and the residue was purified by HPLC to give the title compound (31 mg). LCMS m/z=481.6 [M+H]$^+$.

Example 1.261: Preparation of 2-(((1s,4s)-4-((3-(4-Methoxyphenyl)-5-(methylthio)-4-phenyl-1H-pyrazol-1-yl)methyl)cyclohexyl)methoxy)acetic Acid (Compound 37)

From 3-(4-methoxyphenyl)-5-(methylthio)-4-phenyl-1H-pyrazole and tert-butyl 2-(((1s,4s)-4-(tosyloxymethyl)cyclohexyl)methoxy)acetate, the title compound was obtained using a similar method to the one described in Example 1.260, Step B. LCMS m/z=481.5 [M+H]+.

Example 1.262: Preparation of 2-(((1s,4s)-4-((3-(Methylthio)-4,5-diphenyl-1H-pyrazol-1-yl)methyl)cyclohexyl)methoxy)acetic Acid (Compound 75)

Step A: Preparation of 3,3-Bis(methylthio)-1,2-diphenylprop-2-en-1-one

To a solution of 1,2-diphenylethanone (5.0 g, 25.5 mmol) in anhydrous THF (50 mL), was added a solution of 1.0 M KO-t-Bu in THF (51.0 mL, 51.0 mmol). The reaction was stirred for 15 min at room temperature, and then $K_2CO_3$ (2.095 g, 27.5 mmol) was added. After 10 min, iodomethane (7.92 g, 55.8 mmol) was added and the reaction was stirred for 4 h. The reaction was poured into water and extracted with ethyl acetate. The organic layer was dried over $MgSO_4$ and concentrated under reduced pressure to give the title compound (6.9 g). LCMS m/z=301.3 [M+H]+.

Step B: Preparation of 5-(Methylthio)-3,4-diphenyl-1H-pyrazole

To a suspension of 3,3-bis(methylthio)-1,2-diphenylprop-2-en-1-one (2.5 g, 8.32 mmol) in ethanol (20 mL), was added hydrazine hydrate (1.67 g, 33.3 mmol) at room temperature. The reaction was refluxed for 6 h. After cooling, the reaction was poured into water and extracted with ethyl acetate. The organic extract was dried over $MgSO_4$ and concentrated under reduced pressure. The residue was purified by column chromatography to give the title compound (1.98 g). LCMS m/z=267.0 [M+H]+.

Step C: Preparation of (2-(((1s,4s)-4-((3-(Methylthio)-4,5-diphenyl-1H-pyrazol-1-yl)methyl)cyclohexyl)methoxy)acetic Acid To a solution of 5-(methylthio)-3,4-diphenyl-1H-pyrazole (100 mg, 0.375 mmol) in DMF (3 mL), was added sodium hydride (9.01 mg, 0.375 mmol) at ambient temperature. After stirring for 10 min, a solution of tert-butyl 2-(((1s,4s)-4-(tosyloxymethyl)cyclohexyl)methoxy)acetate (155 mg, 0.375 mmol) in DMF (1 mL) was added at room temperature. The reaction was heated to 45° C. and stirred for 8 h. The reaction was poured into $H_2O$ and extracted with ethyl acetate, which was dried over $MgSO_4$ and concentrated under reduced pressure. The resulting residue was treated with 4.0 M HCl in dioxane and stirred overnight. The reaction was concentrated under reduced pressure and purified by HPLC to give the title compound (19 mg). LCMS m/z=451.6 [M+H]+.

Example 1.263: Preparation of 2-(((1s,4s)-4-((3-(2-Methoxyethylthio)-4,5-diphenyl-1H-pyrazol-1-yl)methyl)cyclohexyl)methoxy)acetic Acid (Compound 188)

Step A: Preparation of 5-(2-Methoxyethylthio)-3,4-diphenyl-1H-pyrazole

To a solution of 3,4-diphenyl-1H-pyrazole-5(4H)-thione (0.5 g, 1.981 mmol) in DMF (5 mL), were added 1-bromo-2-methoxyethane (0.275 g, 1.981 mmol) and $K_2CO_3$ (0.274 g, 1.981 mmol) at room temperature. After stirring for 4 h, the reaction was poured into water and extracted with ethyl acetate. The organic extract was dried over $MgSO_4$ and concentrated under reduced pressure. The resulting residue was purified by column chromatography to give the title compound (0.45 g). LCMS m/z=311.2 [M+H]+; $^1$H NMR (400 MHz, DMSO-$d_6$) δ ppm 3.23 (s, 3H), 3.12-3.54 (m, 4H), 7.22-7.49 (m, 10H), 13.2 (s, 1H).

Step B: Preparation of (2-(((1s,4s)-4-((3-(2-Methoxyethylthio)-4,5-diphenyl-1H-pyrazol-1-yl)methyl)cyclohexyl)methoxy)acetic Acid To a solution of 5-(2-methoxyethylthio)-3,4-diphenyl-1H-pyrazole (180 mg, 0.580 mmol) in DMF (2 mL), was added sodium hydride (13.92 mg, 0.580 mmol) in 0° C. After stirring for 10 min, tert-butyl 2-(((1s,4s)-4-(tosyloxymethyl)cyclohexyl)methoxy)acetate (239 mg, 0.580 mmol) was added and the reaction was warmed to 40° C. After stirring for 12 h, the reaction was poured into water and extracted with ethyl acetate. The organic extract was dried over $MgSO_4$ and concentrated under reduced pressure. The residue was treated with 4.0 M HCl in dioxane (5 mL) and placed for 8 h. The mixture was concentrated under reduced pressure and purified by HPLC to give the title compound (32 mg). LCMS m/z=495.7 [M+H]+.

Example 1.264: Preparation of 2-(((1s,4s)-4-((4-(2,5-Difluorophenyl)-3-(methylthio)-5-phenyl-1H-pyrazol-1-yl)methyl)cyclohexyl)methoxy)acetic Acid (Compound 77)

To a solution of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl)cyclohexyl)methoxy)acetate (110 mg, 0.198 mmol), in dioxane (2 mL), were added 2,5-difluorophenylboronic acid (31.2 mg, 0.198 mmol), Pd(PPh$_3$)$_4$ (11.42 mg, 9.88 μmol), and a 2.0 M aqueous solution of $K_2CO_3$ (54.6 mg, 0.395 mmol) at ambient temperature. The reaction was irradiated under microwave for 1.5 h at 150° C. The reaction was filtered and concentrated under reduced pressure. The residue was treated with 4.0 M HCl (5 mL). After stirring for 10 h, the reaction was concentrated under reduced pressure and purified by HPLC to give the title compound (19 mg). LCMS m/z=487.4 [M+H]+.

Example 1.265: Preparation of 2-(((1s,4s)-4-((4-(2,5-Difluorophenyl)-5-(methylthio)-3-phenyl-1H-pyrazol-1-yl)methyl)cyclohexyl)methoxy)acetic Acid (Compound 78)

From regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl)cyclohexyl)methoxy)acetate, and 2,5-difluorophenylboronic acid, the title compound was obtained using a similar method to the one described in Example 1.264. LCMS m/z=487.8[M+H]+.

Example 1.266: Preparation of 2-(((1s,4s)-4-((4-(2,3-Difluorophenyl)-3-(methylthio)-5-phenyl-1H-pyrazol-1-yl)methyl)cyclohexyl)methoxy)acetic Acid (Compound 82)

To a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl)

cyclohexyl)methoxy)acetate (110 mg, 0.198 mmol), in dioxane (2 mL), were added 2,3-difluorophenylboronic acid (31.2 mg, 0.198 mmol), Pd(PPh$_3$)$_4$ (11.42 mg, 9.88 μmol), and a 2.0 M aqueous solution of K$_2$CO$_3$ (54.6 mg, 0.395 mmol) at ambient temperature. The reaction was irradiated under microwave for 1.5 h at 150° C. After cooling to room temperature, the reaction was poured into water and extracted with ethyl acetate. The organic extract was concentrated under reduced pressure and the resulting residue was treated with 4.0 M HCl in dioxane (5 mL). After standing for 10 h, the reaction was concentrated under reduced pressure and purified by HPLC to give the title compound (13 mg). LCMS m/z=487.4 [M+H]$^+$.

Example 1.267: Preparation of 2-(((1s,4s)-4-((4-(2, 3-Difluorophenyl)-5-(methylthio)-3-phenyl-1H-pyrazol-1-yl)methyl)cyclohexyl)methoxy)acetic Acid (Compound 83)

From a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1r,4r)-4-((4-iodo-5-methylthio-3-phenyl-1H-pyrazol-1-yl)methyl)cyclohexyl)methoxy)acetate, and 2,3-difluorophenylboronic acid, the title compound was obtained using a similar method to the one described in Example 1.266. LCMS m/z=487.4 [M+H]$^+$.

Example 1.268: Preparation of 2-(((1s,4s)-4-((4-(3-Isopropoxyphenyl)-3-(methylthio)-5-phenyl-1H-pyrazol-1-yl)methyl)cyclohexyl)methoxy)acetic Acid (Compound 84)

To a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl)cyclohexyl)methoxy)acetate (110 mg, 0.198 mmol, 1:3 mixture), in dioxane (2 mL), were added 3-isopropoxyphenylboronic acid (35.6 mg, 0.198 mmol), Ph(PPh$_3$)$_4$ (11.42 mg, 9.88 μmol), and a 2.0 M aqueous solution of K$_2$CO$_3$ (54.6 mg, 0.395 mmol) at ambient temperature. The reaction was irradiated under microwave for 1.5 h at 150° C. After cooling to room temperature, the reaction was poured into water and extracted with ethyl acetate. The extract was concentrated under reduced pressure and the resulting residue was treated with 4.0 M HCl in dioxane (5 mL). After standing for 10 h, the reaction was concentrated under reduced pressure and purified by HPLC to give the title compound (21 mg). LCMS m/z=509.5 [M+H]$^+$.

Example 1.269: Preparation of 2-(((1s,4s)-4-((4-(3-Isopropoxyphenyl)-5-(methylthio)-3-phenyl-1H-pyrazol-1-yl)methyl)cyclohexyl)methoxy)acetic Acid (Compound 85)

From a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1r,4r)-4-((4-iodo-5-methylthio-3-phenyl-1H-pyrazol-1-yl)methyl)cyclohexyl)methoxy)acetate, and 3-isopropoxyphenylboronic acid, the title compound was obtained using a similar method to the one described in Example 1.268. LCMS m/z=509.8 [M+H]$^+$.

Example 1.270: Preparation of 2-(((1s,4s)-4-((4-(2, 3-Difluorophenyl)-5-(methylsulfonyl)-3-phenyl-1H-pyrazol-1-yl)methyl)cyclohexyl)methoxy)acetic Acid (Compound 86)

To a solution of 2-(((1s,4s)-4-((4-(2,3-difluorophenyl)-5-(methylthio)-3-phenyl-1H-pyrazol-1-yl)methyl)cyclohexyl)methoxy)acetic acid (10 mg, 0.021 mmol) in CH$_2$Cl$_2$ (2 mL), was added mCPBA (3.55 mg, 0.021 mmol) at room temperature. The reaction was stirred for 3 h at room temperature. The reaction was poured into water and extracted with ethyl acetate. The extract was dried over MgSO$_4$ and concentrated under reduced pressure. The resulting residue was purified by HPLC to give the title compound (9 mg). LCMS m/z=519.7 [M+H]$^+$.

Example 1.271: Preparation of 2-(((1s,4s)-4-((4-(2, 5-Difluorophenyl)-5-(methylsulfonyl)-3-phenyl-1H-pyrazol-1-yl)methyl)cyclohexyl)methoxy)acetic Acid (Compound 87)

To a solution of 2-(((1s,4s)-4-((4-(2,5-difluorophenyl)-5-(methylthio)-3-phenyl-1H-pyrazol-1-yl)methyl)cyclohexyl)methoxy)acetic acid (10 mg, 0.021 mmol) in CH$_2$Cl$_2$ (2 mL), was added mCPBA (7.09 mg, 0.041 mmol) at room temperature. The reaction was stirred for 3 h at room temperature. The reaction was poured into water and extracted with ethyl acetate. The extract was dried over MgSO$_4$ and concentrated under reduced pressure. The resulting residue was purified by HPLC to give the title compound (8 mg). LCMS m/z=519.7 [M+H]$^+$.

Example 1.272: Preparation of 2-(((1s,4s)-4-((4-(3-Fluorophenyl)-5-(methylthio)-3-phenyl-1H-pyrazol-1-yl)methyl)cyclohexyl)methoxy)acetic Acid (Compound 91)

To a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl)cyclohexyl)methoxy)acetate (150 mg, 0.270 mmol), in dioxane (1 mL), were added 3-fluorophenylboronic acid (37.7 mg, 0.270 mmol), Pd(PPh$_3$)$_4$ (1.56 mg, 1.348 μmol) and a 2.0 M aqueous solution of K$_2$CO$_3$ (0.270 mL, 0.539 mmol) at ambient temperature. The reaction was heated under microwave at 120° C. for 1.5 h. The reaction was poured into water and extracted with ethyl acetate. The organic extract was dried over MgSO$_4$ and under reduced pressure. The resulting residue was treated with hydrogen chloride (3.37 mL, 13.48 mmol) and stirred for 5 h. The mixture was concentrated under reduced pressure and purified by HPLC to give the title compound (93 mg). LCMS m/z=469.3 [M+H]$^+$.

Example 1.273: Preparation of 2-(((1s,4s)-4-((4-(2-Fluoro-3-methoxyphenyl)-5-(methylthio)-3-phenyl-1H-pyrazol-1-yl)methyl)cyclohexyl)methoxy)acetic Acid (Compound 92)

To a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl)

cyclohexyl)methoxy)acetate (150 mg, 0.270 mmol), in dioxane (1 mL), were added 2-fluoro-3-methoxyphenylboronic acid (45.8 mg, 0.270 mmol), Pd(PPh$_3$)$_4$ (1.557 mg, 1.348 µmol) and a 2.0 M aqueous solution of K$_2$CO$_3$ (0.270 mL, 0.539 mmol) at ambient temperature. The reaction was heated under microwave at 120° C. for 1.5 h. The reaction was poured into water and extracted with ethyl acetate. The organic extract was dried over MgSO$_4$ and concentrated under reduced pressure. The resulting residue was treated with hydrogen chloride (3.37 mL, 13.48 mmol) and stirred for 5 h. The reaction was concentrated under reduced pressure and purified by HPLC to give the title compound (102 mg). LCMS m/z=499.1 [M+H]$^+$; $^1$H NMR (400 MHz, DMSO-d$_6$) δ ppm 1.34-1.61 (m, 8H), 1.85 (m, 1H), 2.11 (s, 3H), 2.21 (m, 1H), 3.52 (d, J=7.1 Hz, 2H), 3.83 (s, 3H), 3.92 (s, 2H), 4.28 (d, J=7.4 Hz, 2H), 6.80-6.91 (m, 2H), 7.23-7.42 (m, 6H).

Example 1.274: Preparation of 2-(((1s,4s)-4-((4-(4-Fluorophenyl)-5-(methylthio)-3-phenyl-1H-pyrazol-1-yl)methyl)cyclohexyl)methoxy)acetic Acid (Compound 94)

To a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl) cyclohexyl)methoxy)acetate (150 mg, 0.270 mmol), in dioxane (1 mL), was added 4-fluorophenylboronic acid (37.7 mg, 0.270 mmol), Pd(PPh$_3$)$_4$ (15.57 mg, 0.013 mmol) and a 2.0 M aqueous solution of K$_2$CO$_3$ (74.5 mg, 0.539 mmol) at ambient temperature. The reaction was heated under microwave at 120° C. for 1.5 h. The reaction was poured into water and extracted with ethyl acetate. The extract was dried over MgSO$_4$ and concentrated under reduced pressure. The resulting residue was treated with hydrogen chloride (3.37 mL, 13.48 mmol) and stirred for 5 h. The reaction was concentrated under reduced pressure and purified by HPLC to give the title compound (96 mg). LCMS m/z=469.3 [M+H]$^+$; $^1$H NMR (400 MHz, DMSO-d$_6$) δ ppm 1.20-1.35 (m, 8H) 1.63 (m, 1H), 1.95 (s, 3H), 2.09 (m, 1H), 3.48 (d, J=7.0 Hz, 2H), 3.79 (s, 2H), 4.10 (d, J=7.2 Hz, 2H), 6.94-7.09 (m, 9H).

Example 1.275: Preparation of 2-(((1s,4s)-4-((5-(Methylthio)-3-phenyl-4-(3-(trifluoromethyl)phenyl)-1H-pyrazol-1-yl)methyl)cyclohexyl)methoxy) acetic Acid (Compound 96)

To a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl) cyclohexyl)methoxy)acetate (150 mg, 0.270 mmol), in dioxane (1 mL), was added 3-(trifluoromethyl)phenylboronic acid (51.2 mg, 0.270 mmol), Pd(PPh$_3$)$_4$ (15.57 mg, 0.013 mmol) and a 2.0 M aqueous solution of K$_2$CO$_3$ (74.5 mg, 0.539 mmol) at ambient temperature. The reaction was heated under microwave at 120° C. for 1.5 h. The reaction was poured into water and extracted with ethyl acetate. The extract was dried over MgSO$_4$ and concentrated under reduced pressure. The resulting residue was treated with hydrogen chloride (3.37 mL, 13.48 mmol) and stirred for 5 h. The reaction was concentrated under reduced pressure and purified by HPLC to give the title compound (85 mg). LCMS m/z=519.7[M+H]$^+$; $^1$H NMR (400 MHz, DMSO-d$_6$) δ ppm 1.38-1.59 (m, 8H), 1.85 (m, 1H), 2.10 (s, 3H), 2.25 (m, 1H), 3.52 (d, J=7.0 Hz, 2H), 4.01 (s, 2H), 4.31 (d, J=7.2 Hz, 2H), 7.29-7.65 (m, 9H).

Example 1.276: Preparation of 2-(((1s,4s)-4-((4-(4-Chlorophenyl)-5-(methylthio)-3-phenyl-1H-pyrazol-1-yl)methyl)cyclohexyl)methoxy)acetic Acid (Compound 97)

To a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl) cyclohexyl)methoxy)acetate (150 mg, 0.270 mmol), in dioxane (1 mL), was added 4-chlorophenylboronic acid (42.1 mg, 0.270 mmol), Pd(PPh$_3$)$_4$ (15.57 mg, 0.013 mmol) and a 2.0 M aqueous solution of K$_2$CO$_3$ (74.5 mg, 0.539 mmol) at ambient temperature. The reaction was heated under microwave at 120° C. for 1.5 h. The reaction was poured into water and extracted with ethyl acetate. The extract was dried over MgSO$_4$ and concentrated under reduced pressure. The resulting residue was treated with hydrogen chloride (3.37 mL, 13.48 mmol) and was stirred for 5 h. The reaction was concentrated under reduced pressure and purified by HPLC to give the title compound (98 mg). LCMS m/z=485.1 [M+H]$^+$; $^1$H NMR (400 MHz, DMSO-d$_6$) δ ppm 1.21-1.45 (m, 8H), 1.68 (m, 1H), 1.99 (s, 3H), 2.10 (m, 1H), 3.35 (d, J=7.1 Hz, 2H), 3.87 (s, 2H), 4.15 (d, J=7.2 Hz, 2H), 7.12-7.38 (m, 9H).

Example 1.277: Preparation of 2-(((1s,4s)-4-((5-(Methylthio)-3-phenyl-4-(thiophen-2-yl)-1H-pyrazol-1-yl)methyl)cyclohexyl)methoxy)acetic Acid (Compound 108)

To a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl) cyclohexyl)methoxy)acetate (150 mg, 0.270 mmol), in dioxane (1 mL), was added thiophen-2-ylboronic acid (34.5 mg, 0.270 mmol), Pd(PPh$_3$)$_4$ (15.57 mg, 0.013 mmol) and a 2.0 M aqueous solution of K$_2$CO$_3$ (74.5 mg, 0.539 mmol) at ambient temperature. The reaction was heated under microwave at 120° C. for 1.5 h. The reaction was poured into water and extracted with ethyl acetate. The extract was dried over MgSO$_4$ and concentrated under reduced pressure. The resulting residue was treated with hydrogen chloride (3.37 mL, 13.48 mmol) and was stirred for 5 h. The reaction was concentrated under reduced pressure and purified by HPLC to give the title compound (89 mg). LCMS m/z=457.1 [M+H]$^+$.

Example 1.278: Preparation of 2-(((1s,4s)-4-((5-(Methylthio)-3-phenyl-4-(thiophen-3-yl)-1H-pyrazol-1-yl)methyl)cyclohexyl)methoxy)acetic Acid (Compound 110)

To a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl) cyclohexyl)methoxy)acetate (150 mg, 0.270 mmol), in dioxane (1 mL), was added thiophen-3-ylboronic acid (34.5 mg, 0.270 mmol), Pd(PPh$_3$)$_4$ (15.57 mg, 0.013 mmol) and a 2.0 M aqueous solution of K$_2$CO$_3$ (74.5 mg, 0.539 mmol) at ambient temperature. The reaction was heated under microwave at 120° C. for 1.5 h. The reaction was poured into water and extracted with ethyl acetate. The organic extract was dried over MgSO₄ and concentrated under reduced pressure. The resulting residue was treated with hydrogen chloride (3.37 mL, 13.48 mmol) and stirred for 5 h. The mixture was concentrated under reduced pressure and purified by HPLC to give the title compound (106 mg). LCMS m/z=457.2 [M+H]⁺; ¹H NMR (400 MHz, DMSO-d₆) δ ppm 1.34-1.61 (m, 8H), 1.86 (m, 1H), 1.99 (m, 1H), 2.22 (s, 3H), 3.61 (d, J=7.1 Hz, 2H), 3.99 (s, 2H), 4.24 (d, J=7.4 Hz, 2H), 7.01-7.69 (m, 8H).

Example 1.279: Preparation of 2-(((1s,4s)-4-((4-(3-Methoxyphenyl)-5-(methylsulfinyl)-3-phenyl-1H-pyrazol-1-yl)methyl)cyclohexyl)methoxy)acetic Acid (Compound 114)

To a solution of 2-(((1s,4s)-4-((4-(3-methoxyphenyl)-5-(methylthio)-3-phenyl-1H-pyrazol-1-yl)methyl)cyclohexyl)methoxy)acetic acid (52 mg, 0.108 mmol) in DCM (1 mL), was added mCPBA (18.67 mg, 0.108 mmol) portionwise at room temperature. After stirring for 30 min, the reaction was poured into water and extracted with ethyl acetate. The extract was dried over MgSO₄ and concentrated under reduced pressure. The resulting residue was purified by HPLC to provide the title compound (40 mg). LCMS m/z=497.2 [M+H]⁺.

Example 1.280: Preparation of 2-(((1s,4s)-4-((4-(3-Fluoro-5-methylphenyl)-5-(methylthio)-3-phenyl-1H-pyrazol-1-yl)methyl)cyclohexyl)methoxy)acetic Acid (Compound 134)

To a mixture of regioisomers, tert-butyl 2-(((1s,4s)-4-((4-iodo-3-methylthio-5-phenyl-1H-pyrazol-1-yl)methyl)cyclohexyl)methoxy)acetate and tert-butyl 2-(((1s,4s)-4-((4-iodo-5-methylthio-3-phenyl-1H-pyrazol-1-yl)methyl)cyclohexyl)methoxy)acetate (500 mg, 0.898 mmol), in dioxane (5 mL), was added 3-fluoro-5-methylphenylboronic acid (138 mg, 0.898 mmol), Pd(PPh₃)₄ (51.9 mg, 0.045 mmol) and a 2.0 M aqueous solution of K₂CO₃ (248 mg, 1.797 mmol) at ambient temperature. The reaction was heated under Microwave at 120° C. for 1.5 h. The reaction was poured into water and extracted with ethyl acetate. The extract was dried over MgSO₄ and concentrated under reduced pressure. The resulting residue was treated with 4.0 M hydrogen chloride (11.23 mL, 44.9 mmol) in dioxane and stirred for 5 h. The reaction was concentrated under reduced pressure and purified by HPLC. The lyophilized solid was dissolved in acetonitrile (1 mL) and H₂O (2 mL) and added NaOH (14.6 mg, 0.367 mmol) in H₂O (1 mL). The mixture was dried under reduced pressure to give the title compound (185 mg). LCMS m/z=483.4 [M+H]⁺; ¹H NMR (400 MHz, DMSO-d₇) δ ppm 1.30-1.65 (m, 8H), 1.76 (m, 1H), 2.18 (s, 3H), 2.21 (m, 1H), 2.35 (s, 3H), 3.45 (d, J=7.2 Hz, 2H), 3.98 (s, 2H), 4.28 (d, J=7.4 Hz, 2H), 6.85-7.08 (m, 3H), 7.21-7.35 (m, 5H).

Example 1.281: Preparation of 2-(((1r,4s)-4-((3-((S)-3,4-Dihydroxybutyl)-4,5-diphenyl-1H-pyrazol-1-yl)methyl)cyclohexyl)methoxy)acetic Acid (Compound 156)

Step A: Preparation of (R)-4-(3-phenyl-1H-pyrazol-5-yl)butane-1,2-diol

To a solution of 5-(but-3-enyl)-3-phenyl-1H-pyrazole (3.0 g, 15.13 mmol) in iso-propanol (20 mL) and H₂O (20 mL), was added AD-mix-α (20.0 g) at room temperature. The reaction was stirred for 48 h at room temperature. The reaction was poured into saturated Na₂SO₃ (20 mL) and extracted with ethyl acetate The extract was dried over MgSO₄ and concentrated under reduced pressure to give the title compound (2.45 g) as an oil, which was used without further purification. LCMS m/z=232.9 [M+H]⁺.

Step B: Preparation of (R)-5-(2-(2,2-dimethyl-1,3-dioxolan-4-yl)ethyl)-3-phenyl-1H-pyrazole To a solution of (R)-4-(3-phenyl-1H-pyrazol-5-yl)butane-1,2-diol (2.5 g, 10.76 mmol) in acetone (50 mL), were added 2,2-dimethoxypropane (11.21 g, 108 mmol) and PTSA (0.185 g, 1.076 mmol) at room temperature. After stirring for 3 h, the reaction was concentrated under reduced pressure. The resulting residue was poured into water and extracted with ethyl acetate. The extract was dried over MgSO₄ and concentrated under reduced pressure to give the title compound without further purification. LCMS m/z=273.4 [M+H]⁺.

Step C: Preparation of (R)-4-bromo-5-(2-(2,2-dimethyl-1,3-dioxolan-4-yl)ethyl)-3-phenyl-1H-pyrazole To a solution of (R)-5-(2-(2,2-dimethyl-1,3-dioxolan-4-yl)ethyl)-3-phenyl-1H-pyrazole (2.3 g, 8.45 mmol) and MP-carbonate (26 g, 84.5 mmol) in CH₂Cl₂ (100 mL), was added bromine (1.350 g, 8.45 mmol) dropwise at 0° C. After stirring for 1 h, MP-carbonate was filtered off and washed with CH₂Cl₂. The combined organic layer was poured into water, extracted with CH₂Cl₂, dried over MgSO₄, and then concentrated under reduced pressure. The resulting residue was purified by column chromatography to give the title compound (2.81 g) as an oil. LCMS m/z=351.2 [M+H]⁺.

Step D: Preparation of tert-Butyl 2-(((1s,4s)-4-((4-Bromo-5-(2-((R)-2,2-dimethyl-1,3-dioxolan-4-yl)ethyl)-3-phenyl-1H-pyrazol-1-yl)methyl)cyclohexyl)methoxy)acetate and tert-Butyl 2-(((1s,4s)-4-((4-Bromo-3-(2-((R)-2,2-dimethyl-1,3-dioxolan-4-yl)ethyl)-5-phenyl-1H-pyrazol-1-yl)methyl)cyclohexyl)methoxy)acetate as a Mixture of Regioisomers To a solution of (R)-4-bromo-5-(2-(2,2-dimethyl-1,3-dioxolan-4-yl)ethyl)-3-phenyl-1H-pyrazole (1.23 g, 3.50 mmol) in DMF (10 mL), was sodium hydride (0.084 g, 3.50 mmol) added at ambient temperature. After stirring for 30 min, (R)-tert-butyl 2-((4-((4-bromo-3-(2-(2,2-dimethyl-1,3-dioxolan-4-yl)ethyl)-5-phenyl-1H-pyrazol-1-yl)methyl)cyclohexyl)methoxy)acetate (1.45 g, 3.50 mmol) was added and the reaction was heated to 45° C. After stirring for 12 h, the reaction was poured into H₂O and extracted with ethyl acetate, which was dried over MgSO₄ and concentrated under reduced pressure. The resulting residue was purified by column chromatography to give the title compounds (1.82 g, 1:3 ratio) as a mixture of regioisomers. LCMS m/z=591.7 [M+H]⁺.

Step E: Preparation of (2-(((1r,4s)-4-((3-((S)-3,4-dihydroxybutyl)-4,5-diphenyl-1H-pyrazol-1-yl)methyl)cyclohexyl)methoxy)acetic Acid To a solution of regioisomers, tert-butyl 2-(((1r,4s)-4-((4-bromo-3-(2-((S)-2,2-dimethyl-1,3-dioxolan-4-yl)ethyl)-5-phenyl-1H-pyrazol-1-yl)methyl)cyclohexyl)methoxy)acetate and tert-butyl 2-(((1r,4s)-4-((4-bromo-5-(2-((S)-2,2- dimethyl-1,3-dioxolan-4-yl)ethyl)-3-phenyl-1H-pyrazol-1-yl)methyl)cyclohexyl)methoxy)acetate (150 mg, 0.254 mmol), in dioxane (1 mL), were added phenylboronic acid (30.9 mg, 0.254 mmol), Pd(PPh₃)₄ (14.65 mg, 0.013 mmol) and a 2.0 M aqueous solution of K₂CO₃ (70.1 mg, 0.507 mmol) at ambient temperature. The reaction was heated under microwave at 120° C. for 1.5 h. After cooling to room temperature, the reaction was poured into water and extracted with ethyl acetate. The organic extract was dried over MgSO₄ and concentrated under reduced pressure. The residue was treated with 4.0 M HCl in dioxane (5 mL). After standing for 10 h, the reaction was concentrated under reduced pressure and purified by HPLC to give the title compound (12 mg). LCMS m/z=493.5 [M+H]⁺

Example 1.282: Preparation of 2-(((1r,4s)-4-((5-((S)-3,4-Dihydroxybutyl)-3,4-diphenyl-1H-pyrazol-1-yl)methyl)cyclohexyl)methoxy)acetic Acid (Compound 157)

From a mixture of regioisomers, tert-butyl 2-(((1r,4s)-4-((4-bromo-3-(2-((S)-2,2-dimethyl-1,3-dioxolan-4-yl)ethyl)-5-phenyl-1H-pyrazol-1-yl)methyl)cyclohexyl)methoxy)acetate and tert-butyl 2-(((1r,4s)-4-((4-bromo-5-(2-((S)-2,2-dimethyl-1,3-dioxolan-4-yl)ethyl)-3-phenyl-1H-pyrazol-1-yl)methyl)cyclohexyl)methoxy)acetate, and phenylboronic acid, the title compound was obtained by using a similar method to the one described in Example 1.281. LCMS m/z=493.7 [M+H]⁺; ¹H NMR (400 MHz, DMSO-d₆) δ ppm 1.30-1.78 (m, 10H), 1.86 (m, 1H), 2.10 (s, 1H), 2.63 (m, 1H), 2.71 (m, 1H), 3.10 (m, 2H), 3.12-3.22 (m, 1H), 3.35 (d, J=7.2 Hz, 2H), 3.95 (s, 2H), 4.02 (d, J=7.3 Hz, 2H), 7.02-7.35 (m, 10H).

Example 1.283: Preparation of 2-(((1r,4s)-4-((5-((S)-3,4-Dihydroxybutyl)-4-(3-fluorophenyl)-3-phenyl-1H-pyrazol-1-yl)methyl)cyclohexyl)methoxy)acetic Acid (Compound 158)

To a solution of regioisomers, tert-butyl 2-(((1r,4s)-4-((4-bromo-3-(2-((S)-2,2-dimethyl-1,3-dioxolan-4-yl)ethyl)-5-phenyl-1H-pyrazol-1-yl)methyl)cyclohexyl)methoxy)acetate and tert-butyl 2-(((1r,4s)-4-((4-bromo-5-(2-((S)-2,2-dimethyl-1,3-dioxolan-4-yl)ethyl)-3-phenyl-1H-pyrazol-1-yl)methyl)cyclohexyl)methoxy)acetate (150 mg, 0.254 mmol), in dioxane (1 mL), were added 3-fluorophenylboronic acid (35.5 mg, 0.254 mmol), Pd(PPh₃)₄ (14.65 mg, 0.013 mmol) and a 2.0 M aqueous solution of K₂CO₃ (70.1 mg, 0.507 mmol) at ambient temperature. The reaction was heated under microwave at 120° C. for 1.5 h. The reaction was poured into water and extracted with ethyl acetate. The extract was dried over MgSO₄ and concentrated under reduced pressure. The residue was treated with 4.0 M HCl in dioxane. After stirring for 5 h, the reaction was concentrated under reduced pressure and purified by HPLC to give the title compound (45 mg). LCMS m/z=511.5 [M+H]⁺; ¹H NMR (400 MHz, DMSO-d₆) δ ppm 1.10-1.77 (m, 10H), 1.78 (m, 1H), 1.98 (m, 1H), 2.72 (m, 1H), 2.80 (m, 1H), 3.20-3.40 (m, 3H), 3.38 (d, J=7.2 Hz, 2H), 3.97 (s, 2H), 3.99 (d, J=7.3 Hz, 2H), 7.15-7.38 (m, 9H).

Example 1.284: Preparation of 2-(((1r,4s)-4-((4-(3,4-Difluorophenyl)-3-((S)-3,4-dihydroxybutyl)-5-phenyl-1H-pyrazol-1-yl)methyl)cyclohexyl)methoxy)acetic Acid (Compound 159)

To a solution of regioisomers, tert-butyl 2-(((1r,4s)-4-((4-bromo-3-(2-((S)-2,2-dimethyl-1,3-dioxolan-4-yl)ethyl)-5-phenyl-1H-pyrazol-1-yl)methyl)cyclohexyl)methoxy)acetate and tert-butyl 2-(((1r,4s)-4-((4-bromo-5-(2-((S)-2,2-dimethyl-1,3-dioxolan-4-yl)ethyl)-3-phenyl-1H-pyrazol-1-yl)methyl)cyclohexyl)methoxy)acetate (150 mg, 0.254 mmol), in dioxane (1 mL), were added 3,4-difluorophenylboronic acid (40.0 mg, 0.254 mmol), Pd(PPh₃)₄ (14.65 mg, 0.013 mmol) and a 2.0 M aqueous solution of K₂CO₃ (70.1 mg, 0.507 mmol) at ambient temperature. The reaction was heated under microwave at 120° C. for 1.5 h. After cooling to room temperature, the reaction was poured into water and extracted with ethyl acetate. The extract was concentrated under reduced pressure and the resulting residue was treated with 4.0 M HCl in dioxane (5 mL). After standing for 10 h, the reaction was concentrated under reduced pressure and purified by HPLC to give the title compound (12 mg). LCMS m/z=529.7 [M+H]⁺.

Example 1.285: Preparation of 2-(((1r,4s)-4-((4-(3,4-Difluorophenyl)-5-((S)-3,4-dihydroxybutyl)-3-phenyl-1H-pyrazol-1-yl)methyl)cyclohexyl)methoxy)acetic Acid (Compound 160)

From regioisomers, tert-butyl 2-(((1r,4s)-4-((4-bromo-3-(2-((S)-2,2-dimethyl-1,3-dioxolan-4-yl)ethyl)-5-phenyl-1H-pyrazol-1-yl)methyl)cyclohexyl)methoxy)acetate and tert-butyl 2-(((1r,4s)-4-((4-bromo-5-(2-((S)-2,2-dimethyl-1,3-dioxolan-4-yl)ethyl)-3-phenyl-1H-pyrazol-1-yl)methyl)cyclohexyl)methoxy)acetate, and 3,4-difluorophenylboronic acid, the title compound was obtained by using similar method to the one described in Example 1.284. LCMS m/z=529.5 [M+H]⁺; ¹H NMR (400 MHz, DMSO-d₆) δ ppm 1.10-1.77 (m, 10H), 1.75 (m, 1H), 2.10 (m, 1H), 2.70 (m, 1H), 2.75 (m, 1H), 3.15 (m, 1H), 3.21 (m, 1H), 3.32 (m, 1H), 3.35 (d, J=7.2 Hz, 2H), 3.97 (s, 2H), 3.98 (d, J=7.2 Hz, 2H), 6.95 (m, 1H), 7.14-7.41 (m, 7H).

Example 1.286: Preparation of 2-(((1r,4s)-4-((4-(3-Chlorophenyl)-5-((S)-3,4-dihydroxybutyl)-3-phenyl-1H-pyrazol-1-yl)methyl)cyclohexyl)methoxy)acetic Acid (Compound 162)

To a solution of regioisomers, tert-butyl 2-(((1r,4s)-4-((4-bromo-3-(2-((S)-2,2-dimethyl-1,3-dioxolan-4-yl)ethyl)-5-phenyl-1H-pyrazol-1-yl)methyl)cyclohexyl)methoxy)acetate and tert-butyl 2-(((1r,4s)-4-((4-bromo-5-(2-((S)-2,2-dimethyl-1,3-dioxolan-4-yl)ethyl)-3-phenyl-1H-pyrazol-1-yl)methyl)cyclohexyl)methoxy)acetate (150 mg, 0.254 mmol), in dioxane (1 mL), were added 3-chlorophenylboronic acid (39.7 mg. 0.254 mmol), Pd(PPh₃)₄ (14.65 mg, 0.013 mmol) and a 2.0 M aqueous solution of K₂CO₃ (70.1 mg, 0.507 mmol) at ambient temperature. The reaction was heated under microwave at 120° C. for 1.5 h. The reaction was poured into water and extracted with ethyl acetate. The extract was dried over MgSO₄ and concentrated under reduced pressure. The residue was treated with 4.0 M HCl in dioxane (5 mL). After stirring for 5 h, the reaction was concentrated under reduced pressure and purified by HPLC to give the title compound (65 mg). LCMS m/z=528.3 [M+H]⁺; ¹H NMR (400 MHz, DMSO-d₆) δ ppm 1.31-1.65 (m, 10H), 1.80 (m, 1H), 2.12 (m, 1H), 2.72 (m, 1H), 2.80 (m, 1H), 3.20 (m, 1H), 3.25 (m, 1H), 3.42 (m, 1H), 3.45 (d, J=7.2 Hz, 2H), 4.00 (s, 2H), 4.05 (d, J=7.2 Hz, 2H), 7.13-7.42 (m, 9H).

Example 1.287: Preparation of 2-(((1s,4s)-4-((5-((R)-3,4-Dihydroxybutyl)-4-(3-fluorophenyl)-3-phenyl-1H-pyrazol-1-yl)methyl)cyclohexyl)methoxy)acetic Acid (Compound 169)

To a solution of regioisomers, tert-butyl 2-(((1r,4s)-4-((4-bromo-3-(2-((S)-2,2-dimethyl-1,3-dioxolan-4-yl)ethyl)-5- phenyl-1H-pyrazol-1-yl)methyl)cyclohexyl)methoxy)acetate and tert-butyl 2-(((1r,4s)-4-((4-bromo-5-(2-((S)-2,2-dimethyl-1,3-dioxolan-4-yl)ethyl)-3-phenyl-1H-pyrazol-1-yl)methyl)cyclohexyl)methoxy)acetate (150 mg, 0.254 mmol), in dioxane (1 mL), were added 3-fluorophenylboronic acid (35.5 mg, 0.254 mmol), Pd(PPh$_3$)$_4$ (14.65 mg, 0.013 mmol) and a 2.0 M aqueous solution of K$_2$CO$_3$ (70.1 mg, 0.507 mmol) at ambient temperature. The reaction was heated under microwave at 120° C. for 1.5 h. The reaction was poured into water and extracted with ethyl acetate. The organic extract was dried over MgSO$_4$ and concentrated under reduced pressure. The residue was treated with 4.0 M HCl in dioxane (5 mL). After stirring for 5 h, the reaction was concentrated under reduced pressure and purified by HPLC to give the title compound (89 mg). LCMS m/z=511.4 [M+H]$^+$.

Example 1.288: Preparation of 2-(((1s,4s)-4-((4-(3,4-Difluorophenyl)-5-((R)-3,4-dihydroxybutyl)-3-phenyl-1H-pyrazol-1-yl)methyl)cyclohexyl)methoxy)acetic Acid (Compound 170)

To a solution of regioisomers, tert-butyl 2-(((1r,4s)-4-((4-bromo-3-(2-((S)-2,2-dimethyl-1,3-dioxolan-4-yl)ethyl)-5-phenyl-1H-pyrazol-1-yl)methyl)cyclohexyl)methoxy)acetate and tert-butyl 2-(((1r,4s)-4-((4-bromo-5-(2-((S)-2,2-dimethyl-1,3-dioxolan-4-yl)ethyl)-3-phenyl-1H-pyrazol-1-yl)methyl)cyclohexyl)methoxy)acetate (150 mg, 0.254 mmol), in dioxane (1 mL), was added 3,4-difluorophenylboronic acid (40.0 mg, 0.254 mmol), Pd(PPh$_3$)$_4$ (14.65 mg, 0.013 mmol) and a 2.0 M aqueous solution of K$_2$CO$_3$ (70.1 mg, 0.507 mmol) at ambient temperature. The reaction was heated under microwave at 120° C. for 1.5 h. The reaction was extracted with ethyl acetate and concentrated under reduced pressure. The residue was treated with 4.0 M HCl in dioxane and was stirred for 5 h. The reaction was concentrated under reduced pressure and purified by HPLC to give the title compound (72 mg). LCMS m/z=529.3 [M+H]$^+$.

Example 1.289: Preparation of 2-(((1s,4s)-4-((4-(3-Chlorophenyl)-5-((R)-3,4-dihydroxybutyl)-3-phenyl-1H-pyrazol-1-yl)methyl)cyclohexyl)methoxy)acetic Acid (Compound 171)

To a solution of regioisomers, tert-butyl 2-(((1r,4s)-4-((4-bromo-3-(2-((S)-2,2-dimethyl-1,3-dioxolan-4-yl)ethyl)-5-phenyl-1H-pyrazol-1-yl)methyl)cyclohexyl)methoxy)acetate and tert-butyl 2-(((1r,4s)-4-((4-bromo-5-(2-((S)-2,2-dimethyl-1,3-dioxolan-4-yl)ethyl)-3-phenyl-1H-pyrazol-1-yl)methyl)cyclohexyl)methoxy)acetate (150 mg, 0.254 mmol), in dioxane (1 mL), were added 3-chlorophenylboronic acid (39.7 mg, 0.254 mmol), Pd(PPh$_3$)$_4$ (14.65 mg, 0.013 mmol) and a 2.0 M aqueous solution of K$_2$CO$_3$ (70.1 mg, 0.507 mmol) at ambient temperature. The reaction was heated under microwave at 120° C. for 1.5 h. The reaction was extracted with ethyl acetate and concentrated under reduced pressure. The residue was treated with 4.0 M HCl in dioxane and stirred for 5 h. The reaction was concentrated under reduced pressure and purified by HPLC to give the title compound (85 mg). LCMS m/z=528.3 [M+H]$^+$.

Example 1.290: Preparation of 2-(((1s,4s)-4-((3-(Cyanomethylthio)-4,5-diphenyl-1H-pyrazol-1-yl)methyl)cyclohexyl)methoxy)acetic Acid (Compound 183)

Step A: Preparation of 2-(3,4-Diphenyl-1H-pyrazol-5-ylthio)acetonitrile

To a solution of 3,4-diphenyl-1H-pyrazole-5(4H)-thione (0.49 g, 1.981 mmol) in DMF (5 mL), were added 2-bromoacetonitrile (0.253 g, 1.981 mmol) and K$_2$CO$_3$ (0.274 g, 1.981 mmol) at room temperature. After stirring for 2 h, the reaction was poured into water and extracted with ethyl acetate. The organic extract was dried over MgSO$_4$ and concentrated under reduced pressure. The residue was purified by column chromatography to give the title compound (0.52 g). LCMS m/z=292.1

Step B: Preparation of (2-(((1s,4s)-4-((3-(Cyanomethylthio)-4,5-diphenyl-1H-pyrazol-1-yl)methyl) cyclohexyl)methoxy)acetic Acid To a solution of 2-(3,4-diphenyl-1H-pyrazol-5-ylthio)acetonitrile (330 mg, 1.13 mmol) in DMF (2 mL), was added sodium hydride (27.2 mg, 1.133 mmol) in 0° C. After stirring for 10 min, tert-butyl 2-(((1s,4s)-4-(tosyloxymethyl)cyclohexyl)methoxy)acetate (467 mg, 1.13 mmol) was added and the reaction was warmed to 40° C. After stirring for 12 h, the reaction was poured into water and extracted with ethyl acetate. The extract was dried over MgSO$_4$, concentrated under reduced pressure, and then treated with 4.0 M HCl in dioxane (5 mL). After stirring for 8 h, the mixture was concentrated under reduced pressure and purified by HPLC to give the title compound (78 mg). LCMS m/z=476.2 [M+H]$^+$.

Example 1.291: Preparation of 2-(((1s,4s)-4-((5-(2-Methoxyethylthio)-3,4-diphenyl-1H-pyrazol-1-yl) methyl)cyclohexyl)methoxy)acetic Acid (Compound 189)

From 5-(2-methoxyethylthio)-3,4-diphenyl-1H-pyrazole and tert-butyl 2-(((1s,4s)-4-(tosyloxymethyl)cyclohexyl) methoxy)acetate, the title compound was obtained by using similar method to the one described in Example 1.263. LCMS m/z=495.7 [M+H]$^+$; $^1$H NMR (400 MHz, DMSO-d$_6$) δ ppm 1.35-1.52 (m, 8H), 1.85 (m, 1H), 2.31 (m, 1H), 2.43 (t, J=2.5 Hz, 2H), 2.61 (t, J=2.5 Hz, 2H), 3.05 (s, 3H), 3.46 (d, J=7.1 Hz, 2H), 3.98 (s, 2H), 4.31 (d, J=7.2 Hz, 2H), 7.31-7.54 (in, 10H).

Example 1.292: Preparation of 2-(((1s,4s)-4-((3-(2-Ethoxyethylthio)-4,5-diphenyl-1H-pyrazol-1-yl) methyl)cyclohexyl)methoxy)acetic Acid (Compound 185)

Step A: Preparation of 5-(2-Ethoxyethylthio)-3,4-diphenyl-1H-pyrazole

To a solution of 3,4-diphenyl-1H-pyrazole-5(4H)-thione (0.5 g, 1.981 mmol) in DMF (5 mL), were added 1-bromo-2-ethoxyethane (0.303 g, 1.981 mmol) and K$_2$CO$_3$ (0.274 g, 1.981 mmol) at room temperature. After stirring for 4 h, the reaction was poured into water and extracted with ethyl acetate, which was dried over MgSO$_4$ and concentrated under reduced pressure. The residue was purified by column chromatography to give the title compound (0.45 g). LCMS m/z=343.5 [M+H]$^+$; $^1$H NMR (400 MHz, DMSO-d$_6$) δ ppm 1.20 (t, J=7.1 Hz, 3H), 3.25 (m, 2H), 3.45 (m, 2H), 4.25 (q, J=7.1 Hz, 2H), 7.25-7.56 (m, 10H), 13.0 (s, 1H).

Step B: Preparation of (2-(((1s,4s)-4-((3-(2-Ethoxyethylthio)-4,5-diphenyl-1H-pyrazol-1-yl)methyl) cyclohexyl)methoxy)acetic Acid To a solution of 5-(2-ethoxyethylthio)-3,4-diphenyl-1H-pyrazole (320 mg, 0.986 mmol) in DMF (2 mL), was added sodium hydride (23.67 mg, 0.986 mmol) at 0° C. After stirring for 10 min, tert-butyl 2-(((1s,4s)-4-(tosyloxymethyl)cyclohexyl)methoxy)acetate (407 mg, 0.986 mmol) was added and the reaction was warmed to 40° C. After stirring for 12 h, the reaction was poured into water and extracted with ethyl acetate. The extract was dried over $MgSO_4$ and concentrated under reduced pressure. The resulting residue was treated with 4.0 M HCl in dioxane (5 mL) and stirred for 8 h. The reaction was concentrated under reduced pressure and purified by HPLC to give the title compound (70 mg). LCMS m/z=509.5 [M+H]$^+$.

Example 1.293: Preparation of 2-(((1s,4s)-4-((5-(2-Ethoxyethylthio)-3,4-diphenyl-1H-pyrazol-1-yl)methyl)cyclohexyl)methoxy)acetic Acid (Compound 186)

From 5-(2-ethoxyethylthio)-3,4-diphenyl-1H-pyrazole and tert-butyl 2-(((1s,4s)-4-(tosyloxymethyl)cyclohexyl)methoxy)acetate, the title compound was obtained by using a similar method to the one described in Example 1.292. LCMS m/z=509.6 [M+H]$^+$; $^1$H NMR (400 MHz, DMSO-$d_6$) δ ppm 1.01 (t, J=7.1 Hz, 3H), 1.35-1.52 (m, 8H), 1.85 (m, 1H), 2.25 (m, 1H), 2.41 (q, J=7.1 Hz, 2H), 2.60 (t, J=5.0 Hz, 2H), 3.25 (t, J=5.0 Hz, 2H), 3.45 (d, J=7.1 Hz, 2H), 4.00 (s, 2H), 4.35 (d, J=7.2 Hz, 2H), 7.25-7.53 (m, 10H).

Example 1.294: Preparation of 2-(((1s,4s)-4-((5-(3-Hydroxypropylthio)-3,4-diphenyl-1H-pyrazol-1-yl)methyl)cyclohexyl)methoxy)acetic Acid (Compound 187)

Step A: Preparation of 3,4-Diphenyl-5-(2-(tetrahydro-2H-pyran-2-yloxy)ethylthio)-1H-pyrazole To a solution of 3-(4-bromo-3-phenyl-1H-pyrazol-5-yl)propan-1-ol (1.0 g, 3.56 mmol) in THF (10 mL), was added 3,4-dihydro-2H-pyran (0.898 g, 10.67 mmol) followed by PTSA (0.061 g, 0.356 mmol) at room temperature. After stirring for 12 h, the reaction was poured into water and extracted with ethyl acetate. The extract was dried over $MgSO_4$ and concentrated under reduced pressure to give the title compound (1.12 g). LCMS m/z=381.2 [M+H]$^+$.

Step B: Preparation of (2-(((1s,4s)-4-((5-(2-Hydroxyethylthio)-3,4-diphenyl-1H-pyrazol-1-yl)methyl)cyclohexyl)methoxy)acetic Acid To a solution of 3,4-diphenyl-5-(3-(tetrahydro-2H-pyran-2-yloxy)propylthio)-1H-pyrazole (120 mg, 0.304 mmol) in DMF (2 mL), was added sodium hydride (7.30 mg, 0.304 mmol) at 0° C. After stirring for 10 min, tert-butyl 2-(((1s,4s)-4-(tosyloxymethyl)cyclohexyl)methoxy)acetate (125 mg, 0.304 mmol) was added and the reaction was warmed to 40° C. After stirring for 12 h, the reaction was poured into water and extracted with ethyl acetate. The extract was concentrated under reduced pressure and treated with 4.0 M HCl dioxane (5 mL) for 8 h. The mixture was concentrated under reduced pressure and purified by HPLC to give the title compound (105 mg). LCMS m/z=495.6 [M+H]$^+$; $^1$H NMR (400 MHz, DMSO-$d_6$) δ ppm 1.35-1.52 (m, 10H), 1.83 (m, 1H), 2.22 (m, 1H), 2.46 (t, J=5.0 Hz, 2H), 3.22 (t, J=5.0 Hz, 2H), 3.50 (d, J=7.1 Hz, 2H), 3.91 (s, 2H), 4.30 (d, J=7.2 Hz, 2H), 7.23-7.50 (m, 10H).

Example 2: Homogeneous Time-Resolved Fluorescence (HTRF®) Assay For Direct cAMP Measurement Compounds were screened for agonists of the human prostacyclin (PGI2) receptor using the HTRF® assay for direct cAMP measurement (Gabriel et al., ASSAY and Drug Development Technologies, 1:291-303, 2003) and recombinant CHO-K1 cells stably transfected with human prostacyclin receptor. CHO-K1 cells were obtained from ATCC® (Manassas, Va.; Catalog #CCL-61). An agonist of the prostacyclin receptor was detected in HTRF® assay for direct cAMP measurement as a compound which increased cAMP concentration. HTRF® assay also was used to determine $EC_{50}$ values for prostacyclin receptor agonists.

Principle of the assay: The HTRF® assay kit was purchased from Cisbio-US, Inc. (Bedford, Mass.; Catalog #62AM4PEC). The HTRF® assay supported by the kit is a competitive immunoassay between endogenous cAMP produced by the CHO-K1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

Standard curve: The fluorescence ratio (665 nm/620 nm) of the standards (0.17 to 712 nM cAMP) included in the assay was calculated and used to generate a cAMP standard curve according to the kit manufacturer's instructions. The fluorescence ratio of the samples (test compound or compound buffer) was calculated and used to deduce respective cAMP concentrations by reference to the cAMP standard curve.

Setup of the assay: The HTRF® assay was carried out using a two-step protocol essentially according to the kit manufacturer's instructions, in 20 µL total volume per well in 384-well plate format (ProxiPlates; PerkinElmer, Fremont, Calif.; catalog #6008280). To each of the experimental wells was transferred 3000 recombinant CHO-K1 cells in 5 µL assay buffer (phosphate buffered saline containing calcium chloride and magnesium chloride (Invitrogen, Carlsbad, Calif.; catalog #14040) supplemented with IBMX (100 µM) and rolipram (10 µM) (phosphodiesterase inhibitors; Sigma-Aldrich, St. Louis, Mo.; catalog #15879 and catalog #R6520, respectively) and 0.1% bovine serum albumin (BSA) fraction V (Sigma-Aldrich; catalog #A3059)), followed by test compound in 5 µL assay buffer or 5 µL assay buffer. The plate was then incubated at room temperature for 1 h. To each well was then added 5 µL cAMP-d2 conjugate in lysis buffer and 5 µL Cryptate conjugate in lysis buffer according to the kit manufacturer's instructions. The plate was then further incubated at room temperature for 1 h, after which the assay plate was read.

Assay readout: The HTRF® readout was accomplished using a PHERAstar (BMG LABTECH Inc., Durham, N.C.) or EnVision™ (PerkinElmer, Fremont Calif.) microplate reader.

Certain compounds of the present invention and their corresponding activity values are shown in TABLE B.

TABLE B

| Compound No. | human PGI2 receptor $EC_{50}$ (nM) (HTRF®) |
|---|---|
| 90 | 7 |
| 111 | 16 |

TABLE B-continued

| Compound No. | human PGI2 receptor EC$_{50}$ (nM) (HTRF ®) |
|---|---|
| 184 | 11 |
| 198 | 2 |

Certain other compounds of the invention had activity values ranging from about 1.3 nM to about 5 μM in this assay.

Example 3: Human Platelet Aggregation Inhibition Test

Blood collected from healthy human volunteers in aqueous trisodium citrate solution was centrifuged at 150 g for 15 min and the upper layer was recovered to obtain platelet-rich plasma (PRP). The residual blood was centrifuged at 3000 g for 10 min and the supernatant was collected as platelet-poor plasma (PPP). Platelet concentration in the PRP was determined using the Z series Beckman Coulter particle counter (Beckman, Fullerton, Calif.) and adjusted to 250,000 platelets/μL using PPP. 480 μL of PRP was pre-incubated at 37° C. and stirred at 1200 rpm with 10 μL aqueous test compound solution for 1 min prior to induction of aggregation by the addition of 10 μL of aqueous adenosine diphosphate (ADP) solution to adjust the final ADP concentration in the PRP to $1\times10^{-5}$ M. The maximal amplitude of aggregation response within 3 min was determined and measured in triplicate using the Chronolog model 490 aggregometer (Chrono-log Corp., Havertown, Pa.). Percent inhibition of aggregation was calculated from the maximum decrease in optical density of the control (addition of water in place of the test compound solution) sample and of the samples containing test compound. The test compound was added to adjust the final concentration to the range $10^{-9}$ to $10^{-4}$ M, and IC$_{50}$ values were determined by inhibition percentage of aggregation at each concentration. The results are shown in Table C.

TABLE C

| Compound No. | human PRP IC$_{50}$ (nM) |
|---|---|
| 184 | 20 |
| 111 | 28 |
| 146 | 70 |
| 135 | 220 |

Certain other compounds of the invention had activity values ranging from about 10.3 nM to about 810 nM in this assay.

It is apparent that the compounds of the present invention markedly inhibit platelet aggregation in human PRP.

Example 4: Rat Model of Pulmonary Arterial Hypertension

Animals: Male Wistar rats (100-150 g at start of study) (Charles River Laboratories, Wilmington, Mass.) were housed two per cage and maintained in a humidity—(40-60%) and temperature—(68-72° F.) controlled facility on a 12 hr:12 hr light/dark cycle (lights on at 6:30 am) with free access to food (Harlan Teklad, Orange Calif., Rodent Diet 8604) and water. Rats were allowed one week of habituation to the animal facility before testing.

Rat monocrotaline model: The rat monocrotaline (MCT) model is a standard and well-accepted model of pulmonary arterial hypertension. MCT induces acute pulmonary endothelial damage associated with pulmonary vascular inflammation. Subsequently, pulmonary artery smooth muscle cells proliferate, occluding small pulmonary vessels and leading to severe pulmonary arterial hypertension including right ventricular hypertrophy. (See, e.g., Schermuly et al., Circ. Res., 2004, 94:1101-1108.)

Figure 2:
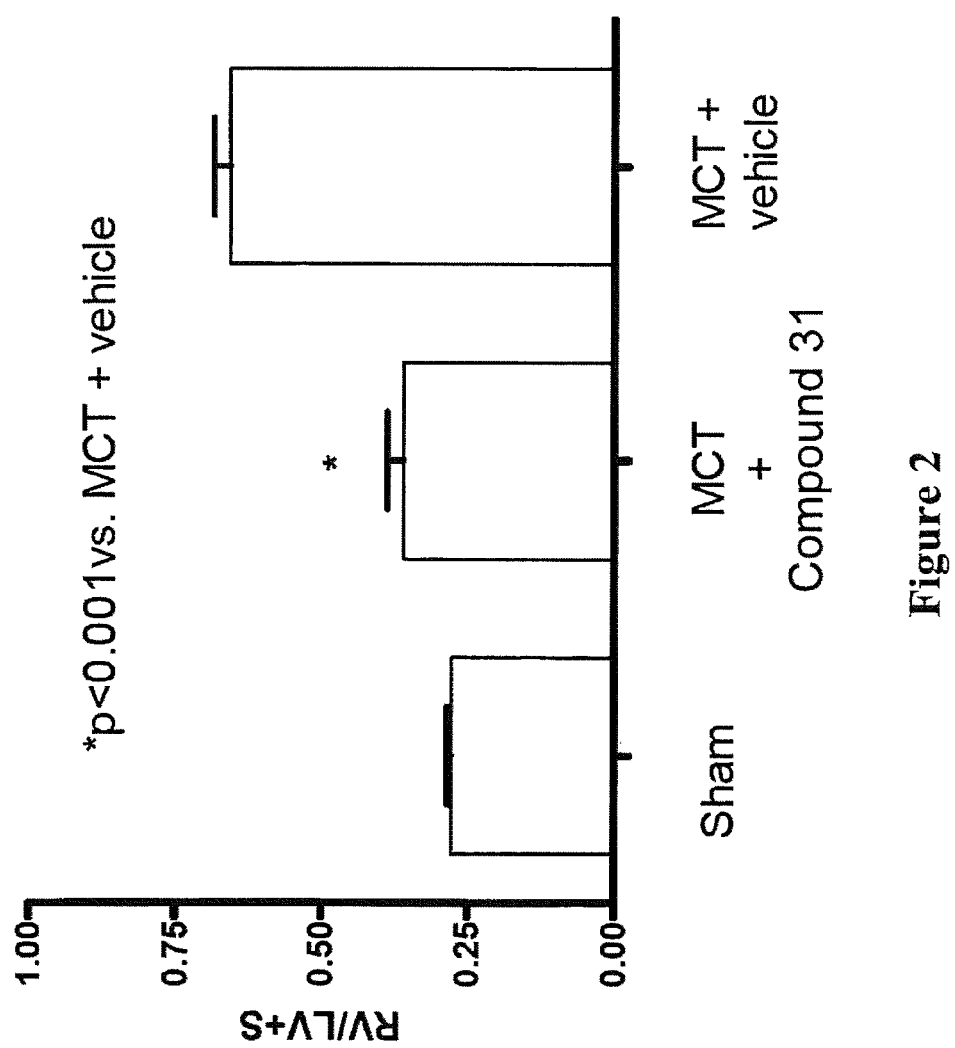
FIG. 2 shows the results of an experiment which measured the ability of Compound 31 to inhibit the right ventricle hypertrophic response to MCT-induced pulmonary arterial hypertension in rat.
Figure 3:
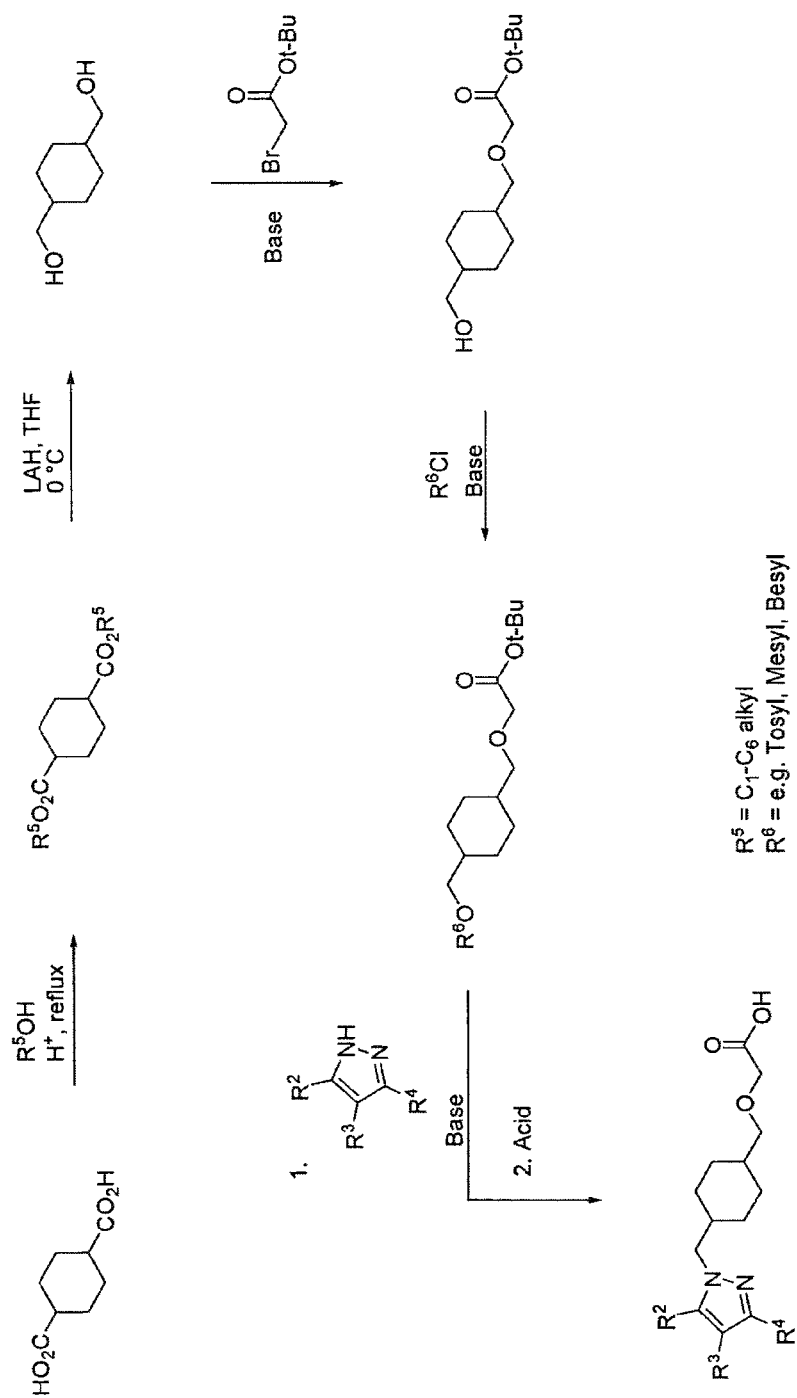
FIG. 3 depicts a general method for the preparation of compounds of the present invention. First, cyclohexane-1,4-dicarboxylic acid is esterified and then reduced to give the corresponding diol. The diol is mono-alkylated with tert-butyl bromoacetate and the free hydroxyl is activated as a sulfonate ester. Coupling of the sulfonate ester with a pyrazole followed by acid hydrolysis affords compounds of Formula Ia.
Figure 4:
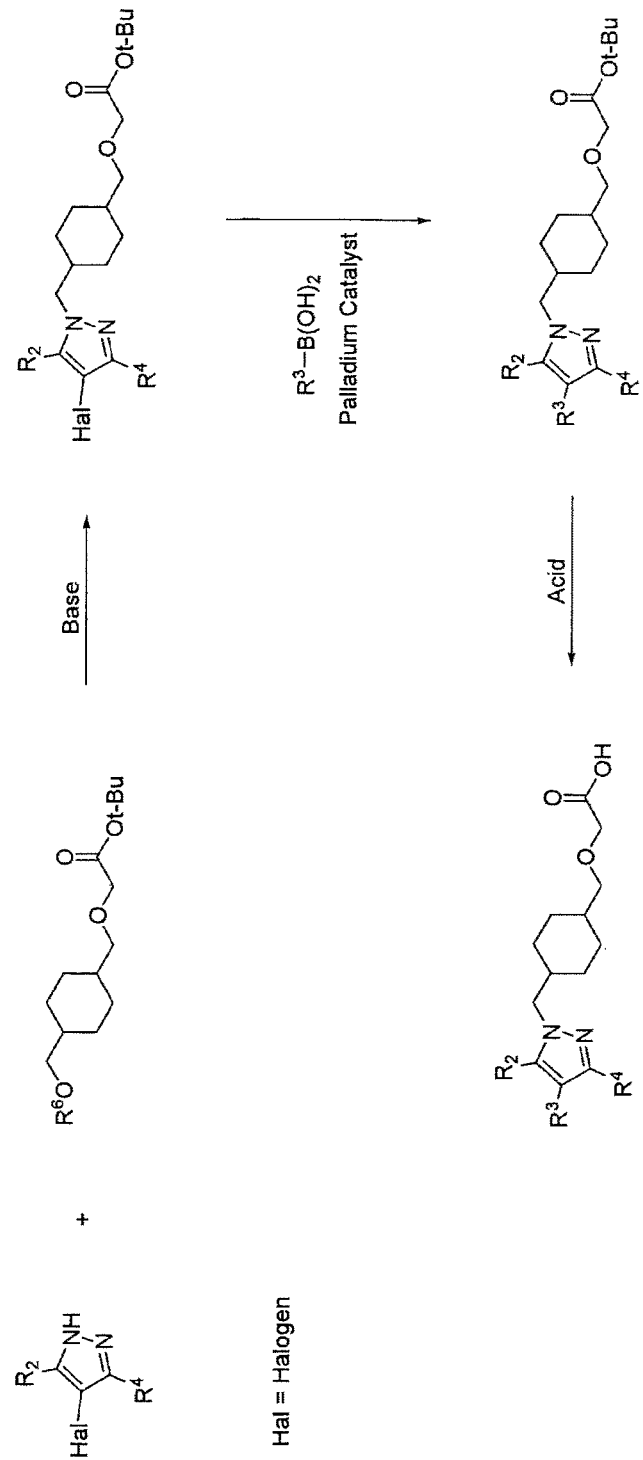
FIG. 4 depicts an alternative general method for the preparation of compounds of the present invention. In this method the sulfonate ester shown in FIG. 3 is reacted in the presence of a base with a pyrazole bearing a halogen at a position equivalent to $R^3$. The product then undergoes a Suzuki coupling with a boronic acid derivative and then acid hydrolysis affords compounds of Formula Ia.
Figure 5:
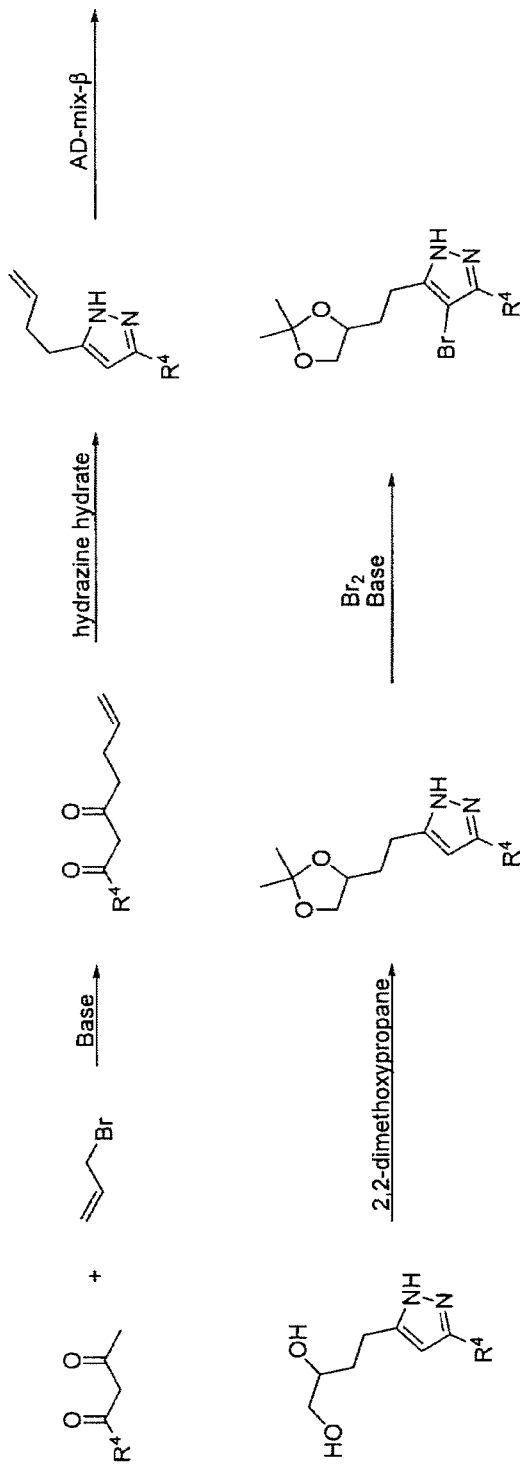
FIG. 5 depicts a method of preparing an intermediate useful in the synthesis of certain dihydroxy compounds of the present invention. First, a 3-oxobutanoyl derivative is reacted with allyl bromide in the presence of base to give a 3-oxohept-6-enoyl derivative. Reaction with hydrazine hydrate gives a 5-(but-3-enyl)-1H-pyrazole which is converted to the diol with AD-mix-β and then protected with 2,2-dimethoxypropane.
Figure 6:
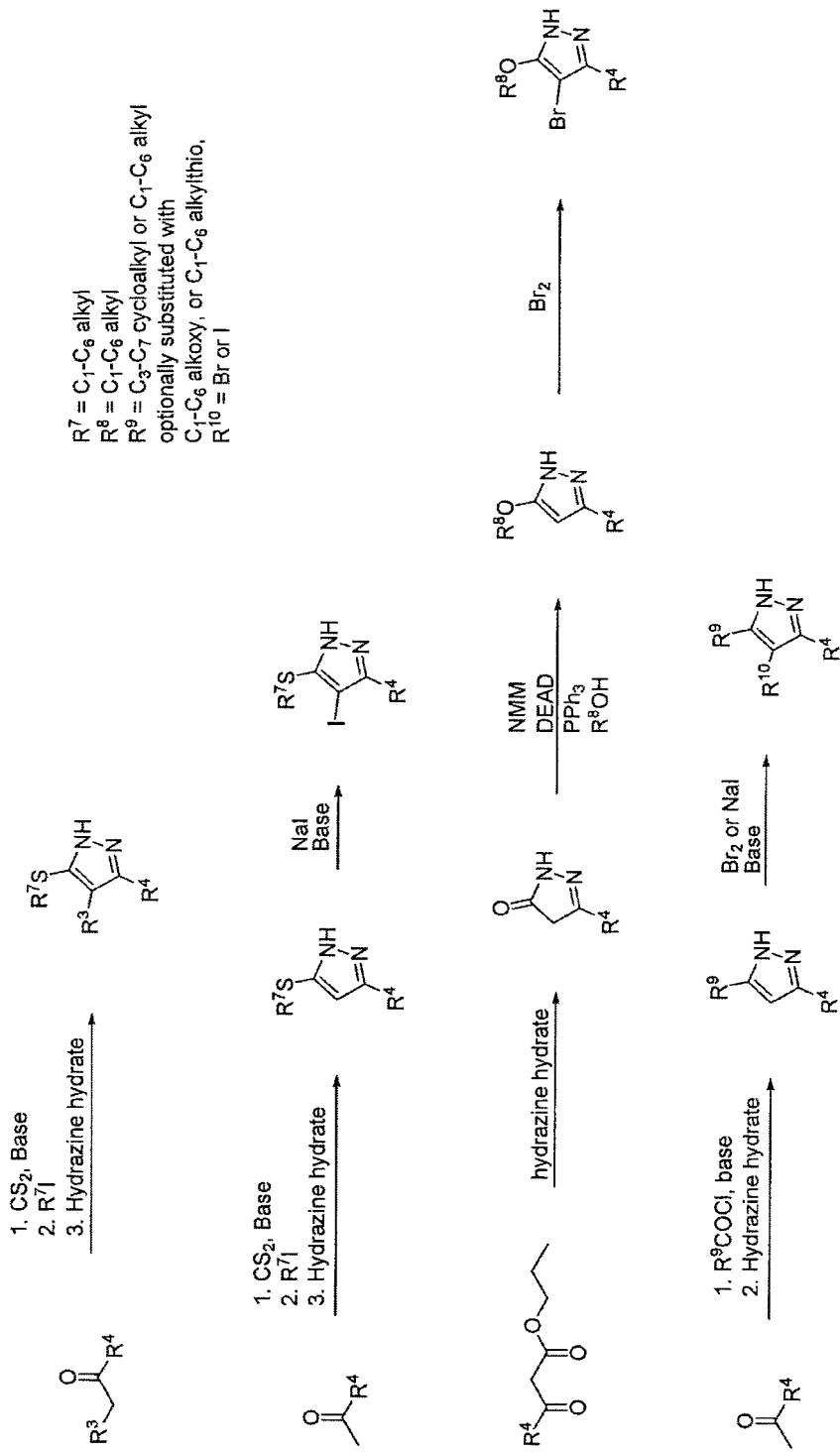
FIG. 6 depicts a number of methods for synthesizing intermediates useful in the preparation of compounds of the present invention. In the first of these methods, a ketone derivative is reacted with carbon disulfide in the presence of base, followed by an alkyl halide, followed by hydrazine hydrate to give a 2-(alkylthio)-substituted pyrazole intermediate. In the second of these methods, a methyl ketone is reacted with carbon disulfide in the presence of base, followed by an alkyl halide, followed by hydrazine hydrate to give a 2-(alkylthio)-substituted pyrazole intermediate in which $R^3$ is hydrogen. This may then be converted to the corresponding iodide by treatment with sodium iodide and base. In the third of these methods, a 3-oxo-3-propoxypropanoyl derivative is treated with hydrazine hydrate to afford a 1H-pyrazol-5(4H)-one. Mitsunobu reaction followed by bromination affords 2-alkoxy-3-bromo pyrazole intermediates. In the fourth of these methods, a methyl ketone is reacted with an acid chloride in the presence of base, then hydrazine hydrate and finally bromine or sodium iodide in the presence of base to give 3-halo-2-alkyl- or 3-halo-2-cycloalkyl-pyrazole intermediates.
Figure 7:
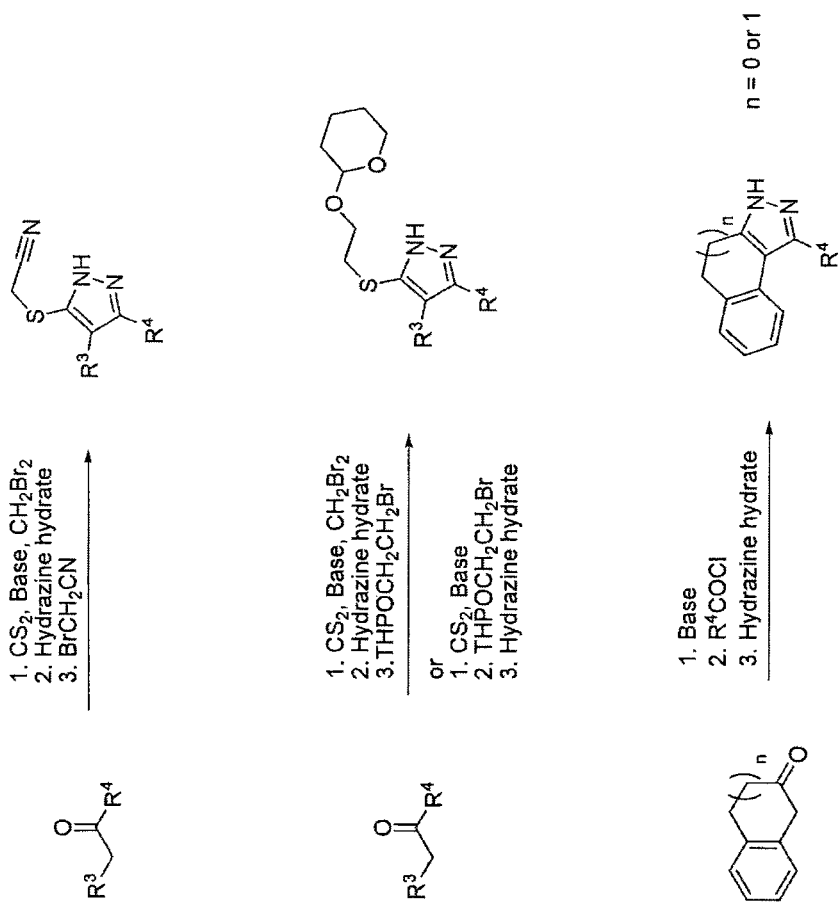
FIG. 7 depicts three methods for the synthesis of certain intermediates useful in the preparation of compounds of the present invention. In the first of these methods a ketone derivative is reacted first with carbon disulfide and methylene bromide in the presence of base, then hydrazine hydrate and finally bromo acetonitrile to give a 2-(cyanomethylthio)-pyrazole intermediate. In the second of these methods, a ketone derivative is converted to a 2-(tetrahydro-2H-pyran-2-yloxy)ethylthio-pyrazole. The transformation may be accomplished by either reaction with carbon disulfide, methylene bromide and base, followed by hydrazine hydrate, followed by 2-(2-bromoethoxy)tetrahydro-2H-pyran, or reaction with carbon disulfide and base, then 2-(2-bromoethoxy)tetrahydro-2H-pyran and finally hydrazine hydrate. The third method describes the preparation of substituted 4,5-dihydro-3H-benzo[e]indazole and 1,8-dihydro indeno[2,1-c]pyrazole intermediates from 3,4-dihydronaphthalen-2(1H)-one or 1H-inden-2(3H)-one respectively via reaction with an acid chloride in the presence of base followed by reaction with hydrazine hydrate.
Figure 8:
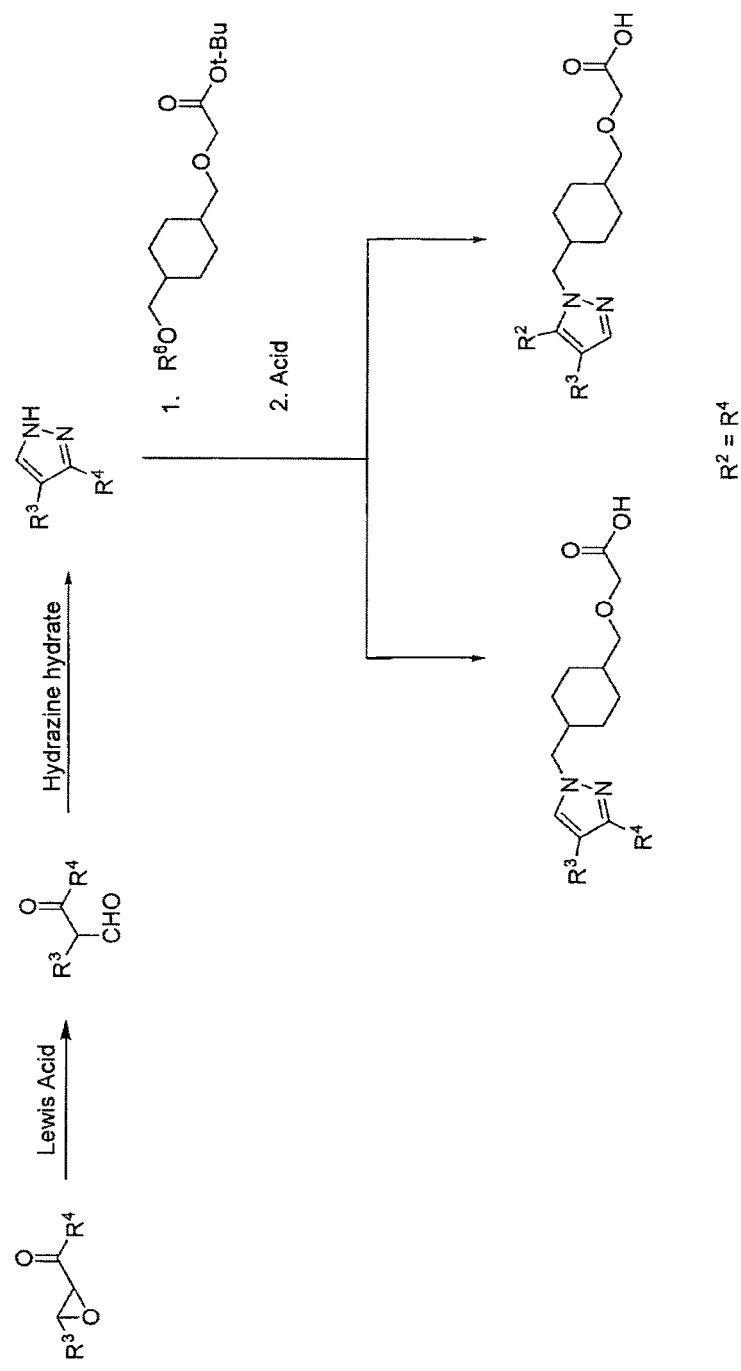
FIG. 8 depicts a method of preparing certain di-substituted compounds of the present invention. β-Keto aldehydes derived from chalcone epoxides by Lewis acid-catalyzed rearrangement are reacted with hydrazine hydrate to give di-substituted pyrazoles. These are reacted with the sulfonate esters described in FIG. 3 to give di-substituted compounds of Formula Ia as mixtures of regioisomers.
Figure 9:
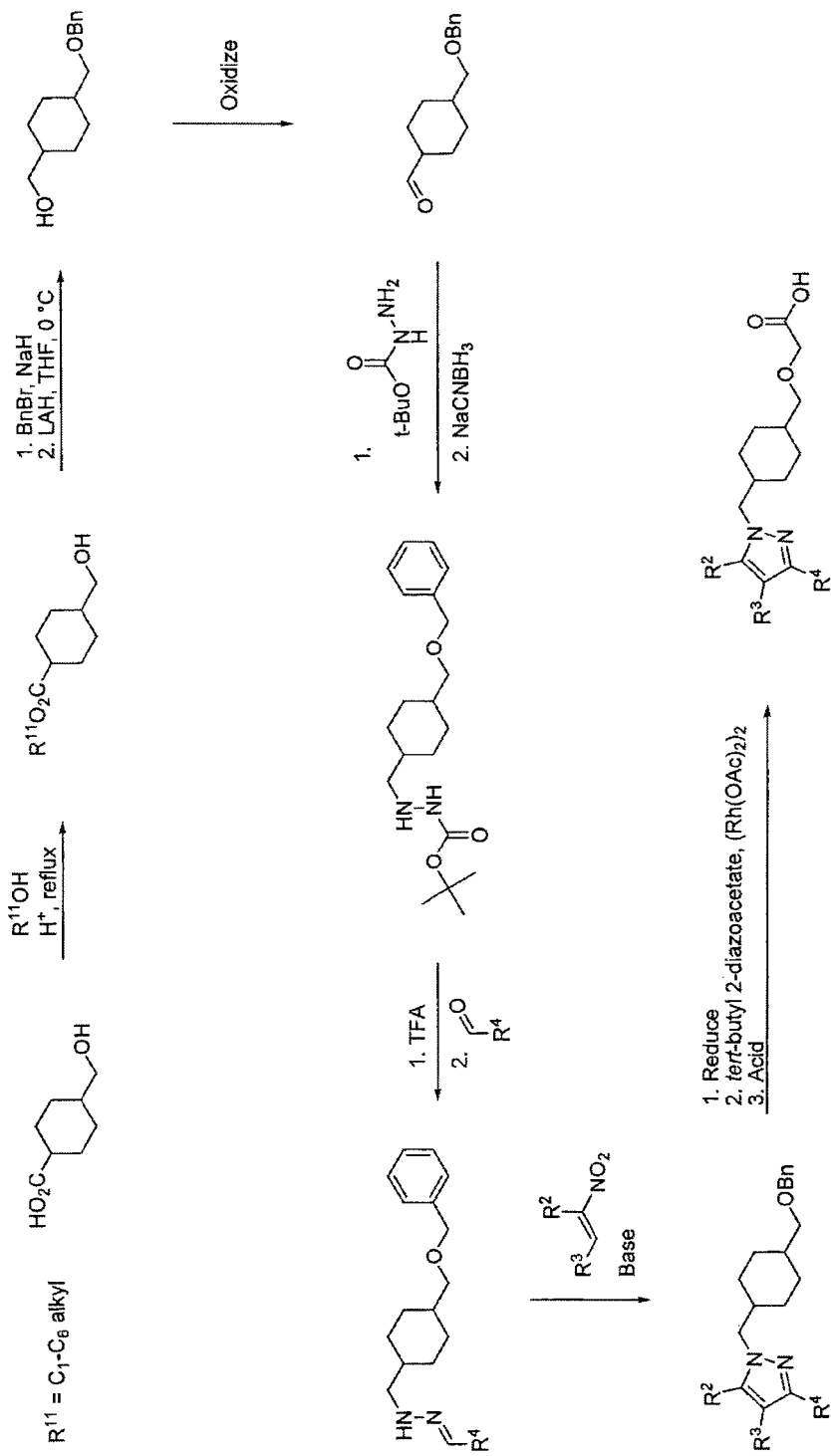
FIG. 9 depicts a general method of preparing compounds of the present invention. Starting from 4-(hydroxymethyl) cyclohexanecarboxylic acid the acid group is esterified and the alcohol is protected with a benzyl group. Next, the ester is reduced and reoxidized to the aldehyde. The aldehyde undergoes reductive animation to give a Boc-protected hydrazine which is subsequently deprotected and then coupled with an aldehyde to give an imine. This is reacted with a nitroalkene is the presence of base to form the pyrazole ring. Next, the benzyl protecting group is removed reductively, the alcohol is reacted with tert-butyl 2-diazoacetate in the presence of rhodium acetate to give the 2-tert-butoxy-2-oxoethoxy derivative which is finally converted to a compound of Formula Ia by treatment with acid.

Rats were randomly given a single subcutaneous injection of either 60 mg/kg MCT (Sigma, St. Louis, Mo.) or 0.9% saline (sham) and assigned to receive oral administration of 20% hydroxypropyl beta-cyclodextrin (vehicle) or test compound (30 mg/kg; FIGS. 1 and 2). 10-11 rats were used per treatment group. 24 h following MCT administration, test compound or vehicle was administered by oral gavage twice a day for 21 consecutive days. Heart chamber weights were measured on Day 22. Rats were anesthetized with intraperitoneal pentobarbital (50 mg/kg), the chest cavity was opened and the heart was excised. The right ventricle was dissected free from the septum and left ventricle and both parts were weighed. The ratio of right ventricular (RV) weight to left ventricle plus septum (LV+S) weight (this ratio is indicated as "RV/(LV+S)" in FIGS. 1 and 2) was calculated as an index of the hypertrophic response to the induced pulmonary arterial hypertension and, as such, as an index of a test compound's therapeutic efficacy for pulmonary arterial hypertension.

It is apparent from inspection of FIGS. 1 and 2 that oral administration of Compounds 14 and 31 inhibited the hypertrophic response to the induced pulmonary arterial hypertension and, as such, evidenced therapeutic efficacy for pulmonary arterial hypertension.

Those skilled in the art will recognize that various modifications, additions, substitutions and variations to the illustrative examples set forth herein can be made without departing from the spirit of the invention and are, therefore, considered within the scope of the invention. All documents referenced above, including, but not limited to, printed publications and provisional and regular patent applications, are incorporated herein by reference in their entirety.

What is claimed is:

1. A method for the treatment of a PGI2 receptor mediated disorder in an individual, comprising administering to said individual in need thereof, a therapeutically effective amount of a 2-((4-((1H-pyrazol-1-yl)methyl)cyclohexyl)methoxy)acetic acid derivative or a pharmaceutically acceptable salt, solvate, or hydrate thereof.

2. A method for the treatment of PAH in an individual, comprising administering to said individual in need thereof, a therapeutically effective amount of a 2-((4-((1H-pyrazol-1-yl)methyl)cyclohexyl)methoxy)acetic acid derivative or a pharmaceutically acceptable salt, solvate, or hydrate thereof.

3. The method according to claim 2, wherein said PAH is selected from:
   idiopathic PAH;
   familial PAH;
   PAH associated with a collagen vascular disease selected from: scleroderma, CREST syndrome, systemic lupus erythematosus (SLE), rheumatoid arthritis, Takayasu's arteritis, polymyositis, and dermatomyositis;
   PAH associated with a congenital heart disease selected from: atrial septic defect (ASD), ventricular septic defect (VSD) and patent ductus arteriosus in an individual;
   PAH associated with portal hypertension;
   PAH associated with HIV infection;

PAH associated with ingestion of a drug or toxin;
PAH associated with hereditary hemorrhagic telangiectasia;
PAH associated with splenectomy;
PAH associated with significant venous or capillary involvement;
PAH associated with pulmonary veno-occlusive disease (PVOD); and
PAH associated with pulmonary capillary hemangiomatosis (PCH) in an individual.

4. A method for the treatment of a disorder selected from: platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD) in an individual, comprising administering to said individual in need thereof, a therapeutically effective amount of a 2-((4-((1H-pyrazol-1-yl)methyl)cyclohexyl)methoxy)acetic acid derivative or a pharmaceutically acceptable salt, solvate, or hydrate thereof.

* * * * *